US009587279B2

(12) United States Patent
Fahey, III et al.

(10) Patent No.: US 9,587,279 B2
(45) Date of Patent: Mar. 7, 2017

(54) THYROID TUMORS IDENTIFIED

(71) Applicant: Cornell University, Ithaca, NY (US)

(72) Inventors: Thomas J. Fahey, III, Larchmont, NY (US); Nimmi Kapoor, Orange, CA (US); Theresa Scognamiglio, Brooklyn, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/087,812

(22) Filed: Nov. 22, 2013

(65) Prior Publication Data

US 2015/0167094 A1 Jun. 18, 2015

Related U.S. Application Data

(63) Continuation of application No. 13/063,429, filed as application No. PCT/US2009/005091 on Sep. 11, 2009, now abandoned.

(60) Provisional application No. 61/191,845, filed on Sep. 12, 2008, provisional application No. 61/207,812, filed on Feb. 17, 2009.

(51) Int. Cl.
*C12Q 1/68* (2006.01)

(52) U.S. Cl.
CPC ......... *C12Q 1/6886* (2013.01); *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2006/0035244 A1 | 2/2006 | Riggins et al. | |
| 2007/0099209 A1 | 5/2007 | Clarke et al. | |
| 2008/0044824 A1* | 2/2008 | Giordano et al. | 435/6 |
| 2008/0292546 A1 | 11/2008 | Clarke | |
| 2009/0298061 A1 | 12/2009 | Wirtz | |
| 2010/0131432 A1* | 5/2010 | Kennedy et al. | 705/500 |
| 2010/0285979 A1* | 11/2010 | Zeiger et al. | 506/8 |
| 2011/0251091 A1 | 10/2011 | Fahey, III et al. | |
| 2012/0172243 A1 | 7/2012 | Davicioni et al. | |

FOREIGN PATENT DOCUMENTS

| | | | |
|---|---|---|---|
| WO | WO-00/63438 A2 | 10/2000 | |
| WO | WO-2005/085471 A2 | 9/2005 | |
| WO | WO-2005/100608 A2 | 10/2005 | |
| WO | WO-2006/020269 A2 | 2/2006 | |
| WO | WO-2010/030365 A3 | 3/2010 | |
| WO | WO 2010030365 A2 * | 3/2010 | C12Q 1/68 |
| WO | WO-2010/124372 A1 | 11/2010 | |

OTHER PUBLICATIONS

"[HG-U133A] Affymetrix Human Genome U133A Array", GEO, XP002528459, (Mar. 11, 2002), 4 pgs.
"U.S. Appl. No. 13/063,429, Non Final Office Action mailed Feb. 21, 2014", 24 pgs.
"U.S. Appl. No. 13/063,429, Response filed Jan. 21, 2014 to Restriction Requirement mailed Nov. 22, 2013", 11 pgs.
"U.S. Appl. No. 13/063,429, Response filed May 20, 2014 to Non Final Office Action mailed Feb. 21, 2014", 17 pgs.
"U.S. Appl. No. 13/063,429, Restriction Requirement mailed Nov. 22, 2013", 11 pgs.
"U.S. Appl. No. 13/063,429, Supplemental Preliminary Amendment filed Feb. 4, 2013", 11 pgs.
"U.S. Appl. No. 13/063,429, Supplemental Preliminary Amendment filed Jun. 25, 2013", 11 pgs.
"International Application Serial No. PCT/US2009/005091, International Preliminary Report on Patentability dated Mar. 15, 2011", 9 pgs.
"International Application Serial No. PCT/US2009/005091, International Search Report mailed Mar. 31, 2010", 9 pgs.
"International Application Serial No. PCT/US2009/005091, Invitation to Pay Additional Fee mailed Jan. 11, 2010"; 9 pgs.
"International Application Serial No. PCT/US2009/005091, Written Opinion mailed Mar. 31, 2010", 9 pgs.
Arora, N., et al., "Identification of Borderline Thyroid Tumors by Gene Expression Array Analysis", *Cancer*, (2009), 11 pgs.
Durand, S., et al., "Evaluation of gene expression profiles in thyroid nodule biopsy material to diagnose thyroid cancer", *Journal of Clinical Endocrinology & Metabolism*, 93(4), (2008), 1195-1202.
Finley, D. J., et al., "Advancing the Molecular Diagnosis of Thyroid Nodules: Defining Benign Lesions by Molecular Profiling"; *Thyroid* 15(6), (2005), 562-568.
Finley, D. J., et al., "Discrimination of Benign and Malignant Thyroid Nodules by Molecular Profiling", *Annuals of Surgery*, 240(3), (2004), 425-437.
Finley, D. J., et al., "Molecular Profiling Distinguishes Papillary Carcinoma from Benign Thyroid Nodules", *The Journal of Clinical Endocrinology & Metabolism*, 89(7). (Jul. 2004), 3214-3223.
Fontaine, J.-F., et al., "Microarray analysis refines classification of non-medullary thyroid tumours of uncertain malignancy". *Oncogene*, 27, (2008), 2228-2236.
Gombos, K., et al., "Characterization of microarray gene expression profiles of early stage thyroid tumours", *Cancer Genomics & Proteomics*, 4(6), (2007), 403-409.
Lubitz, C. C., et al., "Gene expression profiling of thyroid tumors—clinical applicability",*Nature Clinical Practice—Endocrinology & Metabolism*, 2(9), (2006), 472-473.
Lubitz, C. C., et al., "Microarray Analysis of Thyroid Nodule Fine-Needle Aspirates Accurately Classifies Benign and Malignant Lesions", *Journal of Molecular Diagnostics*, 8(4), (2006), 490-498.
Lubitz, C. C., et al., "Molecular analysis of minimally invasive follicular carcinomas by gene profiling", *Surgery*, 138(6), (2005), 1042-1048; Discussion 1048-1049.
Lubitz, C. C., et al., "The Differentiation of Benign and Malignant Thyroid Nodules", *Advances in Surgery*, vol. 39, (2005), 355-376.
Nikolova, D, et al., ""Genome-wide gene expression profiles of thyroid carcinoma: Identification of molecular targets for treatment of thyroid carcinoma"", *Oncology Reports*, 20(1), (2008), 105-121.

(Continued)

*Primary Examiner* — Karen S Weiler
(74) *Attorney, Agent, or Firm* — Schwegman Lundberg & Woessner, P.A.

(57) ABSTRACT

The invention relates to methods and kits for detecting thyroid cancer by detecting differences in the expression of genes that are differentially expressed in thyroid cancer cells.

10 Claims, 5 Drawing Sheets

(56) References Cited

OTHER PUBLICATIONS

Puxeddu, E., et al., "Clinical Implications of BRAF mutation in thyroid carcinoma", *Trends in Endocrinology and Metabolism*, 19(4), (2008), 138-145.

Stolf, B. S., et al., "Expres si on profil e of malignant and non-malignant diseases of the thyroid gland reveals altered expression of a common set of genes in goiter and papillary carcinomas", *Cancer Letters*, 227(1), (2005), 59-73.

"U.S. Appl. No. 13/063,429, Final Office Action mailed Sep. 2, 2014", 20 pgs.

"U.S. Appl. No. 13/063,429, Examiner Interview Summary mailed Mar. 11, 2015", 2 pgs.

"U.S. Appl. No. 13/063,429, Preliminary Amendment filed Mar. 10, 2011", 3 pgs.

"U.S. Appl. No. 13/063,429, Supplemental Preliminary Amendment filed May 31, 2011", 10 pgs.

"U.S. Appl. No. 14/087,812, Response filed Jan. 6, 2016 to Advisory Action mailed Oct. 22, 2015", 7 pgs.

\* cited by examiner

SEQUENCE LISTING

```
<160> NUMBER OF SEQ ID NOS: 172

<210> SEQ ID NO 1
<211> LENGTH: 22
<212> TYPE: DNA
<213> ORGANISM: Homo sapiens

<400> SEQUENCE: 1
tgcttgctct gataggaaaa tg                                           22

<210> SEQ ID NO 2
<211> LENGTH: 22
<212> TYPE: DNA
<213> ORGANISM: Homo sapiens

<400> SEQUENCE: 2
gactttctag taactcagca gc                                           22

<210> SEQ ID NO 3
<211> LENGTH: 19
<212> TYPE: DNA
<213> ORGANISM: Homo sapiens
```

```
<400> SEQUENCE: 3
aatactgtga gaagaagtg                                        19

<210> SEQ ID NO 4
<211> LENGTH: 21
<212> TYPE: DNA
<213> ORGANISM: Homo sapiens

<400> SEQUENCE: 4
gtgccaaagg ctgaggaaat g                                     21

<210> SEQ ID NO 5
<211> LENGTH: 22
<212> TYPE: DNA
<213> ORGANISM: Homo sapiens

<400> SEQUENCE: 5
ctcatgtggt agcagttgat tc                                    22

<210> SEQ ID NO 6
<211> LENGTH: 20
<212> TYPE: DNA
<213> ORGANISM: Homo sapiens

<400> SEQUENCE: 6
gaagtcccgc aaggagaatg                                       20

<210> SEQ ID NO 7
<211> LENGTH: 19
<212> TYPE: DNA
<213> ORGANISM: Homo sapiens

<400> SEQUENCE: 7
aggctggcct catccaaag                                        19

<210> SEQ ID NO 8
<211> LENGTH: 19
<212> TYPE: DNA
<213> ORGANISM: Homo sapiens

<400> SEQUENCE: 8
gatcgtgtgt cgctgcaac                                        19

<210> SEQ ID NO 9
<211> LENGTH: 19
<212> TYPE: DNA
<213> ORGANISM: Homo sapiens

<400> SEQUENCE: 9
aggaaactca ttcagactg                                        19

<210> SEQ ID NO 10
<211> LENGTH: 19
<212> TYPE: DNA
<213> ORGANISM: Homo sapiens

<400> SEQUENCE: 10
atgccaacca agagatgag                                        19

<210> SEQ ID NO 11
<211> LENGTH: 19
<212> TYPE: DNA
<213> ORGANISM: Homo sapiens
```

```
<400> SEQUENCE: 11
aatgggcgag cacatacac                                                  19

<210> SEQ ID NO 12
<211> LENGTH: 19
<212> TYPE: DNA
<213> ORGANISM: Homo sapiens

<400> SEQUENCE: 12 taataggtg tggaatgtc                                                   19

<210> SEQ ID NO 13
<211> LENGTH: 19
<212> TYPE: DNA
<213> ORGANISM: Homo sapiens

<400> SEQUENCE: 13
cttcctaact tattgcctg                                                  19

<210> SEQ ID NO 14
<211> LENGTH: 19
<212> TYPE: DNA
<213> ORGANISM: Homo sapiens

<400> SEQUENCE: 14
ggatctgcga cacctcagc                                                  19

<210> SEQ ID NO 15
<211> LENGTH: 20
<212> TYPE: DNA
<213> ORGANISM: Homo sapiens

<400> SEQUENCE: 15
ggcctacaac aaatccaaac                                                 20

<210> SEQ ID NO 16
<211> LENGTH: 22
<212> TYPE: DNA
<213> ORGANISM: Homo sapiens

<400> SEQUENCE: 16
taggacacgc aggaaagacc ac                                              22

<210> SEQ ID NO 17
<211> LENGTH: 21
<212> TYPE: DNA
<213> ORGANISM: Homo sapiens

<400> SEQUENCE: 17
ttaaacctgt ccacattggt g                                               21

<210> SEQ ID NO 18
<211> LENGTH: 19
<212> TYPE: DNA
<213> ORGANISM: Homo sapiens

<400> SEQUENCE: 18
gataagaggg attagggag                                                  19

<210> SEQ ID NO 19
<211> LENGTH: 20
<212> TYPE: DNA
```

<213> ORGANISM: Homo sapiens

<400> SEQUENCE: 19
atttcctttc taacactgtg                                           20

<210> SEQ ID NO 20
<211> LENGTH: 20
<212> TYPE: DNA
<213> ORGANISM: Homo sapiens

<400> SEQUENCE: 20
tctagttaca gtggatttag                                           20

<210> SEQ ID NO 21
<211> LENGTH: 19
<212> TYPE: DNA
<213> ORGANISM: Homo sapiens

<400> SEQUENCE: 21
atccagagtg acagtgaac                                            19

<210> SEQ ID NO 22
<211> LENGTH: 19
<212> TYPE: DNA
<213> ORGANISM: Homo sapiens

<400> SEQUENCE: 22
gactaaacct aaatgcctc                                            19

<210> SEQ ID NO 23
<211> LENGTH: 23
<212> TYPE: DNA
<213> ORGANISM: Homo sapiens

<400> SEQUENCE: 23
atccagcctc atacctacat cag                                       23

<210> SEQ ID NO 24
<211> LENGTH: 19
<212> TYPE: DNA
<213> ORGANISM: Homo sapiens

<400> SEQUENCE: 24
gcttattcca taccatttc                                            19

<210> SEQ ID NO 25
<211> LENGTH: 20
<212> TYPE: DNA
<213> ORGANISM: Homo sapiens

<400> SEQUENCE: 25
ggctcttctc cctctcccag                                           20

<210> SEQ ID NO 26
<211> LENGTH: 19
<212> TYPE: DNA
<213> ORGANISM: Homo sapiens

<400> SEQUENCE: 26
gttggtaata tcactatgc                                            19

<210> SEQ ID NO 27
<211> LENGTH: 19

```
<212> TYPE: DNA
<213> ORGANISM: Homo sapiens

<400> SEQUENCE: 27
gtaattggat ttcgctatc                                              19

<210> SEQ ID NO 28
<211> LENGTH: 23
<212> TYPE: DNA
<213> ORGANISM: Homo sapiens

<400> SEQUENCE: 28
gatgagaact accacaagtg ctg                                         23

<210> SEQ ID NO 29
<211> LENGTH: 25
<212> TYPE: DNA
<213> ORGANISM: Homo sapiens

<400> SEQUENCE: 29
tgtactttga atcgcttgct tgttg                                       25

<210> SEQ ID NO 30
<211> LENGTH: 20
<212> TYPE: DNA
<213> ORGANISM: Homo sapiens

<400> SEQUENCE: 30
tgcagcaact ccagactgag                                             20

<210> SEQ ID NO 31
<211> LENGTH: 19
<212> TYPE: DNA
<213> ORGANISM: Homo sapiens

<400> SEQUENCE: 31
ttgtgtgttg tcttgaaag                                              19

<210> SEQ ID NO 32
<211> LENGTH: 20
<212> TYPE: DNA
<213> ORGANISM: Homo sapiens

<400> SEQUENCE: 32
gaagcgattc tcccatgctc                                             20

<210> SEQ ID NO 33
<211> LENGTH: 19
<212> TYPE: DNA
<213> ORGANISM: Homo sapiens

<400> SEQUENCE: 33
tacgataaag tttgcacag                                              19

<210> SEQ ID NO 34
<211> LENGTH: 20
<212> TYPE: DNA
<213> ORGANISM: Homo sapiens

<400> SEQUENCE: 34
gaaagaactg tctctaccag                                             20

<210> SEQ ID NO 35
```

-continued

```
<211> LENGTH: 19
<212> TYPE: DNA
<213> ORGANISM: Homo sapiens

<400> SEQUENCE: 35
actacaagca gagactgag                                                     19

<210> SEQ ID NO 36
<211> LENGTH: 20
<212> TYPE: DNA
<213> ORGANISM: Homo sapiens

<400> SEQUENCE: 36
caaggcaggc agattgtttg                                                    20

<210> SEQ ID NO 37
<211> LENGTH: 22
<212> TYPE: DNA
<213> ORGANISM: Homo sapiens

<400> SEQUENCE: 37
ttagcggaca tgggtcaatt tc                                                 22

<210> SEQ ID NO 38
<211> LENGTH: 21
<212> TYPE: DNA
<213> ORGANISM: Homo sapiens

<400> SEQUENCE: 38
gcttgtactg ggacattgtt c                                                  21

<210> SEQ ID NO 39
<211> LENGTH: 19
<212> TYPE: DNA
<213> ORGANISM: Homo sapiens

<400> SEQUENCE: 39
gatccaggac atctatcag                                                     19

<210> SEQ ID NO 40
<211> LENGTH: 19
<212> TYPE: DNA
<213> ORGANISM: Homo sapiens

<400> SEQUENCE: 40
agcacggaca cactggcac                                                     19

<210> SEQ ID NO 41
<211> LENGTH: 19
<212> TYPE: DNA
<213> ORGANISM: Homo sapiens

<400> SEQUENCE: 41
gtgaaagcac cttgtaaac                                                     19

<210> SEQ ID NO 42
<211> LENGTH: 19
<212> TYPE: DNA
<213> ORGANISM: Homo sapiens

<400> SEQUENCE: 42
agtaaggagg taagattgc                                                     19
```

```
<210> SEQ ID NO 43
<211> LENGTH: 20
<212> TYPE: DNA
<213> ORGANISM: Homo sapiens

<400> SEQUENCE: 43
ggtagtgtct aagtggtatg                                           20

<210> SEQ ID NO 44
<211> LENGTH: 19
<212> TYPE: DNA
<213> ORGANISM: Homo sapiens

<400> SEQUENCE: 44
tgactttcaa ctaaccttg                                            19

<210> SEQ ID NO 45
<211> LENGTH: 20
<212> TYPE: DNA
<213> ORGANISM: Homo sapiens

<400> SEQUENCE: 45
gatattgtgt cctaaattgc                                           20

<210> SEQ ID NO 46
<211> LENGTH: 21
<212> TYPE: DNA
<213> ORGANISM: Homo sapiens

<400> SEQUENCE: 46
tgccaatggg acaaacataa g                                         21

<210> SEQ ID NO 47
<211> LENGTH: 26
<212> TYPE: DNA
<213> ORGANISM: Homo sapiens

<400> SEQUENCE: 47
gatgcctgtt tgctatttgg tggaag                                    26

<210> SEQ ID NO 48
<211> LENGTH: 19
<212> TYPE: DNA
<213> ORGANISM: Homo sapiens

<400> SEQUENCE: 48
attgtactct ttaacccag                                            19

<210> SEQ ID NO 49
<211> LENGTH: 22
<212> TYPE: DNA
<213> ORGANISM: Homo sapiens

<400> SEQUENCE: 49
cttcctcagt tgcactaacc ac                                        22

<210> SEQ ID NO 50
<211> LENGTH: 25
<212> TYPE: DNA
<213> ORGANISM: Homo sapiens

<400> SEQUENCE: 50
tctgccagct tacatttacc caaac                                     25
```

```
<210> SEQ ID NO 51
<211> LENGTH: 19
<212> TYPE: DNA
<213> ORGANISM: Homo sapiens

<400> SEQUENCE: 51
gtgaccgctc ttgctcttg                                                    19

<210> SEQ ID NO 52
<211> LENGTH: 19
<212> TYPE: DNA
<213> ORGANISM: Homo sapiens

<400> SEQUENCE: 52
aagagtgaat agttgcctc                                                    19

<210> SEQ ID NO 53
<211> LENGTH: 19
<212> TYPE: DNA
<213> ORGANISM: Homo sapiens

<400> SEQUENCE: 53
ctagaggctg gtttagaac                                                    19

<210> SEQ ID NO 54
<211> LENGTH: 21
<212> TYPE: DNA
<213> ORGANISM: Homo sapiens

<400> SEQUENCE: 54
agtttgtagc caatgtggaa g                                                 21

<210> SEQ ID NO 55
<211> LENGTH: 19
<212> TYPE: DNA
<213> ORGANISM: Homo sapiens

<400> SEQUENCE: 55
tgatttcctg ttatgagtc                                                    19

<210> SEQ ID NO 56
<211> LENGTH: 21
<212> TYPE: DNA
<213> ORGANISM: Homo sapiens

<400> SEQUENCE: 56
ttccatatca tctccggttc g                                                 21

<210> SEQ ID NO 57
<211> LENGTH: 19
<212> TYPE: DNA
<213> ORGANISM: Homo sapiens

<400> SEQUENCE: 57
gactcttgca catcactac                                                    19

<210> SEQ ID NO 58
<211> LENGTH: 21
<212> TYPE: DNA
<213> ORGANISM: Homo sapiens

<400> SEQUENCE: 58
tgtgcccaac gcatgttata g                                                 21
```

<210> SEQ ID NO 59
<211> LENGTH: 19
<212> TYPE: DNA
<213> ORGANISM: Homo sapiens

<400> SEQUENCE: 59
agaaaggact tgtatgctg                                                19

<210> SEQ ID NO 60
<211> LENGTH: 21
<212> TYPE: DNA
<213> ORGANISM: Homo sapiens

<400> SEQUENCE: 60
gtgtgtgtca ccctcctgaa c                                             21

<210> SEQ ID NO 61
<211> LENGTH: 20
<212> TYPE: DNA
<213> ORGANISM: Homo sapiens

<400> SEQUENCE: 61
ttgcagctat gtattgttag                                               20

<210> SEQ ID NO 62
<211> LENGTH: 20
<212> TYPE: DNA
<213> ORGANISM: Homo sapiens

<400> SEQUENCE: 62
gatggcgata cgcttcagta                                               20

<210> SEQ ID NO 63
<211> LENGTH: 20
<212> TYPE: DNA
<213> ORGANISM: Homo sapiens

<400> SEQUENCE: 63
aaggtgatgt gatggcagtg                                               20

<210> SEQ ID NO 64
<211> LENGTH: 20
<212> TYPE: DNA
<213> ORGANISM: Homo sapiens

<400> SEQUENCE: 64
ttggcagctt gaggttgctc                                               20

<210> SEQ ID NO 65
<211> LENGTH: 21
<212> TYPE: DNA
<213> ORGANISM: Homo sapiens

<400> SEQUENCE: 65
cttgatcggt catgcctagc c                                             21

<210> SEQ ID NO 66
<211> LENGTH: 19
<212> TYPE: DNA
<213> ORGANISM: Homo sapiens

<400> SEQUENCE: 66

```
gtaggcaccc tggtagcaa                                                  19

<210> SEQ ID NO 67
<211> LENGTH: 19
<212> TYPE: DNA
<213> ORGANISM: Homo sapiens

<400> SEQUENCE: 67
aagagattgt ttggttcac                                                  19

<210> SEQ ID NO 68
<211> LENGTH: 23
<212> TYPE: DNA
<213> ORGANISM: Homo sapiens

<400> SEQUENCE: 68
ctcgggatct ccaataggct ctc                                             23

<210> SEQ ID NO 69
<211> LENGTH: 19
<212> TYPE: DNA
<213> ORGANISM: Homo sapiens

<400> SEQUENCE: 69
gtgccctccg ttcacagtc                                                  19

<210> SEQ ID NO 70
<211> LENGTH: 21
<212> TYPE: DNA
<213> ORGANISM: Homo sapiens

<400> SEQUENCE: 70
agctttcaac acagtagtat c                                               21

<210> SEQ ID NO 71
<211> LENGTH: 19
<212> TYPE: DNA
<213> ORGANISM: Homo sapiens

<400> SEQUENCE: 71
ataaactcta ccaagggtg                                                  19

<210> SEQ ID NO 72
<211> LENGTH: 19
<212> TYPE: DNA
<213> ORGANISM: Homo sapiens

<400> SEQUENCE: 72
cgtgaggaag caagtgaca                                                  19

<210> SEQ ID NO 73
<211> LENGTH: 22
<212> TYPE: DNA
<213> ORGANISM: Homo sapiens

<400> SEQUENCE: 73
gagaagataa ttggagctgg aa                                              22

<210> SEQ ID NO 74
<211> LENGTH: 22
<212> TYPE: DNA
<213> ORGANISM: Homo sapiens

<400> SEQUENCE: 74
```

```
caatcttaga ctctggcctc aa                                              22

<210> SEQ ID NO 75
<211> LENGTH: 23
<212> TYPE: DNA
<213> ORGANISM: Homo sapiens

<400> SEQUENCE: 75
gctctctgta ccctgaaatc ttc                                             23

<210> SEQ ID NO 76
<211> LENGTH: 20
<212> TYPE: DNA
<213> ORGANISM: Homo sapiens

<400> SEQUENCE: 76
gtttgaatag tctttctcag                                                 20

<210> SEQ ID NO 77
<211> LENGTH: 19
<212> TYPE: DNA
<213> ORGANISM: Homo sapiens

<400> SEQUENCE: 77
gtcaaggtag tagatgcac                                                  19

<210> SEQ ID NO 78
<211> LENGTH: 20
<212> TYPE: DNA
<213> ORGANISM: Homo sapiens

<400> SEQUENCE: 78
gctaccttgc acatatctac                                                 20

<210> SEQ ID NO 79
<211> LENGTH: 20
<212> TYPE: DNA
<213> ORGANISM: Homo sapiens

<400> SEQUENCE: 79
gatacatcaa agtaaagcag                                                 20

<210> SEQ ID NO 80
<211> LENGTH: 20
<212> TYPE: DNA
<213> ORGANISM: Homo sapiens

<400> SEQUENCE: 80
atgatgtaaa cttggatgtc                                                 20

<210> SEQ ID NO 81
<211> LENGTH: 22
<212> TYPE: DNA
<213> ORGANISM: Homo sapiens

<400> SEQUENCE: 81
caatagccgt gcaagatgaa tg                                              22

<210> SEQ ID NO 82
<211> LENGTH: 19
<212> TYPE: DNA
<213> ORGANISM: Homo sapiens
```

```
<400> SEQUENCE: 82
atcgactaca tgattgttc                                              19

<210> SEQ ID NO 83
<211> LENGTH: 23
<212> TYPE: DNA
<213> ORGANISM: Homo sapiens

<400> SEQUENCE: 83
gtatgagacc tacgagcctt acc                                         23

<210> SEQ ID NO 84
<211> LENGTH: 20
<212> TYPE: DNA
<213> ORGANISM: Homo sapiens

<400> SEQUENCE: 84
acccagaatt aagatatacg                                             20

<210> SEQ ID NO 85
<211> LENGTH: 19
<212> TYPE: DNA
<213> ORGANISM: Homo sapiens

<400> SEQUENCE: 85
cttagatgac caaagatgc                                              19

<210> SEQ ID NO 86
<211> LENGTH: 23
<212> TYPE: DNA
<213> ORGANISM: Homo sapiens

<400> SEQUENCE: 86
ctttctggta gtattggagg agg                                         23

<210> SEQ ID NO 87
<211> LENGTH: 23
<212> TYPE: DNA
<213> ORGANISM: Homo sapiens

<400> SEQUENCE: 87
cagaggctgt tatgtttatt gtg                                         23

<210> SEQ ID NO 88
<211> LENGTH: 20
<212> TYPE: DNA
<213> ORGANISM: Homo sapiens

<400> SEQUENCE: 88
catcgaggct tctaccggaa                                             20

<210> SEQ ID NO 89
<211> LENGTH: 19
<212> TYPE: DNA
<213> ORGANISM: Homo sapiens

<400> SEQUENCE: 89
agagcataga actccagtg                                              19

<210> SEQ ID NO 90
<211> LENGTH: 21
<212> TYPE: DNA
<213> ORGANISM: Homo sapiens
```

```
<400> SEQUENCE: 90
cactggagag attggacttt c                                              21

<210> SEQ ID NO 91
<211> LENGTH: 20
<212> TYPE: DNA
<213> ORGANISM: Homo sapiens

<400> SEQUENCE: 91
tatatcaagg taaagtccag                                                20

<210> SEQ ID NO 92
<211> LENGTH: 19
<212> TYPE: DNA
<213> ORGANISM: Homo sapiens

<400> SEQUENCE: 92
caagtgtgta gtcctgttg                                                 19

<210> SEQ ID NO 93
<211> LENGTH: 19
<212> TYPE: DNA
<213> ORGANISM: Homo sapiens

<400> SEQUENCE: 93
ggtttctttc ttcttcttc                                                 19

<210> SEQ ID NO 94
<211> LENGTH: 19
<212> TYPE: DNA
<213> ORGANISM: Homo sapiens

<400> SEQUENCE: 94
aatggcacga tcatgggtc                                                 19

<210> SEQ ID NO 95
<211> LENGTH: 22
<212> TYPE: DNA
<213> ORGANISM: Homo sapiens

<400> SEQUENCE: 95
aagtgtagcc caggttaaga ac                                             22

<210> SEQ ID NO 96
<211> LENGTH: 21
<212> TYPE: DNA
<213> ORGANISM: Homo sapiens

<400> SEQUENCE: 96
gagaaacagc tcagccagtg g                                              21

<210> SEQ ID NO 97
<211> LENGTH: 19
<212> TYPE: DNA
<213> ORGANISM: Homo sapiens

<400> SEQUENCE: 97
aaggtgattt cttgagttc                                                 19

<210> SEQ ID NO 98
<211> LENGTH: 24
<212> TYPE: DNA
```

```
<213> ORGANISM: Homo sapiens

<400> SEQUENCE: 98
ctgatgtatc caccaaacca gtac                                        24

<210> SEQ ID NO 99
<211> LENGTH: 20
<212> TYPE: DNA
<213> ORGANISM: Homo sapiens

<400> SEQUENCE: 99
cagtagtgca taggaaattc                                             20

<210> SEQ ID NO 100
<211> LENGTH: 20
<212> TYPE: DNA
<213> ORGANISM: Homo sapiens

<400> SEQUENCE: 100
cagtgaaaca tctgatacac                                             20

<210> SEQ ID NO 101
<211> LENGTH: 20
<212> TYPE: DNA
<213> ORGANISM: Homo sapiens

<400> SEQUENCE: 101
atagtcatgg acatttacag                                             20

<210> SEQ ID NO 102
<211> LENGTH: 20
<212> TYPE: DNA
<213> ORGANISM: Homo sapiens

<400> SEQUENCE: 102
aagttactaa gactgcacag                                             20

<210> SEQ ID NO 103
<211> LENGTH: 20
<212> TYPE: DNA
<213> ORGANISM: Homo sapiens

<400> SEQUENCE: 103
ctatcgttga atgaatgaac                                             20

<210> SEQ ID NO 104
<211> LENGTH: 21
<212> TYPE: DNA
<213> ORGANISM: Homo sapiens

<400> SEQUENCE: 104
ctgaaggagt ggtgcgatca a                                           21

<210> SEQ ID NO 105
<211> LENGTH: 24
<212> TYPE: DNA
<213> ORGANISM: Homo sapiens

<400> SEQUENCE: 105
gaagacactt tggcaatgca gcgg                                        24

<210> SEQ ID NO 106
<211> LENGTH: 20
```

<212> TYPE: DNA
<213> ORGANISM: Homo sapiens

<400> SEQUENCE: 106
gatacttctg cttggtgtag                                           20

<210> SEQ ID NO 107
<211> LENGTH: 19
<212> TYPE: DNA
<213> ORGANISM: Homo sapiens

<400> SEQUENCE: 107
gacgaccctt gtctccctg                                            19

<210> SEQ ID NO 108
<211> LENGTH: 21
<212> TYPE: DNA
<213> ORGANISM: Homo sapiens

<400> SEQUENCE: 108
gcatcactaa ggtcttcagc a                                         21

<210> SEQ ID NO 109
<211> LENGTH: 23
<212> TYPE: DNA
<213> ORGANISM: Homo sapiens

<400> SEQUENCE: 109
gtggtcagta gccttatgca cct                                       23

<210> SEQ ID NO 110
<211> LENGTH: 19
<212> TYPE: DNA
<213> ORGANISM: Homo sapiens

<400> SEQUENCE: 110
atcatttctc tctccaaag                                            19

<210> SEQ ID NO 111
<211> LENGTH: 20
<212> TYPE: DNA
<213> ORGANISM: Homo sapiens

<400> SEQUENCE: 111
ggaagacaac agacaatatc                                           20

<210> SEQ ID NO 112
<211> LENGTH: 21
<212> TYPE: DNA
<213> ORGANISM: Homo sapiens

<400> SEQUENCE: 112
gattatggcg acactcttgc c                                         21

<210> SEQ ID NO 113
<211> LENGTH: 19
<212> TYPE: DNA
<213> ORGANISM: Homo sapiens

<400> SEQUENCE: 113
tacagtgatg acagacagc                                            19

<210> SEQ ID NO 114

```
<211> LENGTH: 21
<212> TYPE: DNA
<213> ORGANISM: Homo sapiens

<400> SEQUENCE: 114
cttggagagg gtgccattgt c                                              21

<210> SEQ ID NO 115
<211> LENGTH: 19
<212> TYPE: DNA
<213> ORGANISM: Homo sapiens

<400> SEQUENCE: 115
gataaacagg gaaacactg                                                 19

<210> SEQ ID NO 116
<211> LENGTH: 21
<212> TYPE: DNA
<213> ORGANISM: Homo sapiens

<400> SEQUENCE: 116
cttgtaacgt cttctctgcc t                                              21

<210> SEQ ID NO 117
<211> LENGTH: 20
<212> TYPE: DNA
<213> ORGANISM: Homo sapiens

<400> SEQUENCE: 117
tattgacttg gagactattg                                                20

<210> SEQ ID NO 118
<211> LENGTH: 19
<212> TYPE: DNA
<213> ORGANISM: Homo sapiens

<400> SEQUENCE: 118
gaagaaactg agcaaggcc                                                 19

<210> SEQ ID NO 119
<211> LENGTH: 14243
<212> TYPE: DNA
<213> ORGANISM: Homo sapiens

<400> SEQUENCE: 119
ctcctcctcc tgctttcctc cagtaagtgc atacccgcta gtggtctgta caggcggcac    60
ggtttgatgg cagagatatt ttctttccaa actgttcaaa atgatgaacg aagatgcagc   120
tcagaaaagc gacagtggag agaagttcaa cggcagtagt cagaggagaa aaagacccaa   180
gaagtctgac agcaatgcaa gcttcctccg tgctgccaga gcaggcaacc tggacaaagt   240
tgtggaatat ctgaagggggg gcatagacat caatacctgc aatcagaatg gactcaacgc   300
tctccatctg gctgccaagg aaggccacgt ggggctggtg caggagctgc tgggaagagg   360
gtcctctgtg gattctgcca ctaagaaggg aaataccgct cttcacattg catctttggc   420
tggacaagca gaagttgtca agttcttgt taaggaagga gccaatatta atgcacagtc   480
tcagaatggc tttactcctt tatacatggc tgcccaagag aatcacattg atgttgtaaa   540
atatttgctg gaaaatgag ctaatcagag cactgctaca gaggatggct ttactcctct   600
agctgtggca ctccagcaag gacacaacca ggcggtggcc atcctcttgg agaatgacac   660
caaagggaaa gtgaggctgc cagctctgca tattgccgct aggaaagacg acaccaaatc   720
```

```
tgccgcactt ctgcttcaga atgaccacaa tgctgacgta caatccaaga tgatggtgaa      780
taggacaact gagagtggtt ttaccccttt gcacatagct gcacattacg gaaatgtcaa      840
cgtggcaact cttcttctaa accggggagc tgctgtggac ttcacagcca ggaatggaat      900
cactcctctg catgtggctt ccaaaagagg aaatacaaac atggtgaagc tcttactgga      960
tcgaggcggt cagatcgatg ccaaaactag ggatgggttg acaccacttc actgtgctgc     1020
acgaagtggg catgaccaag tggtggaact tctgttggaa cggggtgccc ccttgctggc     1080
aaggactaag aatgggctgt ctccactaca catggctgcc cagggagacc acgtggaatg     1140
tgtgaagcac ctgttacagc acaaggcacc tgttgatgat gtcaccctag actacctgac     1200
agccctccac gttgctgcgc actgtggcca ctaccgtgta accaaactcc ttttagacaa     1260
gagagccaat ccgaacgcca gagccctgaa tggtttttact ccactgcaca ttgcctgcaa     1320
gaaaaaccgc atcaaagtca tggaactgct ggtgaaatat ggggcttcaa tccaagctat     1380
aacagagtct ggcctcacac caatacatgt ggctgccttc atgggccact tgaacattgt     1440
cctccttctg ctgcagaacg gagcctctcc agatgtcact aacattcgtg gtgagacggc     1500
actacacatg gcagcccgag ccgggcaggt ggaagtggtc cgatgcctcc tgagaaatgg     1560
tgcccttgtt gatgccagag ccagggagga acagacacct ttacatattg cctcccgcct     1620
gggtaagaca gaaattgtcc agctgcttct acaacatatg gctcatccag atgcggccac     1680
tacaaatggg tacacaccac tgcacatctc tgcccgggag ggccaggtgg atgtggcatc     1740
agtcctattg gaagcaggag cagcccactc cttagctacc aagaagggtt ttactcccct     1800
gcatgtagca gccaagtatg aagcctggga tgtggcaaaa cttctcttgc aacgccgtgc     1860
tgccgcagat tctgcaggga gaacggcct taccccgctc catgttgctg ctcattatga     1920
caaccagaag gtggcgctgc tgttactgga aagggtgct tcccctcatg ccactgccaa     1980
gaatggctat actccgttac atattgctgc caagaagaat caaatgcaga tagcttccac     2040
actcctgaac tatggagcag agacaaacat tgtgacaaag caaggagtaa ctccactcca     2100
tctggcctcg caggaggggc acacagatat ggttaccttg cttctggata agggagccaa     2160
tatccacatg tcaactaaga gtggactcac atccttacac cttgcagccc aggaagataa     2220
agtgaatgtt gctgatattc tcaccaagca tggagctgat caggatgctc atacaaagct     2280
tggttacaca ccttaattg tggcctgtca ctatggaaat gtgaaaatgg tcaactttct     2340
tctgaagcag ggagcaaatg ttaacgcaaa aaccaagaac ggctacacgc ctttgcacca     2400
ggccgctcag cagggtcaca cgcacatcat caacgtcctg ctccagcatg ggccaagcc     2460 caacgccacc actgcgaatg gcaacactgc cttggcgatt gctaagcgtc tgggctacat     2520
ctccgtggtc gacaccctga aggttgtgac tgaggaggtc accaccacca ccacaactat     2580
tacagaaaaa cacaaactaa atgtacctga gacgatgact gaggttcttg atgtttctga     2640
tgaagagggt gatgacacaa tgactggtga tggggagaa taccttaggc ctgaggacct     2700
aaaagaactg ggtgatgact cactacccag cagtcagttc ctggatggta tgaattacct     2760
gcgatacagc ttggagggag gacgatctga cagccttcga tccttcagtt ccgacaggtc     2820
tcacactctg agccatgcct cctacctgag ggacagtgcc gtgatggatg actcagttgt     2880
gattcccagt caccaggtgt caactctagc caaggaggca gaaaggaatt cttatcgcct     2940
aagctggggc actgagaact tagacaacgt ggctctttct tctagtccta ttcattcagg     3000
tttcctggtt agttttatgg tggatgcccg aggtggtgct atgcgaggat gcagacacaa     3060
```

```
tgggctccga atcattattc cacctcggaa atgtactgct ccaacgcgag tcacctgccg    3120
actggtcaag cgccacagac tggcaacaat gcctccaatg gtggaaggag aaggcctggc    3180
cagtcgcctg atcgaagttg gaccttctgg tgctcagttc cttggtaaac ttcacctgcc    3240
aacggctcct cccccactta atgagggaga aagtttggtc agccgcattc ttcagctggg    3300
gcctcctgga accaaattcc ttgggcctgt gatcgtggag atccctcact ttgcggccct    3360
tcgaggaaag gaaagggaac tggtggtcct gcgcagtgag aatggggaca gctggaaaga    3420
gcatttctgt gactacactg aagatgaatt gaatgaaatt cttaacggca tggatgaagt    3480
actggatagc ccagaagacc tagaaaagaa acgaatctgc cgcatcatca cccgagactt    3540
cccacagtac tttgcagtgg tgtctcgtat caaacaggac agcaatctga ttggcccaga    3600
aggaggtgta ctgagcagca cagtggtgcc ccaggtgcag gccgtcttcc cagagggggc    3660
actcaccaag cggatccgcg taggcctgca ggctcaacct atgcacagtg agctggttaa    3720
gaagatccta ggcaacaaag ctaccttcag ccctatagtc actttggaac ctagaagaag    3780
aaaattccac aaaccaatta ccatgaccat tcctgtcccc aaagcttcaa gtgatgtcat    3840
gttgaatggt tttggggggag atgcaccaac cttaagatta ctatgcagca taacaggtgg    3900
aaccacccct gcccagtggg aagatattac aggaactacg ccattaacat tgtcaatga    3960 atgtgtttcc tttacaacaa acgtgtctgc caggttctgg ctgatagatt gtcgacagat    4020
ccaggaatcc gttacttttg catcacaagt atacagagaa attatctgcg taccttatat    4080
ggccaaattt gtagtgtttg ccaaatcaca tgaccccatt gaagccaggt tgaggtgttt    4140
ctgcatgact gatgataaag tggataagac ccttgaacaa caagaaaatt ttgctgaggt    4200
ggccagaagc agggatgtgg aggtgttaga aggaaaaccc atctacgttg attgtttcgg    4260
caacttggta ccattaacta aaagtggcca gcatcatata ttcagttttt ttgccttcaa    4320
agaaaataga cttcctctat ttgtcaaggt acgcgatacg actcaggaac cttgcggacg    4380
actatcattt atgaaggagc caaaatccac gagaggcctg gtgcatcaag ctatttgcaa    4440
cttaaacatc actttgccga tttatacaaa ggaatcagag tcagatcaag aacaggagga    4500
agagatcgat atgacatcag aaaaaaatga tgagacagaa tctacagaaa catctgtcct    4560
gaaaagtcac ctggttaatg aagttcctgt cctagcaagt ccggacttgc tctctgaagt    4620
ttctgagatg aaacaagatt tgatcaaaat gaccgccatc ttgaccacag atgtgtctga    4680
taaggcaggt tctattaaag tgaaggagct ggtgaaggct gctgaggaag agccaggaga    4740 gcctttgaa atcgttgaaa gagttaaaga ggacttagag aaagtgaatg aaatcctgag    4800
aagtggaacc tgcacaagag atgaaagcag tgtgcagagc tctcggtctg agagaggatt    4860
agttgaagag gaatgggtta ttgtcagtga tgaggaaata aagagggcta ggcaaaaagc    4920
acctttagaa atcactgaat atccatgtgt agaagttaga atagataaag agatcaaagg    4980
aaaagtagag aaagactcaa ctgggctagt gaactacctt actgatgatc tgaatacctg    5040
tgtgcctctt cccaaagagc agctgcagac agttcaagat aaggcaggga agaaatgtga    5100
ggctctggct gttggcagga gctctgaaaa ggaagggaaa gacatacccc cagatgagac    5160
acagagtaca cagaaacagc acaaaccaag cttgggaata agaagccag taagaaggaa    5220 attaaaagaa aagcagaaac aaaaagagga aggtttacaa gctagtgcag agaaagctga    5280
acttaaaaaa ggtagttcag aagagtcatt aggtgaagac ccaggtttag cccctgaacc    5340
ccttcccact gtcaaggcca catctccttt gatagaagaa actcccattg gttccataaa    5400
ggacaaagta aaggcccttc agaagcgagt ggaagatgaa cagaaaggtc gaagcaagtt    5460
```

```
gcccatcaga gtcaaaggca aggaggacgt gccaaaaaag accacccaca ggccacatcc    5520
agctgcgtca ccctctctga agtcagagag acatgcgcca gggtctccct cccctaaaac    5580
agaaagacac tctactcttt cctcttccgc aaaaactgaa aggcaccctc cagtatcacc    5640
atcaagtaaa actgagaaac actccacctgt gtcaccctct gcaaaacgg aaagacattc    5700 acctgcgtca tcatcgagta aaactgagaa acactcacct gtatcaccct cgacaaaaac    5760
tgaaaggcac tctcctgtgt catctacaaa acagaaaga cacccacctg tttcgccttc    5820
aggcaaaaca gacaaacgtc cacctgtatc gccctccggg aggacagaaa acacccgcc    5880 agtatcgcct gggagaacag aaaaacgctt gcctgtttca ccctccggaa gaacggacaa    5940
gcaccaacct gtatcaacag ctgggaaaac tgagaagcac ctgcctgtgt caccttctgg    6000
caaaacagaa aagcaaccac ctgtatcccc cacttcaaaa acagagagga ttgaggaaac    6060
catgtctgtt cgggagctga tgaaggcttt ccagtcaggt caggacccct ctaaacataa    6120
aactggactc tttgagcaca aatcagcaaa acaaaagcag ccacaagaga aaggtaaagt    6180
tcgggtagaa aaagaaaagg ggccgatact aacccagaga gaagctcaga aaacagagaa    6240
tcagacaatc aaacgaggcc agagactccc ggtaacgggc acagcagaat ccaaaagagg    6300
agttcgtgtt tcctccatag gagttaagaa agaagatgca gctggaggaa aggagaaagt    6360
tctcagccac aaaatacctg aacctgttca gtcagtgcct gaagaagaaa gccacagaga    6420
gagcgaagtg cccaaagaaa agatggctga tgagcaggga gacatggatc tacagatcag    6480
cccagatagg aaaaacctcca ctgacttctc tgaggtcatt aagcaagagt tggaagacaa    6540
tgacaaatac caacaattcc gcctgagtga ggagacagaa aaggcacagc ttcacttaga    6600
ccaagtactc actagtcctt tcaacacaac atttccactc gactacatga agatgagtt    6660 ccttccagct ctgtctttac aaagcggtgc tttagatggc agttctgaaa gcctaaagaa    6720 tgaggggta gccggctctc cgtgtggcag cctgatggag gggacccctc agattagttc    6780
agaagaaagc tataagcatg aaggcctagc agagacccct gagacgagcc cagaaagcct    6840
ttctttctca ccaaagaaaa gtgaggagca aactggggaa acaaaggaaa gcaccaagac    6900
agaaaccacc acagaaattc gttcagaaaa agagcatccc acgaccaaag acattactgg    6960
tggctctgaa gagcgaggtg ccacagtcac tgaggactca gagacctcta ctgagagttt    7020
tcagaaagag gccactctag gctctcccaa agacacaagc cctaaaagac aagatgattg    7080
cacaggcagc tgtagtgtag cattagctaa agagacacct acaggactga ctgaggaggc    7140
agcctgtgat gaaggtcaac gtaccttggg tagttcagcc cacaagacac aaactgatag    7200
tgaggttcaa gaatccacag ccacctcaga cgagacaaag gccttgccgc tgcctgaggc    7260
ttctgtaaag acagatacag gaactgaatc aaaacctcag ggagtcatta gaagtcccca    7320
agggttagaa cttgcactcc ctagccgaga tagcgaagtc ctcagcgctg tggctgatga    7380
ctcattagca gtgagccaca agactctct ggaagccagc cctgtgctag aagataactc    7440
ttcacacaaa accctgatt ctctggagcc aagtcctctg aaagaatccc cttgccgtga    7500
ctctctggaa agcagccctg ttgaaccaaa gatgaaggct ggaatttttc caagtcactt    7560
tcctcttcct gcagctgttg ccaaaacaga actcttgacg gaagtggcct ctgtgcggtc    7620
ccggctactc cgagaccctg atggcagtgc tgaggatgac agtcttgagc agacatcgct    7680
catggagagc tcaggaaga gccccctttc tcctgacacc cccagctctg aagaagtcag    7740
ctatgaggtt acacccaaaa ccacagatgt aagtacacca aaaccagctg tgattcatga    7800
```

```
atgtgcagag gaggatgatt cagaaaacgg ggagaaaaag aggttcacac ctgaagagga    7860
gatgtttaaa atggtaacca aaatcaaaat gtttgatgaa cttgaacaag aagcaaagca    7920
gaaaagggac tacaaaaaag aacccaaaca agaagaatct tcttcatctt ctgacccaga    7980
tgctgactgt tcagtagatg tggatgaacc aaaacataca ggcagtgggg aggatgaaag    8040
tggtgtccct gtgttagtaa cttcggagag caggaaggtg tcttcctcct cagaaagtga    8100
acctgagttg gcacagctta aaaaaggtgc tgactcaggc cttttaccag aaccagtgat    8160
tcgagtacaa cctccttctc cacttccatc aagcatggac tccaattcca gtccagaaga    8220
agtacaattc cagcctgtcg tttccaaaca atatactttc aagatgaatg aagatactca    8280
ggaagagcca ggcaaatcag aagaagaaaa agattctgaa tcccatttag ctgaagaccg    8340
tcatgctgtt tccactgagg ctgaagacag gtcttatgat aagctaaaca gagacactga    8400
tcagccaaaa atctgtgatg ccatggatg tgaggccatg agtcctagca gctcagctgc    8460
tcctgtctct tcaggtctac agagtccgac tggtgatgat gttgatgaac agccagtcat    8520
ctataaagaa tcattagctc tccaaggcac tcatgaaaaa gacacagagg gagaagagct    8580
tgatgtttct agagcagaat ctccacaagc agattgcccc agtgaaagct tttcatcttc    8640
atcctctttg cctcattgtt tggtatctga aggaaaagaa ttagatgaag acatatctgc    8700
cacatcttct attcaaaaaa cagaggtcac aaaaactgat gaaacatttg agaacttacc    8760
aaaggactgc ccctctcaag actcatccat tactactcaa acagatagat tttccatgga    8820
tgttcccgtg tctgacctag ctgagaatga tgaaatctat gatccacaaa tcactagccc    8880
ttatgaaaat gtcccttccc aatctttttt ctctagtgaa gaaagcaaaa cccaaacaga    8940
tgcaaatcac accacaagtt ttcactcttc tgaagtgtat tctgttacca tcacatcccc    9000
tgttgaagac gttgtagtgg caagctcctc tagtggaact gttttaagca agaatctaa     9060
ttttgagggc caggacataa aaatggaatc ccaacaggaa agtaccttgt gggaaatgca    9120
atcagacagt gtctcttcat cttttcgagcc tactatgtcc gctacaacaa cagttgttgg    9180
tgaacaaata agcaaagtca tcatcacaaa aactgatgtg gattctgatt cttggagtga    9240
aattcgggaa gacgatgaag cctttgaggc tcgtgtgaaa aggaagaac aaaagatatt    9300
tggtttgatg gtagacagac aatcacaggg taccacccct gacaccactc ctgctaggac    9360
cccaactgaa gaggggaccc caacaagtga gcaaaaccca tttctgtttc aggaaggaaa    9420
attgtttgaa atgacccgaa gtggtgccat tgatatgacc aaaaggtcct atgcagatga    9480
aagtttcac tttttccaaa ttggtcaaga atccagggaa gagactctct ctgaagatgt    9540
gaaagaaggg gctactgggg ctgatcccct accgctggag acatcagctg aatcactagc    9600
actttcagaa tcaaaagaaa cagtggatga tgaggcagac ttacttccag atgacgtgag    9660
tgaggaagta gaggaaatac ctgcttcgga tgctcaactt aactcccaaa tggggatttc    9720
agcctccact gaaacaccta caaaagaagc tgttagtgta gggaccaagg acctccccac    9780
cgtgcaaacg ggtgatatac ctcctctctc tggtgtaaag cagatatcct gccccgactc    9840
ttctgaacca gctgtacaag tccagttaga ttttttccaca ctcaccaggt ctgtttattc    9900
agatagggt gatgattctc ccgattcttc cccagaagaa cagaaatcag taatcgagat    9960
tcctactgca cccatggaga atgtgccttt tactgaaagc aaatccaaaa ttcctgtaag   10020
gactatgccc acttccaccc cagcacctcc atctgcagag tatgagagtt cagtttctga   10080
agattttcta tccagtgtag atgaggaaaa taaggcggat gaagcaaaac caagtccaa    10140
actccctgtc aaagtacccc tccaaagagt tgaacagcag ctctcagatc tagacacctc   10200
```

```
tgtccagaag acagtggctc ctcagggaca ggacatggca agcatcgcac cagataatag   10260
aagcaaatct gaatctgatg ctagttcttt ggattcaaag accaaatgcc cagtaaaaac   10320
ccgaagttac actgagacag aaacagagag cagagagagg gccgaggaac ttgagttaga   10380
atcagaagaa ggggccacaa gaccaaagat acttacatcc cgattgccag ttaagagcag   10440
aagcactaca tcttcctgca gggggggcac gagccccaca aaagaaagta aggagcattt   10500
ctttgacctt tacagaaatt ccatagaatt ctttgaggag attagtgatg aggcttccaa   10560
attagtggat aggctgacac agtcagagag ggagcaggaa atagtttcag acgatgaaag   10620
tagtagtgcc ctggaagtat cagtaattga aaatctgcca cctgttgaga ccgagcactc   10680
agttcctgag gacatctttg acacaaggcc catttgggat gagtctattg agactctgat   10740
tgaacgcatc cctgatgaaa atggccatga ccatgctgaa gatccacagg atgagcagga   10800
acggatcgag gaaaggctgg cttatattgc tgatcacctt ggcttcagct ggacagaatt   10860
agcaagagaa ctggatttca ctgaggagca aattcatcaa attcgaattg aaaatcccaa   10920
ctctcttcaa gaccagagtc atgcactgtt gaagtactgg ctagagaggg atgggaaaca   10980
tgctacagat accaacctcg ttgaatgtct caccaagatc aaccgaatgg atattgttca   11040
tctcatggag accaacacag aacctctcca ggagcgcatc agtcatagtt atgcagaaat   11100
tgaacagacc attacactgg atcatagtga agggttctcg gtacttcaag aggagttatg   11160
cactgcacag cacaagcaga aagaggagca agctgtttct aaagaaagtg agacctgcga   11220
tcaccctcct atcgtctcag aggaagacat ttctgttggt tattccactt ttcaggatgg   11280
cgtccccaaa actgagggg acagctcagc aacagcactc tttccccaaa ctcacaagga   11340
gcaagttcaa caggatttct cagggaaaat gcaagacctg cctgaagagt catctctgga   11400
atatcagcag gaatattttg tgacaactcc aggaacagaa acatcagaga ctcagaaggc   11460
tatgatagta cccagctctc ccagcaagac acctgaggaa gttagcaccc ctgcagagga   11520
ggagaagctg tacctccaga ccccaacatc cagcgagcgg ggaggctctc ccatcataca   11580
agaacccgaa gagccctcag agcacagaga ggagagctct ccgcggaaaa ccagcctcgt   11640
aatagtggag tctgccgata accagcctga gacctgtgaa agactcgatg aagatgcagc   11700
ttttgaaaag ggagacgata tgcctgaaat accccagaa acagtcacag aagaagaata   11760
cattgatgag catggacaca ccgtggtaaa gaaggttact aggaaaatca ttaggcggta   11820
tgtatcctct gaaggcacag agaaagaaga gattatggtg cagggaatgc cacaggaacc   11880
tgtcaacatc gaggaagggg atggctattc caaagttata aagcgtgttg tattgaagag   11940
tgacaccgag cagtcagagg acaacaatga gtaaagccat cacacagaag agggctgtgg   12000
tgaaggacca gcatggaaaa cgcattgact tggagcacct ggaggatgta ccagaagcac   12060
tagaccagga cgacctccag cgcgatctcc agcagctcct tcggcatttc tgcaaggagg   12120
acttgaagca gaggccaag tgaggggctg cccagttctc acaccagaaa ccacacattc   12180
actcaatatg cagcttcctg tttcagtagg ggagtgacct aactggccta attaatggga   12240 tacccccgaca tttccactgt tagcaaatat acggcatttt gctttagttt tccccccatcc   12300 tctttaacta taaagctaat ttgtgaccaa agatggcatc cttcatactg gatgctgtat   12360
ccaatacttt gttgtgtctg tgctaacctg ggaactggcc acctccattg ttctttgctt   12420
ctgcacaaga tccatgaaaa tccattgatc agaagaactt cacctgcaga cctcttcaag   12480
tgacactatg taggaatcct tccaaggaat atctatgtac aatgtatata gctgaaatgc   12540
```

```
tcagatgaac aacatattaa aattaaaacc actgcctatt gtaactacac tgggcatcag   12600
aataaaaggc ctctagaaat tgctgaacaa tggttaatta agatattgct aacacaatcg   12660
agtgataata cagttttact gcaaaagaag cacttcaaac ctattatgtc cttagaactt   12720
ccagagtagc cactgctccc agttaaaggt gggtcagtag ccttgcagaa ctgtcctgag   12780
aagttattgc tggtgctggc cagccatggc ttaggactcc aacagccact ctgagggagg   12840
ggagaaggga gcagaggcca cgcagaatga accgatgggg tattcagttg ctggcagcta   12900
cattgtgtgg cattctagca tcttcaggtc tttagatctt ggacaagttg gcagggtatt   12960
ttaaaagcta taactactgt agttttccag ttttcattgc tgcttagca aaccacgctg    13020 tcttacagtg gtactttctt ctggccactg cactgtagat aattcattgg aaacaagatt   13080
tacccactac ataaaaggtt aaactccttc agtatgttgg agtggtttct ttttttttt    13140 ctttctttct tttttttctt caggtttata tcttctctaa tacctgcatg tggcgtttaa   13200
aaatcaagac cacggtcaaa cccctcttct aatcacatta attgtttcca ttctttttac   13260
cctgagtgag cacttttcac tttccagcta ggtctgtttt tcagcttgca gacaagattg   13320
agaaatcctt gaaaatttgg ttttggttaa aattttttggt ttatttattt gaaatccaca  13380
ctcccttgga aactcttaag tgcatttgtg cacttctgtt tgtttgtctc aaagaaggga   13440
ctgtaacaat ctgagtaatt tccatgtcct cttccttatt cctctagtgg ttgaagctgt   13500
gtagcatttt aacatatata tattcacaaa tatattcata taaacagtat acattttgaa   13560
tcagtcattt gttaaagaaa agtatattca atgaagatga aatttaaata aaaaggaca    13620 gagtctatcc tccagggatt gaacattttc caattatctg gtcttttcct gttgtgcaaa   13680
aatgactcat tgctccgaat gtcaaaaaca aatgcgacaa acaatggcac ttcatcattt   13740
aaagtaatgt tgccaagaga aaaaatttcc tgggagggag gtttcccaca agccaaatct   13800
cctaagcctc aaatgctagc acttttggc agttggatag gaaatgagac attctttggc    13860
agccaaaata agagaggccg atggtgaaac tttttgagac accctatggc cttcttgtca   13920
aaaccttcac tggagctcaa gaaaagcatt tctgttgtgt tatttgcagt gcagatgatg   13980
tctgtgtaac aacataatgg ttattcacct tttttttgatt ttgattttg ctgtgttatc   14040 aaaaacttga atactgtgag aagaagtgaa ttttcagttg acgaatcagc atcttgttcc   14100
catggtgata acactaattg aatatatcta tgagggcatg tattagttaa tggaaaaaaa   14160
aatacaacac taacaataca tagctgcaat gtgtacaatg gctgatttaa ttaaataaaa   14220
tgtacaagtg ttaaatgtgg caa                                           14243
```

<210> SEQ ID NO 120
<211> LENGTH: 5118
<212> TYPE: DNA
<213> ORGANISM: Homo sapiens

<400> SEQUENCE: 120

```
ggctgggctg cgaatagcgt gttcctctcc ggcggaacac acacacccgg ccttggggct     60
gtctcctgag ctccctcctc cacggagagc gctgagcgcc gccgggaatt ccatcccacc    120
gtgggcacgc agtctttgga ggtcccgggc gcagcacgct cggtgtcccc acactgcagc   180
aagacagaga ccccgcggga accttgagct tggaacaacc cttgagcctc tgcagtcgga   240
agagtgggcg cagcagccca gcggaggcca ggcgcgcaac ctcggcgcc ggggcaagga    300 gagagtgcag ggaggcgcag ctcaggcgcc cggctcagga gcgggaggaa gttctcgcgg   360
cgccgggagc gcggtggacg cgccctgggc gcacgcccag gcagccttct ccctggccct   420
```

-continued

```
cgggactgtc ctcgggccgc aaggaggagc ttgctggagt cttagaggcc atccagagcc      480
agcgagcagg agcgctgcgt ctcccgcctc agctaggaag ggggagtggc gctggcaggc      540
tggagctggg aacccagcga gcgcctgacc ttcctcctcc tcttcctgac cctcttcgcg      600
tcttgggctc cggaggaagg ttctagcggc tgcaggaggt ccccagaccc attttcctag      660
aaggctggtg atggatctgc tgctcctgcc gccgccgggg cacttggagc gcaccggcgg      720
cgcgtgagct gggctttgct ctccactgcc ctgggcaaac cccgggccag ccccgcctgg      780
cacctttgcc tgagtccctt tcggttcccg acccaaagcc accagcgtcc agggagggag      840
gaggaggtgg tcctcaggtg cagccccgcc gagatgtccg cgcagagcct gctccacagc      900
gtcttctcct gttcctcgcc cgcttcaagt agcgcggcct cggccaaggg cttctccaag      960
aggaagctgc gccagacccg cagcctggac ccggccctga tcggcggctg cgggagcgac     1020
gaggcgggcg cggagggcag tgcgcgggga ccacggcgg gccgcctcta ctccccatca      1080
ctcccagccg agagtctcgg ccctcgcttg gcgtcctctt cccggggtcc gcccccagg      1140 gccaccaggc taccgcctcc tggacctctt tgctcgtcct tctccacacc cagcaccccg     1200
caggagaagt caccatccgg cagctttcac tttgactatg aggttcccct gggtcgcggc     1260
ggcctcaaga gagcatggc ctgggacctg ccttctgtcc tggccgggcc agccagtagc      1320
cgaagcgctt ccagcatcct ctgttcatcc ggggaggcc caatggcat cttcgcttct      1380 cctaggaggt ggctccagca gaggaagttc cagtccccac ccgacagtcg cgggcacccc     1440
tacgtcgtgt ggaaatccga gggtgatttc acctggaaca gcatgtcagg ccgcagtgta     1500
cggctgaggt cagtccccat ccagagtctc tcagagctgg agagggcccg gctgcaggaa     1560
gtggcttttt atcagttgca acaggactgt gacctgagct gtcagatcac cattcccaaa     1620
gatggacaaa agagaaagaa atctttaaga aagaaactgg attcactagg aaaggagaaa     1680
aacaaagaca aagaattcat cccacaggca tttggaatgc ccttatccca agtcattgcg     1740
aatgacaggg cctataaact caagcaggac ttgcagaggg acgagcagaa agatgcatct     1800
gactttgtgg cttccctcct cccatttgga aataaaagac aaaacaaaga actctcaagc     1860
agtaactcat ctctcagctc aacctcagaa acaccgaatg agtcaacgtc cccaaacacc     1920
ccggaaccgg ctcctcgggc taggaggagg ggtgccatgt cagtggattc tatcaccgat     1980
cttgatgaca atcagtctcg actactagaa gctttacaac tttccttgcc tgctgaggct     2040
caaagtaaaa aggaaaaagc cagagataag aaactcagtc tgaatcctat ttacagacag     2100
gtccctaggc tggtggacag ctgctgtcag cacctagaaa acatggcct ccagacagtg      2160 gggatattcc gagttggaag ctcaaaaaag agagtgagac aattacgtga ggaatttgac     2220
cgtgggattg atgtctctct ggaggaggag cacagtgttc atgatgtggc agccttgctg     2280
aaagagttcc tgagggacat gccagacccc cttctcacca gggagctgta cacagctttc     2340
atcaacactc tcttgttgga gccggaggaa cagctgggca ccttgcagct cctcatatac     2400
cttctacctc cctgcaactg cgacaccctc caccgcctgc tacagttcct ctccatcgtg     2460
gccaggcatg ccgatgacaa catcagcaaa gatgggcaag aggtcactgg gaataaaatg     2520
acatctctaa acttagccac catatttgga cccaacctgc tgcacaagca gaagtcatca     2580
gacaaagaat tctcagttca gagttcagcc cgggctgagg agagcacggc catcatcgct     2640
gttgtgcaaa agatgattga aaattatgaa gccctgttca tggttccccc agatctccag     2700
aacgaagtgc tgatcagcct gttagagacc gatcctgatg tcgtggacta tttactcaga     2760
```

```
agaaaggctt cccaatcatc aagccctgac atgctgcagt cggaagtttc cttttccgtg   2820
ggagggaggc attcatctac agactccaac aaggcctcca gcggagacat ctccccttat   2880
gacaacaact ccccagtgct gtctgagcgc tccctgctgg ctatgcaaga ggacgcggcc   2940
ccgggggct cggagaagct ttacagagtg ccagggcagt ttatgctggt gggccacttg   3000
tcgtcgtcaa agtcaaggga agttctcct ggaccaaggc ttgggaaaga tctgtcagag   3060
gagcctttcg atatctgggg aacttggcat tcaacattaa aaagcggatc caaagaccca   3120
ggaatgacag gttcctctgg agacattttt gaaagcagct ccctaagagc ggggccctgc   3180
tcccttctc aagggaacct gtccccaaat tggcctcggt ggcaggggag ccccgcagag   3240
ctggacagcg acacgcaggg ggctcggagg actcaggccg cagcccccgc gacggagggc   3300
agggcccacc ctgcggtgtc gcgcgcctgc agcacgcccc acgtccaggt ggcagggaaa   3360
gccgagcggc ccacggccag gtcggagcag tacttgaccc tgagcggcgc ccacgacctc   3420
agcgagagtg agctggatgt ggccgggctg cagagccggg ccacacctca gtgccaaaga   3480
ccccatggga gtgggaggga tgacaagcgg ccccccgcct catacccggg cccagggaag   3540
cccgcggcag cggcagcctg gatccagggg ccccccggaag gcgtggagac acccacggac   3600
cagggaggcc aagcagccga gcgagagcag caggtcacgc agaaaaaact gagcagcgcc   3660
aactccctgc cagcgggcga gcaggacagt ccgcgcctgg gggacgctgg ctggctcgac   3720
tggcagagag agcgctggca gatctgggag ctcctgtcga ccgacaaccc cgatgccctg   3780
cccgagacgc tggtctgagc ccgcacccag ccgagccccc cctgccccga gcccccgcc   3840
ctccagccca gggggaccg tgggtggtgg ccactggcac acttagtgtt cttctttcac   3900
acttctcaaa agtgacacaa gagaaatcca gttcacctac agaggtagag cactcacgcc   3960
cccgccattg agaataaggt tccattgcgt agccagcctt aggaaaaaca aacagaaccc   4020
aaaccagatg gcaatgtcca atctaaaaac gtccctcttg gctctataat ataagataca   4080
actcttgctt ggtatagcct aaccgtattt atgtgtcttc ggttttgact attgtgtatt   4140
ctgtaacaga ttatgtataa tcatatatga tatattcaca aagagaaaac aaaaggaact   4200
tttaaaaaaa aaatcacttc acttatatta agcaatgaga tatactaaac aatgagattc   4260
tatagaatgt tctagaatgt gcacaagcgg gtttctgtgc ttttgccata gctttataac   4320
tggggataac ccttccttcg ataccaaaca ctaacaagag gaagcagaat atgagaagcc   4380
atatttttac ataggagtca gatacaaaaa gaaaaatcac tgaatgcttt tagatattga   4440
atacgttttc aggaaaatgc taaatctgat agattacgaa atatatttt agaacttgtt   4500
tagaaaggat tcagttaacc aaacaagaaa aaggcagtgc ctcacaaaga aattaagaag   4560
ttgtccgtcc cacgttacat caaattcagt tttatatagg ccatatataa tatatattta   4620
taatgtataa ttttatgta tttttcaaaa ctacaaactg gaatccaact ataaagtgtt   4680
taagaatcta cacagaatat tcaaattata gaacatgttt tttcccttg ccccataatc   4740
agtatttgcc aaattacatg caattcctta aaaactaaat cacatttggt aaaaggccta   4800
cagctttgta cttacattgt gccaaaggct gaggaaatgt tttctttcgt aattttatgt   4860
gtattgtaaa atgttctacc gtactttagt agtttgaagt ttttcaagtg cataactatt   4920
tttgaccagc agatggcgat acgcttcagt attttatgca attttttttc acttctgaag   4980
ggaaagtgta ttataaaaaa agattttttt ttttttatat aaacatgcta ctcttaattt   5040
tcatgttggt gatgaaattc ccagtggtgt ttcttaaggt tctatcttgt gccatgatga   5100
ataaaaagtt aagcaaag                                                 5118
```

<210> SEQ ID NO 121
<211> LENGTH: 1427
<212> TYPE: DNA
<213> ORGANISM: Homo sapiens

<400> SEQUENCE: 121

```
agatgaaaat ggaaggggcg ggcgcgctag gcctagtcct ggctgggctc ccgctggagt     60
gtgcgttggg ggcggaccag gagcggtggt ctccagggag gtcgaggctg ggctcccac    120
ccggatttgg agcagggtcg ccgcggccca gctgacccgc cggcgtttgt acgttgtgtg    180
cccactcagg gagccatgga caactgtttg gcggccgcag cgctgaatgg ggtggaccga    240
cgttccctgc agcgttcagc aaggctggct ctagaagtgc tggagagggc caagaggagg    300
gcggtggact ggcatgccct ggagcgtccc aaaggctgca tggggtcct tgcccgggag    360
gcgccccacc tagagaaaca gccggcagcc ggcccgcagc gcgttctccc gggagagaga    420
gaagagagac ccccaaccct tagtgcttcc ttcagaacaa tggctgaatt catggactat    480
acttcaagtc agtgtgggaa atattattca tctgtgccag aggaaggagg ggcaacccat    540
gtctatcgtt atcacagagg cgagtcgaag ctgcacatgt gcttggacat agggaatggt    600
cagagaaaag acagaaaaaa gacatcccct tggtcctgga gcagctatca aatatcagag    660
catgctccag aggcatccca gcctgctgag aacatctcta aggacctcta catagaagta    720
tatccaggga cctattctgt cactgtgggc tcaaatgact taaccaagaa gactcatgtg    780
gtagcagttg attctggaca aagcgtggac ctggtcttcc ctgtgtgatg ttgaccatca    840
ctgccatcac atcacctttt tttaagtagt aagaataaag ccactgtatg attctcttaa    900
tagctataca ttaatcctgt ttttagtgct gactgggtca gccttccggg aactggagtc    960
tgtctctttc agtgcttttt tgtttgtttg gttggttttt ttttgagaca gtctcactct   1020
gttgcccagg ctggagtgca gtggcgtgat ctcggctcac tgcaagttcc gcctcccggg   1080
ttcacaccat tctcctgcct cagcctcccg agtagctggc actacaggca cccgccacca   1140
tgcccggcta ttttttttgt attttagta gagacggggt ttcaccatgt tggccaggat   1200
ggtctcgatc tcttgacctc gtgatccacc caccttggcc tcccaaagtg ttgggattac   1260
aggcgtgagc caccgcgccc ggcctcagtg cctttttaa cttgagggtg tagaggtcct   1320
ccacgcttgt ttgcctgaaa gtaatataat gatgctgtct gaacaggttt tactgcttgc   1380
tttccaagta aaggttaatt atgataataa agagatttgg aaatgaa             1427
```

<210> SEQ ID NO 122
<211> LENGTH: 3316
<212> TYPE: DNA
<213> ORGANISM: Homo sapiens

<400> SEQUENCE: 122

```
cactctcttt ctctctccct ctggcatgca tgctgctggt aggagacccc caagtcaaca     60
ttgcttcaga aatcctttag cactcatttc tcaggagaac ttatggcttc agaatcacag    120
ctcggttttt aagatggaca taacctgtac gaccttctga tgggctttca actttgaact    180
ggatgtggac acttttctct cagatgacag aattactcca acttcccctt tgcagttgct    240
tccttttcctt gaaggtagct gtatcttatt ttctttaaaa agcttttttct tccaaagcca    300
cttgccatgc cgaccgtcat tagcgcatct gtggctccaa ggacagcggc tgagccccgg    360
tccccagggc cagttcctca cccggcccag agcaaggcca ctgaggctgg gggtggaaac    420
```

```
ccaagtggca tctattcagc catcatcagc cgcaatttcc ctattatcgg agtgaaagag    480
aagacattcg agcaacttca caagaaatgt ctagaaaaga aagttctttta tgtggaccct    540
gagttcccac cggatgagac ctctctcttt tatagccaga agttccccat ccagttcgtc    600
tggaagagac ctccggaaat ttgcgagaat ccccgattta tcattgatgg agccaacaga    660
actgacatct gtcaaggaga gctaggggac tgctggtttc tcgcagccat tgcctgcctg    720
accctgaacc agcaccttct tttccgagtc atacccatg atcaaagttt catcgaaaac    780
tacgcaggga tcttccactt ccagttctgg cgctatggag agtgggtgga cgtggttata    840
gatgactgcc tgccaacgta caacaatcaa ctggttttca ccaagtccaa ccaccgcaat    900
gagttctgga gtgctctgct ggagaaggct tatgctaagc tccatggttc ctacgaagct    960
ctgaaaggtg ggaacaccac agaggccatg gaggacttca caggaggggt ggcagagttt   1020
tttgagatca gggatgctcc tagtgacatg tacaagatca tgaagaaagc catcgagaga   1080
ggctccctca tgggctgctc cattgatgat ggcacgaaca tgacctatgg aacctctcct   1140
tctggtctga acatggggga gttgattgca cggatggtaa ggaatatgga taactcactg   1200
ctccaggact cagacctcga ccccagaggc tcagatgaaa gaccgacccg acaatcatt   1260
ccggttcagt atgagacaag aatggcctgc gggctggtca gaggtcacgc ctactctgtc   1320
acggggctgg atgaggtccc gttcaaaggt gagaaagtga agctggtgcg gctgcggaat   1380
ccgtggggcc aggtggagtg gaacggttct tggagtgata gatggaagga ctggagcttt   1440
gtggacaaag atgagaaggc ccgtctgcag caccaggtca ctgaggatgg agagttctgg   1500
atgtcctatg aggatttcat ctaccatttc acaaagttgg agatctgcaa cctcacggcc   1560
gatgctctgc agtctgacaa gcttcagacc tggacagtgt ctgtgaacga gggccgctgg   1620
gtacggggtt gctctgccgg aggctgccgc aacttcccag atactttctg gaccaaccct   1680
cagtaccgtc tgaagctcct ggaggaggac gatgaccctg atgactcgga ggtgatttgc   1740
agcttcctgg tggccctgat gcagaagaac cggcggaagg accggaagct aggggccagt   1800
ctcttcacca ttggcttcgc catctacgag gttcccaaag agatgcacgg gaacaagcag   1860
cacctgcaga aggacttctt cctgtacaac gcctccaagg ccaggagcaa aacctacatc   1920
aacatgcggg aggtgtccca gcgcttccgc ctgcctccca gcgagtacgt catcgtgccc   1980
tccacctacg agccccacca ggagggggaa ttcatcctcc gggtcttctc tgaaaagagg   2040
aacctctctg aggaagttga aaataccatc tccgtggatc ggccagtgaa aaagaaaaaa   2100
accaagccca tcatcttcgt ttcggacaga gcaaacagca caaggagct gggtgtggac   2160
caggagtcag aggagggcaa aggcaaaaca agccctgata gcaaaagca gtccccacag   2220
ccacagcctg gcagctctga tcaggaaagt gaggaacagc aacaattccg gaacattttc   2280
aagcagatag caggagatga catggagatc tgtgcagatg agctcaagaa ggtccttaac   2340
acagtcgtga acaaacacaa ggaccctgaag cacacgggt tcacactgga gtcctgccgt   2400
agcatgattg cgctcatgga tacagatggc tctggaaagc tcaacctgca ggagttccac   2460
cacctctgga caagattaa ggcctggcag aaaattttca acactatga cacagaccag   2520
tccggcacca tcaacagcta cgagatgcga aatgcagtca acgacgcagg attccacctc   2580
aacaaccagc tctatgacat cattaccatg cggtacgcag acaaacacat gaacatcgac   2640
tttgacagtt tcatctgctg cttcgttagg ctggagggca tgttcagagc ttttcatgca   2700
tttgacaagg atggagatgg tatcatcaag ctcaacgttc tggagtggct gcagctcacc   2760
atgtatgcct gaaccaggct ggcctcatcc aaagccatgc aggatcactc aggatttcag   2820
```

-continued

| | |
|---|---|
| tttcaccctc tatttccaaa gccatttacc tcaaaggacc cagcagctac acccctacag | 2880 |
| gcttccaggc acctcatcag tcatgctcct cctccatttt accccctacc catccttgat | 2940 |
| cggtcatgcc tagcctgacc ctttagtaaa gcaatgaggt aggaagaaca aacccttgtc | 3000 |
| cctttgccat gtggaggaaa gtgcctgcct ctggtccgag ccgcctcggt tctgaagcga | 3060 |
| gtgctcctgc ttaccttgct ctaggctgtc tgcagaagca cctgccggtg cactcagca | 3120 |
| cctccttgtg ctagagccct ccatcacctt cacgctgtcc caccatgggc caggaaccaa | 3180 |
| accagcactg ggttctactg ctgtggggta aactaactca gtggaatagg gctggttact | 3240 |
| ttgggctgtc caactcataa gtttggctgc attttgaaaa agctgatct aaataaaggc | 3300 |
| atgtgtatgg ctggtc | 3316 |

<210> SEQ ID NO 123
<211> LENGTH: 2833
<212> TYPE: DNA
<213> ORGANISM: Homo sapiens

<400> SEQUENCE: 123

| | |
|---|---|
| gaaggagctc tcttcttgct tggcagctgg accaagggag ccagtcttgg gcgctggagg | 60 |
| gcctgtcctg accatggtcc ctgcctggct gtggctgctt tgtgtctccg tccccaggc | 120 |
| tctcccaag gccagcctg cagagctgtc tgtggaagtt ccagaaaact atggtggaaa | 180 |
| tctcccttta tacctgacca agttgccgct gccccgtgag ggggctgaag ccagatcgt | 240 |
| gctgtcaggg gactcaggca aggcaactga gggcccattt gctatggatc cagattctgg | 300 |
| cttcctgctg gtgaccaggg ccctggaccg agaggagcag gcagagtacc agctacaggt | 360 |
| caccctggag atgcaggatg acatgtctt gtgggtcca cagcctgtgc ttgtgcacgt | 420 |
| gaaggatgag aatgaccagg tgccccattt ctctcaagcc atctacagag ctcggctgag | 480 |
| ccggggtacc aggcctggca tccccttcct cttccttgag gcttcagacc gggatgagcc | 540 |
| aggcacagcc aactcggatc ttcgattcca catcctgagc caggctccag cccagccttc | 600 |
| cccagacatg ttccagctgg agcctcggct gggggctctg gccctcagcc caaggggag | 660 |
| caccagcctt gaccacgccc tggagaggac ctaccagctg ttggtacagg tcaaggacat | 720 |
| gggtgaccag gctcaggcc accaggccac tgccaccgtg gaagtctcca tcatagagag | 780 |
| cacctgggtg tccctagagc ctatccacct ggcagagaat ctcaaagtcc tatcccgca | 840 |
| ccacatggcc caggtacact ggagtggggg tgatgtgcac tatcacctgg agagccatcc | 900 |
| cccgggaccc tttgaagtga atgcagaggg aaacctctac gtgaccagag agctggacag | 960 |
| agaagcccag gctgagtacc tgctccaggt gcgggctcag aattcccatg gcgaggacta | 1020 |
| tgcggcccct ctggagctgc acgtgctggt gatggatgag aatgacaacg tgcctatctg | 1080 |
| ccctccccgt gaccccacag tcagcatccc tgagctcagt ccaccaggta ctgaagtgac | 1140 |
| tagactgtca gcagaggatg cagatgcccc cggctccccc aattcccacg ttgtgtatca | 1200 |
| gctcctgagc cctgagcctg aggatggggt agaggggaga gccttccagg tggacccac | 1260 |
| ttcaggcagt gtgacgctgg gggtgctccc actccgagca ggccagaaca tcctgcttct | 1320 |
| ggtgctggca atggacctgg caggcgcaga gggtggcttc agcagcacgt gtgaagtcga | 1380 |
| agtcgcagtc acagatatca atgatcacgc cctgagttc atcacttccc agattgggcc | 1440 |
| tataagcctc cctgaggatg tggagcccgg gactctggtg ccatgctaa cagccattga | 1500 |
| tgctgacctc gagcccgcct tccgcctcat ggatttttgcc attgagaggg gagacacaga | 1560 |

| | |
|---|---|
| agggactttt ggcctggatt gggagccaga ctctgggcat gttagactca gactctgcaa | 1620 |
| gaacctcagt tatgaggcag ctccaagtca tgaggtggtg gtggtggtgc agagtgtggc | 1680 |
| gaagctggtg gggccaggcc caggccctgg agccaccgcc acggtgactg tgctagtgga | 1740 |
| gagagtgatg ccaccccca agttggacca ggagagctac gaggccagtg tccccatcag | 1800 |
| tgccccagcc ggctctttcc tgctgaccat ccagccctcc gaccccatca gccgaaccct | 1860 |
| caggttctcc ctagtcaatg actcagaggg ctggctctgc attgagaaat tctccgggga | 1920 |
| ggtgcacacc gcccagtccc tgcagggcgc ccagcctggg gacacctaca cggtgcttgt | 1980 |
| ggaggcccag gatacagatg agccgagact gagcgcttct gcaccctgg tgatccactt | 2040 |
| cctaaaggcc cctcctgccc cagccctgac tcttgcccct gtgcctccc aatacctctg | 2100 |
| cacaccccgc caagaccatg gcttgatcgt gagtggaccc agcaaggacc ccgatctggc | 2160 |
| cagtgggcac ggtccctaca gcttcaccct tggtcccaac cccacggtgc aacgggattg | 2220 |
| gcgcctccag actctcaatg gttcccatgc ctacctcacc ttggccctgc attgggtgga | 2280 |
| gccacgtgaa cacataatcc ccgtggtggt cagccacaat gcccagatgt ggcagctcct | 2340 |
| ggttcgagtg atcgtgtgtc gctgcaacgt ggaggggcag tgcatgcgca aggtgggccg | 2400 |
| catgaagggc atgccacga agctgtcggc agtgggcatc cttgtaggca ccctggtagc | 2460 |
| aataggaatc ttcctcatcc tcattttcac ccactggacc atgtcaagga agaaggaccc | 2520 |
| ggatcaacca gcagacagcg tgccctgaa ggcgactgtc tgaatggccc aggcagctct | 2580 |
| agctgggagc ttggcctctg gctccatctg agtccctgg agagagccc agcacccaag | 2640 |
| atccagcagg ggacaggaca gagtagaagc ccctccatct gccctggggt ggaggcacca | 2700 |
| tcaccatcac caggcatgtc tgcagagcct ggacaccaac tttatggact gcccatggga | 2760 |
| gtgctccaaa tgtcagggtg tttgcccaat aataaagccc cagagaactg ggctgggccc | 2820 |
| tatgggattg gta | 2833 |

<210> SEQ ID NO 124
<211> LENGTH: 3981
<212> TYPE: DNA
<213> ORGANISM: Homo sapiens

<400> SEQUENCE: 124

| | |
|---|---|
| tggggcttgt tccgggatcc gcagccttgc tcaggctgtg cattggtgtg gccccgaatt | 60 |
| gcacggagct gccttcctat ttcaaggaaa gacgccaagg taattttgac ccagaggagc | 120 |
| aatgatgtag ccacctccta accttcccu cttgaacccc caggtcccct cttgctgttg | 180 |
| gctgcacatc aggaaggctg tgatgggaat gaaggtgaaa acttggagat ttcacttcag | 240 |
| tcattgcttc tgcctgcaag atcatccttt aaaagtagag aagctgctct gtgtggtggt | 300 |
| taactccaag aggcagaact cgttctagaa ggaaatggat gcaagcagct ccgggggccc | 360 |
| caaacgcatg cttcctgtga tctagcccag ggaagccctt ccgtggggc cccggctttg | 420 |
| agggatgcca ccggttctgg acgcatggct gattcctgaa tgatgatggt tcgccggggg | 480 |
| ctgcttgcgt ggatttcccg ggtggtggtt ttgctggtgc tcctctgctg tgctatctct | 540 |
| gtcctgtaca tgttggcctg caccccaaaa ggtgacgagg agcagctggc actgccagg | 600 |
| gccaacagcc ccacggggaa ggaggggtac caggccgtcc ttcaggagtg ggaggagcag | 660 |
| caccgcaact acgtgagcag cctgaagcgg cagatcgcac agctcaagga ggagctgcag | 720 |
| gagaggagtg agcagctcag gaatgggcag taccaagcca gcgatgctgc tggcctgggt | 780 |
| ctggacagga gccccccaga gaaaacccag gccgacctcc tggccttcct gcactcgcag | 840 |

```
gtggacaagg cagaggtgaa tgctggcgtc aagctggcca cagagtatgc agcagtgcct    900
ttcgatagct ttactctaca gaaggtgtac cagctggaga ctggccttac ccgccacccc    960
gaggagaagc ctgtgaggaa ggacaagcgg gatgagttgg tggaagccat tgaatcagcc   1020
ttggagaccc tgaacaatcc tgcagagaac agccccaatc accgtcctta cacggcctct   1080
gatttcatag aagggatcta ccgaacagaa agggacaaag ggacattgta tgagctcacc   1140
ttcaaagggg accacaaaca tgaattcaaa cggctcatct tatttcgacc attcggcccc   1200
atcatgaaag tggaaaatga aaagctcaac atggccaaca cgcttatcaa tgttatcgtg   1260
cctctagcaa aagggtggac aagttccgg cagttcatgc agaatttcag gcctgctgat    1320
gaagttttta gatgtgtgcc tttaagccct tgattgtgcg tgttggatc ttagaagctg    1380 tgatggctca gatgcacata ttggctgagg ataaccagct aagtgatttc accagcttgt   1440
tttaaacata gaaaatccta ctgtctaatt ataaatcttg aaagatcaag ctgattttt    1500 atttcttttt ttttgagatg gagtcttact ctgtcaccca ggctggagtg cagtggcacg   1560
aactctgctc actgcaacct tcacctccca ggttcaggga gatgtgcatt gagcaggatg   1620
ggagagtcca tctcactgtt gtttactttg ggaaagaaga aataaatgaa gtcaaaggaa   1680
tacttgaaaa cacttccaaa gctgccaact tcaggaactt taccttcatc cagctgaatg   1740
gagaattttc tcggggaaag ggacttgatg ttggagcccg cttctggaag ggaagcaacg   1800
tccttctctt tttctgtgat gtggacatct acttcacatc tgaattcctc aatacgtgta   1860
ggctgaatac acagccaggg aagaaggtat tttatccagt tcttttcagt cagtacaatc   1920
ctggcataat atacggccac catgatgcag tccctcccct ggaacagcag ctggtcataa   1980
agaaggaaac tggattttgg agagactttg gatttgggat gacgtgtcag tatcggtcag   2040
acttcatcaa tataggtggg tttgatctgg acatcaaagg ctggggcgga gaggatgtgc   2100
acctttatcg caagtatctc cacagcaacc tcatagtggt acggacgcct gtgcgaggac   2160
tcttccacct ctggcatgag aagcgctgca tggacgagct gaccccgag cagtacaaga    2220 tgtgcatgca gtccaaggcc atgaacgagg catcccacgg ccagctgggc atgctggtgt   2280
tcaggcacga gatagaggct caccttcgca aacagaaaca gaagacaagt agcaaaaaaa   2340
catgaactcc cagagaagga ttgtgggaga cacttttttct ttccttttgc aattactgaa   2400
agtggctgca acagagaaaa gacttccata aggacgaca aaagaattgg actgatgggt    2460
cagagatgag aaagcctccg atttctctct gttgggcttt ttacaacaga aatcaaaatc   2520
tccgctttgc ctgcaaaagt aacccagttg caccctgtga agtgtctgac aaaggcagaa   2580
tgcttgtgag attataagcc taatggtgtg gaggttttga tggtgtttac aatacactga   2640
gacctgttgt tttgtgtgct cattgaaata ttcatgattt aagagcagtt ttgtaaaaaa   2700
ttcattagca tgaaaggcaa gcatatttct cctcatatga atgagcctat cagcagggct   2760
ctagtttcta ggaatgctaa aatatcagaa ggcaggagag gagataggct tattatgata   2820
ctagtgagta cattaagtaa aataaaatgg accagaaaag aaaagaaacc ataaatatcg   2880
tgtcatattt tccccaagat taaccaaaaa taatctgctt atcttttgg ttgtcctttt    2940 aactgtctcc gttttttct tttatttaaa aatgcacttt ttttcccttg tgagttatag    3000
tctgcttatt taattaccac tttgcaagcc ttacaagaga gcacaagttg gcctacattt   3060 ttatatttt taagaagata ctttgagatg cattatgaga actttcagtt caaagcatca    3120
aattgatgcc atatccaagg acatgccaaa tgctgattct gtcaggcact gaatgtcagg   3180
```

```
cattgagaca tagggaagga atggtttgta ctaatacaga cgtacagata ctttctctga   3240
agagtatttt cgaagaggag caactgaaca ctggaggaaa agaaaatgac actttctgct   3300
ttacagaaaa ggaaactcat tcagactggt gatatcgtga tgtacctaaa agtcagaaac   3360
cacattttct cctcagaagt agggaccgct ttcttacctg tttaaataaa ccaaagtata   3420
ccgtgtgaac caaacaatct cttttcaaaa cagggtgctc ctcctggctt ctggcttcca   3480
taagaagaaa tggagaaaaa tatatatata tatatatata ttgtgaaaga tcaatccatc   3540
tgccagaatc tagtgggatg aagttttttg ctacatgtta tccaccccag gccaggtgga   3600
agtaactgaa ttatttttta aattaagcag ttctactcga tcaccaagat gcttctgaaa   3660
attgcatttt attaccattt caaactattt tttaaaaata aatacagtta acatagagtg   3720
gtttcttcat tcatgtgaaa attattagcc agcaccagat gcatgagcta attatctctt   3780
tgagtccttg cttctgtttg ctcacagtaa actcattgtt taaaagcttc aagaacattc   3840
aagctgttgg tgtgttaaaa aatgcattgt attgatttgt actggtagtt tatgaaattt   3900
aattaaaaca caggccatga atggaaggtg gtattgcaca gctaataaaa tatgatttgg   3960
gatatgaaaa aaaaaaaaaa a                                              3981
```

<210> SEQ ID NO 125
<211> LENGTH: 1251
<212> TYPE: DNA
<213> ORGANISM: Homo sapiens

<400> SEQUENCE: 125

```
acgagccagg acatgtgcta ataatgccct aagccggtta taaagacgtg gaaattgagg     60
ggagaaaaaa aaagggaaaa aaagggtctg tccttcctgg gattcctagc cgaggccagt    120
ctgctgccgt gtgcgtgtgc gtcagggctc tccgggcggc aatgggggct tgagagccgg    180
gtccccagcg ccgggaaggg agcgcggtgg ccgccaccgc caccgccccg gagtccggcg    240
ccgaagctgc gggcgggcgg gcgggcacca gctcggtcag gggctgcttg gcgcggcact    300
gtgcggtgca gcggcggcgc ggcgcggtgc gggcttttcc caggcgcccc ggggtcgggt    360
ggccaacggc gcggccgcgg gcgctgagcg cgaccggttc gcggtagcgg tggcggcggc    420
gtgcgtgcca ggggctgggg gctccgccgc ctctcttgcg gctcaccgag ctccgcgctt    480
ccctctctcc agggcaggcg gcttctcaga gcacaacagc tccagctggc agcatcactt    540
cccgccaatt tatccaactt ctgccaaggc tctgaaatgc caacaacgtc gaggcctgca    600
cttgatgtca agggtggcac ctcacctgcg aaggaggatg ccaaccaaga gatgagctcc    660
gtggcctact ccaaccttgc ggtgaaagat cgcaaagcag tggccattct gcactaccct    720
ggggtagcct caaatggaac caaggccagt ggggctccca ctagttcctc gggatctcca    780
ataggctctc ctacaaccac ccctcccact aaacccccat ccttcaacct gcaccccgcc    840
cctcacttgc tggctagtat gcacctgcag aaacttaata gccagtatca ggggatggct    900
gctgccactc caggccaacc cggggaggca ggacccctgc aaaactggga ctttggggcc    960
caggcgggag gggcagaatc actctctcct tctgctggtg cccagagccc tgctatcatc   1020
gattcggacc cagtggatga ggaagtgctg atgtcgctgg tggtggaact ggggttggac   1080
cgagccaatg agcttccgga gctgtggctg ggcagaatg agtttgactt cactgcggac   1140
tttccatcta gctgctaatg ccaagtgtcc ctaaagatgg aggaataaag ccaccaattc   1200
tgttgtaaat aaaaataaag ttacttacaa agagacgggc caaaaaaaaa a            1251
```

<210> SEQ ID NO 126
<211> LENGTH: 1930
<212> TYPE: DNA
<213> ORGANISM: Homo sapiens

<400> SEQUENCE: 126

```
acagctcatt gttggcagct gccgggcggt cctgccgagc tgtgagggca acggagggga      60
aataaaaggg aacggctccg aatctgcccc agcggccgct gcgagacctc ggcgccgaca     120
tcgcgacagc gaagcgcttt gcacgccagg aaggtcccct ctatgtgctg ctgagccggt     180
cctggacgcg acgagcccgc cctcggtctt cggagcagaa atcgcaaaaa cggaaggact     240
ggaaatggca gaccatatga tggccatgaa ccacggcgc ttccccgacg gcaccaatgg      300
gctgcaccat caccctgccc accgcatggg catgggcag ttcccgagcc ccatcacca       360
ccagcagcag cagccccagc acgccttcaa cgccctaatg ggcgagcaca tacactacgg     420
cgcgggcaac atgaatgcca cgagcggcat caggcatgcg atgggccgg ggactgtgaa      480
cggagggcac ccccgagcg cgctggcccc cgcggccagg tttaacaact cccagttcat      540
gggtccccg gtggccagcc agggaggctc cctgccggcc agcatgcagc tgcagaagct     600
caacaaccag tatttcaacc atcacccta ccccacaac cactacatgc cggatttgca      660
ccctgctgca ggccaccaga tgaacgggac aaaccagcac ttccgagatt gcaaccccaa     720
gcacagcggc ggcagcagca ccccggcgg ctcgggcggc agcagcaccc ccggcggctc     780
tggcagcagc tcgggcggcg gcgcgggcag cagcaacagc ggcggcggca gcggcagcgg    840
caacatgccc gcctccgtgg cccacgtccc cgctgcaatg ctgccgccca atgtcataga     900
cactgatttc atcgacgagg aagttcttat gtccttggtg atagaaatgg gtttggaccg     960
catcaaggag ctgcccgaac tctggctggg gcaaaacgag tttgatttta tgacggactt    1020
cgtgtgcaaa cagcagccca gcagagtgag ctgttgactc gatcgaaacc ccggcgaaag    1080
aaatcaaacc cccaacttct tcggcgtgaa ttaaaagaaa cattcccta gacacagtat     1140
ctcactttc agatcttgaa aggtttgaga acttggaaac aaagtaaact ataaacttgt     1200
acaaattggt tttaaaaaaa attgctgcca ctttttttc ctgttttgt ttcgttttg      1260
tagccttgac attcacccac ctcccttatg tagttgaaat atctagctaa cttggtcttt    1320
ttcgttgttt gttttactc ctttccctca ctttctccag tgctcaactg ttagatatta    1380
atcttggcaa actgcttaat cttgtggatt ttgtagatgg tttcaaatga ctgaactgca    1440
ttcagattta cgagtgaaag gaaaaattgc attagttggt tgcatgaact tcgaagggca    1500
gatattactg cacaaactgc catctcgctt catttttta actatgcatt tgagtacaga    1560
ctaattttta aaatatgcta aactggaaga ttaaacagat gtgggccaaa ctgttctgga    1620
tcaggaaagt catactgttc actttcaagt tggctgtccc cccgccgcc cccccaccc     1680
ccatatgtac agatgataat agggtgtgga atgtcgtcag tggcaaacat ttcacagatt    1740
tttattttgt ttctgtcttc aacattttg acactgtgct aatagttata ttcagtacat     1800
gaaaagatac tactgtgttg aaagcttttt aggaaatttt gacagtattt ttgtacaaaa    1860
cattttttg aaaaaatact tgttaattta ttctatttta atttgccaat gtcaataaaa     1920
agttaagaaa                                                            1930
```

<210> SEQ ID NO 127
<211> LENGTH: 1372
<212> TYPE: DNA
<213> ORGANISM: Homo sapiens

<400> SEQUENCE: 127

```
ccggccgccc gcccgccgcc gccatgccct tctccaacag ccacaacgca ctgaagctgc    60
gcttcccggc cgaggacgag ttccccgacc tgagcgccca caacaaccac atggccaagg   120
tgctgacccc cgagctgtac gcggacgtgc gcgccaagag cacgccgagc ggcttcacgc   180
tggacgacgt catccagaca ggcgtggaca acccgggcca cccgtacatc atgaccgtgg   240
gctgcgtggc gggcgacgag gagtcctacg aagtgttcaa ggatctcttc gaccccatca   300
tcgaggaccg gcaccggcgc tacaagccca gcgatgacga caagaccgac ctcaaccccg   360
acaacctgca gggcggcgac gacctggacc ccaactacgt gctgagctcg cgggtggcca   420
cgggccgcag catccgtggc ttctgcctcc ccccgcactg cagccgcggg gagcgccgag   480
ccatcgagaa gctcgcggtg gaagccctgt ccagcctgga cggcgacctg gcgggccgat   540
actacgcgct caagagcatg acggaggcgg agcagcagca gctcatcgac gaccacttcc   600
tcttcgacaa gcccgtgtcg cccctgctgc tggcctcggg catggcccgc gactggcccg   660
acgccgcgcg tatctggcac aatgacaata agaccttcct ggtgtgggtc aacgaggagg   720
accacctgcg ggtcatctcc atgcagaagg ggggcaacat gaaggaggtg ttcacccgct   780
tctgcaccgg cctcacccag attgaaactc tcttcaagtc taaggactat gagttcatgt   840
ggaaccctca cctgggctac atcctcacct gcccatccaa cctgggcacc gggctgcggg   900
caggtgtcga tatcaagctg cccaacctgg gcaagcatga aagttctcg gaggtgctta   960
agcggctgcg acttcagaag cgaggcacag gcggtgtgga cacggctgcg gtgggcgggg  1020
tcttcgacgt ctccaacgct gaccgcctgg gcttctcaga ggtggagctg gtgcagatgg  1080
tggtggacgg agtgaagctg ctcatcgaga tggaacagcg gctggagcag ggccaggcca  1140
tcgacgacct catgcctgcc cagaaatgaa gcccggccca cccccgacac cagccctgct  1200
gcttcctaac ttattgcctg cagtgcccac catgcacccc tcgatgttgc cgtctggcga  1260
gcccttagcc ttgctgtaag gaaggcttcc gtcacccttg gtagagttta ttttttttgat  1320
ggctaagata ctgctgatgc tgaaataaac tagggttttg gcctgcaaaa aa           1372
```

<210> SEQ ID NO 128
<211> LENGTH: 2485
<212> TYPE: DNA
<213> ORGANISM: Homo sapiens

<400> SEQUENCE: 128

```
gccatggccg ggccgcgcgc gtgcgccccg ctcctgctcc tgctcctgct cggggagctt    60
ctggcggccg ccggggcgca gagagtggga ctccccggcc ccccggcc cccagggccg    120
cccgggaagc ccggccagga cggcattgac ggagaagctg gtcctccagg tctgcctggg   180
cccccgggac caaaggggc cccaggaaag ccggggaaac caggagaggc tgggctgccg   240
ggactgccgg gtgtggatgg tctgactgga cgagatggac ccctggacc caagggtgcc   300
cctggggaac ggggaagtct gggacccccg gggccgcccg gctgggggg caaaggcctc   360
cctggacccc ccggagaggc aggagtgagc ggcccccag gtgggatcgg cctccgcggc   420
ccccgggac cttctggact cccggcctc cctggtcccc caggacctcc cggacccct    480
ggacacccag gagtcctccc tgaaggcgct actgaccttc agtgcccaag tatctgcccg   540
ccaggtcccc cagggccccc tggaatgcca gggttcaagg gacccactgg ctacaaaggc   600
gagcaggggg aagtcggcaa ggacggcgag aaggtgacc ctggcccccc tgggcccgcc   660
ggcctcccgg gcagcgtggg gctgcagggc ccccggggat tacgaggact gccagggcca   720
```

```
ctcgggcccc ctggggaccg gggtcccatt gggttccgag ggccgcctgg gatcccagga      780
gcgcctggga aagcgggtga ccgaggcgag aggggcccag aagggttccg cggcccccaag     840
ggtgacctcg gcagacctgg tcccaaggga accccggag tggccgggcc aagcggagag       900
ccgggcatgc cgggcaagga cggccagaat ggcgtgccag gactcgatgg ccagaaggga      960
gaggctggtc gcaacggtgc tccggagag aagggcccca acgggctgcc gggcctccct      1020
ggacgagcgg ggtccaaagg cgagaaggga gaacggggca gagctgggga gctgggtgag     1080
gccggcccct ctggagagcc aggcgtccct ggagatgctg gcatgcctgg ggagcgcggt     1140
gaggctggcc accggggctc agcggggggcc ctcggcccac aaggccctcc cggagccct    1200
ggtgtccgag gcttccaggg ccagaagggc agcatgggag accccggcct tccaggcccc     1260
cagggcctcc gaggtgacgt gggcgaccgg ggtccgggg gtgccgcagg ccctaaggga     1320
gaccagggta ttgcaggttc cgacggtctt cctggggata aggagaaact gggtcccagc     1380
ggcctggtcg gacccaaagg agagtctggc agtcgagggg agctgggccc caaaggcacc     1440
cagggtccca acggcaccag cggtgttcag ggtgtccccg gccccccgg tcctctgggc      1500
ctgcagggcg tccggggtgt tcctggcatc acggggaagc cggagttcc ggggaaggag     1560
gccagcgagc agcgcatcag ggagctgtgt gggggggatga tcagcgaaca aattgcacag     1620
ttagccgcgc acctaaggaa gccctttggca ccgggtcca ttggtcggcc cggtccagct    1680
ggccccctg gcccccagg accccagc tccattggtc accctggcgc tcgaggaccc     1740
cctggatacc gcggtcccac tggggagctg ggagacccc ggcccagagg aaaccagggt      1800
gacagaggag acaaggcgc ggcaggagca gggctggacg ggcctgaagg agaccagggg     1860
ccccaaggac cccaaggcgt gcccggcacc agcaaggacg gccaggacgg tgctcccggc     1920
gagcctgggc ctcccggaga tcctgggctt ccaggtgcca ttggggccca ggggacaccg     1980
gggatctgcg acacctcagc ctgccaagga gccgtgttag gagggtcgg ggagaaatca     2040
ggctctcgaa gctcataaaa ttcaacgtga ggaagcaagt gacaaggacg cccgaagcac     2100
agtggacggt catgaaggag cggggtgtg gcaggcgggt gacgtccagg agagggagcg     2160
cccctggctg cccctcggcc gccgactgga cgcgcgggcc ttgccagcga gcaccctcat     2220
cgggctgtcg cctgacagca tacctcaaaa ggccctagct aataaacctg taagcccagc     2280
atttgagaga aggtagggtg tgtatatata aaaggttgtg tacaactcca cgaggtgaaa     2340
aatattcagt aacttgttta catagcattt gtgtaaagac tatgatctca tcccaataaa     2400
atgatatatt aaaccttcag attaatgact ggctacagag taacaaaaaa taaagaattt     2460
aatgtacagt aaattctctc ccata                                           2485

<210> SEQ ID NO 129
<211> LENGTH: 901
<212> TYPE: DNA
<213> ORGANISM: Homo sapiens

<400> SEQUENCE: 129
gggatctcgg actccctgga ccctccctcc agcccagcct cgctagctcc gcctgcggta      60
cgtgctcccg cctccgactc aaaatgcctg tctggggagg tggaaacaag tgtgggggcct   120
gtgggaggac cgtgtaccac gcagaagagg tgcagtgtga tggcaggagc ttccaccgct     180
gctgctttct ctgcatggtt tgcaggaaaa atttagatag cacaacagtg gcaattcacg     240
atgaagagat ctactgcaaa tcctgctacg gaaagaagta tgggccaaaa ggctacggtt     300
```

| | |
|---|---|
| atggccaggg cgctggcacg cttaacatgg accgtggcga gaggctgggc atcaaaccag | 360 |
| agagtgttca gcctcacagg cctacaacaa atccaaacac ttctaaattt gctcagaaat | 420 |
| atggaggtgc tgagaagtgt tccagatgtg gggattctgt atatgctgcc gagaagataa | 480 |
| ttggagctgg aaagccctgg cacaaaaact gtttccgatg tgcaaagtgt gggaagagtc | 540 |
| ttgaatcaac aactctgact gaaaaagaag gtgaaatcta ttgtaaagga tgctatgcaa | 600 |
| agaactttgg gccaagggga tttggctatg ccaaggagc aggggctctt gttcatgccc | 660 |
| agtaagatgt aaaccctgaa ctaaacatca cacactgaga atctcttcat aatctaggca | 720 |
| cagataatct ttaacactaa actactgtga aattctacca gcattaagta ctgtatatcg | 780 |
| ccctgtactt ggataggctg gctaactcgt aggaagagag cactgtatgg tatccttttg | 840 |
| ctttattcac cagcattttg ggggaacatt tcttttacat tttaaataaa acttcagctt | 900 |
| g | 901 |

<210> SEQ ID NO 130
<211> LENGTH: 2628
<212> TYPE: DNA
<213> ORGANISM: Homo sapiens

<400> SEQUENCE: 130

| | |
|---|---|
| gaccgcggca gctcagcctc ccgccgattg tatgttccag gcctcaatga ggagtccaaa | 60 |
| catggagcca ttcaagcagc agaaggtgga ggacttttat gacatcggag aggagctggg | 120 |
| gagtggccag tttgccatcg tgaagaagtg ccgggagaag agcacggggc ttgagtatgc | 180 |
| agccaagttc atcaagaagc ggcagagccg ggcgagccgg cgcggtgtga gccgggagga | 240 |
| gatcgagcgg gaggtgagca tcctgcggca ggtgctgcac cacaatgtca tcacgctgca | 300 |
| cgacgtctat gagaaccgca ccgacgtggt gctcatcctt gagctagtgt ctggaggaga | 360 |
| gctcttcgat ttcctggccc agaaggagtc actgagtgag gaggaggcca ccagcttcat | 420 |
| taagcagatc ctggatgggg tgaactacct tcacacaaag aaaattgctc actttgatct | 480 |
| caagccagaa aacattatgt tgttagacaa gaatatttcc cattccacaca tcaagctgat | 540 |
| tgactttggt ctggctcacg aaatagaaga tggagttgaa tttaagaata ttttttgggac | 600 |
| gccggaattt gttgctccag aaattgtgaa ctacgagccc ctgggtctgg aggctgacat | 660 |
| gtggagcata gcgtcatca cctacatcct cttaagtgga gcatcccctt tcctgggaga | 720 |
| cacgaagcag gaaacactgg caaatatcac agcagtgagt tacgactttg atgaggaatt | 780 |
| cttcagccag acgagcgagc tggccaagga ctttattcgg aagcttctgg ttaaagagac | 840 |
| ccggaaacgg ctcacaatcc aagaggctct cagacacccc tggatcacgc cggtggacaa | 900 |
| ccagcaagcc atggtgcgca gggagtctgt ggtcaatctg gagaacttca ggaagcagta | 960 |
| tgtccgcagg cggtggaagc tttccttcag catcgtgtcc ctgtgcaacc acctcacccg | 1020 |
| ctcgctgatg aagaaggtgc acctgaggcc ggatgaggac ctgaggaact gtgagagtga | 1080 |
| cactgaggag gacatcgcca ggaggaaagc cctccaccca cggaggagga gcagcacctc | 1140 |
| ctaactggcc tgacctgcag tggccgccag ggaggtctgg gcccagcggg gctcccttct | 1200 |
| gtgcagactc ttggacccag ctcagcacca gcacccgggc gtcctgagca cttttgcaaga | 1260 |
| gagatgggcc caaggaattc agaagagctt gcaggcaagc caggagaccc tgggagctgt | 1320 |
| ggctgtcttc tgtggaggag gctccagcat tcccaaagct cttaattctc cataaaatgg | 1380 |
| gctttcctct gtctgccatc ctcagagtct ggggtgggga tgtggactta ggaaaacaat | 1440 |
| ataaaggaca tcctcatcat cacggggtga aggtcagact aaggcagcct tcttcacagg | 1500 |

```
ctgaggggt tcagaaccag cctggccaaa aattacacca gagagacaga gtcctcccca    1560
ttgggaacag ggtgattgag gaaagtgaac cttgggtgtg agggaccaat cctgtgacct    1620
cccagaacca tggaagccag gacgtcaggc tgaccaacac ctcagacctt ctgaagcagc    1680
ccattgctgg cccgccatgt tgtaattttg ctcatttta ttaaacttct ggtttacctg     1740
atgcttggct tcttttaggg ctaccccat ctcatttcct ttagcccgtg tgcctgtaac     1800
tctgaggggg ggcacccagt ggggtgctga gtgggcagaa tctcagaagg tcctcctgaa    1860
ccgtccgcgc aggcctgcag tgggcctgcc tcctccttgc ttccctaaca ggaaggtgtc    1920
cagttcaaga gaacccaccc agagactggg agtggtggct cacgcctata tccctgcgc     1980 tttggcagtc cgaggcaggg gaattgcttg aactcaggag ttggagacca gcctgggcaa    2040
catggcaaaa cgcagtctgt acaaaaaata caaaaaatta gccaggtgta ggggtaggca    2100
cctggcatcc cagctactcc aggggctgag gtgacagcat tgcttaagcc cagaaggtcg    2160
aggctgcagt gagctgagat cacgccactg cactccagtc tgggtgacag agagagacca    2220
tatccaaaaa aaaaaaagt tgccagagac gagtatgccc atgctccctc tacctcactg     2280
ccaccactcc tgctgttagg agctgagtgt gtctccctaa aatttctatg ttgaagtctt    2340
aacccttggt accacagaat atcactgtat ttggagatgg ggtctttaga aaggcactta    2400
aattaaaatg agctcactga tatgggcccc gatgcaatat aattggtgtc cttataagaa    2460 gggggaggtta ggacacgcag gaaagaccac atgaaggccc aggagtggga gggggaatag   2520
ccatcgacaa actaaggggg cctcagagga aaccaaccct gctgacacct caatcttaga    2580
ctctggcctc aaaaattgta agaaaataaa cttctgtctt ttaagcca               2628

<210> SEQ ID NO 131
<211> LENGTH: 1876
<212> TYPE: DNA
<213> ORGANISM: Homo sapiens

<400> SEQUENCE: 131
gagcttactc tggctttgcc gagatggggc tgccccagcc agggctgtgg ctgaagaggc      60
tctgggtgct cttggaggtg gctgtgcatg tggtcgtggg taaagtgctt ctgatattgt     120
ttccagacag agtcaagcgg aacatcctgg ccatgggcga aagacgggt atgaccagga      180 accccccattt cagccacgac aactggatac caaccttttt cagcacccag tatttctggt    240
tcgtcttgaa ggtccgttgg cagcgactag aggacacgac tgagctaggg ggtctggccc     300
caaactgccc ggtggtccgc ctctcaggac agaggtgcaa catttgggag tttatgcaag     360
gtaataggcc actggtgctg aattttggaa gttgtacctg accttcattt atgttcaaat     420
ttgaccagtt caagaggctt attgaagact ttagttccat agcagatttt cttgtcattt     480
acattgaaga agcacatgca tcagatggct gggcttttaa gaacaacatg gacatcagaa     540
atcaccagaa cctcaggat cgcctgcagg cagcccatct actgctggcc aggagccccc      600
agtgccctgt ggtggtggac accatgcaga accagagcag ccagctctac gcagcactgc     660
ctgagaggct ctacataatc caggagggca ggatcctcta caagggtaaa tctggccctt     720
ggaactacaa cccagaggaa gttcgtgctg ttctggaaaa gctccacagt taatctggac     780
agatacctca attctaggtg accaacggga gggcttctca aggcttagct ctccctgaga    840
cccagctggc ttttaccctt gacctgtgtc cctagctgaa tcactagctc agattttct     900 gatctaagca aacaactccc agctgaggaa tgcaggccac agcacccaat caagacaaat    960
```

```
tgttattatc agaaaatgaa gcaacacttg agctgttcag gccagttccc tgttgaagaa      1020
acagttccct gttgaagaaa gtagagcctg acactgctcc cactttggag accacattcc      1080
ctgcacacgg tctttgagag agcagttgca ctctacaggc acacttctga ggtacggtat      1140
ctctctccag ccactctgat accaagtaat tcaagctggc attccttcta ttagggaaat      1200
tcattttacc caatttgcat ttatggaatt gatcatttaa gacactaaat tagttttag       1260 aaccaattat gggaagaatt ccagttgtta ggaagagatg aggagttgga agaggaggga      1320
ttagaaacag gaggaggcag tcatcctctc cttgccaaaa gatttaaacc tgtccacatt      1380
ggtggtgatg atgggtgagt ttccatggta acacatccct aattttacca gggaagagga      1440
gagtactcac tttaccatct ttgaatatat ttcatagaaa tctagctctc tgtaccctga      1500
aatcttccac tagcctcact tttcaacaga gtcatctaga agggagggtt ggcttcccaa      1560
aagcataacc ttgaccaaac caaacaatag gcaccagcaa tgctgtcatt cagttatgca      1620
gaagctcatt tgtgaaattc tgtttctctg atttcttcgc aagtctctta atggtcattt      1680
gtgttagatt acatcaaact gatggatagc cattggtatt catctatttt aactctgtgt      1740
ctttacatat ttgtttatga tggccacagc ctaaagtaca cacggctgtg acttgattca      1800
aaagaaaatg ttataagatg cagtaaaacta ataacagaat tattaaaata tatcaggcta     1860
aaaaaaaaaa aaaaaa                                                      1876

<210> SEQ ID NO 132
<211> LENGTH: 3913
<212> TYPE: DNA
<213> ORGANISM: Homo sapiens

<400> SEQUENCE: 132
ctttcactgg caagagacgg agtcctgggt ttcagttcca gttgcctgcg gtgggctgtg        60
tgagtttgcc aaagtcccct gccctctctg ggtctcggtt ccctcgcctg tccacgtgag       120
gttggaggag ctgaacgccg acgtcatttt tagctaagag ggagcagggt ccccgagtcg       180
ccggcccagg gtctgcgcat ccgaggccgc gcgcccttc ccctccccca cggctcctcc        240
gggccccgca ctctgcgccc cggctgccgc ccagcgccct acaccgccct caggggggccc     300 tcgcgggctc ccccggccg ggatgccagt gccccgcgcc acgcgcgcct gctcccgcgc        360
cgcctgccct gcagcctgcc cgcggcgcct ttatacccag cgggctcggc gctcactaat       420
gtttaactcg gggccgaaac ttgccagcgg cgagtgactc caccgcccgg agcagcggtg      480
caggacgcgc gtctccgccg cccgcggtga cttctgcctg cgctcctcct ctgaacgctc      540
acttccgagg agacgccgac gatgaagaca ccgtggaagg ttcttctggg actgctgggt      600
gctgctgcgc ttgtcaccat catcaccgtg cccgtggttc tgctgaacaa aggcacagat      660
gatgctacag ctgacagtcg caaaacttac actctaactg attacttaaa aaatacttat     720
agactgaagt tatactcctt aagatggatt tcagatcatg aatatctcta caaacaagaa     780
aataatatct tggtattcaa tgctgaatat ggaaacagct cagttttctt ggagaacagt     840
acatttgatg agtttggaca ttctatcaat gattattcaa tatctcctga tgggcagttt     900
attctcttag aatacaaacta cgtgaagcaa tggaggcatt cctacacagc ttcatatgac     960
atttatgatt taaataaaag gcagctgatt acagaagaga ggattccaaa caacacacag    1020
tgggtcacat ggtcaccagt gggtcataaa ttggcatatg tttggaacaa tgacatttat    1080
gttaaaattg aaccaaattt accaagttac agaatcacat ggacgggaa agaagatata    1140 atatataatg gaataactga ctgggttat gaagaggaag tcttcagtgc ctactctgct    1200
```

```
ctgtggtggt ctccaaacgg cactttttta gcatatgccc aatttaacga cacagaagtc   1260
ccacttattg aatactcctt ctactctgat gagtcactgc agtacccaaa gactgtacgg   1320
gttccatatc caaaggcagg agctgtgaat ccaactgtaa agttctttgt tgtaaataca   1380
gactctctca gctcagtcac caatgcaact tccatacaaa tcactgctcc tgcttctatg   1440
ttgatagggg atcactactt gtgtgatgtg acatgggcaa cacaagaaag aatttctttg   1500
cagtggctca ggaggattca gaactattcg gtcatggata tttgtgacta tgatgaatcc   1560
agtggaagat ggaactgctt agtggcacgg caacacattg aaatgagtac tactggctgg   1620 gttgaagat ttaggccttc agaacctcat tttaccttg atggtaatag cttctacaag    1680
atcatcagca atgaagaagg ttacagacac atttgctatt ccaaatagc taaaaaagac   1740 tgcacattta ttacaaaagg cacctgggaa gtcatcggga tagaagctct aaccagtgat   1800
tatctatact acattagtaa tgaatataaa ggaatgccag gaggaaggaa tctttataaa   1860
atccaactta gtgactatac aaaagtgaca tgcctcagtt gtgagctgaa tccggaaagg   1920
tgtcagtact attctgtgtc attcagtaaa gaggcgaagt attatcagct gagatgttcc   1980
ggtcctggtc tgcccctcta tactctcacac agcagcgtga atgataaagg gctgagagtc   2040
ctggaagaca attcagcttt ggataaaatg ctgcagaatg tccagatgcc ctccaaaaaa   2100
ctggacttca ttattttgaa tgaaacaaaa ttttggtatc agatgatctt gcctcctcat   2160
tttgataaat ccaagaaata tcctctacta ttagatgtgt atgcaggccc atgtagtcaa   2220
aaagcagaca ctgtcttcag actgaactgg gccacttacc ttgcaagcac agaaaacatt   2280
atagtagcta gcttgatgg cagaggaagt ggttaccaag gagataagat catgcatgca   2340
atcaacagaa gactgggaac atttgaagtt gaagatcaaa ttgaagcagc cagacaattt   2400
tcaaaaatgg gatttgtgga caacaaacga attgcaattt ggggctggtc atatggaggg   2460
tacgtaacct caatggtcct gggatcggga agtggcgtgt tcaagtgtgg aatagccgtg   2520
gcgcctgtat cccggtggga gtactatgac tcagtgtaca cagaacgtta catgggtctc   2580
ccaactccag aagacaacct tgaccattac agaaattcaa cagtcatgag cagagctgaa   2640
aattttaaac aagttgagta cctccttatt catggaacag cagatgataa cgttcacttt   2700
cagcagtcag ctcagatctc caaagccctg gtcgatgttg gagtggattt ccaggcaatg   2760
tggtatactg atgaagacca tggaatagct agcagcacag cacaccaaca tatatatacc   2820
cacatgagcc acttcataaa acaatgtttc tctttacctt agcacctcaa aataccatgc   2880
catttaaagc ttattaaaac tcattttgt tttcattatc tcaaaactgc actgtcaaga   2940
tgatgatgat ctttaaaata cacactcaaa tcaagaaact taaggttacc tttgttccca   3000
aatttcatac ctatcatctt aagtaggac ttctgtcttc acaacagatt attaccttac    3060
agaagtttga attatccggt cgggttttat tgtttaaaat catttctgca tcagctgctg   3120
aaacaacaaa taggaattgt ttttatggag ctttgcata gattccctga gcaggatttt    3180 aatcttttc taactggact ggttcaaatg ttgttctctt ctttaaaggg atggcaagat    3240
gtgggcagtg atgtcactag gcagggaca ggataagagg gattagggag agaagatagc    3300
agggcatggc tgggaaccca agtccaagca taccaacacg agcaggctac tgtcagctcc   3360
cctcggagaa gagctgttca cagccagact ggcacagttt tctgagaaag actattcaaa   3420
cagtctcagg aaatcaaata tgcaaagcac tgacttctaa gtaaaccac agcagttgaa    3480 aagactccaa agaaatgtaa gggaaactgc cagcaacgca ggcccccagg tgccagttat   3540
```

| | |
|---|---|
| ggctataggt gctacaaaaa cacagcaagg gtgatgggaa agcattgtaa atgtgctttt | 3600 |
| aaaaaaaaat actgatgttc ctagtgaaag aggcagcttg aaactgagat gtgaacacat | 3660 |
| cagcttgccc tgttaaaaga tgaaaatatt tgtatcacaa atcttaactt gaaggagtcc | 3720 |
| ttgcatcaat ttttcttatt tcatttcttt gagtgtctta attaaaagaa tattttaact | 3780 |
| tccttggact cattttaaaa aatggaacat aaaatacaat gttatgtatt attattccca | 3840 |
| ttctacatac tatggaattt ctcccagtca tttaataaat gtgccttcat tttttcagaa | 3900 |
| aaaaaaaaaa aaa | 3913 |

<210> SEQ ID NO 133
<211> LENGTH: 5795
<212> TYPE: DNA
<213> ORGANISM: Homo sapiens

<400> SEQUENCE: 133

| | |
|---|---|
| gagcagcggc agcagcagcg accccggcg gcggcggcgg cgcgcggtcc cagccaggcg | 60 |
| gccccggtgt cccggccccg gtggatgcac ggctggggag gagcccatgg gccggagctg | 120 |
| aggctgcccg gggcggcggg gcgcggggca ggggcgcgg tcgaggcccg gaggcggcgg | 180 |
| cgcaggagga agcggaggag gtcgggcgct cggggcccgg gaggcgggcc gcgcagcgcc | 240 |
| gcagccccgg gctcgccatg ctcctggcct cggccgtggt ggtctgggaa tggctgaacg | 300 |
| agcacggccg ctggcgtccc tacagcccag cggtgagcca ccacatcgag gcggtggtcc | 360 |
| gcgccggccc ccgcgcgggg ggcagcgtgg tgctgggcca ggtggacagc cgtctcgcgc | 420 |
| cctacatcat cgacctgcag tccatgaacc agttccgcca agacacggga actctccgcc | 480 |
| cagttcgccg caactactac gaccctcct cggcccctgg gaagggcgtg gtgtgggagt | 540 |
| gggagaacga caatggctcc tggacgccct acgacatgga agtgggcatc accatccagc | 600 |
| atgcctatga gaagcagcac ccctggatcg acctcacttc cattggcttt agctacgtaa | 660 |
| ttgacttcaa caccatgggc cagatcaacc gtcagaccca cgccaacgc cgcgtccgcc | 720 |
| ggcgcctcga cctcatctac cccatggtca cagggacctt gcctaaggct cagtcctggc | 780 |
| cagtcagccc tgggccagcc acctcgcccc ccatgtcccc ctgctcctgt ccccagtgtg | 840 |
| tcttggtgat gagtgttaag gcagccgtgg tcaatggcag cactgggccc ctacagctgc | 900 |
| cagtgacccg caagaacatg ccgcctcctg gagtggtcaa gctaccccca ctgccaggct | 960 |
| ctggggccaa gccactggac agcacaggca ccattcgagg cccactgaag accgcccat | 1020 |
| cgcaggtgat ccggagacaa gcctccagca tgcccactgg acaaccatgg gctctcctg | 1080 |
| ccagtccccc aggacccaac agcaagaccg gaagggtggc cctggccacc ttgaatcgta | 1140 |
| ccaacctgca gcgactggcc attgccagt cccgggtgct gatcgcctct ggggtcccca | 1200 |
| cagtcccagt gaagaaccta aatgggtcca gtcctgtcaa ccctgccttg gcaggaatca | 1260 |
| ctgggatcct catgagtgca gcggggctgc ctgtgtgtct caccaggcca ccaaagctgg | 1320 |
| tcctacaccc accccccgtc agcaagagtg aaataaaatc catcccaggg gtttccaaca | 1380 |
| caagccgcaa gaccaccaaa aaacaagcca agaaggtaa aaccccagag gaagtgctaa | 1440 |
| aaaaatatct acagaaagtc cggcaccca cagatgagga ctgcaccatc tgtatggaac | 1500 |
| gcctcacggc cccctcaggc tacaagggcc cgcagcctac ggtaaaacct gacctggtag | 1560 |
| ggaagctgtc cagatgcggc cacgtctacc acatctactg cttggttgcc atgtacaaca | 1620 |
| atgggaacaa ggatgaagt ttgcagtgtc caacctgcaa gaccatttat ggggtgaaga | 1680 |
| caggcaccca acctccaggg aagatggagt accacctcat cccccactcc ttgcctggcc | 1740 |

-continued

```
acccagactg caaaaccatc cggatcatct acagcatccc ccccggcatt cagggaccgg      1800
aacacccgaa tcctgggaag agtttcagcg cccgaggctt cccacgacac tgttaccttc      1860
cggacagcga gaaagggaga aaagttctga agctgctgct cgtggcctgg gatcgccgcc      1920
tcatttttgc cattggcacc tccagcacca caggcgagtc agacaccgtc atctggaatg      1980
aggtccacca aagacagag tttggctcta atctcactgg ccatggctac cagatgcca       2040 attacctgga taatgtgctg gctgaactgg ctgcccaggg catctctgag acagcactg       2100 cccaggagaa ggactgaggc cagaaaagct ttgaggtggg aggggccatg gagactgcag     2160
gacaggaagt gaggagagtg agtcaatgta aagaagttg tgtcctgcc ctcccaactt       2220 tctatcctcc cctcctgccc tgtgtccatc cctcatccct ccaaccaca gtgggagcca      2280 gactgaatat agcgacatca ttcataaatc tcatccaaca caagggaga tgggatgagg      2340 gccatcctgg gtctgttccc atggagtttt tggtgctggg taggcaggaa tcccctccct     2400
accccacctc ccaagtaggg gcatggtcag cacacctagg gtatgggcag tgcttaggca    2460
ctccatatcc tggctttggg aagccggggt ttcttgcctc agccggcttc ttgctacttc    2520
cactctgctt tgagactgga gtttctgcta ttctccctct gctggaggca gggagctctc    2580
actgtgcaag gttgggggt gggcaaaggg gtgaatcact aaactgctgt gacatcagaa    2640
actgatgcct tggtgtagag caaggaagca cttcttccca gagggtcgg agaaggaaaa     2700 gcctctggga gcacattctg ctgtcatcac agtccttggc ttctctgggc cctcctctcc     2760
tcctcacagc tctcacctgt ccaaagaggc atctggttct tcatgtgga tggatggact     2820 ctggggttcc tctttggagt ggcatcccat gatgctgttt ctagaccctc tctgatcaaa    2880
ccagagcctg catcccactg agcatctgaa ctgtcctcag ggagaggagc ccacagcctt    2940
cttcccaact cattctagac cagctcaaag attccatgag tttcatcgag tcactgtgag    3000
tggagcccat gctgggctct gtgccctctg tgtctgtgca tgcgcgtgtg tgtgtgggcg    3060
tgtgtgcatt gctgggccag cttgaaggga aggcccgtca tgtccctgca ctctgttttg    3120
caagatgcca aaccccagtt ctgatggggc tccaacagcc aggctgtggt cctttgacgt    3180
tcctcacctg ttgccaacct atcccgtagt gaactgaaac cccaatgaag acagaactgt    3240
gcctggggag atgcaatgag gtgagggctg aactcatcct tttatatttc ttttcaagat    3300
tggatcagag ctcatctcca tccagtcttg tttctatgaa ggcttcaatc tgtttccatg    3360
caaatttgct aatcagagcc cagagctgct gggtccctca tctccctcat ctattataga   3420
ttgacttaca gcagggagag aatctcttta gctcattcct aatggagttg ggatcacaat   3480
atggtctggt ccaatctgca tcttgttgtg tcccaagacc ctatctcctc cccaacattc   3540
ttattgcctt tggctcccag taaggaacga attggggggcc aggaggaga acaggggga   3600 tcaagaaggg aaacccaatt ccccctttga aagtgggttc tttgaactat gtgtttgggg   3660
gaagttcctc tggatactaa tttgaattta tatacctcat gttttggggg tttgacgtat   3720
atatatatat atatatatgc atatatatttt cataatattt ggaaggtttt tgatgctaga   3780
aaaatggaaa caagagaacc ttcaaaaatg gtacttagat gggaactgga ggccaatctt    3840
tcataaagcc agcccatag ctgcttgctg ttaggcctcc agccattttg acattgggt      3900 ggatagtcga ttcacctgcc tgtcagtcga ttcacctgcc tgtcacccag ttctgtggat    3960
gtgctggtgc tgagcctttg ctctcttttcc aaatggttac agggatgttg atcagctcca   4020
ccagagggag ctctgatggg aggaattgct ctgccatcct tgtccctgtg tctcctgtcg    4080
```

```
gcaggcagcc attgtatctc accagcagac caggagactg gtcccaaggt tactgcacca    4140
cagggcaatt tcctgccata gttaggaagg aaacacctga actaaatgga agagacatcc    4200
ctgcggtgtt taatatcaca cccatgccct tgtcaggtt accatgtaca gagattactt    4260
ggagagcctc atgccgtctc taccttcgca cactggtcaa gtatctgctg agcttcttgg    4320
ccgcaaggat gcagaaatag gctgagggtc catgggaaga aagacacaat gaggcagtag    4380
gaggtgggga agaaaagaag acagactttc aaaatggaat taggcactgg ggagagatca    4440
gtttccccac atcagggaga agaaggtata ggtgggaag ggggtggcca ggagcagaag     4500
gaagaagact caagatggaa agggagccgc tgtgcctgtg gcaataccac ttggagaggt    4560
cgacttcata ccttcaagcc ttttcccctg ggcttttgat tgtgtctgtg cccccttct     4620 tgtcctctct gcagatgccc agtagggct acctcatcct cgtgctgttc ttgtgtggct     4680
ttctgggcag tagggatctt gaatttcctt tctaacactg tgcccggcaa ggcggggagc    4740
attcctctgc cctttgtctt gtgccaacct ggaaaggtgc agtctagatt tcagtgagaa    4800
ccctgccagc tgagccctgt gcatctacta ccttgacaca gagtgttttc ccactagaag    4860
ctctgctctg ctctcctggc ccaagtaggg gattccatgc cttccctttc atggtcttag    4920
caccagcagc ctagtttctc ccttccagag tctccaggga tgacaaattg gattggagac    4980
aaacctcgtc agatgctcat cccctaaaag gttaattgtg tatttgtggc tgcgtgtgcc    5040
tttgtgtttt cattctcttc ccattttgt acatttggt cttctctgtg gttttatact      5100
tggtcaaaag tactcgtctt ggtattgcac tgttgtgtgc atgagaaaac tgggggaagg    5160
ctcactggta caagaaagga cccctgaccc ctttccttct ctgtggtccc cggcattaga    5220
ttgggggttc tgggagaggc aggtgaatgt cctaagtgaa ttgttctgtt tgtaactgga    5280
atgtttttga agtctttggt gttgctccgt gaaaggacat cgccacctgg tgctcatgag    5340
gtgtctttgc agaacaataa atggcaaatg aacaaccaca aaattgttac tcttgttggc    5400
cttctgctgt ttgtagatta gtgcacctat ctgtgaggga tttgggttac ctccctgagt    5460
ctgtaagcaa ccacaagccc tgccactggg tgggggaagt ccctccccaa ccacttaaaa    5520
acaaattttc cacatattac ccacccacac atttgacctg gctagacttt gtttgcctaa    5580
aggaacagac cacattgctg ggaaaatgag taagtgaacg tgtgggagaa aaacactttt    5640
agaatcacga atattcactt ttaaaggtct ctttgcctgg ctgcaatata gtgtgtgttt    5700
aaattattta caggctgttg tttctcaaat aaatgtttaa tattaatcat tcccaaactg    5760
acaagaacac aaaaataaaa tgcaaataca gagcc                              5795
```

<210> SEQ ID NO 134
<211> LENGTH: 2498
<212> TYPE: DNA
<213> ORGANISM: Homo sapiens

<400> SEQUENCE: 134

```
gctgagcgcc ggaggagcgt aggcagggca gcgctggcgc cagtggcgac aggagccgcg     60
cgaccggcaa aaatacacgg gaggccgtcg ccgaaaagag tccgcggtcc tctctcgtaa    120
acacactctc ctccaccggc gcctccccct ccgctctgcg cgccgcccgg ctgggcgccc    180
gaggccgctc cgactgctat gtgaccgcga ggctgcggga ggaagggac agggaagaag     240 aggctctccc gcgggagccc ttgaggacca agtttgcggc cacttctgca ggcgtccctt    300
cttagctctc gcccgcccct ttctgcagcc taggcggccc gggttctctt ctcttcctcg    360
cgcgcccagc cgcctcggtt cccggcgacc atggtgacga tggaggagct gcgggagatg    420
```

```
gactgcagtg tgctcaaaag gctgatgaac cgggacgaga atggcggcgg cgcgggcggc      480
agcggcagcc acggcaccct ggggctgccg agcggcggca agtgcctgct gctggactgc      540
agaccgttcc tggcgcacag cgcgggctac atcctaggtt cggtcaacgt gcgctgtaac      600
accatcgtgc ggcggcgggc taagggctcc gtgagcctgg agcagatcct gcccgccgag      660
gaggaggtac gcgcccgctt gcgctccggc ctctactcgg cggtcatcgt ctacgacgag      720
cgcagcccgc gcgccgagag cctccgcgag gacagcaccg tgtcgctggt ggtgcaggcg      780
ctgcgccgca acgccgagcg caccgacatc tgcctgctca aaggcggcta tgagaggttt      840
tcctccgagt acccagaatt ctgttctaaa accaaggccc tggcagccat cccaccccg       900 gttccccca gtgccacaga gcccttggac ctgggctgca gctcctgtgg gaccccacta      960
cacgaccagg ggggtcctgt ggagatcctt cccttcctct acctcggcag tgcctaccat     1020
gctgcccgga gagacatgct ggacgccctg gcatcacgg ctctgttgaa tgtctcctcg      1080
gactgcccaa accactttga aggacactat cagtacaagt gcatcccagt ggaagataac     1140
cacaaggccg acatcagctc ctggttcatg gaagccatag agtacatcga tgccgtgaag     1200
gactgccgtg ggcgcgtgct ggtgcactgc caggcgggca tctcgcggtc ggccaccatc     1260
tgcctggcct acctgatgat gaagaaacgg gtgaggctgg aggaggcctt cgagttcgtt     1320
aagcagcgcc gcagcatcat ctcgcccaac ttcagcttca tggggcagct gctgcagttc     1380
gagtcccagg tgctggccac gtcctgtgct gcggaggctg ctagcccctc gggacccctg     1440
cgggagcggg gcaagacccc cgccacccc acctcgcagt tcgtcttcag ctttccggtc      1500
tccgtgggcg tgcactcggc ccccagcagc ctgccctacc tgcacagccc catcaccacc     1560
tctcccagct gttagagccg ccctgggggc cccagaacca gagctggctc ccagcaaggg     1620
taggacgggc cgcatgcggg cagaaagttg ggactgagca gctgggagca ggcgaccgag     1680
ctccttcccc atcatttctc cttggccaac gacgaggcca gccagaatgg caataaggac     1740
tccgaataca taataaaagc aaacagaaca ctccaactta gagcaataac ggctgccgca     1800
gcagccaggg aagaccttgg tttggtttat gtgtcagttt cacttttccg atagaaattt     1860
cttacctcat tttttaagc agtaaggctt gaagtgatga aacccacaga tcctagcaaa     1920
tgtgcccaac cagctttact aaagggggag gaagggaggg caaagggatg agaagacaag     1980
tttcccagaa gtgcctggtt ctgtgtactt gtcccttgt tgtcgttgtt gtagttaaag      2040
gaatttcatt ttttaaaaga aatcttcgaa ggtgtggttt tcatttctca gtcaccaaca     2100
gatgaataat tatgcttaat aataaagtat ttattaagac tttcttcaga gtatgaaagt     2160
acaaaaagtc tagttacagt ggatttagaa tatatttatg ttgatgtcaa acagctgagc     2220
accgtagcat gcagatgtca aggcagttag gaagtaaatg gtgtcttgta gatatgtgca     2280
aggtagcatg atgagcaact tgagtttgtt gccactgaga agcaggcggg ttgggtggga     2340
ggaggaagaa agggaagaat taggtttgaa ttgctttttt aaaaaaaaag aaaagaaaaa     2400
gacagcatct cactatgttg ccaaggctca tcttgagaag caggcgggtt gggtggggagg    2460 aggaagaaag ggaagaatta ggtttgaatt gcttttt                              2498
```

<210> SEQ ID NO 135
<211> LENGTH: 2936
<212> TYPE: DNA
<213> ORGANISM: Homo sapiens

<400> SEQUENCE: 135

```
cgaaggtagc gtgtcgggga cccagactga taagacaaaa gagaatcagt cgctttgggc      60
tgcccctcca cacaacctgg gacttttaaa caaagctgtg cgcagagaaa ggcgtggaaa     120
tgccactttg agagtttgtg ctgggggatg tgagaagctc tgagacatgt gagaaggtct     180
agtattctac tagaactgga agattgctct ccgagttttg ttttgttatt ttgtttaaaa     240
aataaaaagc ttgaggccaa ggcaattcat attggctcac aggtattttt gctgtgctgt     300
gcaaggaact ctgctagctc aagattcaca atgttgaaag ccctttcct aactatgctg      360 actctggcgc tggtcaagtc acaggacacc gaagaaacca tcacgtacac gcaatgcact     420
gacggatatg agtgggatcc tgtgagacag caatgcaaag atattgatga atgtgacatt     480
gtcccagacg cttgtaaagg tggaatgaag tgtgtcaacc actatggagg atacctctgc     540
cttccgaaaa cagcccagat tattgtcaat aatgaacagc tcagcagga aacacaacca      600 gcagaaggaa cctcaggggc aaccaccggg gttgtagctg ccagcagcat ggcaaccagt     660
ggagtgttgc ccgggggtgg ttttgtggcc agtgctgctg cagtcgcagg ccctgaaatg     720
cagactggcc gaaataactt tgtcatccgg cggaacccag ctgaccctca gcgcattccc     780 tccaacctt cccaccgtat ccagtgtgca gcaggctacg agcaaagtga acacaacgtg      840
tgccaagaca tagacgagtg cactgcaggg acgcacaact gtagagcaga ccaagtgtgc     900
atcaatttac ggggatcctt tgcatgtcag tgccctcctg gatatcagaa gcgaggggag     960
cagtgcgtag acatagatga atgtaccatc cctccatatt gccaccaaag atgcgtgaat    1020
acaccaggct catttattg ccagtgcagt cctgggtttc aattggcagc aaacaactat     1080
acctgcgtag atataaatga atgtgatgcc agcaatcaat gtgctcagca gtgctacaac    1140
attcttggtt cattcatctg tcagtgcaat caaggatatg agctaagcag tgacaggctc    1200
aactgtgaag acattgatga atgcagaacc tcaagctacc tgtgtcaata tcaatgtgtc    1260
aatgaacctg ggaaattctc atgtatgtgc ccccagggat accaagtggt gagaagtaga    1320
acatgtcaag atataaatga gtgtgagacc acaaatgaat gccgggagga tgaaatgtgt    1380
tggaattatc atggcggctt ccgttgttat ccacgaaatc cttgtcaaga tccctacatt    1440
ctaacaccag agaaccgatg tgtttgccca gtctcaaatg ccatgtgccg agaactgccc    1500
cagtcaatag tctacaaata catgagcatc cgatctgata ggtctgtgcc atcagacatc    1560
ttccagatac aggccacaac tatttatgcc aacaccatca atacttttcg gattaaatct    1620
ggaaatgaaa atggagagtt ctacctacga caaacaagtc ctgtaagtgc aatgcttgtg    1680
ctcgtgaagt cattatcagg accaagagaa catatcgtgg acctggagat gctgacagtc    1740
agcagtatag ggaccttccg cacaagctct gtgttaagat tgacaataat agtggggcca    1800 ttttcattt agtcttttct aagagtcaac cacaggcatt taagtcagcc aaagaatatt     1860
gttaccttaa agcactattt tatttataga tatatctagt gcatctacat ctctatactg    1920
tacactcacc cataattcaa acaattacac catggtataa agtgggcatt taatatgtaa    1980
agattcaaag tttgtcttta ttactatatg taaattagac attaatccac taaactggtc    2040
ttcttcaaga gagctaagta tacactatct ggtgaaactt ggattctttc ctataaaagt    2100
gggaccaagc aatgatgatc ttctgtggtg cttaaggaaa cttactagag ctccactaac    2160
agtctcataa ggaggcagcc atcataacca ttgaatagca tgcaagggta agaatgagtt    2220
tttaactgct ttgtaagaaa atggaaaagg tcaataaaga tatatttctt tagaaaatgg    2280
ggatctgcca tatttgtgtt ggttttatt ttcatatcca gcctaaaggt ggttgtttat     2340
tatatagtaa taaatcattg ctgtacaata tgctggtttc tgtagggtat ttttaatttt    2400
```

| | |
|---|---|
| gtcagaaatt ttagattgtg aatatttgt aaaaaacagt aagcaaaatt ttccagaatt | 2460 |
| cccaaaatga accagatatc ccctagaaaa ttatactatt gagaaatcta tggggaggat | 2520 |
| atgagaaaat aaattccttc taaaccacat tggaactgac ctgaagaagc aaactcggaa | 2580 |
| aatataataa catccctgaa ttcaggactt ccacaagatg cagaacaaaa tggataaaag | 2640 |
| gtatttcact ggagaagttt taatttctaa gtaaaattta aatcctaaca cttcactaat | 2700 |
| ttataactaa aatttctcat cttcgtactt gatgctcaca gaggaagaaa atgatgatgg | 2760 |
| tttttattcc tggcatccag agtgacagtg aacttaagca aattaccctc tacccaatt | 2820 |
| ctatggaata ttttatacgt ctccttgttt aaaatgtcac tgctttactt tgatgtatca | 2880 |
| tattttaaa taaaaataaa tattcccttta gaagatcaaa aaaaaaaaaa aaaaaa | 2936 |

<210> SEQ ID NO 136
<211> LENGTH: 3727
<212> TYPE: DNA
<213> ORGANISM: Homo sapiens

<400> SEQUENCE: 136

| | |
|---|---|
| aagtgagagc agcggcagcc ggcggtgcag cagccggccg acccagagtg taagtgcgtg | 60 |
| tgctggggcg agcgggagcg ggcgaggatg ggcacaggat agaggcagag ccacccacgc | 120 |
| cgccgcggcc ccacgctggg cgacagagcc tccagttccc cttcaatggt ggcgggtcgc | 180 |
| cggagctctg atcgccggga acccttgccg ctgctgtcct gcgaccccaa gcaggtatag | 240 |
| acacgtgtgg ccgtttacgc tgtaggatcc tcattcccac tggctttgaa cattttgggg | 300 |
| acttacaatg ccgccacccg cggacatcgt caaggtggcc atagaatggc cgggcgccta | 360 |
| ccccaaactc atggaaattg atcagaaaaa accactgtct gcaataataa aggaagtctg | 420 |
| tgatgggtgg tctcttgcca accatgaata ttttgcactc cagcatgccg atagttcaaa | 480 |
| cttctatatc acagaaaaga accgcaatga gataaaaaat ggcactatcc ttcgattaac | 540 |
| cacatctcca gctcagaacg cccagcagct ccatgaacga atccagtcct cgagtatgga | 600 |
| tgccaagctg gaagccctga aggacttggc cagcctctcc cgggatgtca cgtttgccca | 660 |
| ggagtttata aacctggacg gtatctctct cctcacgcag atggtggaga gcggcactga | 720 |
| gcgataccag aaaattgcag agatcatgaa gccttgcttt ggagacatgc tgtccttcac | 780 |
| cctgacggcc ttcgttgagc tgatggacca tggcatagtg tcctgggata catttttcggt | 840 |
| ggcgttcatt aagaagatag caagttttgt gaacaagtca gccatagaca tctcgatcct | 900 |
| gcagcggtcc ttggccatttt tggagtcgat ggtgctcaat agccatgacc tctaccagaa | 960 |
| agtggcgcag gagatcacca tcggccagct cattccacac ctgcaagggt cagatcaaga | 1020 |
| aatccaaacc tatactattg cagtgattaa tgcgcttttc ctgaaggctc ctgatgagag | 1080 |
| gaggcaggag atggcgaata ttttggctca gaagcaactg cgttccatca ttttaacaca | 1140 |
| tgtcatccga gccagcggg ccatcaacaa tgagatggcg caccagctgt atgttctaca | 1200 |
| agtgctcacc tttaacctcc tggaagacag gatgatgacc aaaatggacc cccaggacca | 1260 |
| ggctcagagg gacatcatat ttgaacttcg aagaattgct tttgatgctg agtctgaacc | 1320 |
| taacaacagc agtggcagca tggagaaacg caagtccatg tacacgcgag attataagaa | 1380 |
| gcttgggttc attaatcatg tcaaccctgc catggacttc acgcagactc cacctgggat | 1440 |
| gttggctctg gacaacatgc tgtactttgc caagcaccac caagatgcct acatccggat | 1500 |
| tgtgcttgag aacagtagtc gagaagacaa gcatgaatgt cccctttggcc gcagtagtat | 1560 |

-continued

```
agagctgacc aagatgctat gtgagatctt gaaagtgggc gagttgccta gtgagacctg    1620
caacgacttc cacccgatgt tcttcaccca cgacagatcc tttgaggagt ttttctgcat    1680
ctgtatccag ctcctgaaca agacatggaa ggaaatgagg gcaacttctg aagacttcaa    1740
caaggtaatg caggtggtga aggagcaggt tatgagagca cttacaacca agcctagctc    1800
cctggaccag ttcaagagca aactgcagaa cctgagctac actgagatcc tgaaaatccg    1860
ccagtccgag aggatgaacc aggaagattt ccagtcccgc ccgattttgg aactaaagga    1920
gaagattcag ccagaaatct tagagctgat caaacagcaa cgcctgaacc gccttgtgga    1980
agggacctgc tttaggaaac tcaatgcccg gcggaggcaa gacaagtttt ggtattgtcg    2040
gctttcgcca aatcacaaag tcctgcatta cggagactta aagagagtc ctcagggaga     2100 agtgccccac gattccttgc aggacaaact gccggtggca gatatcaaag ccgtggtgac    2160
gggaaaggac tgccctcata tgaaagagaa aggtgccctt aaacaaaaca aggaggtgct    2220
tgaactcgct ttctccatct tgtatgactc aaactgccaa ctgaacttca tcgctcctga    2280
caagcatgag tactgtatct ggacggatgg actgaatgcg ctactcggga aggacatgat    2340
gagcgacctg acgcggaatg acctggacac cctgctcagc atggaaatca agctccgcct    2400
cctggacctg gaaaacatcc agatccctga cgcacctccg ccgattccca aggagcccag    2460
caactatgac ttcgtctatg actgtaactg aagtggccgg gcccagacat gccccttcca    2520
aaactggaac acctagctaa caggagagag gaatgaaaac acacccacgc cttgaaccg     2580 tcctttggta aagggaagct gtgggtccac attcccttca gcatcacctc tagccctggc    2640
aactttcagc ccctagctgg catcttgctc accgccctga ttctgttcct cggctccact    2700
gcttcaggtc acttcccatg gctgcagtcc actggtggga caagagcaaa gcccactgcc    2760
agtaagaagg ccaaagggcc cttccatcct agccctctgc aggcatgccc ttccttccct    2820
tgggcaggaa agccagcagc cccagactgc ccaaaaactt gcccaccaga ccaagggcag    2880
tgccccaagg cccctgtctg gaggaaatgg cctagctatt tgatgagaag accaaacccc    2940
acatcctcct ttcccctctc tctagaatca tctcgcacca ccagttacac ttgaattaag    3000
atctgcgctc aaatctcctc ccacctctct ccctgctttt gccttgctct gttcctcttt    3060
ggtcccaaga gcagcagccg cagcctcctc gtgatcctcc ctagcataaa tttcccaaac    3120
agtccacagg tccatgccc actttgcgtc tgcactgtga tcgtgacaaa tcttccctcc     3180
tcaccagcta gtctggggtt tcctctccct gccccaggcc agaactgcct tcttcatttc    3240
cacccacgct cccagcctct tagctgaaag cacaaatggt gaaatcagta gtctcgctcc    3300
atctctaata gactaaacct aaatgcctct aggacggact gttgctatcc aagcgtttgg    3360
tgttaccttc tcctgggagg tcctgctgca actcaagttc cacaggatgg tcaagctgtc    3420
agacatccaa gtttacatca ttgtaattat tactggtatt tacaatttgc aagagttttg    3480
ggttagtttt ttttttttt ttgctttgt ttttgtacaa aagagtctaa cattttttgc       3540
caaacagata tatatttaat gaaagaagaa gatacataaa tgtgtgaatt ccagttttt     3600 ttttaattat tttaatccca aacatcttcc tgaaaataac attcccttaa acatgctgtg    3660
gaataaaatg gattgtgatg atttggaaaa aaaaaaaaaa aaaaaaaaaa aaaaaaaaaa    3720
aaaaaaa                                                               3727
```

<210> SEQ ID NO 137
<211> LENGTH: 4654
<212> TYPE: DNA
<213> ORGANISM: Homo sapiens

<400> SEQUENCE: 137

```
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg gacaacaca ggtcgcggag      480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga gaggaccggg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaagagcc accaaccaaa taccaaatct     780
ctcaaccaga agtgtacgtg gctgcgccag gggagtcgct agaggtgcgc tgcctgttga     840
aagatgccgc cgtgatcagt tggactaagg atggggtgca cttggggccc aacaatagga     900
cagtgcttat tggggagtac ttgcagataa agggcgccac gcctagagac tccggcctct     960
atgcttgtac tgccagtagg actgtagaca gtgaaacttg gtacttcatg gtgaatgtca    1020
cagatgccat ctcatccgga gatgatgagg atgacaccga tggtgcggaa gattttgtca    1080
gtgagaacag taacaacaag agagcaccat actggaccaa cacagaaaag atggaaaagc    1140
ggctccatgc tgtgcctgcg gccaacactg tcaagtttcg ctgcccagcc ggggggaacc    1200
caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga tgaatacgg gtccatcaat cacacgtacc     1380
acctggatgt tgtggagcga tcgcctcacc ggcccatcct ccaagccgga ctgccggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgcccta cctcaaggtt ctcaaggccg ccggtgttaa caccacggac aaagagattg    1620
aggttctcta tattcggaat gtaacttttg aggacgctgg ggaatatacg tgcttggcgg    1680
gtaattctat tgggatatcc tttcactctg catggttgac agttctgcca gcgcctggaa    1740
gagaaaagga gattacagct tccccagact acctggagat agccatttac tgcatagggg    1800
tcttcttaat cgcctgtatg gtggtaacag tcatcctgtg ccgaatgaag aacacgacca    1860
agaagccaga cttcagcagc cagccggctg tgcacaagct gaccaaacgt atccccctgc    1920
ggagacaggt aacagtttcg gctgagtcca gctcctccat gaactccaac accccgctgg    1980
tgaggataac aacacgcctc tcttcaacgg cagacacccc catgctggca gggtctccg     2040
agtatgaact tccagaggac ccaaaatggg agtttccaag agataagctg acactgggca    2100
agcccctggg agaaggttgc tttgggcaag tggtcatggc ggaagcagtg ggaattgaca    2160
aagcaagcc caaggaggcg gtcaccgtgg ccgtgaagat gttgaaagat gatgccacag    2220
agaaagacct ttctgatctg gtgtcagaga tggagatgat gaagatgatt gggaaacaca    2280
```

```
agaatatcat aaatcttctt ggagcctgca cacaggatgg gcctctctat gtcatagttg    2340
agtatgcctc taaaggcaac ctccgagaat acctccgagc ccggaggcca cccgggatgg    2400
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttagggggc tcgccctacc    2760
cagggattcc cgtggaggaa cttttttaagc tgctgaagga aggacacaga atggataagc    2820
cagccaactg caccaacgaa ctgtacatga tgatgaggga ctgttggcat gcagtgccct    2880
cccagagacc aacgttcaag cagttggtag aagacttgga tcgaattctc actctcacaa    2940
ccaatgagga atacttggac ctcagccaac ctctcgaaca gtattcacct agttaccctg    3000
acacaagaag ttcttgttct tcaggagatg attctgtttt ttctccagac ccatgccttt    3060
acgaaccatg ccttcctcag tatccacaca taaacggcag tgttaaaaca tgaatgactg    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcacc    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
tatttacaag gagttatttt ttgtattgat tttaaatgga tgtcccaatg cacctagaaa    3600
attggtctct cttttttttaa tagctatttg ctaaatgctg ttcttacaca taatttctta    3660
attttcaccg agcagaggtg gaaaaatact tttgctttca gggaaaatgg tataacgtta    3720
atttattaat aaaattggtaa tatacaaaac aattaatcat ttatagtttt ttttgtaatt    3780
taagtggcat ttctatgcag gcagcacagc agactagtta atctattgct tggacttaac    3840
tagttatcag atccttttgaa aagagaatat ttacaatata tgactaattt ggggaaaatg    3900
aagtttttgat ttatttgtgt ttaaatgctg ctgtcagacg attgttctta gacctcctaa    3960
atgccccata ttaaaagaac tcattcatag gaaggtgttt cattttggtg tgcaaccctg    4020
tcattacgtc aacgcaacgt ctaactggac ttcccaagat aaatggtacc agcgtcctct    4080
taaaagatgc cttaatccat tccttgagga cagaccttag ttgaaatgat agcagaatgt    4140
gcttctctct ggcagctggc cttctgcttc tgagttgcac attaatcaga ttagcctgta    4200
ttctcttcag tgaattttga taatggcttc cagactcttt ggcgttggag acgcctgtta    4260
ggatcttcaa gtcccatcat agaaaattga aacacagagt tgttctgctg atagttttgg    4320
ggatacgtcc atcttttttaa gggattgctt tcatctaatt ctggcaggac ctcaccaaaa    4380
gatccagcct catacctaca tcagacaaaa tatcgccgtt gttccttctg tactaaagta    4440
ttgtgttttg ctttggaaac acccactcac tttgcaatag ccgtgcaaga tgaatgcaga    4500
ttacactgat cttatgtgtt acaaaattgg agaaagtatt taataaaacc tgttaatttt    4560
tatactgaca ataaaaatgt ttctacagat attaatgtta acaagacaaa ataaatgtca    4620
cgcaacttat tttttttaata aaaaaaaaaa aaaa                              4654
```

<210> SEQ ID NO 138
<211> LENGTH: 3252
<212> TYPE: DNA
<213> ORGANISM: Homo sapiens

<400> SEQUENCE: 138

| | | | | | |
|---|---|---|---|---|---|
| caaggaggct | gctgattgtg | gcccacagcc | tcatctgaac | gccaggagac | caggataccg | 60 |
| aggcaccgga | tccctctct | gtgccctggga | gagcccagt | gctgcccagt | caccccaggg | 120 |
| ctgaggtctg | cgtccctagt | ggtgcaaggc | ctggtaggac | cacggggcag | ggaatgtgag | 180 |
| cgccatctga | gctcacggtg | tcctgagtcg | cggcttcgtg | actttggcag | gggcctccgg | 240 |
| accagtgacc | ccagtcaaac | ccagagggtc | ttgggcggca | gcgacgaagg | aggtattcag | 300 |
| gctccaggcc | aggtggggcc | ggacgccccc | agccatccac | catggtggtg | gcacacccca | 360 |
| ccgccactgc | caccaccacg | cccactgcca | ctgtcacggc | caccgttgtg | atgaccacgg | 420 |
| ccaccatgga | cctgcgggac | tggctgttcc | tctgctacgg | gctcatcgcc | ttcctgacgg | 480 |
| aggtcatcga | cagcaccacc | tgcccctcgg | tgtgccgctg | cgacaacggc | ttcatctact | 540 |
| gcaacgaccg | ggactcaca | tccatccccg | cagatatccc | tgatgatgcc | accccctct | 600 |
| acctgcagaa | caaccagatc | aacaacgccg | gcatccccca | ggacctcaag | accaaggtca | 660 |
| acgtgcaggt | catctaccta | tacgagaatg | acctggatga | gttccccatc | aacctgcccc | 720 |
| gctccctccg | ggagctgcac | ctgcaggaca | caatgtgcg | caccattgcc | agggactcgc | 780 |
| tggcccgcat | cccgctgctg | gagaagctgc | acctggatga | caactccgtg | tccaccgtca | 840 |
| gcattgagga | ggacgccttc | gccgacagca | aacagctcaa | gctgctcttc | ctgagccgga | 900 |
| accacctgag | cagcatcccc | tcggggctgc | cgcacacgct | ggaggagctg | cggctggatg | 960 |
| acaaccgcat | ctccaccatc | ccgctgcatg | ccttcaaggg | cctcaacagc | ctgcggcgcc | 1020 |
| tggtgctgga | cggtaacctg | ctggccaacc | agcgcatcgc | cgacgacacc | ttcagccgcc | 1080 |
| tacagaacct | cacagagctc | tcgctggtgc | gcaattcgct | ggccgcgcca | cccctcaacc | 1140 |
| tgcccagcgc | ccacctgcag | aagctctacc | tgcaggacaa | tgccatcagc | acatcccct | 1200 |
| acaacacgct | ggccaagatg | cgtgagctgg | agcggctgga | cctgtccaac | aacaacctga | 1260 |
| ccacgctgcc | ccgcggcctg | ttcgacgacc | tggggaacct | ggcccagctg | ctgctcagga | 1320 |
| acaacccttg | gttttgtggc | tgcaacctca | tgtggctgcg | ggactgggtg | aaggcacggg | 1380 |
| cggccgtggt | caacgtgcgg | ggcctcatgt | gccagggccc | tgagaaggtc | cggggcatgg | 1440 |
| ccatcaagga | cattaccagc | gagatggacg | agtgttttga | gacggggccg | cagggcggcg | 1500 |
| tggccaatgc | ggctgccaag | accacggcca | gcaaccacgc | ctctgccacc | acgcccccagg | 1560 |
| gttccctgtt | taccctcaag | gccaaaaggc | cagggctgcg | cctccccgac | tccaacattg | 1620 |
| actaccccat | ggccacgggt | gatggcgcca | agaccctggc | catccacgtg | aaggccctga | 1680 |
| cggcagactc | catccgcatc | acgtggaagg | ccacgctccc | cgcctcctct | ttccggctca | 1740 |
| gttggctgcg | cctgggccac | agcccagccg | tgggctccat | cacggagacc | ttggtgcagg | 1800 |
| gggacaagac | agagtacctg | ctgacagccc | tggagcccaa | gtccacctac | atcatctgca | 1860 |
| tggtcaccat | ggagaccagc | aatgcctacg | tagctgatga | gacacccgtg | tgtgccaagg | 1920 |
| cagagacagc | cgacagctat | ggccctacca | ccacactcaa | ccaggagcag | aacgctggcc | 1980 |
| ccatggcgag | cctgccctg | gcgggcatca | tcggcggggc | agtggctctg | gtcttcctct | 2040 |
| tcctggtcct | gggggccatc | tgctggtacg | tgcaccaggc | tggcgagctg | ctgacccggg | 2100 |

| | |
|---|---:|
| agagggccta caaccggggc agcaggaaaa aggatgacta tatggagtca gggaccaaga | 2160 |
| aggataactc catcctggaa atccgcggcc ctgggctgca gatgctgccc atcaacccgt | 2220 |
| accgcgccaa agaggagtac gtggtccaca ctatcttccc ctccaacggc agcagcctct | 2280 |
| gcaaggccac acacaccatt ggctacggca ccacgcgggg ctaccgggac ggcggcatcc | 2340 |
| ccgacataga ctactcctac acatgatgcc cgcccacccg ggctgccccg cctcagcccc | 2400 |
| agctgccctg gcgtggccat gtggctttgc ccagcctgct gcaatccaag agagcaagga | 2460 |
| agagaaattc catgggtgac tttcctccgc agaaagcaaa gtttggggag ggctgacgat | 2520 |
| tttgtagaac acaacagtga caattttttt taaaagaata gaaggcagga gggggaattc | 2580 |
| gacattgttg aagacataat ttataccaag ttatgccagt tggggaggga aggactaaaa | 2640 |
| ataatattgc aggcagggct gggttgggtt ttttttttt cccccctgaa ctggaaggat | 2700 |
| actacctgta caacatctgt ggacacctca tgctctgttc aaggccatca caaaggaacc | 2760 |
| gccaggagaa agcagccggc tctcaaagct cccacgcagc tctcccgcca ctggccactc | 2820 |
| gctggcgacc cgatggaagg ttttcaggct cctcacaaag gagagaggga agaaaagatc | 2880 |
| ttttgccctg gagatatggt cctgaaatct ctcccctggc ttattccata ccatttccct | 2940 |
| tgcagatttg cagaaacatg gcatctttca ctgcattctt tgaacaatca tgtagtcgat | 3000 |
| taaaaaaaaa aaacaaactt tttttttccta ggctgaagcc ctcttcagtt ccatgcacca | 3060 |
| cgctccgtag aagccccggc ggaagccgta gctttccctg ccacctggag gtgcatctgt | 3120 |
| ctgcctgtct atccctgtcg cggtgtctct aagtacagat gggtagatag agccacatgc | 3180 |
| acggtcctta ccgttcttct tgggtcagtt cttaccattt cctgaacaat agaattgtga | 3240 |
| aagtgttaaa aa | 3252 |

<210> SEQ ID NO 139
<211> LENGTH: 3005
<212> TYPE: DNA
<213> ORGANISM: Homo sapiens

<400> SEQUENCE: 139

| | |
|---|---:|
| ggtctggcac aggcacgcac actctcagta gactcttca ctcctctctc tcttcctctc | 60 |
| tcacacgttc tccaacccaa ggaggccaga cagagggacg tggtcactct ctgaaaagtt | 120 |
| caacttgaga gacaaaatgc agtggacctc cctcctgctg ctggcagggc tcttctccct | 180 |
| ctcccaggcc cagtatgaag atgaccctca ttggtggttc cactacctcc gcagccagca | 240 |
| gtccacctac tacgatccct atgaccctta cccgtatgag acctacgagc ttacccccta | 300 |
| tggggtggat gaagggccag cctacaccta cggctctcca tcccctccag atccccgcga | 360 |
| ctgcccccag gagtgcgact gcccacccaa cttccccacg gccatgtact gtgacaatcg | 420 |
| caacctcaag tacctgccct tcgttccctc ccgcatgaag tatgtgtact ccagaacaa | 480 |
| ccagatcacc tccatccagg aaggcgtctt tgacaatgcc acagggctgc tctggattgc | 540 |
| tctccacggc aaccagatca ccagtgataa ggtgggcagg aaggtcttct ccaagctgag | 600 |
| gcacctggag aggctgtacc tggaccacaa caacctgacc cggatgcccg gtcccctgcc | 660 |
| tcgatccctg agagagctcc atctcgacca caaccagatc tcacgggtcc caacaatgc | 720 |
| tctggagggg ctgagaacc tcacggcctt gtacctccaa cacaatgaga tccaggaagt | 780 |
| gggcagttcc atgagggggcc tccggtcact gatcttgctg gacctgagtt ataaccacct | 840 |
| tcggaaggtg cctgatgggc tgccctcagc tcttgagcag ctgtacatgg agcacaacaa | 900 |
| tgtctacacc gtccccgata gctacttccg ggggcgcccc aagctgctgt atgtgcggct | 960 |

```
gtcccacaac agtctaacca acaatggcct ggcctccaac accttcaatt ccagcagcct    1020
ccttgagcta gacctctcct acaaccagct gcagaagatc cccccagtca acaccaacct    1080
ggagaacctc tacctccaag gcaataggat caatgagttc tccatcagca gcttctgcac    1140
cgtggtggac gtcgtgaact tctccaagct gcaggtgctg cgcctggacg ggaacgagat    1200
caagcgcagc gccatgcctg ccgacgcgcc cctctgcctg cgccttgcca gcctcatcga    1260
gatctgagca gccctggcac cgggtactgg gcggagagcc ccgtggcat ttggcttgat     1320 ggtttggttt ggcttttgct ggaaggtcca ggatggacca tgtgacagaa gtccacgggc    1380
accctctgta gtcttctttc ctgtaggtgg ggttagggggg gcgatcagg acaggcagc    1440 cttctgctga ggacataggc agaagctcac tcttttccag ggacagaagt ggtggtagat    1500
ggaaggatcc ctggatgttc aaccccata aatctcacgg ctcttaagtt cttcccaatg    1560
atctgaggtc atggaacttc aaaagtggca tgggcaatag tatataacca tactttcta     1620 acaatccctg gctgtctgtg agcagcactt gacagctctc cctctgtgct gggctggtcg    1680
tgcagttact ctgggctccc atttgttgct tctcaaaata tacctcttgc ccagctgcct    1740
cttctgaaat ccacttcacc cactccactt tcctccacag atgcctcttc tgtgccttaa    1800
gcagagtcag gagaccccaa ggcatgtgag catctgccca gcaacctgtg gagacaaccc    1860
acactgtgtc tgagggtgaa aggacaccag gagtcacttc tatacctccc taacctcacc    1920
cctggaaagc caccagattg gaggtcacca gcatgatgat aatattcatg acctgatgtg    1980
ggaggagaca gccaacctca ggcttagatc aatgtatagg ctatattttt ggcagctggg    2040
tagctctttg aaggtggata agacttcaga agaggaaagg ccagactttg cttaccatca    2100
gcatctgcaa tgggccaaac acacctcaaa ttggctgagt tgagaaagca gccccagtag    2160
ttccattctt gcccagcact ttctgcattc caaacagcat cctacctggg tttttatcca    2220
caaaggtagc ggccacatgg ttttaaagt atgagaaaca cagtttgtcc tctccttta     2280 tccaagcagg aagattctat atcctgatgg tagagacaga ctccaggcag ccctggactt    2340
gctagcccaa agaaggagga tgtggttaat ctgtttcacc tggtttgtcc taaggccata    2400
gttaaaaagt accagctctg ctggggtcc gtgaagccca ggccaggcag ccaaatcttg     2460
cctgtgctgg gcatacaacc ctctgctttc acatctctga gctatatcct cattagtgaa    2520
ggtggctttt gctttatagt ttggctgggg agcacttaat tcttcccatt tcaaaaggta    2580
atgttgcctg ggcttaacc cacctgccct ttgggcaagg ttgggacaaa gccatctggg     2640
cagtcagggg caaggactgt tggaggagag ttagcccaag tataggctct gcccagatgc    2700
catcacatcc ctgatactgt gtatgctttg aagcaccttc cctgagaagg gaagagggga    2760
tctttggact acgttcttgg ctccagacct ggaatccaca aaagccaaac cagctcattt    2820
caacaaagga gctccgatgt gaggggcaag gctgccccct gccccagggc tcttcagaaa    2880
gcatctgcat gtgaacacca tcatgccttt ataaaggatc cttattacag gaaaagcatg    2940
agtggtggct aacctgacca ataaagttat tttatgattg catctaaaaa aaaaaaaaaa    3000
aaaaa                                                                3005
```

<210> SEQ ID NO 140  
<211> LENGTH: 4339  
<212> TYPE: DNA  
<213> ORGANISM: Homo sapiens

<400> SEQUENCE: 140

```
agagccggag gaggggggaag gagggagggg agagcggtgg cggcggctgc gccgggctgt    60
gagtctctcg ccgccggagg aagatgaggc tgaagattgg gttcatctta cgcagtttgc   120
tggtggtggg aagcttcctg gggctagtgg tcctctggtc ttccctgacc ccgcggccgg   180
acgacccaag cccgctgagc aggatgaggg aagacagaga tgtcaatgac cccatgccca   240
accgaggcgg caatggacta gctcctgggg aggacagatt caaacctgtg gtaccatggc   300
ctcatgttga aggagtagaa gtggacttag agtctattag aagaataaac aaggccaaaa   360
atgaacaaga gcaccatgct ggaggagatt cccagaaaga tatcatgcag aggcagtatc   420
tcacatttaa gcctcagaca ttcacctacc atgatcctgt gcttcgccca gggatcctcg   480
gtaactttga acccaaagaa cctgagcctc ctggagtggt tggtggccct ggagagaaag   540
ccaagccatt ggttttggga ccagaattca acaagcaat tcaagccagc attaaagagt   600
ttggatttaa catggtggca agtgacatga tctcactgga ccgcagcgtc aatgacttac   660
gccaagaaga atgcaagtat tggcattatg atgaaaactt gctcacttcg agcgttgtca   720
ttgtcttcca taatgaagga tggtcaaccc tcatgagaac agtccacagt gtaattaaaa   780
ggactccaag gaaatattta gcagaaattg tgttaattga cgatttcagt aataaagaac   840
acttaaaaga aaaactggat gaatatatta gctgtggaa tggcctagtg aaggtatttc   900
gaaatgaaag aagggaaggt ttaattcaag cacgaagtat tggtgctcag aaggctaaac   960
ttggacaggt tttgatatac cttgatgccc actgtgaggt ggcagttaac tggtatgcac  1020
cacttgtagc tcccatatct aaggacagaa ccatttgcac tgtgccgctt atagatgtca  1080
taaatggcaa cacatatgaa attatacccc aaggggtgg tgatgaagat gggtatgccc  1140
gaggagcatg ggattggagt atgctctgga acgggtgcc tctgacccct caagagaaga  1200
gactgagaaa gacaaaaact gaaccgtatc ggtccccagc catggctggg ggattatttg  1260
ccattgaacg agagttcttc tttgaattgg gtctctatga tccaggtctc cagatttggg  1320
gtggtgaaaa ctttgagatc tcatacaaga tatggcagtg tggtggcaaa ttattatttg  1380
ttccttgttc tcgtgttgga catatctacc gtcttgaggg ctggcaagga aatcctccgc  1440
ccatttatgt tgggtcttct ccaactctga agaattatgt tagagttgtg gaggtttggt  1500
gggatgaata taaagactac ttctatgcta gtcgtcctga atcgcaggca ttaccatatg  1560
gggatatatc ggagctgaaa aaatttcgag aagatcacaa ctgcaaaagt ttaagtggt  1620
tcatggaaga aatagcttat gatatcacct cacactaccc tttgccaccc aaaaatgttg  1680
actgggggaga aatcagaggc ttcgaaactg cttactgcat tgatagcatg ggaaaaacaa  1740
atggaggctt tgttgaacta ggaccctgcc acaggatggg aggggaatcag cttttcagaa  1800
tcaatgaagc aaatcaactc atgcagtatg accagtgttt gacaaaggga gctgatggat  1860
caaaagttat gattacacac tgtaatctaa atgaatttaa ggaatggcag tacttcaaga  1920
acctgcacag atttactcat attccttcag gaaagtgttt agatcgctca gaggtcctgc  1980
atcaagtatt catctccaat tgtgactcca gtaaaacgac tcaaaaatgg gaaatgaata  2040
acatccatag tgtttagaga gaaaaaaata aaccaataac ctacctactg acaagtaaat  2100
ttatacagga ctgaaaaccg cctgaaacct gctgcaacta ttgttattaa ctctgtatag  2160
ctccaaaacct ggaacctcct gatcagtttg aaggacattg ataaactgtg attttacaat  2220
aacattatca tctgcagtta ctgttttacaa gactgctttt accttaaaact ttgtagatgt  2280
ttacatcttt ttgttgtgtt ttaagatgat gttggtaatt tgtgccttta gctctgttttt  2340
attagacaga gttaaagcat gttgtcttct ttgggattac actcagggt ctgaaaggca   2400
```

```
gtttgatttt tattttttaac acacttgaaa aaaggttgga gtagccagac tttcatatat    2460
aacttggtga ttatcaacct gttgtgtctt tatttaattt tacatctttt tgaagcactg    2520
ccacaggtta ttagccaagg tggccttcct tcacagtcat gctgcttttt tgaaaggtga    2580
atttcaacac atttagtgcc tctttcattt ctcagtatat atttcaagag cttgtgatga    2640
aatctatagg atggtaatga tggacttgtc acctgtatgg ggaatacttt tactactcag    2700
aaatgaattt atgtgctgcc atttgctata agttgaact ttgtatggct tgaaaagaa    2760 atgacaatat ggaacatccc aaggctgtcc catagggttg gaagttgtgt agcattcact    2820
cccttaccta ctggcattcc cagtgccctc tgtccatacc tacttctagg attgcaaagg    2880
agtcttccaa ctagagaaaa attgtccact gacatttggg atttactttt ctccaatacc    2940
tgccaataca gaaaactatt atcagttgtt attgttatcc cttgaaagcg agggtgacaa    3000
aaacaacaaa acaccgttat aaacacatca aaggttcatt ctgactgagg taagactttc    3060
caagcccttg ttagattagg ccttataaaa cttgtgtgca ttataaccta agctgtgcaa    3120
cctgtgaagc caagagtgaa ctgatgtttc atttatattt tcatccaaat gacattatct    3180
gcacgttttt aaaatttaaa aacaaaggac tatttaaaaa tacagtttat taacaaacgt    3240
gaactacttt ctgttacatt aggtgttccc tagtgtttct taatttcttt ttagaaagtg    3300 tattttatt agtattttc cggtgaacag aagatttgtt tggatttaaa catttactaa    3360
gacagtacct attaggaaaa ccaaatattg caaatggtca attcgatttt aatttctcaa    3420
aagatactct gttatccaga agattaaaat gcctacattg agtgcttaaa aaaaaaaaa    3480 caactgtgat gatgtgagca gaatggcaag taagttaagc attttgatc ctgtaatcat    3540 ggtatcatta caatgaaagg aattcacaaa ctactgccag aggaagtttg tttttttaatt    3600 taagagggaa atataaccta taaatttgtt tcttccaagc ttagctctta aatttggaga    3660
ctcaaagtta aacatcctca acagagtttt atttataatt ttgaattgtc aatttgtatt    3720
ttgctactga tctgtgatca accatttaa ctttcatctc tagggatgtt taacatttat    3780
aattgcaaaa taaccaact ataaaaaaag aaactaagag agaattggta ctttaattac    3840
ttgtgtgttt gcaaataggc tccatttcc atgttgagta gattataacc ttattaacta    3900
tgcataggcc taagaaaggt ggcaatgaac tgtgcatgta aatttaaat gggtactttg    3960 tgcaattcgt taaagaaga tactctatga atatgattct atatattgaa atcagaaaac    4020
ctaccaaaca aaaacatcag aagctgctgc cataatgact atttttctact gtaggctgct    4080 ttggaaataa ttcccatatc cttgctttgt aagttggtaa tatcactatg catttctaca    4140
cattttataa atttgattta tgcagatttt gatacactgt atgtttctgt agaaattgta    4200
taaatattca aaattttatt aggataaatt tgagaaactt acgtatatct taattctggg    4260
ttgcttgttt tttaggtgac aaaaataaaa tattgtattt taattcaaaa aaaaaaaaa    4320 aaaaaaaaaa aaaaaaaaa                                                 4339

<210> SEQ ID NO 141
<211> LENGTH: 2602
<212> TYPE: DNA
<213> ORGANISM: Homo sapiens

<400> SEQUENCE: 141
ttgcgacgct cgggtctggg tccgggtccg gacgtgcaac agaagccgtc agtggcccg      60 ctggctaaaa aagggcaagc atcggaggct cgagccagcg gccgcggcgc ttcccgacag    120
```

| | |
|---|---|
| ttcctaattc ggggcgctac gccggcccca ccacctgttc ccggcagcca atggggccgc | 180 |
| ggggggcggc cggggcggag cgcggctaca aaaggcctcg ggccccgcgc gcccgcccac | 240 |
| cccgctccgg gcgcgctctc gggaaggctt ggaccgacgc ggcccagagg ccaggaacat | 300 |
| tccgcgcgtg gaccagccgg gccagggcga tgctgcgggt gcggtgtctg cgcggcggga | 360 |
| gccgcggcgc cgaggcggtg cactacatcg gatctcggct tggacgaacc ttgacaggat | 420 |
| gggtgcagcg aactttccag agcacccagg cagctacggc ttcctcccgg aactcctgtg | 480 |
| cagctgacga caaagccact gagcctctgc ccaaggactg ccctgtctct tcttacaacg | 540 |
| aatgggaccc cttagaggaa gtgatagtgg gcagagcaga aaacgcctgt gttccaccgt | 600 |
| tcaccatcga ggtgaaggcc aacacatatg aaaagtactg gccattttac cagaagcaag | 660 |
| gagggcatta ttttcccaaa gatcatttga aaaaggctgt tgctgaaatt gaagaaatgt | 720 |
| gcaatatttt aaaaacggaa ggagtgacag taaggaggcc tgaccccatt gactggtcat | 780 |
| tgaagtataa aactcctgat tttgagtcta cgggttata cagtgcaatg cctcgagaca | 840 |
| tcctgatagt tgtgggcaat gagattatcg aggctcccat ggcatggcgt tcacgcttct | 900 |
| ttgagtaccg agcgtacagg tcaattatca aagactactt ccaccgtggc gccaagtgga | 960 |
| caacagctcc taagcccaca atggctgatg agctttataa ccaggattat cccatccact | 1020 |
| ctgtagaaga cagacacaaa ttggctgctc agggaaaatt tgtgacaact gagtttgagc | 1080 |
| catgctttga tgctgctgac ttcattcgag ctggaagaga tatttttgca cagagaagcc | 1140 |
| aggttacaaa ctacctaggc attgaatgga tgcgtaggca tcttgctcca gactacagag | 1200 |
| tgcatatcat ctcctttaaa gatcccaatc ccatgcatat tgatgctacc ttcaacatca | 1260 |
| ttggacctgg tattgtgctt tccaaccctg accgaccatg tcaccagatt gatctttca | 1320 |
| agaaagcagg atgactatc attactcctc caacaccaat catcccagac gatcatccac | 1380 |
| tctggatgtc atccaaatgg ctttccatga atgtcttaat gctagatgaa aaacgtgtta | 1440 |
| tggtggatgc caatgaagtt ccaattcaaa agatgtttga aaagctgggt atcactacca | 1500 |
| ttaaagttaa cattcgtaat gccaattccc tgggaggagg cttccattgc tggacctgcg | 1560 |
| atgtccggcg ccgaggcacc ttacagtcct acttggactg aacaggcctg atggagcttg | 1620 |
| tggctggcct cagatacacc taagaagctt aggggcaagg ttcattctcc tgctttaaaa | 1680 |
| agtgcatgaa ctgtagtgct ttaaacaatc atctccttaa caggggtcgt aagcctggtt | 1740 |
| tgcttctatt acttttcttt gacataaaga aaataacttc tgctaggtat tactctctac | 1800 |
| tcctaaagtt atttactatt tggcttcaag tataaaattt tggtgaatgt gtaccaagaa | 1860 |
| aaaattagtc acctgagtaa cttggccact aataattaac catctaccte tgtttttaat | 1920 |
| tttctttcca aaaggcagct tgaaatgttg gtcctaatct taatttttt tcctcttcta | 1980 |
| tagacttgag aatgtttttc tctaaatgag agaaagactt agaatgtaca cagatccaaa | 2040 |
| atagaatcag attatctctt tttttctaaa ggagagaaag acttagaaca tacacagatc | 2100 |
| ctaagtagaa ccaggtaatt gtctcttttt ctaataagga atttgggtaa tttttaattt | 2160 |
| tttgttttt aaaaaataac ctagactatg caaaacatca aagtgaattt ccatgaatg | 2220 |
| tttttaatat tctcatctca acattgtgat atatgctact aaaaaccttt tcatatacat | 2280 |
| cttacctcat ttcaagtgaa ttattttaat ctttttctct ctttccaaaa atttaggaat | 2340 |
| gtttagtgta attggatttc gctatcagtt cccatcctta agttttgata ttcaatatct | 2400 |
| gatagataca ctgcatcttt ggtcatctaa gatttgttta caaatgtgca aattatttag | 2460 |
| agcatagact ttataagcat taaaaaaaac taatggaggt aaaacctaaa tgcgatgtga | 2520 |

|   |   |
|---|---|
| aataatttta gtgttgatac cgtatgtgta tttttattct aataaacttt tgtgttccag | 2580 |
| attgaaaaaa aaaaaaaaaa aa | 2602 |

<210> SEQ ID NO 142
<211> LENGTH: 1920
<212> TYPE: DNA
<213> ORGANISM: Homo sapiens

<400> SEQUENCE: 142

|   |   |
|---|---|
| ccacagttcc tttccccgat agcttcaaat tctctgcctt ttgaaataag cctactttta | 60 |
| actggaataa ataattggtc aatctctacc tcaggtgaag aggaaccaag cctctggaaa | 120 |
| cacttaggaa caaactgtaa aaaccaaagg caattgtgta accggttaaa taagcttgct | 180 |
| ggactttgtc cctgtgtatg agttagacaa ttctttcagc tagtttgagt gacgcactga | 240 |
| ccagtgaagc gcagtgaagc agtgggaacc ggaatatcca aagagtggtt tgaaggagaa | 300 |
| agaagcattg tggctttata tcctctgggc ctgggtttcc tgaagtcacc acacatagag | 360 |
| gagagagaaa atggctgagt taaagtacat ttctggattt gggaatgagt gttcttcaga | 420 |
| ggatcctcgc tgcccaggtt ccctgccaga aggacagaat aatcctcagg tctgcccta | 480 |
| caatctctat gctgagcagc tctcaggatc ggctttcact tgtccacgga gcaccaataa | 540 |
| gagaagctgg ctgtatagga ttctaccttc agtttctcac aagccctttg aatccattga | 600 |
| cgaaggccaa gtcactcaca actgggatga agttgatcct gatcctaacc agcttagatg | 660 |
| gaaaccattt gagattccaa aagcatctca gaagaaagta gactttgtga gtggcctgca | 720 |
| taccttgtgt ggagctggag acataaagtc taacaatggg cttgctatcc acattttcct | 780 |
| ctgcaatacc tccatggaga acagatgctt ttacaattca gatggggact tcttgattgt | 840 |
| tccgcagaaa gggaaccttc tcatttacac cgagtttggc aagatgcttg tacagcccaa | 900 |
| tgagatctgc gtcattcaga gaggaatgcg gttcagcata gatgtctttg aggagaccag | 960 |
| gggctacatc ttggaggtct atggtgtcca ctttgagtta cctgaccttg gaccaattgg | 1020 |
| ggccaatggc ttggccaatc ctcgtgattt cttgataccc attgcctggt atgaggatcg | 1080 |
| ccaagtacca ggtggttaca cggtcattaa taaataccag ggcaagctgt ttgctgccaa | 1140 |
| acaggatgtc tccccgttca atgttgtggc ctggcacggg aattatacac cctacaagta | 1200 |
| caacctgaag aatttcatgg ttatcaactc agtggccttt gaccatgcag acccatccat | 1260 |
| tttcacagta ttgactgcta agtctgtccg ccctggagtg gccattgctg attttgtcat | 1320 |
| cttcccacct cgatgggggg ttgctgataa gaccttcagg cctccttatt accataggaa | 1380 |
| ctgcatgagt gagttcatgg gactcatccg aggtcactat gaggcaaagc aaggtggtt | 1440 |
| cctgccaggg ggagggagtc tacacagcac aatgaccccc catggacctg atgctgactg | 1500 |
| ctttgagaag gccagcaagg tcaagctggc acctgagagg attgccgatg caccatggc | 1560 |
| atttatgttt gaatcatctt taagtctggc ggtcacaaag tggggactca aggcctccag | 1620 |
| gtgtttggat gagaactacc acaagtgctg ggagccactc aagagccact tcactcccaa | 1680 |
| ctccaggaac ccagcagaac ctaattgaga ctggaacatt gctaccataa ttaagagtag | 1740 |
| atttgtgaag atttcttcag aatctcatgc tttctggtag tattggagga gggggttggt | 1800 |
| taaaatgaaa attcactttt catagtcaag taactcagaa cttttatgga aacgcatttg | 1860 |
| caaagttcta tggctgtcac cttaattact caataaactt gctggtgttc tgtggacgta | 1920 |

<210> SEQ ID NO 143

<211> LENGTH: 4150
<212> TYPE: DNA
<213> ORGANISM: Homo sapiens

<400> SEQUENCE: 143

```
cttgaatctt ggggcaggaa ctcagaaaac ttccagcccg ggcagcgcgc gcttggtgca      60
agactcagga gctagcagcc cgtccccctc cgactctccg gtgccgccgc tgcctgctcc     120
cgccacccta ggaggcgcgg tgccacccac tactctgtcc tctgcctgtg ctccgtgccc     180
gaccctatcc cggcggagtc tccccatcct cctttgcttt ccgactgccc aaggcacttt     240
caatctcaat ctcttctctc tctctctctc tctctctctc tctctctctc tctctctctc     300
tctctctctc gcagggtggg gggaagagga ggaggaattc tttccccgcc taacatttca     360
agggacacaa ttcactccaa gtctcttccc tttccaagcc gcttccgaag tgctcccggt     420
gcccgcaact cctgatccca acccgcgaga ggagcctctg cgacctcaaa gcctctcttc     480
cttctccctc gcttccctcc tcctcttgct acctccacct ccaccgccac ctccacctcc     540
ggcacccacc caccgccgcc gccgccaccg gcagcgcctc ctcctctcct cctcctcctc     600
ccctcttctc tttttggcag ccgctggacg tccggtgttg atggtggcag cggcggcagc     660
ctaagcaaca gcagccctcg cagcccgcca gctcgcgctc gccccgccgg cgtccccagc     720
cctatcacct catctcccga aaggtgctgg gcagctccgg ggcggtcgag gcgaagcggc     780
tgcagcggcg gtagcggcgg cgggaggcag gatgagcgca cgcggtgagg gcgcggggca     840
gccgtccact tcagcccagg gacaacctgc cgccccagcg cctcagaaga gaggacgcgg     900
ccgcccagg aagcagcagc aagaaccaac cggtgagccc tctcctaaga gacccagggg     960
aagacccaaa ggcagcaaaa acaagagtcc ctctaaagca gctcaaaaga aagcagaagc    1020
cactggagaa aaacggccaa gaggcagacc taggaaatgg ccacaacaag ttgttcagaa    1080
gaagcctgct caggaggaaa ctgaagagac atcctcacaa gagtctgccg aagaggacta    1140
gggggcgcca acgttcgatt tctacctcag cagcagttgg atcttttgaa gggagaagac    1200
actgcagtga ccacttattc tgtattgcca tggtctttcc actttcatct ggggtggggt    1260
ggggtggggt gggggagggg ggggtggggt gggagaaaat cacataacct taaaaaggac    1320
tatattaatc accttctttg taatcccttc acagtcccag gtttagtgaa aaactgctgt    1380
aaacacaggg gacacagctt aacaatgcaa cttttaatta ctgttttctt ttttcttaac    1440
ctactaatag tttgttgatc tgataagcaa gagtgggcgg gtgagaaaaa ccgaattggg    1500
tttagtcaat cactgcactg catgcaaaca agaaacgtgt cacacttgtg acgtcgggca    1560
ttcatatagg aagaacgcgg tgtgtaacac tgtgtacacc tcaaatacca ccccaaccca    1620
ctccctgtag tgaatcctct gtttagaaca ccaaagataa ggactagata ctactttctc    1680
tttttcgtat aatcttgtag acacttactt gatgattttt aacttttat ttctaaatga    1740
gacgaaatgc tgatgtatcc tttcattcag ctaacaaact agaaaaggtt atgttcattt    1800
ttcaaaaagg gaagtaagca aacaaatatt gccaactctt ctatttatgg atatcacaca    1860
tatcagcagg agtaataaat ttactcacag cacttgtttt caggacaaca cttcattttc    1920
aggaaatcta cttcctacag agccaaaatg ccatttagca ataaataaca cttgtcagcc    1980
tcagagcatt taaggaaact agacaagtaa aattatcctc tttgtaattt aatgaaaagg    2040
tacaacagaa taatgcatga tgaactcacc taattatgag gtgggaggag cgaaatctaa    2100
atttcttttg ctatagttat acatcaattt aaaaagcaaa aaaaaaaaag ggggggcaa    2160
tctctctctg tgtctttctc tctctctctt cctctccctc tctcttttca ttgtgtatca    2220
```

```
gtttccatga aagacctgaa taccacttac ctcaaattaa gcatatgtgt tacttcaagt   2280
aatacgtttt gacataagat ggttgaccaa ggtgcttttc ttcggcttga gttcaccatc   2340
tcttcattca aactgcactt ttagccagag atgcaatata tccccactac tcaatactac   2400
ctctgaatgt tacaacgaat ttacagtcta gtacttatta catgctgcta tacacaagca   2460
atgcaagaaa aaaacttact gggtaggtga ttctaatcat ctgcagttct ttttgtacac   2520
ttaattacag ttaaagaagc aatctcctta ctgtgtttca gcatgactat gtattttttct   2580 atgttttttt aattaaaaat ttttaaaata cttgtttcag cttctctgct agatttctac   2640
attaacttga aaattttta accaagtcgc tcctaggttc ttaaggataa ttttcctcaa   2700
tcacactaca catcacacaa gatttgactg taatatttaa atattaccct ccaagtctgt   2760
acctcaaatg aattctttaa ggagatggac taattgactt gcaaagacct acctccagac   2820
ttcaaaagga atgaacttgt tacttgcagc attcatttgt tttttcaatg tttgaaatag   2880
ttcaaactgc agctaaccct agtcaaaact attttttgtaa aagacatttg atagaaagga   2940
acacgttttt acatactttt gcaaaataag taaataataa ataaaataaa agccaacctt   3000
caaagaaact tgaagctttg taggtgagat gcaacaagcc ctgcttttgc ataatgcaat   3060
caaaaatatg tgtttttaag attagttgaa tataagaaaa tgcttgacaa atatttttcat   3120 gtattttaca caaatgtgat ttttgtaata tgtctcaacc agattyattt taaacgcttc   3180
ttatgtagag ttttttatgcc tttctctcct agtgagtgtg ctgactttt aacatggtat   3240 tatcaactgg gccaggaggt agtttctcat gacggctttt gtcagtatgg cttttagtac   3300
tgaagccaaa tgaaactcaa aaccatctct cttccagctg cttcagggag gtagtttcaa   3360
aggccacata cctctctgag actggcagat cgctcactgt tgtgaatcac caaaggagct   3420
atggagagaa ttaaaactca acattactgt taactgtgcg ttaaataagc aaataaacag   3480
tggctcataa aaataaagt cgcattccat atctttggat gggccttttta gaaacctcat   3540 tggccagctc ataaaatgga agcaattgct catgttggcc aaacatggtg caccgagtga   3600
tttccatctc tggtaaagtt acactttat ttcctgtatg ttgtacaatc aaaacacact   3660
actacctctt aagtcccagt atacctcatt tttcatactg aaaaaaaaag cttgtggcca   3720
atggaacagt aagaacatca taaaattttt atatatatag tttatttttg tgggagataa   3780
attttatagg actgttcttt gctgttgttg gtcgcagcta cataagactg gacatttaac   3840
ttttctacca tttctgcaag ttaggtatgt ttgcaggaga aaagtatcaa gacgtttaac   3900
tgcagttgac tttctccctg ttcctttgag tgtcttctaa ctttattctt tgttctttat   3960
gtagaattgc tgtctatgat tgtactttga atcgcttgct tgttgaaaat atttctctag   4020
tgtattatca ctgtctgttc tgcacaataa acataacagc ctctgtgatc cccatgtgtt   4080
ttgattcctg ctctttgtta cagttccatt aaatgagtaa taaagtttgg tcaaaacaga   4140
aaaaaaaaa                                                          4150
```

<210> SEQ ID NO 144
<211> LENGTH: 980
<212> TYPE: DNA
<213> ORGANISM: Homo sapiens

<400> SEQUENCE: 144

```
gcggcggcgg gcagcagctg cgctgcgact gctctggaag gagaggacgg ggcacaaacc    60
ctgaccatga cccccacag gctgctgcca ccgctgctgc tgctgctagc tctgctgctc   120
```

```
gctgccagcc caggaggcgc cttggcgcgg tgcccaggct gcgggcaagg ggtgcaggcg      180
ggttgtccag ggggctgcgt ggaggaggag gatggggggt cgccagccga gggctgcgcg      240
gaagctgagg gctgtctcag gagggagggg caggagtgcg gggtctacac ccctaactgc      300
gccccaggac tgcagtgcca tccgcccaag gacgacgagg cgcctttgcg ggcgctgctg      360
ctcggccgag gccgctgcct tccggcccgc gcgcctgctg ttgcagagga gaatcctaag      420
gagagtaaac cccaagcagg cactgcccgc ccacaggatg tgaaccgcag agaccaacag      480
aggaatccag gcacctctac cacgccctcc cagcccaatt ctgcgggtgt ccaagacact      540
gagatgggcc catgccgtag acatctggac tcagtgctgc agcaactcca gactgaggtc      600
taccgagggg ctcaaacact ctacgtgccc aattgtgacc atcgaggctt ctaccggaag      660
cggcagtgcc gctcctccca ggggcagcgc cgaggtccct gctggtgtgt ggatcggatg      720
ggcaagtccc tgccagggtc tccagatggc aatggaagct cctcctgccc cactgggagt      780
agcggctaaa gctgggggat agaggggctg caggccact ggaaggaaca tggagctgtc        840
atcactcaac aaaaaaccga ggccctcaat ccaccttcag gccccgcccc atgggccct         900 caccgctggt tggaaagagt gttggtgttg gctggggtgt caataaagct gtgcttgggg      960
tcgctgaaaa aaaaaaaaaa                                                   980

<210> SEQ ID NO 145
<211> LENGTH: 5190
<212> TYPE: DNA
<213> ORGANISM: Homo sapiens

<400> SEQUENCE: 145
tctgggggct cggctttgcc gcgctcgctg cacttgggcg agagctggaa cgtggaccag       60
agctcggatc ccatcgcagc taccgcgatg agaggcgctc gcggcgcctg ggattttctc      120
tgcgttctgc tcctactgct tcgcgtccag acaggctctt ctcaaccatc tgtgagtcca      180
ggggaaccgt ctccaccatc catccatcca ggaaaatcag acttaatagt ccgcgtgggc      240
gacgagatta ggctgttatg cactgatccg ggctttgtca aatggacttt tgagatcctg      300
gatgaaacga atgagaataa gcagaatgaa tggatcacgg aaaaggcaga agccaccaac      360
accggcaaat acacgtgcac caacaaacac ggcttaagca attccattta tgtgtttgtt      420
agagatcctg ccaagctttt ccttgttgac cgctccttgt atgggaaaga agacaacgac      480
acgctggtcc gctgtcctct cacagaccca gaagtgacca attattccct caagggggtgc      540 caggggaagc tcttcccaa ggacttgagg tttattcctg accccaaggc gggcatcatg       600
atcaaaagtg tgaaacgcgc ctaccatcgg ctctgtctgc attgttctgt ggaccaggag      660
ggcaagtcag tgctgtcgga aaaattcatc ctgaaagtga ggccagcctt caaagctgtg      720
cctgttgtgt ctgtgtccaa agcaagctat cttcttaggg aaggggaaga attcacagtg      780
acgtgcacaa taaagatgt gtctagttct gtgtactcaa cgtggaaaag agaaaacagt      840
cagactaaac tacaggagaa atataatagc tggcatcacg gtgacttcaa ttatgaacgt      900
caggcaacgt tgactatcag ttcagcgaga gttaatgatt ctggagtgtt catgtgttat      960
gccaataata cttttggatc agcaaatgtc acaacaacct ggaagtagt agataaagga     1020 ttcattaata tcttccccat gataaacact acagtatttg taaacgatgg agaaaatgta     1080
gatttgattg ttgaatatga agcattcccc aaacctgaac accagcagtg gatctatatg     1140
aacagaacct tcactgataa atgggaagat tatcccaagt ctgagaatga agtaatatc      1200 agatacgtaa gtgaacttca tctaacgaga ttaaaaggca ccgaaggagg cacttacaca    1260
```

```
ttcctagtgt ccaattctga cgtcaatgct gccatagcat ttaatgttta tgtgaataca      1320
aaaccagaaa tcctgactta cgacaggctc gtgaatggca tgctccaatg tgtggcagca      1380
ggattcccag agcccacaat agattggtat ttttgtccag gaactgagca gagatgctct      1440
gcttctgtac tgccagtgga tgtgcagaca ctaaactcat ctgggccacc gtttggaaag      1500
ctagtggttc agagttctat agattctagt gcattcaagc acaatggcac ggttgaatgt      1560
aaggcttaca cgatgtggg caagacttct gcctatttta actttgcatt taaaggtaac      1620
aacaaagagc aaatccatcc ccacaccctg ttcactcctt tgctgattgg tttcgtaatc      1680
gtagctggca tgatgtgcat tattgtgatg attctgacct acaaatattt acagaaaccc      1740
atgtatgaag tacagtggaa ggttgttgag gagataaatg gaaacaatta tgtttacata      1800
gacccaacac aacttcctta tgatcacaaa tgggagtttc ccagaaacag gctgagtttt      1860
gggaaaaccc tgggtgctgg agctttcggg aaggttgttg aggcaactgc ttatggctta      1920
attaagtcag atgcggccat gactgtcgct gtaaagatgc tcaagccgag tgcccatttg      1980
acagaacggg aagccctcat gtctgaactc aaagtcctga gttaccttgg taatcacatg      2040
aatattgtga atctacttgg agcctgcacc attggagggc ccaccctggt cattacagaa      2100
tattgttgct atggtgatct tttgaatttt ttgagaagaa aacgtgattc atttatttgt      2160
tcaaagcagg aagatcatgc agaagctgca ctttataaga tcttctgca ttcaaaggag      2220 tcttcctgca gcgatagtac taatgagtac atggacatga acctggagt tcttatgtt      2280 gtcccaacca aggccgacaa aaggagatct gtgagaatag gctcatacat agaaagagat      2340
gtgactcccg ccatcatgga ggatgacgag ttggccctag acttagaaga cttgctgagc      2400
ttttcttacc aggtggcaaa gggcatggct ttcctcgcct ccaagaattg tattcacaga      2460
gacttggcag ccagaaatat cctccttact catggtcgga tcacaaagat ttgtgatttt      2520
ggtctagcca gagacatcaa gaatgattct aattatgtgg ttaaaggaaa cgctcgacta      2580
cctgtgaagt ggatggcacc tgaaagcatt ttcaactgtg tatacacgtt tgaaagtgac      2640
gtctggtcct atgggatttt ctttgggag ctgttctctt taggaagcag ccccatcct      2700 ggaatgccgg tcgattctaa gttctacaag atgatcaagg aaggcttccg gatgctcagc      2760
cctgaacacg cacctgctga aatgtatgac ataatgaaga cttgctggga tgcagatccc      2820
ctaaaaagac caacattcaa gcaaattgtt cagctaattg agaagcagat ttcagagagc      2880
accaatcata tttactccaa cttagcaaac tgcagcccca accgacagaa gcccgtggta      2940
gaccattctg tgcggatcaa ttctgtcggc agcaccgctt cctcctccca gcctctgctt      3000
gtgcacgacg atgtctgagc agaatcagtg tttgggtcac ccctccagga atgatctctt      3060
cttttggctt ccatgatggt tattttcttt tctttcaact tgcatccaac tccaggatag      3120
tgggcacccc actgcaatcc tgtctttctg agcacacttt agtggccgat gattttgtc      3180 atcagccacc atcctattgc aaaggttcca actgtatata ttcccaatag caacgtagct      3240
tctaccatga acagaaaaca ttctgatttg gaaaagagaa gggaggtatg gactgggggc      3300
cagagtcctt tccaaggctt ctccaattct gcccaaaat atggttgata gtttacctga      3360
ataaatggta gtaatcacag ttggccttca gaaccatcca tagtagtatg atgatacaag      3420
attagaagct gaaaacctaa gtcctttatg tggaaaacag aacatcatta gaacaaagga      3480
cagagtatga acacctgggc ttaagaaatc tagtatttca tgctgggaat gagacatagg      3540
ccatgaaaaa aatgatcccc aagtgtgaac aaaagatgct cttctgtgga ccactgcatg      3600
```

| | |
|---|---|
| agcttttata ctaccgacct ggttttaaa tagagtttgc tattagagca ttgaattgga | 3660 |
| gagaaggcct ccctagccag cacttgtata tacgcatcta taaattgtcc gtgttcatac | 3720 |
| atttgagggg aaaacaccat aaggtttcgt ttctgtatac aaccctggca ttatgtccac | 3780 |
| tgtgtataga agtagattaa gagccatata agtttgaagg aaacagttaa taccatttt | 3840 |
| taaggaaaca atataaccac aaagcacagt ttgaacaaaa tctcctcttt tagctgatga | 3900 |
| acttattctg tagattctgt ggaacaagcc tatcagcttc agaatggcat tgtactcaat | 3960 |
| ggatttgatg ctgtttgaca aagttactga ttcactgcat ggctcccaca ggagtgggaa | 4020 |
| aacactgcca tcttagtttg gattcttatg tagcaggaaa taaagtatag gtttagcctc | 4080 |
| cttcgcaggc atgtcctgga caccgggcca gtatctatat atgtgtatgt acgtttgtat | 4140 |
| gtgtgtagac aaatatttgg aggggtattt ttgccctgag tccaagaggg tcctttagta | 4200 |
| cctgaaaagt aacttggctt tcattattag tactgctctt gtttcttttc acatagctgt | 4260 |
| ctagagtagc ttaccagaag cttccatagt ggtgcagagg aagtggaagg catcagtccc | 4320 |
| tatgtatttg cagttcacct gcacttaagg cactctgtta tttagactca tcttactgta | 4380 |
| cctgttcctt agaccttcca taatgctact gtctcactga acatttaaa tttaccctt | 4440 |
| tagactgtag cctggatatt attcttgtag tttacctctt taaaaacaaa acaaaacaaa | 4500 |
| acaaaaaact cccttcctc actgcccaat ataaaaggca aatgtgtaca tggcagagtt | 4560 |
| tgtgtgttgt cttgaaagat tcaggtatgt tgccttatg gtttccccct tctacatttc | 4620 |
| ttagactaca tttagagaac tgtggccgtt atctggaagt aaccatttgc actggagttc | 4680 |
| tatgctctcg cacctttcca aagttaacag atttttgggt tgtgttgtca cccaagagat | 4740 |
| tgttgtttgc catactttgt ctgaaaaatt cctttgtgtt tctattgact tcaatgatag | 4800 |
| taagaaaagt ggttgttagt tatagatgtc taggtacttc aggggcactt cattgagagt | 4860 |
| tttgtcttgg atattcttga aagtttatat ttttataatt ttttcttaca tcagatgttt | 4920 |
| ctttgcagtg gcttaatgtt tgaaattatt ttgtggcttt ttttgtaaat attgaaatgt | 4980 |
| agcaataatg tcttttgaat attcccaagc ccatgagtcc ttgaaaatat ttttatata | 5040 |
| tacagtaact ttatgtgtaa atacataagc ggcgtaagtt taaaggatgt tggtgttcca | 5100 |
| cgtgttttat tcctgtatgt tgtccaattg ttgacagttc tgaagaattc taataaaatg | 5160 |
| tacatatata aatcaaaaaa aaaaaaaaaa | 5190 |

<210> SEQ ID NO 146
<211> LENGTH: 7998
<212> TYPE: DNA
<213> ORGANISM: Homo sapiens

<400> SEQUENCE: 146

| | |
|---|---|
| gcggcggcgg cccgagggcg acttgcgggg cgcgcaggcc gccgtgcacc cgggacgctt | 60 |
| ccccctcggg gaccctccgc gggcttctcc gccgcgccgt ccggcgggag ccggcgggac | 120 |
| cccgggcgag cggcgcgggc ggcaccatga ggcggcagtg gggcgcgctg ctgcttggcg | 180 |
| ccctgctctg cgcacacggc ctggccagca gccccgagtg tgcttgtggt cggagccact | 240 |
| tcacatgtgc agtgagtgct cttggagagt gtacctgcat ccctgcccag tggcagtgtg | 300 |
| atggagacaa tgactgcggg gaccacagcg atgaggatgg atgtatacta cctacctgtt | 360 |
| cccctcttga ctttcactgt gacaatggca agtgcatccg ccgctcctgg gtgtgtgacg | 420 |
| ggacaacga ctgtgaggat gactcggatg agcaggactg tcccccccgg gagtgtgagg | 480 |
| aggacgagtt tccctgccag aatggctact gcatccggag tctgtggcac tgcgatggtg | 540 |

```
acaatgactg tggcgacaac agcgatgagc agtgtgacat gcgcaagtgc tccgacaagg    600
agttccgctg tagtgacgga agctgcattg ctgagcattg gtactgcgac ggtgacaccg    660
actgcaaaga tggctccgat gaggagaact gtccctcagc agtgccagcg cccccctgca    720
acctggagga gttccagtgt gcctatggac gctgcatcct cgacatctac cactgcgatg    780
gcgacgatga ctgtggagac tggtcagacg agtctgactg ctcctcccac cagccctgcc    840
gctctgggga gttcatgtgt gacagtggcc tgtgcatcaa tgcaggctgg cgctgcgatg    900
gtgacgcgga ctgtgatgac cagtctgatg agcgcaactg caccacctcc atgtgtacgg    960
cagaacagtt ccgctgtcac tcaggccgct gtgtccgcct gtcctggcgc tgtgatgggg   1020
aggacgactg tgcagacaac agcgatgaag agaactgtga aatacagga agcccccaat    1080
gtgccttgga ccagttcctg tgttggaatg ggcgctgcat tgggcagagg aagctgtgca    1140
acggggtcaa cgactgtggt gacaacagcg acgaaagccc acagcagaat tgccggcccc    1200
ggacgggtga ggagaactgc aatgttaaca acggtggctg tgcccagaag tgccagatgg    1260
tgcgggggc agtgcagtgt acctgccaca caggctaccg gctcacagag gatgggcaca    1320
cgtgccaaga tgtgaatgaa tgtgccgagg aggggtattg cagccagggc tgcaccaaca   1380
gcgaaggggc tttccaatgc tggtgtgaaa caggctatga actacggccc gaccggcgca   1440
gctgcaaggc tctggggcca gagcctgtgc tgctgttcgc caatcgcatc gacatccggc   1500
aggtgctgcc acaccgctct gagtacacac tgctgcttaa caacctggag aatgccattg   1560
cccttgattt ccaccaccgc cgcgagcttg tcttctggtc agatgtcacc ctggaccgga   1620
tcctccgtgc caacctcaac ggcagcaacg tggaggaggt tgtgtctact gggctggaga   1680
gcccagggg cctggctgtg gattgggtcc atgacaaact ctactggacc gactcaggca   1740
cctcgaggat tgaggtggcc aatctggatg gggcccaccg gaaagtgttg ctgtggcaga   1800
acctggagaa gccccgggcc attgccttgc atcccatgga gggtaccatt tactggacag   1860
actgggcaa caccccccgt attgaggcct ccagcatgga tggctctgga cgccgcatca   1920
ttgccgatac ccatctcttc tggcccaatg gcctcaccat cgactatgcc gggcgccgta   1980
tgtactgggt ggatgctaag caccatgtca tcgagagggc caatctggat gggagtcacc   2040
gtaaggctgt cattagccag ggcctcccgc atcccttcgc catcacagtg tttgaagaca   2100
gcctgtactg gacagactgg cacaccaaga gcatcaatag cgctaacaaa tttacgggga   2160
agaaccagga aatcattcgc aacaaactcc acttccctat ggacatccac accttgcacc   2220
cccagccgcca acctgcaggg aaaaaccgct gtggggacaa caacgaggc tgcacgcacc   2280
tgtgtctgcc cagtggccag aactacacct gtgcctgccc cactggcttc cgcaagatca   2340
gcagccacgc ctgtgcccag agtcttgaca agttcctgct ttttgcccga aggatggaca   2400
tccgtcgaat cagctttgac acagaggacc tgtctgatga tgtcatccca ctggctgacg   2460
tgcgcagtgc tgtggccctt gactgggact cccgggatga ccacgtgtac tggacagatg   2520
tcagcactga taccatcagc agggccaagt gggatggaac aggacaggag gtggtagtgg   2580
ataccagttt ggagagccca gctggcctgg ccattgattg ggtcaccaac aaactgtact   2640
ggacagatgc aggtacagac cggattgaag tagccaacac agatggcagc atgagaacag   2700
tactcatctg ggagaacctt gatcgtcctc gggacatcgt ggtggaaccc atgggcgggt   2760
acatgtattg gactgactgg ggtgcagagc ccaagattga acgagctggc atggatgcct   2820
caggccgcca agtcattatc tcttctaatc tgacctggcc taatgggtta gctattgatt   2880
```

```
atgggtccca gcgtctatac tgggctgacg ccggcatgaa gacaattgaa tttgctggac    2940
tggatggcag taagaggaag gtgctgattg gaagccagct cccccaccca tttgggctga    3000
ccctctatgg agagcgcatc tattggactg actggcagac caagagcata cagagcgctg    3060
accggctgac agggctggac cgggagactc tgcaggagaa cctggaaaac ctaatggaca    3120
tccatgtctt ccaccgccgc cggccccag tgtctacacc atgtgctatg gagaatggcg     3180
gctgtagcca cctgtgtctt aggtccccaa atccaagcgg attcagctgt acctgcccca    3240
caggcatcaa cctgctgtct gatggcaaga cctgctcacc aggcatgaac agtttcctca    3300
tcttcgccag gaggatagac attcgcatgg tctcccctgga catcccttat tttgctgatg   3360
tggtggtacc aatcaacatt accatgaaga acaccattgc cattggagta gaccccagg     3420
aaggaaaggt gtactggtct gacagcacac tgcacaggat cagtcgtgcc aatctgatg     3480
gctcacagca tgaggacatc atcaccacag ggctacagac cacagatggg ctcgcggttg    3540
atgccattgg ccggaaagta tactggacag acacgggaac aaaccggatt gaagtgggca    3600
acctggacgg gtccatgcgg aaagtgttgg tgtggcagaa ccttgacagt ccccgggcca    3660
tcgtactgta ccatgagatg gggtttatgt actggacaga ctgggggag aatgccaagt     3720
tagagcggtc cggaatggat ggctcagacc gcgcggtgct catcaacaac aacctaggat    3780
ggcccaatgg actgactgtg gacaaggcca gctcccaact gctatgggcc gatgcccaca    3840
ccgagcgaat tgaggctgct gacctgaatg gtgccaatcg gcatacattg gtgtcaccgg    3900
tgcagcaccc atatggcctc accctgctcg actcctatat ctactggact gactggcaga    3960
ctcggagcat ccaccgtgct gacaagggta ctggcagcaa tgtcatcctc gtgaggtcca    4020
acctgccagg cctcatggac atgcaggctg tggaccgggc acagccacta ggtttttaaca   4080
agtgcggctc gagaaatggc ggctgctccc acctctgctt gcctcggcct tctggcttct    4140
cctgtgcctg ccccactggc atccagctga agggagatgg gaagacctgt gatccctctc    4200
ctgagaccta cctgctcttc tccagccgtg gctccatccg gcgtatctca ctggacacca    4260
gtgaccacac cgatgtgcat gtccctgttc ctgagctcaa caatgtcatc tccctggact    4320
atgacagcgt ggatggaaag gtctattaca cagatgtgtt cctggatgtt atcaggcgag    4380
cagacctgaa cggcagcaac atggagacag tgatcgggcg agggctgaag accactgacg    4440
ggctggcagt ggactgggtg gccaggaacc tgtactggac agacacaggt cgaaatacca    4500
ttgaggcgtc caggctggat ggttcctgcc gcaaagtact gatcaacaat agcctggatg    4560
agccccgggc cattgctgtt ttccccagga aggggtacct cttctggaca gactgggcc     4620
acattgccaa gatcgaacgg gcaaacttgg atggttctga gcggaaggtc ctcatcaaca    4680
cagacctggg ttggcccaat ggccttaccc tggactatga tacccgcagg atctactggg    4740
tggatgcgca tctggaccgg atcgagagtg ctgacctcaa tgggaaactg cggcaggtct    4800
tggtcagcca tgtgtcccac ccctttgccc tcacacagca agacaggtgg atctactgga    4860
cagactggca gaccaagtca atccagcgtg ttgacaaata tcaggccgg aacaaggaga     4920
cagtgctggc aaatgtggaa ggactcatgg atatcatcgt ggtttcccct cagcggcaga    4980
cagggaccaa tgcctgtggt gtgaacaatg gtggctgcac ccacctctgc tttgccagag    5040
cctcggactt cgtatgtgcc tgtcctgacg aacctgatag ccggccctgc tcccttgtgc    5100
ctggcctggt accaccagct cctagggcta ctggcatgag tgaaaagagc ccagtgctac    5160
ccaacacacc acctaccacc ttgtattctt caaccacccg gacccgcacg tctctggagg    5220
aggtggaagg aagatgctct gaaagggatg ccaggctggg cctctgtgca cgttccaatg    5280
```

```
acgctgttcc tgctgctcca ggggaaggac ttcatatcag ctacgccatt ggtggactcc    5340
tcagtattct gctgattttg gtggtgattg cagctttgat gctgtacaga cacaaaaaat    5400
ccaagttcac tgatcctgga atggggaacc tcacctacag caaccccctcc taccgaacat   5460 ccacacagga agtgaagatt gaagcaatcc ccaaaccagc catgtacaac cagctgtgct    5520
ataagaaaga gggagggcct gaccataact acaccaagga gaagatcaag atcgtagagg    5580
gaatctgcct cctgtctggg gatgatgctg agtgggatga cctcaagcaa ctgcgaagct    5640
cacggggggg cctcctccgg gatcatgtat gcatgaagac agacacggtg tccatccagg    5700
ccagctctgg ctccctggat gacacagaga cggagcagct gttacaggaa gagcagtctg    5760
agtgtagcag cgtccatact gcagccactc cagaaagacg aggctctctg ccagacacgg    5820
gctggaaaca tgaacgcaag ctctcctcag agagccaggt ctaaatgccc acattctctt    5880
ccctgcctgc ctgttccttc tcctttatgg acgtctagtc cttgtgctcg cttacaccgc    5940
aggccccgct tctgtgtgct tgtcctcctc ctcctcccac cccataactg ttcctaagcc    6000
ttcaccggag ctgtttacca cgtgagtcca taactacctg tgcacaagaa atgatggcac    6060
atcacgagaa tttagacctg gattttacca tgaacctcac atcttgtact ccatcctggg    6120 cccccctgaaa ctgcttattc gtgattcctc accagcgtag agctccacct ccccttcccc    6180
cagtaccctc agtgcctgct tctcagtgct gatgcagctg atgacccagg actgcgctct    6240
gccccatcac agccagcatg actgcttctc tgagagaact tgcccatcag gggctgggac    6300 atggggtgt gggtaaagac agggatgaag gatagaggct gagagaagaa ggaagaatca     6360
gcccagcagg tatgggcatc tgggaaacct ccagcctcaa gtgtgttggt aacatgaaaa    6420
agctttgggg ggtagttgga tctggtgtc tggtccattg ctggcagtgg acattattct     6480
tgccctaaga gacactgcct tttcagcagc agatactggt gagatggggg tggctcaggc    6540
tgttcttcct cctcctagaa tgtctggagc tgttctacta ttcagataac tgggtcccct    6600
atcacaaggc tactggctaa taggaattcc ctcctggtgc caccactggc cagtacctt     6660 cctaagtctt tgctcaaatt aaccaggttg tgagccagtg gcttgagtga atgttaggcc    6720
ttgggggctg agtctctgaa aagtctaaga agctctgcct agaccaaata tggtatacct    6780
cctgacccct ctctccctca tgtcctggga ttctggggaa gagacctaga aacaagcttt    6840
caaagaaaaa ccagaagttg tcataaatgg tcagaaagaa cgatcaggtt ggagacttgg    6900
gaaacccagg gcctaaagag aagtatccat gagggtcaaa cttcctgttg aacttcctat    6960
gttctttctc aagtgctcag ggatctaagt tagtggacag caagcctgtg gctacggggt    7020
ggtgatgttc ctcttccagc tgtcccctca gctaaggggc ttagtttcca tgtgggatgc    7080
catcacttgg ttcatgctca ttcacacaaa gggcacgtgt ctcagcctgg tatcagggaa    7140
attgagactt attttgccc taaaacgtct ccctagctgt tcttcgtggg gttttttgt      7200 ttgttttttt gcctaatttg cttttctga ccaagccttg tggcaccagc aatctccaaa     7260
gtcctgtggt gggagggctg aataaataaa aatacaaaga ggtgggtaag gagtaggaag    7320
gtagagagca ccactgatga ggccctccta gcccatggca gacccagacc tcttctcccc    7380
caggaattag aagtggcagg agagaacaac aggggctggg aatggagggg agaatttcta    7440
ggggaagttt cctgagttga aacttctcct gtggttactg gtattgagaa atcagctacc    7500
aaagtgaaaa aggacaagat caattctttt ctagtcagtt ctaagactgc tagagagaga    7560
taccaggccc ttagccttgc tctcagtagc gtcagcccca gttctgagcc tccccacatt    7620
```

-continued

| | | |
|---|---|---|
| acacttaaca agcagtaaag gagtgagcac tttgggtcct tagactcatg tctggggagg | 7680 |
| aagagcaagt agaaaagtgg cattttcttg attggaaagg gggaaggatc ttattgcact | 7740 |
| tgggctgttc agaatgtaga aaggacatat ttgaggaagt atctatttga gcactgattt | 7800 |
| actctgtaaa aagcaaaatc tctctgtcct aaactaatgg aagcgattct cccatgctca | 7860 |
| tgtgtaatgg ttttaacgtt actcactgga gagattggac tttctggagt tatttaacca | 7920 |
| ctatgttcag tattttagga ctttatgata atttaatata aatttagctt ttcttaatca | 7980 |
| aaaaaaaaaa aaaaaaaa | 7998 |

<210> SEQ ID NO 147
<211> LENGTH: 4122
<212> TYPE: DNA
<213> ORGANISM: Homo sapiens

<400> SEQUENCE: 147

| | | |
|---|---|---|
| gcgagcgaag ggagcgctct gggatgggac ttggagcaag cggcggcggc ggagacagag | 60 |
| gcagaggcag aagctggggc tccgtcctcg cctcccacga gcgatccccg aggagagccg | 120 |
| cggccctcgg cgaggcgaag aggccgacga ggaagacccg ggtggctgcg cccctgcctc | 180 |
| gcttcccagg cgccggcggc tgcagccttg cccctcttgc tcgccttgaa aatggaaaag | 240 |
| atgctcgcag gctgctttct gctgatcctc ggacagatcg tcctcctccc tgccgaggcc | 300 |
| agggagcggt cacgtgggag gtccatctct aggggcagac acgctcggac ccaccccgcag | 360 |
| acggcccttc tggagagttc ctgtgagaac aagcgggcag acctggtttt catcattgac | 420 |
| agctctcgca gtgtcaacac ccatgactat gcaaaggtca aggagttcat cgtggacatc | 480 |
| ttgcaattct tggacattgg tcctgatgtc acccgagtgg gcctgctcca atatggcagc | 540 |
| actgtcaaga atgagttctc cctcaagacc ttcaaggaga agtccgaggt ggagcgtgct | 600 |
| gtcaagagga tgcggcatct gtccacgggc accatgactg ggctggccat ccagtatgcc | 660 |
| ctgaacatcg cattctcaga agcagagggg gcccggcccc tgagggagaa tgtgccacgg | 720 |
| gtcataatga tcgtgacaga tgggagacct caggactccg tggccgaggt ggctgctaag | 780 |
| gcacgggaca cgggcatcct aatctttgcc attggtgtgg gccaggtaga cttcaacacc | 840 |
| ttgaagtcca ttgggagtga gccccatgag gaccatgtct tccttgtggc caatttcagc | 900 |
| cagattgaga cgctgacctc cgtgttccag aagaagttgt gcacggccca catgtgcagc | 960 |
| accctggagc ataactgtgc ccacttctgc atcaacatcc ctggctcata cgtctgcagg | 1020 |
| tgcaaacaag gctacattct caactcggat cagacgactt gcagaatcca ggatctgtgt | 1080 |
| gccatggagg accacaactg tgagcagctc tgtgtgaatg tgccgggctc cttcgtctgc | 1140 |
| cagtgctaca gtggctacgc cctggctgag gatgggaaga ggtgtgtggc tgtgactac | 1200 |
| tgtgcctcag aaaaccacgg atgtgaacat gagtgtgtaa atgctgatgg ctcctacctt | 1260 |
| tgccagtgcc atgaaggatt tgctcttaac ccagataaaa aaacgtgcac aaagatagac | 1320 |
| tactgtgcct catctaatca cggatgtcag cacgagtgtg ttaacacaga tgattcctat | 1380 |
| tcctgccact gcctgaaagg ctttacccctg aatccagata agaaaacctg cagaaggatc | 1440 |
| aactactgtg cactgaacaa accgggctgt gagcatgagt cgtcaacat ggaggagagc | 1500 |
| tactactgcc gctgccaccg tggctacact ctggacccca atggcaaaac ctgcagccga | 1560 |
| gtggaccact gtgcacagca ggaccatggc tgtgagcagc tgtgtctgaa cacggaggat | 1620 |
| tccttcgtct gccagtgctc agaaggcttc ctcatcaacg aggacctcaa gacctgctcc | 1680 |
| cgggtggatt actgcctgct gagtgaccat ggttgtgaat actcctgtgt caacatggac | 1740 |

```
agatcctttg cctgtcagtg tcctgaggga cacgtgctcc gcagcgatgg gaagacgtgt   1800
gcaaaattgg actcttgtgc tctggggac  cacggttgtg aacattcgtg tgtaagcagt   1860
gaagattcgt ttgtgtgcca gtgctttgaa ggttatatac tccgtgaaga tggaaaaacc   1920
tgcagaagga aagatgtctg ccaagctata gaccatggct gtgaacacat ttgtgtgaac   1980
agtgatgact catacacgtg cgagtgcttg gagggattcc ggctcgctga ggatgggaaa   2040
cgctgccgaa ggaaggatgt ctgcaaatca acccaccatg gctgcgaaca catttgtgtt   2100
aataatggga attcctacat ctgcaaatgc tcagagggat tgttctagc  tgaggacgga   2160 agacggtgca agaaatgcac tgaaggccca attgacctgg tctttgtgat cgatggatcc   2220
aagagtcttg gagaagagaa ttttgaggtc gtgaagcagt tgtcactgg  aattatagat   2280 tccttgacaa tttcccccaa agccgctcga gtggggctgc tccagtattc cacacaggtc   2340
cacacagagt tcactctgag aaacttcaac tcagccaaag acatgaaaaa agccgtggcc   2400
cacatgaaat acatgggaaa gggctctatg actgggctgg ccctgaaaca catgtttgag   2460
agaagtttta cccaaggaga aggggccagg ccccttttcca aagggtgcc  cagagcagcc   2520 attgtgttca ccgacggacg ggctcaggat gacgtctccg agtgggccag taaagccaag   2580
gccaatggta tcactatgta tgctgttggg gtaggaaaag ccattgagga ggaactacaa   2640
gagattgcct ctgagcccac aaacaagcat ctcttctatg ccgaagactt cagcacaatg   2700
gatgagataa gtgaaaaact caagaaaggc atctgtgaag ctctagaaga ctccgatgga   2760
agacaggact ctccagcagg ggaactgcca aaaacggtcc aacagccaac agaatctgag   2820
ccagtcacca taaatatcca agacctactt tcctgttcta attttgcagt gcaacacaga   2880
tatctgtttg aagaagacaa tcttttacgg tctacacaaa agctttccca ttcaacaaaa   2940
ccttcaggaa gcccttttgga agaaaaacac gatcaatgca aatgtgaaaa ccttataatg   3000
ttccagaacc ttgcaaacga agaagtaaga aaattaacac agcgcttaga agaaatgaca   3060
cagagaatgg aagccctgga aaatcgcctg agatacagat gaagattaga aatcgcgaca   3120
catttgtagt cattgtatca cggattacaa tgaacgcagt gcagagcccc aaagctcagg   3180
ctattgttaa atcaataatg ttgtgaagta aaacaatcag tactgagaaa cctggtttgc   3240
cacagaacaa agacaagaag tatacactaa cttgtataaa tttatctagg aaaaaaatcc   3300
ttcagaattc taagatgaat ttaccaggtg agaatgaata agctatgcaa ggtattttgt   3360
aatatactgt ggacacaact tgcttctgcc tcatcctgcc ttagtgtgca atctcatttg   3420
actatacgat aaagtttgca cagtcttact tctgtagaac actggccata ggaaatgctg   3480
tttttttgta ctggacttta ccttgatata tgtatatgga tgtatgcata aaatcatagg   3540
acatatgtac ttgtggaaca agttggattt tttatacaat attaaaattc accacttcag   3600
agaatggtat tcagtgcaaa aattcttagt ttaactttaa atggaagata tgtatgtatg   3660
agaaatggcc aacatgccta tgaaaaaaat gctgaatctc atcagtaatc aggaaaatgc   3720
aggttaaaac aataccattt ttcacccatc agcttagcaa aaatgagtat attttttaac   3780
aagtgttggt aaggatgtgg aaatgtgagg ttcttgtagt aagaatgcaa atggcactct   3840
ttgtagagta agtctgttga catctcataa aactgaaaat gcacacaacc ctgtaaatct   3900
agcaactgca ctcagttgat ttcagcccat acatacaaag agacctgcat aagaatgtta   3960
ctaggctttg taaagcaaaa aataaggaa  caacttaaac atcatcagaa ggggaactga   4020
taaactctgg tgtaatccat accacagaaa tacaacaccg catgtacagg aatgtgctac   4080
```
atctatacaa ataaatggtc aaactcaaaa aaaaaaaaaa aa                    4122

<210> SEQ ID NO 148
<211> LENGTH: 6695
<212> TYPE: DNA
<213> ORGANISM: Homo sapiens

<400> SEQUENCE: 148
gccctcgccg cccgcggcgc cccgagcgct ttgtgagcag atgcggagcc gagtggaggg     60
cgcgagccag atgcggggcg acagctgact tgctgagagg aggcggggag gcgcggagcg    120
cgcgtgtggt ccttgcgccg ctgacttctc cactggttcc tgggcaccga aagataaacc    180
tctcataatg aaggcccccg ctgtgcttgc acctggcatc ctcgtgctcc tgtttacctt    240
ggtgcagagg agcaatgggg agtgtaaaga ggcactagca aagtccgaga tgaatgtgaa    300
tatgaagtat cagcttccca acttcaccgc ggaaacaccc atccagaatg tcattctaca    360
tgagcatcac attttccttg gtgccactaa ctacatttat gttttaaatg aggaagacct    420
tcagaaggtt gctgagtaca agactgggcc tgtgctggaa cacccagatt gtttcccatg    480
tcaggactgc agcagcaaag ccaatttatc aggaggtgtt tggaaagata acatcaacat    540
ggctctagtt gtcgacacct actatgatga tcaactcatt agctgtggca gcgtcaacag    600
agggacctgc cagcgacatg tctttcccca caatcatact gctgacatac agtcggaggt    660
tcactgcata ttctccccac agatagaaga gcccagccag tgtcctgact gtgtggtgag    720
cgccctggga gccaaagtcc tttcatctgt aaaggaccgg ttcatcaact tctttgtagg    780
caataccata aattcttctt atttcccaga tcatccattg cattcgatat cagtgagaag    840
gctaaaggaa acgaaagatg gttttatgtt tttgacggac cagtcctaca ttgatgtttt    900
acctgagttc agagattctt accccattaa gtatgtccat gcctttgaaa gcaacaattt    960
tatttacttc ttgacggtcc aaagggaaac tctagatgct cagactttc acacaagaat   1020
aatcaggttc tgttccataa actctggatt gcattcctac atggaaatgc ctctggagtg   1080
tattctcaca gaaaagagaa aaaagagatc cacaaagaag gaagtgttta atatacttca   1140
ggctgcgtat gtcagcaagc ctgggggccca gcttgctaga caaataggag ccagcctgaa   1200
tgatgacatt cttttcgggg tgttcgcaca aagcaagcca gattctgccg aaccaatgga   1260
tcgatctgcc atgtgtgcat tccctatcaa atatgtcaac gacttcttca caagatcgt   1320
caacaaaaac aatgtgagat gtctccagca tttttacgga cccaatcatg agcactgctt   1380
taataggaca cttctgagaa attcatcagg ctgtgaagcg cgccgtgatg aatatcgaac   1440
agagtttacc acagctttgc agcgcgttga cttattcatg ggtcaattca gcgaagtcct   1500
cttaacatct atatccacct tcattaaagg agacctcacc atagctaatc ttgggacatc   1560
agagggtcgc ttcatgcagg ttgtggtttc tcgatcagga ccatcaaccc ctcatgtgaa   1620
ttttctcctg gactcccatc cagtgtctcc agaagtgatt gtggagcata cattaaacca   1680
aaatggctac acactggtta tcactgggaa gaagatcacg aagatcccat tgaatggctt   1740
gggctgcaga catttccagt cctgcagtca atgcctctct gccccaccct tgttcagtg   1800
tggctggtgc cacgacaaat gtgtgcgatc ggaggaatgc ctgagcggga catggactca   1860
acagatctgt ctgcctgcaa tctacaaggt ttcccaaat agtgcacccc ttgaaggagg   1920
gacaaggctg accatatgtg gctgggactt tggattcggg aggaataata aatttgattt   1980
aaagaaaact agagttctcc ttggaaatga gagctgcacc ttgactttaa gtgagagcac   2040
gatgaataca ttgaaatgca cagttggtcc tgccatgaat aagcatttca atatgtccat   2100

```
aattatttca aatggccacg ggacaacaca atacagtaca ttctcctatg tggatcctgt    2160
aataacaagt atttcgccga aatacggtcc tatggctggt ggcactttac ttactttaac    2220
tggaaattac ctaaacagtg ggaattctag acacatttca attggtggaa aaacatgtac    2280
tttaaaaagt gtgtcaaaca gtattcttga atgttatacc ccagcccaaa ccatttcaac    2340
tgagtttgct gttaaattga aaattgactt agccaaccga gagacaagca tcttcagtta    2400
ccgtgaagat cccattgtct atgaaattca tccaaccaaa tcttttatta gtacttggtg    2460
gaaagaacct ctcaacattg tcagttttct attttgcttt gccagtggtg ggagcacaat    2520
aacaggtgtt gggaaaaacc tgaattcagt tagtgtcccg agaatggtca taaatgtgca    2580
tgaagcagga aggaacttta cagtggcatg tcaacatcgc tctaattcag agataatctg    2640
ttgtaccact ccttccctgc aacagctgaa tctgcaactc cccctgaaaa ccaaagcctt    2700
tttcatgtta gatgggatcc tttccaaata ctttgatctc atttatgtac ataatcctgt    2760
gtttaagcct tttgaaaagc cagtgatgat ctcaatgggc aatgaaaatg tactggaaat    2820
taagggaaat gatattgacc ctgaagcagt taaaggtgaa gtgttaaaag ttggaaataa    2880
gagctgtgag aatatacact tacattctga agccgtttta tgcacggtcc ccaatgacct    2940
gctgaaattg aacagcgagc taaatataga gtggaagcaa gcaatttctt caaccgtcct    3000
tggaaaagta atagttcaac cagatcagaa tttcacagga ttgattgctg gtgttgtctc    3060
aatatcaaca gcactgttat tactacttgg gttttcctg tggctgaaaa agagaaagca    3120
aattaaagat ctgggcagtg aattagttcg ctacgatgca agagtacaca ctcctcattt    3180
ggataggctt gtaagtgccc gaagtgtaag cccaactaca gaaatggttt caaatgaatc    3240
tgtagactac cgagctactt ttccagaaga tcagtttcct aattcatctc agaacggttc    3300
atgccgacaa gtgcagtatc ctctgacaga catgtccccc atcctaacta gtggggactc    3360
tgatatatcc agtccattac tgcaaaatac tgtccacatt gacctcagtg ctctaaatcc    3420
agagctggtc caggcagtgc agcatgtagt gattgggccc agtagcctga ttgtgcatttt   3480 caatgaagtc ataggaagag ggcattttgg ttgtgtatat catgggactt tgttggacaa    3540
tgatggcaag aaaattcact gtgctgtgaa atccttgaac agaatcactg acataggaga    3600
agtttcccaa tttctgaccg agggaatcat catgaaagat tttagtcatc ccaatgtcct    3660
ctcgctcctg gaatctgcc tgcgaagtga agggtctccg ctggtggtcc taccatacat    3720
gaaacatgga gatcttcgaa atttcattcg aaatgagact cataatccaa ctgtaaaaga    3780
tcttattggc tttggtcttc aagtagccaa aggcatgaaa tatcttgcaa gcaaaaagtt    3840
tgtccacaga gacttggctg caagaaactg tatgctggat gaaaaattca cagtcaaggt    3900
tgctgatttt ggtcttgcca gagacatgta tgataaagaa tactatagtg tacacaacaa    3960
aacaggtgca aagctgccag tgaagtggat ggctttggaa agtctgcaaa ctcaaaagtt    4020
taccaccaag tcagatgtgt ggtcctttgg cgtgctcctc tgggagctga tgacaagagg    4080
agccccacct tatcctgacg taaacacctt tgatataact gtttacttgt tgcaagggag    4140
aagactccta caacccgaat actgcccaga cccttatat gaagtaatgc taaaatgctg    4200
gcaccctaaa gccgaaatgc gcccatcctt ttctgaactg tgtcccgga tatcagcgat    4260 cttctctact ttcattgggg agcactatgt ccatgtgaac gctacttatg tgaacgtaaa    4320
atgtgtcgct ccgtatcctt ctctgttgtc atcagaagat aacgctgatg atgaggtgga    4380
cacacgacca gcctccttct gggagacatc atagtgctag tactatgtca aagcaacagt    4440
```

```
ccacactttg tccaatggtt tttttcactgc ctgacctttta aaaggccatc gatattcttt    4500
gctcttgcca aaattgcact attataggac ttgtattgtt atttaaatta ctggattcta    4560
aggaatttct tatctgacag agcatcagaa ccagaggctt ggtcccacag gccacggacc    4620
aatggcctgc agccgtgaca acactcctgt catattggag tccaaaactt gaattctggg    4680
ttgaattttt taaaaatcag gtaccacttg atttcatatg ggaaattgaa gcaggaaata    4740
ttgagggctt cttgatcaca gaaaactcag aagagatagt aatgctcagg acaggagcgg    4800
cagccccaga acaggccact catttagaat tctagtgttt caaaacactt ttgtgtgttg    4860
tatggtcaat aacattttc attactgatg gtgtcattca cccattaggt aaacattccc    4920
ttttaaatgt ttgtttgttt tttgagacag gatctcactc tgttgccagg gctgtagtgc    4980
agtggtgtga tcatagctca ctgcaacctc cacctcccag gctcaagcct cccgaatagc    5040
tgggactaca ggcgcacacc accatccccg gctaattttt gtatttttg tagagacggg    5100 gttttgccat gttgccaagg ctggtttcaa actcctggac tcaagaaatc cacccacctc    5160
agcctcccaa agtgctagga ttacaggcat gagccactgc gcccagccct tataaatttt    5220
tgtatagaca ttcctttggt tggaagaata tttataggca atacagtcaa agtttcaaaa    5280
tagcatcaca caaaacatgt ttataaatga acaggatgta atgtacatag atgacattaa    5340
gaaaatttgt atgaaataat ttagtcatca tgaaatattt agttgtcata taaaaaccca    5400
ctgtttgaga atgatgctac tctgatctaa tgaatgtgaa catgtagatg ttttgtgtgt    5460
atttttttaa atgaaaactc aaaataagac aagtaatttg ttgataaaata ttttttaaaga   5520 taactcagca tgtttgtaaa gcaggataca ttttactaaa aggttcattg gttccaatca    5580
cagctcatag gtagagcaaa gaaagggtgg atggattgaa aagattagcc tctgtctcgg    5640
tggcaggttc ccacctcgca agcaattgga aacaaaactt tggggagtt ttattttgca    5700 ttagggtgtg ttttatgtta agcaaaacat actttagaaa caaatgaaaa aggcaattga    5760
aaatcccagc tatttcacct agatggaata gccaccctga gcagaacttt gtgatgcttc    5820
attctgtgga attttgtgct tgctactgta tagtgcatgt ggtgtaggtt actctaactg    5880
gttttgtcga cgtaaacatt taaagtgtta tatttttat aaaaatgttt attttttaatg    5940 atatgagaaa aattttgtta ggccacaaaa acactgcact gtgaacattt tagaaaaggt    6000
atgtcagact gggattaatg acagcatgat tttcaatgac tgtaaattgc gataaggaaa    6060
tgtactgatt gccaatacac cccacccctca ttacatcatc aggacttgaa gccaagggtt    6120
aacccagcaa gctacaaaga gggtgtgtca cactgaaact caatagttga gtttggctgt    6180
tgttgcagga aaatgattat aactaaaagc tctctgatag tgcagagact taccagaaga    6240
cacaaggaat tgtactgaag agctattaca atccaaatat tgccgtttca taaatgtaat    6300
aagtaatact aattcacaga gtattgtaaa tggtggatga caaaagaaaa tctgctctgt    6360
ggaaagaaag aactgtctct accagggtca agagcatgaa cgcatcaata gaaagaactc    6420
ggggaaacat cccatcaaca ggactacaca cttgtatata cattcttgag aacactgcaa    6480
tgtgaaaatc acgtttgcta tttataaact tgtccttaga ttaatgtgtc tggacagatt    6540
gtgggagtaa gtgattcttc taagaattag atacttgtca ctgcctatac ctgcagctga    6600
actgaatggt acttcgtatg ttaatagttg ttctgataaa tcatgcaatt aaagtaaagt    6660
gatgcaacat cttgtaaaaa aaaaaaaaaa aaaaa                                6695
```

<210> SEQ ID NO 149
<211> LENGTH: 7619

<212> TYPE: DNA
<213> ORGANISM: Homo sapiens

<400> SEQUENCE: 149

```
actgaggcgc tggatctgtg gtcgcggctg gggacgtgcg cccgcgccac catcttcggc    60
tgaagaggca attgcttttg gatcgttcca tttacaatgg cgcagagaac tggactcgag   120
gatccagaga ggtatctctt tgtggacagg gctgtcatct acaaccctgc cactcaagct   180
gattggacag ctaaaaagct agtgtggatt ccatcagaac gccatggttt tgaggcagct   240
agtatcaaag aagaacgggg agatgaagtt atggtggagt tggcagagaa tggaaagaaa   300
gcaatggtca acaaagatga tattcagaag atgaacccac ctaagttttc caaggtggag   360
gatatggcag aattgacatg cttgaatgaa gcttccgttt tacataatct gaaggatcgc   420
tactattcag gactaatcta tacttattct ggactcttct gtgtagttat aaacccttac   480
aagaatcttc caatttactc tgagaatatt attgaaatgt acagagggaa gaagcgtcat   540
gagatgcctc cacacatcta tgctatatct gaatctgctt acagatgcat gcttcaagat   600
cgtgaggacc agtcaattct ttgcacgggt gagtcaggtg ctgggaagac agaaaataca   660
aagaaagtta ttcagtacct tgcccatgtt gcttcttcac ataaaggaag aaaggaccat   720
aatattcctg gggaacttga acggcagctt ttgcaagcaa atccaattct ggaatcattt   780
ggaaatgcga agactgtgaa aaatgataac tcatctcgtt ttggcaaatt tattcggatc   840
aactttgatg taactggcta tatcgttggg gccaacattg aaacatacct tctggaaaag   900
tctcgtgctg ttcgtcaagc aaaagatgaa cgtacttttc atatcttttc ccagttgtta   960
tctggagcag gagaacacct aaagtctgat ttgcttcttg aaggatttaa taactacagg  1020
tttctctcca atggctatat tcctattccg ggacagcaag acaaagataa tttccaggag  1080
accatggaag caatgcacat aatgggcttc tcccatgaag agattctgtc aatgcttaaa  1140
gtagtatctt cagtgctaca gtttggaaat atttctttca aaaaggagag aaatactgat  1200
caagcttcca tgccagaaaa tacagttgcg cagaagctct gccatcttct tgggatgaat  1260
gtgatggagt ttactcgggc catcctgact ccccggatca aggtcggccg agactatgtg  1320
caaaaagccc agaccaaaga acaggcagat tttgcagtag aagcattggc aaaagctacc  1380
tatgagcggc tctttcgctg gctcgttcat cgcatcaata agctctggga taggaccaaa  1440
cgtcagggag catctttcat tggaatcctg gatattgctg gatttgaaat ttttgagctg  1500
aactcctttg aacaactttg catcaactac accaatgaga gctgcagca gctgttcaac  1560
cacaccatgt ttatcctaga acaagaggaa taccagcgcg aaggcatcga gtggaacttc  1620
atcgatttcg ggctggatct gcagccatgc atcgacctaa tagagagacc tgcgaaccct  1680
cctggtgtac tggcccttt ggatgaagaa tgctggttcc ctaaagccac agataaaacc  1740
tttgttgaaa aactggttca agagcaaggt tcccactcca gtttcagaa acctcgacaa  1800
ttaaaagaca aagctgattt ttgcattata cattatgcag ggaaggtgga ctataaggca  1860
gatgagtggc tgatgaagaa tatggaccc ctgaatgaca acgtggccac ccttttgcac  1920
cagtcatcag acagatttgt ggcagagctt tggaaagatg tggaccgtat cgtgggtctg  1980
gatcaagtca ctggtatgac tgagacagct tttggctccg catataaaac caagaagggc  2040
atgtttcgta ccgttgggca actctacaaa gaatctctca ccaagctgat ggcaactctc  2100
cgaaacacca accctaactt tgttcgttgt atcattccaa atcacgagaa gagggctgga  2160
aaattggatc cacacctagt cctagatcag cttcgctgta atggtgtcct ggaagggatc  2220
```

```
cgaatctgtc gccagggctt ccctaaccga atagttttcc aggaattcag acagagatat    2280
gagatcctaa ctccaaatgc tattcctaaa ggttttatgg atggtaaaca ggcctgtgaa    2340
cgaatgatcc gggctttaga attggaccca aacttgtaca gaattggaca gagcaagata    2400
tttttcagag ctggagttct ggcacactta gaggaagaaa gagatttaaa aatcaccgat    2460
atcattatct tcttccaggc cgtttgcaga ggttacctgg ccagaaaggc ctttgccaag    2520
aagcagcagc aactaagtgc cttaaaggtc ttgcagcgga actgtgccgc gtacctgaaa    2580
ttacggcact ggcagtggtg gcgagtcttc acaaaggtga agccgcttct acaagtgact    2640
cgccaggagg aagaacttca ggccaaagat gaagagctgt tgaaggtgaa ggagaagcag    2700
acgaaggtgg aaggagagct ggaggagatg gagcggaagc accagcagct tttagaagag    2760
aagaatatcc ttgcagaaca actacaagca gagactgagc tctttgctga agcagaagag    2820
atgagggcaa gacttgctgc taaaaagcag gaattagaag agattctaca tgacttggag    2880
tctagggttg aagaagaaga agaaagaaac caaatcctcc aaaatgaaaa gaaaaaaatg    2940
caagcacata ttcaggacct ggaagaacag ctagacgagg aggaagggc tcggcaaaag    3000 ctgcagctgg aaaaggtgac agcagaggcc aagatcaaga agatggaaga ggagattctg    3060
cttctcgagg accaaaattc caagttcatc aaagaaaaga aactcatgga agatcgcatt    3120
gctgagtgtt cctctcagct ggctgaagag gaagaaaagg cgaaaaactt ggccaaaatc    3180
aggaataagc aagaagtgat gatctcagat ttagaagaac gcttaaagaa ggaagaaaag    3240
actcgtcagg aactggaaaa ggccaaaaga aaactcgacg gggagacgac cgacctgcag    3300
gaccagatcg cagagctgca ggcgcagatt gatgagctca agctgcagct ggccaagaag    3360
gaggaggagc tgcagggcgc actggccaga ggtgatgatg aaacactcca taagaacaat    3420
gcccttaaag ttgtgcgaga gctacaagcc caaattgctg aacttcagga agactttgaa    3480
tccgagaagg cttcacggaa caaggccgaa aagcagaaaa gggacttgag tgaggaactg    3540
gaagctctga aaacagagct ggaggacacg ctggacacca cggcagccca gcaggaacta    3600
cgtacaaaac gtgaacaaga agtggcagag ctgaagaaag ctcttgagga ggaaactaag    3660
aaccatgaag ctcaaatcca ggacatgaga caaagcacg caacagccct ggaggagctc    3720
tcagagcagc tggaacaggc caagcggttc aaagcaaatc tagagaagaa caagcagggc    3780
ctggagacag ataacaagga gctggcgtgt gaggtgaagg tcctgcagca ggtcaaggct    3840
gagtctgagc acaagaggaa gaagctcgac gcgcaggtcc aggagctcca tgccaaggtc    3900
tctgaaggcg acaggctcag ggtggagctg gcggagaaag caagtaagct gcagaatgag    3960
ctagataatg tctccaccct tctggaagaa gcagagaaga agggtattaa atttgctaag    4020
gatgcagcta gtcttgagtc tcaactacag gatacacagg agcttcttca ggaggagaca    4080
cgccagaaac taaacctgag cagtcggatc cggcagctgg aagaggagaa gaacagtctt    4140
caggagcagc aggaggagga ggaggaggcc aggaagaacc tggagaagca agtgctggcc    4200
ctgcagtccc agttggctga taccaagaag aaagtagatg acgacctggg aacaattgaa    4260
agtctggaag aagccaagaa gaagcttctg aaggacgcgg aggccctgag ccagcgcctg    4320
gaggagaagg cactggcgta tgacaaactg gagaagacca agaaccgcct gcagcaggag    4380
ctggacgacc tcacggtgga cctggaccac cagcgccagg tcgcctccaa cttggagaag    4440
aagcagaaga gtttgaccca gctgttagca gaagagaaga gcatctctgc tcgctatgcc    4500
gaagagcggg accgggccga agccgaggcc agagagaaag aaaccaaagc cctgtcactg    4560 gccccgggccc tcgaggaagc cctggaggcc aaggaggagt ttgagaggca gaacaagcag    4620
```

```
ctccgagcag acatggaaga cctcatgagc tccaaagatg atgtgggaaa aaacgttcac   4680
gaacttgaaa aatccaaacg ggccctagag cagcaggtgg aggaaatgag gacccagctg   4740
gaggagctgg aagacgaact ccaggccacg gaagatgcca agcttcgtct ggaggtcaac   4800
atgcaggcca tgaaggcgca gttcgagaga gacctgcaaa ccagggatga gcagaatgaa   4860
gagaagaagc ggctgctgat caaacaggtg cgggagctcg aggcggagct ggaggatgag   4920
aggaaacagc gggcgcttgc tgtagcttca aagaaaaaga tggagataga cctgaaggac   4980
ctcgaagccc aaatcgaggc tgcgaacaaa gctcgggatg aggtgattaa gcagctccgc   5040
aagctccagg ctcagatgaa ggattaccaa cgtgaattag aagaagctcg tgcatccaga   5100
gatgagattt ttgctcaatc caaagagagt gaaaagaaat tgaagagtct ggaagcagaa   5160
atccttcaat tgcaggagga acttgcctca tctgagcgag cccgccgaca cgccgagcag   5220
gagagagatg agctggcgga cgagatcacc aacagcgcct ctggcaagtc cgcgctgctg   5280
gatgagaagc ggcgtctgga agctcggatc gcacagctgg aggaggagct ggaagaggag   5340
cagagcaaca tggagctgct caacgaccgc ttccgcaaga ccactctaca ggtggacaca   5400
ctgaacgccg agctagcagc cgagcgcagc gccgcccaga agagtgacaa tgcacgccag   5460
caactggagc ggcagaacaa ggagctgaag gccaagctgc aggaactcga gggtgctgtc   5520
aagtctaagt tcaaggccac catctcagcc ctggaggcca agattgggca gctggaggag   5580
cagcttgagc aggaagccaa ggaacgagca gccgccaaca aattagtccg tcgcactgag   5640
aagaagctga agaaaatctt catgcaggtt gaggatgagc gtcgacacgc ggaccagtat   5700
aaagagcaga tggagaaggc caacgctcgg atgaagcagc ttaaacgcca gctggaggaa   5760
gcagaagaag aagcgacgcg tgccaacgca tctcggcgta aactccagcg ggaactggat   5820
gatgccaccg aggccaacga gggcctgagc cgcgaggtca gcaccctgaa gaaccggctg   5880
aggcggggtg gccccatcag cttctcttcc agccgatctg gccggcgcca gctgcacctt   5940
gaaggagctt ccctggagct ctccgacgat gacacagaaa gtaagaccag tgatgtcaac   6000
gagacgcagc caccccagtc agagtaaagt tgcaggaagc cagaggaggc aatacagtgg   6060
gacagttagg aatgcacccg gggcctcctg cagatttcgg aaattggcaa gctacgggat   6120
tccttcctga agatcaact gtgtcttaag gctctccagc ctatgcatac tgtatcctgc   6180
ttcagactta ggtacaattg ctccccttt tatatataga cacacacagg acacatatat   6240
taaacagatt gtttcatcat tgcatctatt ttccatatag tcatcaagag accatttat   6300
aaaacatggt aagacccttt ttaaaacaaa ctccaggccc ttggttgcgg gtcgctgggt   6360
tattgggca gcgccgtggt cgtcactcag tcgctctgca tgctctctgt catacagaca   6420
ggtaacctag ttctgtgttc acgtggcccc cgactcctca gccacatcaa gtctcctaga   6480
ccactgtgga ctctaaactg cacttgtctc tctcatttcc ttcaaataat gatcaatgct   6540
atttcagtga gcaaactgtg aaaggggctt tggaaagagt aggagggtg ggctggatcg   6600
gaagcaacac ccatttgggg ttaccatgtc catcccccaa ggggggccct gccctcgag   6660
tcgatggtgt cccgcatcta ctcatgtgaa ctggccttgg cgagggctgg tctgtgcata   6720
gaagggatag tggccacact gcagctgagg ccccaggtgg cagccatgga tcatgtagac   6780
ttccagatgg tctcccgaac cgcctggctc tgccggcgcc ctcctcacgt caggagcaag   6840
cagccgtgga cccctaagcc gagctggtgg aaggcccctc cctgtcgcca gccgggccct   6900
catgctgacc ttgcaaattc agccgctgct ttgagcccaa aatgggaata ttggttttgt   6960
```

| | |
|---|---|
| gtccgaggct tgttccaagt tgtcaatga ggtttatgga gcctccagaa cagatgccat | 7020 |
| cttcctgaat gttgacatgc cagtgggtgt gactccttca ttttt ccttc tcccttccct | 7080 |
| ttggacagtg ttacagtgaa cacttagcat cctgttttg gttggtagtt aagcaaactg | 7140 |
| acattacgga aagtgcctta gacactcag tactaagaca atgttgaata tatcattcgc | 7200 |
| ctctataaca atttaatgta ttcagttttg actgtgcttc atatcatgta cctctctagt | 7260 |
| caaagtggta ttacagacat tcagtgacaa tgaatcagtg ttaattctaa atccttgatc | 7320 |
| ctctgcaatg tgcttgaaaa cacaaacctt tgggttaaa agctttaaca tctattagga | 7380 |
| agaatttgtc ctgtgggttt ggaatcttgg attttccccc tttatgaact gtactggctg | 7440 |
| ttgaccacca gacacctgac cgcaaatatc ttttcttgta ttcccatatt tctagacaat | 7500 |
| gattttgta agacaataaa tttattcatt atagatattt gcgcctgctc tgtttacttg | 7560 |
| aagaaaaaag cacccgtgga gaataaagag acctcaataa caagaataa tcatgtgaa | 7619 |

<210> SEQ ID NO 150
<211> LENGTH: 1752
<212> TYPE: DNA
<213> ORGANISM: Homo sapiens

<400> SEQUENCE: 150

| | |
|---|---|
| atgtcttatg gtgaaattga aggtaaattc ttgggaccta gagaagaagt aacgagtgag | 60 |
| ccacgctgta aaaattgaa gtcaaccaca gagtcgtatg ttttcacaa tcatagtaat | 120 |
| gctgattttc acagaatcca agagaaaact ggaaatgatt gggtccctgt gaccatcatt | 180 |
| gatgtcagag acatagtta tttgcaggag aacaaaatca aaactacaga tttgcataga | 240 |
| cctttgcatg atgagatgcc tggtaataga ccagatgtta ttgaatccat tgattcacag | 300 |
| gttttacagg aagcacgtcc tccattagta tccgcagacg atgagatata tagcacaagt | 360 |
| aaagcattta taggacccat ttacaaaccc cctgagaaaa agaaacgtaa tgaagggagg | 420 |
| aatgaggcac atgttctaaa tggtataaat gacagaggag gacaaaaaga gaaacagaaa | 480 |
| tttaactctg aaaaatcaga gattgacaat gaattattcc agttttacaa agaaattgaa | 540 |
| gagcttgaaa aggaaaaaga tggttttgag aacagttgta aagaatctga accttctcag | 600 |
| gaacaatttg ttccatttta tgagggtcat aataatggtc tcttaaaacc tgatgaagaa | 660 |
| aagaaagatc ttagtaataa agctatgcca tcacattgtg attatcagca gaacttgggg | 720 |
| aatgagccag acaaatatcc ctgtaatgga caagtaatac ctacattttg tgacacttca | 780 |
| tttacttctt tcaggcctga atggcagtca gtatatcctt ttatagtgcc ctatggtccc | 840 |
| cctcttccca gtttgaacta tcatttaaac attcagagat tcagtggtcc accaaatcca | 900 |
| ccatcaaata ttttccaagc ccaagatgac tctcagatac aaaatggata ttatgtaaat | 960 |
| aattgtcatg ttaactggaa ttgcatgact tttgatcaga caatgaata tactgactgt | 1020 |
| agtgagaata ggagtagtgt tcatccctct ggaaatggct gcagtatgca agatcgatat | 1080 |
| gtgagtaatg gtttctgtga agtcagagaa agatgctgga agatcattg tatggacaag | 1140 |
| cataatggaa cagacaggtt tgtgaaccag cagtttcaag aggaaaagtt aaataaattg | 1200 |
| cagaagttac ttattctttt aagaggtctg cctggttctg ggaaaacaac attgtctcga | 1260 |
| attctgcttg gtcagaatcg tgatggcatt tgttcagca ctgatgacta ttttcaccat | 1320 |
| caagatgggt acaggtataa tgttaatcaa cttggtgatg cccatgactg gaaccagaac | 1380 |
| agagcaaaac aagctatcga tcagggaaga tctccagtta taatagataa cactaatata | 1440 |
| caagcttggg aaatgaagcc atatgtggaa gtggccatag gaaaaggata cagagtagag | 1500 |

-continued

| | |
|---|---|
| tttcatgaac ctgaaacttg gtggaaattt gatcctgaag aattagaaaa gaggaataaa | 1560 |
| catggtgtgt ctcgaaagaa gattgctcag atgttggatc gttatgaata tcaaatgtcc | 1620 |
| atttctattg taatgaattc agtggaacca tcacacaaaa gcacacaaag acctcctcct | 1680 |
| ccacagggga gacagaggtg gggaggctct cttggctcac ataatcgtgt ctgtgtcaca | 1740 |
| aataatcatt aa | 1752 |

<210> SEQ ID NO 151
<211> LENGTH: 1758
<212> TYPE: DNA
<213> ORGANISM: Homo sapiens

<400> SEQUENCE: 151

| | |
|---|---|
| ctgctgtctg cggaggaaac tgcatcgacg gacggccgcc cagctacggg aggacctgga | 60 |
| gtggcactgg gcgcccgacg gaccatcccc gggacccgcc tgcccctcgg cgccccgccc | 120 |
| cgccggccg ctccccgtcg ggttcccag ccacagcctt acctacgggc tcctgactcc | 180 |
| gcaaggcttc cagaagatgc tcgaaccacc ggccggggcc tcggggcagc agtgagggag | 240 |
| gcgtccagcc ccccactcag ctcttctcct cctgtgccag gggctccccg ggggatgagc | 300 |
| atggtggttt tccctcggag cccctggct cgggacgtct gagaagatgc cggtcatgag | 360 |
| gctgttccct tgcttcctgc agctcctggc cgggctggcg ctgcctgctg tgccccccca | 420 |
| gcagtgggcc ttgtctgctg gaacggctc gtcagaggtg gaagtggtac ccttccagga | 480 |
| agtgtgggc cgcagctact gccgggcgct ggagaggctg gtggacgtcg tgtccgagta | 540 |
| ccccagcgag gtggagcaca tgttcagccc atcctgtgtc tccctgctgc gctgcaccgg | 600 |
| ctgctgcggc gatgagaatc tgcactgtgt gccggtggag acggccaatg tcaccatgca | 660 |
| gctcctaaag atccgttctg ggaccggcc ctcctacgtg gagctgacgt tctctcagca | 720 |
| cgttcgctgc gaatgccggc ctctgcggga gaagatgaag ccggaaagga ggagacccaa | 780 |
| gggcaggggg aagaggagga gagagaagca gagacccaca gactgccacc tgtgcggcga | 840 |
| tgctgttccc cggaggtaac ccacccttg gaggagagag accccgcacc cggctcgtgt | 900 |
| atttattacc gtcacactct tcagtgactc ctgctggtac ctgccctcta tttattagcc | 960 |
| aactgtttcc ctgctgaatg cctcgctccc ttcaagacga ggggcaggga aggacaggac | 1020 |
| cctcaggaat tcagtgcctt caacaacgtg agagaaagag agaagccagc cacagacccc | 1080 |
| tgggagcttc cgctttgaaa gaagcaagac acgtggcctc gtgaggggca agctaggccc | 1140 |
| cagaggccct ggaggtctcc aggggcctgc agaaggaaag aagggggccc tgctacctgt | 1200 |
| tcttgggcct caggctctgc acagacaagc agcccttgct ttcggagctc ctgtccaaag | 1260 |
| tagggatgcg gatcctgctg gggccgccac ggcctggctg gtgggaaggc cggcagcggg | 1320 |
| cggagggat ccagccactt ccccctcttc ttctgaagat cagaacattc agctctggag | 1380 |
| aacagtggtt gcctggggc ttttgccact ccttgtcccc cgtgatctcc cctcacactt | 1440 |
| tgccatttgc ttgtactggg acattgttct ttccggccaa ggtgccacca ccctgccccc | 1500 |
| cctaagagac acatacagag tgggcccccgg gctggagaaa gagctgcctg gatgagaaac | 1560 |
| agctcagcca gtgggatga ggtcaccagg ggaggagcct gtgcgtccca gctgaaggca | 1620 |
| gtggcagggg agcaggttcc ccaagggccc tggcaccccc acaagctgtc cctgcagggc | 1680 |
| catctgactg ccaagccaga ttctcttgaa taaagtattc tagtgtggaa aaaaaaaaa | 1740 |
| aaaaaaaaaa aaaaaaaa | 1758 |

<210> SEQ ID NO 152
<211> LENGTH: 1622
<212> TYPE: DNA
<213> ORGANISM: Homo sapiens

<400> SEQUENCE: 152

```
gtttaagtag aatcctcaag cttggcctca gagtactatg aggcttctga atccaggaat      60
aagactgctc ttggatttac tctctttgta ttgcatgtca aaggcaacag aactggacca     120
agaaaattca aacttttttg cgtttgtttc tactaagatg acatcataca tggctattga     180
tggcagtgct cttgttccct tgcgtcagaa gcccaggagg aaaactcaag gttttctcac     240
gatgagtcgg aggaggatat cgtgtaaaga tctgggccat gctgactgcc aagggtggct     300
gtataagaaa aaggaaaagg aagtttcct aagcaacaaa tggaaaagt tctgggtgat      360
actgaagggg tcgtcactgt actggtatag caatcaaatg gcagagaaag ctgatggatt     420
tgtcaacctg cctgatttca ctgtggaaag agcatctgaa tgcaagaaaa agcatgcttt     480
taagatcagc catccacaga tcaagacctt ttattttgca gctgagaatg tgcaggaaat     540
gaacgtgtgg ttaaataaac ttggatcggc tgtaatccat caggaatcca ctacaaagga     600
tgaagaatgt tacagtgaaa gtgaacagga agatccagaa atagctgcgg agacaccacc     660
ccctcctcac gcttcccaga ctcagtcttt gactgcacag caggcatctt catcctcacc     720
cagcctgagt ggaacgtcgt attctttctc ttccctggaa aatacagtga agacacccag     780
cagtttttcct tcctccttat ctaaagagag acaatccttg cctgacacag ttaacagttt     840
gtctgctgct gaagatgagg gacaaccaat aacgtttgct gtgcaagttc attcacctgt     900
accctcagag gcaggcatcc acaaggccct ggaaaacagt tttgtcacat cagaaagtgg     960
attttttgaac tctttatcta gtgatgatac ttcttcattg agtagcaatc atgaccatct    1020
tactgtccca gataagcctg ctggatcaaa gatcatggac aaagaagaga caaaagtgtc    1080
tgaagatgat gaaatggaga agctgtacaa atcattagag caagctagtc tatctcctct    1140
tggggaccga cgaccttcga ctaaaaagga gttgagaaaa tcctttgtta agcggtgtaa    1200
aaatccatct ataaacgaga aactccacaa aatccgaaca ttgaatagca cattaaagtg    1260
taaagaacat gatctggcca tgattaacca gttgctggat gacccgaagc tgacagccag    1320
gaaatacaga gagtggaaag tcatgaacac cctgctgatc caggacatct atcagcagca    1380
gcgggcttcg cctgcccctg atgacactga tgacacccccc caggaactca gaaaatcacc    1440
ttcttctccc tctgttgaaa attccatttg agacaaagtc agggttttct cctcttatat    1500
tttatcacaa gcaactcttc aagatgttgc aaaagcttac attttccctt aaaaggaaaa    1560
ctgaaaccca gtccttcaag catcagcttc ccatctaaag atgcacgtta gatgaagata    1620
at                                                                    1622
```

<210> SEQ ID NO 153
<211> LENGTH: 3730
<212> TYPE: DNA
<213> ORGANISM: Homo sapiens

<400> SEQUENCE: 153

```
gtgtgaaggg ggggtccggg gggcgggtcc ctgtgccgct gacgtcccga gcagtgctgg      60
gaagtatagg ctgtgttgtc acgccggtgt cagtctgatg aagattggca tcaggtgaag     120
tctggagcag gacttctgag gctttctatc ctccatgctg ctcactagaa aagggggctgt    180
gaactgtgct ttggctctag cagacaggaa gaaattctgg cccagctgga agtagaaaga    240
```

```
ggggagtgag tctcctgagg accatctcag aggccccggg atcacccgaa cagtcctcca      300
tgtgaatcaa tcccatgatg caacatgcct cccagcccc cgctctgacg atgatggcca       360
cgcagaatgt cccgcccca ccctaccagg acagcccaca gatgacggca accgcccagc       420
caccctccaa ggcccaggct gtccacatct ctgcccctc agctgctgcc agcacacctg       480
tgcccagtgc ccatcgac ccccaggccc agctggaggc tgacaagcga gctgtataca       540
ggcaccctct tttccgctc ctgacgctgc tgtttgagaa atgtgaacag gccacccagg       600
gctctgagtg catcacctcc gccagctttg atgtggacat cgagaacttt gtccaccagc     660
aggaacagga gcacaaaccc ttcttcagcg atgacccaga actggacaat ctgatggtga     720
aggcaatcca ggtcctgaga atccacctgc tggagctgga aaagtcaat gaactctgca      780 aggacttttg taaccgttac atcacctgcc tcaaaaccaa gatgcacagc gacaacctgc     840
tcaggaatga tctaggggg ccctactccc ccaaccagcc ctccatcaac cttcactcac      900
aggacctcct gcagaattcc cccaattcca tgtccggagt ctccaataac ccccagggga     960
ttgtggtccc agcctcagcg ctccagcagg gcaacatcgc catgacaacc gtcaactcac    1020
aagttgtgtc aggtggagcc ttataccaac cggttaccat ggtaacctcc cagggtcagg    1080
tggtcaccca agcaatcccc cagggagcca tccagatcca gaacacacag gttaaccttg    1140
acctcacctc cctcctggac aatgaggata agaagtccaa gaacaaacga ggagtcttgc    1200
ccaagcatgc caccaatata atgcgttctt ggctcttcca gcatctcatg caccccctacc   1260 ccacggagga tgagaagagg cagatcgcag cccagaccaa cctcaccctc ctgcaagtaa    1320
acaactggtt catcaatgcc cggaggcgca tcctgcagcc catgcttgat gccagcaacc    1380
cagatcctgc ccccaaagcc aagaagatca agtctcagca ccggcccacc caaagattct    1440
ggcccaactc catcgctgcg ggggtgctgc agcagcaggg cggtgcccca gggacaaacc    1500
ccgatggttc catcaacttg gacaacctgc agtccctgtc ctcagacagt gccaccatgg    1560
ccatgcagca ggctatgatg gctgcacacg atgactcatt ggatgggaca aagaagagg    1620 atgaggatga gatggaagag gaggaggagg aggagctgga ggaggaggtc gacgagctgc    1680
agacgacaaa tgtcagcgac ctgggcttgg aacacagtga ctccctggag tagtcgggca    1740
gcccagatgg cactgatcac tgagcaggag aggagtgtcg ccgggaggcc ttcagggtgg    1800 ggggaaggg gacatgggca ggaagcaccg agggagttgg gccctagctt ccccaaaatca    1860 gtagcttgaa gaaaggcaaa ggagacacct gttccttccc aaccaccgag cttcaatgag    1920
gaccccagcc ccacttccct ggaactgccg aggactctgt ttggcggggc cagtcgagca    1980
gcctgtgtgg aaagacagga gtgagatctg gactcaccaa atccctgagg atagatggca    2040
cccatggccc ccacccacgg aaggacttga gttgtttaca agccctgcac tgaggcagat    2100
tggtgctgtt cgcagagtag gcctttgccc ggggcagac ttagaaggaa ggggagagac    2160 aaaggggac tgagttcat ccccagaagt ttctcagctc cttttgacaga cattcaaggg    2220 caggagggag ccccaaagca taaccagtgg ccagaggagt gggagggcct gaggcatcac    2280
atcttgcaga tcagaatggg atggaatcca ccaggctcca gctcatccct ccaaggccct   2340
gtctctgcgc acagcaacca tggacatggg agaaagggat gggagccaca gtgcccttca    2400
ctctctcctg gaaaccaact gtaagctggt gggctcaacc tgtgggaggt taagaggagt    2460
cccttctggg ttgactccaa gagccaagga gatggcagac cctgggctag gaaccatatg   2520
gaggtgactt tgaggccaca gctgtcccta ggtgatcaca gaacttagct cctttaacaa    2580
```

```
caggacaatg gttttttacc ctagatgttc ccaccttcag tgctccacgc cctccataga    2640
ccttcagaga aggtgaaacc aggttatctg ggaatctttc cagcccgcag gtcgccacgg    2700
ccatcccttt gctcccagcc tggctccatc agcctccagc ttcctttctt cattctgtcc    2760
ttcagggaag gcagaagaaa cattgggaaag catctagtcc agtgggaagc caggggttgg    2820
agaaggtgct acatccctct tcccatcaat atcctaaatg tgggggaggg cccagagaat    2880
ggcacccaag agcctgcggg gatgcccatc ccacacaccc cacccagctg ttctaaccct    2940
gctatccaca gccctggagg aactggggct cctggaagga ggaggaggct ctccactgtc    3000
caccctaaca catacccctcc cacccacctt ccagaccccc ttggttggca ccctctcctc    3060
cggttccctc tcaccccatg gctgtgaatg acaggacagg tcacacgtgt gttttccatt    3120
gggtttaatt taatggacgt gcagtttcat ttgtaaattg tgcattggcc acctccttca    3180
gtggcaggat gtgagtggct acctggctca actggagggg acccccttggg ccctctgggg   3240 cttcccctcc cccacctggt tggggtagag caaaaggatg gtcactcttc cgaggtctcc    3300
ctgaaatgaa tgtatttctc ccccaaaaga gctgatattt aatgttttaa taaggatttt    3360
tgagaaacaa ataaccttat ttataatctg ggtgatccaa tcatttttta ctcccttttg    3420
atgccataca tagaggaaag tctagctttt ttggcgtgag acttttgcaa tgtgcagtgg    3480
gataaaatgc atttccttt ctggttcgtt tttcttgtta acacgcgcac acagacacac     3540
acacacaccg ttccactcac cacctggaca ggcgtccccc agcacggaca cactggcaca    3600
caggtgccca catctcttcc tctcagcccc tccacctgcc taatgttatg caacctcctt    3660
ctgatgtatc caccaaacca gtactgaatg tggccgagac gttttcagta aatcttatta    3720
cctaccgtaa                                                           3730

<210> SEQ ID NO 154
<211> LENGTH: 4499
<212> TYPE: DNA
<213> ORGANISM: Homo sapiens

<400> SEQUENCE: 154
acacatgcat agctcttagc ttctgtgtaa gaagttgtga gctccttctg gaaacatttg      60
cagttacatt aagtaaagtg taaatgcaca tgaatggcag cttatagaga accaccttgt     120
aaccagtata caggtacaac tacagctctt cagaaattgg aaggttttgc tagccggtta     180
tttcatagac actctaaagg tactgcacat gatcagaaaa cagctctgga aaatgacagc     240
cttcatttct ctgaacatac tgccttatgg gacagatcaa tgaaagagtt tctagccaaa     300
gccaaagaag acttttttgaa aaaatgggag aatccaactc agaataatgc cggacttgaa    360
gattttgaaa ggaaaaaaac ccttggaaca ggttcatttg gaagagtcat gttggtaaaa    420
cacaaagcca ctgaacagta ttatgccatg aagatcttag ataagcagaa ggttgttaaa    480
ctgaagcaaa tagagcatac tttgaatgag aaaagaatat tacaggcagt gaattttcct    540
ttccttgttc gactggagta tgcttttaag gataattcta atttatacat ggttatggaa    600
tatgtccctg ggggtgaaat gttttcacat ctaagaagaa ttggaaggtt cagtgagccc    660
catgcacggt tctatgcagc tcagatagtg ctaacattcg agtacctcca ttcactagac    720
ctcatctaca gagatctaaa acctgaaaat ctcttaattg accatcaagg ctatatccag    780
gtcacagact tgggtttgc caaaagagtt aaaggcagaa cttggacatt atgtggaact    840
ccagagtatt tggctccaga aataattctc agcaagggct acaataaggc agtggattgg    900
tgggcattag gagtgctaat ctatgaaatg gcagctggct atccccccatt ctttgcagac    960
```

```
caaccaattc agatttatga aaagattgtt tctggaaagg tccgattccc atcccacttc    1020
agttcagatc tcaaggacct tctacggaac ctgctgcagg tggatttgac caagagattt    1080
ggaaatctaa agaatggtgt cagtgatata aaaactcaca agtggttttgc cacgacagat   1140 tggattgcta tttaccagag gaaggttgaa gctccattca taccaaagtt tagaggctct    1200
ggagatacca gcaactttga tgactatgaa gaagaagata tccgtgtctc tataacagaa    1260
aaatgtgcaa aagaatttgg tgaattttaa agaggaacaa gatgacatct gagctcacac    1320
tcagtgtttg cactctgttg agagataagg tagagctgag accgtccttg ttgaagcagt    1380
tacctagttc cttcattcca acgactgagt gaggtcttta ttgccatcat cccgtgtgcg    1440
cactctgcat ccacctatgt aacaaggcac cgctaagcaa gcattgtctg tgccataaca    1500
cagtactaga ccactttctt acttctcttt gggttgtctt tctcctctcc tatatccatt    1560
tcttcctttt ccaatttcat tggttttctc taaacagtgc tccattttat tttgttggtg    1620
tttcagatgg gcagtgttat ggctacgtga tatttgaagg gaaggataag tgttgctttc    1680
agtagttatt gccaatattg ttgttggtca atggcttgaa gataaacttt ctaataatta    1740
ttatttcttt gagtagctca gacttggttt tgccaaaact cttggtaatt tttgaagata    1800
gactgtctta tcaccaagga aatttataca aattaagact aactttcttg gaattcacta    1860
ttctggcaat aaattttggt agactaatac agtacagcta gacccagaaa tttggaaggc    1920
tgtagatcag aggttctagt tccctttccc tccttttata tcctcctctc cttgagtaat    1980
gaagtgacca gcctgtgtag tgtgacaaac gtgtctcatt cagcaggaaa aactaatgat    2040
atggatcatc acccagattc tctcacttgg taccagcatt tctgtaggta ttagagaaga    2100
gttctaagtt ttctaaacct taactgttcc ttaaggattt tagccagtat tttaatagaa    2160
catgattaat gaaagtgaca aatttttaaat tttctctaat agtcctcatc ataaactttt    2220
taaaggaaaa taagcaaact aaaaagaaca ttggtttaga taaatactta tactttgcaa    2280
agtcaaaaat ggcttgattt ttggaaacaa tatagaggta ttcatattta aatgagggtt    2340
tacatttgtt ttgttttgta accgttaaaa agaagttgtt tccagctaat tattgtggtg    2400
tactatattt gtgagcctag ggtaggggca ctgctgcaac ttctgctttc atcccatgcc    2460
tcatcaatga ggaaagggaa caaagtgtat aaaactgcca caattgtatt ttaattttga    2520
ggtatgatat tttcagatat ttcataattt ctaacctctg ttctctcagt aaacagaatg    2580
tctgatcgat catgcagata caatgttggt atttgagagg ttagtttttt tcctacactt    2640 tttttgcca actgacttaa caacattgct gtcaggtgga aatttcaagc acttttgcac    2700
atttagttca gtgtttgttg agaatccatg gcttaaccca cttgttttgc tattttttc     2760 tttgctttta attttcccca tctgatttta tctctgcgtt tcagtgacct accttaaaac    2820
aacacacgag aagagttaaa ctgggttcat tttaatgatc aatttacctg catataaaat    2880
ttatttttaa tcaagctgat cttaatgtat ataatcattc tatttgcttt attatcggtg    2940
caggtaggtc attaacacca cttctttttca tctgtaccac accctggtga aacctttgaa    3000
gacataaaaa aaacctgtct gagatgttct ttctaccaat ctatatgtct ttcggttatc    3060
aagtgtttct gcatggtaat gtcatgtaaa tgctgatatt gatttcactg gtccatctat    3120
atttaaaacg tgcaagaaaa aaataaaata ctctgctcta gcaagttttg tgtaacaaag    3180
gcatatcgtc atgttaataa atttaaaaca tcattcgtat aaaatatttt aattttcttg    3240
tatttcattt agacccaaga acatgctgac caatgtgttc tatatgtaaa ctacaaattc    3300
```

| | |
|---|---|
| tatggtagct tgttgtata ttattgtaaa attattttaa taagtcatgg ggatgacaat | 3360 |
| ttgattatta caatttagtt ttcagtaatc aaaaagattt ctatgaattc taaaaaatat | 3420 |
| ttttttctat gaaattacta gtgcccagct gtagaatcta ccttaggtag atgatcccta | 3480 |
| gacatacgtt ggttttgagg gctattcagc cattccatttt tactctctat ttaaaggccg | 3540 |
| tgagcaagct tgtcatgagc aaatatgtca agggagtcaa tttctgacca atcaagtaca | 3600 |
| ctaaattaga atattttaa agtatgtaac attcccagtt tcagccacaa tttagccaag | 3660 |
| aataagataa aaacttgaat aagaagtaag tagcataaat cagtatttaa cctaaaatta | 3720 |
| catatttgaa acagaagata ttatgttatg ctcagtaaat aattaagaga tggcattgtg | 3780 |
| taagaaggag ccctagactg aaagtcaaga catctgaatt tcaggctgga aaactatcag | 3840 |
| tatgatctca gcctcagttc tcttgtctgt aaaatggaag aactggatta ggcagtttgt | 3900 |
| aagattcctc ctaactttca cagtcgatga caagattgtc ttttatctg atattttgaa | 3960 |
| gggtatattg ctttgaagta agtctcaata aggcaatata ttttagggca tctttcttct | 4020 |
| tatctctgac agtgttctta aaattatttg aatatcataa gagccttggt gtctgtccta | 4080 |
| attcctttct cactcaccga tgctgaatac ccagttgaat caaactgtca acctaccaaa | 4140 |
| aacgatattg tggcttatgg gtattgctgt ctcattcttg gtatattctt tgttaactg | 4200 |
| cccattggcc tgaaaatact cattgtaagc ctgaaaaaaa aaatctttcc cactgttttt | 4260 |
| tctgcttgtt gtaagaatca aatgaaataa tgtatgtgaa agcaccttgt aaactgtaac | 4320 |
| ctatcaatgt aaaatgttaa ggtgtgttgt tatttcatta attacttctt tgtttagaat | 4380 |
| ggaatttcct atgcactact gtagctagga aatgctgaaa acaactgtgt ttttttaatta | 4440 |
| atcaataact gcaaaattaa agtaccttca atggataaga caaaaaaaaa aaaaaaaa | 4499 |

<210> SEQ ID NO 155
<211> LENGTH: 3595
<212> TYPE: DNA
<213> ORGANISM: Homo sapiens

<400> SEQUENCE: 155

| | |
|---|---|
| tttggaaacg tcacactgtg gaggaaaagc agcaactagg gagctggtga agaaggatgt | 60 |
| ctcagcagtg tttactaggc ctccaacact agagcccatc ccccagctcc gaaaagcttc | 120 |
| ctggaaatgt ccttgttatc acttcccctc tcgggctggg cgctgggagc gggcggtctc | 180 |
| ctccgccccc ggctgttccg ccgaggctcg ctgggtcgct ggcgccgccg cgcagcacgg | 240 |
| ctcagaccga ggcgcacagg ctcgcagctc cgcggcgcct agcgctccgg tccccgccgc | 300 |
| gacgcgccac cgtccctgcc ggcgcctccg cgcgcttcga aatgagggtc ctgggtgggc | 360 |
| gctgcggggc gctgctggcg tgtctcctcc tagtgcttcc cgtctcagag gcaaacttt | 420 |
| tgtcaaagca acaggcttca caagtcctgg ttaggaagcg tcgtgcaaat tctttacttg | 480 |
| aagaaaccaa acagggtaat cttgaaagag aatgcatcga agaactgtgc aataagaag | 540 |
| aagccaggga ggtctttgaa aatgacccgg aaacggatta ttttttatcca aaatacttag | 600 |
| tttgtcttcg ctcttttcaa actgggttat tcactgctgc acgtcagtca actaatgctt | 660 |
| atcctgacct aagaagctgt gtcaatgcca ttccagacca gtgtagtcct ctgccatgca | 720 |
| atgaagatgg atatatgagc tgcaaagatg gaaaagcttc ttttacttgc acttgtaaac | 780 |
| caggttggca aggagaaaag tgtgaatttg acataaatga atgcaaagat ccctcaaata | 840 |
| taaatggagg ttgcagtcaa atttgtgata atacacctgg aagttaccac tgttcctgta | 900 |
| aaaatggttt tgttatgctt tcaaataaga agattgtaa agatgtggat gaatgctctt | 960 |

```
tgaagccaag catttgtggc acagctgtgt gcaagaacat cccaggagat tttgaatgtg   1020
aatgccccga aggctacaga tataatctca aatcaaagtc ttgtgaagat atagatgaat   1080
gctctgagaa catgtgtgct cagctttgtg tcaattaccc tggaggttac acttgctatt   1140
gtgatgggaa gaaaggattc aaacttgccc aagatcagaa gagttgtgag gttgtttcag   1200
tgtgccttcc cttgaacctt gacacaaagt atgaattact ttacttggcg gagcagtttg   1260
caggggttgt tttatattta aaatttcgtt tgccagaaat cagcagattt tcagcagaat   1320
ttgatttccg gacatatgat tcagaaggcg tgatactgta cgcagaatct atcgatcact   1380
cagcgtggct cctgattgca cttcgtggtg gaaagattga agttcagctt aagaatgaac   1440
atacatccaa aatcacaact ggaggtgatg ttattaataa tggtctatgg aatatggtgt   1500
ctgtggaaga attagaacat agtattagca ttaaaatagc taaagaagct gtgatggata   1560
taaataaacc tggaccccct tttaagccgg aaaatggatt gctggaaacc aaagtatact   1620
ttgcaggatt ccctcggaaa gtggaaagtg aactcattaa accgattaac cctcgtctag   1680
atggatgtat acgaagctgg aatttgatga agcaaggagc ttctggaata aaggaaatta   1740
ttcaagaaaa acaaaataag cattgcctgg ttactgtgga gaagggctcc tactatcctg   1800
gttctggaat tgctcaattt cacatagatt ataataatgt atccagtgct gagggttggc   1860
atgtaaatgt gaccttgaat attcgtccat ccacgggcac tggtgttatg cttgccttgg   1920
tttctggtaa caacacagtg ccctttgctg tgtccttggt ggactccacc tctgaaaaat   1980
cacaggatat tctgttatct gttgaaaata ctgtaatata tcggatacag gccctaagtc   2040
tatgttccga tcaacaatct catctggaat ttagagtcaa cagaaacaat ctggagttgt   2100
cgacaccact taaatagaa accatctccc atgaagacct tcaaagacaa cttgccgtct   2160
tggacaaagc aatgaaagca aaagtggcca catacctggg tggccttcca gatgttccat   2220
tcagtgccac accagtgaat gccttttata atggctgcat ggaagtgaat attaatggtg   2280
tacagttgga tctggatgaa gccatttcta acataatga tattagagct cactcatgtc   2340
catcagtttg gaaaaagaca aagaattctt aaggcatctt ttctctgctt ataatacctt   2400
ttccttgtgt gtaattatac ttatgtttca ataacagctg aagggtttta tttacaatgt   2460
gcagtctttg attatttgt ggtccttttcc tgggattttt aaaaggtcct ttgtcaagga   2520
aaaaaattct gttgtgatat aaatcacagt aaagaaattc ttacttctct tgctatctaa   2580
gaatagtgaa aaataacaat tttaaatttg aattttttc ctacaaatga cagtttcaat   2640
ttttgtttgt aaaactaaat tttaattta tcatcatgaa ctagtgtcta aatacctatg   2700
tttttttcag aaagcaagga agtaaactca aacaaagtg cgtgtaatta aatactatta   2760
atcataggca gatactattt tgtttatgtt tttgtttttt tcctgatgaa ggcagaagag   2820
atggtggtct attaaatatg aattgaatgg agggtcctaa tgccttattt caaaacaatt   2880
cctcaggggg aacagctttg gcttcatctt tctcttgtgt ggcttcacat ttaaaccagt   2940
atctttattg aattagaaaa caagtgggac atattttcct gagagcagca caggaatctt   3000
cttcttggca gctgcagtct gtcaggatga gatatcagat taggttggat aggtggggaa   3060
atctgaagtg ggtacatttt ttaaattttg ctgtgtgggt cacacaaggt ctacattaca   3120
aaagacagaa ttcagggatg gaaaggagaa tgaacaaatg tgggagttca tagttttcct   3180
tgaatccaac ttttaattac cagagtaagt tgccaaaatg tgattgttga agtacaaaag   3240
gaactatgaa aaccagaaca aattttaaca aaaggacaac cacagaggga tatagtgaat   3300
```

```
atcgtatcat tgtaatcaaa gaagtaagga ggtaagattg ccacgtgcct gctggtactg    3360
tgatgcattt caagtggcag ttttatcacg tttgaatcta ccattcatag ccagatgtgt    3420
atcagatgtt tcactgacag ttttttaacaa taaattcttt tcactgtatt ttatatcact    3480
tataataaat cggtgtataa ttttaaaatg catgtgaata tctttattat atcaactgtt    3540
tgaataaaac aaaattacat aatagacatt taactcttca aaaaaaaaaa aaaaa         3595

<210> SEQ ID NO 156
<211> LENGTH: 11687
<212> TYPE: DNA
<213> ORGANISM: Homo sapiens

<400> SEQUENCE: 156
aacaaagagc acgcggcgct ggccgccggc actcgcgccc tgaggctgcg gccccggagc      60
gcccggcggc ggtttcggcg cgcggccggg ctggcgatgg aagatggaag gaaggagcgc     120
agcggcagag acatttgttt gggtgaacaa tgcatctgca cattcccaga gtgttgccaa     180
ggccaaatat gaatttttat ttggcagatc tgaagggaaa gctccagata ctagtgatca     240
tggaggaagc actttactcc caccaaatgt cacaaatgaa tttccagaat atgggaccat     300
ggaggaaggt ggagaaggcc taagggcttc tctggaattt gatggtgagg ctctgccatg     360
ccacccacaa gagcagcagg gtgtccagcc tcttactggc tgccactctg ggctcgacag     420
tgttacagaa ggaccaaaag atgtcagaga ggcccctct caaagtcatc tcaaggaaca      480
aagtttacag cccattgact ctttgatttc agctctgaaa gccacagaag ccagaatcat     540
ttccggaaca ttacaggcta caaaggtact ggaccaagat gctgtttcta gttttttcagt   600 tcagcaggtg gaaaaagagc tggacactgc cagtcgtaaa acacagagag tcaacaaaac     660
gctccctgct ggccaaaaaa atttaccaga aatacctctt tcagctgaag taacaacgga     720
ggaaagtttt tatttgagca tccagaaaga tctcaccgcg ctgttaactg agacactca     780 ggcagagatt tccagataa tgaataatgg gaggaaaggg ctgtctgtg tgcaggagcc       840 atcttgtcct ttggcctccc tcgggagctc agcagtgacc tgccactctg caggcagtgt     900
tggtttcttg aaagagcaga ggtctgctct tgggagagag cacccagggg gatgtgatcg     960
aagcagctcc atgggacgcc caggccgggt caaacatgtg gaatttcaag gagtggaaat    1020
actgtggaca ggaggagaca agagagagac ccagcatcct atagattttg agacatcact    1080
gcaaagaaca gcctctcctg acagcaaaga gtcttccaaa gtgccacgcc atctcatctc    1140
atcagctggt ttgtgtaatt caagtagttt aactgagaat gtttgggatg aatcctggaa    1200
agctccttca gagaggcctg gcactagctc ggggacattt tcccctgtgc gtcttgatga    1260
gagtggagag gatgaagtct tcctacagga aaacaaacag catcttgaga agacacctaa    1320
accagagaga gacagggaaa ggatcagcga acaagaggag cacgttaagg gggaagatga    1380
agacatcctt gggcctggat atacggagga ctccaccgac gtgtacagct cccagtttga    1440
aaccattttg gacaacactt ctttatacta cagtgcagag tccctggaga cattatactc    1500
agagcctgat agctattta gctttgaaat gccctcact ccaatgatac aacagcgcat      1560
taaagaaggt ggtcagttct tggagaggac atcaggggga ggacatcagg atatcctgag    1620
tgtgtctgca gatggtggca tcgtgatggg ctattctagt ggcgtcacca atggggctgaa   1680 tgatgccagc gactccatct acacgaaagg caccccggag attgcttttct ggggaagcaa   1740 tgctgggggtg aaaacaacac ggctagaagc tcattctgaa atggggagca ctgaaatttt    1800
ggaaaaggag accccagaaa atctcagtaa tggtaccagc agcaatgtgg aagcagccaa    1860
```

```
aaggttggcc aaacgccttt atcagctgga cagattcaaa agatcagatg ttgcaaaaca   1920
ccttggcaag aacaacgaat ttagcaaact agttgcagaa gaatatctga agttttttga   1980
ttttacagga atgacgctgg atcagtcact caggtatttc tttaaagcat tctctcttgt   2040
gggagaaact caagaacgag agagagtttt aatacacttc tccaatagat atttttattg   2100
taacccagat accattgctt cacaagatgg agtccattgc cttacctgtg caataatgct   2160
tcttaatacc gatctacatg gccacaatat tggaaagaag atgacctgtc aggagttcat   2220
tgcaaatctg caaggggtaa atgagggtgt tgatttctcc aaggatctgc tgaaagctct   2280
gtacaactca atcaagaatg agaagcttga atgggcagta gatgatgaag agaaaaaaaa   2340
gtctccctca gaaagtactg aggagaaagc taacggaaca catccaaaga ccatcagtcg   2400
tattggaagt actactaacc cattttggga cattcctcat gatccaaatg ctgctgtgta   2460
caaaagtgga ttcttggctc ggaaaattca tgcagatatg gatggaaaga agactccaag   2520
aggaaaacga ggatggaaaa ccttttatgc tgtactgaag ggaacagttc tttacttgca   2580
aaaggatgaa tacaagccag aaaaggcctt gtctgaagag gacttgaaaa acgctgtgag   2640
tgtgcaccac gcattggcat ccaaggccac ggactatgag aagaaaccaa acgtgtttaa   2700
acttaaaact gccgactgga gggtcttgct ttttcaaact cagagcccag aggaaatgca   2760
agggtggata aacaaaatca attgtgtggc agctgtattt tctgcaccac catttccagc   2820
agcaatcggc tctcagaaga gtttagccg cccacttctg cctgccacta acaaaaact    2880 gtctcaggag gagcaactga agtcacatga aagtaagctg aagcagatca ccaccgagct   2940
ggccgagcac cgctcatatc cccccgacaa gaaggtcaaa gccaaggacg tcgatgagta   3000
caaactgaaa gaccactatc tggagtttga gaaaacccgc tatgaaatgt atgtcagcat   3060
tctcaaggaa ggaggcaaag agctactgag taacgatgaa agcgaggctg caggactgaa   3120
gaagtcgcac tcgagtcctt cgctgaaccc ggatacttct ccaatcactg ccaaagtcaa   3180
gcgtaacgtg tcagagagga aggatcaccg acctgaaaca ccaagcatta agcaaaaagt   3240
tacttagagt ccatctgcgg ccaggaagtg ctggtcatgg agcaaaatag gttttttcaa   3300
gatctttctg gtaatccgtg aatatattta aaaaaaaaa gtctgtgaca aaacggtgca   3360
ttagtaattt tttctattgt atattttgt tagtttctgt acagattgtc tttgctcttg    3420
atttcttttg ctttgatgat ttttgcaact tgatagctaa tgcacctttt ctgtgaggag   3480
gaggggatcg tgatttcaga atgaattatg tatcccttct cttttggttt tctcttgttt   3540
gcagtctgct cagttgtttt atgtattctc atatcaactg ttaaacttt ttttaaggtt   3600 aaagaattta atccattgtg aaacacttaa ctggacaaac tgtagtttta gtaaattcta   3660
gctggagtta atatacgcct ttatatgtga aatcttgccc agtcacagag gtagaattga   3720
gcactcacag atgctccagt aagaatcaca gtgctgggaa tctagttgct ccaatatgag   3780
gcagcttcat gtgcagctta gcacttgttg ttgagatcgg accctgctgg aagcagggaa   3840
aagaagcgtg aagatcgtag gattgagaac ttagggaagc acattagctt gcttgaagtg   3900
ctgattccat ttcagccaag caagggaaag aggaagtgga gtcattttgc ctttgaaggc   3960
tgaggaaaga ttgataccca gttaatttg tttgctaaag gatgggggca ataatcggcc   4020
cttgaggagc tgcagcagta ggcatgtgct cagtctgcag gaattgttac ctcactccca   4080
cagggtctag actagaaatc catcatctct atcgttgata tccttccatc aggaatagaa   4140
tttttcttac tctacatatg tgtgtgtgcg tgcgtgtgtg tgcgtgtgtg ggcatgggg t   4200
```

```
tgtgtcctgg ttgtgatatt gaggtcttcc ttcctaacaa attaatacta aaatgaaaca      4260
gcttttcttg tgtccttaag acaaaataag gaaggaaaac gtagctgcag ttgtccacga      4320
tggatattgg ttcttaaaa tatatctgaa agtagtagtc agaatgaatt atggttggaa       4380
aactgaggaa tcttctggtt gcaggtgcaa agtgactttg tttattcttg tctcagtctc      4440
cttgatagcc acttcactct gctactactc aactttctcc taaaaatact tcatctattt     4500
tcagtccttt ctttctgtct actcaaaatg gttctattaa ctttgcagtc atgagcttgt      4560
tccagttaca gtccctttga agttcagggt gataaacaga atattcttct gtagaggaag     4620
agaaaggagt gaaagtttag cccactgaga cctagagctt tgtgatttcc taaccttgaa     4680
actctgtaat ccctaaagtt aaaatctccg caagtggcac aacttcagaa ctaatagtat      4740
cactttgatt tttcttttc ctcccttaga agtttctct agttctatag tttatttgtt        4800
gaaggtacta tgaccaaaga atcagctgct ctacaggaat agcatggttc cagtgaatta      4860
gagaaaacct gctgtaaagc catggtagtg tctaagtggt atgttattat gatgtactag     4920
catttattta cagaattatt tattaacgtt tacttccttc ccctctgtaa atgtccatga     4980
ctattgccca gagaaggctt acccctctct agggttgcag ttgctttctt tgtaataagt    5040
attttgccac acctgtaaaa aaaaaaacct cacttttaac tctctgcctt gtttgggtaa    5100
aggcagtaac taagtttatg tttcagaact gcaaaacaaa caggatagtt accaatatgg    5160
cccatgtatc agattgattt tgtagcctc tcactgaatc caacatatcc acaagcaagt     5220
tatctgtctt tctacctgat aatctaaatt atcaggatat tgttttctg cctaaatgtt     5280 tatactaagc cgaggggaga gaggtaccta gaccatgtca tctacaagct tcagtaacta   5340
aagaaaaagg aacttccctg agtggcttga atgtgtttgc ccacagtcta tatctatgta    5400
tatagaatgt ctgtatgtat tttacttatt taatatacat tgaatggtac cttgctacag    5460
tatttctgac atttagagta gtgttgaaat actcggctag catcagcacc actatagcac    5520
tgtccgtgtc atatgagtca ctaatattaa ctccagggac ttctggatag gctaatagat    5580
cattggatac gaagggctct tttgaagctt cagtatacca tgtttgcata gtttatcttt    5640
aaaaacaact ttaaaggttc ttttgtgagc caggatctca gactgccgta gcatgatgct   5700
gtccatcttt agcgcatggg ctgagaacac ctcttccctg aggcttctga aggttgctgt    5760
ctgtcatgag tgcatgaagg aggccaagag tttatgctat gggaggaaac agtcactgat    5820
ttgcctagat tctgagagtc tggcccatag ccaaccacat tttccttgg gataaattat     5880 ttcctgtggc atctagccag aagaaattga ggatgtttcc tttcacagct gctccaagcc    5940
tgttgcccaa ttcacggtac aagggagcac cccttccctt tcctctgaag gtacgccacc    6000
cacctccgtc gcccacctca gcgcccagga gccttgggac ttccttccat atgataaatc    6060
attcttcttc acgtcaatac acttcatatt aatttctagt acagaaaatc ttgacagcta    6120
tcagaatgcc ttggtcatag tgttgttgca aaattgacca tacaggtggc ccatgtataa    6180
aatctgaatt ttaggggttt gtccccacct cgcatgctgg cttttacagg gaggtgtctg    6240
ggattcctca ttagcaatca aaacttaatt actgggatgc agagtcctta ctttatcgcc    6300
agcccgtagg catttctgaa gtgcactttt ttgaaacatc attttgctaa ctctcagcag    6360
tgtctaatta aactgagcaa tacttttgtg aattttaatt aatctcagca aaccatgat     6420 gggagagagt cctctgatgg aaatgtagtc cctggattat gtgtaacctt tttattcctc    6480
ttagatgcag aggatagaaa gcatttttg gtgcagtggt cttgtggcaa acacaagacc     6540
ctctatgcgt ctccaactgt tatcctaatc tagaaaatga ggactggccc ctgggcaaaa    6600
```

```
gtgacatgag gaatttactc tggaagagga aaatctgggt ggcttttccaa ggctaagata   6660 ggtttgtatt tcaccctgtg gccaagctac agaacttctg agattgtgga agaattttttg  6720 caaccagcag ggaaagaggc ctcttactgc ctaaacacaa agttacactg agcttttcta   6780
ctgtcctttg cctattgctc cctctatcat gtaaagatct gggaaggatg agaggcaggg   6840
cctgcttgtc atgagctgca ctcttttctt tttaactaat cattgacaat tggaagaaaa   6900
ttgacgttaa agaagtttct ccattgtctt actaacaaaa cctttttgggt ttcattaatt  6960 gtccttgaaa ttgagttcct ttggcatttt tccttgcagt catcagttaa gcatgttgca   7020
tcctgaattc acagaagttt agctttgcag gtttgaatct ctgtaattta actcccgtgg   7080
acttggtcga gttttcagca ggttgggagc cacctctctt catttcagca gtgagtcatc   7140
ccttgacttt tcaaatgaca gaatttttc caattgtaaa attagcactg taaaacaaag    7200
aaccaaagtg gcatcctaag agttgttaaa cctgaagtct agtttatgag gaattgtcca   7260
agttggagtt taaatagtat ctgcttttgt ctcaaagcat ctaagttatt ctgacagaaa   7320
atggtaagtc agctttgcag gcagatgcgc ctctgggcct cctaccttgc tccacagctt   7380
tctggccatc ttgtctccca ggccatgcca ctgctctgcc acatgtcagc aaatttcttt   7440
ccaccagtct tatagcatct tacatgatca aatcatcaca gaataacccc gtgatagatt   7500
attgatagca atagagaggg gctttgtcac tgattttttct ctcagattcc ttttccatct  7560
ctcatccata aaggaaggac tgaaatccaa aggcattctc cttttgtacc tacagtatcc   7620
agaacccacg tgggcagcct tctgcttatg acaataattg gcccattgca tgcagagaga   7680
atgtcttcat agagagaatg tcattaaata cttgaatctg catgacagtt tgacttgaat   7740
gcaacagcag gaaaattttg caagttacat aattgtatat acagtaggtt ttcttaagtc   7800
tcttcggttc atcctttgta atttgtgtgt gtatctgtag tattgcaggc ttttggagac   7860
tattcttaca ggcagtatgt cagtcatcaa agaaaatgct gtcacctgcc attgttgtat   7920
ttgtgggtat ttatagttgt atgtatgtaa atgcatcagt gtgtagattg catatcagtg   7980
tatggtacat gtacatcaaa attatttttg tccttaatca gtgtgatatg aaaagcaagt   8040
acaacctcat aggactgatt atataatgaa gttgttgaga gtatatatag tggtattgtt   8100
ttattaaact taaactcaaa taatattttg attaaaattt ttaataagac tttatgctag   8160
aaaattcttt gagctttgaa tcaccagggc aaaaatgact ttcaactaac cttgtgaatc   8220
ttttgcagtg tactgtgtgc aataccaagg gcatagctcc ctgtaatttg ggaaatacag   8280
aaagaaaaga aaaaaaaaaa aaaggcagc ctgtgcagtc ttagtaactt tagtattaag    8340
agcacttaaa gtcaaactga caattttggg cttattacaa aatgtgatgc tttaaagcac   8400 acgttctttta ttgttgttgt aattagtcca taaaaaatat agcttcgga agaattaagt   8460 acccaccata tcatttatgt atttgtgtat gttttacggg agatcaaacc actctcgtgg   8520
tgccgcatcc gtactcgctt gacttggaag aaatatcaca agcactaaag tatatcaggg   8580
catcccagga ttgggtactg tatcctaggt ttgcagttgc agaaattagc atctagtgtc   8640
acaggtaaaa gaatttcagg accaggttta aactttattt taaatatttt tatacttagg   8700
tctctttttc ctgcctctcc ccaaagaaga gccactggcc ttagttgttt gagcttactg   8760
cttatattat agagtgtaaa taggtaacta gagactaaaa ttttattaac cagcatgttt   8820
ggtatattta aagcagtgac tgagtgtgtt tgagtgagtg gctgagtgca gtgtcttttg   8880
tttaaacaca ctgcctcgtg tctttgtagc tgattcagag agtttgaatt gtggggtggg   8940
```

```
agactaactt cagctccagg ctgcagtaat gtgttggtag ttacacttga ggcattttt    9000
tgttgttgtt aattaactct atagtctcaa actattttg caaatatatc attttcctta   9060
attggttctt gacgtgcagt ggactggctc tgtgaatgat tggcagggtc ttagttttgc   9120
gagagtattt ccttctaaga attattgtga tctgcagaaa cagccatttg attcaaaaat   9180
catgtagaaa aggagtagga gaagcaaaac gtttcatttt tgggccttaa ccatttgaaa   9240
tgtttggact ttaaacataa agccatggag tttataaagc caagtaacca tttgatatgg   9300
ataataatat ctactctaga gagagtatat atatgcacat tgattttaa tgctgttaag    9360
atacttttgt aaaactgtag gaacaagagt aattagacca aattgaagct tagggacag    9420
taaagtggtt gctttccatt tagggtaacc atgcatgtgg ttagtcctct cctcctgaga   9480
ttcagaacca gttgactgtc cccttaggtg tataaggaga aaagttgaca tgtctgggac   9540
ctctgacatg tgtacacatg cttgcacaca tgcacacaca gtgaatgttt taagttatac   9600
aaacataaga ccttaagatg caaagagcca gaatattcta aagaggtgat gaacagaggg   9660
ggtggaaact gcatcacaga tgttttccaa gggccagggt ggaatctgag ctctagtgtc   9720
tgactttgag atgcattata ttttaacac ataatgagg ggatccatat cacattcttt     9780
cttgtggacc accaaattga aggctttctt gtaattcaca agcagcagct ctccagcatc   9840
tctccgtagc ctgggtgaag tcccagaagc tggtgtgcat cattttccaa ggtggcagag   9900
ctgcttgctc tgcagatcat tcctttgaga gaggagtaca agtgaagaaa caaggaggca   9960
cttcctgtag gagcactgat gtgccttgtc cacactcccc tctgagcttt actggtaaga  10020
gagctccgac tgaacatgct gagcagttga gcacttttcc atcagcaaca acagcgagga  10080
tggaaatgga aaggaaccga actaaaatgc atttcccttt gcagggcaga gagctaagct  10140
cttaggaata gtgttataga aataagcacc ctaacttcaa ttcctgaaaa tgttggttaa  10200
tggagagaat tttggagttt cacttaatat tttcccatcg gtcgccataa ataagtcttc  10260
aggcgctcct agaagagtcc cagcccaagg ctcgattaag gaccacactg caggtctgag  10320
gctcactgct ctgagtcctg aacaccagag ccctgcagag agtggtgata acacatcatc  10380
tctgcaaaga ggaacctctc ccccggccgc cacttcactc aggcttctac tgagcagcaa  10440
ggacagcctg ggtttcaaat gccacttccc ctgctttagg gatccaggtg tcctgatagc  10500
gtgaccctgc tgaggcaagg tatcaactcc gagagtgact gagtcactga gcgtggcaca  10560
tgaacaaacg tcatgacaaa gattctctga gtgaagttaa caccacgtat tttacctttg  10620
caaaaaacaa actggcaccc tgagttctaa ctacggacgg acgatatctt tgcctccaca  10680
cccagattcc tggaaatggc taacgtttcc tttctagggg aagggtcgag gaatactcaa  10740
gtgctagctt agcagctttg ttcagtccag atcagagctg ttaggtaaag gcctaaccac  10800
ctccctgcag tctcttatat ctcaagcttt aggaacccat ttctaaatgt acactagcgg  10860
agaatttata ttgtcagcct tgattaccat aggacaggca gaaaggcgat aatttgtatc  10920
ttttaatata aaagaagctt ttaacttttc cagcctatta taatactga gttatattca   10980
ctgtggctca aactaattgg cattgtggaa catttcttta ccttcaaagt tttctccacc  11040
aatcatttca gttctattgc agtcctggtg ccatatgtcc cctgcaaatt gtgaaagtaa  11100
ttagtgacaa aatagcagcc tgctcctttt caatggcgaa actgtcggca ttagcagttt  11160
tgggtaagct ggcggtacta taacacgtac tggaaacctg ttcctcatca ccacctacca  11220
gattctggaa atgccgtctt ctagaaaacg atggcgtttt tggtggtctt cttttgaaag  11280
gaacagtaat ttgtgtggat attgttaaag tgtttaaaga atattttgac aattaagttt  11340
```

```
acattttaca attgctttat tttttattaa aatagttgta tataaatatt accctatttc    11400
actgttgttc aagtaaatct aaaccttgta gacaagtgag tcatctgata tgtatagaag    11460
ctgtgatata tagagtacat ttattgtgta aatgtttatg aatataattg ttcctgtgtt    11520
tttataagtt ggggatattt tgttgtttta cggcaacaaa atttattgca tttaaatggt    11580
ttttatgtaa tagaaatcac gcaaaatagt gaaggattta aaatatgtat atgatacatg    11640
taaatgtaca aactttagaa agaaataaat ccaacaaatt tcaatca                 11687

<210> SEQ ID NO 157
<211> LENGTH: 1719
<212> TYPE: DNA
<213> ORGANISM: Homo sapiens

<400> SEQUENCE: 157
ggcgatggga aggcgggcgc agtcgaccca agggtggaga agagggaagg cgaaggacgc      60
gcgttcccgg gctcgtgacc gccagcggcc cggggaaccc gctcccagac agactcggag     120
agatggcagg cggaagacac cggcgcgtcg tgggcaccct ccacctgctg ctgctggtgg     180
ccgccctgcc ctgggcatcc aggggggtca gtccgagtgc ctcagcctgg ccagaggaga     240
agaattacca ccagccagcc attttgaatt catcggctct tcggcaaatt gcagaaggca     300
ccagtatctc tgaaatgtgg caaaatgact acagccatt gctgatagag cgatacccgg      360
gatcccctgg aagctatgct gctcgtcagc acatcatgca gcgaattcag aggcttcagg     420
ctgactgggt cttggaaata gacaccttct tgagtcagac accctatggg taccggtctt     480
tctcaaatat catcagcacc ctcaatccca ctgctaaacg acatttggtc ctcgcctgcc     540
actatgactc caagtatttt tcccactgga caacagagt gtttgtagga gccactgatt      600
cagccgtgcc atgtgcaatg atgttggaac ttgctcgtgc cttagacaag aaactccttt     660
ccttaaagac tgtttcagac tccaagccag atttgtcact ccagctgatc ttctttgatg     720
gtgaagaggc ttttcttcac tggtctcctc aagattctct ctatgggtct cgacacttag     780
ctgcaaagat ggcatcgacc ccgcacccac ctggagcgag aggcaccagc caactgcatg     840
gcatggattt attggtctta ttggatttga ttggagctcc aaacccaacg tttcccaatt     900
tttttccaaa ctcagccagg tggttcgaaa gacttcaagc aattgaacat gaacttcatg     960
aattgggttt gctcaaggat cactctttgg aggggcggta tttccagaat tacagttatg    1020
gaggtgtgat tcaggatgac catattccat ttttaagaag aggtgttcca gttctgcatc    1080
tgataccgtc tccttttcct gaagtctggc acaccatgga tgacaatgaa gaaaatttgg    1140
atgaatcaac cattgacaat ctaaacaaaa tcctacaagt cttgtgttg gaatatcttc      1200 atttgtaata ctctgattta gtttaggata attggttcta gaattgaatt caaaagtcaa    1260
ggcatcattt aaaataatct gatttcagac aaatgctgtg tggaaacatc tatcctatag    1320
atcatcctat tcttatgtgt ctttggttat cagatcaatt acagaataat tgtgttgtga    1380
tattgtgtcc taaattgctc attaattttt atttacagat tgaaaagag ggaccgtgta     1440 aagaaaatgg aaaataaata tctttcaaag actcttttag ataaacacga tgaggcaaaa    1500
tcaggttcat tcattcaacg atagtttctc aacagtactt aaatagcggt tggaaaacgt    1560
agccttcatt ttatgatttt ttcatatgtg gaaatctatt acatgtaata caaaacaaac    1620
atgtagtttg aaggcggtca gatttctttg agaaatcttt gtagagttaa ttttatggaa    1680
attaaaatca gaattaaatg ctaaaaaaaa aaaaaaaaa                           1719
```

<210> SEQ ID NO 158
<211> LENGTH: 2824
<212> TYPE: DNA
<213> ORGANISM: Homo sapiens

<400> SEQUENCE: 158

```
gttttgaaag ttgatggagc gaactgcttt tccaaagact cttttgaaaa acttttttaag      60
taggccattc tgactttaac atttctcttt gtcttaacat tagacaaaaa gtaaccttcc     120
tgaagaggac atgtgattgg aagttgtcaa ttgttgaagc attggtaact ccagtctcta     180
acgttttaga aaatcataac aagcggttct ctaccctgta aaggtgaact actgagttct     240
tcattatgtc tgatggagat tatgattacc tcatcaagtt tttagctttg ggagactctg     300
gtgtagggaa gaccagtgta ctttaccaat atacagatgg taaatttaac tccaaattta     360
tcacaacagt gggcattgat ttcagggaaa aaagagtggt gtacagagcc agtgggccgg     420
atggagccac tggcagaggc cagagaatcc acctgcagtt atgggacaca gcagggcagg     480
agaggtttcg tagcttaacg acagcgttct tcagagatgc tatgggtttt cttctacttt     540
ttgatctgac aaatgagcaa agtttcctca atgtcagaaa ctggataagc cagctacaga     600
tgcatgcata ttgtgaaaac ccagatatag tgctgtgtgg aaacaagagt gatctggagg     660
accagagagt agtgaaagag gaggaagcca tagcactcgc agagaaatat ggaatcccct     720
actttgaaac tagtgctgcc aatgggacaa acataagcca agcaattgag atgcttctgg     780
acctgataat gaagcgaatg gaacggtgtg tggacaagtc ctggattcct gaaggagtgg     840
tgcgatcaaa tggtcatgcc tctacggatc agttaagtga agaaaaggag aaaggggcat     900
gtggctgttg agaagtcaag taagcgacat agtagttcag gtggcccatg cctgggatct     960
tctctatgat tgatacatgg cacagtgaga gattaatggg cattgtgtac aaattgcttc    1020
tcaccatccc cattagacct acgaataaag catccggttc taaaattaat ttgttgcagc    1080
tttgtaaaata tttctttaag attcagcctg agagttagga gaaatatttc agagccaaaa    1140
gtgccttata caaccttagc ctattatagt aaatcattca aggattcaga attttgcagt    1200
cacagaagag tgtatttatt atgtagaatg aatgagggta ctgtcacctg ccttaatgta    1260
ggtaggccca gagtcttaca tttaagatct tacatgcagt tataaaaccg ccacagtctt    1320
caatccagat ttgaagactc atgccatagg tgacattcta aaataccatt aaagccactt    1380
aaatgttaaa taagaatata catgcacatc agctcaatgt ctttgagtat taattttatg    1440
taagcattct atttaacatg aatataggac aaatcatggc tatatctata gaccttggat    1500
aaactggatt gaccaattat acactcacgg tgactttttt attggtggga aggggattgg    1560
ggtggggcag gctggcttaa tgtaatatga gcaaccaaag tgggacttct gtctccccgc    1620
tatattccca ttgctctgaa tggttgattg aagggtcagg gaactagatt ttatggcttt    1680
agttcactgt gattgtacat ttatacttgg cctatgtgct ggccgcacct gaacatagct    1740
ggtgcttatg ccgagttatt tgcgatgagt aaatatttag tttcttttc ttcatattta    1800
taatgttgat ctggcatcct caggctgcag ctttattagc ttataactta ctcatctcta    1860
tctttaccag caggctctgt attgttgata tttgcaactt gttttgcttt tccattggtg    1920
gaattgaaat aattagtttt taattacata agatgcctgt ttgctatttg gtggaagata    1980
gatgttcata ttgaagcagt cacatttgta ctgtagttca ataaaagaaa atgaagtat    2040
tctgtagcct atatttttca tagagctcat gagcatttac tgtacttgct gggtcttgcc    2100
aagatcattt attccgctgc attgccaaag tgtcttcata ccaaattaaa ggtggtttta    2160
```

```
atatatgttt catggaagtt gtttataaaa ttcaaaggta tttcatttag gtgaaaagtc    2220
ttatttatta aagtggtttg aataaagtag atcaaaactt ccagagatct taatggctat    2280
ataggaagaa atatcactca ccataattta aataaagaat aaaaatactt gtattttgtg    2340
gtggcaaatg tttggtagaa ctgtaattag aaaaatacaa gtatatttgc gtgatggtta    2400
cactagaagc ccagacttta cgactacaca atatattcat gtatctaaac tgtacttgta    2460 cccctaaat  ttattttaa  aaaggaaaa  ataaagtat  catgaaaaaa  cctatttttt    2520
tttccactgt ccttccacta ctcccataac aaacttatcc atggttggta aaattttaca    2580
tatttctatc cttgaaatga aggcttcttt taaattccaa agaagtcatg gaggcctgtg    2640
catttgaatt gtatatgcta gtgaggaaaa gatttagaca tttcaagagc agggttggcc    2700
aggcgcggtg gctcacacct gtaatcccag cactttggga ggccgaggag gcggatcac     2760 gaggtcagga gatcgagacc atcctggcta acacagtgaa accccatctc tactaaaaaa    2820
aaaa                                                                 2824
```

<210> SEQ ID NO 159
<211> LENGTH: 1856
<212> TYPE: DNA
<213> ORGANISM: Homo sapiens

<400> SEQUENCE: 159

```
gtggcaagag tagcggtgac ggcggcggcg gcggcggcgg cagcattatg cgtgattact      60
gacaggcacc agctgctgcc gccacagccg tctcaaacgc actatgtgga ctctccgatc     120
tagaggcaga ttcctgacta atcccagagg gctggcccag cctgtgctcc ccgggctgct    180
aggaagcgat gaccactctt gttagcccaa gttgaagaaa gccgggctgt gcctgggagc    240
cgagagaggc ggtaatattt agaagctgca caggagagga acatgaactg acgagtaaac    300
atgtatggaa attattctca cttcatgaag tttcccgcag gctatggagg ctcccctggc    360
cacactggct ctacatccat gagcccatca gcagccttgt ccacagggaa gccaatggac    420
agccacccca gctacacaga tacccccagtg agtgccccac ggactctgag tgcagtgggg    480 accccctca  atgccctggg ctctccatat cgagtcatca cctctgccat gggcccaccc     540
tcaggagcac ttgcagcgcc tccaggaatc aacttggttg ccccacccag ctctcagcta    600
aatgtggtca acagtgtcag cagttcagag gacatcaagc ccttaccagg gcttcccggg    660
attggaaaca tgaactaccc atccaccagc cccggatctc tggttaaaca catctgtgcc    720
atctgtggag acagatcctc aggaaagcac tacggggtat acagttgtga aggctgcaaa    780
gggttcttca agaggacgat aaggaaggac ctcatctaca cgtgtcggga taataaagac    840
tgcctcattg acaagcgtca gcgcaaccgc tgccagtact gtcgctatca gaagtgcctt    900
gtcatgggca tgaagaggga agctgtgcaa gaagaaagac agaggagccg agagcgagct    960
gagagtgagg cagaatgtgc taccagtggt catgaagaca tgcctgtgga gaggattcta    1020
gaagctgaac ttgctgttga accaaagaca gaatcctatg gtgacatgaa tatggagaac    1080
tcgacaaatg accctgttac caacatatgt catgctgctg acaagcagct tttcaccctc    1140
gttgaatggg ccaagcgtat tccccacttc tctgacctca ccttggagga ccaggtcatt    1200
ttgcttcggg cagggtggaa tgaattgctg attgcctctt tctcccaccg ctcagtttcc    1260
gtgcaggatg gcatccttct ggccacgggt ttacatgtcc accggagcag tgcccacagt    1320
gctggggtcg gctccatctt tgacagagtc ctaactgagc tggtttccaa aatgaaagac    1380
```

```
atgcagatgg acaagtcgga actgggatgc ctgcgagcca ttgtactctt taacccagat    1440
gccaagggcc tgtccaaccc ctctgaggtg gagactctgc gagagaaggt ttatgccacc    1500
cttgaggcct acaccaagca gaagtatccg gaacagccag gcaggtttgc caagctgctg    1560
ctgcgcctcc cagctctgcg ttccattggc ttgaaatgcc tggagcacct cttcttcttc    1620
aagctcatcg gggacacccc cattgacacc ttcctcatgg agatgttgga gacccgctg     1680 cagatcacct gagccccacc agccacagcc tccccaccca ggatgacccc tgggcaggtg    1740
tgtgtggacc cccaccctgc actttcctcc acctcccacc ctgaccccct tcctgtcccc    1800
aaaatgtgat gcttataata aagaaaacct ttctacacat gaaaaaaaaa aaaaaa        1856

<210> SEQ ID NO 160
<211> LENGTH: 2640
<212> TYPE: DNA
<213> ORGANISM: Homo sapiens

<400> SEQUENCE: 160
actcgccgca gcctgcgcgc cttctccagt ccgcggtgcc atggccccg cccgtctgtt      60 cgcgctgctg ctgttcttcg taggcggagt cgccgagtcg atccgagaga ctgaggtcat    120 cgaccccag gacctcctag aaggccgata cttctccgga gccctaccag acgatgagga    180
tgtagtgggg cccgggcagg aatctgatga cttttgagctg tctggctctg gagatctgga   240
tgacttggaa gactccatga tcggccctga agttgtccat cccttggtgc ctctagataa    300
ccatatccct gagagggcag ggtctgggag ccaagtcccc accgaaccca gaaaactaga    360
ggagaatgag gttatcccca agagaatctc acccgttgaa gagagtgagg atgtgtccaa    420
caaggtgtca atgtccagca ctgtgcaggg cagcaacatc tttgagagaa cggaggtcct    480
ggcagctctg attgtgggtg gcatcgtggg catcctctt gccgtcttcc tgatcctact     540
gctcatgtac cgtatgaaga agaaggatga aggcagctat gacctgggca agaaacccat    600
ctacaagaaa gccccccacca atgagttcta cgcgtgaagc ttgcttgtgg gcactggctt    660
ggactttagc ggggagggaa gccaggggat tttgaagggt ggacattagg gtagggtgag    720
gtcaacctaa tactgacttg tcagtatctc cagctctgat tacctttgaa gtgttcagaa    780
gagacattgt cttctactgt tctgccaggt tcttcttgag ctttgggcct cagttgccct    840
ggcagaaaaa tggattcaac ttggcctttc tgaaggcaag actgggattg gatcacttct    900
taaacttcca gttaagaatc taggtccgcc ctcaagccca tactgaccat gcctcatcca    960
gagctcctct gaagccaggg ggctaacgga tgttgtgtgg agtcctggct ggaggtcctc    1020
ccccagtggc cttcctccct tcctttcaca gccggtctct ctgccaggaa atgggggaag    1080
gaactagaac cacctgcacc ttgagatgtt tctgtaaatg ggtacttgtg atcacactac    1140
gggaatctct gtggtatata cctggggcca ttctaggctc tttcaagtga cttttggaaa    1200
tcaacctttt ttatttgggg gggaggatgg ggaaaagagc tgagagttta tgctgaaatg    1260
gatttataga atatttgtaa atctattttt agtgtttgtt cgttttttta actgttcatt    1320
cctttgtgca gagtgtatat ctctgcctgg gcaagagtgt ggaggtgccg aggtgtcttc    1380
attctctcgc acatttccac agcacctgct aagtttgtat ttaatggttt ttgttttttgt   1440 ttttgtttgt ttcttgaaaa tgagagaaga gccggagaga tgattttat taattttttt     1500 tttttttttt tttttttact atttatagct ttagataggg cctcccttcc cctcttcttt    1560
ctttgttctc tttcattaaa ccccttcccc agtttttttt ttatactta aacccgctc      1620 ctcatggcct tggcccttc tgaagctgct tcctcttata aaatagcttt tgccgaaaca     1680
```

```
tagttttttt ttagcagatc ccaaaatata atgaagggga tggtgggata tttgtgtctg    1740
tgttcttata atatattatt attcttcctt ggttctagaa aaatagataa atatatttt     1800 ttcaggaaat agtgtggtgt ttccagtttg atgttgctgg gtggttgagt gagtgaattt    1860
tcatgtggct gggtgggttt ttgccttttt ctcttgccct gttcctggtg ccttctgatg    1920
gggctggaat agttgaggtg gatggttcta cccttttctgc cttctgtttg ggacccagct   1980
ggtgttcttt ggtttgcttt cttcaggctc tagggctgtg ctatccaata cagtaaccac    2040
atgcggctgt ttaaagttaa gccaattaaa atcacataag attaaaaatt ccttcctcag    2100
ttgcactaac cacgtttcta gaggcgtcac tgtatgtagt tcatggctac tgtactgaca    2160
gcgagagcat gtccatctgt tggacagcac tattctagag aactaaactg gcttaacgag    2220
tcacagcctc agctgtgctg gacgacccct tgtctccctg ggtagggggg ggggaatggg    2280
ggagggctga tgaggcccca gctggggcct gttgtctggg accctccctc tcctgagagg    2340
ggaggcctgg tggcttagcc tgggcaggtc gtgtctcctc ctgacccccag tggctgcggt   2400 gagggaacc accctccctt gctgcaccag tggccattag ctcccgtcac cactgcaacc     2460
cagggtccca gctggctggg tcctcttctg cccccagtgc ccttcccctt gggctgtgtt    2520
ggagtgagca cctcctctgt aggcacctct cacactgttg tctgttactg attttttttg    2580
ataaaaagat aataaaacct ggtactttct aaaaaaaaaa aaaaaaaaa aaaaaaaaa      2640
```

<210> SEQ ID NO 161
<211> LENGTH: 3300
<212> TYPE: DNA
<213> ORGANISM: Homo sapiens

<400> SEQUENCE: 161

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaagcctc    240
ccccgttgcc cctctggatc cactgcttaa atacggacga ggacagggcc ctgtctcctc    300
agcttcaggc accaccactg acctgggaca gtgaatcgac aatgccgtct tctgtctcgt    360
ggggcatcct cctgctggca ggcctgtgct gcctggtccc tgtctccctg ctgaggatc     420 cccagggaga tgctgcccag aagacagata catcccacca tgatcaggat cacccaacct    480
tcaacaagat caccccccaac ctggctgagt tcgccttcag cctataccgc cagctggcac   540
accagtccaa cagcaccaat atcttcttct ccccagtgag catcgctaca gcctttgcaa    600
tgctctccct ggggaccaag gctgacactc acgatgaaat cctggagggc ctgaatttca    660
acctcacgga gattccggag gctcagatcc atgaaggctt ccaggaactc ctccgtaccc    720
tcaaccagcc agacagccag ctccagctga ccaccggcaa tggcctgttc ctcagcgagg    780
gcctgaagct agtgggataag ttttttggagg atgttaaaaa gttgtaccac tcagaagcct   840
tcactgtcaa cttcggggac accgaagagg ccaagaaaca gatcaacgat tacgtggaga    900
agggtactca agggaaaatt gtggatttgg tcaaggagct tgacagagac acagttttg     960 ctctggtgaa ttacatcttc tttaaaggca atgggagag accctttgaa gtcaaggaca    1020
ccgaggaaga ggacttccac gtggaccagg tgaccaccgt gaaggtgcct atgatgaagc    1080
gtttaggcat gtttaacatc cagcactgta agaagctgtc cagctgggtg ctgctgatga    1140
```

```
aatacctggg caatgccacc gccatcttct tcctgcctga tgaggggaaa ctacagcacc   1200
tggaaaatga actcacccac gatatcatca ccaagttcct ggaaaatgaa gacagaaggt   1260
ctgccagctt acatttaccc aaactgtcca ttactggaac ctatgatctg aagagcgtcc   1320
tgggtcaact gggcatcact aaggtcttca gcaatgggGC tgacctctcc ggggtcacag   1380
aggaggcacc cctgaagctc tccaaggccg tgcataaggc tgtgctgacc atcgacgaga   1440
aagggactga agctgctggg gccatgtttt tagaggccat acccatgtct atccccccg    1500 aggtcaagtt caacaaaccc tttgtcttct taatgattga acaaaatacc aagtctcccc   1560
tcttcatggg aaaagtggtg aatcccaccc aaaaataact gcctctcgct cctcaacccc   1620
tcccctccat ccctggcccc ctccctggat gacattaaag aagggttgag ctggtccctg   1680
cctgcatgtg actgtaaatc cctcccatgt tttctctgag tctcccttg cctgctgagg    1740 ctgtatgtgg gctccaggta acagtgctgt cttcgggccc cctgaactgt gttcatggag   1800
catctggctg ggtaggcaca tgctgggctt gaatccaggg gggactgaat cctcagctta   1860
cggacctggg cccatctgtt tctggagggc tccagtcttc cttgtcctgt cttggagtcc   1920
ccaagaagga atcacagggg aggaaccaga taccagccat gaccccaggc tccaccaagc   1980
atcttcatgt cccctgctc atcccccact cccccccacc cagagttgct catcctgcca    2040
gggctggctg tgcccacccc aaggctgccc tcctgggggc cccagaactg cctgatcgtg   2100
ccgtggccca gttttgtggc atctgcagca acacaagaga gaggacaatg tcctcctctt   2160
gacccgctgt cacctaacca gactcgggcc ctgcacctct caggcacttc tggaaaatga   2220
ctgaggcaga ttcttcctga gcccattct ccatggggca acaaggacac ctattctgtc    2280
cttgtccttc catcgctgcc ccagaaagcc tcacatatct ccgtttagaa tcaggtccct   2340
tctccccaga tgaagaggag ggtctctgct ttgttttctc tatctcctcc tcagacttga   2400
ccaggcccag caggcccag aagaccatta ccctatatcc cttctcctcc ctagtcacat    2460
ggccataggc ctgctgatgg ctcaggaagg ccattgcaag gactcctcag ctatgggaga   2520
ggaagcacat cacccattga ccccgcaac ccctcccttt cctcctctga gtcccgactg    2580
gggccacatg cagcctgact tctttgtgcc tgttgctgtc cctgcagtct tcagagggcc   2640
accgcagctc cagtgccacg gcaggaggct gttcctgaat agccctgtg gtaagggcca    2700 ggagagtcct tccatcctcc aaggccctgc taaaggacac agcagccagg aagtcccctg   2760
ggcccctagc tgaaggacag cctgctccct ccgtctctac caggaatggc cttgtcctat   2820
ggaaggcact gccccatccc aaactaatct aggaatcact gtctaaccac tcactgtcat   2880
gaatgtgtac ttaaaggatg aggttgagtc ataccaaata gtgatttcga tagttcaaaa   2940
tggtgaaatt agcaattcta catgattcag tctaatcaat ggataccgac tgtttcccac   3000
acaagtctcc tgttctctta agcttactca ctgacagcct ttcactctcc acaaatacat   3060
taaagatatg gccatcacca agcccctag gatgacacca gacctgagag tctgaagacc    3120
tggatccaag ttctgacttt tccccctgac agctgtgtga ccttcgtgaa gtcgccaaac   3180
ctctctgagc cccagtcatt gctagtaaga cctgcctttg agttggtatg atgttcaagt   3240
tagataacaa aatgtttata cccattagaa cagagaataa atagaactac atttcttgca   3300
```

<210> SEQ ID NO 162
<211> LENGTH: 4038
<212> TYPE: DNA
<213> ORGANISM: Homo sapiens

<400> SEQUENCE: 162

-continued

```
tgggggcggt ggcagggccg gtgggcggtg gcggctcccg gtctcggctc gggcacggcc      60
ctgggcaggc cgcccgccag ccgcaggggc gctcctgagc ttcgcggggc cgcagtccgg     120
gatgcctgcg cgaagggagg ggcgaagggc cggccgttgc cgacgtgggt gttaagtggc     180
cgccccagcc ggcgacccgg agccgagagc gggcggcgga gcctgagctg gacgcggcca     240
cgccggcgcg gcgggatatg tggtgcctgt cataagctcc agagagctgc cttccacaag     300
accagcagaa gagtgggcaa acatgaaatc caatcctgct atccaggctg ccattgacct     360
cacagcgggg gctgcaggag gtacagcatg tgtactgacc gggcagccct ttgacacaat     420
gaaagtgaag atgcagacgt tccctgacct gtaccggggc ctcaccgact gctgcctgaa     480
gacttactcc caggtgggct tccgtggctt ctacaagggt accagtccag cactaatcgc     540
caacatcgct gagaactcag tcctcttcat gtgctacggc ttctgccagc aggtggtgcg     600
gaaagtggct ggattggaca agcaggcaaa gctgagtgat ctgcagaatg cagccgccgg     660
ttccttcgcc tctgcctttg ctgcactggt gctctgcccc acggagctcg tgaagtgccg     720
gctgcagacc atgtatgaga tggagacatc agggaagata gccaagagcc agaatacagt     780
gtggtctgtc atcaaaagta ttcttaggaa agatggcccc ttggggttct accatggact     840
ctcaagcact ttacttcgag aagtaccagg ctatttcttc ttcttcggtg gctatgaact     900
gagccggtcc ttttttgcat cagggagatc aaaagatgaa ttaggccctg tacctttgat     960
gttaagtggt ggagttggtg ggatttgcct ctggcttgcg gtatacccag tggattgtat    1020
caaatccaga attcaagttc tttccatgtc tggaaaacag gcaggattta tcagaacctt    1080
tataaatgtt gtgaaaaatg aaggaataac ggccttatat tctggactga acctactat    1140 gattcgagca ttccctgcca atggagcact cttttttggcc tacgaatata gcaggaagtt    1200
gatgatgaac cagttggaag catactgaag tgtcttggtg ggcctgagcc aagcacaggt    1260
gtttgaggac tacagttcat ctcagggttt cttggagtac aagaccagtg tgaagttatt    1320
ctgatttctt gggaattttg cttttttgtct tcccttctac cctacatctt aaactttatg    1380
gaagaacctc tattttgcat catatcattt ctgtccataa ttgtactgaa atagaaaagt    1440
gaccgctctt gctcttggta aaatatagag tggtcagtag cettatgcac ctaattcaaa    1500 aggtggaata tagttctgtc agggctttta cgtaaacctc cacttgtaca tgcaatttgg    1560
acagttatgt gttgagggaa atacagtttg gtaccttgtt tatttcaaat atcagaaaaa    1620
cccagaggtg atcatttctc atgaagatgc ttataaatgg ttgcttaacc cattctagat    1680
gtagggtctg cttaatgtgt gtactttttct aagtggttga ttatttttta ttttttgat    1740 acagagtctc actctgtcac ccagactgga gtgcagtggc acgatctcgg ctcactgcaa    1800
cctccgcctc ctgggttcaa gcgattctct cacctcagcc tcctgagtag ctgggattac    1860
aggtacgcgc caccatgtcc agctaatttt ttttggtatt ttttgtagag acgaggtttc    1920
accatgttgt ccaggttggt ctcgaactcc tgacctcaag tgatccgccc acctcggcct    1980
cccaaagtgc tgggattact ggtgtgagcc accatgccca gccagtggtt gaattttta    2040 aaaagtgttc atggggtgct tgaaaactaa aatatccttc tagatttgta agacagtata    2100
cctgcatact ggtgtggctt ccacacttga gtaaaagctt cagagtaggt atcctagatt    2160
tccccaagat gctctactct taaaatagtg ccattcattt tctaggtggg atcatattcc    2220
acgctgacta tattgctagg ggtggcccag agggtcaggc cttggggaaa tagcatggcc    2280
tttaccagct tcccttctct cccaaagaac ttcccttctt gggctttaga ttgaggaagg    2340
```

| | |
|---|---|
| ggctgagtgg taggcggtgc tgctgtgctc tgatgaagac ccatgtggct agcaacagcg | 2400 |
| cttaccttttt gtctctgggt cctggcctgg ggccatcaat ccactttggg ccactcactg | 2460 |
| tctgctctgc ctccaccaat cagaaaccct tccaaggaac agtgagagcc aaagccaaga | 2520 |
| gaagccttct tccctgtttg gtgattgtgt gacagtgggt gaacctctct cagagagaac | 2580 |
| tagaaagaac tcagtgcttg tactccacag tgagtaatgt caggtctgac ccatcctgaa | 2640 |
| gcctgtcttg ccatgctttt acagtgttgg aggcttctac atttggtact tgcagtcagt | 2700 |
| aagtcttaat gatgactgta tatgtgatat gagtttataa agcaatggaa cataagaaaa | 2760 |
| gcaattgtag gccaggcgca gtggctcacg cctataatcc cagcactttg ggaggctgag | 2820 |
| gcgggcgggt cacaaggtca ggagttcgag aacagcctga ccaacatggt gaaacccccat | 2880 |
| ctctactaaa aatacaaaaa ttagctgggc gtggtggcac gtgcctgtaa tcccagctac | 2940 |
| tcaggaggct gaggcaggag aatcgcttga acccgggagg cagaggttgc agtgaactga | 3000 |
| gattgtgcca ctgcactcca gactgggtga cacagcgaga cttcatctca aaaaaaaaaa | 3060 |
| gaaaagaaaa gcaattgtac ttcactatgc catatgtatg tattcactga ccaaaaattc | 3120 |
| actgaccaac caaccaaact ccacacttca tctgatcccc catagacttg gggatggaca | 3180 |
| gctgttcttt ggccatatgg tataagagga tcattcttgt cactacttaa gttagcctca | 3240 |
| tcattttgtg ctgctccaac accagcaggg tatctcccaa taaagtgttc ctaagcagcc | 3300 |
| tgtatactga gtgcaagcag gctatcaatt ttaataatag tccataccat gtatgtgttt | 3360 |
| ctgtcagcag aatgtacatg ttgtacaaaa cctccaggtt ccttaagctt tttgctgtcc | 3420 |
| atgaatcctc tgtggcaact gtaatcacag agccagaagc cagagggcca gggatatgag | 3480 |
| aggctgacaa acatcagggg acatctgggg aggagatccc tgtcatgtct cttgtgccat | 3540 |
| ggagctatta tggctggtct tccatttgct ttttctttaa gtgaaaacca tttttctact | 3600 |
| ttgcttttct ctccatactt aaatggtcag tagctactga gtggtgcttt atctgaatag | 3660 |
| gcctggatcg aagtaaaata gaaatgggac tggctttcca caggaagtaa actgcttcag | 3720 |
| agcccacagt cccctgctca gtgtccggaa agaagtcagt catccctgtt ggcagtaaat | 3780 |
| cttcccacag gccgtccatt agagatttaa ctagatatgt tcaatagaaa gagtctgagg | 3840 |
| caagtggaaa tgaggaacgg aaacttaggt tgggagaata ttttttttttt attcattctg | 3900 |
| tttgcttaat tcagagtaca gtttgtgcta tttcatatct gtactccagg cagaaatata | 3960 |
| acttgaaaat actgtgtcta aagaaatttc agtgttctat cattaaatta tttacttaat | 4020 |
| aaaaaaaaaa aaaaaaaa | 4038 |

<210> SEQ ID NO 163
<211> LENGTH: 7693
<212> TYPE: DNA
<213> ORGANISM: Homo sapiens

<400> SEQUENCE: 163

| | |
|---|---|
| gcggcggcgg ccgcggtggc agcgaaggcg gcggcggcgg cggcagtggc agtggccgct | 60 |
| gcagccccac actccgccgc caaactggag gagcgacgga agccagaccc caggaggatg | 120 |
| gaggatgaag ctgtcctgga cagagggggct tccttcctca gcatgtgtg tgatgaagaa | 180 |
| gaagtagaag gccaccatac catttacatc ggagtccatg tgccgaagag ttacaggaga | 240 |
| aggagacgtc acaagagaaa gacagggcac aaagaaaaga aggaaaagga gagaatctct | 300 |
| gagaactact ctgacaaatc agatattgaa aatgctgatg aatccagcag cagcatccta | 360 |
| aaacctctca tctctcctgc tgcagaacgc atccgattca tcttgggaga ggaggatgac | 420 |

-continued

```
agcccagctc cccctcagct cttcacggaa ctggatgagc tgctggccgt ggatgggcag    480
gagatggagt ggaaggaaac agccaggtgg atcaagtttg aagaaaaagt ggaacagggt    540
ggggaaagat ggagcaagcc ccatgtggcc acattgtccc ttcatagttt atttgagctg    600
aggacatgta tggagaaagg atccatcatg cttgatcggg aggcttcttc tctcccacag    660
ttggtggaga tgattgttga ccatcagatt gagacaggcc tattgaaacc tgaacttaag    720
gataaggtga cctatacttt gctccggaag caccggcatc aaaccaagaa atccaacctt    780
cggtccctgg ctgacattgg gaagacagtc tccagtgcaa gtaggatgtt taccaaccct    840
gataatggta gcccagccat gacccatagg aatctgactt cctccagtct gaatgacatt    900
tctgataaac cggagaagga ccagctgaag aataagttca tgaaaaaatt gccacgtgat    960
gcagaagctt ccaacgtgct tgttggggag gttgactttt tggatactcc tttcattgcc   1020
tttgttaggc tacagcaggc tgtcatgctg ggtgccctga ctgaagttcc tgtgcccaca   1080
aggttcttgt tcattctctt aggtcctaag gggaaagcca agtcctacca cgagattggc   1140
agagccattg ccaccctgat gtctgatgag gtgttccatg acattgctta taaagcaaaa   1200
gacaggcacg acctgattgc tggtattgat gagttcctag atgaagtcat cgtccttcca   1260
cctggggaat gggatccagc aattaggata gagcctccta agagtcttcc atcctctgac   1320
aaaagaaaga atatgtactc aggtggagag aatgttcaga tgaatgggga tacgccccat   1380
gatggaggtc acggaggagg aggacatggg gattgtgaag aattgcagcg aactggacgg   1440
ttctgtggtg gactaattaa agacataaag aggaaagcgc cattttttgc cagtgatttt   1500
tatgatgctt taaatattca agctctttcg gcaattctct tcatttatct ggcaactgta   1560
actaatgcta tcacttttgg aggactgctt ggggatgcca ctgacaacat gcagggcgtg   1620
ttggagagtt tcctgggcac tgctgtctct ggagccatct tttgcctttt tgctggtcaa   1680
ccactcacta ttctgagcag caccggacct gtcctagttt tgagaggct tctatttaat   1740
ttcagcaagg acaataattt tgactatttg gagtttcgcc tttggattgg cctgtggtcc   1800
gccttcctat gtctcatttt ggtagccact gatgccagct tcttggttca atacttcaca   1860
cgtttcacgg aggagggctt ttcctctctg attagcttca tctttatcta tgatgctttc   1920
aagaagatga tcaagcttgc agattactac cccatcaact ccaacttcaa agtgggctac   1980
aacactctct tttcctgtac ctgtgtgcca cctgacccag ctaatatctc aatatctaat   2040
gacaccacac tggccccaga gtatttgcca actatgtctt ctactgacat gtaccataat   2100
actaccttg actgggcatt tttgtcgaag aaggagtgtt caaatacgg aggaaacctc   2160
gtcgggaaca actgtaattt tgttcctgat atcacactca tgtcttttat cctcttcttg   2220
ggaacctaca cctcttccat ggctctgaaa aaattcaaaa ctagtcctta ttttccaacc   2280
acagcaagaa aactgatcag tgattttgcc attatcttgt ccattctcat cttttgtgta   2340
atagatgccc tagtaggcgt ggacacccca aaactaattg tgccaagtga gttcaagcca   2400
acaagtccaa accgaggttg gttcgttcca ccgtttggag aaaaccctg gtgggtgtgc   2460
cttgctgctg ctatcccggc tttgttggtc actatactga ttttcatgga ccaacaaatt   2520
acagctgtga ttgtaaacag gaaagaacat aaactcaaga aaggagcagg gtatcacttg   2580
gatctctttt gggtggccat cctcatggtt atatgctccc tcatggctct tccgtggtat   2640
gtagctgcta cggtcatctc cattgctcac atcgacagtt tgaagatgga gacagagact   2700
tctgcacctg gagaacaacc aaagtttcta ggagtgaggg aacaaagagt cactggaacc   2760
```

```
cttgtgttta ttctgactgg tctgtcagtc tttatggctc ccatcttgaa gtttataccc    2820
atgcctgtac tctatggtgt gttcctgtat atgggagtag catcccttaa tggtgtgcag    2880
ttcatggatc gtctgaagct gcttctgatg cctctgaagc atcagcctga cttcatctac    2940
ctgcgtcatg ttcctctgcg cagagtccac ctgttcactt tcctgcaggt gttgtgtctg    3000
gccctgcttt ggatcctcaa gtcaacggtg gctgctatca ttttccagt aatgatcttg     3060 gcacttgtag ctgtcagaaa aggcatggac tacctcttct cccagcatga cctcagcttc    3120
ctggatgatg tcattccaga aaggacaag aaaagaagg aggatgagaa gaaaaagaaa      3180
aagaagaagg gaagtctgga cagtgacaat gatgattctg actgcccata ctcagaaaaa    3240
gttccaagta ttaaaattcc aatggacatc atggaacagc aacctttcct aagcgatagc    3300
aaaccttctg acagagaaag atcaccaaca ttccttgaac gccacacatc atgctgataa    3360
aattcctttc cttcagtcac tcggtatgcc aagtcctcct agaactccag taaaagttgt    3420
gcctcaaatt agaatagaac ttgaacctga agacaatgat tatttctgga ggagcaaggg    3480
aacagaaact acattgtaac ctgtttgtct ttcttaaaac tgacatttgt tgttaatgtc    3540
atttgttttt gtttggctgt tgttttattt tttaactttt atttcgtctc agttttgt     3600 cacaggccaa ataatacagc gctctctctg cttctctctt gcatagatac aatcaagaca    3660
atagtgcacc gttccttaaa aacagcatct gaggaatccc ccttttgttc ttaaactttc    3720
agatgtgtcc tttgataacc aaattctgtc actcaagaca cagacacgca cagaccctgt    3780
cctttgcctc tattaagcag aggatggaag tattaaggat tttgtaacac ctttttatgaa   3840 aatgttgaag gaacttaaaa ctttagcttt ggagctgtgc ttactggctt gtctttgtct    3900
ggtagaacaa accttgacct ccagacagag tcccttctca cttatagagc tctccaggac    3960
tggaaaaagt gctgctattt taacttgctc ttgcttgtaa atcctaatct tagagttatc    4020
aaaagaagaa aaaactgaag gtactttact ccctatagag aaaccattgc catcattgta    4080
gcaagtgctg gaatgtccct ttttcctat gcaactttt ttaacccttt aatgaactta      4140
tctgttgagt acattgaaga atattttct tcctagattt tgttgtttaa attatggggc     4200
ctaacctgcc acttatttt tgtcaatttt taaaactttt tttaattac tgtaaagaaa      4260 atgaattttt tcctgcagca ggaaacatag ttttgagtag ttctacctct tatttgtagc    4320
tgccaggctt tctgtaaaaa ttgtattgta tataatgtga tttttacaca tacatacaca    4380
cacaaataca caatctctag ggtaagccag aaggcaagat cagattaaaa acaccatgtt    4440
tctaagcatc cattttccc tttctttaaa agaaacttaa ctgttctatg aaggagattg     4500
agggagaaga gacaaactcc tatgtcatga gaataaccga tgttctgata atagtagcat    4560
ctaggtacag atgctggttg tattaccacg tcaatgtcct atgcagtatt gttagacatt    4620
ttctcatttt gaaatatttg tgtgtttgtg tatgtgctct gtgccatggc tggtgtatat    4680
atgtgcaatg ttagaaggca aaagagtgat ggtaggcaga gggcaaagtc attgaatctc    4740
ttatgccagt tttcataaaa cccaaaccac atatgaaaaa atccattaag ggtccaagaa    4800
gtctgtccat atgaaaatga gggtaaatat agtttatttc ccaggtatca gtcattataa    4860
ttgatataat agctctaaca tgcaatataa aattcatagg agtattaata gcccatttac    4920
acatctataa aatgtaatgg gattgcagag ctgcagagta cagtgtaaca gtactctcat    4980 gcaattttt tcaggatgca aaggcaatta ttctttgtaa gcgggacatt tagaatatat     5040
ttgtgtacat attatatgta tgtatatttc aaagtaccac actgaaaatt agacatttat    5100
taaccaaatt taacgtggta tttaaaggta atatttttaa tatgatacat tacatattgt    5160
```

```
gaatgtatac taaaaaaaca ttttaaatgt taaaattata atttcagatt catataacca   5220
caactgtgat atatcctaac tataaccagt tgttgagggg tatactagaa gcagaatgaa   5280
accacatttt ttggtttgat aatatgcact tattgactcc cactcattgt tatgttaatt   5340
aagttattat tctgtctcct tgtaattttg attacaaaaa ttttattatc ctgagttagc   5400
tgttactttt acagtacctg atactcctaa aactttttaac ttatacaaat tagtcaataa   5460
tgaccccaat ttttttcatta aaataatagt ggtgaattat atgttattgt gttaaaacct   5520
cacttgccaa attctggctt cacatttgta tttagggcta tccttaaaat gatgagtcta   5580
tattatctag ctttctatta ccctaatata aactggtata agaagacttt ccttttttct   5640
ttatgcatgg aagcatcaat aaattgttta aaaccatgt atagtaaatt cagcttaacc    5700
cgtgatcttc ttaagttaaa ggtacttttg ttttataaaa gctctagata aactttcttt   5760
ttctgatcat gaatcaagta tctgtggttt catgcccctc tctataccttc tcaaagaact   5820 cctgaagcaa cttaactcat catttcagcc tctgagtaga ggtaaaacct atgtgtactt   5880
ctgtttatga tccatattga tatttatgac atgaacacag aatagtacct tacatttgct   5940
aaacagacag ttaatatcaa atcctttcaa tattctggga acccagggaa gttttttaaaa   6000 atgtcattac tttcaaagga acagaagtag ttaaccaaac taacaagcaa aacctgaggt   6060
ttacctagtg acaccaaatt atcggtatt taactgaatt tacccattga ctaagaatga    6120
accagatttg gtggtggttt tgtttctatg caaactggac acaaattaca acagtaaatt   6180
tttttataag tgcttctccc ttctccatga tgtgacttcc ggagataaag gattcaaaag   6240
ataaagacaa agtacgctca gagttgttaa ccagaaagtc ctggctgtgg ttgcagaaac   6300
actgttggaa gaaagagat gactaagtca agtgtctgcc ttatcaaaag agcaaaaatg    6360
cctctggttt tgtgtttggg agaaaaatat cttggacgca ctgttttcct tgataaaagt   6420
catcttctct actgtgtgaa atgaatactt ggaattctaa ttgttttgtg tgccaggggc   6480
agtaatgtcc ctgcctcttc tcccaatcaa ggttgaggag tggggctggg gagaggactt   6540
aactgactta agaagtagga aaacaaaaac ctctctcctc agccttccac ctccaagaga   6600
ggaggaaaaa cagttgtctg ctgtctgtaa ttcagtttgc gtgtatttta tgctcatgca   6660
ccaacccata cagagtaaat cttttatcaa ctatatactg gtgtttaata gagaatgatt   6720
gtcttccgag tttttttggtt ccttttttaa ctgtgttaaa gtacttgaaa tgtattgact   6780
gctgactata ttttaaaaac aaaatgaaat aatttgagtt gtattacaga ggttgacatt   6840
gttcagggat gggacaaagc cttcttcaat ccttttcata ctacttaatg attttggtgc   6900
aggaacctga gattttctga tttatatttc atgatatttc acatttgctc ttcacagcat   6960
gagcatgaag cccagtggca ccaaatggct gggtacaatc aagtgatatt ttgtagcacc   7020
tcactatctg aaaggccatg agttttcaga tgatttcatt gagcttcatt gcagcctgaa   7080 atttttaaaaa agttgtgtaa tacgccaacc agtcaagttg tgttttggcc agagatttag   7140
atatgtccaa tttcctggct catttcattg tgctctatgg gtacgtataa aaagcaagaa   7200
ttctgtttcc taggcaaaca ttgcaactca gggctaaagt catccagtga aacttttaga   7260
gccagaagta actttgtccc agtcctacaa tgtgaaaaga gtgaatagtt gcctcttttt   7320 agccatttc atggctggta catattcgta cgcattactt ttcagaatca atacgcactt    7380
tcagatattc ttattttttat tctcttaagt ctttattaac tttggagaga gaatgatgc    7440 atctttttat tttaaatgaa gtagatcaac atggtggaac aaaatgataa agaacagaaa   7500
```

-continued

| | |
|---|---:|
| acatttcaat atattactaa taacttttc caatataaat cctaaaattc ctataacata | 7560 |
| gtattttaca gttttatgaa gctttctatt gtgacttta tggaattaag agatgaagaa | 7620 |
| gatgagatat tttagcattt atattttca aaattatatg tatacttaaa aataaagtaa | 7680 |
| ctttatgcat tta | 7693 |

<210> SEQ ID NO 164
<211> LENGTH: 7949
<212> TYPE: DNA
<213> ORGANISM: Homo sapiens

<400> SEQUENCE: 164

| | |
|---|---:|
| gggagaggga gacgcaggcg gcgaaacggc agaggagccg agccccctcc gcccaaggcg | 60 |
| ccctccctcc gtccgcgcac aggcgccgtc gcttggagga gcaaggtgcc tcccagcccg | 120 |
| caggggcgcc gcgcgcaagc ccgcgggctc ttcggtggct ctgccccggg actgcacctg | 180 |
| gaggcggccc cggacgggga tggtcagcgg ctgctgccgt ctggctcgcg agcgggacgc | 240 |
| tgtgagggca ccatggcgct gactcccggg tggggtcct cggcggggcc ggtccggccg | 300 |
| gagctctggc tgctgctgtg ggcagccgcg tggcgcctgg gtgcctcggc gtgccccgcc | 360 |
| ctctgcacct gcaccggaac cacggtggac tgccacggca cggggctgca ggccattccc | 420 |
| aagaatatac ctcggaacac cgagcgcctg gaactcaatg caacaacat cactcggatc | 480 |
| cataagaatg actttgcggg gctcaagcag ctgcgggtgc tgcagctgat ggagaaccag | 540 |
| attggagcag tggaacgtgg tgcttttgat gacatgaagg agctggagcg gctgcgactg | 600 |
| aaccgaaaacc agctgcacat gttaccggaa ctgctgttcc agaacaacca ggctttgtca | 660 |
| agactggact tgagtgagaa cgccatccag gccatcccca ggaaagcttt tcggggagct | 720 |
| acggacctta aaaatttaca gctggacaag aaccagatca gctgcattga ggaaggggcc | 780 |
| ttccgtgctc tgcgggggct ggaggtgctg accctgaaca caacaatat caccaccatc | 840 |
| cccgtgtcca gctcaacca tatgcccaag ctacggacct tccgcctgca ctccaaccac | 900 |
| ctgttttgcg actgccacct ggcctggctc tcgcagtggc tgaggcagcg gccaaccatc | 960 |
| gggctcttca cccagtgctc gggcccagcc agctgcgtg gcctcaatgt ggcagaggtc | 1020 |
| cagaagagtg agttcagctg ctcaggccag ggagaagcgg ggcgcgtgcc cacctgcacc | 1080 |
| ctgtcctccg gctcctgccc ggccatgtgc acctgcagca atggcatcgt ggactgtcgt | 1140 |
| ggaaaaggcc tcactgccat cccggccaac ctgcccgaga ccatgacgga gatacgcctg | 1200 |
| gagctgaacg gcatcaagtc catccctcct ggagccttct caccctacag aaagctacgg | 1260 |
| aggatagacc tgagcaacaa tcagatcgct gagattgcac ccgacgcctt ccagggcctc | 1320 |
| cgctccctga actcgctggt cctctatgga aacaagatca gagacctccc ccgtggtgtg | 1380 |
| tttgaggcc tatacaccct acagctcctg ctcctgaatg ccaacaagat caactgcatc | 1440 |
| cggcccgatg ccttccagga cctgcagaac ctctcactgc tctccctgta tgacaacaag | 1500 |
| atccagagcc tcgccaaggg cacttcacc tccctgcggg ccatccagac tctgcacctg | 1560 |
| gcgcagaacc ctttcatttg cgactgtaac ctcaagtggc tggcagactt cctgcgcacc | 1620 |
| aatcccatcg agacgagtgg tgcccgctgt gccagtcccc ggcgcctcgc caacaagcgc | 1680 |
| atcgggcaga tcaagagcaa gaagttccgg tgctcagcca aagagcagta cttcattcca | 1740 |
| ggcacggagg attaccagct gaacagcgag tgcaacagcg acgtggtctg tcccacaaag | 1800 |
| tgccgctgtg aggccaacgt ggtggagtgc tccagcctga agctcaccaa gatccctgag | 1860 |
| cgcatccccc agtccacggc agaactgcga ttgaataaca tgagatttc catcctggag | 1920 |

```
gccactggga tgtttaaaaa acttacacat ctgaagaaaa tcaatctgag caacaacaag    1980
gtgtcagaaa ttgaagatgg ggccttcgag ggcgcagcct ctgtgagcga gctgcaccta    2040
actgccaacc agctggagtc catccggagc ggcatgttcc ggggtctgga tggcttgagg    2100
accctaatgc tgcggaacaa ccgcatcagc tgcatccaca acgacagctt cacgggcctg    2160
cgcaacgtcc ggctcctctc gctctacgac aaccagatca ccaccgtatc cccaggagcc    2220
ttcgacaccc tccagtccct ctccacactg aatctcctgg ccaaccottt caactgcaac    2280
tgccagctgg cctggctagg aggctggcta cggaagcgca agatcgtgac ggggaaccocg    2340
cgatgccaga accctgactt tttgcggcag attcccctgc aggacgtggc cttccctgac    2400
ttcaggtgtg aggaaggcca ggaggagggg ggctgcctgc cccgcccaca gtgcccacag    2460
gagtgcgcct gcctggacac cgtggtccga tgcagcaaca agcacctgcg ggccctgccc    2520
aagggcattc ccaagaatgt cacagaactc tatttggacg ggaaccagtt cacgctggtt    2580
ccgggacagc tgtctacctt caagtacctg cagctcgtgg acctgagcaa caacaagatc    2640
agttccttaa gcaattcctc cttcaccaac atgagccagc tgaccactct gatcctcagc    2700
tacaatgccc tgcagtgcat cccgcctttg gccttccagg actccgctc cctgcgcctg    2760
ctgtctctcc acggcaatga catctccacc ctccaagagg gcatctttgc agacgtgacc    2820
tccctgtctc acctggccat ggtgccaac ccctatact gtgactgcca cctccgctgg    2880
ctgtccagct gggtgaagac tggctacaag gaaccgggca ttgctcgttg tgctgggccc    2940
caggacatgg agggcaagct gctcctcacc acgcctgcca agaagtttga atgccaaggt    3000
cctccaacgc tggctgtcca ggccaagtgt gatctctgct tgtccagtcc gtgccagaac    3060
cagggcacct gccacaacga ccccccttgag gtgtacaggt gcgcctgccc cagcggctat    3120
aagggtcgag actgtgaggt gtccctggac agctgttcca gtggccctg tgaaaatggg    3180
ggcacctgcc atgcacagga gggcgaggat gccccgttca cgtgctcctg tccaccggc    3240
tttgaaggac caacctgtgg ggtgaacaca gatgactgtg tggatcatgc ctgtgccaat    3300
gggggcgtct gtgtggatgg tgtgggcaac tacacctgcc agtgccccct gcagtatgag    3360
ggaaaggcct gtgagcagct ggtggacttg tgctctccgg atctgaaccc atgtcaacac    3420
gaggcccagt gtgtgggcac cccggatggg cccaggtgtg agtgcatgcc aggttatgca    3480
ggtgacaact gcagtgagaa ccaggatgac tgcagggacc accgctgcca gaatggggcc    3540
cagtgtatgg atgaagtcaa cagctactcc tgcctctgtg ctgagggcta cagtggacag    3600
ctctgtgaga tccctcccca tctgcctgcc cccaagagcc cctgtgaggg gactgagtgc    3660
cagaatgggg ccaactgtgt ggaccagggc aacaggcctg tgtgccagtg cctcccaggc    3720
ttcggtggcc ctgagtgtga aagttgctc agtgtcaact tgtgatcg gacacttac    3780
ctgcagttca ctgacctgca aaactggcca cgggccaaca tcacgttgca ggtctccacg    3840
gcagaggaca tgggatcct tctgtacaac ggggacaacg accacattgc agttgagctg    3900
taccagggcc atgtgcgtgt cagctacgac ccaggcagct accccagctc tgccatctac    3960
agtgctgaga cgatcaacga tgggcaattc cacaccgttg agctggttgc ctttgaccag    4020
atggtgaatc tctccattga tggcgggagc cccatgacca tggacaactt tggcaaacat    4080
tacacgctca acagcgaggc gccactctat gtgggagga tgcccgtgga tgtcaactca    4140
gctgccttcc gcctgtggca gatcctcaac ggcaccggct tccacggttg catccgaaac    4200
ctgtacatca acaacgagct gcaggacttc accaagacgc agatgaagcc aggcgtggtg    4260
```

```
ccaggctgcg aaccctgccg caagctctac tgcctgcatg gcatctgcca gcccaatgcc    4320
accccagggc ccatgtgcca ctgcgaggct ggctgggtgg gcctgcactg tgaccagccc    4380
gctgacggcc cctgccatgg ccacaagtgt gtccatgggc aatgcgtgcc cctcgacgct    4440
ctttcctaca gctgccagtg ccaggatggg tactcggggg cactgtgcaa ccaggccggg    4500
gccctggcag agccctgcag aggcctgcag tgcctgcatg ccactgcca ggcctcaggc     4560
accaaggggg cacactgtgt gtgtgacccc ggcttttcgg gcgagctgtg tgagcaagag    4620
tccgagtgcc gggggggaccc tgtccgggac tttcaccagg tccagagggg ctatgccatc    4680
tgccagacca cgcgccccct gtcatgggtg gagtgccggg gctcgtgccc aggccagggc    4740
tgctgccagg gccttcggct gaagcggagg aagttcacct ttgagtgcag cgatgggacc    4800
tcttttgccg aggaggtgga aaagcccacc aagtgtggct gtgccctctg cgcatagcgc    4860
tgggcgtgga caggccggtg agggcgggca agggccccca gccgctgcag cagcggagac    4920
agtcgccagc agctgggctg gggtgcaggt catcacagga cggctcctgg gcagctgggc    4980
cctcctgggt ggggtggtgc cagagcagcc ttttaaaagc aaattgcgcc atagctgggg    5040
gcagcggggg tgggcgaggc ctgagctgcg ggctgccctc tccggaagtg ccttgcacaa    5100
ataggcgctt aataaatatt tgttgagtga atgtgtgcgt gaggtcaggc caagaagtgc    5160
agaacgatga cacccctcct tacctgctat ctgaatctgg agaagaaaaa tgacagcctt    5220
ccaaaccaac ccttcccttt ggcctgtggc ccaggctggc ttggaactgg gtctgtggcc    5280
ccagaagcct cttacccctc tgcgggcaac catgaagtac tgtcagcctc cccgggaagc    5340
cagcctggtt cattctgctg ctacagaatc tgctggtggt aggccaggct ctggagcggg    5400
ggtgccgcct cctgctggcc agggagggtc ggacccttgc cccctgggct gactggcagc    5460
tctgcagcca cggcttggga acgaggctgt gggtggaggt ggttcttagg accaggcctc    5520
tgaatcctaa agttctagca tgactactgt agctgcgagg cttatgtgg aggaaacagt      5580
cacaggggct gctcagggtg gcagacccca ctaaagaggg cagagggttc tttgctctag    5640
ataaacaaac atcatctgcc tccagacact ggccacagta ggagtattgg tcctgggctt    5700
ccccagccac cagtcagcca caagctgtcg gtgacctatt ggtagaggga ctgggtgtga    5760
gggtctgggc cagggtgctt gacctgggag cagctggttc agagtccttc acaccgcagg    5820
ccagtaggga gcagtggaag ggacagtgct ccaggcattg gaagtccct gctggctcta     5880
tcactcgggg caaacttctc cccacctggg ccttgggttc ttcagctata aaatggccag    5940
aggtgggggg cggatgact aaaggaacag tgcagactcc cccactgtgg tcttgggagg     6000
ccagaggagt tagaagacct atctatctat ctatctatct acattgatca catcaaaagt    6060
atttatgtgc ctaacccggg gctgggatt gtggacgttc tggcctaatg gacagatgtg     6120
aactcatccc agagcatcgc aggaatgacc aggatgcccg ggaagagttg agctgagtgg    6180
gggctccagc cacagacagc ggcccaggcc agggagttgc tggcaacgaa ggagccagtg    6240
gtggaagaag aagaggccct gaatatacga ttgcctgccc acgttgtctt ctcttccata    6300
cacagtgaaa atgtagaaag atggtttgtg aggccaaact gtgaatgggc taaagggagg    6360
caaagttgca ctctccttcc ccagagggct caccaagagg gcacaccccc ggggttctg     6420
gtgggcaacg ggggtgagca tgtccctgcc ctggctccct ccatctgtga ccaggaggca    6480
tggctgggtg tatgttcagg tgaggctcag agtggcattg tgtccctgtc ccctgcccag    6540
ggcagtgagg ggagcccttg atgctgatta gaaggctaga actgggggtag aggtgcctgg    6600
catgtctcat gccatgggga ctcaatctag caactgtgag tcctggggtc cctgtgatgg    6660
```

| | |
|---|---|
| gaagagggca gtgccctgcc caatgtggca ggtgtcctca tggcaggatc tgcccctcac | 6720 |
| caggggctg ggatctactt gcttggagct ctgagcaagg ccacaatgcc cgcccccacc | 6780 |
| cccaagtaga ctgcagcctg ggcctcatgg ggcttctccc aggcccacat ggcatccctc | 6840 |
| tctgagtttc caggccaccg tgggaccctg cagagcatct gcaccgggct ggatagggca | 6900 |
| gaaaagctca agggcagcta gcttgcctct tccctggaag aaaggtgctc tgggactcac | 6960 |
| caaccctgag aaagatagct ttcctggcca ccaccattcc ccaccaccct ggagaagcca | 7020 |
| attcccaggc ttgaagggca ctggctggca ggaggcctct tcattctgca ggaggtggaa | 7080 |
| aggacacctg tagacaggtg atgctcaccc ctcacctggc gccatggggc tgggaggtga | 7140 |
| gcggctggca tgtttgttcc tagggagcac catgtgagct taaggctccc ctgaccggcc | 7200 |
| ccaccacatg gcccagcctc ctagcacagc agcgctgacc tcagtgcagt ctgaggattg | 7260 |
| gaatccacca tgagatgatg tgagagctgt gtgccccagg atcaactttt tctccaactt | 7320 |
| ggccatcagc cagcgagttg ctaaggacct gagtcagcac tcacgttgcc tattcacact | 7380 |
| ccgcttgaaa gtccggaagg tggctactgc aaaatcaccc ctctgagaag tcctctctcc | 7440 |
| acatcttgtc ccccttgtg aagacccta gttcgctctg catttaggc atgaagagat | 7500 |
| acagcagggt gcgtccggag ggagctgtgg ccttgcaaca ccactggcaa cagggccggg | 7560 |
| gctcccggtg aaggtgtcag gaagtggaaa aggctggact ttgtctcctc tttgcctgct | 7620 |
| ggtagcctaa ccgcaaaagt atctctttat acagaatact tacagattct aatatatatt | 7680 |
| tgtatttcat tttgttacag tatttttata tgttaaagtc aacatccagc gtcttgtttt | 7740 |
| gcctttcaga tgctatgtgg tcgtggcacg ttttgttggg ggtttctgta gtcgtcttgt | 7800 |
| ttggatcaac tcctagaggc tggtttagaa caggcccatg agggagctgc acctgccctg | 7860 |
| gaagtattgt tttagactat gtcgatattg tctgttgtct tccatgtgaa catgacattg | 7920 |
| agtcactctg caaaaaaaaa aaaaaaaaa | 7949 |

<210> SEQ ID NO 165
<211> LENGTH: 7924
<212> TYPE: DNA
<213> ORGANISM: Homo sapiens

<400> SEQUENCE: 165

| | |
|---|---|
| gccactaccc gctgcggagt gaacggtgtg gagcggaggc cgcggaggct cctcggtcct | 60 |
| tcagcacccc tcggcccgac gcacccacgc ccctcacccc ccgagagccg aaaatggacc | 120 |
| caagtggggt caaagtgctg gaaacagcag aggacatcca ggagaggcgg cagcaggtcc | 180 |
| tagaccgata ccaccgcttc aaggaactct caacccttag gcgtcagaag ctggaagatt | 240 |
| cctatcgatt ccagttcttt caagagatg ctgaagagct ggagaaatgg atacaggaaa | 300 |
| aacttcagat tgcatctgat gagaattata agacccaac caacttgcag ggaaagcttc | 360 |
| agaagcatca agcatttgaa gctgaagtgc aggccaactc aggagccatt gttaagctgg | 420 |
| atgaaactgg aaacctgatg atctcagaag ggcattttgc atctgaaacc atacggaccc | 480 |
| gtttgatgga gctgcaccgc cagtgggaat tacttttgga gaagatgcga gaaaaggaa | 540 |
| tcaaactgct gcaggcccag aagttggtgc agtacttacg agaatgtgag gacgtgatgg | 600 |
| actggatcaa tgacaaggaa gcaattgtta cttctgaaga gctgggccag gatctggagc | 660 |
| atgtagaggt tttacagaag aaatttgaag agtttcaaac agatatggct gctcatgaag | 720 |
| aaagagttaa tgaagtgaac cagtttgctg ccaaactcat acaggagcag caccctgagg | 780 |

| | |
|---|---|
| aggaactgat caagactaag caggatgaag tcaatgcagc ctggcagcgg ctgaagggcc | 840 |
| tggctctgca gaggcagggg aagctctttg gggcagcaga agttcagcgc tttaacaggg | 900 |
| atgtggatga gactatcagt tggattaagg aaaaggagca gttaatggcc tctgatgatt | 960 |
| ttggccgaga cctggcaagt gttcaggctc tgcttcggaa gcacgagggt ctggagagag | 1020 |
| atcttgctgc tctagaagac aaggtcaaag ccctgtgtgc tgaggctgac cgcctgcaac | 1080 |
| agtcccaccc tctgagtgca acacagattc aagtgaagcg agaggaactg attacaaact | 1140 |
| gggagcagat ccgcaccttg gcggcagaga gacatgcacg gctcaatgat tcatacaggc | 1200 |
| ttcaacgctt ccttgctgac ttccgtgacc tcaccagctg ggtgactgag atgaaagccc | 1260 |
| tcatcaatgc agatgagctt gccagtgatg tggctggggc tgaagccctg ctagatagac | 1320 |
| accaagagca aagggtgaa attgatgccc atgaagacag cttcaaatct gcagatgaat | 1380 |
| ctggacaggc actgcttgct gctggtcact atgcctcaga tgaagtgagg gagaagctga | 1440 |
| ccgtcctttc cgaggagaga gcggcgctgc tggagctgtg ggagctgcgc aggcagcagt | 1500 |
| acgagcagtg catggacctg cagctcttct accgggacac tgagcaggtg acaactggaa | 1560 |
| tgagcaagca ggaggcgttc ctgttgaatg aagacttggg agattccttg gatagtgtgg | 1620 |
| aagcgcttct taagaagcac gaagactttg agaaatccct tagtgcccag gaggaaaaga | 1680 |
| ttacagcatt agatgaattt gcaaccaagc taattcagaa caaccactat gcaatggaag | 1740 |
| atgtggccac tcgccgagat gctctgttga gccgccgcaa tgcccttcac gagagagcca | 1800 |
| tgcgtcgccg ggcccagcta gccgattctt ccatctgca gcagttttttc cgtgattctg | 1860 |
| atgagctcaa gagttgggtc aatgagaaga tgaaaactgc cacagatgaa gcttataaag | 1920 |
| atccatccaa cctacaagga aaagtacaga agcatcaggc ttttgaggct gagctctcag | 1980 |
| caaaccagag ccgaattgat gccttggaga agctggccaa aaagctgatt gatgtcaacc | 2040 |
| actatgccaa ggatgaagtg gcagctcgta tgaatgaggt gatcagtttg tggaagaaac | 2100 |
| tgctagaggc cactgaactg aaaggaataa agcttcgtga agccaaccag caacagcaat | 2160 |
| taatcgcaa tgttgaggat attgaattgt ggctatatga agtagaaggt cacttggctt | 2220 |
| cggatgatta cggcaaagat cttaccaatg tgcagaaccc tccagaagaaa catgccctgc | 2280 |
| tagaggcaga tgtggctgct caccaggacc gaattgatgg catcaccatt caggcccgcc | 2340 |
| agttccaaga tgctggccat tttgatgcag aaaacatcaa gaagaaacag gaagccctcg | 2400 |
| tggctcgcta tgaggcactc aaggagccca tggttgcccg gaagcagaag ctggccgatt | 2460 |
| ctctgcggtt gcagcagctc ttccgggatg ttgaggatga ggacgtgg attcgagaga | 2520 |
| aagagcccat tgccgcatct accaacagag gtaaggattt aattggggtc cagaatctgc | 2580 |
| taaagaaaca tcaagcctta caagcagaaa ttgctggaca tgaaccacgc atcaaagcag | 2640 |
| ttacacagaa ggggaatgcc atggtggagg aaggccattt tgctgcagag gatgtgaagg | 2700 |
| ccaagcttca cgagctgaac caaaagtggg aggcactgaa agccaaagct tcccagcgtc | 2760 |
| ggcaggacct ggaggactct ctgcaggccc agcagtactt tgctgatgct aacgaggctg | 2820 |
| aatcctggat gcgggagaag gaacccattg tgggcagcac tgactatggc aaggacgaag | 2880 |
| actctgctga ggctctactg aagaaacacg aagctttgat gtcagatctc agtgcctacg | 2940 |
| gcagcagcat ccaggctttg cgagaacaag cacagtcctg ccggcaacaa gtggcccca | 3000 |
| cggatgatga gactgggaag gagctggtct tggctctcta cgactatcag gagaagagtc | 3060 |
| cccgagaggt caccatgaag aagggagata tccttacctt actcaacagc accaacaagg | 3120 |
| attggtggaa agtggaagtg aacgatcgtc agggttttgt gccggctgcg tacgtgaaga | 3180 |

-continued

```
aattggaccc cgcccagtca gcctcccggg agaatctcct ggaggagcaa ggcagcatag    3240
cactgcggca ggagcagatt gacaatcaga cacgcataac taaggaggcc ggcagtgtat    3300
ctctgcgtat gaagcaggtg gaagaactat atcattctct gctggaactg ggtgagaagc    3360
gtaaaggcat gttggagaag agttgcaaga agtttatgtt gttccgtgaa gcgaatgaac    3420
tacagcaatg gatcaatgag aaggaagccg ctctgacaag tgaggaggtc ggagcagact    3480
tggagcaggt tgaggtgctc cagaagaagt ttgatgactt ccagaaggac ctgaaggcca    3540
atgagtcacg gttgaaggac attaacaagg tagctgaaga cctggagtct gaaggtctca    3600
tggcagagga ggtgcaggct gtgcaacaac aggaagtgta tggcatgatg cccagggatg    3660
aaactgattc caagacagcc tccccgtgga agtctgctcg tctgatggtt cacaccgtgg    3720
ccacctttaa ttccatcaag gagctgaatg acgctggcg gtccctacag cagctggccg    3780
aggaacggag ccagctcttg ggcagcgccc atgaagtaca gaggttccac agagatgctg    3840
atgaaaccaa agaatggatt gaagagaaga atcaagctct aaacacagac aattatggac    3900
atgatctcgc cagtgtccag gccctgcaac gcaagcatga gggcttcgag agggaccttg    3960
cggctctcgg tgacaaggta aactcccttg gtgaaacagc agagcgcctg atccagtccc    4020
atcccgagtc agcagaagac ctgcaggaaa agtgcacaga gttaaaccag gcctggagca    4080
gcctggggaa acgtgcagat cagcgcaagg caaagttggg tgactcccac gacctgcagc    4140
gcttccttag cgatttccgg gacctcatgt cttggatcaa tggaatacgg gggttggtgt    4200
cctcagatga gctagccaag gatgtcaccg gagctgaggc attgctggag cgacaccagg    4260
aacaccggac agaaatcgat gccagggctg gcactttcca ggcatttgag cagtttggac    4320
agcagctgtt ggctcacgga cactatgcca gccctgagat caagcagaaa cttgatattc    4380
ttgaccagga gcgtgcagac ctggagaagg cctgggttca gcgcaggatg atgctggatc    4440
agtgccttga actgcagctg ttccatcggg actgtgagca agctgagaac tggatggctg    4500
cccgggaggc cttcttgaat accgaagaca aggagactc actggacagc gtagaggctc    4560
tgatcaaaaa acatgaagac tttgacaaag cgattaacgt ccaggaagag aagattgctg    4620
ctctgcaggc cttttgccgac cagctcatcg ctgccggcca ttatgccaag ggagacattt    4680
ctagccggcg caatgaggtc ttggacaggt ggcgacgtct gaaagcccag atgattgaga    4740
aaaggtcaaa gctaggagaa tctcaaaccc tccaacagtt cagccgggat gtggatgaga    4800
ttgaggcttg gatcagtgaa aaattgcaaa cagcgagtga tgagtcgtac aaggatccca    4860
ccaacatcca gctttccaag ctgctgagca agcaccagaa gcaccaggct tttgaagcag    4920
agctgcatgc caacgctgac cggatccgtg gggttatcga catgggcaac tccctcattg    4980
aacgtggagc ctgtgccggc agtgaggatg ctgtcaaggc ccgcctggct gccttagctg    5040
accagtggca gttcttggtg caaaagtcag cggaaaagag ccagaaactg aaagaagcca    5100
acaagcagca gaacttcaac acagggatca aggactttga cttctggctg tctgaggtgg    5160
aggccctgct ggcatccgaa gattatggca aagacctggc ttctgtgaac aacctgctga    5220
aaaagcatca actgctggaa gcagatatat ctgcccatga ggatcgcctg aaggacctga    5280
acagccaggc agacagcctg atgaccagca gtgccttcga cacctcccaa gtaaaggaca    5340
agagggacac catcaacggg cgcttccaga agatcaagag catggcggcc tcccggcgag    5400
ccaagctgaa tgaatcccat cgcctgcacc agttcttccg ggacatggat gacgaggagt    5460
cctggatcaa ggagaagaag ctgctggtgg gctcagagga ctacggccgg gacctaaccg    5520
```

```
gcgtgcagaa cctgaggaag aagcacaagc ggctggaagc agaactggct gcgcatgagc   5580
cggctattca gggtgtcctg gacactggca agaagctgtc cgatgacaac accatcggga   5640
aagaggagat ccagcagcgg ctggcgcagt tgtggagca ctggaaagag ctgaagcagc    5700
tggcagctgc ccggggtcag cggctggaag agtccttgga atatcagcag tttgtagcca   5760
atgtggaaga ggaagaagcc tggatcaatg agaaaatgac cctggtggcc agcgaagatt   5820
atggcgacac tcttgccgcc atccagggct tactgaagaa acatgaagct tttgagacag   5880
acttcaccgt ccacaaggat cgcgtgaatg atgtctgcac caatggacaa gacctcatta   5940
agaagaacaa tcaccatgag gagaacatct cttcaaagat gaagggcctg aacgggaaag   6000
tgtcagacct ggagaaagct gcagcccaga gaaaggcgaa gctggatgag aactcggcct   6060
tccttcagtt caactggaag gcggacgtgg tggagtcctg gatcggtgaa aaggagaaca   6120
gcttgaagac agatgattat ggccgagacc tgtcttctgt gcagacgctc ctcaccaaac   6180
aggaaacttt tgacgctggg ctgcaggcct ccagcagga aggcattgcc aacatcactg    6240
ccctcaaaga tcagcttctc gccgccaaac acgttcagtc caaggccatc gaggcccggc   6300
acgcctccct catgaagagg tggagccagc ttctggccaa ctcagccgcc cgcaagaaga   6360
agcttctgga ggctcagagt cacttccgca aggtggagga cctcttcctg accttcgcca   6420
aaaaggcttc tgccttcaac agctggtttg aaaatgcaga ggaggactta acagaccccg   6480
tgcgctgcaa ctccttggaa gaaatcaaag ctttgcgcga ggcccacgac gccttccgct   6540
cctccctcag ctctgcccag gctgacttca accagctggc cgagctggac cgccagatca   6600
agagcttccg cgtagcctcc aaccctaca cctggtttac catggaggcc ctggaggaga    6660
cctggaggaa cctacagaaa atcatcaagg agagggagct ggagctgcag aaggaacagc   6720
ggcggcagga ggagaacgac aagctgcgcc aggagtttgc ccagcacgcc aacgccttcc   6780
accagtggat ccaagagacc aggacatacc tcctcgatgg gtcctgtatg gtggaagagt   6840
cggggaccct cgaatcccag cttgaagcta ccaaacgcaa gcaccaggaa atccgagcca   6900
tgagaagtca gctcaaaaag atcgaggacc tgggggccgc catggaggag gccctcatcc   6960
tggacaacaa gtacacggag cacagcaccg tgggcctcgc ccagcagtgg gaccagctgg   7020
accagctggg catgcgcatg cagcacaacc tggagcagca gatccaggcc aggaacacaa   7080
caggtgtgac tgaggaggcc ctcaaagaat tcagcatgat gtttaaacac tttgacaagg   7140
acaagtctgg caggctgaac catcaggagt tcaaatcttg cctgcgctcc ctgggctatg   7200
acctgcccat ggtggaggaa ggggaacctg accctgagtt cgaggcaatc ctggacacgg   7260
tggatccgaa cagagatggc catgtctcct tgcaagaata catggctttc atgatcagcc   7320
gcgaaactga gaacgtcaag tccagcgagg agattgagag cgccttccgg gccctcagct   7380
cagagggaaa gccttacgtg accaaggagg agctctacca gaacctgacc cgggaacaag   7440
ccgactactg cgtctcccac atgaagccct acgtggacgg caagggccgc gagctcccca   7500
ccgcgttcga ctacgtggag ttcacccgct cgcttttcgt gaactgagcc actccctggg   7560
tcacccaccc ctcgctgctt gccctgcgtc gccttgctgc atgtccgctc ctctgtgtgc   7620
tctcactttc cactgtaacc ttaagcctgc ttagcttgga ataagactta ggagaaaatg   7680
gtgcttcact aacccgcttc cggtccagtc acaatcatca tgtcactgtg ggacccaga    7740
tctgtgtctt gaagcagctg ccctcattcc gacttcagaa aatcgaagca gctggctcct   7800
ccccttgttc tctctcccac cctcccccaa atctgttttc atgtaaaaga caaataaatg   7860
atgacttccc ccaaaaaaaa aaaaaaaaa aaaaaaaaaa aaaaaaaaaa aaaaaaaaaa    7920
```

| | |
|---|---:|
| aaaa | 7924 |

<210> SEQ ID NO 166
<211> LENGTH: 9306
<212> TYPE: DNA
<213> ORGANISM: Homo sapiens

<400> SEQUENCE: 166

| | | | | | |
|---|---|---|---|---|---:|
| gggttcggag | cgcgaagccg | ccgctgggtc | ctcggcgcgc | cccgcgtctg | 60 |
| | | | | cgcttgctgc | |
| cgcgccccgg | tcggcgcgct | gggagttcca | gccatgctct | tctggcacac | 120 |
| | | | | gcagcccgag | |
| cactacaacc | agcacaactc | cggcagctac | ctgcgtgatg | tgctcgctct | 180 |
| | | | | gcccatcttc | |
| aagcaggagg | aaccccagct | gtcccccgag | aacgaggccc | gcctgccacc | 240 |
| | | | | cctgcaatat | |
| gtgttgtgtg | ctgccacgtc | cccagccgtg | aagctgcatg | aagagacgct | 300 |
| | | | | gacctacctc | |
| aaccaaggtc | agtcttatga | aatccgacta | ctggagaatc | ggaagctggg | 360 |
| | | | | agactttcaa | |
| gatctgaaca | caaatatgt | caagagcatc | atccgtgtgg | tcttccatga | 420 |
| | | | | ccgccggctg | |
| cagtatacgg | agcaccagca | gctggagggc | tggcggtgga | gtcggccagg | 480 |
| | | | | ggaccggatc | |
| ctggacatcg | atattccact | gtctgttggt | atcttggacc | ccagggccag | 540 |
| | | | | cccgacccag | |
| ctgaatgcag | tcgagttttt | gtgggaccct | gcgaagagag | cttctgcatt | 600 |
| | | | | cattcaggta | |
| cactgcatca | gcacagaatt | caccccccagg | aagcacgggg | gcgagaaggg | 660 |
| | | | | agtgcccttt | |
| cgagtccaga | ttgacacgtt | taagcagaac | gagaatgggg | agtacacgga | 720 |
| | | | | gcacctgcac | |
| tcagccagct | gccagatcaa | ggtgttcaag | ccgaagggag | ccgatcggaa | 780 |
| | | | | acagaagact | |
| gaccgggaga | agatggagaa | aagaactgcc | caagagaagg | agaaatacca | 840 |
| | | | | gccgtcctat | |
| gaaaccacca | tcctcacaga | gtgctctcca | tgggcccgacg | tggcctacca | 900 |
| | | | | ggtgaacagc | |
| gccccgtccc | caagctacaa | tggttctcca | aacagctttg | gcctcggcga | 960 |
| | | | | aggcaacgcc | |
| tctccgaccc | accgggtgga | ggccctgccc | gtgggcagtg | accacctgct | 1020 |
| | | | | cccatcagct | |
| tcgatccagg | atgcccagca | gtggcttcac | cgcaacaggt | tctcgcagtt | 1080 |
| | | | | ctgccggctc | |
| tttgccagct | tctcaggtgc | tgacttgctg | aagatgtccc | gagatgattt | 1140 |
| | | | | ggtccagatc | |
| tgtggtcccg | cagatgggat | ccggctcttc | aacgccatca | aaggccggaa | 1200 |
| | | | | tgtgaggcca | |
| aagatgacca | tttatgtctg | tcaggagctg | gagcagaatc | gagtgcccct | 1260 |
| | | | | gcagcagaag | |
| cgggacggca | gtggagacag | caacctgtct | gtgtaccacg | ccatcttcct | 1320 |
| | | | | ggaagagctg | |
| accaccttgg | agctgattga | gaagatcgcc | aacctgtaca | gcatctcccc | 1380 |
| | | | | ccagcacatc | |
| caccgagtct | accggcaggg | ccccacgggc | atccatgtgg | tggtgagcaa | 1440 |
| | | | | cgagatggtg | |
| cagaacttcc | aagatgaatc | ctgttttgtc | ctcagcacaa | ttaaagctga | 1500 |
| | | | | gagcaatgat | |
| ggctaccaca | tcatcctgaa | atgtggactc | tgagcagcag | tggacctcat | 1560 |
| | | | | acctgtctcc | |
| agctcccagc | cctgtggatc | cccgtggatg | tagacattgc | cccactgtaa | 1620 |
| | | | | gctgtggcct | |
| caccaggcaa | gctgaggcca | ggagggaccc | tgcccagtct | gtgaaagcta | 1680 |
| | | | | cagagcacca | |
| accagcagaa | gcctgtggac | accaagtacg | gtgtacagaa | agccagtggc | 1740 |
| | | | | tcctttctcc | |
| cttcctcttg | gcctcagat | tttgaatggt | tccttgttct | tttctattgg | 1800 |
| | | | | tccaaccctg | |
| acgttctaaa | agggcaaaca | gtggagacgt | ctgctctgaa | atccctcatc | 1860 |
| | | | | ccttagttgg | |
| aagctgattg | ggtatcttgg | tgctgcctgt | attggtccct | tctgaccact | 1920 |
| | | | | ctcctgcctc | |
| cagagaaagc | tctgcttcac | cctggaagct | ggtacctttta | cctcctcctc | 1980 |
| | | | | tgggagttgg | |
| ctgcatggcc | agcactgccg | acttgatggg | agcagtttgc | cctcattctc | 2040 |
| | | | | ctgtttcagg | |

```
tttgcttccc ttctcagtga ccctggtgag catccgcctt tcctgttctt ggatgaattg    2100 atggagtgg ggctattctg tgccttctac ctctttcttc tctacgttgt ttctaaggat    2160
ctgctgctgc ggaacccaaa gatgtgctcc tgtctctgca ctggcgcatt ggcatggtag    2220
atgccacaat gtatgtgcac ggcctttctc agagacatta gttctgaggc cctttgtggg    2280
gaggttaggg ggatggtaat agaaaaagac tattttattt cctggcaatc acgggtaagg    2340
aggattagga atgagtattc cattcctagg tgtcatcaga tgaccttgac caccacaata    2400
ccaggccctc ttggatggac ttatagaaag ttagagaaga ccttgttgaa ccgctgctaa    2460
acttgccaca ggagcgatgt gttttctctg agtgccsctc acttacatgt ttatctttgt    2520
ttgtagaggc tatgtttagg atattttgcc tgcatcagaa tgggtgcatc atctttctta    2580
atggcctaac tatcgggaaa tttgagtgtc agtaactgtg gtagactcag aaattcgtct    2640
ttgtcttgcc tctggttcct gggatccagt gatctctact ggcccagggc ttcagctctt    2700
ggttaattta ggttcatggg gaaccctctg accacctgaa tgggatgtca tagcttctaa    2760
atggagcttc tgtggaatga agtgctagac tgaaggacta ccagaataaa acagggtcta    2820
caatggggag aacttgtttt atagatgagg aaaccaaggc tcagaggggc aaagtcacct    2880
gcatggtagc acatagtgat agggtagcga tataaattta tcatataaac caggacatct    2940
cggaataaaa ggggctctgt tagtcattat gtttgggtaat agccgtggca ttcctacaga    3000
acagagtgag acaggctcc tgattcctct tccttcttta gaggagaagc ggggagtggg    3060
ttaactaaca gctttattga gatgtcattc acatgccatt cagtttaccc attgctagtg    3120
tccaattgta ttcacagaac caccatcaat tcacagaatt acagtcaacg ttggtacatt    3180
ttcatcaccc ccagtaaaac cccgtaccct tggtctgtca ctcctgcttt cctaactcct    3240
gcagtccaag gcagccatga atctactttc tatgtaagat taacctactc tggacatttc    3300
atatatctgg aatcatgtga tatctctttt gtgactggct tcttccactg aatgttttct    3360
agggccgtcc aagttgagga tgtatcagta cttcattctt ttgtattgct gaataatact    3420
tcattgtata gatagaccac atttgtttat tgattcatca gttgatggac atttgtgtgt    3480
ttttactttt tggctactct gaatgatgct gctatgaaca tatttctaca agattttgtg    3540
tggacatatg ttttcatttc ttttagcaat atacatagga gtggaattgc taggtcttac    3600
agtaactccg tgttttaact ttttgagaaa ctgccagact gttttctata gcagctgtac    3660
cattttacat tcccaccagc aatgtatcca ggtttcaatt tgtctacatc ctcatcaaca    3720
cttgctatta tctgtctttt tgcttttagc atcctaatga gtatgaaatg ctatcttgtg    3780
gttttgattt gcattcccct gatggcaact gatgctgagt gtcttttcct gtgcttacgg    3840
gccatgcgta tttctttgga gaaaggtcta tccaggtcct ttgcctattt ttaattgagt    3900 tgtcttttt tttttaagtt ttctgttttc ctaaccacta gactaccagg gatgagcctt    3960 cttttatta ttgagttggg tgagctattt gtatattcta gacgccagtc ttttatcagg    4020
tatatgactg gtaaaaatgt tctccccttc tgtggattgt tttcagtttc ttgttggtgt    4080
cctttgagac acaaaacttt ttaactttga tgatttccaa gatacgtatt ttttttctat    4140
tgtcacttgt gcttttggtg ccatatctag aaaaccattg cctaatccaa ggtcaagaag    4200
attaatgcct gtgttttctt ctaagaacta tacttttagt tctcacaatg gtctttgatc    4260
catttcgagt atattttat atatgatgtg atgtagggt ccagcttcat tcttttgctt    4320
gtggatctcc acttgtccca ctgctgatta ttgagaaaaa tatcctttct ccacggaatt    4380
gtcttggcat ccttgctaaa ggcctctgct tcttactgga tcttctttcc tgggacatgg    4440
```

```
tgtcgttggg aagcttacct tttttttttt tttacttagt ctgtgtttgg ttccaccagt    4500
tttatgctgc ctttctactc tgttcttgct gtctccctct ttacctgagt caacggtact    4560
gagtcctatc tctctctgat gttccccagt cttccttggt gcatgttcta gctccacaca    4620
ctagtccttg gaggaaggtt gagaccaatg atttcctgtt atgagtcatg aggaaactga    4680
atcacctaga agtggaataa tgtgctcagg gtcaccatag cccattagtg gaaggaccag    4740
gactagacct ttagtcttct gaggtccagc cccttaggct gtctgtcatc actgtaccca    4800
agtgatgtca ctaccaaggc caaatgatgg tgggctaaat tttaattctc aaaagtgtag    4860
gaggctaata ttgtcttcta agttccaaaa gaagatgtaa taaagtctg ttaccttaag     4920 tgtgctatta gtagagtctt ccattttct ggcatgcccc tggcatctgc tcttcttacc     4980
ttctcgtggt tgtagttaaa gcttatagct tatgaaagaa tagaaaataa taaataccaa    5040
aaaaaagtac acatggtaat ttggtaccaa aatatctcag ctgcctaatt tagcagctca    5100
tcccttccac aggggtcaga tgagctaaag ctccaggttt tatttttcat ttgattgaca    5160
tacagaaaag ccatagccct tcccacagct gtccagggtc tttcctgtga gtccggaggt    5220
gctggcctat tgagcaggac agctcttccc agggcattcc caccaacctg tggcttctga    5280
actgtagctt cttttacag tgaaccccag agggaaataa gacagacaca tgtgctcagg     5340
ccaccatctt gaactggaag cccaaagctg agttccttac tcttaggtcg tcacggtttt    5400
tgcggggtat ctgcaaggtt gagataaacc cttcctgtt taccaggttg tccttctgg     5460 atgaagggac agaggctgtt gaatggagga ataataggtt tgctggagga ggggcatggt    5520
atgcctgtgg aaaggacagg atggggtggg gaggtcgagg ctttgacttg gggtcctaaa    5580
caaaggtcag gtgttgccct agtgacctct tgcccagaca gcccagagcc cttacacag     5640 agctattaac ctagggaagg cttaccagc agtggactgg agccagccag ggtcacaagt     5700
ttccaagtcc agcattgctt caggggctgg cctgagtaac tgaagatctg aaaatcatta    5760
acaagtcgat gaaataaacg gaaaagcctc ttaggctgtt gtcagtggag cagagggaga    5820
aagtccctag gcgctcagag gggtgagaa agcagtggat gattgggcgg gggtggggga     5880
ttagatgttg acactgcctg gggtgtagga agaggaacag agaacccaga gtcagggtcc    5940
tagatcccag accctcgctc agtatgagtc tctttgcctc tctgggtctc tatctcctcc    6000
tcttacaaat acaggcttgg tgatctctga agatggcacc aacctgccat gaaatgaatc    6060 tgagggtt tcccattttt ccctccatca aaatcgtaca aaaagctgga cgtggtggcc      6120
catgcctcta atcctagcat tttgggaggc cgaggtggga gaatcacttg acgccaagag    6180
ttcgagacca gcctgggcat cgtagtgaga ctccatctct gtcttttga aaataaaaaa     6240 tctttgaaaa ttgcacaaca ggcagggac ctttacgtgt gcccatcctg gttgtacaca     6300
gtgccaccag tgctcctgca gtgcaaggcg gcatgcttct tgacatgggt cagattgtgt    6360
ccatcgtgtc tttgggaatc agccctagct cctaactggg ctgactactt cctccgcaaa    6420
cttatggggg ctcccagata ttccttgcca gccagggcc agacacagtg caggcacagt     6480
ctgtgtcatt ggtgcacatg tgcgtgttta catgtgtacc tgggttcctt cccttgccca    6540
tgaatttgcc atgagcacag ccagaagcag cctcagcttg gcaaggtgtg gagatgactg    6600
ctgttccctt cgcatttggg gaaacaggc tccctcggta gctcgatgat cctcttttga     6660
tcttgtgtga cctcctggag agtggatgaa gctggtggcc ttagcttttc tagacagtgt    6720
aagtggcact gggcaaggcc cccagagcag ggcaaggtct ctagagcggg tctcccacat    6780
```

```
gactggcttc acacaggcac ttccgctcgg gttgcatgct ctgtgtcatc ttaccggtcc    6840
agggttgcag gtaggaaatg tttgtaccct cttctgattg ccacctcctt cccatcgccc    6900
cttagggaca gggcttgagg gccagtgagg cgctggtcag gcaccccagg cctccttggg    6960
acctgcccag gggcaccctg agagctcctg aaacccccac ttagcttcca gacctttctg    7020
caaaagctcc tcctggcttt cctccctccc ccaatctatg gtcacagct aacagatctg    7080 agggcaactg ctgtgctagt ggccagggct gcacctgcca tccccggctc tgccacttta    7140
gggccttcta gaggcagtgt ccttaggaag tagctctgag gcatgggttt tctgctcctg    7200
tgcagggcag ctgatgggat aaggtgggga aggacggtca gtgcttgggc ccagctggc    7260 cagcctggcg atggggaaac caaaccatgt ccccagcga agggccagag tgggaacctg    7320
tcctcatgcc cttcgtcctg aggagccctg aggtgggcag caggggccag gggaagtttt    7380
caggccttca tcaaagagaa caacatcctc agctccgcac ccctcatcct gtatcagcac    7440
ttaccggtgt gtgactgccc ttgtcagcta gcatacggtg ggcccacctg gcccactggc    7500
tgtttatgcc actgatttat gatagggaat attatctttg aacccaatga agtgttttct    7560
cccccatcac aaaaaaaaaa attcttattt ttagtagaca tgtatttacc aaaaatatgt    7620
actcaattat tgtattttgg attttatcaa tttaaaaatt gtggaaattt gtttgctctt    7680
acgccaacat aatattgatt ttgcctcttg gctctgaaag cccaaaatat ttaccgtcta    7740
gcccgttaca gaaaaagtct gctgactact gagccagacc tccattaccct ccatccctgt    7800 tggattattt aaagaaagcc tcagacagta agggcttttt taaaagaata aaatgacttg    7860
gtttgcgctt ggaagcaggg gaagcattca gatgagcggt ttctgcatta accctgccta    7920
tcacgcatct cgtgtcctgt gtggctggcg agccccctt ggaaggttct ggtgcttcag    7980
ctggctcctg cagagtccac cccgcctcgt ggtgggaatg cagagccctt tgctttcctt    8040
cttgccgcct gcttcctgtt cctggggacc cgctgggcct ttggtctgca tcccctggcc    8100
aggtccctca gggttgatgc gtggagaagg actttgagca gtggtgggca gcagtggcct    8160
cctggccagc tcacactctt gtcctgggag gggcagcctg atctcacctc cacctagtac    8220
cttggggact gaggaccttt tggcttctct ggagcctgca agcctcttcc catgtgtcca    8280
gctgctcttc ctgctacaaa ggggactgct cacagtggcc tcagcttggt ggttttgagg    8340
ggccgccccc cggccctcca taagggtatc ctgggcctga gaattctgca tctgccattg    8400
gaggatggac agcctcaaat ggaaggagtc ccacgggaga tgggtccgag gtccggctgt    8460
ggccatccag cccctgtgg cttgtccagc ctctgtgcac ccctggtgtc ttcactccag    8520
gggcagacag cagccactgc agttcctttc ttcgtgagta acagtagtga tagcagctgg    8580
ggctaacagg ctaggctttg tgttctgcgc atttggtcag cttctcactc gatcctccct    8640
aaagcaatgg ggaggccccc actagcccag ttttcaggaa gtcaactggg aggttagatg    8700
ggggccaggg tccacagct actgatggcc cgagccaggt tgagcttcct ggtgtccagt    8760
ccggatccca cttgcagatc tcatgctctc agataggtgg gacaagttct tttgtcacag    8820
tgctggctct gtcctgaggc ctcattgctg gctgggtgtg ctctgctggg aaaagctttg    8880
cggggcttgc ttggttaacc acagaagaga aggggactgt ttggggtgcc tctctgcagc    8940
ctccccgtgc tgggtggaag cacggttact gtgttctcta atgttcatgt atttaaaatg    9000
atttctttct aaagatgtaa cctccacacc tttctccaga ttgggtgact cttttctaaa    9060
ggtggtggga gtatcgtcg gggtggtgtg gcccttggat gggtcaggtg ggtgtgagag    9120
gtcctgggga ggtgggcgtt gagctcaaag ttgtcctact gccatgtttt tgtacctgaa    9180
```

```
ataaagcata ttttgcactt gttactgtac catagtgcgg acgagaagtc tgtatgtggg    9240
atctgtgctt gggttagaat gcaaataaaa ctcacatttg taagaaaaaa aaaaaaaaaa    9300
aaaaaa                                                               9306
```

<210> SEQ ID NO 167
<211> LENGTH: 7218
<212> TYPE: DNA
<213> ORGANISM: Homo sapiens

<400> SEQUENCE: 167

```
gccccgcatc gtgcccggcc ccgtcgcgga gatcccggac gaccgtcgcg ggttgatggt      60
cgcattccag atgtaaacag cttcagaagc ctgacggtca tatggtagaa tcactgtgga     120
ctgagaccca cctttctaga cctgaagccc aggaggagga agaggaggct ggttggtacc     180
atgggcataa tgctctgaat cctagtctct cacctagtat gtgagcagtc cctgcagatg     240
gcccatttgg agatcttgac aaagcctctt ctgtttccaa tggggttttt ggcgcattct     300
cacagactta gatgaaactg tgatggccac cgcagggggc aggtgctgac atcgtcccca     360
gccctgtggc tgttcatccg gacatcattt ccaacctcaa tatctaaatg ccacagtgct     420
cttggagcaa gttgggctgg ggaccactgt tgccttttaa gaccataaaa ccatgggaaa     480
cgcagaaagt caacatgtag agcacgagtt ttatggagaa aagcatgcca gcctggggcg     540
caagcacact tcccgctccc tgcgcctctc gcacaagacg cggaggacca ggcacgcttc     600
ctcggggaag gtgatccaca ggaactccga agtgagcacc cgatccagca gcaccccag      660 catcccccag tccctggctg aaaatggcct ggagcccttc tcccaagatg gtaccctaga     720
agacttcggg agccccatct gggtggaccg agtggacatg ggcttgagac ctgtgtctta     780
cactgactct tctgtcactc ccagcgtaga cagcagcatc gtcctcacag cagcctctgt     840
gcagagcatg ccagacactg aggagagcag gctttacggg gatgacgcta catatttggc     900
tgagggaggc aggaggcagc attcctatac atccaatggg cccactttca tggagacggc     960
gagctttaag aagaaacgct ccaaatctgc agacatctgg cgggaggaca gcctggaatt    1020
ctcactctct gatctgagcc aagaacattt aacaagcaac gaagaaatct tgggttccgc    1080
cgaagagaag gactgcgagg aggctcgggg gatggaaacg cgggcgagtc cgcggcagct    1140
cagcacctgt cagagagcca attccttggg tgacttgtat gctcagaaaa actctggagt    1200
gacagcaaac gggggggccgg ggagcaaatt tgcaggctac tgtcggaatt tggtgtctga    1260
tattcccaat cttgcaaacc ataagatgcc accagctgct gctgaagaga ctcctccgta    1320
cagtaattat aacacacttc cctgtaggaa atctcactgt ctctctgaag gtgccaccaa    1380
cccacaaatt agccatagca acagcatgca aggcagaaga gctaaaacaa ctcaggatgt    1440
taatgcaggc gagggcagtg agtttgcaga cagtgggatt gaaggggcca ctaccgacac    1500
ggacctcctg tccaggcgat ctaatgccac caactccagc tactcaccca ccacaggccg    1560
ggcctttgtg ggcagcgaca gcggcagcag ctccaccggg gatgcggctc gtcaggggt     1620 gtacgagaac ttccggcggg agctggagat gagcaccacc aacagcgaga gcctggagga    1680
ggccggctcg gcgcacagcg atgagcagag cagcggcacc ctgagctctc cgggccagtc    1740
ggacatcctg ctgaccgccg cacagggcac ggtgcgcaag gccggcgccc tggccgtcaa    1800
gaacttcctg gtgcacaaga gaacaagaa ggtggagtca gccacccgga ggaagtggaa    1860
gcactactgg gtgtccctga aggatgcac gctatttttc tacgagagcg acggcaggtc    1920
```

```
tgggatagac cacaacagca tccccaaaca cgccgtctgg gtggagaaca gcattgtgca    1980
ggcggtgcct gagcacccca agaaggactt tgtcttctgc ctcagcaatt ccctgggtga    2040
tgccttcctt tttcagacca ctagccagac ggagcttgaa aactggatca ccgccatcca    2100
ctctgcctgc gccactgcgg tcgcgaggca ccaccacaag gaagacacgc tccgactcct    2160
gaaatcagag atcaaaaaac tggaacagaa gattgacatg gatgaaaaga tgaagaaaat    2220
gggtgaaatg cagctgtctt cagtcactga ctcaaagaaa aagaaaacaa tattagatca    2280
gatctttgtc tgggagcaaa atctcgagca gttccaaatg gacctgtttc gtttccgctg    2340
ttatttagcc agccttcagg gtggggagct gccaaacccc aaaaggcttc tcgcttttgc    2400
aagtcgacca acgaaagtgg ccatgggccg ccttggaatc ttttcggtat catcgtttca    2460
tgccctggtg gcagcacgca ctggtgaaac tggagtgaga agacgtactc aggccatgtc    2520
cagatccgcg agcaagcgaa ggagcaggtt ttcttctctg tggggtctgg atactacctc    2580
caaaaagaag cagggacggc caagcatcaa tcaggtgttt ggagagggaa ccgaagctgt    2640
aaagaaatct ttagagggaa tatttgatga cattgttcca gatggcaaga gggagaaaga    2700
agtggtctta cctaacgttc accagcacaa ccctgactgc gacatttggg tccacgagta    2760
tttcactcca tcctggttct gtctgcccaa taatcagcct gccctgacgg tcgtccggcc    2820
aggcgacact gcacgggaca ccctggagct gatttgcaag acacatcaac tggatcattc    2880
tgctcattac ctgcgcctga aatttctaat agaaaacaaa atgcagctct atgttccaca    2940
gcccgaggaa gacatctatg agctgctgta caagaaatt gaaatctgtc aaaagtcac    3000
tcagagcatc cacattgaga gtcagatac agctgctgat acttacgggt tttcactttc    3060
ttctgtggaa gaagatggta ttcgaaggct gtacgtgaat agtgtgaagg aaaccggttt    3120
agcttccaag aaaaggcctga aagcaggaga tgagattctt gagatcaata atcgtgctgc    3180
tgacgccctg aactcttcta tgctcaaaga tttcctctca cagccctcgc tgggcctcct    3240
ggtgaggacc taccccgagc tggaggaagg agtggagctg ctggaaagcc cgccccaccg    3300
agtggacggc cctgccgacc ttggcgagag cccctcgcc tttctcacca gcaacccagg    3360
gcacagcctt tgcagcgagc agggcagcag tgctgagacc gctccagagg agaccgaggg    3420
gccagacttg gaatcctcag atgagactga tcacagcagc aagagtacag aacaggtggc    3480
cgcatttttgc cgcagtttgc atgagatgaa ccccctctgac cagagcccat ctcctcagga    3540
ctccacgggg cctcagctgg cgaccatgag acaactctcg gatgcagata agctgcgcaa    3600
ggtgatctgc gagctcctgg agacggagcg cacctacgtg aaggatttaa actgtcttat    3660
ggagagatac ctaaagcctc ttcaaaaaga aactttctc acccaggatg agcttgacgt    3720
gcttttttgga aatttaacgg aaatggtaga gtttcaagta gaattcctta aaactctaga    3780
agatggagtg agactggtac ctgatttgga aaagcttgag aaggttgatc aatttaagaa    3840
agtgctgttc tctctggggg gatcattcct gtattatgct gaccgcttca agctctacag    3900
tgccttctgc gccagccaca caaaagttcc caaggtcctg gtgaaagcca agacagacac    3960
ggctttcaag gcattcttgg atgcccagaa cccgaagcag cagcactcat ccacgctgga    4020
gtcgtacctc atcaagccca tccagaggat cctcaagtac ccacttctgc tcagggagct    4080
gttcgccctg accgatgcgg agagcgagga gcactaccac ctggacgtgg ccatcaagac    4140
catgaacaag gttgccagtc acatcaatga gatgcagaaa atccatgaag agtttgggc    4200
tgtgtttgac cagctgattg ctgaacagac tggtgagaaa aaagaggttg cagatctgag    4260
catgggagac ctgcttttgc acactaccgt gatctggctg aacccgccgg cctcgctggg    4320
```

```
caagtggaaa aaggaaccag agttggcagc attcgtcttc aaaactgctg tggtccttgt    4380
gtataaagat ggttccaaac agaagaagaa acttgtagga tctcacaggc tttccattta    4440
tgaggactgg gacccccttca gatttcgaca catgatcccc acggaagcgc tgcaggttcg    4500
agctttggcg agtgcagatg cagaggcaaa tgccgtgtgt gaaattgtcc atgtaaaatc    4560
cgagtctgaa gggaggccgg agagggtctt tcacttgtgc tgcagctccc cagagagccg    4620
aaaggatttc ctaaaggctg tgcattcaat cctgcgtgat aagcacagaa gacagctcct    4680
caaaaccgag agccttccct catcccagca atatgtccct tttggaggca aagattgtg     4740
tgcactgaag ggggccaggc cggccatgag cagggcagtg tctgcccccaa gcaagtctct   4800
tgggaggagg aggcggcggc tggctcgaaa caggtttacc attgattctg atgccgtctc    4860
cgcaagcagc ccggagaaag agtcccagca gccccccggt ggtggggaca ctgaccgatg    4920
ggtagaggag cagtttgatc ttgctcagta tgaggagcaa gatgacatca aggagacaga    4980
catcctcagt gacgatgatg agttctgtga gtccgtgaag ggtgcctcag tggacagaga    5040
cctgcaggag cggcttcagg ccacctccat cagtcagcgg aaagaggcc ggaaaaccct     5100
ggatagtcac gcgtcccgca tggcacagct caagaagcaa gctgccctgt cggggatcaa    5160
tggaggcctg gagagcgcaa gcgaggaagt catttgggtt aggcgtgaag actttgcccc    5220
ctccaggaaa ctgaacactg agatctgact gcgtcacctg ccccgtagag aatgtgtgta    5280
gatacttcct gccctaactc tgcccaccct cctgtaccgt cgacaagaat gtccccttag    5340
gtcgcgctct tgcacacacg gttttggcag ctgacttggt tctgaagcca tgtagccacc    5400
caactttgtc attttcaaca acatcagaaa gaattgatca gaatcccaaa taagcttgag    5460
tcctatcttc tgtatattac taagggcttt tatttattct caataaatca gggcctgaac    5520
aattaaaaga aaaagattc tatagcactg gaaagcaaat caccccagga gttaacggat     5580
gtacaacaga ttaatttaag ggatagtagc acacacacga tccttctatc tgaaatcagt    5640
ctcctagctg gggaaacctc tttcacacac aaaatgaaat gtgtacagct tgccgtgttc    5700
tgactgtacc cttccctctt ccatgtctga aatctccgt gtattttaag aatgtgtgag     5760
gagagggtgg cgattcatgt ttcaatgagc ctctttttt ttttccttcc tgttttggtc     5820
tatggctggt cttactctgt gtccatgttc ggaagctcta gttttgcata gaattataga    5880
gatgccaaac tctttgaaaa gagatccaaa tttatcgctt gagagaaaga aaagaaacac    5940
tatttttgt atttaccctg agatacaggg gcacaaatag atgagaattt tacagtgtta     6000
gtgtatgtat ccctgagcct aaaaaatgag gatataacct tttacagaga gagtgaggcg    6060
tggtggtttt atatttatat atgaaaggcc agcaagctca tgcgaaggat atacttttct    6120
tccaaaaagc ggatttttt tttttaatgt ttgaatctat atttgagatg ggagtttggt     6180
tggattaaac atgacacccc ggtgggcggt gtgtgtgtct gttgcacatg gcaggagggg    6240
gagcctcctt ctcatggggt tgccatggtg atcattggtt tttccatcaa aattgcatct    6300
tcatccatag attaccttcc ccttccctga cagtccataa ccaaaccttt aaacagaaca    6360
acctctttaa aaacttctct tgtgtttaac actttcttca tgccaacgaa acagggtaaa    6420
catgctcaaa acattaacag tctaaacaga tatccaaata ctaagaagaa aaacaagtta    6480
tagcactttc aattttttt ttttttttaa aaaaggttt atagcttttt cttttcccat      6540
gtcacaatgt ccacttccta agaagggttt aaaatactat gaaaactttc ttttgggga    6600
aaatatctat ttggtgtttg acacatcagt aggtacttta aagacctgaa ttttatagta    6660
```

```
gctttaggag ttatatttta taaaaatcag ttatgacttt atatttccag acaatagaga    6720
gttcagtaca tcatgctctt gtgcctctgc ctgcttttcc tgcgttccca ccctgtattc    6780
cccccgcctt tcgggtttcc agggcttcga gcttgatctt ttgaaagttt tattctatta    6840
aattttttgct atatcttctg gttttctgaa aaagctttag aatggtttct atacccttttg  6900
tatcactgca tttttccata tcatctccgg ttcgatcgcg tccagatgga aaacggaagc    6960
agaggcttct aatcgtcgca tttactggct ccagtgcaac acatccatct gaaacactc     7020
ggaagtctgg tgcttggaga gggtgccatt gtctcttgta cataaggtca tgacgtgtct    7080
atgtcaaaag ttcttatata tttctttttat aagctgaaag aaggtctatt tttatgttttt  7140
taggtctatg aatggaacgt tgtaaatgct tgtcaaacaa taaaaataac gaaaagtgaa    7200
aaaaaaaaaa aaaaaaaa                                                  7218

<210> SEQ ID NO 168
<211> LENGTH: 931
<212> TYPE: DNA
<213> ORGANISM: Homo sapiens

<400> SEQUENCE: 168
tttcgtcggc cgccccttg gcttctgcac tgatggtggg tggatgagta atgcatccag      60
gaagcctgga ggcctgtggt ttccgcaccc gctgccaccc ccgcccctag cgtggacatt    120
tatcctctag cgctcaggcc ctgccgcat cgccgcagat ccagcgccca gagagacacc    180
agagaaccca ccatggcccc ctttgagccc ctggcttctg catcctgtt gttgctgtgg    240
ctgatagccc ccagcagggc ctgcacctgt gtcccacccc acccacagac ggccttctgc    300
aattccgacc tcgtcatcag ggccaagttc gtggggacac cagaagtcaa ccagaccacc    360
ttataccagc gttatgagat caagatgacc aagatgtata aagggttcca agccttaggg    420
gatgccgctg acatccggtt cgtctacacc cccgccatgg agagtgtctg cggatacttc    480
cacaggtccc acaaccgcag cgaggagttt ctcattgctg gaaaactgca ggatggactc    540
ttgcacatca ctacctgcag ttttgtggct ccctggaaca gcctgagctt agctcagcgc    600
cggggcttca ccaagaccta cactgttggc tgtgaggaat gcacagtgtt tccctgttta    660
tccatcccct gcaaactgca gagtggcact cattgcttgt ggacggacca gctcctccaa    720
ggctctgaaa agggcttcca gtcccgtcac cttgcctgcc tgcctcggga gccagggctg    780
tgcacctggc agtccctgcg gtcccagata gcctgaatcc tgcccggagt ggaagctgaa    840
gcctgcacag tgtccaccct gttcccactc ccatctttct tccggacaat gaaataaaga    900
gttaccaccc agcagaaaaa aaaaaaaaaa a                                    931

<210> SEQ ID NO 169
<211> LENGTH: 7697
<212> TYPE: DNA
<213> ORGANISM: Homo sapiens

<400> SEQUENCE: 169
agaatgggaa actgccttgg gagaagcccc aagtgagccc aagggcgcag agcagaagga     60
ccctggagtg taagagccta gattgcaagc ctggcaggag gagccggaag aattaacctc    120
gagtctgcac gcttttaaga acaaggcctt taaaaaatcc aaagtgtgtg gagtttgcaa    180
acaaattatt gacggtcaag gtatttcatg ccgagcctgc aagtattcct gccacaagaa    240
atgtgaagcc aaggtggtga ttccctgcgg tgtgcaagtc cgactggaac aggctccagg    300
gagttccacg ctgtccagtt ctctctgccg tgataaacct ctgcggcccg tcatcctgag    360
```

```
tcccaccatg gaggagggcc atgggctgga cctcacttac atcacggagc gcatcatcgc      420
tgtgtccttc cctgccggct gctctgagga gtcctacctg cacaacctac aggaggtcac      480
gcgcatgctc aagtccaagc acggggacaa ctacctggta ttaaacctttt cagaaaagag    540
atatgacctt acgaagctta acccaaagat catggatgtg ggctggccag agctccacgc      600
accgcccctg gataagatgt gtaccatatg caaggcgcag gagtcctggc tgaacagcaa      660
cctccagcat gtggtcgtca ttcactgcag gggcgggaaa ggacgcatag gagtggtcat      720
atcatcctac atgcatttca ccaacgtctc agccagcgcc gaccaggccc ttgacaggtt      780
tgcaatgaag aagttttatg atgacaaagt ttcagcttta atgcagcctt cccaaaaacg      840
gtatgttcag ttcctcagtg ggctcctgtc cggatcggtg aaaatgaatg cctctcccct      900
gttcctgcat tttgtcatcc tccacggcac ccccaacttc gacacaggtg gagtgtgccg      960
gcccttctg aagctctacc aagccatgca gcctgtgtac acctccggga tctacaacgt       1020
tggcccagaa aaccccagca ggatctgcat cgtcatcgag ccggcccagc ttctgaaggg     1080
agatgtcatg gtgaaatgct accacaagaa ataccgctcg gccacccgtg acgtcatttt     1140
ccgcctgcag tttcacactg gggctgtgca gggctacggg ctggtgtttg gaaggagga      1200
tctggacaat gccagcaaag atgaccgttt tcctgactat gggaaggttg aattagtctt     1260
ctctgccacg cctgagaaga ttcaagggtc cgaacacttg tacaacgacc acggtgtgat     1320
tgtggactac aacacaacag acccactgat acgctgggac tcgtacgaga acctcagtgc     1380
agatggagaa gtgctacaca cgcagggccc tgtcgatggc agcctttacg cgaaggtgag     1440
gaagaaaagc tcctcggatc ctggcatccc aggtggcccc caggcaatcc cggccaccaa     1500
cagcccagac cacagtgacc acaccttgtc tgtcagcagt gactccggcc actctacagc     1560
ctctgccagg acggataaga cggaagagcg cctggcccca ggaaccagga ggggcctgag     1620
tgcccaggag aaggcagagt tggaccagct gctcagtggc tttggcctgg aagatcctgg     1680
aagctccctc aaggaaatga ctgatgctcg aagcaagtac agtgggaccc gccacgtggt     1740
gccagcccag gttcacgtga atggagacgc tgctctgaag gatcgggaga cagacattct     1800
ggatgacgag atgccccacc acgacctgca cagtgtggac agccttggga ccctgtcctc     1860
ctcggaaggg cctcagtcgg cccacctggg tccttcacc tgccacaaga gcagccagaa      1920
ctcactccta tctgacggtt ttggcagcaa cgttggtgaa gatccgcagg caccctcgt     1980
tccggacctg ggccttggca tggacggccc ctatgagcgg gagcggactt ttgggagtcg     2040
agagcccaag cagcccccagc ccctgctgag aaagcccctca gtgtccgccc agatgcaggc   2100
ctatgggcag agcagctact ccacacagac ctgggtgcgc cagcagcaga tggttgtagc     2160
tcaccagtat agcttcgccc cagatgggga ggccggctg gtgagccgct gccctgcaga      2220
caatcctggc ctcgtccagg cccagcccag agtgccactc acccccaccc gagggaccag     2280
cagtagggtg gctgtccaga ggggtgtagg cagtgggcca catccccctg acacacagca     2340
gccctctccc agcaaagcgt tcaaacccag gtttccagga gaccaggttg tgaatggagc     2400
cggcccagag ctgagcacag gcccctcccc aggctcgccc accctggaca tcgaccagtc     2460
catcgagcag ctcaacaggc tgatcctgga gctggatccc accttcgagc ccatccctac    2520
ccacatgaac gccctcggta gccaggccaa tggctctgtg tctccagaca gcgtgggagg    2580
tgggctccgg gcaagcagca ggctgcctga cacaggagag ggcccagca gggccaccgg     2640
gcggcaaggc tcctctgctg aacagccct gggcgggaga ctcaggaagc tgagcctggg     2700
```

```
gcagtacgac aacgatgctg gggggcagct gcccttctcc aaatgtgcat ggggaaaggc    2760
tggtgtggac tatgcccaa acctgccgcc attcccctca ccagcggacg tcaaagagac    2820
gatgacccct ggctatcccc aggacctcga tattatcgat ggcagaattt taagtagcaa    2880
ggagtccatg tgttcaactc cagcatttcc tgtgtctcca gagacaccgt atgtgaaaac    2940
agcgctgcgc catcctccgt tcagcccacc tgagcccccg ctgagcagcc cagccagtca    3000
gcacaaagga ggacgtgaac cacgaagctg ccctgagacg ctcactcacg ctgtggggat    3060
gtcagagagc cccatcggac ccaaatccac gatgctccgg gctgatgcgt cctcgacgcc    3120
ctcctttcag caggcttttg cttcttcctg caccatttcc agcaacggcc ctgggcagag    3180
gagagagagc tcctcttctg cagaacgcca gtgggtggag agcagcccca agcccatggt    3240
ttccctgctg gggagcggcc ggcccaccgg aagtcccctc agcgctgagt ctccggtac    3300 caggaaggac tccccagtgc tgtcctgctt cccgccgtca gagctccagg ctcctttcca    3360
cagccatgag ctgtccctag cagagccacc ggactccctg gcgcctccca gcagccaggc    3420
cttcctgggc ttcggcaccg ccccagtggg aagtggcctt ccgcccgagg aggacctggg    3480
ggccttgctg gccaattctc atggagcgtc accgaccccc agcatcccgc tgacagcgac    3540
aggggctgcc gacaatggct tcctgtccca caactttctc acggtggcgc ctggacacag    3600
cagccaccac agtccaggcc tgcagggcca gggtgtgacc ctgcccgggc agccacccct    3660
ccctgagaag aagcgggcct cggaggggga tcgttctttg ggctcagtct ctccctcctc    3720
cagtggcttc tccagcccgc acagcgggag caccatcagt atcccctcc caaatgtcct    3780 tcccgacttt tccaaggctt cagaagcggc ctcacctctg ccagatagtc caggtgataa    3840
acttgtgatc gtgaaatttg ttcaagacac ttccaagttc tggtacaagg cggatatttc    3900
aagagaacaa gccatcgcca tgttaaggga caaggagccg ggctcattca ttgttcgaga    3960
cagccattcc ttccgagggg cctatggcct ggccatgaag gtggccacgc ccccaccttc    4020
agtcctgcag ctgaacaaga aagctggaga tttggccaat gaactcgtcc ggcacttttt    4080
gatcgagtgt accccgaagg gagtgcggtt gaaagggtgc tcgaatgaac catatttcgg    4140
gagcctgacg gccttggtgt gccagcattc catcacgccc ttggccttgc cgtgcaagct    4200
gcttatccca gagagagatc cattggagga aatagcagaa agttctcccc agacggcagc    4260
caattcagca gctgagctgt tgaagcaggg ggcagcctgc aatgtgtggt acttgaactc    4320
tgtggagatg gagtccctca ccggccacca ggcgatccag aaggccctga gcatcaccct    4380
ggtccaggag cctccacctg tgtccacagt tgtgcacttc aaggtgtcag cccagggcat    4440
caccctgaca gacaatcaga ggaagctctt cttccggagg cattacccccg tgaacagtgt    4500 gatttttctgt gccttggacc cacaagacag gaagtggatc aaagatggcc cttcctcaaa    4560
agtctttgga tttgtggccc ggaagcaggg cagtgccacg gataatgtgt gccacctgtt    4620
tgcagagcat gaccctgagc agcctgccag tgccattgtc aacttcgtat caaaggtcat    4680
gattggttcc ccaaagaagg tctgagaact cccctccctc cctggaccca ccgatgcctc    4740
tcgaagccct ggagacagcc gttgggtgag ggtggggccc ccactttta ccaaactagt    4800 aaacctgaca ttccaggccc atgaggggaa agaggatctt ccagctctgc aaaaacaaga    4860
acaaacaaca tcaccgtgaa ttggccttc ctgaaagtga cttatctgac acatctctgt    4920
agccacatgc tttttgggta aagaagctg gcatgggtg cacccaccc ctagggtcc    4980 ccatgggaaa gggacatgca aggaaacagc acagaacacg aggtggtccc catgtccctg    5040
gcacactagc attccggggg atgaggaatc cccagccctt gaggcagagg tgccgagtga    5100
```

```
ctgccatgct tcgcccgtcc gcatgggcgc ttctgtccag ctgcacccga ggccggggt    5160 ttccctcacc tcggtcttcc caagatggag atgctaacga aactgagaag ggggcgtatg    5220
tttgacgaag gtttgtgcaa gtcaggccct tctggaacac agcagggcct acaacgaggg    5280
gcctttgcga tgggctgtga ggatgggggt ggtgggaaga attggccacg ttggagaccc    5340
catgccaccc caccatggtg agtgctctgt gcctcctgct cacctgtggt gagctgggcg    5400
agctgggcga gctgggcgag ctgggctggg gagagcctgt gaggaccgag aggagaaatg    5460
agaagaagga acaaaaatat tatttctatg taatttatat tttacttatg ccaaattatt    5520
tatgataatt tgccattgct atactgtacc agtgtcaaat gctgcagcct gccaagctgt    5580
gattttgtga ggcttgtccc tatgtaggat gcaccgcagg cccctggcca ctgaaagagt    5640
gtgcagtgga ctgtgggtct cccatatgcg gtgccgccca aggtggctt tgcctcaagc      5700 aacctaccct gatgttttac tcattggaat gttttttcccc gattgtggat gacttctttt    5760
ctgatggaga gagtccagga gggatggaaa actcctggat ttaagctcag catcccccac    5820
atgggctttt cgatcatctt caggcctgaa gctgcacgac ctgaagttcg cctgcattta    5880
tcagccctct ttgtgctgct ccttgccacc ttggggttcc tgctggggac catgtgtggt    5940
tgtggcatgt gtgagcagaa gggaggatga ggaaaaagag aagaaacccc ggtactgaca    6000
agctgttttt gagtgccact gtttgccatc atctaagcca ctgaatcaag tgtatttcag    6060
gcttatttca acattccaat gccctggttt cctgcttga atctgttcgt ggtcaaaggt    6120
ttgggggaat ttgtgaccct ggaacatccc cagagtgaaa gatggagctg gccacatca    6180 gaataaggcc ttggccccat cctctcacag cctaggtgct ctgcaggcat gctgactgtc    6240
ctgattgcga tccagcccga aattccctcc tctgctttca aaagtcaaat cccccattct    6300
taggccacac tggtgtcaca agctcctgtc agggagctgg ggtttgggaa tgtgctttgt    6360
gaactctgct ttaaagtgag gggccgagga aaacttagaa acaggcagag ttggaagcag    6420
ccaaatcaca gtgggtgttg tgtgtgtgtg cgtgtgtgca tgcgtgcgtg tatgcgtgtg    6480
tgaaagcagg tggaccattc cactttttag ctcctattga tgcaccaaac caagtgcctc    6540
atttctgtgc caaatgtttg ccttggtcgt tgtggacctc cttctctaac ttgcggtggc    6600
atgactgtca ggaggtgctg gcattttcag cagatcctca tgtgttgacc ctgatgtctt    6660
tagcagaggc ctctagcatc tcggtttttc atccactgca ggaatgtggc cacagggagc    6720
agaggtttgt actttcccca agaggtcctc atcctgagac ggtctctacc catgtttaac    6780
ccaaagagtg caggccaggt tccttatcct tctgatgaag gatgagagag ctcatttaga    6840
agtcagagca aactagggtc tcagtattga gaaacgcagc ctgccaggga atcacagaga    6900
catcggggtg cccgcgatgg ccctcatgaa gccatgcctc gacggcattc aggaagccct    6960
gcaaacgtgc ttttgaact cattggccag gtgtgatttt tacacaaggt aaacgtggtc      7020
aagggcatcg gggaatttgc tccaagcaga tagctccctc tgaggaacca aaggaagcaa    7080
gtttccacga tttctgaaga gctggtatag gaagtttctt tcttcctttt gtgttacatg    7140
tgcattaaac agaacaagct gtgtgtcatc acagattgta ctgtgggctc agaaaccgtg    7200
agagagcccc caccgtggac accggctcta gggccacagg aaaaggaacg tttccaggca    7260
ttttgtctcc agggctcccg ctggacaggc acgtactgcc ctgggagta aatgcggaga    7320 gttcacgaac tgtgcccaac gcatgttata gccagggtcc tactaactac tcagtaaaag    7380
aacgtattgt tgtattcctc cagtgttaag ctatagccat gttaaaagtc actgtgcatt    7440
```

-continued

| | |
|---|---|
| tattctcagc atcaaatacc ttgtaacgtc ttctctgcct tgttagtgca tatttttact | 7500 |
| tttctgatac tgtaaagaat atatccagta tgtaaatgaa tgttctataa atcttttgta | 7560 |
| tagtcatttt ctctgctcct taaatatcat ctctattcag agtataataa aattatgaac | 7620 |
| ttggtaaaaa aaaaaaaaaa aaaaaaaaaa aaaaaaaaaa aaaaaaaaaa aaaaaaaaaa | 7680 |
| aaaaaaaaaa aaaaaaa | 7697 |

<210> SEQ ID NO 170
<211> LENGTH: 2579
<212> TYPE: DNA
<213> ORGANISM: Homo sapiens

<400> SEQUENCE: 170

| | |
|---|---|
| ggccctggct gccgccgctg cctcgtccgg actcggagag gacttgggag ggacagcggc | 60 |
| gctgggaggt ggcttagcag agactttcca gcaactgctg cccaggactt tttttttttt | 120 |
| ttttcttttt cccaggaggc ggcgacggcg gcggcggggg gagaggaaga gaaagaagcg | 180 |
| tctccagctg aagccaatgc agccctccgg ctctccgcga agaagttccc tgccccgatg | 240 |
| agcccccgcc gtgcgtcccc gactatcccc aggcgggcgt ggggcaccgg gcccagcgcc | 300 |
| gacgatcgct gccgttttgc ccttgggagt aggatgtggt gaaggatgg ggcttctccc | 360 |
| ttacggggct cacaatggcc agagaagatt ccgtgaagtg tctgcgctgc ctgctctacg | 420 |
| ccctcaatct gctcttttgg ttaatgtcca tcagtgtgtt ggcagtttct gcttggatga | 480 |
| gggactacct aaataatgtt ctcactttaa ctgcagaaac gagggtagag aagcagtca | 540 |
| ttttgactta ctttcctgtg gttcatccgg tcatgattgc tgtttgctgt ttccttatca | 600 |
| ttgtggggat gttaggatat tgtggaacgg tgaaagaaa tctgttgctt cttgcatggt | 660 |
| actttggaag tttgcttgtc atttctctgtg tagaactggc ttgtggcgtt tggacatatg | 720 |
| aacaggaact tatggttcca gtacaatggt cagatatggt cactttgaaa gccaggatga | 780 |
| caaattatgg attacctaga tatcggtggc ttactcatgc ttggaatttt tttcagagag | 840 |
| agtttaagtg ctgtggagta gtatatttca ctgactggtt ggaaatgaca gagatggact | 900 |
| ggcccccaga ttcctgctgt gttagagaat tcccaggatg ttccaaacag gcccaccagg | 960 |
| aagatctcag tgacctttat caagagggtt gtgggaagaa aatgtattcc ttttttgagag | 1020 |
| gaaccaaaca actgcaggtg ctgaggtttc tgggaatctc cattggggtg acacaaatcc | 1080 |
| tggccatgat tctcaccatt actctgctct gggctctgta ttatgataga agggagccgg | 1140 |
| ggacagacca aatgatgtcc ttgaagaatg acaactctca gcacctgtca tgtccctcag | 1200 |
| tagaactgtt gaaaccaagc ctgtcaagaa tctttgaaca cacatccatg gcaaacagct | 1260 |
| ttaatacaca ctttgagatg gaggagttat aaaaagaaat gtcacagaag aaaaccacaa | 1320 |
| acttgttta ctggacttgt gaatttttga gtacatacta tgtgtttcag aaatatgtag | 1380 |
| aaataaaat gttgccataa aataacacct aagcatatac tattctatgc tttaaaatga | 1440 |
| ggatggaaaa gtttcatgtc ataagtcacc acctggacaa taattgatgc ccttaaaatg | 1500 |
| ctgaagacag atgtcatacc cactgtgtag cctgtgtatg acttttactg aacacagtta | 1560 |
| tgttttgagg cagcatggtt tgattagcat ttccgcatcc atgcaaacga gtcacatatg | 1620 |
| gtgggactgg agccatagta aaggttgatt tacttctacc aactagtata taaagtacta | 1680 |
| attaaatgct aacataggaa gttagaaaat actaataact tttattactc agcgatctat | 1740 |
| tcttctgatg ctaaataaat tatatatcag aaaacttttca atattggtga ctacctaaat | 1800 |
| gtgattttg ctggttacta aaatattctt accacttaaa agagcaagct aacacattgt | 1860 |

| | |
|---|---|
| cttaagctga tcagggattt tttgtatata agtctgtgtt aaatctgtat aattcagtcg | 1920 |
| atttcagttc tgataatgtt aagaataacc attatgaaaa ggaaaatttg tcctgtatag | 1980 |
| catcattatt tttagccttt cctgttaata aagctttact attctgtcct gggcttatat | 2040 |
| tacacatata actgttattt aaatacttaa ccactaattt tgaaaattac cagtgtgata | 2100 |
| cataggaatc attattcaga atgtagtctg gtctttagga agtattaata agaaaatttg | 2160 |
| cacataactt agttgattca gaaaggactt gtatgctgtt tttctcccaa atgaagactc | 2220 |
| tttttgacac taaacacttt ttaaaaagct tatctttgcc ttctccaaac aagaagcaat | 2280 |
| agtctccaag tcaatataaa ttctacagaa aatagtgttc tttttctcca gaaaaatgct | 2340 |
| tgtgagaatc attaaaacat gtgacaattt agagattctt tgttttattt cactgattaa | 2400 |
| tatactgtgg caaattacac agattattaa atttttttac aagagtatag tatatttatt | 2460 |
| tgaaatggga aaagtgcatt ttactgtatt ttgtgtattt tgtttatttc tcagaatatg | 2520 |
| gaaagaaaat taaaatgtgt caataaatat tttctagaga gtaaaaaaaa aaaaaaaaa | 2579 |

<210> SEQ ID NO 171
<211> LENGTH: 1796
<212> TYPE: DNA
<213> ORGANISM: Homo sapiens

<400> SEQUENCE: 171

| | |
|---|---|
| ggtcagctga gttcgccggc ccagggcagg cggggcccga gcctagcggt aaccccgggg | 60 |
| cagggcgggg ccgctcgcag actccatatg agattcacct cgcaggtggt tccctcattc | 120 |
| gagtgctccg gcgcacagac ccgcgccccg ccgtctgcga gcctcccgag agccgtccct | 180 |
| tcgtccggcc ctggagcatt gcgtttgtcg ccggtgtcgc agtgcgagga tggcgccgcg | 240 |
| ggtgtagcgg ctctctgcgc aggccgagtg ggcccagaga agcgaggaac tccgcagctc | 300 |
| gtcgacacgt ctcgtctcct gtcccaattc agggcttggt gaggtgactc gcggtcgcgg | 360 |
| gtgactcgcc ggcaggacac tgcctggaac gcctggagcg cctcccactg cagacgtctg | 420 |
| tccgcctcca gccgctctcc tctgacgggt cctgcctcag ttggcggaat ggcggccacg | 480 |
| ggagccaatg cagagaaagc tgaaagtcac aatgattgcc ccgtcagact tttaaatcca | 540 |
| aacatagcaa aaatgaaaga agatattctc tatcatttca atctcaccac tagcagacac | 600 |
| aatttcccag ccttgtttgg agatgtgaag tttgtgtgtg ttggtggaag ccctcccgg | 660 |
| atgaaagcct tcatcaggtg cgttggtgca gagctgggcc ttgactgccc aggtagagac | 720 |
| tatcccaaca tctgtgcggg aactgaccgc tatgccatgt ataaagtagg accggtgctg | 780 |
| tctgtcagtc atggtatggg cattccttct atctcaatca tgttgcatga gctcataaag | 840 |
| ctgctgtact atgccggtg ctccaacgtc actatcatcc gcattggcac ttctggtggg | 900 |
| ataggtctgg agcccggcac tgtggtcata acagagcagg cagtggatac ctgcttcaag | 960 |
| gcagagtttg agcagattgt cctggggaag cgggtcatcc ggaaaacgga ccttaacaag | 1020 |
| aagctggtgc aggagctgtt gctgtgttct gcagagctga gcgagttcac cacagtggtg | 1080 |
| gggaacacca tgtgcacctt ggacttctat gaagggcaag gccgtctgga tggggctctc | 1140 |
| tgctcctaca cggagaagga caagcaggcg tatctggagg cagcctatgc agccggcgtc | 1200 |
| cgcaatatcg agatggagtc ctcggtgttt gccgccatgt gcagcgcctg cggcctccaa | 1260 |
| gcggccgtgt gtgtgtcac cctcctgaac gccctggaag gggaccagat cagcagccct | 1320 |
| cgcaatgtgc tcagcgagta ccagcagagg ccgcagcggc tggtgagcta cttcatcaag | 1380 |

-continued

| | |
|---|---|
| aagaaactga gcaaggcctg agcgctgccc tgcacctccg cagacctgct gtgatgactt | 1440 |
| gccattaaaa gcattgtcca aaatcccctg ttgtgtggac tttgagcaca ctttacacaa | 1500 |
| gaatctagaa aatcagatcg cgattaagag acagagaatc ttggattaac cgcatgggag | 1560 |
| atgttcttcc ttttgaagtt tcattggagc attttcaatg atgttagcct gatttggggt | 1620 |
| ttcttcaaga acattctacc aaattttgt actatttcta gggaaatttt tcagacttta | 1680 |
| aaattctaat ggtagtcaga tttcatgtca ctaaacaaga aatctgacaa tagtgccagg | 1740 |
| aaactaattt cctgatacat taaaaaaatt ccatgcaaaa aaaaaaaaaa aaaaaa | 1796 |

<210> SEQ ID NO 172
<211> LENGTH: 3443
<212> TYPE: DNA
<213> ORGANISM: Homo sapiens

<400> SEQUENCE: 172

| | |
|---|---|
| gtgctttact gcgcgctctg gtactgctgt ggctccccgt cctggtgcgg gacctgtgcc | 60 |
| ccgcgcttca gccctccccg cacagcctac tgattcccct gccgcccttg ctcacctcct | 120 |
| gctcgccatg gagtcgctgg ttttcgcgcg gcgctccggc cccactccct cggccgcaga | 180 |
| gctagcccgg ccgctggcgg aagggctgat caagtcgccc aagcccctaa tgaagaagca | 240 |
| ggcggtgaag cggcaccacc acaagcacaa cctgcggcac cgctacgagt tcctggagac | 300 |
| cctgggcaaa ggcacctacg ggaaggtgaa gaaggcgcgg gagagctcgg ggcgcctggt | 360 |
| ggccatcaag tcaatccgga aggacaaaat caaagatgag caagatctga tgcacatacg | 420 |
| gagggagatt gagatcatgt catcactcaa ccaccctcac atcattgcca tccatgaagt | 480 |
| gtttgagaac agcagcaaga tcgtgatcgt catggagtat gccagccggg gcgacccttta | 540 |
| tgactacatc agcgagcggc agcagctcag tgagcgcgaa gctaggcatt tcttccggca | 600 |
| gatcgtctct gccgtgcact attgccatca gaacagagtt gtccaccgag atctcaagct | 660 |
| ggagaacatc ctcttggatg ccaatgggaa tatcaagatt gctgacttcg gcctctccaa | 720 |
| cctctaccat caaggcaagt tcctgcagac attctgtggg agccccctct atgcctcgcc | 780 |
| agagattgtc aatgggaagc cctacacagg cccagaggtg gacagctggt ccctgggtgt | 840 |
| tctcctctac atcctggtgc atggcaccat gcccttttga gggcatgacc ataagatcct | 900 |
| agtgaaacag atcagcaacg gggcctaccg ggagccacct aaaccctctg atgcctgtgg | 960 |
| cctgatccgg tggctgttga tggtgaaccc cacccgccgg gccaccctgg aggatgtggc | 1020 |
| cagtcactgg tgggtcaact ggggctacgc caccccgagtg ggagagcagg aggctccgca | 1080 |
| tgagggtggg caccctggca gtgactctgc ccgcgcctcc atggctgact ggctccggcg | 1140 |
| ttcctcccgc cccctcctgg agaatggggc caaggtgtgc agcttcttca gcagcatgc | 1200 |
| acctggtggg ggaagcacca cccctggcct ggagcgccag cattcgctca agaagtcccg | 1260 |
| caaggagaat gacatggccc agtctctcca cagtgacacg gctgatgaca ctgcccatcg | 1320 |
| ccctggcaag agcaacctca gctgccaaa gggcattctc aagaagaagg tgtcagcctc | 1380 |
| tgcagaaggg gtacaggagg accctccgga gctcagccca atccctgcga gcccagggca | 1440 |
| ggctgccccg ctgctcccca agaagggcat tctcaagaag cccgacagc gcgagtctgg | 1500 |
| ctactactcc tctcccgagc ccagtgaatc tggggagctc ttggacgcag gcgacgtgtt | 1560 |
| tgtgagtggg gatcccaagg agcagaagcc tccgcaagct tcaggctgc tcctccatcg | 1620 |
| caaaggcatc ctcaaactca atggcaagtt ctcccagaca gccttggagc tcgcggcccc | 1680 |
| caccaccttc ggctccctgg atgaactcgc cccacctcgc ccctggcccc gggccagccg | 1740 |

-continued

```
acccctcaggg gctgtgagcg aggacagcat cctgtcctct gagtcctttg accagctgga    1800
cttgcctgaa cggctcccag agcccccact gcggggctgt gtgtctgtgg acaacctcac    1860
ggggcttgag gagcccccct cagagggccc tggaagctgc ctgaggcgct ggcggcagga    1920
tcctttgggg gacagctgct tttccctgac agactgccag gaggtgacag cgacctaccg    1980
acaggcactg agggtctgct caaagctcac ctgagtggag taggcattgc cccagcccgg    2040
tcaggctctc agatgcagct ggttgcaccc cgaggggaga tgccttctcc cccacctccc    2100
aggacctgca tcccagctca gaaggctgag agggtttgca gtggagccct gagcagggct    2160
ggatatggga agtaggcaaa tgaaatgcgc caagggttca gtgtctgtct tcagccctgc    2220
tgaacgaaga ggatactaaa gagaggggaa cgggaatgcc cgcgacagag tccacattgc    2280
ctgtttcttg tgtacatggg ggggccacag agacctggaa agagaactct cccagggccc    2340
atctcctgca tcccatgaat actctgtaca catggtgcct tctaaggaca gctccttccc    2400
tactcattcc ctgcccaagt ggggccagac ctctttacac acacattccc gttcctacca    2460
accaccagaa ctggatggtg gcaccccctaa tgtgcatgag gcatcctggg aatggtctgg    2520
agtaacgctt cgttattttt attttttattt ttatttattt atttattttt ttgagacgga    2580
gtttcgctct tggtgcccag gctagagtgc aatggcgcga tctcagctca cctcaacctc    2640
cgcctcccgg gttcaagcga ttctcctgcc tcagcctccc tagtagctgg gattacaggc    2700
gcccgccacc atgcccggct aattttgtat ttttagtaga cagggtttt ctccatgttg    2760
gtcaggctgg tctcaaactc ccgacctcag gtgatccacc cacctcggcc tcccaaagtg    2820
ctgggattac aggcgtgagc caccgcgccc cacctaaccc ttccttattt agcctaggag    2880
taagagaaca caatctctgt ttcttcaatg gttctcttcc ctttttccatc ctccaaacct    2940
ggcctgagcc tcctgaagtt gctgctgtga atctgaaaga cttgaaaagc ctccgcctgc    3000
tgtgtggact tcatctcaag gggcccagcc tcctctggac tccaccttgg acctcagtga    3060
ctcagaactt ctgcctctaa gctgctctaa agtccagact atggatgtgt tctctaggcc    3120
ttcaggactc tagaatgtcc atatttattt ttatgttctt ggctttgtgt tttaggaaaa    3180
gtgaatcttg ctgttttcaa taatgtgaat gctatgttct gggaaaatcc actatgacat    3240
ctaagttttg tgtacagaga gatatttttg caactatttc cacctcctcc cacaacccc     3300
cacactccac tccacactct tgagtctctt tacctaatgg tctctaccta atggacctcc    3360
gtggccaaaa agtaccatta aaaccagaaa ggtgattgga aaaaaaaaaa aaaaaaaaaa    3420
aaaaaaaaaa aaaaaaaaaa aaa                                           3443
```

US 9,587,279 B2

THYROID TUMORS IDENTIFIED

CROSS-REFERENCE TO RELATED APPLICATIONS

This patent application is a continuation of U.S. patent application Ser. No. 13/063,429, filed Jun. 2, 2011, which is a National Stage application under 35 U.S.C. 371 of PCT/US2009/005091, filed Sep. 11, 2009 and published as WO 2010/030365 A2 on Mar. 18, 2010 which claims the benefit of priority, under 35 U.S.C. Section 119(e), to U.S. Provisional Patent Application Ser. No. 61/191,845 filed on Sep. 12, 2008, and U.S. Provisional Patent Application Ser. No. 61/207,812 filed Feb. 17, 2009, the contents of all of which applications are specifically incorporated by reference herein in their entireties.

FIELD OF THE INVENTION

The invention relates to detection and diagnosis of thyroid cancer. In some embodiments, the methods of the invention can be used to distinguish between benign thyroid cells or tissues, malignant thyroid cells or tissues, and follicular adenomas with nuclear atypia (FANA).

BACKGROUND OF THE INVENTION

Thyroid nodules are common in the United States, occurring in greater than 60% of individuals. Moreover, their incidence is steadily increasing, mainly because of the increased detection of smaller, asymptomatic nodules. Although the majority of these nodules are benign, a significant numbers of patients undergo surgical excision. Upon pathologic review of such thyroid tumors, clear-cut benign or malignant diagnoses often can be rendered. However, follicular lesions of the thyroid often pose a diagnostic challenge.

A particular diagnostic dilemma is presented in a subset of encapsulated follicular lesions with partial nuclear features of papillary thyroid carcinoma (PTC) (occasional nuclear grooves, focal nuclear clearing, and overlapping nuclei) and with histological features that fail to place them reliably in either the benign category or the malignant category. In the inventors' experience, these tumors represent approximately 10% of all follicular-patterned lesions observed at surgical pathology (see also, Arora et al. World J Surg. 32:1237-1246 (2008)). The difficulty of classifying this group of tumors is exemplified further by several studies in which poor interobserver agreement was demonstrated among expert endocrine pathologists ranging from 39% to 58% when they reviewed follicular-patterned lesions of the thyroid (Chan et al., Am J Clin Pathol. 117:16-18 (2002); Franc et al., Hum Pathol. 34:1092-1100 (2003); Lloyd et al., Am J Surg Pathol. 28:1336-1340 (2004); Saxen et al. Acta Pathol Microbiol Scand [A]. 1978; 86A:483-4864-8 (1978); Hirokawa et al. Am J Surg Pathol. 26:1508-1514 (2002)). This diagnostic difficulty in classifying such borderline tumors with standard terminology led Williams to propose the term well differentiated tumor of uncertain malignant potential (WDT-UMP) as a separate diagnostic category (Int J Surg Pathol. 8:181-183 (2000)).

No matter what terminology is used for these tumors, additional tools are needed to determine whether thyroid nodules and/or tumors are actually malignant or simply benign, and/or whether such nodules and/or tumors can progress to become malignant tumors.

SUMMARY OF THE INVENTION

The invention relates to methods for improved diagnosis of thyroid cancer that can distinguish not only benign nodules from malignant thyroid tumors but can also identify borderline, pre-cancerous tumors (e.g., encapsulated follicular lesions that may have partial nuclear features of PTC) that may not need aggressive treatment. For example, in one study conducted by the inventors using the methods described herein, the majority of histologically uncertain tumors (66.7%) were determined to be premalignant tumors, while a smaller number of tumors were determined to be benign tumors (26.7%) and only a even smaller number of tumors were actually malignant tumors (6.7%). By using the methods and kits of the invention, the malignant thyroid tumors can be identified with greater certainty, thereby avoiding unnecessary, expensive and invasive medical procedures that might otherwise have been used to treat histologically uncertain tumors.

Thus, one aspect of the invention is a method of detecting whether thyroid cancer cells are present in a test tissue or cell sample which comprises (a) observing test levels of RNA or protein expression in the test tissue or cell sample for any differentially expressed gene, and (b) comparing the test levels of expression to one or more standard or control levels of expression, to ascertain whether higher or lower levels of expression of any of the genes is present in the test tissue or cell sample, and thereby detecting whether thyroid cancer cells are present in the test tissue or cell sample; wherein the differentially expressed gene is selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof.

In some embodiments, the differentially expressed gene can be selected from the group consisting of DIO1, DTX4, GALNT7, HMGA2, IGFBP6, MET, PROS1, SDC4, SERPINA1, SLC4A4, TIAM1, TIMP1, UPP1 and a combination thereof. In other embodiments, the differentially expressed gene can be selected from the group consisting of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, TIAM1 and a combination thereof. In further embodiments, the differentially expressed gene can be selected from the group consisting of C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 and a combination thereof.

Any methods available to one of skill in the art can be used to detect and/or quantify the test levels of RNA. For example, the test levels of RNA expressed can be detected by microarray analysis or by nucleic acid amplification. In some embodiments, the test levels of RNA expressed are detected by microarray analysis that includes use of one or more probes on the microarray that can hybridize to one or more of the differentially expressed genes, or an RNA or DNA copy of the one or more differentially expressed genes. For example, such methods can employ one or more probes that can hybridize to any of SEQ ID NO:119-172. In some embodiments, the one or more probes hybridize to one or more of the differentially expressed genes, or an RNA or DNA copy of the one or more differentially expressed genes under moderate to highly stringent hybridization conditions. For example, the hybridization conditions can be highly stringent hybridization conditions.

In other embodiments, nucleic acid amplification can be employed. Such nucleic acid amplification can include reverse transcription polymerase chain reaction, real time polymerase chain reaction, or quantitative polymerase chain reaction. For example, the test levels of RNA expressed can be detected by nucleic acid amplification using one or more primers that hybridize to one or more of the differentially expressed genes, or an RNA or DNA copy of the one or more differentially expressed genes under moderate to highly stringent hybridization conditions. The one or more primers employed can, for example, hybridize to any of SEQ ID NO:119-172. Such hybridization conditions can in some instances be highly stringent hybridization conditions.

The one or more standard or control levels of expression can include: an expression level observed for a malignant thyroid cancer cell or tissue; an expression level observed for a benign thyroid cell or tissue; an expression level observed for a follicular adenoma with nuclear atypia; an expression level observed for a borderline thyroid cell or tissue; an expression level observed for a normal non-cancerous thyroid cell or tissue; or an expression level observed for a constitutively expressed gene.

These methods can distinguish between benign, malignant and borderline thyroid cells or tissues. For example, these methods can distinguish between benign thyroid cells or tissues, malignant thyroid cells or tissues, and follicular adenomas with nuclear atypia (FANA). For example, the test tissue or cell sample is obtained from a patient with thyroid cancer or suspected of having thyroid cancer.

Another aspect of the invention is a kit comprising: (a) at least one set of oligonucleotide primers, wherein a first primer in the set contains a sequence complementary to a region in one strand of a nucleic acid sequence template and primes the synthesis of a first extension product, and a second primer contains a sequence complementary to a region in said first extension product and primes the synthesis of a nucleic acid strand complementary to said first extension product, and wherein the template is a differentially expressed gene, or an RNA or DNA copy of the differentially expressed gene; and (b) instructions for using the at least one set of oligonucleotide primers; wherein the differentially expressed gene is selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof.

In some embodiments, the differentially expressed gene can be selected from the group consisting of DIO1, DTX4, GALNT7, HMGA2, IGFBP6, MET, PROS1, SDC4, SERPINA1, SLC4A4, TIAM1, TIMP1, UPP1 and a combination thereof. In other embodiments, the differentially expressed gene can be selected from the group consisting of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, TIAM1 and a combination thereof. In further embodiments, the differentially expressed gene can be selected from the group consisting of C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 and a combination thereof. The first primer and/or the second primer can include a label. A container of nucleotides can also be included in the kit where the nucleotides are used as subunits in the synthesis of and amplified product. For example, the nucleotides can be ribonucleotides and/or deoxyribonucleotides. One or more of such nucleotides can include a label.

The instructions can describe a method for amplifying an mRNA, cRNA or cDNA corresponding to the differentially expressed gene(s). In some embodiments, the first primer and/or the second primer may hybridize to an mRNA, cRNA or cDNA corresponding to the differentially expressed gene under moderate to highly stringent hybridization conditions. For example, the hybridization conditions can be highly stringent hybridization conditions in some instances.

Another aspect of the invention is a kit that includes (a) a microarray with covalently attached probes that can hybridize to a differentially expressed gene selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof; and (b) instructions for using the microarray.

In some embodiments, the differentially expressed gene can be selected from the group consisting of DIO1, DTX4, GALNT7, HMGA2, IGFBP6, MET, PROS1, SDC4, SERPINA1, SLC4A4, TIAM1, TIMP1, UPP1 and a combination thereof. In other embodiments, the differentially expressed gene can be selected from the group consisting of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, TIAM1 and a combination thereof. In further embodiments, the differentially expressed gene can be selected from the group consisting of C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 and a combination thereof. Such probes can, in some embodiments, hybridize to an mRNA, cRNA or cDNA corresponding to the differentially expressed gene, for example, under moderate to highly stringent hybridization conditions. In some embodiments, the hybridization conditions are highly stringent hybridization conditions. Such a kit can also include one or more standard or control probes. For example, the kit can include one or more probes for a constitutively expressed gene.

Another aspect of the invention is a method of detecting a mutation in a human BRAF gene that includes: (a) obtaining a test sample of genomic DNA from a human; (b) amplifying a segment of BRAF DNA from the genomic DNA using primers with SEQ ID NO: 1 and SEQ ID NO:2; and (c) detecting whether the mutation exists in the segment amplified; wherein the mutation consists of a glutamate substituted for valine at codon 600.

Such a method can also include detecting or confirming whether the human has thyroid cancer by observing test levels of RNA or protein expression in the test tissue or cell sample for any of the differentially expressed genes described herein, using any of the methods and/or kits described herein.

DETAILED DESCRIPTION OF THE INVENTION

The invention relates to methods of detecting malignant thyroid tumors and/or distinguishing whether thyroid tumors are benign, malignant, and/or pre-cancerous borderline tumors. While currently available histological and/or cytological procedures can sometimes distinguish benign and malignant thyroid tumors, there are many thyroid tumors that cannot readily be classified as either malignant or benign by such histological procedures. Patients with such unclassified tumors are often aggressively treated as though their tumors were malignant. However, by employing the methods and kits described herein, these unclassified tumors can be properly identified as either benign, malignant, or pre-cancerous borderline tumors, thereby reducing the need for expensive, invasive and unpleasant medical treatment when it is unnecessary.

The application describes an analysis of fifty histologically-unequivocal benign and malignant tumors, which led to the identification of a list of sixty-one genes that are differentially expressed in benign and malignant thyroid tumors. These differentially expressed genes are listed in Table 1.

Figure 4:
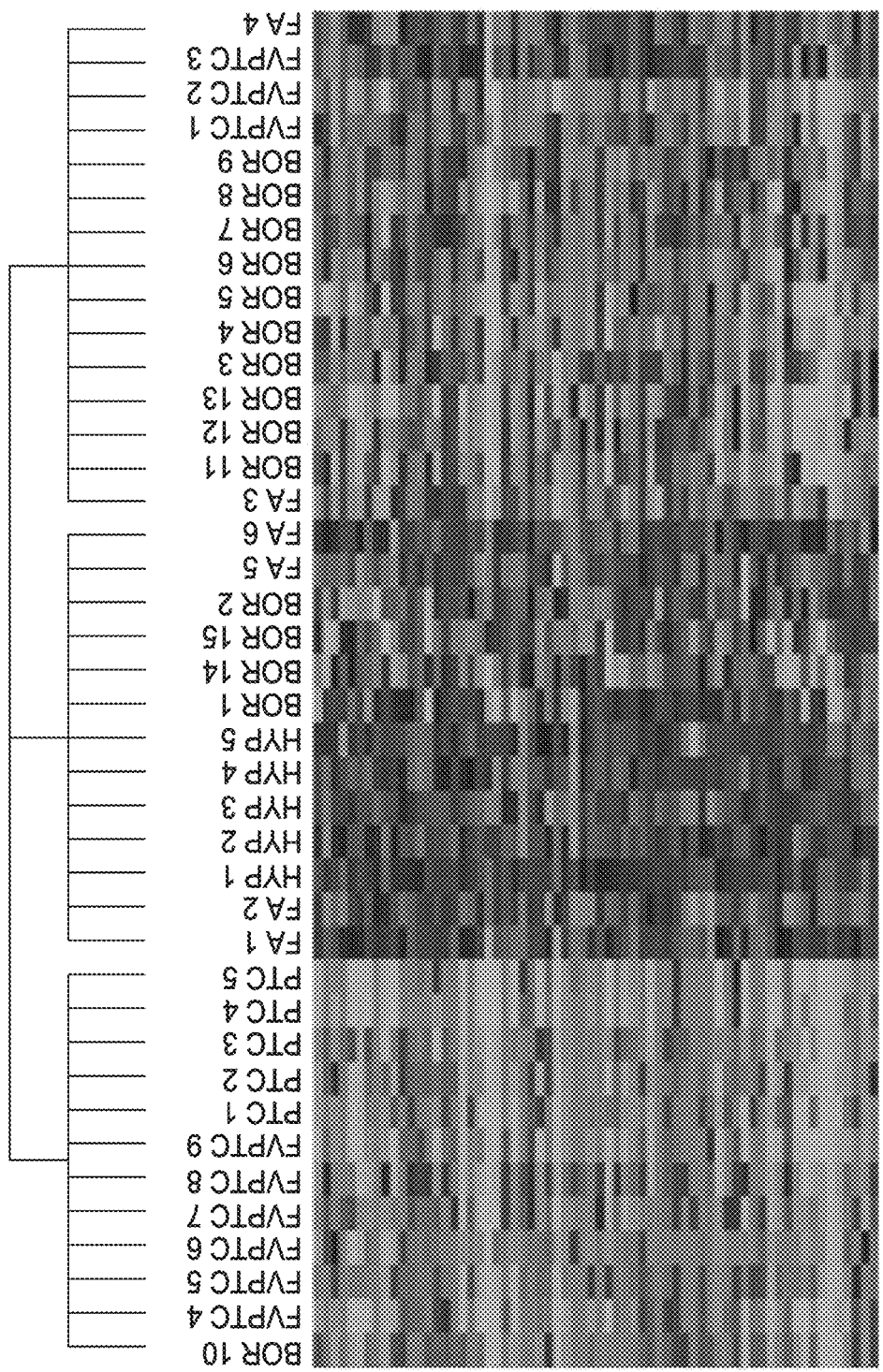
FIG. 4 is graphic generated by three-group K-means cluster analysis that identified 3 distinct groups of tumors based upon their gene expression patterns: malignant (left), benign (center), and intermediate (right). BOR indicates borderline tumor; FVPTC, follicular variant of papillary thyroid carcinoma; PTC, papillary thyroid carcinoma; FA, follicular adenoma; HYP, hyperplastic lesion.

By using probes for the fifty to sixty differentially expressed genes described herein, forty additional tumors were evaluated, including 15 histologically intermediate tumors, 11 benign tumors, and 14 papillary thyroid carcinomas (PTCs). Differential gene expression was used to detect whether the histologically intermediate thyroid tumors were malignant or not. As illustrated herein, the majority of histologically intermediate tumors (66.7%) were actually borderline, premalignant tumors that exhibited gene expression similarities with benign tumors (26.7%) and malignant tumors (6.7%) (FIG. 4). This third category of borderline tumors (encapsulated follicular tumors with cytological atypia) does not fit into previously proposed benign or malignant classification schemes using standard histological, immuno-histochemical, or mutation analyses. Instead, these borderline tumors are premalignant tumors that may warrant monitoring but do not generally need immediate aggressive medical treatment.

Twenty-seven genes were expressed differentially between the benign and borderline groups, including the cyclic AMP response element binding protein/p300-interactivator with glutamic acid/aspartic acid-rich carboxy-terminal domain 1 or CITED1 gene and the fibroblast growth factor receptor 2 or FGFR2 gene. Fourteen genes were expressed differentially between the borderline group and malignant tumors, for example, the met proto-oncogene and of the high-mobility group adenine/thymine-hook 2 or HMGA2 gene in malignancies. Mutations of the v-raf murine sarcoma viral oncogene homolog B1 or BRAF gene were identified in 4 of 14 malignant tumors but not in benign or borderline tumors.

Patients who had histologically or molecularly borderline tumors did not have metastasis or recurrences. These data indicate that encapsulated thyroid follicular lesions with partial nuclear features of PTC are biologically borderline tumors that are molecularly distinct from benign and malignant tumors. Moreover, the data indicate that such borderline tumors identified by the methods and kits of the invention are pre-cancerous with no immediate need for aggressive cancer treatment.

The gene expression profiling methods described herein are more accurate than existing procedures for diagnosing problematic thyroid tumors. For example, the methods of the invention can identify malignant thyroid tumors with greater than 90% sensitivity and 80% specificity. In some embodiments, the methods of the invention can identify malignant thyroid tumors with greater than 93% sensitivity and greater than 82% specificity.

DEFINITIONS

"Genes" are the units of heredity in living organisms. They are encoded in the organism's genetic material (DNA or RNA), and control the physical development and behavior of the organism. Genes encode the information necessary to construct the proteins (etc.) needed for the organism to function. The term "genes" generally refers to the region of DNA (or RNA, in the case of some viruses) that determines the structure of a protein (the coding sequence), together with the region of DNA that controls when and where the protein will be produced (the regulatory sequences).

As used herein, the phrase "expression profiling" refers to differential gene expression analysis/techniques. Examples of such techniques include microarray analyses, real time PCR and qPCR. Microarray technology allows for the comparison of gene expression between, for example, normal and diseased (e.g., cancerous) cells or cells which express different cell markers. There are several names for microarray technology including DNA microarrays, DNA arrays, DNA chips, gene chips, and others.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not deleteriously changed by the presence of more than that which is recited.

Other definitions may appear throughout this disclosure in the appropriate context.

Genes that are Differentially Expressed in Benign and Malignant Thyroid Tumors

The expression levels of one or more of the genes listed in Table 1 can be detected using the methods and kits of the invention. In some embodiments, the expression levels of two or more, or three or more, or four or more, or five or more of the genes listed in Table 1 are detected to assess whether a thyroid nodule contains benign or malignant cancer cells. In other embodiments, the expression levels of seven or more, or eight or more, or ten or more, or twelve or more of the genes listed in Table 1 are detected to assess whether a thyroid nodule contains benign or malignant cancer cells. In further embodiments, the expression levels of no more than ten, no more than twelve, no more than fifteen, no more than twenty of the genes listed in Table 1 are detected to assess whether a thyroid nodule contains benign or malignant cancer cells.

Differential expression of these genes means that the mRNA or transcript levels produced by these genes increases or decreases in a test tissue or cell sample (e.g., a thyroid tissue biopsy) relative to a control, thereby indicating the presence of benign thyroid cells or tissues, malignant thyroid cells or tissues, and/or borderline tumors (e.g., encapsulated thyroid follicular lesions with partial nuclear features of PTC) in the test tissue or cell sample from which the RNA/transcripts were obtained.

Genes whose expression changes in thyroid tumor cells include one or more of the following genes: ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC4A4, SLC25A15, SLIT1, SPTAN1, TFCP2L1, TIAM1, TIMP1, TNS3, TSPAN12, UPP1, or a combination thereof.

The following genes were expressed at higher levels in malignant thyroid cancer tissues and cells than in benign thyroid lesions: CAPN3, CITED 1, DAPK2, DPP4, DUSP4, DTX4, GALNT7, HMGA2, IGFBP6, LRP4, MET, MYH10, PFAAP5, PROS1, PSD3, QPCT, RAB27A, RXRG, SERPINA1, SLIT1, SPTAN1, TIAM1, TIMP1, and UPP1. Thus, detection of an increase in the expression of one or more of these genes in a tissue or cell sample, relative to a benign control tissue sample, is indicative of thyroid cancer.

On the other hand, the following genes are expressed at lower levels in malignant thyroid cancer tissues than in benign thyroid lesions: ANK2, ARHGAP6, C11orf17, CDH16, CITED 2, COL9A3, ChGn, CKB, CSRP2, DIO1, EFEMP1, ELMO1, FGFR2, FLRT1, FMOD, GATM, HGD, KIT, MATN2, NAUK2, PGF, PIP3-E, PKNOX2, PRKACB, SDC4, SLC4A4, SLC25A15, TFCP2L1, TNS3, and TSPAN12. Thus, detection of a decrease in the expression of one or more of these genes in a tissue or cell sample, relative to a benign control tissue sample, is indicative of thyroid cancer.

However, as described herein, the inventors have discovered a third type of thyroid tumor that is pre-cancerous and may not need aggressive medical treatment when initially detected. As described herein, these borderline tumors can be distinguished from benign and malignant by their expression patterns.

The following genes are differentially expressed between malignant and borderline/benign tumors: DIO1, DTX4, GALNT7, HMGA2, IGFBP6, MET, PROS1, SDC4, SERPINA1, SLC4A4, TIAM1, TIMP1, and/or UPP1. Each of these genes exhibit increased expression in malignant tumors relative to borderline and benign tumors, except DIO1, SDC4, and SLC4A4, which are expressed at lower levels in malignant thyroid tissues and cells when compared to their expression in benign and borderline tumors. Thus, when differential expression of one or more of these genes is detected in a thyroid test or cell sample, such differential expression is indicative of the presence of malignant tumor cells.

The following genes are differentially expressed between benign and borderline/malignant lesions: ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, and/or TIAM1. Each of these genes exhibit decreased expression in malignant tumors relative to borderline/malignant tumors, except CITED 1, DUSP4, LRP4, PSD3, SLIT1, SPTAN1, and TIAM1, which are expressed at higher levels in malignant tissues and cells compared to borderline/malignant tissues and cells. Thus, benign thyroid lesions can be identified and distinguished from borderline/malignant tumors by their differential expression patterns in a thyroid test tissue or cell sample.

The following genes are differentially expressed between benign and malignant lesions: C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15. Each of these genes are expressed at higher levels in malignant thyroid tumors relative to their expression levels in benign thyroid lesions, except the following genes: C11orf17, CKB, CSRP2, HGD, PGF, PKNOX2, PRKACB, and SLC25A15, which are expressed at lower levels in malignant thyroid tissues relative to benign thyroid lesions. Thus, to definitively distinguish between benign and malignant thyroid tissues, the expression of these genes can be evaluated.

The difference in expression levels between a differentially expressed gene in malignant thyroid tissues relative to the expression levels for that gene in a control (e.g., normal thyroid tissues) can be at least a 20% difference in expression levels, at least a 30% difference in expression levels, at least a 40% difference in expression levels, at least a 50% difference in expression levels, at least a 60% difference in expression levels, at least a 70% difference in expression levels, at least an 80% difference in expression levels, at least a 90% difference in expression levels, at least a 100% difference in expression levels, and/or a more than a 100% difference in expression levels. Thus, in some embodiments, the difference in expression levels between a differentially expressed gene in malignant thyroid tissues relative to the expression levels for that gene in a control (e.g., normal thyroid tissues) can be at least 1.5 fold, at least 1.7 fold, at least 1.8 fold, at least 2-fold, at least 2.2 fold, at least at least 2.3 fold, at least 2.4 fold, at least 2.5 fold, or more than 2.5 fold. Table 1 provides examples of the differences in expression levels that can readily be determined and observed.

Gene expression data may be gathered in any way that is available to one of skill in the art. For example, gene expression levels can be detected and quantified by employing an array of probes that hybridize to the different transcripts of one or more of the genes listed in Table 1, by using nucleic acid amplification (e.g., quantitative polymerase chain reaction) and through nucleic acid hybridization procedures. Other methods of determining expression of the genes include traditional Northern blotting, nuclease protection, RT-PCR and differential display methods can be used for detecting gene expression levels. Such methods are described in the following sections and in the Examples.

Probes and primers that can hybridize to an RNA, cDNA corresponding to any of the following genes can be used to detect differential gene expression: ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC4A4, SLC25A15, SLIT1, SPTAN1, TFCP2L1, TIAM1, TIMP1, TNS3, TSPAN12, UPP1, or a combination thereof.

Sequences for these differentially expressed genes are available and can be used to make probes and primers for detecting expression levels. Examples of sequences that can be used to make probes and primers for these are provided hereinbelow. Any probe or primer that can hybridize to an RNA or cDNA of any of these genes can be used in the methods of the invention. In some embodiments, such a probe or primer hybridizes such to an RNA or cDNA of a differentially expressed gene under moderately stringent conditions. In other embodiments, such a probe or primer hybridizes such to an RNA or cDNA of a differentially expressed gene under highly stringent conditions. Such conditions are known to one of skill in the art and are described herein.

RNA Manipulation

One of skill in the art will appreciate that in order to assess the mRNA transcript levels (and thereby the expression levels) of a gene or genes, it is desirable to provide a RNA sample or a nucleic acid sample derived from the mRNA transcript(s). As used herein, a nucleic acid derived from an mRNA transcript refers to a nucleic acid ultimately synthesized from the mRNA transcript. Thus, the original mRNA obtained from a test tissue or cell sample can serve as a template for generating a nucleic acid derived from an mRNA. For example, such a nucleic acid derived from an mRNA can be a cDNA reverse transcribed from an mRNA, an RNA transcribed from the cDNA, a DNA amplified from the cDNA, an RNA transcribed from the amplified DNA, and the like. Detection of such derived products is indicative of the presence and abundance of the original mRNA transcript in a test tissue or cell sample. Thus, suitable samples include, but are not limited to, mRNA transcripts of the gene or genes, cDNA reverse transcribed from the mRNA, cRNA transcribed from the cDNA, and the like.

Where it is desired to quantify the transcription level of one or more genes in a sample, the concentration of the mRNA transcript(s) of the gene or genes is proportional to the transcription level of that gene. Similarly, when hybridization is employed to quantify transcription levels, the hybridization signal intensity can be proportional to the amount of hybridized nucleic acid. As described herein, controls can be run to correct for variations introduced during sample preparation and/or hybridization.

The nucleic acid may be isolated from a test tissue or cell sample (and/or a control tissue sample) according to any of a number of methods well known to those of skill in the art.

One of skill in the art will appreciate that where expression levels of a gene or genes are to be detected, RNA (mRNA) is isolated. Methods of isolating total mRNA are well known to those of skill in the art. For example, methods of isolation and purification of nucleic acids are described in Sambrook et al. (1989) MOLECULAR CLONING: A LABORATORY MANUAL, Cold Spring Harbor Laboratory Press; and Sambrook et al. (2001). MOLECULAR CLONING: A LABORATORY MANUAL (3rd ed.). Cold Spring Harbor Laboratory Press, which are both incorporated herein by reference in their entireties. Filter based methods for the isolation of mRNA are also available in the art and can be used for isolating mRNA from biological samples. Examples of commercially available filter-based RNA isolation systems include RNAqueous™ (Ambion) and RNeasy™ (Qiagen). One of skill in the art would appreciate that it is desirable to inhibit or destroy RNase present in homogenates of biological samples soon after obtaining the samples so that the mRNA is not degraded by nucleases during testing.

Frequently, it is desirable to amplify the nucleic acid sample prior to evaluation. If a quantitative result is desired care can be taken to use an amplification method that maintains or controls for the relative frequencies of the amplified nucleic acids.

Methods of "quantitative" amplification are well known to those of skill in the art. For example, quantitative PCR involves simultaneously co-amplifying a known quantity of an internal control nucleic acid. This provides an internal standard that may be used to calibrate the PCR reaction. Detection of the internal control sequence along with the mRNAs of interest (e.g., those from any of the genes in Table 1) allows one of skill in the art to monitor whether the mRNA isolation, purification and quantification procedures accurately reflect actual expression levels or whether there is a problem with any of these procedures (e.g., the mRNA has become degraded during one of the procedures).

Suitable amplification methods include, but are not limited to polymerase chain reaction (PCR) (Innis & Gelfand, *Optimization of PCRs*. In: PCR PROTOCOLS: A GUIDE TO METHODS AND APPLICATIONS (eds. M. A. Innis, et al.), pp. 3-12. Academic Press, San Diego (1990); ligase chain reaction (LCR) (see, Wu and Wallace, Genomics (1989)); Landegren, et al., *Science* 241: 1077-1080 (1988); Barringer, et al., *Gene* 89: 117-122 (1990); transcription amplification (Kwoh, et al., *Proc. Natl. Acad. Sci. USA* 86, 1173-1177 (1989)), and self-sustained sequence replication (Guatelli, et al., *Proc. Natl. Acad. Sci.* 87: 1874-1878 (1990)).

In one embodiment, a nucleic acid sample is the total mRNA isolated from a biological sample (e.g., a test tissue or cell sample). The term "biological sample," as used herein, refers to a sample obtained from an organism or from components (e.g., cells) of an organism, including normal tissue (e.g., as a control) and diseased tissue such as a tumor, a neoplasia or a hyperplasia. The sample may be of any biological tissue or fluid or cells from any organism as well as cells raised in vitro, such as cell lines and tissue culture cells. The biological sample may also be referred to as a "clinical sample" derived from a patient. Such samples include, but are not limited to, tissue biopsy or fine needle aspiration biopsy samples, blood, blood cells (e.g., white cells), urine, peritoneal fluid, and pleural fluid, or cells therefrom. Biological samples may also include sections of tissues such as frozen sections or formalin fixed sections taken for histological purposes.

In some embodiments, the sample mRNA is reverse transcribed with a reverse transcriptase, such as SuperScript II (Invitrogen), and a primer consisting of an oligo-dT to generate first-strand cDNA. Other desirable sequences can be incorporsated into the first-strand cDNA by linking those sequences onto the oligo-dT primer (e.g., a restriction site sequence, a sequence encoding a promoter such as a phage T7 promoter, etc.). A second-strand DNA is polymerized in the presence of a DNA polymerase, DNA ligase, and RNase H. The resulting double-stranded cDNA may be blunt-ended using T4 DNA polymerase and purified by phenol/chloroform extraction. The double-stranded cDNA can then be then transcribed into cRNA or amplified to generate a pool of amplified cDNAs. Methods for the in vitro transcription of RNA are known in the art and describe in, for example, Van Gelder, et al. (1990) and U.S. Pat. Nos. 5,545,522; 5,716,785; and 5,891,636, all of which are incorporated herein by reference.

If desired, a label may be incorporated into the cRNA or cDNA when it is transcribed. Those of skill in the art are familiar with methods for labeling nucleic acids. For example, the cRNA may be transcribed in the presence of biotin-ribonucleotides or the cDNA may be synthesized in the presence of biotin-deoxyribonucleotides. The BioArray High Yield RNA Transcript Labeling Kit (Enzo Diagnostics) is a commercially available kit for biotinylating cRNA.

It will be appreciated by one of skill in the art that the direct transcription method described above provides an antisense (aRNA) pool. Where antisense RNA is used with a microarray for detection, the antisense RNA can be the "target nucleic acid" that is hybridized to an array of the oligonucleotide probes provided in the microarray. In that case the oligonucleotide probes on the microarray are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense, or both senses, as the target nucleic acids include both sense and antisense strands.

To detect hybridization, it may be advantageous to employ nucleic acids in combination with an appropriate detection means. Recognition moieties incorporated into primers, incorporated into the amplified product during amplification, or attached to probes that can hybridize to the amplified product are useful in the identification of nucleic acid molecules. A number of different labels may be used for this purpose including, but not limited to, fluorophores, chromophores, radiophores, enzymatic tags, antibodies, chemiluminescence, electroluminescence, and affinity labels. One of skill in the art will recognize that these and other labels can be used with success in this invention.

Examples of affinity labels include, but are not limited to the following: an antibody, an antibody fragment, a receptor protein, a hormone, biotin, Dinitrophenyl (DNP), or any polypeptide/protein molecule that binds to an affinity label. Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. Examples of fluorophores include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluoroscein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Means of detecting such labels are well known to those of skill in the art. For example, radiolabels may be detected using photographic film or scintillation counters. In other examples, fluorescent markers may be detected using a photodetector to detect emitted light. In still further examples, enzymatic labels are detected by providing the enzyme with a substrate and detecting the reaction product produced by the action of the enzyme on the substrate, and colorimetric labels are detected by simply visualizing the colored label or by use of spectrometer.

So called "direct labels" are detectable labels that are directly attached to or incorporated into the target (sample) nucleic acid prior to hybridization to a probe or microarray. In contrast, so called "indirect labels" are joined to the hybrid duplex after hybridization. In some embodiments, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin-bearing hybrid duplexes providing a label that is easily detected. For a detailed review of methods of labeling nucleic acids and detecting labeled hybridized nucleic acids see, for example, Peter C. van der Vliet & Shiv Pillai, eds., LABORATORY TECHNIQUES IN BIOCHEMISTRY AND MOLECULAR BIOLOGY (1993).

Methods for Detecting Differential Expression

The present invention includes a method for detecting and/or quantifying expression of any combination of the genes listed in Table 1 (e.g., a target nucleic acid) in a biological sample.

Such detection and quantification methods can involve nucleic acid amplification (e.g., reverse transcription PCR, quantitative PCR and/or real-time PCR), wherein a sample containing a target nucleic acid that is to be amplified (e.g. a cDNA generated from an RNA sample by reverse transcription) is mixed with 1) primers that are complementary to sequences within the target sequence to be amplified, 2) a thermostable polymerase, and 3) four different nucleoside triphosphates. The normal steps of nucleic acid amplification are then followed—melting, annealing and synthesis—by thermal cycling of the mixture. The primers employed can be linked to a label. In some embodiments, a fluorescent intercalating agent is used in the reaction. The labeled primers and/or fluorescent intercalating agents allow quantification of the amounts of amplified products generated in various test reactions.

When nucleic acid amplification is used to detect gene expression, any procedure that amplifies RNA can be used, for example, reverse transcription-polymerase chain reaction (RT-PCR) assays, strand displacement amplification and other amplification procedures. Strand displacement amplification can be used as described in Walker et al (1992) Nucl. Acids Res. 20, 1691-1696. The term "polymerase chain reaction" ("PCR") refers to the method of K. B. Mullis U.S. Pat. Nos. 4,683,195; 4,683,202; and 4,965,188, hereby incorporated by reference, which describe a method for increasing the concentration of target nucleic acid in a mixture of genomic DNA or other DNA or RNA without cloning or purification.

The steps involved in PCR nucleic acid amplification method are described in more detail below. For ease of discussion, the nucleic acid to be amplified is described as being double-stranded. However, the process is readily adapted to amplify a single-stranded nucleic acid, such as an mRNA from any of the genes listed in Table 1. In the amplification of a single-stranded nucleic acid, the first step involves the synthesis of a complementary strand, for example, by reverse transcription so that two complementary target strands are available for amplification.

When PCR is performed on double-stranded DNA or cDNA generated from one or more of the RNAs expressed from the genes of Table 1, two primers are employed, each primer hybridizing to a different DNA strand at opposite ends of the DNA target. One of skill in the art can readily make and use probes and primers for the genes listed in Table 1, for example, by examining available nucleic acid sequences for these genes that are available in the sequence database maintained by the National Center for Biotechnology Information (see website at ncbi"dot"nlm"dot"nih-"dot"). Examples of some sequences for the genes listed in Table 1 are provided herein and below.

The PCR process for amplifying a target nucleic acid consists of introducing a large excess of the two primers to a mixture that may contain the mRNA (or cDNA generated therefrom) from any of the genes listed in Table 1, followed by a precise sequence of thermal cycling in the presence of a nucleic acid polymerase. For PCR amplification, each of the two primers is complementary to a distinct region in one of the two strands of the double stranded target sequence. Primers are selected so that they hybridize just outside the region of interest to be amplified and so that, upon primer extension, one primer will be extended towards the hybridization site of a second primer hybridized on the opposite target strand.

To effect amplification, the nucleic acid (RNA or cDNA) is denatured to open up double-stranded target sites and the temperature is lowered so that the primers anneal to their complementary sequences within the target molecule. Following annealing, the primers are extended with a polymerase. Such primer extension forms a new pair of complementary strands that likely have different ends than the original target. Such complementary strands can hybridize together to form an "amplicon" that can also be a target for amplification. The steps of denaturation, primer annealing and primer extension can be repeated many times. Each round of denaturation, annealing and extension constitutes one "cycle." There can be numerous cycles, and the amount of amplified DNA produced increases with the number of cycles. Hence, to obtain a high concentration of an amplified target nucleic acid, many cycles are performed.

The following steps are generally employed during nucleic acid amplification with the inhibitors of the invention:

(a) Each target nucleic acid strand is contacted with four different nucleoside triphosphates and one oligonucleotide primer, wherein each primer is selected to be substantially complementary to a portion the nucleic acid strand to be amplified (hmgn3), such that the extension product synthesized from one primer, when it is separated from its complement, can serve as a template for synthesis of the extension product of the other primer. To promote the proper annealing of primer(s) and the nucleic acid strands to be amplified, a selected primer-hybridization temperature is used that allows hybridization of each primer to a complementary nucleic acid strand. The inhibitors of the invention can be added or included in this melting/annealing reaction.

(b) After primer annealing, a nucleic acid polymerase is used for primer extension. The nucleic acid polymerase incorporates the nucleoside triphosphates into a growing nucleic acid strand to form a new strand that is complementary to the template strand hybridized by the primer. In general, this primer extension reaction is performed at a temperature and for a time effective to promote the activity of the nucleic acid enzyme and to synthesize a "full length" complementary nucleic acid strand that extends into and through a complete second primer binding site. However, the temperature is not so high as to separate each extension product from its nucleic acid template strand. The polymerase may be added after the first melting/annealing reaction.

(c) The mixture from step (b) is then heated for a time and at a temperature sufficient to separate the primer extension products from their complementary templates. The temperature chosen is not so high as to irreversibly denature the nucleic acid polymerase present in the mixture.

(d) The mixture from (c) is cooled for a time and at a temperature effective to promote hybridization of a primer to each of the single-stranded molecules produced in step (b).

(e) The mixture from step (d) is maintained at a temperature and for a time sufficient to promote primer extension by the polymerase to produce a "full length" extension product. The temperature used is not so high as to separate each extension product from the complementary strand template. Steps (c)-(e) are repeated until the desired level of amplification is obtained.

In some embodiments, real-time polymerase chain reaction (real time PCR; also called quantitative real time polymerase chain reaction (Q-PCR/qPCR) or kinetic polymerase chain reaction) is employed to quantify the expression of genes. Real-time PCR amplifies and simultaneously quantifies a targeted nucleic acid (e.g., an RNA expressed by one of the genes listed in Table 1). Thus, real-time PCR permits both detection and quantification (as absolute number of copies or relative amount when normalized to DNA input or additional normalizing genes) of a specific nucleic acid (e.g., RNA) in a sample.

Real-time PCR employs many of the same steps as polymerase chain reaction but the amplified DNA product is quantified as it accumulates in the reaction in real time after each amplification cycle. Methods that are often used to quantify the amplified DNA include the use of fluorescent dyes intercalate with double-stranded DNA product, and the use of modified DNA primers that fluoresce when hybridized with a complementary nucleic acid template.

For example, any of the SEQ ID NO:3-118 primers can be used in a real-time PCR assay for evaluating expression levels of the differentially expressed genes. One type of real-time PCR assay that can be employed involves use of SYBRGreen dye. SYBR Green is a dye that binds the minor groove of double stranded DNA. When SYBR Green dye binds to double stranded DNA, the intensity of the fluorescent emissions increases. As more double stranded amplicons are produced, SYBR Green dye signal will increase. During the PCR assay, such a fluorescent signal is directly proportional to the number of amplicons generated.

To detect RNA expression levels, real-time polymerase chain reaction is combined with reverse transcription PCR, where the RNA in a sample is first treated with reverse transcriptase to generate a cDNA that can then be amplified. Reverse transcription PCR and real-time PCR can be used to quantify relative levels of expression from any of the genes listed in Table 1.

The present invention therefore includes a method for detecting and/or quantifying expression of any of the genes listed in Table 1 (a target nucleic acid) that involves nucleic acid amplification (e.g., reverse transcription PCR and real-time PCR), wherein a sample containing a target nucleic acid that is to be amplified (e.g. a cDNA generated from an RNA sample by reverse transcription) is mixed with 1) primers that are complementary to sequences within the target sequence to be amplified, 2) a thermostable polymerase, and 3) four different nucleoside triphosphates. The normal steps of nucleic acid amplification are then followed—melting, annealing and synthesis—by thermal cycling of the mixture. The primers employed can be linked to a label. In some embodiments, a fluorescent intercalating agent is used in the reaction. The labeled primers and/or fluorescent intercalating agents allow quantification of the amounts of amplified products generated in various test reactions.

Microarrays exploit the preferential binding of complementary nucleic acid sequences. A microarray is typically a glass slide, on to which DNA molecules are attached at fixed locations (spots or features). There may be tens of thousands of spots on an array, each containing a huge number of identical DNA molecules (or fragments of identical molecules), of lengths from twenty to hundreds of nucleotides. The spots on a microarray are either printed on the microarrays by a robot, or synthesized by photo-lithography (similar to computer chip productions) or by ink-jet printing. There are commercially available microarrays, however many labs produce their own microarrays.

Hybridization

Nucleic acid hybridization simply involves contacting a probe and target nucleic acid under conditions where the probe and its complementary target can form stable hybrid duplexes through complementary base pairing (see Lockhart et al., 1999, WO 99/32660, for example). The nucleic acids that do not form hybrid duplexes are then washed away leaving the hybridized nucleic acids to be detected, for example, through detection of an attached detectable label. It is generally recognized that nucleic acids are denatured by increasing the temperature and/or decreasing the salt concentration of the buffer containing the nucleic acids.

Under low stringency conditions (e.g., low temperature and/or high salt) hybrid duplexes (e.g., DNA-DNA, RNA-RNA or RNA-DNA) will form even where the annealed sequences are not perfectly complementary. Thus specificity of hybridization is reduced at lower stringency. Conversely, at higher stringency (e.g., higher temperature or lower salt) successful hybridization occurs with fewer mismatches.

One of skill in the art will appreciate that hybridization conditions may be selected to provide any degree of stringency. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in some embodiments, the wash is performed at the highest stringency that produces consistent results and that provides a signal intensity greater than approximately 10% of the background intensity. To better distinguish between the signal and the background, the hybridized sequences (e.g., on a microarray) may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al. (1989); NUCLEIC ACID HYBRIDIZATION, A PRACTICAL APPROACH, IRL Press, Washington D.C. 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" include conditions equivalent to binding or hybridization at 42EC in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The term "homology" refers to a degree of sequence identity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

The hybridization conditions selected also depend on the particular circumstances (depending, for example, on the G+C content, type of target nucleic acid, source of nucleic acid, and size of hybridization probe). Optimization of hybridization conditions for the particular application of interest is well known to those of skill in the art. Representative solid phase hybridization methods are disclosed in U.S. Pat. Nos. 5,843,663, 5,900,481, and 5,919,626, which are incorporated herein by reference in their entireties. Other methods of hybridization that may be used in the practice of the present invention are disclosed in U.S. Pat. Nos. 5,849, 481, 5,849,486, and 5,851,772, which are also incorporated herein by reference in their entireties.

Signal Detection

The hybridized nucleic acids are typically detected by detecting one or more labels attached to either the nucleic acids derived from a test sample (e.g., an amplified product) or to a probe that is hybridized to the mRNA or an amplified product of the mRNA. The labels may be incorporated by any of a number of means well known to those of skill in the art (for example, see Affymetrix GeneChip™ Expression Analysis Technical Manual).

DNA arrays and gene chip technology provide a means of rapidly screening a large number of nucleic acid samples for their ability to hybridize to a variety of single stranded DNA probes immobilized on a solid substrate. These techniques involve quantitative methods for analyzing large numbers of genes rapidly and accurately. The technology capitalizes on the complementary binding properties of single stranded DNA to screen nucleic acid samples by hybridization (Pease et al., 1994; Fodor et al., 1991). Basically, a DNA array or gene chip consists of a solid substrate with an attached array of single-stranded DNA molecules. For screening, the chip or array is contacted with a single stranded nucleic acid sample (e.g., cRNA or cDNA), which is allowed to hybridize under stringent conditions. The chip or array is then scanned to determine which probes have hybridized.

Methods for directly synthesizing on or attaching polynucleotide probes to solid substrates are available in the art. See, e.g., U.S. Pat. Nos. 5,837,832 and 5,837,860, both of which are expressly incorporated by reference herein in their entireties. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bifunctional crosslinking reagents (Running et al., 1990; Newton et al., 1993). When immobilized onto a substrate, the probes are stabilized and therefore may be used repeatedly.

In general terms, hybridization is performed on an immobilized nucleic acid target or a probe molecule that is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules).

The Affymetrix GeneChip system may be used for hybridization and evaluation of the probe arrays, where the probes have been selected to hybridize to any combination of the genes listed in Table 1 (or a cRNA or cDNA obtained from an mRNA generated by any of those genes). In some embodiments, the Affymetrix U95A or U133A array is used in conjunction with Microarray Suite 5.0 for data acquisition and preliminary analysis of gene expression patterns and/or levels.

Normalization Controls

Normalization controls are oligonucleotide probes that are complementary to labeled reference oligonucleotides that are added to the nucleic acid sample. The signals obtained from the normalization controls after hybridization provide a control for variations in hybridization conditions, label intensity, "reading" efficiency and other factors that may cause the hybridization signal to vary between arrays. For example, signals read from all other probes in the array can be divided by the signal from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes. Normalization probes can be localized at any position in the array or at multiple positions throughout the array to control for spatial variation in hybridization efficiently.

In a some embodiments, a standard probe cocktail supplied by Affymetrix is added to the hybridization to control for hybridization efficiency when using Affymetrix Gene Chip arrays.

Expression Level Controls

Expression level controls are probes that hybridize specifically with constitutively expressed genes in the sample. The expression level controls can be used to evaluate the efficiency of cRNA preparation.

Virtually any constitutively expressed gene provides a suitable target for expression level controls. Typically expression level control probes have sequences complementary to subsequences of constitutively expressed "housekeeping genes."

In one embodiment, the ratio of the signal obtained for a 3' expression level control probe and a 5' expression level control probe that specifically hybridize to a particular housekeeping gene is used as an indicator of the efficiency of cRNA preparation. A ratio of 1-3 indicates an acceptable preparation.

Databases

Any appropriate computer platform may be used to perform the necessary comparisons between sequence information, gene expression information and any other information in a database or provided as an input. For example, a large number of computer workstations and programs are available from a variety of manufacturers, such as those available from Affymetrix.

Statistical Methods

Combining profiles of gene expression over a wide array of transcripts has potentially more classification prediction power than relying on any single gene. The significance of the difference between the levels of gene expression between tissue sample types can be assessed using expression data and any number of statistical tests such as those described in the Examples and by using published methods (e.g., the Significance Analysis of Microarrays (SAM) method, see, Tusher V G, et al., 2001, Proc. Natl. Acad. Sci. USA 98(9):5116-21). SAM identifies genes with statistically significant changes in expression by assimilating a set of gene-specific t-tests. Each gene is assigned a score on the basis of its change in gene expression relative to the standard deviation of repeated measurements for that gene. Genes with scores greater than a threshold are deemed potentially significant. The percentage of such genes identified by chance is the false discovery rate (FDR). To estimate the FDR, nonsense genes are identified by analyzing permutations of the measurements. The threshold can be adjusted to identify smaller or larger sets of genes, and FDRs are calculated for each set.

Kits

The methods described herein can be practiced using a kit. Such kits generally include probes and/or primers for detecting and/or quantifying expression of the differentially expressed genes described herein, and instructions for performing the detection and/or quantification methods.

Thus, one aspect of the invention is a kit that includes, for example, (a) at least one set of oligonucleotide primers, wherein a first primer in the set contains a sequence complementary to a region in one strand of a nucleic acid sequence template and primes the synthesis of a first extension product, and a second primer contains a sequence complementary to a region in said first extension product and primes the synthesis of a nucleic acid strand complementary to said first extension product, and wherein the template is a differentially expressed gene, or an RNA or DNA copy of the differentially expressed gene; and (b) instructions for using the at least one set of oligonucleotide primers; wherein differentially expressed gene is selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof.

The first primer and/or the second primer provided in the kit can have a covalently attached label. For example, the first primer and/or the second primer can be selected from any of SEQ ID NO:3-118.

Another kit that can be made and/or used for detecting differential expression can include (a) a microarray with covalently attached probes that can hybridize to a differentially expressed gene selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof; and (b) instructions for using the microarray.

Probes useful in the microarray of this kit can hybridize to any of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, or a combination thereof The kit can include other useful components. For example, the kit can include a container of nucleotides for use as subunits in the synthesis of and amplified product. In some embodiments, the one or more nucleotides provided can have a covalently attached label. The nucleotides provided with the kit can be ribonucleotides or deoxyribonucleotides. Other components provided by the kit include reagents or devices for isolating and/or purifying mRNA, enzymes such as reverse transcriptase, ligase, DNA polymerase (e.g., Taq polymerase), solutions and buffers for performing enzymatic reaction, and/or solutions for performing hybridization. Thus, the kits can include one or more buffers, such as a DNA isolation buffers, an amplification buffer or a hybridization buffer. The kit may also contain compounds and reagents to prepare DNA templates and isolate RNA from a test sample. The kit may also include various labeling reagents and compounds.

The kit of can also include one or more standard or control probes. For example, one or more of the standard or control probes can be a probe or probes for one or more constitutively expressed genes.

In some embodiments the instructions provided with the kit can describe a method for amplifying an mRNA, cRNA or cDNA corresponding to the differentially expressed gene(s). One of skill in the art may choose to utilize the kit for detecting differential expression by hybridization of a first primer and/or a second primer to an mRNA, cRNA or cDNA corresponding to the differentially expressed gene under moderate to highly stringent hybridization conditions. When using the kit with the microarray, one of skill in the art may choose to utilize the kit for detecting differential expression by hybridization of a probe to an mRNA, cRNA or cDNA corresponding to the differentially expressed gene under moderate to highly stringent hybridization conditions. For example, the instructions provided in the kit can inform one of skill in the art to employ hybridization conditions that are moderately to highly stringent hybridization conditions.

The kit can include primers and/or probes for detecting some or all of the differentially expressed genes. For example, the kits can detect and/or quantify expression of a subset of differentially expressed genes such as any one of DIO1, DTX4, GALNT7, HMGA2, IGFBP6, MET, PROS1, SDC4, SERPINA1, SLC4A4, TIAM1, TIMP1, UPP1 or a combination thereof. The kits can detect and/or quantify expression of other subsets of differentially expressed genes, for example, any one of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, TIAM1 or a combination thereof. Alternatively, for example, the kits can be used to detect another subset of differentially expressed genes such as one or more of the following genes C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 or a combination thereof.

Thus, probes and/or primers for detecting mRNA expression of any of the genes listed in Table 1 may be included in a kit. The kit may further include individual nucleic acids that can be amplified with the nucleic acids of interest. The kit can also include probes and/or primers for detecting particular control nucleic acid sequences. The control nucleic acids included in the kit can be mRNA(s) and/or control cDNA(s). The probes, primers and/or control RNA and/or DNA sequences can be provided on a microarray. Alternatively, the probes, primers and/or control RNA and/or DNA sequences can be provided in separate vials or wells of an assay plate (e.g., a microtiter plate).

Some of the components of the kits may be packaged either in aqueous media or in lyophilized form. When the components of the kit are provided in one and/or more liquid solutions, the liquid solution is an aqueous solution, with a sterile aqueous solution being particularly preferred. However, the components of the kit may also be provided as dried powder(s). When reagents and/or components are provided as a dry powder, the powder can be reconstituted by the addition of a suitable solvent. It is envisioned that the solvent may also be provided in another container or by the user.

The containers for the kits can include at least one vial, test tube, flask, bottle, syringe or other container means, into which a component may be placed, and/or suitably aliquoted. A labeling reagent and label may be included and packaged separately or together. There can be more than one component or container in the kit. For example, the kit can also contain a second, third or other additional container into which the additional components may be separately placed. However, various combinations of components may be included together in a vial. The kits of the present invention can also include a means for containing the nucleic acids, and any other reagent containers in close confinement for commercial sale. Such containers may include injection or blow-molded plastic containers into which the desired vials are retained.

A kit will also include instructions for employing the kit components as well the use of any other reagent not included in the kit. Instructions may include variations that can be implemented.

The following non-limiting examples further illustrate aspects of the invention.

EXAMPLE 1

Materials and Methods

Tumor Samples

Tissue samples were collected at time of surgery, snap-frozen in liquid nitrogen, and stored at −80° C. Representative slides for all tumors were reviewed by two dedicated pathologists. A total of 90 thyroid tumor samples, including 16 papillary thyroid carcinoma (PTC), 22 follicular variants of papillary thyroid carcinoma (FVPTC), 15 hyperplastic nodules, 22 follicular adenomas, and 15 histologically borderline tumors were analyzed in this study. This study was approved by our Institutional Review Board.

Figure 1:
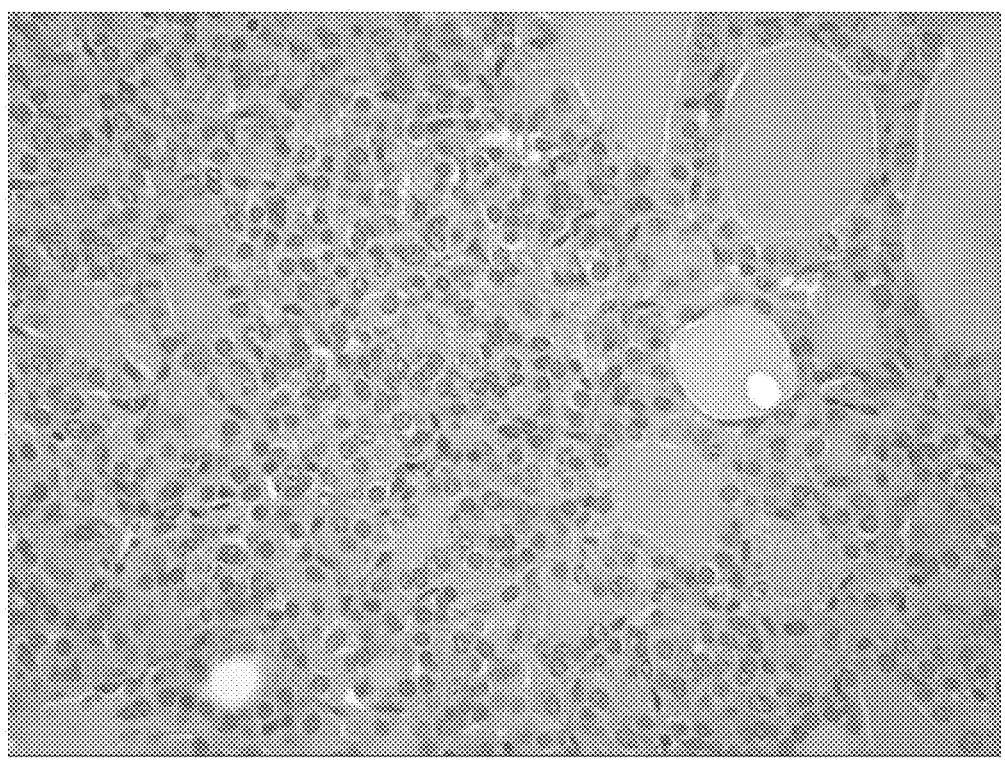
FIG. 1 is an image of a histologically borderline lesion. Note the follicular architecture with focal nuclear clearing and occasional nuclear grooves.

Borderline tumors were defined as encapsulated lesions with follicular architecture in which the morphologic features of papillary thyroid carcinoma were qualitatively incomplete and the lesions did not demonstrate evidence of capsular and/or vascular invasion. The incomplete features of papillary thyroid carcinoma were widespread in the lesions that were analyzed in this study and did not represent focal findings in an otherwise benign nodule. An example of such a borderline tumor sample is shown in FIG. 1. In essence, these cases could be classified as well differentiated tumors of uncertain malignant potential (WDT-UMP) as proposed by Williams et al. (Int J Surg Pathol. 8:181-183 (2000)). The officially reported final diagnosis of the 15 borderline tumors, all rendered prior to the onset of this study, was 7 follicular adeonomas and 8 FVPTCs.

RNA Isolation and GeneChip Hybridization

RNA was extracted using RNeasy Mini kit (Qiagen, Valencia, Calif.) from frozen tissue following manufacturer's protocol. RNA purity was confirmed by spectrophotometry. Total RNA was reverse transcribed to complementary DNA (cDNA) according to manufacturer's protocol (NuGEN Ovation RNA Amplification System V2) and then labeled with biotin. cDNA was then hybridized to genechips for microarray analysis, using either GeneChip U95A or U133A (Affymetrix, Santa Clara, Calif.).

Microarray Data Analysis

ArrayAssist 5.2.2 (Stratagene, Inc., La Jolla, Calif.) was used for gene chip analysis. Interchip and intrachip normalization was performed via robust multichip analysis (RMA). After RMA, hybridization signals underwent variance stabilization, log transformation, and baseline transformation. Advanced significance analysis was performed on 50 U95A GeneChips including 10 hyperplastic nodules, 16 follicular adenomas, 13 follicular variants of papillary thyroid carcinomas (FVPTCs), and 11 papillary thyroid carcinomas. This formed the training set. Gene expression of benign tumors was compared to that of malignant tumors. After Benjamini-Hochberg correction for false-discovery, gene probe sets with significant differential expression (2-fold or more with p<0.05) were identified. This probe list was then converted to correspond to probes on the U133A Gene Chips (array comparison software; available from Affymetrix.com). The remaining 40 tumor samples, all analyzed with U133A Gene Chips, formed the test set. The test set was then assessed using unsupervised hierarchical cluster analysis and K-means cluster analysis with both 2- and 3-group cluster algorithms. Genes that were differentially expressed between borderline tumors and classic benign and malignant tumors were further identified with advanced significance analysis.

Detection of BRAF Mutations

All 40 tumors forming the test group were analyzed for v-raf murine sarcoma viral oncogene homolog B1 (BRAF) mutations in which glutamate was substituted for valine at codon 600. One microgram of RNA was reverse-transcribed in a 20 µl reaction and a 1 µl aliquot of cDNA was used for polymerase chain reaction (PCR). The following PCR primers were used:

```
                                            (SEQ ID NO: 1)
forward primer, 5'-TGCTTGCTCTGATAGGAAAATG-3';
and
                                            (SEQ ID NO: 2)
reverse primer, 5'-GACTTTCTAGTAACTCAGCAGC-3'.
```

Amplification was carried out for 35 cycles (at 94° C. for 15 seconds, at 60° C. for 1 minute, and at 72° C. for 1 minute). All PCR products were visualized by electrophoresis on a 2% agarose gel and purified using a PCR purification kit (Qiagen Inc). BRAF mutations were detected by direct sequencing of PCR products. All sequencing was performed bidirectionally using the Big Dye Terminator cycle-sequencing kit and the Applied Biosystems Automated 3730 DNA Analyzer (Applied Biosystems, Foster City, Calif.).

EXAMPLE 2

Accurate Diagnosis of Thyroid Tumors as Benign or Malignant

This Example illustrates that gene expression analysis can be used to identify whether tumors of uncertain malignancy are benign or malignant. Based on their benign clinical behavior, it is proposed that these encapsulated thyroid follicular lesions with partial nuclear features of papillary thyroid carcinoma be called 'follicular adenomas with nuclear atypia' and the data indicate that these lesions may not need to be treated as cancers.

Differentiation of Benign and Malignant Tumors

The training set consisted of 50 tumors including 26 unequivocal benign tumors (16 follicular adenoma and 10 hyperplastic nodules) and 24 unequivocal malignancies (11 PTC and 13 FVPTC). A total of 66 probe sets corresponding to 56 genes showed significant differential expression between benign and malignant tumors. Thirty-one genes had up-regulated expression in malignancies compared to benign tumors, and 30 genes were down-regulated (Table 1).

TABLE 1

Genes differentially expressed between benign, borderline, and/or malignant thyroid lesions

| Gene Name | Gene Symbol | Fold Change* | P |
|---|---|---|---|
| Differentially expressed between benign and borderline/malignant lesions | | | |
| Ankyrin 2, neuronal | ANK2 | −2.70 | .0281 |
| Rho GTPase activating protein 6 | ARHGAP6 | −2.42 | .0329 |
| Cadherin 16, kidney-specific cadherin | CDH16 | −2.28 | .0185 |
| Cbp/p300-interacting | CITED1 | +6.44 | .0252 |
| Cbp/p300-interacting | CITED2 | −2.06 | .0261 |
| Cbp/p300-interacting | CITED2 | −2.76 | .0182 |
| Collagen, type IX, alpha 3 | COL9A3 | −5.87 | .0160 |
| Chondroitin beta 1,4 | ChGn | −3.72 | .0111 |
| Dual-specificity phosphatase 4 | DUSP4 | +3.69 | .0206 |
| EGF-containing fibulin-like | EFEMP1 | −2.60 | .0464 |
| engulfment and cell motility 1 | ELMO1 | −2.60 | .0261 |
| Fibroblast growth factor receptor 2 | FGFR2 | −2.13 | .0343 |
| Fibronectin leucine rich transmembrane protein 1 | FLRT1 | −2.10 | .0252 |
| Fibromodulin | FMOD | −3.09 | .0063 |
| Glycine amidinotransferase | GATM | −2.41 | .0482 |
| V-kit Hardy-Zuckerman 4 feline | KIT | −3.85 | .0039 |
| Low-density lipoprotein | LRP4 | +5.89 | .016 |
| Matrilin 2 | MATN2 | −3.38 | .0127 |
| Slit homolog 1 (*Drosophila*) | SLIT1 | +3.35 | .0258 |
| Spectrin, alpha, nonerythrocytic 1 | SPTAN1 | +2.66 | .0160 |
| Transcription factor CP2-like 1 | TFCP2L1 | −3.54 | .0029 |
| Phosphoinositide-binding protein | PIP3-E | −3.14 | .0343 |
| Pleckstrin and Sec7 domain | PSD3 | +2.40 | .0169 |
| Pleckstrin and Sec7 domain | PSD3 | +2.55 | .0214 |
| Tensin 3 | TNS3 | −2.41 | .0029 |
| Tetraspanin 12 | TSPAN12 | −2.35 | .0047 |
| T-cell lymphoma invasion and metastasis | TIAM1 | +3.91 | .0160 |
| Differentially expressed between malignant and borderline/benign lesions | | | |
| Deiodinase, iodonthyronine, type 1 | DIO1 | −4.47 | .0321 |
| Deltex 4 homolog (*Drosophila*) | DTX4 | +3.68 | .0111 |
| Uridine diphosphate-N-acetyl-alpha-D-galactosamine | GALNT7 | +2.07 | .0213 |
| High-mobility group AT-hook 2 | HMGA2 | +3.56 | .0204 |
| Insulin-like growth factor binding protein 6 | IGFBP6 | +3.18 | .0160 |
| Met proto-oncogene | MET | +2.35 | .0182 |
| Protein S | PROS1 | +3.97 | .0089 |
| Syndecan 4 | SDC4 | −3.26 | .0049 |
| Serpin peptidase inhibitor, clade A | SERPINA1 | +5.64 | .0252 |
| Serpin peptidase inhibitor, clade A | SERPINA1 | +4.81 | .0233 |
| Solute carrier family 4 | SLC4A4 | −4.03 | .0034 |
| TIMP metallopeptidase inhibitor 1 | TIMP1 | +2.72 | .0446 |
| Uridine phosphorylase 1 | UPP1 | +2.25 | .0127 |
| T-cell lymphoma invasion and metastasis 1 | TIAM1 | +3.91 | .0160 |
| Differentially expressed only between benign and malignant lesions | | | |
| Chromosome 11 open reading frame 17 | C11orf17 | −2.12 | .0239 |
| Calpain 3 | CAPN3 | +2.00 | .0263 |
| Calpain 3 | CAPN3 | +2.10 | .0410 |
| Creatine kinase, brain | CKB | −2.46 | .0189 |
| Cysteine and glycine-rich protein 2 | CSRP2 | −2.41 | .0189 |
| Death-associated protein kinase | DAPK2 | +2.23 | .0322 |
| Dipeptidyl-peptidase 4 | DPP4 | +2.83 | .0127 |
| Dipeptidyl-peptidase 4 | DPP4 | +2.51 | .0117 |
| Homogentisate 1,2-dioxygenase | HGD | −3.17 | .0149 |
| Myosin, heavy chain 10 | MYH10 | +2.73 | .0214 |
| Phosphonoformate immunoassociated protein 5 | PFAAP5 | +2.59 | .0189 |

TABLE 1-continued

Genes differentially expressed between benign,
borderline, and/or malignant thyroid lesions

| Gene Name | Gene Symbol | Fold Change* | P |
|---|---|---|---|
| Phosphonoformate immunoassociated protein 5 | PFAAP5 | +2.28 | .0258 |
| Placental growth factor | PGF | −2.22 | .0301 |
| Myosin, heavy chain 10 | MYH10 | +2.73 | .0214 |
| PBX/knotted 1 homeobox 2 | PKNOX2 | −2.31 | .0455 |
| Protein kinase, cAMP-dependent | PRKACB | −2.20 | .0241 |
| Glytaminyl-peptide cyclotransferase | QPCT | +3.43 | .0136 |
| RAB27A, member RAS oncogene | RAB27A | +2.41 | .0111 |
| RAB27A, member RAS oncogene | RAB27A | +2.08 | .0063 |
| Retinoid X receptor, gamma | RXRG | +2.57 | .0261 |
| Solute carrier family 25 | SLC25A15 | −2.75 | .0261 |

GTP indicates guanine triphosphate; Cpb, cyclic adenosine monophosphate response element-binding protein; EGF, epidermal growth factor; Sec7, a guanine-nucleotide-exchange factor (also called ARNO3 and cytohesion 3); AT, adenine and thymine; TIMP, tissue inhibitor of metalloproteinase; cAMP, cyclic adenosine monophosphate.
*Fold change is shown relative to benign lesions.

Unsupervised Hierarchical Cluster Analysis

Figure 2:
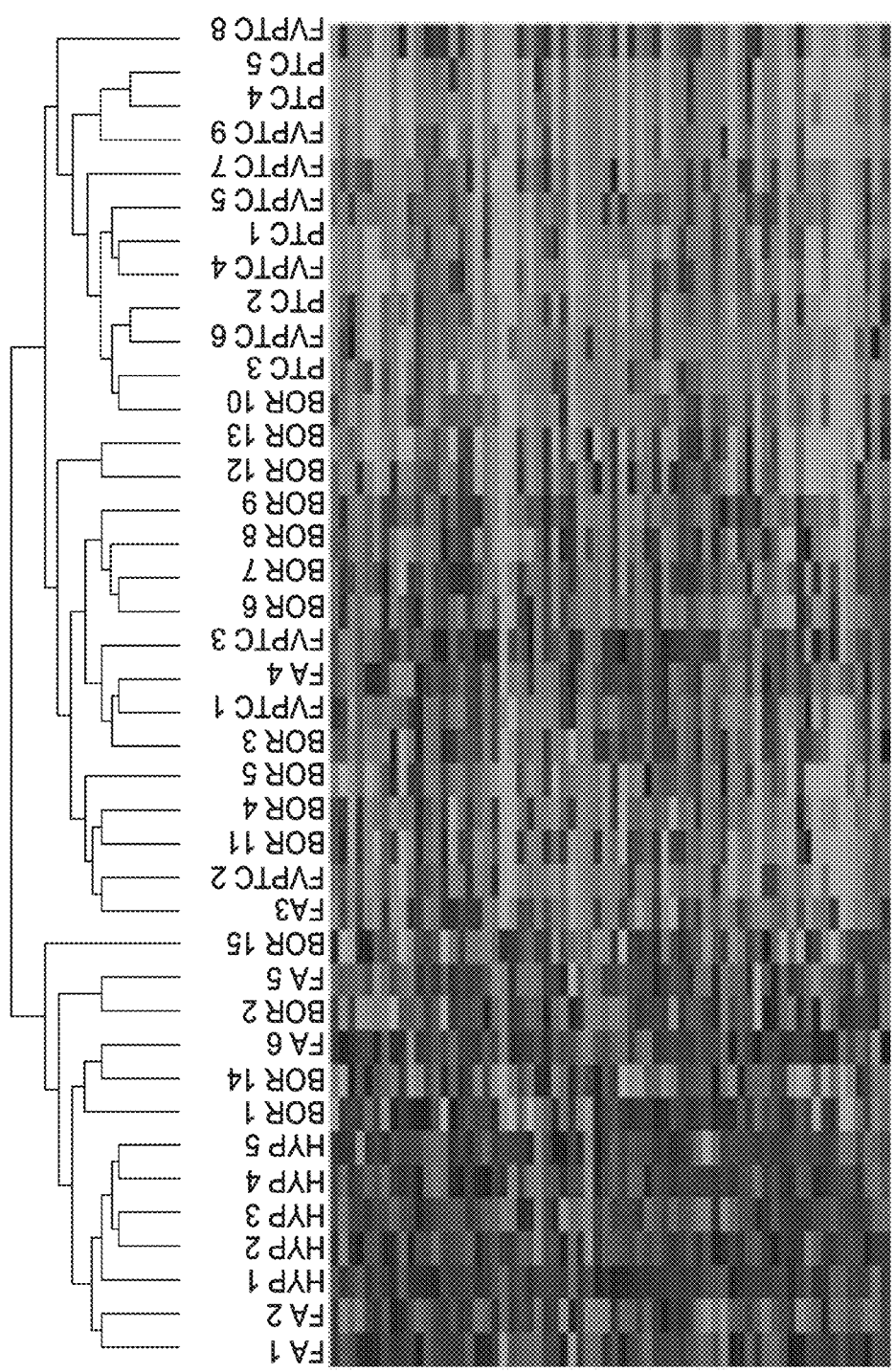
FIG. 2 is a graphic generated by an unsupervised hierarchical cluster analysis. FA indicates follicular adenoma; HYP, hyperplastic lesion; BOR, borderline tumor; FVPTC, follicular variant of papillary thyroid carcinoma; PTC, papillary thyroid carcinoma.

An independent set of 40 test samples was then characterized by observing the expression of genes from the list generated by the training set. The test set included 15 borderline tumors as well as a second group of unequivocal benign (n=11) and malignant (n=14) tumors, including 6 follicular adenomas, 5 hyperplastic nodules, 9 FVPTCs and 5 PTCs. In an unsupervised hierarchical cluster analysis, all benign tumors were distinguished from malignant tumors as expected (FIG. 2).

In addition to these two groups of tumor types, a third intermediate group was identified. This tumor group involved 15 tumors, where the vast majority (10 cases) were histologically borderline tumors. Three FVPTCs and 2 follicular adenomas were also identified in this borderline group of tumor types. Of the 5 remaining borderline tumors, 4 clustered with the benign group and 1 with the malignant group. It is noteworthy that these tumors were the most peripheral nodes in these two groups, indicating an expression profile closer to the intermediate group than other benign and malignant tumors (FIG. 2).

K-Means Cluster Analysis

Figure 3:
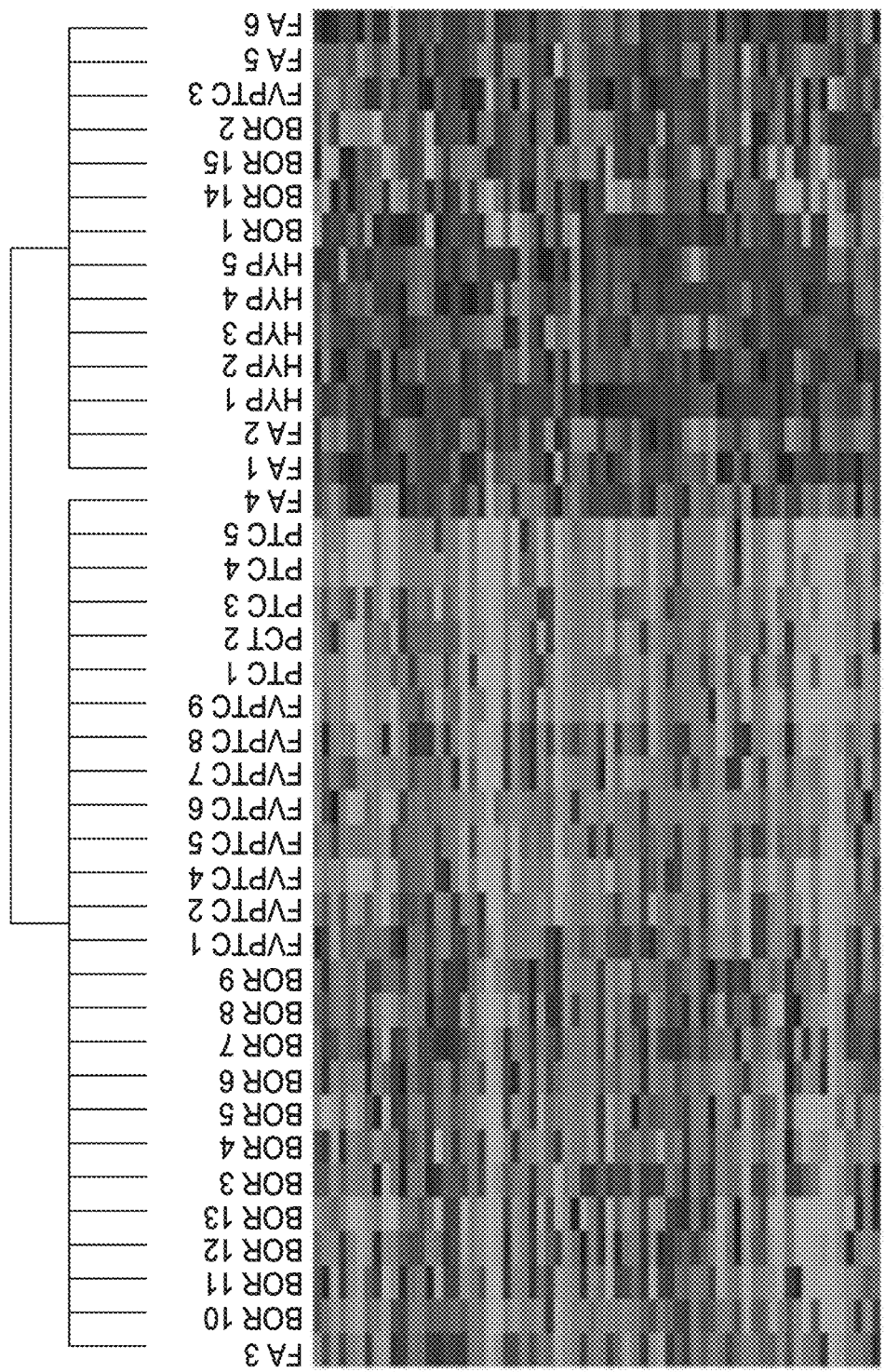
FIG. 3 is a graphic generated by a 2-group K-means cluster analysis. FA indicates follicular adenoma; BOR, borderline tumor; FVPTC, follicular variant of papillary thyroid carcinoma; PTC, papillary thyroid carcinoma; HYP, hyperplastic lesion.

To help elucidate the differences in gene expression between the three groups of tumors (benign, borderline and malignant), the test set was also subjected to K-means cluster analysis using both 2- and 3-groups. In the 2-group cluster algorithm, tumors were separated into two groups based on their gene expression of the genes of interest. This algorithm distinguished benign and malignant tumors with 93% sensitivity and 82% specificity (FIG. 3). Borderline tumors were divided, with four tumors (27%) grouped with benign tumors while eleven (73%) were grouped with the malignant tumors.

In the 3-group cluster algorithm, tumors were separated into three designated groups based on their expression profile. With this algorithm, malignant tumors primarily formed one group (with 1 borderline tumors), benign tumors formed a second group (with 4 borderline tumors), and a third group was composed of 10 borderline tumors, 2 follicular adenoma, and 3 FVPTC (FIG. 4). These 2 follicular adenomas were previously grouped with malignancies in the 2-group algorithm (FA-3 and FA-4) and one of the three FVPTCs that was grouped with the borderline tumors (FVPTC-3) had previously clustered with the benign tumors in the 2-group algorithm.

Correlation with Final Clinical Diagnosis and Patient Follow-Up

Of 15 borderline tumors included in this study, 7 tumors were officially diagnosed and reported as follicular adenomas (47%) and 8 (53%) as FVPTCs. Upon review of the 2-group K-means cluster analysis of these 15 borderline tumors, a correlation between the reported diagnosis and cluster group was observed in only 6 out of 15 tumors (40%), underscoring the diagnostic dilemmas that pathologists face with these tumors (Table 2).

TABLE 2

Comparison of Final Diagnosis with 2-Group Clustering
of Borderline Tumor Samples BOR1-15

| Sample | Pathologic Diagnosis | Cluster Group | Concordance |
|---|---|---|---|
| BOR 1 | FVPTC | Benign | No |
| BOR 2 | FA | Benign | Yes |
| BOR 3 | FA | Malignant* | No |
| BOR 4 | FVPTC | Malignant* | Yes |
| BOR 5 | FA | Malignant* | No |
| BOR 6 | FA | Malignant* | No |
| BOR 7 | FVPTC | Malignant* | Yes |
| BOR 8 | FVPTC | Malignant* | Yes |
| BOR 9 | FA | Malignant* | No |
| BOR 10 | FA | Malignant | No |
| BOR 11 | FVPTC | Malignant* | Yes |
| BOR 12 | FVPTC | Malignant* | Yes |
| BOR 13 | FA | Malignant* | No |
| BOR 14 | FVPTC | Benign | No |
| BOR 15 | FVPTC | Benign | No |

None of the borderline tumors were associated with lymph node metastasis or distant metastasis. Of the 9 patients with histologically borderline tumors who were followed, 6 patients were officially diagnosed with FVPTC, and none developed a recurrence after surgery (mean follow-up 1.7 years; range 2 months to 4.4 years) based on thyroglobulin level, ultrasound studies, or a combination of both methods. Similarly, among the 3 patients with FVPTC in the molecularly intermediate group (FVPTC-1, FVPTC-2, and FVPTC-3), none had lymph node metastasis, extranodal extension, or recurrent disease at follow-up periods of 23 months, 23 months, and 25 months, respectively.

Gene Signature of Borderline Tumors

Figure 5:
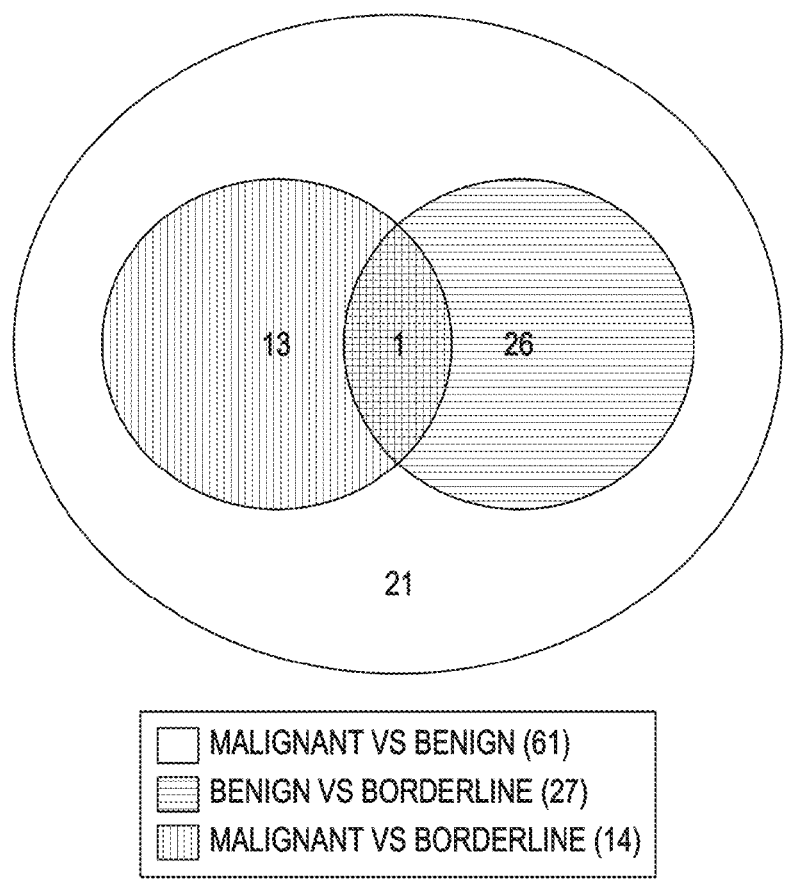
FIG. 5 shows a Venn diagram illustrating the differentially expressed genes relating 61 genes to benign, borderline, and malignant tumors.
Figure 6:
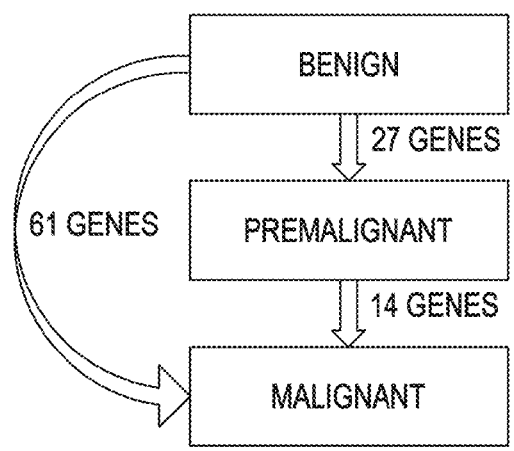
FIG. 6 is a schematic diagram showing proposed gene expression changes during tumorigenesis of follicular-patterned lesions of the thyroid.

To identify gene expression profiles that distinguish borderline tumors from either benign or malignant tumors, another advanced significance analysis was performed. Twenty-seven of the 61 genes had significant differential expression between benign and borderline tumors, while 14 of the 61 genes had significant differential expression between malignancies and borderline tumors. Only one of these genes, T-cell lymphoma invasion and metastasis 1 (TIAM1), overlapped between the two comparisons (FIG. 5). Of the 27 genes that distinguished benign from borderline tumors, 8 genes had up-regulated expression in borderline tumors including, CITED-1, and 19 genes were down-regulated including fibroblast growth factor receptor 2 (FGFR-2) (Table 1). Of the 14 genes that distinguished malignant tumors from borderline tumors, 11 genes were up-regulated in malignant tumors, including met proto-oncogene (MET) and the high-mobility group adenine/thymine-hook 2 gene (HMGA2), whereas 2 genes were relatively down-regulated, notably deiodinase-1 (DIO1) (Table 1).

Mutational Analysis of v-Raf Murine Sarcoma Viral Oncogene Homolog B1

BRAF mutational analysis was performed on all tumors in the test set. BRAF mutations were identified in 4 of 14 of the malignant tumors (29%) (Table 3). No borderline tumors or benign tumors had BRAF mutations.

TABLE 3

Presence of BRAF mutation in tumors

|  | BRAF mutation | Percent |
| --- | --- | --- |
| PTC (n = 5) | 3 | 60% |
| FVPTC (n = 9) | 1 | 11% |
| BOR (n = 15) | 0 | 0% |
| Follicular Adenoma (n = 6) | 0 | 0% |
| Hyperplastic Nodule (n = 5) | 0 | 0% |

PTC = papillary thyroid carcinoma;
FVPTC = follicular variant of papillary thyroid carcinoma;
BOR = borderline tumor Encapsulated follicular lesions with cytologic atypia remain a diagnostic challenge for pathologists. The foregoing experiments employed molecular profiling to identify a third category of thyroid tumors that, based on gene expression data, is likely to be premalignant. This third category of encapsulated follicular tumors with cytologic atypia typically did not fit into previously proposed benign or malignant classification schemes using standard histology, immunohistochemistry, or mutation analysis. The majority of histologically borderline tumors (66.7%) fell into an intermediate group and only a small number share gene expression similarities with benign tumors (26.7%) or malignant tumors (6.7%; Kmeans cluster analysis) (FIG. 4).

Many genes that were expressed differentially between benign tumors and malignant tumors in the training set were classic markers of PTC, including CITED1; dipeptidyl-peptidase 4 (DPP4); FGFR2; and serpin peptidase inhibitor, Glade A (SERPINA1) (see also, Prasad et al., Mod. Pathol. 2005; 18:48-57 (2005); Huang et al., Proc. Natl. Acad. Sci. USA. 98:15044-49 (2001); Jarzab et al., Cancer Res. 65:1587-1597 (2005)).

It is noteworthy that borderline tumors, like malignant tumors, exhibited up-regulated gene expression of CITED1 and pleckstrin and Sec7 domain 3 (PSD3) and down-regulated gene expression of FGFR2 relative to benign tumors (Table 1). These genes and others listed in Table 1 are potential markers of early tumorigenesis.

In contrast, some genes with expression that was consistently altered in malignant tumors exhibited unchanged expression in the borderline group of tumors. For example, DIO1, a differentiation marker that was consistently lost in PTC, was retained in this borderline group. Conversely, MET, SERPINA1, tissue inhibitor of metalloproteinase 1 (TIMP1), and HMGA2, which are genes that were often activated or over-expressed in PTC, exhibited lower expression in the borderline group of tumors relative to the malignant group. These genes may represent gene expression changes that are involved in the later stages of cancer development. These findings indicate that the histologically borderline tumors are premalignant and still lack the complete phenotype of PTC.

The results of BRAF mutation analysis also were in agreement with other studies (see, Nikiforova et al., J Clin Endocrinol Metab. 2003; 88:5399-5404 (2003)), with mutations identified in 29% of malignancies. To date, BRAF mutations have not been identified in benign lesions or in borderline encapsulated follicular tumors (see, Arora et al., World J Surg. 32:1237-1246 (2008); Fontaine et al., Oncogene 27:2228-2236 (2008)). Some studies indicate that BRAF mutations are associated with more aggressive tumors (Frasca et al., Endocr Relat Cancer. 15:191-205 (2008); Kebebew et al., Ann Surg. 246:466-471 (2007)) indicating that borderline tumors are more likely to be indolent tumors.

The finding that BRAF mutation is more frequent in classic PTC than in FVPTC also indicates that, for FVPTCs derived from FAs, BRAF either is uninvolved in carcinogenesis or is involved only as a late event. In addition, because of its higher frequency in classic PTC versus FVPTC, BRAF mutational analysis remains of limited usefulness in the diagnostic evaluation of these lesions.

Of the 15 histologically-defined borderline tumors in this study, 10 were clustered in an intermediate group, separate from benign and malignant clusters (FIG. 3). It is noteworthy that not all borderline tumors were separated into this third group: One tumor was clustered with malignant tumors, and 4 tumors were clustered with benign tumors. Conversely, 3 histologically-unequivocal FVPTCs and 2 FAs were identified in the molecularly intermediate group. Given the data provided herein that FAs, borderline tumors, and FVPTCs are stages of a biologic continuum, such an imperfect correlation between the histological classification and molecular data illustrates that accurate diagnosis should not be based on histological analysis alone.

Immunohistochemical markers have been studied in a few well differentiated tumors of uncertain malignant potential (WDT-UMP) with variable results. Papotti et al. (Mod Pathol. 18:541-546 (2005)) studied the expression of galectin-3 and HBME1 in 13 WDT-UMPs and noted some degree of staining with either antibody in 12 of 13 tumors. Immunohistochemical staining for HBME1, Galectin-3, and CK19 (data not shown) in the histologically borderline tumors that were studied as described herein revealed heterogeneous staining patterns. This variability, again, may reflect the biologically borderline nature of these tumors.

Unfortunately, part of the problem with standard diagnostic tools is the need by clinicians to separate tumors into benign or malignant categories. Partially for that reason, the term WDT-UMP proposed by Williams and by Rosai has not been embraced in practice and certainly is not in use at most institutions (Williams et al., Int J Surg Pathol. 8:181-183 (2000); Rosai, Endocr Pathol. 16:279-283 (2005)). Consequently, the majority of borderline tumors, as in the current study, probably are diagnosed as FVPTCs because of pathologists' general preference to err on the side of over-diagnosis for potential legal concerns. Patients are then often subjected, perhaps unnecessarily, to completion thyroidectomies, central neck dissections, and even radioactive iodine therapy. With the current 2-tiered classification (benign and malignant), our 2-Kmeans cluster would place 73% of histologically borderline tumors in the malignant category. However, such classification is somewhat simplistic and does not correlate with the clinical behavior of these tumors.

Several groups have reviewed the outcome of patients with encapsulated PTC, including both classic PTC and FVPTC (Liu et al., Cancer. 107:1255-1264 (2006); Vickery et al., Am J Surg Pathol. 7: 797-807 (1983); Evans et al., Am J Surg Pathol. 11:592-597 (1987). Liu et al. reviewed the outcome data from 42 patients with encapsulated, noninvasive FVPTCs who had a median 10-year follow-up and reported that no patients had recurrences and that none had lymph node metastasis. Vickery identified 10 patients who had encapsulated papillary cancers; in those patients, none had a recurrence, and only 1 patient had developed lymph node metastasis at a median follow-up of 15 years. Evans identified 7 patients who had encapsulated PTC and reported no recurrences or distant metastases at a median follow-up of 13.5 years. The number of studies that specifically have investigated tumors with borderline features is limited, although no tumor recurrences have been reported (Fusco et al., Am J Pathol. 160:2157-2167 (2002)). Likewise, none of the patients with borderline tumors in the current study had lymph node metastasis, and none of those with clinical follow-up developed recurrent disease or distant metastasis. The data presented here provide evidence that borderline tumors represent a molecularly distinct group of tumors that may not need aggressive treatment.

EXAMPLE 3

Real Time PCR Methods

This example describes procedures for performing reverse transcription, real-time, quantitative PCR (RT-qPCR).

Total RNA from human cells is isolated by a standard mini-column method, RNAeasy® Mini Kit (Qiagen, Valencia, Calif.). RNA sample quality is evaluated based on electrophoretic integrity of 18S and 28S rRNA bands on a 2100 Bioanalyzer instrument (Agilent, Santa Clara, Calif.) and by standard spectrophotometric absorbance methods at 230, 260 and 280 nm wavelengths on a NanoDrop 1000 (NanoDrop/Thermo Scientific, Wilmington, Del.).

Preparation of cDNA from the RNA samples is carried out using 1.0 μg of total RNA into a standard 20 μl MMLV reverse transcriptase (Promega, Madison, Wis.) reaction according to the manufacturer's instructions using Promega buffers with a combination of 50 μg/ml random hexamers (Integrated DNA Technologies, Coralville, Iowa) and 2.5 ng/μl oligo d(T16) (Integrated DNA Technologies, Coralville, Iowa) to prime the first strand synthesis. Upon completion of the reverse transcription protocol, the cDNA sample is diluted with 91 μl nuclease-free water (~5 fold) so that 1 μl (~1/100) is used as the template for individual 25 μl PCR reactions.

SYBR® Green real-time PCR is set up by combining 12.5 μl 2× SYBR® Green PCR Master Mix (Applied Biosystems, Foster City, Calif.) with 1 μl cDNA sample, 1 μl PCR primer mix (10 μM each forward and reverse primers from Tables 4 and 5) and 10 μl nuclease-free water in an appropriate reaction tube or plate. Real-time PCR thermal cycling and detection is performed on either an ABI 7500 (Applied Biosystems, Foster City, Calif.) or Stratagene Mx3005P (Agilent, Santa Clara, Calif.) instrument for 1 cycle of 10 minutes at 95° C., then 40 cycles of 15 seconds at 95° C. and 60 seconds at 60° C., followed by the instrument specific dissociation analysis steps.

Using the instrument's software and a consistent selection of measurement variables, Ct values are determined and relative expression measurements obtained by the ΔΔCt calculation method (Livak, K J, Schmittgen, T D. 2001, *Methods* 25, 402-408).

EXAMPLE 4

Primers and Probes for Detection of Differential Expression

This Example describes primers and probes for detecting expression of the differentially expressed genes described herein.

Thus, the sequences of primers with SEQ ID NO:3-118 are shown below in Tables 4 and 5.

Examples of human sequences (SEQ ID NO:119-172) for the differentially expressed genes ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, and UPP1 are shown in Table 6.

TABLE 4

Forward Primers for Nucleic Acid Amplification
Of Differentially Expressed Genes

| Gene Symbol HGNC Standard | NIH/NCBI Transcript ID | Forward Primer Sequence | SEQ ID NO: |
|---|---|---|---|
| ANK2 | NM_001127493 | AATACTGTGAGAAGAAGTG | 3 |
| ARHGAP6 | NM_001174 | GTGCCAAAGGCTGAGGAAATG | 4 |
| C11orf17 | NM_182901 | CTCATGTGGTAGCAGTTGATTC | 5 |
| NAUK2 | NM_030952 | GAAGTCCCGCAAGGAGAATG | 6 |
| CAPN3 | NM_173090 | AGGCTGGCCTCATCCAAAG | 7 |
| CDH16 | NM_004062 | GATCGTGTGTCGCTGCAAC | 8 |
| CSGALNACT1 (ChGn) | NR_024040 | AGGAAACTCATTCAGACTG | 9 |
| CITED1 | NM_004143 | ATGCCAACCAAGAGATGAG | 10 |
| CITED2 | NM_006079 | AATGGGCGAGCACATACAC | 11 |
| CITED2 | NM_006079 | TAATAGGGTGTGGAATGTC | 12 |
| CKB | NM_001823 | CTTCCTAACTTATTGCCTG | 13 |

TABLE 4-continued

Forward Primers for Nucleic Acid Amplification
Of Differentially Expressed Genes

| Gene Symbol HGNC Standard | NIH/NCBI Transcript ID | Forward Primer Sequence | SEQ ID NO: |
|---|---|---|---|
| COL9A3 | NM_001853 | GGATCTGCGACACCTCAGC | 14 |
| CSRP2 | NM_001321 | GGCCTACAACAAATCCAAAC | 15 |
| DAPK2 | NM_014326 | TAGGACACGCAGGAAAGACCAC | 16 |
| DIO1 | NM_000792 | TTAAACCTGTCCACATTGGTG | 17 |
| DPP4 | NM_001935 | GATAAGAGGGATTAGGGAG | 18 |
| DTX4 | NM_015177 | ATTTCCTTTCTAACACTGTG | 19 |
| DUSP4 | NM_001394 | TCTAGTTACAGTGGATTTAG | 20 |
| EFEMP1 | NM_001039348 | ATCCAGAGTGACAGTGAAC | 21 |
| ELMO1 | NM_001039459 | GACTAAACCTAAATGCCTC | 22 |
| FGFR2 | NM_000141 | ATCCAGCCTCATACCTACATCAG | 23 |
| FLRT1 | NM_013280 | GCTTATTCCATACCATTTC | 24 |
| FMOD | NM_002023 | GGCTCTTCTCCCTCTCCCAG | 25 |
| GALNT7 | NM_017423 | GTTGGTAATATCACTATGC | 26 |
| GATM | NM_001482 | GTAATTGGATTTCGCTATC | 27 |
| HGD | NM_000187 | GATGAGAACTACCACAAGTGCTG | 28 |
| HMGA2 | NM_003483 | TGTACTTTGAATCGCTTGCTTGTTG | 29 |
| IGFBP6 | NM_002178 | TGCAGCAACTCCAGACTGAG | 30 |
| KIT | NM_001093772 | TTGTGTGTTGTCTTGAAAG | 31 |
| LRP4 | NM_002334 | GAAGCGATTCTCCCATGCTC | 32 |
| MATN2 | NM_030583 | TACGATAAAGTTTGCACAG | 33 |
| MET | NM_001127500 | GAAAGAACTGTCTCTACCAG | 34 |
| MYH10 | NM_005964 | ACTACAAGCAGAGACTGAG | 35 |
| PFAAP5 | U50535 | CAAGGCAGGCAGATTGTTTG | 36 |
| PFAAP5 | CR601845 | TTAGCGGACATGGGTCAATTTC | 37 |
| PGF | NM_002632 | GCTTGTACTGGGACATTGTTC | 38 |
| IPCEF1 (PIP3-E) | NM_001130700 | GATCCAGGACATCTATCAG | 39 |
| PKNOX2 | NM_022062 | AGCACGGACACACTGGCAC | 40 |
| PRKACB | NM_002731 | GTGAAAGCACCTTGTAAAC | 41 |
| PROS1 | NM_000313 | AGTAAGGAGGTAAGATTGC | 42 |
| PSD3 | NM_206909 | GGTAGTGTCTAAGTGGTATG | 43 |
| PSD3 | NM_206909 | TGACTTTCAACTAACCTTG | 44 |
| QPCT | NM_012413 | GATATTGTGTCCTAAATTGC | 45 |
| RAB27A | NM_183236 | TGCCAATGGGACAAACATAAG | 46 |
| RAB27A | NM_183236 | GATGCCTGTTTGCTATTGGTGGAAG | 47 |
| RXRG | NM_006917 | ATTGTACTCTTTAACCCAG | 48 |
| SDC4 | NM_002999 | CTTCCTCAGTTGCACTAACCAC | 49 |

TABLE 4-continued

Forward Primers for Nucleic Acid Amplification
Of Differentially Expressed Genes

| Gene Symbol HGNC Standard | NIH/NCBI Transcript ID | Forward Primer Sequence | SEQ ID NO: |
|---|---|---|---|
| SERPINA1 | NM_000295 | TCTGCCAGCTTACATTTACCCAAAC | 50 |
| SLC25A15 | NM_014252 | GTGACCGCTCTTGCTCTTG | 51 |
| SLC4A4 | NM_003759 | AAGAGTGAATAGTTGCCTC | 52 |
| SLIT1 | NM_003061 | CTAGAGGCTGGTTTAGAAC | 53 |
| SPTAN1 | NM_003127 | AGTTTGTAGCCAATGTGGAAG | 54 |
| TFCP2L1 | NM_014553 | TGATTTCCTGTTATGAGTC | 55 |
| TIAM1 | NM_003253 | TTCCATATCATCTCCGGTTCG | 56 |
| TIMP1 | NM_003254 | GACTCTTGCACATCACTAC | 57 |
| TNS3 | NM_022748 | TGTGCCCAACGCATGTTATAG | 58 |
| TSPAN12 | NM_012338 | AGAAAGGACTTGTATGCTG | 59 |
| UPP1 | NM_181597 | GTGTGTGTCACCCTCCTGAAC | 60 |

TABLE 5

Reverse Primers for Nucleic Acid Amplification
of Differentially Expressed Genes

| Gene Symbol HGNC Standard | NIH/NCBI Transcript ID | Reverse Primer Sequence | SEQ ID NO: |
|---|---|---|---|
| ANK2 | NM_001127493 | TTGCAGCTATGTATTGTTAG | 61 |
| ARHGAP6 | NM_001174 | GATGGCGATACGCTTCAGTA | 62 |
| C11orf17 | NM_182901 | AAGGTGATGTGATGGCAGTG | 63 |
| NAUK2 | NM_030952 | TTGGCAGCTTGAGGTTGCTC | 64 |
| CAPN3 | NM_173090 | CTTGATCGGTCATGCCTAGCC | 65 |
| CDH16 | NM_004062 | GTAGGCACCCTGGTAGCAA | 66 |
| CSGALNACT1 (ChGn) | NR_024040 | AAGAGATTGTTTGGTTCAC | 67 |
| CITED1 | NM_004143 | CTCGGGATCTCCAATAGGCTCTC | 68 |
| CITED2 | NM_006079 | GTGCCCTCCGTTCACAGTC | 69 |
| CITED2 | NM_006079 | AGCTTTCAACACAGTAGTATC | 70 |
| CKB | NM_001823 | ATAAACTCTACCAAGGGTG | 71 |
| COL9A3 | NM_001853 | CGTGAGGAAGCAAGTGACA | 72 |
| CSRP2 | NM_001321 | GAGAAGATAATTGGAGCTGGAA | 73 |
| DAPK2 | NM_014326 | CAATCTTAGACTCTGGCCTCAA | 74 |
| DIO1 | NM_000792 | GCTCTCTGTACCCTGAAATCTTC | 75 |
| DPP4 | NM_001935 | GTTTGAATAGTCTTTCTCAG | 76 |
| DTX4 | NM_015177 | GTCAAGGTAGTAGATGCAC | 77 |
| DUSP4 | NM_001394 | GCTACCTTGCACATATCTAC | 78 |
| EFEMP1 | NM_001039348 | GATACATCAAAGTAAAGCAG | 79 |

TABLE 5-continued

Reverse Primers for Nucleic Acid Amplification of Differentially Expressed Genes

| Gene Symbol HGNC Standard | NIH/NCBI Transcript ID | Reverse Primer Sequence | SEQ ID NO: |
|---|---|---|---|
| ELMO1 | NM_001039459 | ATGATGTAAACTTGGATGTC | 80 |
| FGFR2 | NM_000141 | CAATAGCCGTGCAAGATGAATG | 81 |
| FLRT1 | NM_013280 | ATCGACTACATGATTGTTC | 82 |
| FMOD | NM_002023 | GTATGAGACCTACGAGCCTTACC | 83 |
| GALNT7 | NM_017423 | ACCCAGAATTAAGATATACG | 84 |
| GATM | NM_001482 | CTTAGATGACCAAAGATGC | 85 |
| HGD | NM_000187 | CTTTCTGGTAGTATTGGAGGAGG | 86 |
| HMGA2 | NM_003483 | CAGAGGCTGTTATGTTTATTGTG | 87 |
| IGFBP6 | NM_002178 | CATCGAGGCTTCTACCGGAA | 88 |
| KIT | NM_001093772 | AGAGCATAGAACTCCAGTG | 89 |
| LRP4 | NM_002334 | CACTGGAGAGATTGGACTTTC | 90 |
| MATN2 | NM_030583 | TATATCAAGGTAAAGTCCAG | 91 |
| MET | NM_001127500 | CAAGTGTGTAGTCCTGTTG | 92 |
| MYH10 | NM_005964 | GGTTTCTTTCTTCTTCTTC | 93 |
| PFAAP5 | U50535 | AATGGCACGATCATGGGTC | 94 |
| PFAAP5 | CR601845 | AAGTGTAGCCCAGGTTAAGAAC | 95 |
| PGF | NM_002632 | GAGAAACAGCTCAGCCAGTGG | 96 |
| IPCEF1 (PIP3-E) | NM_001130700 | AAGGTGATTTCTTGAGTTC | 97 |
| PKNOX2 | NM_022062 | CTGATGTATCCACCAAACCAGTAC | 98 |
| PRKACB | NM_002731 | CAGTAGTGCATAGGAAATTC | 99 |
| PROS1 | NM_000313 | CAGTGAAACATCTGATACAC | 100 |
| PSD3 | NM_206909 | ATAGTCATGGACATTTACAG | 101 |
| PSD3 | NM_206909 | AAGTTACTAAGACTGCACAG | 102 |
| QPCT | NM_012413 | CTATCGTTGAATGAATGAAC | 103 |
| RAB27A | NM_183236 | CTGAAGGAGTGGTGCGATCAA | 104 |
| RAB27A | NM_183236 | GAAGACACTTTGGCAATGCAGCGG | 105 |
| RXRG | NM_006917 | GATACTTCTGCTTGGTGTAG | 106 |
| SDC4 | NM_002999 | GACGACCCTTGTCTCCCTG | 107 |
| SERPINA1 | NM_000295 | GCATCACTAAGGTCTTCAGCA | 108 |
| SLC25A15 | NM_014252 | GTGGTCAGTAGCCTTATGCACCT | 109 |
| SLC4A4 | NM_003759 | ATCATTTCTCTCTCCAAAG | 110 |
| SLIT1 | NM_003061 | GGAAGACAACAGACAATATC | 111 |
| SPTAN1 | NM_003127 | GATTATGGCGACACTCTTGCC | 112 |
| TFCP2L1 | NM_014553 | TACAGTGATGACAGACAGC | 113 |
| TIAM1 | NM_003253 | CTTGGAGAGGGTGCCATTGTC | 114 |
| TIMP1 | NM_003254 | GATAAACAGGGAAACACTG | 115 |

TABLE 5-continued

Reverse Primers for Nucleic Acid Amplification of Differentially Expressed Genes

| Gene Symbol HGNC Standard | NIH/NCBI Transcript ID | Reverse Primer Sequence | SEQ ID NO: |
|---|---|---|---|
| TNS3 | NM_022748 | CTTGTAACGTCTTCTCTGCCT | 116 |
| TSPAN12 | NM_012338 | TATTGACTTGGAGACTATTG | 117 |
| UPP1 | NM_181597 | GAAGAAACTGAGCAAGGCC | 118 |

Sequences of the coding regions of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, and/or UPP1 can be used to develop probes and primers for detecting differential expression of these genes. Such sequences are available in the database maintained by the National Center for Biotechnology Information (NCBI). See website at ncbi.nlm.nih.gov. A few examples of such sequences are provided below.

One example of a nucleic acid sequence for human ANK2 is available as NCBI accession number NM_001148 (gi: 188595661). This sequence is recited below for easy reference as SEQ ID NO:119.

```
   1 ctcctcctcc tgctttcctc cagtaagtgc ataccgcta gtggtctgta caggcggcac
  61 ggtttgatgg cagagatatt ttctttccaa actgttcaaa atgatgaacg aagatgcagc
 121 tcagaaaagc gacagtggag agaagttcaa cggcagtagt cagaggagaa aaagacccaa
 181 gaagtctgac agcaatgcaa gcttcctccg tgctgccaga gcaggcaacc tggacaaagt
 241 tgtggaatat ctgaagggg gcatagacat caataccctgc aatcagaatg gactcaacgc
 301 tctccatctg gctgccaagg aaggccacgt ggggctggtg caggagctgc tgggaagagg
 361 gtcctctgtg gattctgcca ctaagaaggg aaataccgct cttcacattg catctttggc
 421 tggacaagca gaagttgtca aagttcttgt taaggaagga gccaatatta atgcacagtc
 481 tcagaatggc tttactcctt tatacatggc tgcccaagag aatcacattg atgttgtaaa
 541 atatttgctg gaaaatggag ctaatcagag cactgctaca gaggatggct ttactcctct
 601 agctgtggca ctccagcaag gacacaacca ggcggtggcc atcctcttgg agaatgacac
 661 caaagggaaa gtgaggctgc cagctctgca tattgccgct aggaaagacg acaccaaatc
 721 tgccgcactt ctgcttcaga atgaccacaa tgctgacgta caatccaaga tgatggtgaa
 781 taggacaact gagagtggtt ttacccctttt gcacatagct gcacattacg gaaatgtcaa
 841 cgtggcaact cttcttctaa accggggagc tgctgtggac ttcacagcca ggaatggaat
 901 cactcctctg catgtggctt ccaaaagagg aaatacaaac atggtgaagc tcttactgga
 961 tcgaggcggt cagatcgatg ccaaaactag ggatgggttg acaccacttc actgtgctgc
1021 acgaagtggg catgaccaag tggtggaact tctgttggaa cggggtgccc ccttgctggc
1081 aaggactaag aatgggctgt ctccactaca catggctgcc cagggagacc acgtggaatg
1141 tgtgaagcac ctgttacagc acaaggcacc tgttgatgat gtcaccctag actacctgac
1201 agccctccac gttgctgcgc actgtggcca ctaccgtgta accaaactcc ttttagacaa
1261 gagagccaat ccgaacgcca gagccctgaa tggttttact ccactgcaca ttgcctgcaa
1321 gaaaaaccgc atcaaagtca tggaactgct ggtgaaatat ggggcttcaa tccaagctat
1381 aacagagtct ggcctcacac caatacatgt ggctgccttc atgggccact tgaacattgt
1441 cctccttctg ctgcagaacg gagcctctcc agatgtcact aacattcgtg gtgagacggc
```

```
-continued
1501  actacacatg gcagcccgag ccgggcaggt ggaagtggtc cgatgcctcc tgagaaatgg
1561  tgcccttgtt gatgccagag ccagggagga acagacacct ttacatattg cctcccgcct
1621  gggtaagaca gaaattgtcc agctgcttct acaacatatg gctcatccag atgcggccac
1681  tacaaatggg tacacaccac tgcacatctc tgcccgggag ggccaggtgg atgtggcatc
1741  agtcctattg gaagcaggag cagcccactc cttagctacc aagaagggtt ttactcccct
1801  gcatgtagca gccaagtatg gaagcctgga tgtggcaaaa cttctcttgc aacgccgtgc
1861  tgccgcagat tctgcaggga agaacggcct taccccgctc catgttgctg ctcattatga
1921  caaccagaag gtggcgctgc tgttactgga aagggtgct tcccctcatg ccactgccaa
1981  gaatggctat actccgttac atattgctgc caagaagaat caaatgcaga tagcttccac
2041  actcctgaac tatggagcag agacaaacat tgtgacaaag caaggagtaa ctccactcca
2101  tctggcctcg caggaggggc acacagatat ggttaccttg cttctggata agggagccaa
2161  tatccacatg tcaactaaga gtggactcac atccttacac cttgcagccc aggaagataa
2221  agtgaatgtt gctgatattc tcaccaagca tggagctgat caggatgctc atacaaagct
2281  tggttacaca cctttaattg tggcctgtca ctatggaaat gtgaaaatgg tcaactttct
2341  tctgaagcag ggagcaaatg ttaacgcaaa aaccaagaac ggctacacgc ctttgcacca
2401  ggccgctcag cagggtcaca cgcacatcat caacgtcctg ctccagcatg gggccaagcc
2461  caacgccacc actgcgaatg caacactgc cttggcgatt gctaagcgtc tgggctacat
2521  ctccgtggtc gacaccctga aggttgtgac tgaggaggtc accaccacca ccacaactat
2581  tacagaaaaa cacaaactaa atgtacctga gacgatgact gaggttcttg atgtttctga
2641  tgaagagggt gatgacacaa tgactggtga tggggagaa taccttaggc ctgaggacct
2701  aaaagaactg ggtgatgact cactacccag cagtcagttc ctggatggta tgaattacct
2761  gcgatacagc ttggagggag gacgatctga cagccttcga tccttcagtt ccgacaggtc
2821  tcacactctg agccatgcct cctacctgag ggacagtgcc gtgatggatg actcagttgt
2881  gattcccagt caccaggtgt caactctagc caaggaggca gaaaggaatt cttatcgcct
2941  aagctggggc actgagaact tagacaacgt ggctctttct tctagtccta ttcattcagg
3001  tttcctggtt agttttatgg tggatgcccg aggtggtgct atgcgaggat gcagacacaa
3061  tgggctccga atcattattc cacctcggaa atgtactgct ccaacgcgag tcacctgccg
3121  actggtcaag cgccacagac tggcaacaat gcctccaatg gtggaaggag aaggcctggc
3181  cagtcgcctg atcgaagttg gaccttctgg tgctcagttc cttggtaaac ttcacctgcc
3241  aacggctcct cccccactta atgagggaga agtttggtc agccgcattc ttcagctggg
3301  gcctcctgga accaaattcc ttgggcctgt gatcgtggag atccctcact ttgcggccct
3361  tcgaggaaag gaaagggaac tggtggtcct gcgcagtgag aatgggggaca gctggaaaga
3421  gcatttctgt gactacactg aagatgaatt gaatgaaatt cttaacggca tggatgaagt
3481  actggatagc ccagaagacc tagaaaagaa acgaatctgc cgcatcatca cccgagactt
3541  cccacagtac tttgcagtgg tgtctcgtat caaacaggac agcaatctga ttgcccaga
3601  aggaggtgta ctgagcagca cagtggtgcc ccaggtgcag gccgtcttcc cagagggggc
3661  actcaccaag cggatccgcg taggcctgca ggctcaacct atgcacagtg agctggttaa
3721  gaagatccta ggcaacaaag ctaccttcag ccctatagtc actttggaac ctagaagaag
3781  aaaattccac aaaccaatta ccatgaccat tcctgtcccc aaagcttcaa gtgatgtcat
3841  gttgaatggt tttggggag atgcaccaac cttaagatta ctatgcagca taacaggtgg
3901  aaccacccct gcccagtggg aagatattac aggaactacg ccattaacat ttgtcaatga
```

-continued

```
3961  atgtgtttcc tttacaacaa acgtgtctgc caggttctgg ctgatagatt gtcgacagat
4021  ccaggaatcc gttacttttg catcacaagt atacagaaa attatctgcg taccttatat
4081  ggccaaattt gtagtgtttg ccaaatcaca tgaccccatt gaagccaggt tgaggtgttt
4141  ctgcatgact gatgataaag tggataagac ccttgaacaa caagaaaatt ttgctgaggt
4201  ggccagaagc agggatgtgg aggtgttaga aggaaaaccc atctacgttg attgtttcgg
4261  caacttggta ccattaacta aaagtggcca gcatcatata ttcagttttt ttgccttcaa
4321  agaaaataga cttcctctat ttgtcaaggt acgcgatacg actcaggaac cttgcggacg
4381  actatcattt atgaaggagc caaaatccac gagaggcctg gtgcatcaag ctatttgcaa
4441  cttaaacatc actttgccga tttatacaaa ggaatcagag tcagatcaag aacaggagga
4501  agagatcgat atgcatcag aaaaaaatga tgagacagaa tctacagaaa catctgtcct
4561  gaaaagtcac ctggttaatg aagttcctgt cctagcaagt ccggacttgc tctctgaagt
4621  ttctgagatg aaacaagatt tgatcaaaat gaccgccatc ttgaccacag atgtgtctga
4681  taaggcaggt tctattaaag tgaaggagct ggtgaaggct gctgaggaag agccaggaga
4741  gccttttgaa atcgttgaaa gagttaaaga ggacttagag aaagtgaatg aaatcctgag
4801  aagtggaacc tgcacaagag atgaaagcag tgtgcagagc tctcggtctg agagaggatt
4861  agttgaagag aatgggttaa ttgtcagtga tgaggaaata gaagaggcta ggcaaaaagc
4921  acctttagaa atcactgaat atccatgtgt agaagttaga atagataaag agatcaaagg
4981  aaaagtagag aaagactcaa ctgggctagt gaactacctt actgatgatc tgaatacctg
5041  tgtgcctctt cccaaagagc agctgcagac agttcaagat aaggcaggga agaaatgtga
5101  ggctctggct gttggcagga gctctgaaaa ggaagggaaa gacatacccc cagatgagac
5161  acagagtaca cagaaacagc acaaaccaag cttgggaata agaagccag taagaaggaa
5221  attaaaagaa agcagaaac aaaaagagga aggtttacaa gctagtgcag agaaagctga
5281  acttaaaaaa ggtagttcag aagagtcatt aggtgaagac ccaggtttag cccctgaacc
5341  ccttcccact gtcaaggcca catctccttt gatagaagaa actcccattg gttccataaa
5401  ggacaaagta aaggcccttc agaagcgagt ggaagatgaa cagaaaggtc gaagcaagtt
5461  gcccatcaga gtcaaaggca aggaggacgt gccaaaaaag accacccaca ggccacatcc
5521  agctgcgtca ccctctctga agtcagagag acatgcgcca gggtctccct cccctaaaac
5581  agaaagacac tctactcttt cctcttccgc aaaaactgaa aggcaccctc cagtatcacc
5641  atcaagtaaa actgagaaac actcacctgt gtcaccctct gcaaaaacgg aaagacattc
5701  acctgcgtca tcatcgagta aaactgagaa acactcacct gtatcaccct cgacaaaaac
5761  tgaaaggcac tctcctgtgt catctacaaa aacagaaaga cacccacctg tttcgccttc
5821  aggcaaaaca gacaaacgtc cacctgtatc gccctccggg aggacagaaa acacccgcc
5881  agtatcgcct gggagaacag aaaaacgctt gcctgtttca ccctccggaa aacggacaa
5941  gcaccaacct gtatcaacag ctgggaaaac tgagaagcac ctgcctgtgt caccttctgg
6001  caaaacgaaa agcaaccac ctgtatcccc cacttcaaaa acagagagga ttgaggaaac
6061  catgtctgtt cgggagctga tgaaggcttt ccagtcaggt caggacccctt ctaaacataa
6121  aactggactc tttgagcaca aatcagcaaa acaaaagcag ccacaagaga aggtaaagt
6181  tcgggtagaa aaagaaaagg ggccgatact aacccagaga gaagctcaga aaacagagaa
6241  tcagacaatc aaacgaggcc agagactccc ggtaacgggc acagcagaat ccaaaagagg
6301  agttcgtgtt tcctccatag gagttaagaa agaagatgca gctggaggaa aggagaaagt
```

```
6361  tctcagccac aaaatacctg aacctgttca gtcagtgcct gaagaagaaa gccacagaga
6421  gagcgaagtg cccaaagaaa gatggctga tgagcaggga gacatggatc tacagatcag
6481  cccagatagg aaaacctcca ctgacttctc tgaggtcatt aagcaagagt tggaagacaa
6541  tgacaaatac caacaattcc gcctgagtga ggagacagaa aaggcacagc ttcacttaga
6601  ccaagtactc actagtcctt tcaacacaac atttccactc gactacatga aagatgagtt
6661  ccttccagct ctgtctttac aaagcggtgc tttagatggc agttctgaaa gcctaaagaa
6721  tgaggggta gccggctctc cgtgtggcag cctgatggag ggaccctc agattagttc
6781  agaagaaagc tataagcatg aaggcctagc agagacccct gagcgagcc cagaaagcct
6841  ttctttctca ccaaagaaaa gtgaggagca aactggggaa acaaaggaaa gcaccaagac
6901  agaaaccacc acagaaattc gttcagaaaa agagcatccc acgaccaaag acattactgg
6961  tggctctgaa gagcgaggtg ccacagtcac tgaggactca gagacctcta ctgagagttt
7021  tcagaaagag gccactctag gctctcccaa agacacaagc cctaaaagac aagatgattg
7081  cacaggcagc tgtagtgtag cattagctaa agacacct acaggactga ctgaggaggc
7141  agcctgtgat gaaggtcaac gtacctttgg tagttcagcc cacaagacac aaactgatag
7201  tgaggttcaa gaatccacag ccacctcaga cgagacaaag gccttgccgc tgcctgaggc
7261  ttctgtaaag acagatacag gaactgaatc aaaacctcag ggagtcatta aagtcccca
7321  agggttagaa cttgcactcc ctagccgaga tagcgaagtc ctcagcgctg tggctgatga
7381  ctcattagca gtgagccaca aagactctct ggaagccagc cctgtgctag aagataactc
7441  ttcacacaaa acccctgatt ctctggagcc aagtcctctg aaagaatccc cttgccgtga
7501  ctctctggaa agcagccctg ttgaaccaaa gatgaaggct ggaattttc caagtcactt
7561  tcctcttcct gcagctgttg ccaaaacaga actcttgacg gaagtggcct ctgtgcggtc
7621  ccggctactc cgagaccctg atggcagtgc tgaggatgac agtcttgagc agacatcgct
7681  catggagagc tcagggaaga gccccctttc tcctgacacc cccagctctg aagaagtcag
7741  ctatgaggtt acacccaaaa ccacagatgt aagtacacca aaaccagctg tgattcatga
7801  atgtgcagag gaggatgatt cagaaaacgg ggagaaaaag aggttcacac ctgaagagga
7861  gatgtttaaa atggtaacca aaatcaaaat gtttgatgaa cttgaacaag aagcaaagca
7921  gaaaagggac tacaaaaaag aacccaaaca agaagaatct tcttcatctt ctgacccaga
7981  tgctgactgt tcagtagatg tggatgaacc aaaacataca ggcagtgggg aggatgaaag
8041  tggtgtccct gtgttagtaa cttcggagag caggaaggtg tcttcctcct cagaaagtga
8101  acctgagttg gcacagctta aaaaaggtgc tgactcaggc ctttaccag aaccagtgat
8161  tcgagtacaa cctccttctc cacttccatc aagcatggac tccaattcca gtccagaaga
8221  agtacaattc cagcctgtcg tttccaaaca atatactttc aagatgaatg aagatactca
8281  ggaagagcca ggcaaatcag aagaagaaaa agattctgaa tcccatttag ctgaagaccg
8341  tcatgctgtt tccactgagg ctgaagacag gtcttatgat aagctaaaca gagacactga
8401  tcagccaaaa atctgtgatg ccatggatg tgaggccatg agtcctagca gctcagctgc
8461  tcctgtctct tcaggtctac agagtccgac tggtgatgat gttgatgaac agccagtcat
8521  ctataaagaa tcattagctc tccaaggcac tcatgaaaaa gacacagagg gagaagagct
8581  tgatgtttct agagcagaat ctccacaagc agattgcccc agtgaaagct tttcatcttc
8641  atcctctttg cctcattgtt tggtatctga aggaaaagaa ttagatgaag acatatctgc
8701  cacatcttct attcaaaaaa cagaggtcac aaaaactgat gaaacatttg agaacttacc
8761  aaaggactgc ccctctcaag actcatccat tactactcaa acagatagat tttccatgga
```

-continued

```
 8821 tgttcccgtg tctgacctag ctgagaatga tgaaatctat gatccacaaa tcactagccc
 8881 ttatgaaaat gtcccttccc aatctttttt ctctagtgaa gaaagcaaaa cccaaacaga
 8941 tgcaaatcac accacaagtt ttcactcttc tgaagtgtat tctgttacca tcacatcccc
 9001 tgttgaagac gttgtagtgg caagctcctc tagtggaact gttttaagca aagaatctaa
 9061 ttttgagggc caggacataa aaatggaatc ccaacaggaa agtaccttgt gggaaatgca
 9121 atcagacagt gtctcttcat ctttcgagcc tactatgtcc gctacaacaa cagttgttgg
 9181 tgaacaaata agcaaagtca tcatcacaaa aactgatgtg gattctgatt cttggagtga
 9241 aattcgggaa gacgatgaag cctttgaggc tcgtgtgaaa gaggaagaac aaaagatatt
 9301 tggtttgatg gtagacagac aatcacaggg taccacccct gacaccactc ctgctaggac
 9361 cccaactgaa gaggggaccc caacaagtga gcaaaaccca tttctgtttc aggaaggaaa
 9421 attgtttgaa atgacccgaa gtggtgccat tgatatgacc aaaaggtcct atgcagatga
 9481 aagttttcac ttttttccaaa ttggtcaaga atccaggaa gagactctct ctgaagatgt
 9541 gaaagaaggg gctactgggg ctgatcccct accgctggag acatcagctg aatcactagc
 9601 actttcagaa tcaaaagaaa cagtggatga tgaggcagac ttacttccag atgacgtgag
 9661 tgaggaagta gaggaaatac ctgcttcgga tgctcaactt aactcccaaa tggggatttc
 9721 agcctccact gaaacaccta caaaagaagc tgttagtgta gggaccaagg acctccccac
 9781 cgtgcaaacg ggtgatatac ctcctctctc tggtgtaaag cagatatcct gccccgactc
 9841 ttctgaacca gctgtacaag tccagttaga ttttccaca ctcaccaggt ctgtttattc
 9901 agatagggt gatgattctc ccgattcttc cccagaagaa cagaaatcag taatcgagat
 9961 tcctactgca cccatggaga atgtgccttt tactgaaagc aaatccaaaa ttcctgtaag
10021 gactatgccc acttccaccc cagcacctcc atctgcagag tatgagagtt cagtttctga
10081 agattttcta tccagtgtag atgaggaaaa taaggcggat gaagcaaaac caaagtccaa
10141 actccctgtc aaagtacccc tccaaagagt tgaacagcag ctctcagatc tagacacctc
10201 tgtccagaag acagtggctc ctcagggaca ggacatggca agcatcgcac cagataatag
10261 aagcaaatct gaatctgatg ctagttcttt ggattcaaag accaaatgcc cagtaaaaac
10321 ccgaagttac actgagacag aaacagagag cagagagagg gccgaggaac ttgagttaga
10381 atcagaagaa ggggccacaa gaccaaagat acttacatcc cgattgccag ttaagagcag
10441 aagcactaca tcttcctgca gggggggcac gagccccaca aagaaagta aggagcattt
10501 cttttgacctt tacagaaatt ccatagaatt ctttgaggag attagtgatg aggcttccaa
10561 attagtggat aggctgacac agtcagagag ggagcaggaa atagtttcag acgatgaaag
10621 tagtagtgcc ctggaagtat cagtaattga aaatctgcca cctgttgaga ccgagcactc
10681 agttcctgag gacatctttg acacaaggcc catttgggat gagtctattg agactctgat
10741 tgaacgcatc cctgatgaaa atggccatga ccatgctgaa gatccacagg atgagcagga
10801 acggatcgag gaaaggctgg cttatattgc tgatcacctt ggcttcagct ggacagaatt
10861 agcaagagaa ctggatttca ctgaggagca aattcatcaa attcgaattg aaaatcccaa
10921 ctctcttcaa gaccagagtc atgcactgtt gaagtactgg ctagagaggg atgggaaaca
10981 tgctacagat accaacctcg ttgaatgtct caccaagatc aaccgaatgg atattgttca
11041 tctcatggag accaacacag aacctctcca ggagcgcatc agtcatagtt atgcagaaat
11101 tgaacagacc attcactgg atcatagtga agggttctcg gtacttcaag aggagttatg
11161 cactgcacag cacaagcaga aagaggagca agctgtttct aaagaaagtg agacctgcga
```

-continued

```
11221 tcaccctcct atcgtctcag aggaagacat ttctgttggt tattccactt ttcaggatgg 11281 cgtccccaaa actgagggg acagctcagc aacagcactc tttccccaaa ctcacaagga 11341 gcaagttcaa caggatttct cagggaaaat gcaagacctg cctgaagagt catctctgga 11401 atatcagcag gaatattttg tgacaactcc aggaacagaa acatcagaga ctcagaaggc 11461 tatgatagta cccagctctc ccagcaagac acctgaggaa gttagcaccc ctgcagagga 11521 ggagaagctg tacctccaga ccccaacatc cagcgagcgg ggaggctctc catcatacca 11581 agaacccgaa gagccctcag agcacagaga ggagagctct ccgcggaaaa ccagcctcgt 11641 aatagtggag tctgccgata accagcctga gacctgtgaa agactcgatg aagatgcagc 11701 ttttgaaaag ggagacgata tgcctgaaat accccagaa acagtcacag aagaagaata 11761 cattgatgag catggacaca ccgtggtaaa gaaggttact aggaaaatca ttaggcggta 11821 tgtatcctct gaaggcacag agaaagaaga gattatggtg cagggaatgc cacaggaacc 11881 tgtcaacatc gaggaagggg atggctattc caaagttata aagcgtgttg tattgaagag 11941 tgacaccgag cagtcagagg acaacaatga gtaaagccat cacacagaag agggctgtgg 12001 tgaaggacca gcatggaaaa cgcattgact tggagcacct ggaggatgta ccagaagcac 12061 tagaccagga cgacctccag cgcgatctcc agcagctcct tcggcatttc tgcaaggagg 12121 acttgaagca agaggccaag tgaggggctg cccagttctc acaccagaaa ccacacattc 12181 actcaatatg cagcttcctg tttcagtagg ggagtgacct aactggccta attaatggga 12241 taccccgaca tttccactgt tagcaaatat acggcatttt gctttagttt tccccatcc 12301 tctttaacta taaagctaat ttgtgaccaa agatggcatc cttcatactg gatgctgtat 12361 ccaatacttt gttgtgtctg tgctaacctg gaactggcc acctccattg ttctttgctt 12421 ctgcacaaga tccatgaaaa tccattgatc agaagaactt cacctgcaga cctcttcaag 12481 tgacactatg taggaatcct tccaaggaat atctatgtac aatgtatata gctgaaatgc 12541 tcagatgaac aacatattaa aattaaaacc actgcctatt gtaactacac tgggcatcag 12601 aataaaaggc ctctagaaat tgctgaacaa tggttaatta agatattgct aacacaatcg 12661 agtgataata cagtttact gcaaaagaag cacttcaaac ctattatgtc cttagaactt 12721 ccagagtagc cactgctccc agttaaaggt gggtcagtag ccttgcagaa ctgtcctgag 12781 aagttattgc tggtgctggc cagccatggc ttaggactcc aacagccact ctgagggagg 12841 ggagaaggga gcagaggcca cgcagaatga accgatgggg tattcagttg ctggcagcta 12901 cattgtgtgg cattctagca tcttcaggtc tttagatctt ggacaagttg gcagggtatt 12961 ttaaaagcta taactactgt agttttccag ttttcattgc tgctttagca aaccacgctg 13021 tcttacagtg gtactttctt ctggccactg cactgtagat aattcattgg aaacaagatt 13081 tacccactac ataaaaggtt aaactccttc agtatgttgg agtggtttct ttttttttt 13141 cttctttct ttttttttctt caggtttata tcttctctaa tacctgcatg tggcgtttaa 13201 aaatcaagac cacggtcaaa cccctcttct aatcacatta attgtttcca ttcttttac 13261 cctgagtgag cacttttcac tttccagcta ggtctgtttt tcagcttgca gacaagattg 13321 agaaatcctt gaaaatttgg ttttggttaa aattttggt ttatttattt gaaatccaca 13381 ctcccttgga aactcttaag tgcatttgtg cacttctgtt tgtttgtctc aaagaaggga 13441 ctgtaacaat ctgagtaatt tccatgtcct cttccttatt cctctagtgg ttgaagctgt 13501 gtagcatttt aacatatata tattcacaaa tatattcata taaacagtat acattttgaa 13561 tcagtcattt gttaaagaaa agtatattca atgaagatga aattttaaata aaaaaggaca 13621 gagtctatcc tccagggatt gaacattttc caattatctg gtctttttcct gttgtgcaaa
```

-continued

```
13681 aatgactcat tgctccgaat gtcaaaaaca aatgcgacaa acaatggcac ttcatcattt 13741 aaagtaatgt tgccaagaga aaaaatttcc tgggagggag gtttcccaca agccaaatct 13801 cctaagcctc aaatgctagc acttttttggc agttggatag gaaatgagac attctttggc 13861 agccaaaata agagaggccg atggtgaaac ttttttgagac accctatggc cttcttgtca 13921 aaaccttcac tggagctcaa gaaaagcatt tctgttgtgt tatttgcagt gcagatgatg 13981 tctgtgtaac aacataatgg ttattcacct ttttttgatt ttgattttttg ctgtgttatc 14041 aaaaacttga atactgtgag aagaagtgaa ttttcagttg acgaatcagc atcttgttcc 14101 catggtgata acactaattg aatatatcta tgagggcatg tattagttaa tggaaaaaaa 14161 aatacaacac taacaataca tagctgcaat gtgtacaatg gctgatttaa ttaaataaaa 14221 tgtacaagtg ttaaatgtgg caa
```

One example of a nucleic acid sequence for human ARHGAP6 is available as NCBI accession number NM_013427 (gi: 95091874). This sequence is recited below for easy reference as SEQ ID NO:120.

```
   1 ggctgggctg cgaatagcgt gttcctctcc ggcggaacac acacacccgg ccttggggct 61 gtctcctgag ctccctcctc cacgagagag gctgagcgcc gccgggaatt ccatcccacc 121 gtgggcacgc agtctttgga ggtcccgggc gcagcacgct cggtgtcccc acactgcagc 181 aagacagaga ccccgcggga accttgagct tggaacaacc cttgagcctc tgcagtcgga 241 agagtgggcg cagcagccca gcggaggcca ggcgcgcaac ctcgggcgcc ggggcaagga 301 gagagtgcag ggaggcgcag ctcaggcgcc cggctcagga gcgggaggaa gttctcgcgg 361 cgccgggagc gcggtggacg cgccctgggc gcacgcccag gcagccttct ccctggccct 421 cgggactgtc ctcgggccgc aaggaggagc ttgctggagt cttagaggcc atccagagcc 481 agcgagcagg agcgctgcgt ctcccgcctc agctaggaag ggggagtggc gctggcaggc 541 tggagctggg aacccagcga gcgcctgacc ttcctcctcc tcttcctgac cctcttcgcg 601 tcttgggctc cggaggaagg ttctagcggc tgcaggaggt ccccagaccc attttcctag 661 aaggctggtg atggatctgc tgctcctgcc gccgccgggg cacttggagc gcaccggcgg 721 cgcgtgagct gggcttttgct ctccactgcc ctgggcaaac cccgggccag ccccgcctgg 781 cacctttgcc tgagtccctt tcggttcccg acccaaagcc accagcgtcc agggagggag 841 gaggaggtgg tcctcaggtg cagccccgcc gagatgtccg cgcagagcct gctccacagc 901 gtcttctcct gttcctcgcc cgcttcaagt agcgcggcct cggccaaggg cttctccaag 961 aggaagctgc gccagacccg cagcctggac ccgccctga tcggcggctg cgggagcgac 1021 gaggcgggcg cggagggcag tgcgcgggga gccacggcgg gccgcctcta ctccccatca 1081 ctcccagccg agagtctcgg ccctcgcttg gcgtcctctt cccggggtcc gccccccagg 1141 gccaccaggc taccgcctcc tggacctctt tgctcgtcct tctccacacc cagcaccccg 1201 caggagaagt caccatccgg cagctttcac tttgactatg aggttcccct gggtcgcggc 1261 ggcctcaaga agagcatggc ctgggacctg ccttctgtcc tggccgggcc agccagtagc 1321 cgaagcgctt ccagcatcct ctgttcatcc ggggagggcc ccaatggcat cttcgcttct 1381 cctaggaggt ggctccagca gaggaagttc cagtccccac ccgacagtcg cgggcacccc 1441 tacgtcgtgt ggaaatccga gggtgatttc acctggaaca gcatgtcagg ccgcagtgta 1501 cggctgaggt cagtccccat ccagagtctc tcagagctgg agagggcccg gctgcaggaa 1561 gtggcttttt atcagttgca acaggactgt gacctgagct gtcagatcac cattcccaaa
```

-continued

```
1621 gatggacaaa agagaaagaa atctttaaga aagaaactgg attcactagg aaaggagaaa 1681 aacaaagaca aagaattcat cccacaggca tttggaatgc ccttatccca agtcattgcg 1741 aatgacaggg cctataaact caagcaggac ttgcagaggg acgagcagaa agatgcatct 1801 gactttgtgg cttccctcct cccatttgga aataaaagac aaaacaaaga actctcaagc 1861 agtaactcat ctctcagctc aacctcagaa acaccgaatg agtcaacgtc cccaaacacc 1921 ccggaaccgg ctcctcgggc taggaggagg ggtgccatgt cagtggattc tatcaccgat 1981 cttgatgaca atcagtctcg actactagaa gctttacaac tttccttgcc tgctgaggct 2041 caaagtaaaa aggaaaaagc cagagataag aaactcagtc tgaatcctat ttacagacag 2101 gtccctaggc tggtggacag ctgctgtcag cacctagaaa acatggcct ccagacagtg 2161 gggatattcc gagttggaag ctcaaaaaag agagtgagac aattacgtga ggaatttgac 2221 cgtgggattg atgtctctct ggaggaggag cacagtgttc atgatgtggc agccttgctg 2281 aaagagttcc tgagggacat gccagacccc cttctcacca gggagctgta cacagctttc 2341 atcaacactc tcttgttgga gccggaggaa cagctgggca ccttgcagct cctcatatac 2401 cttctacctc cctgcaactg cgacaccctc caccgcctgc tacagttcct ctccatcgtg 2461 gccaggcatg ccgatgacaa catcagcaaa gatgggcaag aggtcactgg aataaaatg 2521 acatctctaa acttagccac catatttgga cccaacctgc tgcacaagca gaagtcatca 2581 gacaaagaat tctcagttca gagttcagcc cgggctgagg agagcacggc catcatcgct 2641 gttgtgcaaa agatgattga aaattatgaa gccctgttca tggttccccc agatctccag 2701 aacgaagtgc tgatcagcct gttagagacc gatcctgatg tcgtggacta tttactcaga 2761 agaaaggctt cccaatcatc aagccctgac atgctgcagt cggaagtttc cttttccgtg 2821 ggagggaggc attcatctac agactccaac aaggcctcca gcggagacat ctccccttat 2881 gacaacaact ccccagtgct gtctgagcgc tccctgctgg ctatgcaaga ggacgcggcc 2941 ccgggggggct cggagaagct ttacagagtg ccagggcagt ttatgctggt gggccacttg 3001 tcgtcgtcaa agtcaaggga aagttctcct ggaccaaggc ttgggaaaga tctgtcagag 3061 gagcctttcg atatctgggg aacttggcat tcaacattaa aaagcggatc caaagaccca 3121 ggaatgacag gttcctctgg agacattttt gaaagcagct ccctaagagc ggggccctgc 3181 tcccttctc aagggaacct gtccccaaat tggcctcgtc ggcaggggag ccccgcagag 3241 ctggacagcg acacgcaggg ggctcggagg actcaggccg cagcccccgc gacggagggc 3301 agggcccacc ctgcggtgtc gcgcgcctgc agcacgcccc acgtccaggt ggcagggaaa 3361 gccgagcggc ccacggccag gtcggagcag tacttgaccc tgagcggcgc ccacgacctc 3421 agcgagagtg agctggatgt ggccgggctg cagagccggg ccacacctca gtgccaaaga 3481 ccccatggga gtgggaggga tgacaagcgg cccccgcctc catacccggg cccagggaag 3541 cccgcggcag cggcagcctg gatccagggg ccccgaag gcgtggagac acccacggac 3601 cagggaggcc aagcagccga gcgagagcag caggtcacgc agaaaaaact gagcagcgcc 3661 aactccctgc cagcgggcga gcaggacagt ccgcgcctgg gggacgctgg ctggctcgac 3721 tggcagagag agcgctggca gatctgggag ctcctgtcga ccgacaaccc cgatgccctg 3781 cccgagacgc tggtctgagc ccgcacccag ccgagccccc cctgccccga gcccccgcc 3841 ctccagccca gggggaccg tgggtggtgg ccactggcac acttagtgtt cttctttcac 3901 acttctcaaa agtgacacaa gagaaatcca gttcacctac agaggtagag cactcacgcc 3961 cccgccattg agaataaggt tccattgcgt agccagcctt aggaaaaaca aacagaaccc 4021 aaaccagatg gcaatgtcca atctaaaaac gtccctcttg gctctataat ataagataca
```

-continued

```
4081 actcttgctt ggtatagcct aaccgtattt atgtgtcttc ggttttgact attgtgtatt
4141 ctgtaacaga ttatgtataa tcatatatga tatattcaca aagagaaaac aaaaggaact
4201 tttaaaaaaa aaatcacttc acttatatta agcaatgaga tatactaaac aatgagattc
4261 tatagaatgt tctagaatgt gcacaagcgg gtttctgtgc ttttgccata gctttataac
4321 tggggataac ccttccttcg ataccaaaca ctaacaagag gaagcagaat atgagaagcc
4381 atatttttac ataggagtca gatacaaaaa gaaaaatcac tgaatgcttt tagatattga
4441 atacgttttc aggaaaatgc taaatctgat agattacgaa atatatttt agaacttgtt
4501 tagaaaggat tcagttaacc aaacaagaaa aaggcagtgc ctcacaaaga aattaagaag
4561 ttgtccgtcc cacgttacat caaattcagt tttatatagg ccatatataa tatatattta
4621 taatgtataa tttttatgta tttttcaaaa ctacaaactg gaatccaact ataaagtgtt
4681 taagaatcta cacagaatat tcaaattata gaacatgttt tttcccttttg ccccataatc
4741 agtatttgcc aaattacatg caattcctta aaaactaaat cacatttggt aaaaggccta
4801 cagctttgta cttacattgt gccaaaggct gaggaaatgt tttctttcgt aattttatgt
4861 gtattgtaaa atgttctacc gtactttagt agtttgaagt ttttcaagtg cataactatt
4921 tttgaccagc agatggcgat acgcttcagt attttatgca attttttttc acttctgaag
4981 ggaaagtgta ttataaaaaa agatttttt tttttttata aaacatgcta ctcttaattt
5041 tcatgttggt gatgaaattc ccagtggtgt ttcttaaggt tctatcttgt gccatgatga
5101 ataaaaagtt aagcaaag
```

One example of a nucleic acid sequence for human C11orf17 is available as NCBI accession number NM_182901 (gi: 116174739). This sequence is recited below for easy reference as SEQ ID NO:121.

```
   1 agatgaaaat ggaaggggcg ggcgcgctag gcctagtcct ggctgggctc ccgctggagt
  61 gtgcgttggg ggcggaccag gagcggtggt ctccagggag gtcgaggctg gggctcccac
 121 ccggatttgg agcagggtcg ccgcggccca gctgacccgc cggcgtttgt acgttgtgtg
 181 cccactcagg gagccatgga caactgtttg gcggccgcag cgctgaatgg ggtggaccga
 241 cgttccctgc agcgttcagc aaggctggct ctagaagtgc tggagagggc aagaggagg
 301 gcggtggact ggcatgccct ggagcgtccc aaaggctgca tgggggtcct tgcccgggag
 361 gcgccccacc tagagaaaca gccggcagcc ggcccgcagc gcgttctccc gggagagaga
 421 gaagagagac ccccaacccct tagtgcttcc ttcagaacaa tggctgaatt catggactat
 481 acttcaagtc agtgtgggaa atattattca tctgtgccag aggaaggagg ggcaacccat
 541 gtctatcgtt atcacagagg cgagtcgaag ctgcacatgt gcttggacat agggaatggt
 601 cagagaaaag acagaaaaaa gacatccctt ggtcctggag gcagctatca aatatcagag
 661 catgctccag aggcatccca gcctgctgag aacatctcta aggacctcta catagaagta
 721 tatccaggga cctattctgt cactgtgggc tcaaatgact taaccaagaa gactcatgtg
 781 gtagcagttg attctggaca aagcgtggac ctggtcttcc ctgtgtgatg ttgaccatca
 841 ctgccatcac atcacctttt tttaagtagt aagaataaag ccactgtatg attctcttaa
 901 tagctataca ttaatcctgt ttttagtgct gactgggtca gccttccggg aactggagtc
 961 tgtctctttc agtgcttttt tgtttgtttg gttggttttt ttttgagaca gtctcactct
1021 gttgcccagg ctggagtgca gtggcgtgat ctcggctcac tgcaagttcc gcctcccggg
1081 ttcacaccat tctcctgcct cagcctcccg agtagctggc actacaggca cccgccacca
```

-continued

```
1141 tgcccggcta tttttttttgt attttttagta gagacggggt ttcaccatgt tggccaggat 1201 ggtctcgatc tcttgacctc gtgatccacc caccttggcc tcccaaagtg ttgggattac 1261 aggcgtgagc caccgcgccc ggcctcagtg cctttttaa cttgagggtg tagaggtcct 1321 ccacgcttgt ttgcctgaaa gtaatataat gatgctgtct gaacaggttt tactgcttgc 1381 tttccaagta aaggttaatt atgataataa agagatttgg aaatgaa
```

One example of a nucleic acid sequence for human CAPN3 is available as NCBI accession number NM_000070 (gi: 27765081). This sequence is recited below for easy reference as SEQ ID NO:122.

```
   1 cactctcttt ctctctccct ctggcatgca tgctgctggt aggagacccc caagtcaaca 61 ttgcttcaga aatcctttag cactcatttc tcaggagaac ttatggcttc agaatcacag 121 ctcggttttt aagatggaca taacctgtac gaccttctga tgggctttca actttgaact 181 ggatgtggac acttttctct cagatgacag aattactcca acttcccctt tgcagttgct 241 tcctttcctt gaaggtagct gtatcttatt ttctttaaaa agcttttct tccaaagcca 301 cttgccatgc cgaccgtcat tagcgcatct gtggctccaa ggacagcggc tgagccccgg 361 tccccagggc cagttcctca cccggcccag agcaaggcca ctgaggctgg gggtggaaac 421 ccaagtggca tctattcagc catcatcagc cgcaattttc ctattatcgg agtgaaagag 481 aagacattcg agcaacttca caagaaatgt ctagaaaaga aagttcttta tgtggaccct 541 gagttcccac cggatgagac ctctctcttt tatagccaga agttccccat ccagttcgtc 601 tggaagagac ctccggaaat ttgcgagaat ccccgattta tcattgatgg agccaacaga 661 actgacatct gtcaaggaga gctagggac tgctggtttc tcgcagccat tgcctgcctg 721 accctgaacc agcaccttct tttccgagtc atacccatg atcaaagttt catcgaaaac 781 tacgcaggga tcttccactt ccagttctgg cgctatggag agtgggtgga cgtggttata 841 gatgactgcc tgccaacgta caacaatcaa ctggttttca ccaagtccaa ccaccgcaat 901 gagttctgga gtgctctgct ggagaaggct tatgctaagc tccatggttc ctacgaagct 961 ctgaaaggtg gaacaccac agaggccatg gaggacttca caggaggggt ggcagagttt 1021 tttgagatca gggatgctcc tagtgacatg tacaagatca tgaagaaagc catcgagaga 1081 ggctccctca tgggctgctc cattgatgat ggcacgaaca tgacctatgg aacctctcct 1141 tctggtctga acatggggga gttgattgca cggatggtaa ggaatatgga taactcactg 1201 ctccaggact cagacctcga ccccagaggc tcagatgaaa gaccgacccg gacaatcatt 1261 ccggttcagt atgagacaag aatggcctgc gggctggtca gaggtcacgc ctactctgtc 1321 acggggctgg atgaggtccc gttcaaaggt gagaaagtga agctggtgcg gctgcggaat 1381 ccgtggggcc aggtggagtg gacggttct tggagtgata gatggaagga ctggagcttt 1441 gtggacaaag atgagaaggc ccgtctgcag caccaggtca ctgaggatgg agagttctgg 1501 atgtcctatg aggatttcat ctaccatttc acaaagttgg agatctgcaa cctcacggcc 1561 gatgctctgc agtctgacaa gcttcagacc tggacagtgt ctgtgaacga gggccgctgg 1621 gtacggggtt gctctgccgg aggctgccgc aacttcccag atactttctg gaccaaccct 1681 cagtaccgtc tgaagctcct ggaggaggac gatgaccctg atgactcgga ggtgatttgc 1741 agcttcctgg tggccctgat gcagaagaac cggcggaagg accggaagct aggggccagt 1801 ctcttcacca ttggcttcgc catctacgag gttcccaaag agatgcacgg gaacaagcag 1861 cacctgcaga aggacttctt cctgtacaac gcctccaagg ccaggagcaa aacctacatc 1921 aacatgcggg aggtgtccca gcgcttccgc ctgcctccca gcgagtacgt catcgtgccc
```

```
1981 tccacctacg agccccacca ggaggggaa ttcatcctcc gggtcttctc tgaaaagagg 2041 aacctctctg aggaagttga aaataccatc tccgtggatc ggccagtgaa aaagaaaaaa 2101 accaagccca tcatcttcgt ttcggacaga gcaaacagca acaaggagct gggtgtggac 2161 caggagtcag aggagggcaa aggcaaaaca agccctgata agcaaaagca gtccccacag 2221 ccacagcctg gcagctctga tcaggaaagt gaggaacagc aacaattccg gaacattttc 2281 aagcagatag caggagatga catggagatc tgtgcagatg agctcaagaa ggtccttaac 2341 acagtcgtga acaaacacaa ggacctgaag acacacgggt tcacactgga gtcctgccgt 2401 agcatgattg cgctcatgga tacagatggc tctggaaagc tcaacctgca ggagttccac 2461 cacctctgga acaagattaa ggcctggcag aaaattttca acactatgac acagaccag 2521 tccggcacca tcaacagcta cgagatgcga aatgcagtca acgacgcagg attccacctc 2581 aacaaccagc tctatgacat cattaccatg cggtacgcag acaaacacat gaacatcgac 2641 tttgacagtt tcatctgctg cttcgttagg ctggagggca tgttcagagc ttttcatgca 2701 tttgacaagg atggagatgg tatcatcaag ctcaacgttc tggagtggct gcagctcacc 2761 atgtatgcct gaaccaggct ggcctcatcc aaagccatgc aggatcactc aggatttcag 2821 tttcaccctc tatttccaaa gccatttacc tcaaggacc cagcagctac accctacag 2881 gcttccaggc acctcatcag tcatgctcct cctccatttt accccctacc catccttgat 2941 cggtcatgcc tagcctgacc ctttagtaaa gcaatgaggt aggaagaaca aaccttgtc 3001 cctttgccat gtggaggaaa gtgcctgcct ctggtccgag ccgcctcggt tctgaagcga 3061 gtgctcctgc ttaccttgct ctaggctgtc tgcagaagca cctgccggtg gcactcagca 3121 cctccttgtg ctagagccct ccatcacctt cacgctgtcc caccatgggc caggaaccaa 3181 accagcactg ggttctactg ctgtggggta aactaactca gtggaatagg gctggttact 3241 tgggctgtc caactcataa gtttggctgc attttgaaaa agctgatct aaataaaggc 3301 atgtgtatgg ctggtc
```

One example of a nucleic acid sequence for human CDH16 is available as NCBI accession number NM_004062 (gi: 16507958). This sequence is recited below for easy reference as SEQ ID NO:123.

```
  1 gaaggagctc tcttcttgct tggcagctgg accaagggag ccagtcttgg gcgctggagg 61 gcctgtcctg accatggtcc ctgcctggct gtggctgctt tgtgtctccg tcccccaggc 121 tctccccaag gcccagcctg cagagctgtc tgtggaagtt ccagaaaact atggtggaaa 181 tttcccttta tacctgacca agttgccgct gccccgtgag ggggctgaag gccagatcgt 241 gctgtcaggg gactcaggca aggcaactga gggcccattt gctatggatc cagattctgg 301 cttcctgctg gtgaccaggg ccctggaccag agaggagcag gcagagtacc agctacaggt 361 caccctggag atgcaggatg acatgtcttg tggggtcca cagcctgtgc ttgtgcacgt 421 gaaggatgag aatgaccagg tgccccattt ctctcaagcc atctacagag ctcggctgag 481 ccggggtacc aggcctggca tccccttcct cttccttgag gcttcagacc gggatgagcc 541 aggcacagcc aactcggatc ttcgattcca catcctgagc caggctccag cccagccttc 601 cccagacatg ttccagctgg agcctcggct ggggctctg gccctcagcc caaggggag 661 caccagcctt gaccacgccc tggagaggac ctaccagctg ttggtacagg tcaaggacat 721 gggtgaccag gcctcaggcc accaggccac tgccaccgtg gaagtctcca tcatagagag 781 cacctgggtg tccctagagc ctatccacct ggcagagaat ctcaaagtcc tatacccgca
```

-continued

```
 841 ccacatggcc caggtacact ggagtggggg tgatgtgcac tatcacctgg agagccatcc 901 cccgggaccc tttgaagtga atgcagaggg aaacctctac gtgaccagag agctggacag 961 agaagcccag gctgagtacc tgctccaggt gcgggctcag aattcccatg gcgaggacta 1021 tgcggcccct ctggagctgc acgtgctggt gatggatgag aatgacaacg tgcctatctg 1081 ccctccccgt gaccccacag tcagcatccc tgagctcagt ccaccaggta ctgaagtgac 1141 tagactgtca gcagaggatg cagatgcccc cggctccccc aattcccacg ttgtgtatca 1201 gctcctgagc cctgagcctg aggatggggt agaggggaga gccttccagg tggacccccac 1261 ttcaggcagt gtgacgctgg gggtgctccc actccgagca ggccagaaca tcctgcttct 1321 ggtgctggcc atggacctgg caggcgcaga gggtggcttc agcagcacgt gtgaagtcga 1381 agtcgcagtc acagatatca atgatcacgc ccctgagttc atcacttccc agattgggcc 1441 tataagcctc cctgaggatg tggagcccgg gactctggtg gccatgctaa cagccattga 1501 tgctgacctc gagcccgcct tccgcctcat ggattttgcc attgagaggg agacacaga 1561 agggactttt ggcctggatt gggagccaga ctctgggcat gttagactca gactctgcaa 1621 gaacctcagt tatgaggcag ctccaagtca tgaggtggtg gtggtggtgc agagtgtggc 1681 gaagctggtg gggccaggcc caggccctgg agccaccgcc acggtgactg tgctagtgga 1741 gagagtgatg ccaccccccca agttggacca ggagagctac gaggccagtg tccccatcag 1801 tgccccagcc ggctctttcc tgctgaccat ccagccctcc gacccatca gccgaaccct 1861 caggttctcc ctagtcaatg actcagaggg ctggctctgc attgagaaat tctccgggga 1921 ggtgcacacc gcccagtccc tgcagggcgc ccagcctggg gacacctaca cggtgcttgt 1981 ggaggcccag gatacagatg agccgagact gagcgcttct gcaccctgg tgatccactt 2041 cctaaaggcc cctcctgccc cagccctgac tcttgcccct gtgccctccc aatacctctg 2101 cacaccccgc caagaccatg gcttgatcgt gagtggaccc agcaaggacc ccgatctggc 2161 cagtgggcac ggtccctaca gcttcaccct tggtcccaac cccacggtgc aacgggattg 2221 gcgcctccag actctcaatg gttcccatgc ctacctcacc ttggccctgc attgggtgga 2281 gccacgtgaa cacataatcc ccgtggtggt cagcccacaat gcccagatgt ggcagctcct 2341 ggttcgagtg atcgtgtgtc gctgcaacgt ggaggggcag tgcatgcgca aggtgggccg 2401 catgaagggc atgcccacga agctgtcggc agtgggcatc cttgtaggca ccctggtagc 2461 aataggaatc ttcctcatcc tcattttcac ccactggacc atgtcaagga agaaggaccc 2521 ggatcaacca gcagacagcg tgcccctgaa ggcgactgtc tgaatggccc aggcagctct 2581 agctgggagc ttggcctctg gctccatctg agtcccctgg gagagagccc agcacccaag 2641 atccagcagg ggacaggaca gagtagaagc ccctccatct gccctgggt ggaggcacca 2701 tcaccatcac caggcatgtc tgcagagcct ggacaccaac tttatggact gcccatggga 2761 gtgctccaaa tgtcagggtg tttgcccaat aataaagccc cagagaactg ggctgggccc 2821 tatgggattg gta
```

One example of a nucleic acid sequence for human ChGn is available as NCBI accession number BC060772 (gi: 38174239). This sequence is recited below for easy reference as SEQ ID NO:124.

```
  1 tggggcttgt tccgggatcc gcagccttgc tcaggctgtg cattggtgtg gccccgaatt 61 gcacggagct gccttcctat ttcaaggaaa gacgccaagg taattttgac ccagaggagc 121 aatgatgtag ccacctccta accttccctt cttgaacccc caggtcccct cttgctgttg
```

-continued

```
 181 gctgcacatc aggaaggctg tgatgggaat gaaggtgaaa acttggagat ttcacttcag
 241 tcattgcttc tgcctgcaag atcatccttt aaaagtagag aagctgctct gtgtggtggt
 301 taactccaag aggcagaact cgttctagaa ggaaatggat gcaagcagct ccgggggccc
 361 caaacgcatg cttcctgtga tctagcccag ggaagccctt ccgtggggc cccggctttg
 421 agggatgcca ccggttctgg acgcatggct gattcctgaa tgatgatggt tcgccggggg
 481 ctgcttgcgt ggatttcccg ggtggtggtt ttgctggtgc tcctctgctg tgctatctct
 541 gtcctgtaca tgttggcctg caccccaaaa ggtgacgagg agcagctggc actgcccagg
 601 gccaacagcc ccacggggaa ggaggggtac caggccgtcc ttcaggagtg ggaggagcag
 661 caccgcaact acgtgagcag cctgaagcgg cagatcgcac agctcaagga ggagctgcag
 721 gagaggagtg agcagctcag gaatgggcag taccaagcca gcgatgctgc tggcctgggt
 781 ctggacagga gcccccaga gaaaacccag gccgacctcc tggccttcct gcactcgcag
 841 gtggacaagg cagaggtgaa tgctggcgtc aagctggcca cagagtatgc agcagtgcct
 901 ttcgatagct ttactctaca gaaggtgtac cagctggaga ctggccttac ccgccacccc
 961 gaggagaagc ctgtgaggaa ggacaagcgg gatgagttgg tggaagccat tgaatcagcc
1021 ttggagaccc tgaacaatcc tgcagagaac agccccaatc accgtcctta cacggcctct
1081 gatttcatag aagggatcta ccgaacagaa agggacaaag gacattgta tgagctcacc
1141 ttcaaggggg accacaaaca tgaattcaaa cggctcatct tatttcgacc attcggcccc
1201 atcatgaaag tggaaaatga aaagctcaac atggccaaca cgcttatcaa tgttatcgtg
1261 cctctagcaa aagggtgga caagttccgg cagttcatgc agaatttcag gcctgctgat
1321 gaagttttta gatgtgtgcc tttaagccct tgattgtgcg gtgttggatc ttagaagctg
1381 tgatggctca gatgcacata ttggctgagg ataaccagct aagtgatttc accagcttgt
1441 tttaaacata gaaaatccta ctgtctaatt ataaatcttg aaagatcaag ctgatttttt
1501 atttcttttt ttttgagatg gagtcttact ctgtcaccca ggctggagtg cagtggcacg
1561 aactctgctc actgcaacct tcacctccca ggttcaggga gatgtgcatt gagcaggatg
1621 ggagagtcca tctcactgtt gtttactttg gaaagaagaa aataaatgaa gtcaaaggaa
1681 tacttgaaaa cacttccaaa gctgccaact tcaggaactt taccttcatc cagctgaatg
1741 gagaattttc tcggggaaag ggacttgatg ttggagcccg cttctggaag ggaagcaacg
1801 tccttctctt tttctgtgat gtggacatct acttcacatc tgaattcctc aatacgtgta
1861 ggctgaatac acagccaggg aagaaggtat tttatccagt tcttttcagt cagtacaatc
1921 ctggcataat atacggccac catgatgcag tccctccctt ggaacagcag ctggtcataa
1981 agaaggaaac tggattttgg agagactttg gatttgggat gacgtgtcag tatcggtcag
2041 acttcatcaa tataggtggg tttgatctgg acatcaaagg ctggggcgga gaggatgtgc
2101 acctttatcg caagtatctc cacagcaacc tcatagtggt acggacgcct gtgcgaggac
2161 tcttccacct ctggcatgag aagcgctgca tggacgagct gaccccccgag cagtacaaga
2221 tgtgcatgca gtccaaggcc atgaacgagg catcccacgg ccagctgggc atgctggtgt
2281 tcaggcacga gatagaggct caccttcgca aacagaaaca gaagacaagt agcaaaaaaa
2341 catgaactcc cagagaagga ttgtgggaga cactttttct ttcctttttgc aattactgaa
2401 agtggctgca acagagaaaa gacttccata aggacgaca aaagaattgg actgatgggt
2461 cagagatgag aaagcctccg atttctctct gttgggcttt ttacaacaga atcaaaatc
2521 tccgctttgc ctgcaaaagt aacccagttg caccctgtga agtgtctgac aaaggcagaa
```

-continued

```
2581 tgcttgtgag attataagcc taatggtgtg gaggttttga tggtgtttac aatacactga
2641 gacctgttgt tttgtgtgct cattgaaata ttcatgattt aagagcagtt ttgtaaaaaa
2701 ttcattagca tgaaaggcaa gcatatttct cctcatatga atgagcctat cagcagggct
2761 ctagtttcta ggaatgctaa aatatcagaa ggcaggagag gagataggct tattatgata
2821 ctagtgagta cattaagtaa aataaaatgg accagaaaag aaaagaaacc ataaatatcg
2881 tgtcatattt tccccaagat taaccaaaaa taatctgctt atcttttgg ttgtccttt
2941 aactgtctcc gttttttct tttatttaaa aatgcacttt ttttcccttg tgagttatag
3001 tctgcttatt taattaccac tttgcaagcc ttacaagaga gcacaagttg gcctacattt
3061 ttatatttt taagaagata ctttgagatg cattatgaga actttcagtt caaagcatca
3121 aattgatgcc atatccaagg acatgccaaa tgctgattct gtcaggcact gaatgtcagg
3181 cattgagaca taggaagga atggtttgta ctaatacaga cgtacagata ctttctctga
3241 agagtatttt cgaagaggag caactgaaca ctggaggaaa agaaaatgac actttctgct
3301 ttacagaaaa ggaaactcat tcagactggt gatatcgtga tgtacctaaa agtcagaaac
3361 cacattttct cctcagaagt agggaccgct ttcttacctg tttaaataaa ccaaagtata
3421 ccgtgtgaac caaacaatct cttttcaaaa cagggtgctc ctcctggctt ctggcttcca
3481 taagaagaaa tggagaaaaa tatatatata tatatatata ttgtgaaaga tcaatccatc
3541 tgccagaatc tagtgggatg gaagttttg ctacatgtta tccaccccag gccaggtgga
3601 agtaactgaa ttatttttta aattaagcag ttctactcga tcaccaagat gcttctgaaa
3661 attgcatttt attaccattt caaactatt tttaaaaata aatacagtta acatagagtg
3721 gtttcttcat tcatgtgaaa attattagcc agcaccagat gcatgagcta attatctctt
3781 tgagtccttg cttctgtttg ctcacagtaa actcattgtt taaagcttc aagaacattc
3841 aagctgttgg tgtgttaaaa aatgcattgt attgatttgt actggtagtt tatgaaattt
3901 aattaaaaca caggccatga atggaaggtg gtattgcaca gctaataaaa tatgattg
3961 ggatatgaaa aaaaaaaaaa aa
```

One example of a nucleic acid sequence for human CITED1 is available as NCBI accession number NM_004143 (gi: 222136685). This sequence is recited below for easy reference as SEQ ID NO:125.

```
  1 acgagccagg acatgtgcta ataatgccct aagccggtta taaagacgtg gaaattgagg
 61 ggagaaaaaa aaaggaaaa aaagggtctg tccttcctgg gattcctagc cgaggccagt
121 ctgctgccgt gtgcgtgtgc gtcagggctc tccgggcggc aatgggggct tgagagccgg
181 gtccccagcg ccgggaaggg agcgcggtgg ccgccaccgc caccgccccg gagtccggcg
241 ccgaagctgc gggcgggcgg gcgggcacca gctcggtcag gggctgcttg gcgcggcact
301 gtgcggtgca gcggcggcgc ggcgcggtgc gggcttttcc caggcgcccc ggggtcgggt
361 ggccaacggc gcggccgcgg gcgctgagcg cgaccggttc gcggtagcgg tggcggcgc
421 gtgcgtgcca ggggctgggg gctccgccgc ctctcttgcg gctcaccgag ctccgcgctt
481 ccctctctcc agggcaggcg gcttctcaga gcacaacagc tccagctggc agcatcactt
541 cccgccaatt tatccaactt ctgccaaggc tctgaaatgc caacaacgtc gaggcctgca
601 cttgatgtca agggtggcac ctcacctgcg aaggaggatg ccaaccaaga gatgagctcc
661 gtggcctact ccaaccttgc ggtgaaagat cgcaaagcag tggccattct gcactaccct
721 ggggtagcct caaatggaac caaggccagt ggggctccca ctagttcctc gggatctcca
781 ataggctctc ctacaaccac ccctcccact aaaccccat ccttcaacct gcaccccgcc
```

```
 841 cctcacttgc tggctagtat gcacctgcag aaacttaata gccagtatca ggggatggct 901 gctgccactc caggccaacc cggggaggca ggacccctgc aaaactggga ctttggggcc 961 caggcgggag gggcagaatc actctctcct tctgctggtg cccagagccc tgctatcatc 1021 gattcggacc cagtggatga ggaagtgctg atgtcgctgg tggtggaact ggggttggac 1081 cgagccaatg agcttccgga gctgtggctg gggcagaatg agtttgactt cactgcggac 1141 tttccatcta gctgctaatg ccaagtgtcc ctaaagatgg aggaataaag ccaccaattc 1201 tgttgtaaat aaaaataaag ttacttacaa agagacgggc caaaaaaaaa a
```

One example of a nucleic acid sequence for human CITED2 is available as NCBI accession number NM_006079 (gi: 51807294). This sequence is recited below for easy reference as SEQ ID NO:126.

```
   1 acagctcatt gttggcagct gccgggcggt cctgccgagc tgtgagggca acggaggga 61 aataaaggg aacggctccg aatctgcccc agcggccgct gcgagacctc ggcgccgaca 121 tcgcgacagc gaagcgcttt gcacgccagg aaggtcccct ctatgtgctg ctgagccggt 181 cctggacgcg acgagcccgc cctcggtctt cggagcagaa atcgcaaaaa cggaaggact 241 ggaaatggca gaccatatga tggccatgaa ccacgggcgc ttccccgacg gcaccaatgg 301 gctgcaccat caccctgccc accgcatggg catggggcag ttcccgagcc ccatcacca 361 ccagcagcag cagccccagc acgccttcaa cgccctaatg ggcgagcaca tacactacgg 421 cgcgggcaac atgaatgcca cgagcggcat caggcatgcg atggggccgg ggactgtgaa 481 cggagggcac cccccgagcg cgctggcccc cgcggccagg tttaacaact cccagttcat 541 gggtcccccg gtggccagcc agggaggctc cctgccggcc agcatgcagc tgcagaagct 601 caacaaccag tatttcaacc atcacccta cccccacaac cactacatgc cggatttgca 661 ccctgctgca ggccaccaga tgaacgggac aaaccagcac ttccgagatt gcaaccccaa 721 gcacagcggc ggcagcagca ccccggcgg ctcgggcggc agcagcaccc ccggcggctc 781 tggcagcagc tcgggcggcg gcgcgggcag cagcaacagc ggcggcggca gcggcagcgg 841 caacatgccc gcctccgtgg cccacgtccc cgctgcaatg ctgccgccca atgtcataga 901 cactgatttc atcgacgagg aagttcttat gtccttggtg atagaaatgg gtttggaccg 961 catcaaggag ctgcccgaac tctggctggg gcaaaacgag tttgatttta tgacggactt 1021 cgtgtgcaaa cagcagccca gcagagtgag ctgttgactc gatcgaaacc ccggcgaaag 1081 aaatcaaacc cccaacttct tcggcgtgaa ttaaagaaa cattcccta gacacagtat 1141 ctcactttc agatcttgaa aggtttgaga acttggaaac aaagtaaact ataaacttgt 1201 acaaattggt tttaaaaaaa attgctgcca ctttttttc ctgtttttgt ttcgtttttg 1261 tagccttgac attcacccac ctcccttatg tagttgaaat atctagctaa cttggtcttt 1321 ttcgttgttt gttttttactc ctttccctca ctttctccag tgctcaactg ttagatatta 1381 atcttggcaa actgcttaat cttgtggatt ttgtagatgg tttcaaatga ctgaactgca 1441 ttcagattta cgagtgaaag gaaaaattgc attagttggt tgcatgaact tcgaagggca 1501 gatattactg cacaaactgc catctcgctt cattttttta actatgcatt tgagtacaga 1561 ctaatttta aaatatgcta aactggaaga ttaaacagat gtgggccaaa ctgttctgga 1621 tcaggaaagt catactgttc actttcaagt tggctgtccc cccgccgcc cccccaccc 1681 ccatatgtac agatgataat agggtgtgga atgtcgtcag tgcaaacat ttcacagatt 1741 tttatttgt ttctgtcttc aacattttg acactgtgct aatagttata ttcagtacat
```

```
1801 gaaaagatac tactgtgttg aaagcttttt aggaaatttt gacagtattt ttgtacaaaa 1861 catttttttg aaaaaatact tgttaattta ttctatttta atttgccaat gtcaataaaa 1921 agttaagaaa
```

One example of a nucleic acid sequence for human CKB is available as NCBI accession number M16451 (gi: 180571). This sequence is recited below for easy reference as SEQ ID NO:127.

```
   1 ccggccgccc gcccgccgcc gccatgcccct tctccaacag ccacaacgca ctgaagctgc
  61 gcttcccggc cgaggacgag ttccccgacc tgagcgccca caacaaccac atggccaagg
 121 tgctgacccc cgagctgtac gcggacgtgc gcgccaagag cacgccgagc ggcttcacgc
 181 tggacgacgt catccagaca ggcgtggaca acccgggcca cccgtacatc atgaccgtgg
 241 gctgcgtggc gggcgacgag gagtcctacg aagtgttcaa ggatctcttc gacccccatca
 301 tcgaggaccg gcaccggcgc tacaagccca gcgatgacga caagaccgac ctcaaccccg
 361 acaacctgca gggcggcgac gacctggacc ccaactacgt gctgagctcg cgggtggcca
 421 cgggccgcag catccgtggc ttctgcctcc ccccgcactg cagccgcggg gagcgccgag
 481 ccatcgagaa gctcgcggtg gaagccctgt ccagcctgga cggcgacctg gcgggccgat
 541 actacgcgct caagagcatg acggaggcgg agcagcagca gctcatcgac gaccacttcc
 601 tcttcgacaa gcccgtgtcg cccctgctgc tggcctcggg catggcccgc gactggcccg
 661 acgccgcgcg tatctggcac aatgacaata gaccttcct ggtgtgggtc aacgaggagg
 721 accacctgcg ggtcatctcc atgcagaagg ggggcaacat gaaggaggtg ttcacccgct
 781 tctgcaccgg cctcacccag attgaaactc tcttcaagtc taaggactat gagttcatgt
 841 ggaaccctca cctgggctac atcctcacct gcccatccaa cctgggcacc gggctgcggg
 901 caggtgtcga tatcaagctg cccaacctgg gcaagcatga aagttctcg gaggtgctta
 961 agcggctgcg acttcagaag cgaggcacag gcggtgtgga cacggctgcg gtgggcgggg
1021 tcttcgacgt ctccaacgct gaccgcctgg gcttctcaga ggtggagctg gtgcagatgg
1081 tggtggacgg agtgaagctg ctcatcgaga tggaacagcg gctggagcag gccaggcca
1141 tcgacgacct catgcctgcc cagaaatgaa gcccggccca cacccgacac cagccctgct
1201 gcttcctaac ttattgcctg cagtgcccac catgcacccc tcgatgttgc cgtctggcga
1261 gcccttagcc ttgctgtaag gaaggcttcc gtcaccttg gtagagttta ttttttgat
1321 ggctaagata ctgctgatgc tgaaataaac tagggttttg gcctgcaaaa aa
```

One example of a nucleic acid sequence for human COL9A3 is available as NCBI accession number NM_001853 (gi: 119508425). This sequence is recited below for easy reference as SEQ ID NO:128.

```
   1 gccatggccg ggccgcgcgc gtgcgccccg ctcctgctcc tgctcctgct cggggagctt
  61 ctggcggccg ccggggcgca gagagtggga ctccccggcc cccccggccc ccagggccg
 121 cccgggaagc ccggccagga cggcattgac ggagaagctg gtcctccagg tctgcctggg
 181 cccccgggac caaaggggc cccaggaaag ccggggaaac caggagaggc tgggctgccg
 241 ggactgccgg gtgtggatgg tctgactgga cgagatggac ccctggacc caagggtgcc
 301 cctggggaac ggggaagtct gggaccccg gggccgccg gctgggggg caaaggcctc
 361 cctggacccc ccggagaggc aggagtgagc ggcccccag gtgggatcgg cctccgcggc
 421 ccccgggac cttctggact ccccggcctc cctggtcccc caggacctcc cggacccct
```

```
 481 ggacacccag gagtcctccc tgaaggcgct actgaccttc agtgcccaag tatctgcccg 541 ccaggtcccc cagggccccc tggaatgcca gggttcaagg gacccactgg ctacaaaggc 601 gagcaggggg aagtcggcaa ggacggcgag aagggtgacc ctggcccccc tgggcccgcc 661 ggcctcccgg gcagcgtggg gctgcagggc ccccggggat tacgaggact gccagggcca 721 ctcgggcccc ctggggaccg gggtcccatt gggttccgag ggccgcctgg gatcccagga 781 gcgcctggga aagcgggtga ccgaggcgag aggggcccag aagggttccg cggcccccaag 841 ggtgacctcg gcagacctgg tcccaaggga accccggag tggccgggcc aagcggagag 901 ccgggcatgc cgggcaagga cggccagaat ggcgtgccag gactcgatgg ccagaaggga 961 gaggctggtc gcaacggtgc tccgggagag aagggcccca acgggctgcc gggcctccct 1021 ggacgagcgg ggtccaaagg cgagaaggga aacggggca gagctgggga gctgggtgag 1081 gccggcccct ctggagagcc aggcgtccct ggagatgctg catgcctgg ggagcgcggt 1141 gaggctggcc accggggctc agcggggggcc ctcggcccac aaggccctcc cggagcccct 1201 ggtgtccgag gcttccaggg ccagaagggc agcatgggga accccggcct tccaggcccc 1261 cagggcctcc gaggtgacgt gggcgaccgg ggtccgggag gtgccgcagg ccctaaggga 1321 gaccagggta ttgcaggttc cgacggtctt cctggggata aaggagaact gggtcccagc 1381 ggcctggtcg gacccaaagg agagtctggc agtcgagggg agctgggccc caaaggcacc 1441 cagggtccca acgcaccag cggtgttcag ggtgtccccg gcccccccgg tcctctgggc 1501 ctgcagggcg tcccggtgt tcctggcatc acggggaagc cgggagttcc ggggaaggag 1561 gccagcgagc agcgcatcag ggagctgtgt ggggggatga tcagcgaaca aattgcacag 1621 ttagccgcgc acctaaggaa gcctttggca cccgggtcca ttggtcggcc cggtccagct 1681 ggccccctg ggcccccagg accccaggc tccattggtc accctggcgc tcgaggaccc 1741 cctggatacc gcggtcccac tggggagctg ggagaccccg ggcccagagg aaaccagggt 1801 gacagaggag acaaaggcgc ggcaggagca gggctggacg ggcctgaagg agaccaggg 1861 ccccaaggac cccaaggcgt gcccggcacc agcaaggacg gccaggacgg tgctcccggc 1921 gagcctgggc ctcccggaga tcctgggctt ccaggtgcca ttggggccca ggggacaccg 1981 gggatctgcg acacctcagc ctgccaagga gccgtgttag gaggggtcgg ggagaaatca 2041 ggctctcgaa gctcataaaa ttcaacgtga ggaagcaagt gacaaggacg cccgaagcac 2101 agtggacggt catgaaggag cggggtgtg gcaggcgggt gacgtccagg agagggagcg 2161 cccctggctg cccctcggcc gccgactgga cgcgcgggcc ttgccagcga gcaccctcat 2221 cgggctgtcg cctgacagca tacctcaaaa ggccctagct aataaacctg taagcccagc 2281 atttgagaga aggtagggtg tgtatatata aaaggttgtg tacaactcca cgaggtgaaa 2341 aatattcagt aacttgttta catagcattt gtgtaaagac tatgatctca tcccaataaa 2401 atgatatatt aaaccttcag attaatgact ggctacagag taacaaaaaa taaagaattt 2461 aatgtacagt aaattctctc ccata
```

One example of a nucleic acid sequence for human CSRP2 is available as NCBI accession number NM_001321 (gi: 4503100). This sequence is recited below for easy reference as SEQ ID NO:129.

```
  1 gggatctcgg actccctgga ccctccctcc agcccagcct cgctagctcc gcctgcggta 61 cgtgctcccg cctccgactc aaaatgcctg tctggggagg tggaaacaag tgtgggcct 121 gtgggaggac cgtgtaccac gcagaagagg tgcagtgtga tggcaggagc ttccaccgct 181 gctgctttct ctgcatggtt tgcaggaaaa atttagatag cacaacagtg gcaattcacg
```

```
241 atgaagagat ctactgcaaa tcctgctacg gaagaagta tgggccaaaa ggctacggtt 301 atggccaggg cgctggcacg cttaacatgg accgtggcga gaggctgggc atcaaaccag 361 agagtgttca gcctcacagg cctacaacaa atccaaacac ttctaaattt gctcagaaat 421 atggaggtgc tgagaagtgt tccagatgtg gggattctgt atatgctgcc gagaagataa 481 ttggagctgg aaagccctgg cacaaaaact gtttccgatg tgcaaagtgt gggaagagtc 541 ttgaatcaac aactctgact gaaaagaag gtgaaatcta ttgtaaagga tgctatgcaa 601 agaactttgg gcccaaggga tttggctatg ccaaggagc aggggctctt gttcatgccc 661 agtaagatgt aaaccctgaa ctaaacatca cacactgaga atctcttcat aatctaggca 721 cagataatct ttaacactaa actactgtga aattctacca gcattaagta ctgtatatcg 781 ccctgtactt ggataggctg gctaactcgt aggaagagag cactgtatgg tatcctttg 841 ctttattcac cagcattttg ggggaacatt tcttttacat tttaaataaa acttcagctt 901 g
```

One example of a nucleic acid sequence for human DAPK2 is available as NCBI accession number NM_0014326 (gi: 71774012). This sequence is recited below for easy reference as SEQ ID NO:130.

```
   1 gaccgcggca gctcagcctc ccgccgattg tatgttccag gcctcaatga ggagtccaaa 61 catggagcca ttcaagcagc agaaggtgga ggactttat gacatcggag aggagctggg 121 gagtggccag tttgccatcg tgaagaagtg ccgggagaag agcacggggc ttgagtatgc 181 agccaagttc atcaagaagc ggcagagccg ggcgagccgg cgcggtgtga gccgggagga 241 gatcgagcgg gaggtgagca tcctgcggca ggtgctgcac cacaatgtca tcacgctgca 301 cgacgtctat gagaaccgca ccgacgtggt gctcatcctt gagctagtgt ctggaggaga 361 gctcttcgat ttcctggccc agaaggagtc actgagtgag gaggaggcca ccagcttcat 421 taagcagatc ctggatgggg tgaactacct tcacacaaag aaaattgctc actttgatct 481 caagccagaa acattatgt tgttagacaa gaatattccc attccacaca tcaagctgat 541 tgactttggt ctggctcacg aaatagaaga tggagttgaa tttaagaata tttttgggac 601 gccggaattt gttgctccag aaattgtgaa ctacgagccc ctgggtctgg aggctgacat 661 gtggagcata ggcgtcatca cctacatcct cttaagtgga gcatcccctt tcctgggaga 721 cacgaagcag gaaacactgg caaatatcac agcagtgagt tacgactttg atgaggaatt 781 cttcagccag acgagcgagc tggccaagga ctttattcgg aagcttctgg ttaaagagac 841 ccggaaacgg ctcacaatcc aagaggctct cagacacccc tggatcacgc cggtggacaa 901 ccagcaagcc atggtgcgca gggagtctgt ggtcaatctg gagaacttca ggaagcagta 961 tgtccgcagg cggtggaagc tttccttcag catcgtgtcc ctgtgcaacc acctcacccg 1021 ctcgctgatg aagaaggtgc acctgaggcc ggatgaggac ctgaggaact gtgagagtga 1081 cactgaggag acatcgcca ggaggaaagc cctccaccca cggaggagga gcagcacctc 1141 ctaactggcc tgacctgcag tggccgccag ggaggtctgg gcccagcggg gctcccttct 1201 gtgcagactt ttggacccag ctcagcacca gcacccgggc gtcctgagca ctttgcaaga 1261 gagatgggcc caaggaattc agaagagctt gcaggcaagc caggagaccc tgggagctgt 1321 ggctgtcttc tgtggaggag gctccagcat tcccaaagct cttaattctc cataaaatgg 1381 gctttcctct gtctgccatc ctcagagtct ggggtgggag tgtggactta ggaaaacaat 1441 ataaaggaca tcctcatcat cacggggtga aggtcagact aaggcagcct tcttcacagg
```

-continued

```
1501 ctgaggggt tcagaaccag cctggccaaa aattacacca gagagacaga gtcctcccca
1561 ttgggaacag ggtgattgag gaaagtgaac cttgggtgtg agggaccaat cctgtgacct
1621 cccagaacca tggaagccag gacgtcaggc tgaccaacac ctcagacctt ctgaagcagc
1681 ccattgctgg cccgccatgt tgtaattttg ctcatttta ttaaacttct ggtttacctg
1741 atgcttggct tcttttaggg ctaccccat ctcatttcct ttagcccgtg tgcctgtaac
1801 tctgaggggg ggcacccagt ggggtgctga gtgggcagaa tctcagaagg tcctcctgaa
1861 ccgtccgcgc aggcctgcag tgggcctgcc tcctccttgc ttccctaaca ggaaggtgtc
1921 cagttcaaga gaacccaccc agagactggg agtggtggct cacgcctata atccctgcgc
1981 tttggcagtc cgaggcaggg gaattgcttg aactcaggag ttggagacca gcctgggcaa
2041 catggcaaaa cgcagtctgt acaaaaaata caaaaaatta gccaggtgta ggggtaggca
2101 cctggcatcc cagctactcc aggggctgag gtgacagcat tgcttaagcc cagaaggtcg
2161 aggctgcagt gagctgagat cacgccactg cactccagtc tgggtgacag agagagacca
2221 tatccaaaaa aaaaaaagt tgccagagac gagtatgccc atgctccctc tacctcactg
2281 ccaccactcc tgctgttagg agctgagtgt gtctccctaa aatttctatg ttgaagtctt
2341 aacccttggt accacagaat atcactgtat ttggagatgg ggtctttaga aaggcactta
2401 aattaaaatg agctcactga tatgggcccc gatgcaatat aattggtgtc cttataagaa
2461 ggggaggtta ggacacgcag gaaagaccac atgaaggccc aggagtggga gggggaatag
2521 ccatcgacaa actaaggggg cctcagagga aaccaaccct gctgacacct caatcttaga
2581 ctctggcctc aaaaattgta agaaaataaa cttctgtctt ttaagcca
```

One example of a nucleic acid sequence for human DIO1 is available as NCBI accession number NM_00972 (gi: 89357933). This sequence is recited below for easy reference as SEQ ID NO:131.

```
   1 gagcttactc tggctttgcc gagatggggc tgccccagcc agggctgtgg ctgaagaggc
  61 tctgggtgct cttggaggtg gctgtgcatg tggtcgtggg taaagtgctt ctgatattgt
 121 ttccagacag agtcaagcgg aacatcctgg ccatgggcga aagacgggt atgaccagga
 181 accccatttt cagccacgac aactggatac caacctttt cagcacccag tatttctggt
 241 tcgtcttgaa ggtccgttgg cagcgactag aggacacgac tgagctaggg ggtctggccc
 301 caaactgccc ggtggtccgc ctctcaggac agaggtgcaa catttgggag tttatgcaag
 361 gtaataggcc actggtgctg aattttggaa gttgtacctg accttcattt atgttcaaat
 421 ttgaccagtt caagaggctt attgaagact ttagttccat agcagatttt cttgtcattt
 481 acattgaaga agcacatgca tcagatggct gggcttttaa gaacaacatg gacatcagaa
 541 atcaccagaa ccttcaggat cgcctgcagg cagcccatct actgctggcc aggagccccc
 601 agtgccctgt ggtggtggac accatgcaga accagagcag ccagctctac gcagcactgc
 661 ctgagaggct ctacataatc caggagggca ggatcctcta caagggtaaa tctggcccctt
 721 ggaactacaa cccagaggaa gttcgtgctg ttctggaaaa gctccacagt taatctggac
 781 agatacctca attctaggtg accaacggga gggcttctca aggcttagct ctccctgaga
 841 cccagctggc ttttacccctt gacctgtgtc cctagctgaa tcactagctc agattttct
 901 gatctaagca aacaactccc agctgaggaa tgcaggccac agcacccaat caagacaaat
 961 tgttattatc agaaaatgaa gcaacacttg agctgttcag gccagttccc tgttgaagaa
1021 acagttccct gttgaagaaa gtagagcctg acactgctcc cactttggag accacattcc
```

-continued

```
1081 ctgcacacgg tctttgagag agcagttgca ctctacaggc acacttctga ggtacggtat 1141 ctctctccag ccactctgat accaagtaat tcaagctggc attccttcta ttagggaaat 1201 tcattttacc caatttgcat ttatggaatt gatcatttaa gacactaaat tagtttttag 1261 aaccaattat gggaagaatt ccagttgtta ggaagagatg aggagttgga agaggaggga 1321 ttagaaacag gaggaggcag tcatcctctc cttgccaaaa gatttaaacc tgtccacatt 1381 ggtggtgatg atgggtgagt ttccatggta acacatccct aattttacca gggaagagga 1441 gagtactcac tttaccatct ttgaatatat ttcatagaaa tctagctctc tgtaccctga 1501 aatcttccac tagcctcact tttcaacaga gtcatctaga agggagggtt ggcttcccaa 1561 aagcataacc ttgaccaaac caaacaatag gcaccagcaa tgctgtcatt cagttatgca 1621 gaagctcatt tgtgaaattc tgtttctctg atttcttcgc aagtctctta atggtcattt 1681 gtgttagatt acatcaaact gatggatagc cattggtatt catctatttt aactctgtgt 1741 ctttacatat ttgtttatga tggccacagc ctaaagtaca cacggctgtg acttgattca 1801 aaagaaaatg ttataagatg cagtaaacta ataacagaat tattaaaata tatcaggcta 1861 aaaaaaaaaa aaaaaa
```

One example of a nucleic acid sequence for human DPP4 is available as NCBI accession number NM_001935 (gi: 47078262). This sequence is recited below for easy reference as SEQ ID NO:132.

```
  1 ctttcactgg caagagacgg agtcctgggt ttcagttcca gttgcctgcg gtgggctgtg 61 tgagtttgcc aaagtcccct gccctctctg ggtctcggtt ccctcgcctg tccacgtgag 121 gttggaggag ctgaacgccg acgtcatttt tagctaagag ggagcagggt ccccgagtcg 181 ccggcccagg gtctgcgcat ccgaggccgc gcgcccttc ccctccccca cggctcctcc 241 gggccccgca ctctgcgccc cggctgccgc ccagcgccct acacgccct caggggccc 301 tcgcgggctc ccccggccg ggatgccagt gccccgcgcc acgcgcgcct gctcccgcgc 361 cgcctgccct gcagcctgcc cgcggcgcct ttatacccag cgggctcggc gctcactaat 421 gtttaactcg gggccgaaac ttgccagcgc cgagtgactc caccgcccgg agcagcggtg 481 caggacgcgc gtctccgccg cccgcggtga cttctgcctg cgctccttct ctgaacgctc 541 acttccgagg agacgccgac gatgaagaca ccgtggaagg ttcttctggg actgctgggt 601 gctgctgcgc ttgtcaccat catcaccgtg cccgtggttc tgctgaacaa aggcacagat 661 gatgctacag ctgacagtcg caaaacttac actctaactg attacttaaa aaatacttat 721 agactgaagt tatactcctt aagatggatt tcagatcatg aatatctcta caaacaagaa 781 aataatatct tggtattcaa tgctgaatat ggaaacagct cagttttctt ggagaacagt 841 acatttgatg agtttggaca ttctatcaat gattattcaa tatctcctga tgggcagttt 901 attctcttag aatacaacta cgtgaagcaa tggaggcatt cctacacagc ttcatatgac 961 atttatgatt taaataaaag gcagctgatt acagaagaga ggattccaaa caacacacag 1021 tgggtcacat ggtcaccagt gggtcataaa ttggcatatg tttggaacaa tgacatttat 1081 gttaaaattg aaccaaattt accaagttac agaatcacat ggacggggaa agaagatata 1141 atatataatg gaataactga ctgggtttat gaagaggaag tcttcagtgc ctactctgct 1201 ctgtggtggt ctccaaacgg cacttttta gcatatgccc aatttaacga cacagaagtc 1261 ccacttattg aatactcctt ctactctgat gagtcactgc agtacccaaa gactgtacgg
```

-continued

```
1321 gttccatatc caaaggcagg agctgtgaat ccaactgtaa agttctttgt tgtaaataca
1381 gactctctca gctcagtcac caatgcaact tccatacaaa tcactgctcc tgcttctatg
1441 ttgatagggg atcactactt gtgtgatgtg acatgggcaa cacaagaaag aatttctttg
1501 cagtggctca ggaggattca gaactattcg gtcatggata tttgtgacta tgatgaatcc
1561 agtggaagat ggaactgctt agtggcacgg caacacattg aaatgagtac tactggctgg
1621 gttggaagat ttaggccttc agaacctcat tttaccctcg atggtaatag cttctacaag
1681 atcatcagca atgaagaagg ttacagacac atttgctatt ccaaataga taaaaaagac
1741 tgcacattta ttacaaaagg cacctgggaa gtcatcggga tagaagctct aaccagtgat
1801 tatctatact acattagtaa tgaatataaa ggaatgccag gaggaaggaa tctttataaa
1861 atccaactta gtgactatac aaaagtgaca tgcctcagtt gtgagctgaa tccggaaagg
1921 tgtcagtact attctgtgtc attcagtaaa gaggcgaagt attatcagct gagatgttcc
1981 ggtcctggtc tgcccctcta tactctacac agcagcgtga atgataaagg gctgagagtc
2041 ctggaagaca attcagcttt ggataaaatg ctgcagaatg tccagatgcc ctccaaaaaa
2101 ctggacttca ttattttgaa tgaaacaaaa ttttggtatc agatgatctt gcctcctcat
2161 tttgataaat ccaagaaata tcctctacta ttagatgtgt atgcaggccc atgtagtcaa
2221 aaagcagaca ctgtcttcag actgaactgg gccacttacc ttgcaagcac agaaaacatt
2281 atagtagcta gctttgatgg cagaggaagt ggttaccaag gagataagat catgcatgca
2341 atcaacagaa gactgggaac atttgaagtt gaagatcaaa ttgaagcagc cagacaattt
2401 tcaaaaatgg gatttgtgga caacaaacga attgcaattt ggggctggtc atatggaggg
2461 tacgtaacct caatggtcct gggatcggga agtggcgtgt tcaagtgtgg aatagccgtg
2521 gcgcctgtat cccggtggga gtactatgac tcagtgtaca cagaacgtta catgggtctc
2581 ccaactccag aagacaacct tgaccattac agaaattcaa cagtcatgag cagagctgaa
2641 aattttaaac aagttgagta cctccttatt catggaacag cagatgataa cgttcacttt
2701 cagcagtcag ctcagatctc caaagccctg gtcgatgttg gagtggattt ccaggcaatg
2761 tggtatactg atgaagacca tggaatagct agcagcacag cacaccaaca tatatatacc
2821 cacatgagcc acttcataaa acaatgtttc tctttacctt agcacctcaa ataccatgc
2881 catttaaagc ttattaaaac tcattttgt tttcattatc tcaaaactgc actgtcaaga
2941 tgatgatgat ctttaaaata cacactcaaa tcaagaaact taaggttacc tttgttccca
3001 aatttcatac ctatcatctt aagtagggac ttctgtcttc acaacagatt attaccttac
3061 agaagtttga attatccggt cgggttttat tgtttaaaat catttctgca tcagctgctg
3121 aaacaacaaa taggaattgt ttttatggag gctttgcata gattcccctga gcaggatttt
3181 aatcttttc taactggact ggttcaaatg ttgttctctt ctttaaaggg atggcaagat
3241 gtgggcagtg atgtcactag ggcagggaca ggataagagg gattagggag agaagatagc
3301 agggcatggc tgggaaccca agtccaagca taccaacacg agcaggctac tgtcagctcc
3361 cctcggagaa gagctgttca cagccagact ggcacagttt tctgagaaag actattcaaa
3421 cagtctcagg aaatcaaata tgcaaagcac tgacttctaa gtaaaaccac agcagttgaa
3481 aagactccaa agaatgtaa gggaaactgc cagcaacgca ggcccccagg tgccagttat
3541 ggctataggt gctacaaaaa cacagcaagg gtgatgggaa agcattgtaa atgtgctttt
3601 aaaaaaaaat actgatgttc ctagtgaaag aggcagcttg aaactgagat gtgaacacat
3661 cagcttgccc tgttaaaaga tgaaatatt tgtatcacaa atcttaactt gaaggagtcc
3721 ttgcatcaat ttttcttatt tcatttcttt gagtgtctta attaaaagaa tattttaact
```

-continued

```
3781 tccttggact cattttaaaa aatggaacat aaaatacaat gttatgtatt attattccca
3841 ttctacatac tatggaattt ctcccagtca tttaataaat gtgccttcat tttttcagaa
3901 aaaaaaaaaa aaa
```

One example of a nucleic acid sequence for human DTX4 is available as NCBI accession number NM_015177 (gi: 148237497). This sequence is recited below for easy reference as SEQ ID NO:133.

```
   1 gagcagcggc agcagcagcg gaccccggcg gcggcggcgg cgcgcggtcc cagccaggcg
  61 gccccggtgt cccggccccg gtggatgcac ggctggggag gagcccatgg gccggagctg
 121 aggctgcccg gggcggcggg gcgcggggca gggggcgcgg tcgaggcccg gaggcggcgg
 181 cgcaggagga agcggaggag gtcgggcgct cggggcccgg gaggcgggcc gcgcagcgcc
 241 gcagccccgg gctcgccatg ctcctggcct cggccgtggt ggtctgggaa tggctgaacg
 301 agcacggccg ctggcgtccc tacagcccag cggtgagcca ccacatcgag gcggtggtcc
 361 gcgccggccc ccgcgcgggg ggcagcgtgg tgctgggcca ggtggacagc cgtctcgcgc
 421 cctacatcat cgacctgcag tccatgaacc agttccgcca agacacggga actctccgcc
 481 cagttcgccg caactactac gacccctcct cggcccctgg gaagggcgtg gtgtgggagt
 541 gggagaacga caatggctcc tggacgccct acgacatgga agtgggcatc accatccagc
 601 atgcctatga gaagcagcac ccctggatcg acctcacttc cattggcttt agctacgtaa
 661 ttgacttcaa caccatgggc cagatcaacc gtcagaccca cgccaacgc cgcgtccgcc
 721 ggcgcctcga cctcatctac cccatggtca cagggacctt gcctaaggct cagtcctggc
 781 cagtcagccc tgggccagcc acctcgcccc ccatgtcccc ctgctcctgt ccccagtgtg
 841 tcttggtgat gagtgttaag gcagccgtgg tcaatggcag cactgggccc ctacagctgc
 901 cagtgacccg caagaacatg ccgcctcctg gagtggtcaa gctaccccca ctgccaggct
 961 ctggggccaa gccactggac agcacaggca ccattcgagg cccactgaag accgccccat
1021 cgcaggtgat ccggagacaa gcctccagca tgcccactgg gacaaccatg ggctctcctg
1081 ccagtccccc aggacccaac agcaagaccg gaagggtggc cctggccacc ttgaatcgta
1141 ccaacctgca gcgactggcc attgcccagt cccgggtgct gatcgcctct ggggtcccca
1201 cagtcccagt gaagaaccta aatgggtcca gtcctgtcaa ccctgccttg gcaggaatca
1261 ctgggatcct catgagtgca gcggggctgc ctgtgtgtct caccaggcca ccaaagctgg
1321 tcctacaccc accccccgtc agcaagagtg aaataaaatc catcccaggg gtttccaaca
1381 caagccgcaa gaccaccaaa aaacaagcca agaaaggtaa aaccccagag gaagtgctaa
1441 aaaaatatct acagaaagtc cggcacccac cagatgagga ctgcaccatc tgtatggaac
1501 gcctcacggc cccctcaggc tacaagggcc cgcagcctac ggtaaaacct gacctggtag
1561 ggaagctgtc cagatgcggc cacgtctacc acatctactg cttggttgcc atgtacaaca
1621 atgggaacaa ggatggaagt ttgcagtgtc caacctgcaa gaccatttat ggggtgaaga
1681 caggcaccca acctccaggg aagatggagt accacctcat cccccactcc ttgcctggcc
1741 acccagactg caaaaccatc cggatcatct acagcatccc ccccggcatt cagggaccgg
1801 aacacccgaa tcctgggaag agtttcagcg cccgaggctt cccacgacac tgttaccttc
1861 cggacagcga gaaagggaga aaagttctga gctgctgct cgtggcctgg gatcgccgcc
1921 tcattttgc cattggcacc tccagcacca caggcgagtc agacaccgtc atctggaatg
```

-continued

```
1981 aggtccacca caagacagag tttggctcta atctcactgg ccatggctac ccagatgcca 2041 attacctgga taatgtgctg gctgaactgg ctgcccaggg catctctgag acagcactg 2101 cccaggagaa ggactgaggc cagaaaagct ttgaggtggg aggggccatg gagactgcag 2161 gacaggaagt gaggagagtg agtcaatgta gaagaagttg gtgtcctgcc ctcccaactt 2221 tctatcctcc cctcctgccc tgtgtccatc cctcatccct cccaaccaca gtgggagcca 2281 gactgaatat agcgacatca ttcataaatc tcatccaaca caaagggaga tgggatgagg 2341 gccatcctgg gtctgttccc atggagtttt tggtgctggg taggcaggaa tcccctccct 2401 accccacctc ccaagtaggg gcatggtcag cacacctagg gtatgggcag tgcttaggca 2461 ctccatatcc tggctttggg aagccggggt ttcttgcctc agccggcttc ttgctacttc 2521 cactctgctt tgagactgga gtttctgcta ttctccctct gctggaggca gggagctctc 2581 actgtgcaag gttgggggt gggcaaaggg gtgaatcact aaactgctgt gacatcagaa 2641 actgatgcct tggtgtagag caaggaagca cttcttccca agagggtcgg agaaggaaaa 2701 gcctctggga gcacattctg ctgtcatcac agtccttggc ttctctgggc cctcctctcc 2761 tcctcacagc tctcacctgt ccaaagaggc atctggttct ctcatgtgga tggatggact 2821 ctggggttcc tctttggagt ggcatcccat gatgctgttt ctagaccctc tctgatcaaa 2881 ccagagcctg catcccactg agcatctgaa ctgtcctcag ggagaggagc ccacagcctt 2941 cttcccaact cattctagac cagctcaaag attccatgag tttcatcgag tcactgtgag 3001 tggagcccat gctgggctct gtgccctctg tgtctgtgca tgcgcgtgtg tgtgtgggcg 3061 tgtgtgcatt gctgggccag cttgaaggga aggcccgtca tgtccctgca ctctgttttg 3121 caagatgcca aaccccagtt ctgatggggc tccaacagcc aggctgtggt cctttgacgt 3181 tcctcacctg ttgccaacct atcccgtagt gaactgaaac cccaatgaag acagaactgt 3241 gcctggggag atgcaatgag gtgagggctg aactcatcct tttatatttc ttttcaagat 3301 tggatcagag ctcatctcca tccagtcttg tttctatgaa ggcttcaatc tgtttccatg 3361 caaatttgct aatcagagcc cagagctgct gggtccctca tctccctcat ctattataga 3421 ttgacttaca gcagggagag aatctcttta gctcattcct aatggagttg ggatcacaat 3481 atggtctggt ccaatctgca tcttgttgtg tcccaagacc ctatctcctc cccaacattc 3541 ttattgcctt tggctcccag taaggaacga attgggggcc agggaggaga acaggggga 3601 tcaagaaggg aaacccaatt cccccttga aagtgggttc tttgaactat gtgtttgggg 3661 gaagttcctc tggatactaa tttgaattta tatacctcat gttttggggg tttgacgtat 3721 atatatatat atatatatgc atatatattt cataatattt ggaaggtttt tgatgctaga 3781 aaaatggaaa caagagaacc ttcaaaaatg gtacttagat gggaactgga ggccaatctt 3841 tcataaagcc agcccatag ctgcttgctg ttaggcctcc agccattttg acattgggt 3901 ggatagtcga ttcacctgcc tgtcagtcga ttcacctgcc tgtcacccag ttctgtggat 3961 gtgctggtgc tgagcctttg ctctctttcc aaatggttac agggatgttg atcagctcca 4021 ccagagggag ctctgatggg aggaattgct ctgccatcct tgtccctgtg tctcctgtcg 4081 gcaggcagcc attgtatctc accagcagac caggagactg gtcccaaggt tactgcacca 4141 cagggcaatt tcctgccata gttaggaagg aaacacctga actaaatgga agagacatcc 4201 ctgcggtgtt taatatcaca cccatgccct ttgtcaggtt accatgtaca gagattactt 4261 ggagagcctc atgccgtctc taccttcgca cactggtcaa gtatctgctg agcttcttgg 4321 ccgcaaggat gcagaaatag gctgagggtc catgggaaga aagacacaat gaggcagtag 4381 gaggtgggga agaaaagaag acagactttc aaaatggaat taggcactgg ggagagatca
```

-continued

```
4441 gtttccccac atcagggaga agaaggtata ggtggggaag ggggtggcca ggagcagaag 4501 gaagaagact caagatggaa agggagccgc tgtgcctgtg gcaataccac ttggagaggt 4561 cgacttcata ccttcaagcc ttttcccctg ggcttttgat tgtgtctgtg ccccctttct 4621 tgtcctctct gcagatgccc agtaggggct acctcatcct cgtgctgttc ttgtgtggct 4681 ttctgggcag tagggatctt gaatttcctt tctaacactg tgcccggcaa ggcggggagc 4741 attcctctgc cctttgtctt gtgccaacct ggaaaggtgc agtctagatt tcagtgagaa 4801 ccctgccagc tgagccctgt gcatctacta ccttgacaca gagtgttttc ccactagaag 4861 ctctgctctg ctctcctggc ccaagtaggg gattccatgc cttcccttc atggtcttag 4921 caccagcagc ctagtttctc ccttccagag tctccaggga tgacaaattg gattggagac 4981 aaacctcgtc agatgctcat cccctaaaag gttaattgtg tatttgtggc tgcgtgtgcc 5041 tttgtgtttt cattctcttc ccattttgt acattttggt cttctctgtg gttttatact 5101 tggtcaaaag tactcgtctt ggtattgcac tgttgtgtgc atgagaaaac tgggggaagg 5161 ctcactggta caagaaagga cccctgaccc ctttccttct ctgtggtccc cggcattaga 5221 ttggggttc tgggagaggc aggtgaatgt cctaagtgaa ttgttctgtt tgtaactgga 5281 atgttttga agtctttggt gttgctccgt gaaaggacat cgccacctgg tgctcatgag 5341 gtgtctttgc agaacaataa atggcaaatg aacaaccaca aaattgttac tcttgttggc 5401 cttctgctgt ttgtagatta gtgcacctat ctgtgaggga tttgggttac ctccctgagt 5461 ctgtaagcaa ccacaagccc tgccactggg tgggggaagt ccctccccaa ccacttaaaa 5521 acaaattttc cacatattac ccacccacac atttgacctg gctagacttt gtttgcctaa 5581 aggaacagac cacattgctg ggaaaatgag taagtgaacg tgtgggagaa aaacactttt 5641 agaatcacga atattcactt ttaaaggtct ctttgcctgg ctgcaatata gtgtgtgttt 5701 aaattattta caggctgttg tttctcaaat aaatgtttaa tattaatcat tcccaaactg 5761 acaagaacac aaaaataaaa tgcaaataca gagcc
```

One example of a nucleic acid sequence for human DUSP4 is available as NCBI accession number NM_001394 (gi: 58331238). This sequence is recited below for easy reference as SEQ ID NO:134.

```
  1 gctgagcgcc ggaggagcgt aggcagggca gcgctggcgc cagtggcgac aggagccgcg 61 cgaccggcaa aaatacacgg gaggccgtcg ccgaaaagag tccgcggtcc tctctcgtaa 121 acacactctc ctccaccggc gcctccccct ccgctctgcg cgccgcccgg ctgggcgccc 181 gaggccgctc cgactgctat gtgaccgcga ggctgcggga ggaagggac agggaagaag 241 aggctctccc gcgggagccc ttgaggacca agtttgcggc cacttctgca ggcgtccctt 301 cttagctctc gcccgcccct ttctgcagcc taggcggccc gggttctctt ctcttcctcg 361 cgcgcccagc cgcctcggtt cccggcgacc atggtgacga tggaggagct gcgggagatg 421 gactgcagtg tgctcaaaag gctgatgaac cggacgagag atggcggcgg cgcgggcggc 481 agcggcagcc acggcaccct ggggctgccg agcggcggca agtgcctgct gctggactgc 541 agaccgttcc tggcgcacag cgcgggctac atcctaggtt cggtcaacgt gcgctgtaac 601 accatcgtgc ggcggcgggc taagggctcc gtgagcctgg agcagatcct gcccgccgag 661 gaggaggtac gcgccgctt gcgctccggc ctctactcgg cggtcatcgt ctacgacgag 721 cgcagcccgc gcgccgagag cctccgcgag gacagcaccg tgtcgctggt ggtgcaggcg 781 ctgcgccgca acgccgagcg caccgacatc tgcctgctca aaggcggcta tgagaggttt
```

```
 841 tcctccgagt acccagaatt ctgttctaaa accaaggccc tggcagccat cccacccccg 901 gttccccca  gtgccacaga gcccttggac ctgggctgca gctcctgtgg accccacta 961 cacgaccagg ggggtcctgt ggagatcctt cccttcctct acctcggcag tgcctaccat 1021 gctgcccgga gagacatgct ggacgccctg ggcatcacgg ctctgttgaa tgtctcctcg 1081 gactgcccaa accactttga aggacactat cagtacaagt gcatcccagt ggaagataac 1141 cacaaggccg acatcagctc ctggttcatg gaagccatag agtacatcga tgccgtgaag 1201 gactgccgtg ggcgcgtgct ggtgcactgc caggcgggca tctcgcggtc ggccaccatc 1261 tgcctggcct acctgatgat gaagaaacgg gtgaggctgg aggaggcctt cgagttcgtt 1321 aagcagcgcc gcagcatcat ctcgcccaac ttcagcttca tggggcagct gctgcagttc 1381 gagtcccagg tgctggccac gtcctgtgct gcggaggctg ctagccctc  gggacccctg 1441 cgggagcggg gcaagacccc cgccacccc  acctcgcagt tcgtcttcag ctttccggtc 1501 tccgtgggcg tgcactcggc ccccagcagc ctgccctacc tgcacagccc catcaccacc 1561 tctcccagct gttagagccg ccctgggggc cccagaacca gagctggctc ccagcaaggg 1621 taggacgggc cgcatgcggg cagaaagttg ggactgagca gctgggagca ggcgaccgag 1681 ctccttcccc atcatttctc cttggccaac gacgaggcca gccagaatgg caataaggac 1741 tccgaataca taataaaagc aaacagaaca ctccaactta gagcaataac ggctgccgca 1801 gcagccaggg aagaccttgg tttggtttat gtgtcagttt cacttttccg atagaaattt 1861 cttacctcat tttttaagc  agtaaggctt gaagtgatga acccacaga  tcctagcaaa 1921 tgtgcccaac cagcttact  aaaggggag  gaagggaggg caaagggatg agaagacaag 1981 tttcccagaa gtgcctggtt ctgtgtactt gtccctttgt tgtcgttgtt gtagttaaag 2041 gaatttcatt ttttaaaaga aatcttcgaa ggtgtggttt tcatttctca gtcaccaaca 2101 gatgaataat tatgcttaat aataaagtat ttattaagac tttcttcaga gtatgaaagt 2161 acaaaaagtc tagttacagt ggatttagaa tatatttatg ttgatgtcaa acagctgagc 2221 accgtagcat gcagatgtca aggcagttag gaagtaaatg gtgtcttgta gatatgtgca 2281 aggtagcatg atgagcaact tgagtttgtt gccactgaga agcaggcggg ttgggtggga 2341 ggaggaagaa agggaagaat taggtttgaa ttgctttta  aaaaaaaaag aaaagaaaaa 2401 gacagcatct cactatgttg ccaaggctca tcttgagaag caggcgggtt gggtgggagg 2461 aggaagaaag ggaagaatta ggtttgaatt gcttttttt
```

One example of a nucleic acid sequence for human EFEMP1 is available as NCBI accession number NM_004105 (gi: 86787911). This sequence is recited below for easy reference as SEQ ID NO:135.

```
   1 cgaaggtagc gtgtcgggga cccagactga taagacaaaa gagaatcagt cgctttgggc 61 tgcccctcca cacaacctgg gacttttaaa caaagctgtg cgcagagaaa ggcgtggaaa 121 tgccactttg agagtttgtg ctggggatg  tgagaagctc tgagacatgt gagaaggtct 181 agtattctac tagaactgga agattgctct ccgagttttg ttttgttatt ttgtttaaaa 241 aataaaaagc ttgaggccaa ggcaattcat attggctcac aggtattttt gctgtgctgt 301 gcaaggaact ctgctagctc aagattcaca atgttgaaag ccctttttcct aactatgctg 361 actctggcgc tggtcaagtc acaggacacc gaagaaacca tcacgtacac gcaatgcact 421 gacggatatg agtgggatcc tgtgagacag caatgcaaag atattgatga atgtgacatt 481 gtcccagacg cttgtaaagg tggaatgaag tgtgtcaacc actatggagg atacctctgc 541 cttccgaaaa cagcccagat tattgtcaat aatgaacagc ctcagcagga aacacaacca
```

-continued

```
 601 gcagaaggaa cctcagggc aaccaccggg gttgtagctg ccagcagcat ggcaaccagt
 661 ggagtgttgc ccggggtgg ttttgtggcc agtgctgctg cagtcgcagg ccctgaaatg
 721 cagactggcc gaaataactt tgtcatccgg cggaacccag ctgaccctca gcgcattccc
 781 tccaaccctt cccaccgtat ccagtgtgca gcaggctacg agcaaagtga acacaacgtg
 841 tgccaagaca tagacgagtg cactgcaggg acgcacaact gtagagcaga ccaagtgtgc
 901 atcaatttac ggggatcctt tgcatgtcag tgccctcctg gatatcagaa gcaggggag
 961 cagtgcgtag acatagatga atgtaccatc cctccatatt gccaccaaag atgcgtgaat
1021 acaccaggct cattttattg ccagtgcagt cctgggtttc aattggcagc aaacaactat
1081 acctgcgtag atataaatga atgtgatgcc agcaatcaat gtgctcagca gtgctacaac
1141 attcttggtt cattcatctg tcagtgcaat caaggatatg agctaagcag tgacaggctc
1201 aactgtgaag acattgatga atgcagaacc tcaagctacc tgtgtcaata tcaatgtgtc
1261 aatgaacctg ggaaattctc atgtatgtgc ccccagggat accaagtggt gagaagtaga
1321 acatgtcaag atataaatga gtgtgagacc acaaatgaat gccgggagga tgaaatgtgt
1381 tggaattatc atggcggctt ccgttgttat ccacgaaatc cttgtcaaga tccctacatt
1441 ctaacaccag agaaccgatg tgtttgccca gtctcaaatg ccatgtgccg agaactgccc
1501 cagtcaaatg tctacaaata catgagcatc cgatctgata ggtctgtgcc atcagacatc
1561 ttccagatac aggccacaac tatttatgcc aacaccatca atacttttcg gattaaatct
1621 ggaaatgaaa atggagagtt ctacctacga caaacaagtc ctgtaagtgc aatgcttgtg
1681 ctcgtgaagt cattatcagg accaagagaa catatcgtgg acctggagat gctgacagtc
1741 agcagtatag ggaccttccg cacaagctct gtgttaagat tgacaataat agtggggcca
1801 ttttcatttt agtcttttct aagagtcaac cacaggcatt taagtcagcc aaagaatatt
1861 gttaccttaa agcactattt tatttataga tatatctagt gcatctacat ctctatactg
1921 tacactcacc cataattcaa acaattacac catggtataa agtgggcatt taatatgtaa
1981 agattcaaag tttgtcttta ttactatatg taaattagac attaatccac taaactggtc
2041 ttcttcaaga gagctaagta tacactatct ggtgaaactt ggattctttc ctataaaagt
2101 gggaccaagc aatgatgatc ttctgtggtg cttaaggaaa cttactagag ctccactaac
2161 agtctcataa ggaggcagcc atcataacca ttgaatagca tgcaagggta agaatgagtt
2221 tttaactgct ttgtaagaaa atggaaaagg tcaataaaga tatatttctt tagaaaatgg
2281 ggatctgcca tatttgtgtt ggtttttatt ttcatatcca gcctaaaggt ggttgtttat
2341 tatatagtaa taaatcattg ctgtacaata tgctggtttc tgtagggtat ttttaatttt
2401 gtcagaaatt ttagattgtg aatatttgt aaaaaacagt aagcaaaatt ttccagaatt
2461 cccaaaatga accagatatc ccctagaaaa ttatactatt gagaaatcta tggggaggat
2521 atgagaaaat aaattccttc taaaccacat tggaactgac ctgaagaagc aaactcggaa
2581 aatataataa catccctgaa ttcaggactt ccacaagatg cagaacaaaa tggataaaag
2641 gtatttcact ggagaagttt taatttctaa gtaaaattta aatcctaaca cttcactaat
2701 ttataactaa aatttctcat cttcgtactt gatgctcaca gaggaagaaa atgatgatgg
2761 tttttattcc tggcatccag agtgacagtg aacttaagca aattaccctc ctacccaatt
2821 ctatggaata ttttatacgt ctccttgttt aaaatgtcac tgctttactt tgatgtatca
2881 tatttttaaa taaaaataaa tattcccttta gaagatcaaa aaaaaaaaaa aaaaaa
```

One example of a nucleic acid sequence for human ELMO1 is available as NCBI accession number NM_014800 (gi: 86787650). This sequence is recited below for easy reference as SEQ ID NO:136.

```
   1 aagtgagagc agcggcagcc ggcggtgcag cagccggccg acccagagtg taagtgcgtg
  61 tgctggggcg agcgggagcg ggcgaggatg ggcacaggat agaggcagag ccacccacgc
 121 cgccgcggcc ccacgctggg cgacagagcc tccagttccc cttcaatggt ggcgggtcgc
 181 cggagctctg atcgccggga acccttgccg ctgctgtcct gcgacccaa gcaggtatag
 241 acacgtgtgg ccgtttacgc tgtaggatcc tcattcccac tggctttgaa cattttgggg
 301 acttacaatg ccgccacccg cggacatcgt caaggtggcc atagaatggc cgggcgccta
 361 ccccaaactc atggaaattg atcagaaaaa accactgtct gcaataataa aggaagtctg
 421 tgatgggtgg tctcttgcca accatgaata ttttgcactc cagcatgccg atagttcaaa
 481 cttctatatc acagaaaaga accgcaatga gataaaaaat ggcactatcc ttcgattaac
 541 cacatctcca gctcagaacg cccagcagct ccatgaacga atccagtcct cgagtatgga
 601 tgccaagctg gaagccctga aggacttggc cagcctctcc cgggatgtca cgtttgccca
 661 ggagtttata aacctggacg gtatctctct cctcacgcag atggtggaga gcggcactga
 721 gcgataccag aaattgcaga agatcatgaa gccttgcttt ggagacatgc tgtccttcac
 781 cctgacggcc ttcgttgagc tgatggacca tggcatagtg tcctgggata cattttcggt
 841 ggcgttcatt aagaagatag caagttttgt gaacaagtca gccatagaca tctcgatcct
 901 gcagcggtcc ttggccattt tggagtcgat ggtgctcaat agccatgacc tctaccagaa
 961 agtggcgcag gagatcacca tcggccagct cattccacac ctgcaagggt cagatcaaga
1021 aatccaaacc tatactattg cagtgattaa tgcgcttttc ctgaaggctc ctgatgagag
1081 gaggcaggag atggcgaata ttttggctca gaagcaactg cgttccatca ttttaacaca
1141 tgtcatccga gcccagcggg ccatcaacaa tgagatggcg caccagctgt atgttctaca
1201 agtgctcacc tttaacctcc tggaagacag gatgatgacc aaaatggacc cccaggacca
1261 ggctcagagg gacatcatat ttgaacttcg aagaattgct tttgatgctg agtctgaacc
1321 taacaacagc agtggcagca tggagaaacg caagtccatg tacacgcgag attataagaa
1381 gcttgggttc attaatcatg tcaaccctgc catggacttc acgcagactc cacctgggat
1441 gttggctctg gacaacatgc tgtactttgc caagcaccac caagatgcct acatccggat
1501 tgtgcttgag aacagtagtc gagaagacaa gcatgaatgt ccctttggcc gcagtagtat
1561 agagctgacc aagatgctat gtgagatctt gaaagtgggc gagttgccta gtgagacctg
1621 caacgacttc cacccgatgt tcttcaccca cgacagatcc tttgaggagt ttttctgcat
1681 ctgtatccag ctcctgaaca agacatgaa ggaaatgagg gcaacttctg aagacttcaa
1741 caaggtaatg caggtggtga aggagcaggt tatgagagca cttacaacca gcctagctc
1801 cctggaccag ttcaagagca aactgcagaa cctgagctac actgagatcc tgaaaatccg
1861 ccagtccgag aggatgaacc aggaagattt ccagtcccgc ccgattttgg aactaaagga
1921 gaagattcag ccagaaatct tagagctgat caaacagcaa cgcctgaacc gccttgtgga
1981 agggacctgc tttaggaaac tcaatgcccg gcggaggcaa gacaagtttt ggtattgtcg
2041 gctttcgcca aatcacaaag tcctgcatta cggagactta aagagagtc ctcagggaga
2101 agtgccccac gattccttgc aggacaaact gccggtggca gatatcaaag ccgtggtgac
2161 gggaaaggac tgccctcata tgaaagagaa aggtgccctt aaacaaaaca aggaggtgct
2221 tgaactcgct ttctccatct tgtatgactc aaactgccaa ctgaacttca tcgctcctga
2281 caagcatgag tactgtatct ggacggatgg actgaatgcg ctactcggga aggacatgat
2341 gagcgacctg acgcggaatg acctggacac cctgctcagc atggaaatca agctccgcct
2401 cctggaccta gaaaacatcc agatccctga cgcacctccg ccgattccca aggagcccag
```

-continued

```
2461 caactatgac ttcgtctatg actgtaactg aagtggccgg gcccagacat gcccttcca
2521 aaactggaac acctagctaa caggagagag gaatgaaaac acacccacgc cttggaaccg
2581 tcctttggta aagggaagct gtgggtccac attcccttca gcatcacctc tagccctggc
2641 aactttcagc ccctagctgg catcttgctc accgccctga ttctgttcct cggctccact
2701 gcttcaggtc acttcccatg gctgcagtcc actggtggga caagagcaaa gcccactgcc
2761 agtaagaagg ccaaagggcc cttccatcct agccctctgc aggcatgccc ttccttccct
2821 tgggcaggaa agccagcagc cccagactgc ccaaaaactt gcccaccaga ccaagggcag
2881 tgccccaagg cccctgtctg gaggaaatgg cctagctatt tgatgagaag accaaacccc
2941 acatcctcct ttcccctctc tctagaatca tctcgcacca ccagttacac ttgaattaag
3001 atctgcgctc aaatctcctc ccacctctct ccctgctttt gccttgctct gttcctcttt
3061 ggtcccaaga gcagcagccg cagcctcctc gtgatcctcc ctagcataaa tttcccaaac
3121 agtccacagg tccatgccc actttgcgtc tgcactgtga tcgtgacaaa tcttccctcc
3181 tcaccagcta gtctggggtt tcctctccct gccccaggcc agaactgcct tcttcatttc
3241 cacccacgct cccagcctct tagctgaaag cacaaatggt gaaatcagta gtctcgctcc
3301 atctctaata gactaaacct aaatgcctct aggacggact gttgctatcc aagcgtttgg
3361 tgttaccttc tcctggggag tcctgctgca actcaagttc cacaggatgg tcaagctgtc
3421 agacatccaa gtttacatca ttgtaattat tactggtatt tacaatttgc aagagttttg
3481 ggttagtttt ttttttttttt tttgctttgt ttttgtacaa aagagtctaa cattttttgc
3541 caaacagata tatatttaat gaaaagaaga gatacataaa tgtgtgaatt tccagttttt
3601 ttttaattat tttaatccca aacatcttcc tgaaaataac attcccttaa acatgctgtg
3661 gaataaaatg gattgtgatg atttggaaaa aaaaaaaaa aaaaaaaaa aaaaaaaaa
3721 aaaaaaa
```

One example of a nucleic acid sequence for human FGFR2 is available as NCBI accession number NM_000141 (gi: 189083823). This sequence is recited below for easy reference as SEQ ID NO:137.

```
   1 ggcggcggct ggaggagagc gcggtggaga gccgagcggg cgggcggcgg gtgcggagcg
  61 ggcgagggag cgcgcgcggc cgccacaaag ctcgggcgcc gcggggctgc atgcggcgta
 121 cctggcccgg cgcggcgact gctctccggg ctggcggggg ccggccgcga gccccggggg
 181 ccccgaggcc gcagcttgcc tgcgcgctct gagccttcgc aactcgcgag caaagtttgg
 241 tggaggcaac gccaagcctg agtcctttct tcctctcgtt ccccaaatcc gagggcagcc
 301 cgcgggcgtc atgcccgcgc tcctccgcag cctggggtac gcgtgaagcc cgggaggctt
 361 ggcgccggcg aagacccaag gaccactctt ctgcgtttgg agttgctccc gcaaccccg
 421 ggctcgtcgc tttctccatc ccgacccacg cggggcgcgg ggacaacaca ggtcgcggag
 481 gagcgttgcc attcaagtga ctgcagcagc agcggcagcg cctcggttcc tgagcccacc
 541 gcaggctgaa ggcattgcgc gtagtccatg cccgtagagg aagtgtgcag atgggattaa
 601 cgtccacatg gagatatgga agaggaccgg ggattggtac cgtaaccatg gtcagctggg
 661 gtcgtttcat ctgcctggtc gtggtcacca tggcaacctt gtccctggcc ggccctcct
 721 tcagtttagt tgaggatacc acattagagc cagaagagcc accaaccaaa taccaaatct
 781 ctcaaccaga agtgtacgtg gctgcgccag gggagtcgct agaggtgcgc tgcctgttga
 841 aagatgccgc cgtgatcagt tggactaagg atggggtgca cttggggccc aacaatagga
```

-continued

```
 901 cagtgcttat tggggagtac ttgcagataa agggcgccac gcctagagac tccggcctct
 961 atgcttgtac tgccagtagg actgtagaca gtgaaacttg gtacttcatg gtgaatgtca
1021 cagatgccat ctcatccgga gatgatgagg atgacaccga tggtgcggaa gattttgtca
1081 gtgagaacag taacaacaag agagcaccat actggaccaa cacagaaaag atggaaaagc
1141 ggctccatgc tgtgcctgcg gccaacactg tcaagtttcg ctgcccagcc gggggggaacc
1201 caatgccaac catgcggtgg ctgaaaaacg gaaggagtt taagcaggag catcgcattg
1261 gaggctacaa ggtacgaaac cagcactgga gcctcattat ggaaagtgtg gtcccatctg
1321 acaagggaaa ttatacctgt gtagtggaga atgaatacgg gtccatcaat cacacgtacc
1381 acctggatgt tgtggagcga tcgcctcacc ggcccatcct ccaagccgga ctgccggcaa
1441 atgcctccac agtggtcgga ggagacgtag agtttgtctg caaggtttac agtgatgccc
1501 agccccacat ccagtggatc aagcacgtgg aaaagaacgg cagtaaatac gggcccgacg
1561 ggctgcccta cctcaaggtt ctcaaggccg ccggtgttaa caccacggac aaagagattg
1621 aggttctcta tattcggaat gtaacttttg aggacgctgg ggaatatacg tgcttggcgg
1681 gtaattctat tgggatatcc tttcactctg catggttgac agttctgcca gcgcctggaa
1741 gagaaaagga gattacagct tccccagact acctggagat agccatttac tgcatagggg
1801 tcttcttaat cgcctgtatg gtggtaacag tcatcctgtg ccgaatgaag aacacgacca
1861 agaagccaga cttcagcagc cagccggctg tgcacaagct gaccaaacgt atccccctgc
1921 gggagacaggt aacagtttcg gctgagtcca gctcctccat gaactccaac accccgctgg
1981 tgaggataac aacacgcctc tcttcaacgg cagacacccc catgctggca ggggtctccg
2041 agtatgaact tccagaggac ccaaaatggg agtttccaag agataagctg acactgggca
2101 agccctgg gagaaggttgc tttgggcaag tggtcatggc ggaagcagtg ggaattgaca
2161 aagacaagcc caaggaggcg gtcaccgtgg ccgtgaagat gttgaaagat gatgccacag
2221 agaaagacct ttctgatctg gtgtcagaga tggagatgat gaagatgatt gggaaacaca
2281 agaatatcat aaatcttctt ggagcctgca cacaggatgg gcctctctat gtcatagttg
2341 agtatgcctc taaaggcaac ctccgagaat acctccgagc ccggaggcca cccgggatgg
2401 agtactccta tgacattaac cgtgttcctg aggagcagat gaccttcaag gacttggtgt
2461 catgcaccta ccagctggcc agaggcatgg agtacttggc ttcccaaaaa tgtattcatc
2521 gagatttagc agccagaaat gttttggtaa cagaaaacaa tgtgatgaaa atagcagact
2581 ttggactcgc cagagatatc aacaatatag actattacaa aaagaccacc aatgggcggc
2641 ttccagtcaa gtggatggct ccagaagccc tgtttgatag agtatacact catcagagtg
2701 atgtctggtc cttcggggtg ttaatgtggg agatcttcac tttagggggc tcgccctacc
2761 cagggattcc cgtggaggaa ctttttaagc tgctgaagga aggacacaga atggataagc
2821 cagccaactg caccaacgaa ctgtacatga tgatgaggga ctgttggcat gcagtgccct
2881 cccagagacc aacgttcaag cagttggtag aagacttgga tcgaattctc actctcacaa
2941 ccaatgagga atacttggac ctcagccaac ctctcgaaca gtattcacct agttaccctg
3001 acacaagaag ttcttgttct tcaggagatg attctgtttt ttctccagac ccatgccttt
3061 acgaaccatg ccttcctcag tatccacaca taaacggcag tgttaaaaca tgaatgactg
3121 tgtctgcctg tccccaaaca ggacagcact gggaacctag ctacactgag cagggagacc
3181 atgcctccca gagcttgttg tctccacttg tatatatgga tcagaggagt aaataattgg
3241 aaaagtaatc agcatatgtg taaagattta tacagttgaa aacttgtaat cttccccagg
3301 aggagaagaa ggtttctgga gcagtggact gccacaagcc accatgtaac ccctctcacc
```

-continued

```
3361 tgccgtgcgt actggctgtg gaccagtagg actcaaggtg gacgtgcgtt ctgccttcct
3421 tgttaatttt gtaataattg gagaagattt atgtcagcac acacttacag agcacaaatg
3481 cagtatatag gtgctggatg tatgtaaata tattcaaatt atgtataaat atatattata
3541 tatttacaag gagttatttt ttgtattgat tttaaatgga tgtcccaatg cacctagaaa
3601 attggtctct ctttttttaa tagctatttg ctaaatgctg ttcttacaca taatttctta
3661 attttcaccg agcagaggtg gaaaaatact tttgctttca gggaaaatgg tataacgtta
3721 atttattaat aaattggtaa tatacaaaac aattaatcat ttatagtttt ttttgtaatt
3781 taagtggcat ttctatgcag gcagcacagc agactagtta atctattgct tggacttaac
3841 tagttatcag atcctttgaa aagagaatat ttacaatata tgactaattt ggggaaaatg
3901 aagttttgat ttatttgtgt ttaaatgctg ctgtcagacg attgttctta gacctcctaa
3961 atgccccata ttaaaagaac tcattcatag gaaggtgttt cattttggtg tgcaaccctg
4021 tcattacgtc aacgcaacgt ctaactggac ttcccaagat aaatggtacc agcgtcctct
4081 taaaagatgc cttaatccat tccttgagga cagaccttag ttgaaatgat agcagaatgt
4141 gcttctctct ggcagctggc cttctgcttc tgagttgcac attaatcaga ttagcctgta
4201 ttctcttcag tgaattttga taatggcttc cagactcttt ggcgttggag acgcctgtta
4261 ggatcttcaa gtcccatcat agaaaattga aacacagagt tgttctgctg atagttttgg
4321 ggatacgtcc atctttttaa gggattgctt tcatctaatt ctggcaggac ctcaccaaaa
4381 gatccagcct catacctaca tcagacaaaa tatcgccgtt gttccttctg tactaaagta
4441 ttgtgttttg ctttggaaac acccactcac tttgcaatag ccgtgcaaga tgaatgcaga
4501 ttacactgat cttatgtgtt acaaaattgg agaaagtatt taataaaacc tgttaatttt
4561 tatactgaca ataaaaatgt ttctacagat attaatgtta acaagacaaa ataaatgtca
4621 cgcaacttat ttttttaata aaaaaaaaaa aaaa
```

One example of a nucleic acid sequence for human FLRT1 is available as NCBI accession number NM_013280 (gi: 48762940). This sequence is recited below for easy reference as SEQ ID NO:138.

```
  1 caaggaggct gctgattgtg gcccacagcc tcatctgaac gccaggagac caggataccg
 61 aggcaccgga tcccctctct gtgccctggg gagccccagt gctgcccagt caccccaggg
121 ctgaggtctg cgtccctagt ggtgcaaggc ctggtaggac cacggggcag ggaatgtgag
181 cgccatctga gctcacggtg tcctgagtcg cggcttcgtg actttggcag gggcctccgg
241 accagtgacc ccagtcaaac ccagagggtc ttgggcggca gcgacgaagg aggtattcag
301 gctccaggcc aggtggggcc ggacgccccc agccatccac catggtggtg gcacacccca
361 ccgccactgc caccaccacg cccactgcca ctgtcacggc caccgttgtg atgaccacgg
421 ccaccatgga cctgcgggac tggctgttcc tctgctacgg gctcatcgcc ttcctgacgg
481 aggtcatcga cagcaccacc tgcccctcgg tgtgccgctg cgacaacggc ttcatctact
541 gcaacgaccg gggactcaca tccatccccg cagatatccc tgatgatgcc accaccctct
601 acctgcagaa caaccagatc aacaacgccg gcatccccca ggacctcaag accaaggtca
661 acgtgcaggt catctaccta tacgagaatg acctggatga gttccccatc aacctgcccc
721 gctccctccg ggagctgcac ctgcaggaca acaatgtgcg caccattgcc agggactcgc
781 tggcccgcat cccgctgctg gagaagctgc acctggatga caactccgtg tccaccgtca
841 gcattgagga ggacgccttc gccgacagca aacagctcaa gctgctcttc ctgagccgga
```

-continued

```
 901 accacctgag cagcatcccc tcggggctgc cgcacacgct ggaggagctg cggctggatg
 961 acaaccgcat ctccaccatc ccgctgcatg ccttcaaggg cctcaacagc ctgcggcgcc
1021 tggtgctgga cggtaacctg ctggccaacc agcgcatcgc cgacgacacc ttcagccgcc
1081 tacagaacct cacagagctc tcgctggtgc gcaattcgct ggccgcgcca ccctcaacc
1141 tgcccagcgc ccacctgcag aagctctacc tgcaggacaa tgccatcagc cacatcccct
1201 acaacacgct ggccaagatg cgtgagctgg agcggctgga cctgtccaac aacaacctga
1261 ccacgctgcc ccgcggcctg ttcgacgacc tggggaacct ggcccagctg ctgctcagga
1321 acaacccttg gttttgtggc tgcaacctca tgtggctgcg ggactgggtg aaggcacggg
1381 cggccgtggt caacgtgcgg ggcctcatgt gccagggccc tgagaaggtc cggggcatgg
1441 ccatcaagga cattaccagc gagatggacg agtgttttga cggggccg cagggcggcg
1501 tggccaatgc ggctgccaag accacggcca gcaaccacgc ctctgccacc acgcccagg
1561 gttccctgtt taccctcaag gccaaaaggc cagggctgcg cctccccgac tccaacattg
1621 actaccccat ggccacgggt gatggcgcca agaccctggc catccacgtg aaggccctga
1681 cggcagactc catccgcatc acgtggaagg ccacgctccc cgcctcctct ttccggctca
1741 gttggctgcg cctgggccac agcccagccg tgggctccat cacggagacc ttggtgcagg
1801 gggacaagac agagtacctg ctgacagccc tggagcccaa gtccacctac atcatctgca
1861 tggtcaccat ggagaccagc aatgcctacg tagctgatga cacccgtg tgtgccaagg
1921 cagagacagc cgacagctat ggccctacca ccacactcaa ccaggagcag aacgctggcc
1981 ccatggcgag cctgccctg gcgggcatca tcggcgggc agtggctctg gtcttcctct
2041 tcctggtcct gggggccatc tgctggtacg tgcaccaggc tggcgagctg ctgacccggg
2101 agagggccta caaccggggc agcaggaaaa aggatgacta tatggagtca gggaccaaga
2161 aggataactc catcctggaa atccgcggcc ctgggctgca gatgctgccc atcaacccgt
2221 accgcgccaa agaggagtac gtggtccaca ctatcttccc ctccaacggc agcagcctct
2281 gcaaggccac acacaccatt ggctacggca ccacgcgggg ctaccgggac ggcggcatcc
2341 ccgacataga ctactcctac acatgatgcc cgcccacccg ggctgccccg cctcagcccc
2401 agctgccctg gcgtggccat gtggctttgc ccagcctgct gcaatccaag agagcaagga
2461 agagaaattc catgggtgac tttcctccgc agaaagcaaa gtttgggag ggctgacgat
2521 tttgtagaac acaacagtga caatttttt taaaagaata gaaggcagga gggggaattc
2581 gacattgttg aagacataat ttataccaag ttatgccagt tggggaggga aggactaaaa
2641 ataatattgc aggcagggct gggttgggtt ttttttttt cccccctgaa ctggaaggat
2701 actacctgta caacatctgt ggacacctca tgctctgttc aaggccatca caaggaacc
2761 gccagggaga agcagccggc tctcaaagct cccacgcagc tctcccgcca ctggccactc
2821 gctggcgacc cgatggaagg ttttcaggct cctcacaaag gagagaggga agaaaagatc
2881 ttttgccctg gagatatggt cctgaaatct ctccctggc ttattccata ccatttccct
2941 tgcagatttg cagaaacatg gcatctttca ctgcattctt tgaacaatca tgtagtcgat
3001 taaaaaaaaa aaacaaactt ttttttccta ggctgaagcc ctcttcagtt ccatgcacca
3061 cgctccgtag aagccccggc ggaagccgta gctttccctg ccacctggag gtgcatctgt
3121 ctgcctgtct atccctgtcg cggtgtctct aagtacagat gggtagatag agccacatgc
3181 acggtcctta ccgttcttct tgggtcagtt cttaccattt cctgaacaat agaattgtga
3241 aagtgttaaa aa
```

One example of a nucleic acid sequence for human FMOD is available as NCBI accession number NM_002023 (gi: 71040110). This sequence is recited below for easy reference as SEQ ID NO:139.

```
   1 ggtctggcac aggcacgcac actctcagta gactctttca ctcctctctc tcttcctctc
  61 tcacacgttc tccaacccaa ggaggccaga cagagggacg tggtcactct ctgaaaagtt
 121 caacttgaga gacaaaatgc agtggacctc cctcctgctg ctggcaggc  tcttctccct
 181 ctcccaggcc cagtatgaag atgaccctca ttggtggttc cactacctcc gcagccagca
 241 gtccacctac tacgatccct atgaccctta cccgtatgag acctacgagc cttaccccta
 301 tgggtggat gaagggccag cctacaccta cggctctcca tcccctccag atccccgcga
 361 ctgcccccag gagtgcgact gcccaccaa cttccccacg gccatgtact gtgacaatcg
 421 caacctcaag tacctgccct tcgttccctc ccgcatgaag tatgtgtact ccagaacaa
 481 ccagatcacc tccatccagg aaggcgtctt tgacaatgcc acagggctgc tctggattgc
 541 tctccacggc aaccagatca ccagtgataa ggtgggcagg aaggtcttct ccaagctgag
 601 gcacctggag aggctgtacc tggaccacaa caacctgacc cggatgcccg gtccctgcc
 661 tcgatccctg agagagctcc atctcgacca caaccagatc tcacgggtcc ccaacaatgc
 721 tctggagggg ctggagaacc tcacggcctt gtacctccaa cacaatgaga tccaggaagt
 781 gggcagttcc atgagggggcc tccggtcact gatcttgctg gacctgagtt ataaccacct
 841 tcggaaggtg cctgatgggc tgccctcagc tcttgagcag ctgtacatgg agcacaacaa
 901 tgtctacacc gtccccgata gctacttccg gggggcgccc aagctgctgt atgtgcggct
 961 gtcccacaac agtctaacca acaatggcct ggcctccaac accttcaatt ccagcagcct
1021 ccttgagcta gacctctcct acaaccagct gcagaagatc cccccagtca acaccaacct
1081 ggagaacctc tacctccaag gcaataggat caatgagttc tccatcagca gcttctgcac
1141 cgtggtggac gtcgtgaact tctccaagct gcaggtgctg cgcctggacg gaacgagat
1201 caagcgcagc gccatgcctg ccgacgcgcc cctctgcctg cgccttgcca gcctcatcga
1261 gatctgagca gccctggcac cgggtactgg gcggagagcc cccgtggcat ttggcttgat
1321 ggtttggttt ggcttttgct ggaaggtcca ggatggacca tgtgacagaa gtccacgggc
1381 accctctgta gtcttctttc ctgtaggtgg ggttaggggg ggcgatcagg acaggcagc
1441 cttctgctga ggacataggc agaagctcac tcttttccag ggacagaagt ggtggtagat
1501 ggaaggatcc ctggatgttc caccccata aatctcacgg ctcttaagtt cttcccaatg
1561 atctgaggtc atggaacttc aaaagtggca tgggcaatag tatataacca tacttttcta
1621 acaatccctg gctgtctgtg agcagcactt gacagctctc cctctgtgct gggctggtcg
1681 tgcagttact ctgggctccc atttgttgct tctcaaaata tacctcttgc ccagctgcct
1741 cttctgaaat ccacttcacc cactccactt tcctccacag atgcctcttc tgtgccttaa
1801 gcagagtcag gagacccaa ggcatgtgag catctgccca gcaacctgtg gagacaaccc
1861 acactgtgtc tgagggtgaa aggacaccag gagtcacttc tatacctccc taacctcacc
1921 cctggaaagc caccagattg gaggtcacca gcatgatgat aatattcatg acctgatgtg
1981 ggaggagaca gccaacctca ggcttagatc aatgtatagg ctatatttt ggcagctggg
2041 tagctctttg aaggtggata agacttcaga agaggaaagg ccagactttg cttaccatca
2101 gcatctgcaa tgggccaaac acacctcaaa ttggctgagt tgagaaagca gccccagtag
2161 ttccattctt gcccagcact ttctgcattc caaacagcat cctacctggg ttttatcca
2221 caaaggtagc ggccacatgg tttttaaagt atgagaaaca cagtttgtcc tctccttta
2281 tccaagcagg aagattctat atcctgatgg tagagacaga ctccaggcag ccctggactt
```

```
2341 gctagcccaa agaaggagga tgtggttaat ctgtttcacc tggtttgtcc taaggccata 2401 gttaaaaagt accagctctg gctggggtcc gtgaagccca ggccaggcag ccaaatcttg 2461 cctgtgctgg gcatacaacc ctctgctttc acatctctga gctatatcct cattagtgaa 2521 ggtggctttt gctttatagt ttggctgggg agcacttaat tcttcccatt tcaaaggta 2581 atgttgcctg gggcttaacc cacctgccct ttgggcaagg ttgggacaaa gccatctggg 2641 cagtcagggg caaggactgt tggaggagag ttagcccaag tataggctct gcccagatgc 2701 catcacatcc ctgatactgt gtatgctttg aagcaccttc cctgagaagg gaagagggga 2761 tctttggact acgttcttgg ctccagacct ggaatccaca aaagccaaac cagctcattt 2821 caacaaagga gctccgatgt gagggggcaag gctgccccct gccccagggc tcttcagaaa 2881 gcatctgcat gtgaacacca tcatgccttt ataaggatc cttattacag gaaaagcatg 2941 agtggtggct aacctgacca ataaagttat tttatgattg catctaaaaa aaaaaaaaaa 3001 aaaaa
```

One example of a nucleic acid sequence for human GALNT7 is available as NCBI accession number NM_017423 (gi: 157502211). This sequence is recited below for easy reference as SEQ ID NO:140.

```
   1 agagccggag gaggggggaag gagggagggg agagcggtgg cggcggctgc gccgggctgt 61 gagtctctcg ccgccggagg aagatgaggc tgaagattgg gttcatctta cgcagtttgc 121 tggtggtggg aagcttcctg gggctagtgt tcctctggtc ttccctgacc ccgcggccgg 181 acgacccaag cccgctgagc aggatgaggg aagacagaga tgtcaatgac cccatgccca 241 accgaggcgg caatggacta gctcctgggg aggacagatt caaacctgtg gtaccatggc 301 ctcatgttga aggagtagaa gtggacttag agtctattag aagaataaac aaggccaaaa 361 atgaacaaga gcaccatgct ggaggagatt cccagaaaga tatcatgcag aggcagtatc 421 tcacatttaa gcctcagaca ttcacctacc atgatcctgt gcttcgccca gggatcctcg 481 gtaactttga acccaaagaa cctgagcctc ctggagtggt tggtggccct ggagagaaag 541 ccaagccatt ggttttggga ccagaattca acaagcaat tcaagccagc attaaagagt 601 ttggatttaa catggtggca agtgacatga tctcactgga ccgcagcgtc aatgacttac 661 gccaagaaga atgcaagtat tggcattatg atgaaaactt gctcacttcg agcgttgtca 721 ttgtcttcca taatgaagga tggtcaaccc tcatgagaac agtccacagt gtaattaaaa 781 ggactccaag gaaatattta gcagaaattg tgttaattga cgatttcagt aataaagaac 841 acttaaaaga aaaactggat gaatatatta gctgtggaa tggcctagtg aaggtatttc 901 gaaatgaaag aagggaaggt ttaattcaag cacgaagtat tggtgctcag aaggctaaac 961 ttggacaggt tttgatatac cttgatgccc actgtgaggt ggcagttaac tggtatgcac 1021 cacttgtagc tcccatatct aaggacagaa ccatttgcac tgtgccgctt atagatgtca 1081 taaatggcaa cacatatgaa attatacccc aaggggggtgg tgatgaagat gggtatgccc 1141 gaggagcatg ggattggagt atgctctgga acgggtgcc tctgaccct caagagaaga 1201 gactgagaaa gacaaaaact gaaccgtatc ggtccccagc catggctggg ggattatttg 1261 ccattgaacg agagttcttc tttgaattgg gtctctatga tccaggtctc cagatttggg 1321 gtggtgaaaa ctttgagatc tcatacaaga tatggcagtg tggtggcaaa ttattatttg 1381 ttccttgttc tcgtgttgga catatctacc gtcttgaggg ctggcaagga atcctccgc 1441 ccatttatgt tgggtcttct ccaactctga gaattatgt tagagttgtg gagggtttggt 1501 gggatgaata taaagactac ttctatgcta gtcgtcctga atcgcaggca ttaccatatg
```

-continued

```
1561 gggatatatc ggagctgaaa aaatttcgag aagatcacaa ctgcaaaagt tttaagtggt
1621 tcatggaaga aatagcttat gatatcacct cacactaccc tttgccaccc aaaaatgttg
1681 actggggaga atcagaggc ttcgaaactg cttactgcat tgatagcatg ggaaaaacaa
1741 atggaggctt tgttgaacta ggaccctgcc acaggatggg agggaatcag cttttcagaa
1801 tcaatgaagc aaatcaactc atgcagtatg accagtgttt gacaaaggga gctgatggat
1861 caaaagttat gattacacac tgtaatctaa atgaatttaa ggaatggcag tacttcaaga
1921 acctgcacag atttactcat attccttcag gaaagtgttt agatcgctca gaggtcctgc
1981 atcaagtatt catctccaat tgtgactcca gtaaaacgac tcaaaaatgg gaatgaata
2041 acatccatag tgtttagaga gaaaaaaata aaccaataac ctacctactg acaagtaaat
2101 ttatacagga ctgaaaaccg cctgaaacct gctgcaacta ttgttattaa ctctgtatag
2161 ctccaaacct ggaacctcct gatcagtttg aaggacattg ataaactgtg attttacaat
2221 aacattatca tctgcagtta ctgtttacaa gactgctttt accttaaaact ttgtagatgt
2281 ttacatcttt ttgttgtgtt ttaagatgat gttggtaatt tgtgccttta gctctgtttt
2341 attagacaga gttaaagcat gttgtcttct ttgggattac actcaggggt ctgaaaggca
2401 gtttgatttt tattttaac acacttgaaa aaaggttgga gtagccagac tttcatatat
2461 aacttggtga ttatcaacct gttgtgtctt tatttaattt tacatcttt tgaagcactg
2521 ccacaggtta ttagccaagg tggccttcct tcacagtcat gctgctttt tgaaaggtga
2581 atttcaacac atttagtgcc tctttcattt ctcagtatat atttcaagag cttgtgatga
2641 aatctatagg atggtaatga tggacttgtc acctgtatgg ggaatacttt tactactcag
2701 aaatgaattt atgtgctgcc atttgctata aagttgaact ttgtatggct tgaaaaagaa
2761 atgacaatat ggaacatccc aaggctgtcc catagggttg gaagttgtgt agcattcact
2821 cccttaccta ctggcattcc cagtgccctc tgtccatacc tacttctagg attgcaaagg
2881 agtcttccaa ctagagaaaa attgtccact gacatttggg atttactttt ctccaatacc
2941 tgccaataca gaaaactatt atcagttgtt attgttatcc cttgaaagcg agggtgacaa
3001 aaacaacaaa acaccgttat aaacacatca aaggttcatt ctgactgagg taagactttc
3061 caagcccttg ttagattagg ccttataaaa cttgtgtgca ttataaccta agctgtgcaa
3121 cctgtgaagc caagagtgaa ctgatgtttc atttatattt tcatccaaat gacattatct
3181 gcacgttttt aaaatttaaa aacaaaggac tatttaaaaa tacagtttat taacaaacgt
3241 gaactacttt ctgttacatt aggtgttccc tagtgtttct taatttcttt ttagaaagtg
3301 tatttttatt agtattttt cggtgaacag aagatttgtt tggatttaaa catttactaa
3361 gacagtacct attaggaaaa ccaaatattg caaatggtca attcgatttt aatttctcaa
3421 aagatactct gttatccaga agattaaaat gcctacattg agtgcttaaa aaaaaaaaa
3481 caactgtgat gatgtgagca gaatggcaag taagttaagc attttttgatc ctgtaatcat
3541 ggtatcatta caatgaaagg aattcacaaa ctactgccag aggaagtttg ttttttaatt
3601 taagagggaa atataaccta taaatttgtt tcttccaagc ttagctctta aatttggaga
3661 ctcaaagtta aacatcctca acagagtttt atttataatt ttgaattgtc aatttgtatt
3721 ttgctactga tctgtgatca accattttaa cttttcatctc tagggatgtt taacatttat
3781 aattgcaaaa taaaccaact ataaaaaaag aaactaagag agaattggta ctttaattac
3841 ttgtgtgttt gcaaataggc tccattttcc atgttgagta gattataacc ttattaacta
3901 tgcataggcc taagaaaggt ggcaatgaac tgtgcatgta aatttaaat gggactttg
```

```
3961 tgcaattcgt taaaagaaga tactctatga atatgattct atatattgaa atcagaaaac 4021 ctaccaaaca aaaacatcag aagctgctgc cataatgact attttctact gtaggctgct 4081 ttggaaataa ttcccatatc cttgctttgt aagttggtaa tatcactatg catttctaca 4141 cattttataa atttgattta tgcagatttt gatacactgt atgtttctgt agaaattgta 4201 taaatattca aaattttatt aggataaatt tgagaaactt acgtatatct taattctggg 4261 ttgcttgttt tttaggtgac aaaaataaaa tattgtattt taattcaaaa aaaaaaaaa 4321 aaaaaaaaaa aaaaaaaa
```

One example of a nucleic acid sequence for human GATM is available as NCBI accession number NM_001482 (gi: 126090880). This sequence is recited below for easy reference as SEQ ID NO:141.

```
   1 ttgcgacgct cgggtctggg tccgggtccg gacgtgcaac agaagccgtc agtggccccg 61 ctggctaaaa aagggcaagc atcggaggct cgagccagcg gccgcggcgc ttcccgacag 121 ttcctaattc gggcgctac gccggcccca ccacctgttc ccggcagcca atggggccgc 181 gggggcggc cggggcggag cgcggctaca aaaggcctcg ggccccgcgc gcccgcccac 241 cccgctccgg gcgcgctctc gggaaggctt ggaccgacgc ggcccagagg ccaggaacat 301 tccgcgcgtg gaccagccgg gccagggcga tgctgcgggt gcggtgtctg cgcggcggga 361 gccgcggcgc cgaggcggtg cactacatcg gatctcggct tggacgaacc ttgacaggat 421 gggtgcagcg aactttccag agcacccagg cagctacggc ttcctcccgg aactcctgtg 481 cagctgacga caaagccact gagcctctgc ccaaggactg ccctgtctct tcttacaacg 541 aatgggaccc cttagaggaa gtgatagtgg gcagagcaga aaacgcctgt gttccaccgt 601 tcaccatcga ggtgaaggcc aacacatatg aaaagtactg gccattttac cagaagcaag 661 gagggcatta ttttcccaaa gatcatttga aaaaggctgt tgctgaaatt gaagaaatgt 721 gcaatatttt aaaaacggaa ggagtgacag taaggaggcc tgaccccatt gactggtcat 781 tgaagtataa aactcctgat tttgagtcta cgggtttata cagtgcaatg cctcgagaca 841 tcctgatagt tgtgggcaat gagattatcg aggctcccat ggcatggcgt tcacgcttct 901 ttgagtaccg agcgtacagg tcaattatca aagactactt ccaccgtggc gccaagtgga 961 caacagctcc taagcccaca atggctgatg agctttataa ccaggattat cccatccact 1021 ctgtagaaga cagacacaaa ttggctgctc agggaaaatt tgtgacaact gagtttgagc 1081 catgctttga tgctgctgac ttcattcgag ctggaagaga tattttttgca cagagaagcc 1141 aggttacaaa ctacctaggc attgaatgga tgcgtaggca tcttgctcca gactacagag 1201 tgcatatcat ctcctttaaa gatcccaatc ccatgcatat tgatgctacc ttcaacatca 1261 ttggacctgg tattgtgctt tccaaccctg accgaccatg tcaccagatt gatcttttca 1321 agaaagcagg atggactatc attactcctc caacaccaat catcccagac gatcatccac 1381 tctggatgtc atccaaatgg ctttccatga atgtcttaat gctagatgaa aaacgtgtta 1441 tggtggatgc caatgaagtt ccaattcaaa agatgtttga aaagctgggt atcactacca 1501 ttaaagttaa cattcgtaat gccaattccc tgggaggagg cttccattgc tggacctgcg 1561 atgtccggcg ccgaggcacc ttacagtcct acttggactg aacaggcctg atggagcttg 1621 tggctggcct cagatacacc taagaagctt aggggcaagg ttcattctcc tgctttaaaa 1681 agtgcatgaa ctgtagtgct ttaaacaatc atctccttaa cagggggtcgt aagcctggtt 1741 tgcttctatt acttttcttt gacataaaga aaataacttc tgctaggtat tactctctac 1801 tcctaaagtt atttactatt tggcttcaag tataaaattt tggtgaatgt gtaccaagaa
```

-continued

```
1861 aaaattagtc acctgagtaa cttggccact aataattaac catctacctc tgttttaat
1921 tttctttcca aaaggcagct tgaaatgttg gtcctaatct taattttttt tcctcttcta
1981 tagacttgag aatgttttc tctaaatgag agaaagactt agaatgtaca cagatccaaa
2041 atagaatcag attatctctt tttttctaaa ggagagaaag acttagaaca tacacagatc
2101 ctaagtagaa ccaggtaatt gtctcttttt ctaataagga atttgggtaa ttttaattt
2161 tttgtttttt aaaaataac ctagactatg caaaacatca aagtgaattt tccatgaatg
2221 tttttaatat tctcatctca acattgtgat atatgctact aaaaaccttt tcatatacat
2281 cttacctcat ttcaagtgaa ttattttaat cttttctct ctttccaaaa atttaggaat
2341 gtttagtgta attggatttc gctatcagtt cccatcctta agttttgata ttcaatatct
2401 gatagataca ctgcatcttt ggtcatctaa gatttgttta caaatgtgca aattatttag
2461 agcatagact ttataagcat taaaaaaac taatggaggt aaaacctaaa tgcgatgtga
2521 aataatttta gtgttgatac cgtatgtgta tttttattct aataaacttt tgtgttccag
2581 attgaaaaaa aaaaaaaaaa aa
```

One example of a nucleic acid sequence for human HGD is available as NCBI accession number NM_000187 (gi: 115527116). This sequence is recited below for easy reference as SEQ ID NO:142.

```
   1 ccacagttcc tttccccgat agcttcaaat tctctgcctt ttgaaataag cctacttta
  61 actggaataa ataattggtc aatctctacc tcaggtgaag aggaaccaag cctctggaaa
 121 cacttaggaa caaactgtaa aaaccaaagg caattgtgta accggttaaa taagcttgct
 181 ggactttgtc cctgtgtatg agttagacaa ttctttcagc tagtttgagt gacgcactga
 241 ccagtgaagc gcagtgaagc agtgggaacc ggaatatcca aagagtggtt tgaaggagaa
 301 agaagcattg tggctttata tcctctgggc ctgggtttcc tgaagtcacc acacatagag
 361 gagagagaaa atggctgagt taaagtacat ttctggattt gggaatgagt gttcttcaga
 421 ggatcctcgc tgcccaggtt ccctgccaga aggacagaat aatcctcagg tctgcccta
 481 caatctctat gctgagcagc tctcaggatc ggctttcact tgtccacgga gcaccaataa
 541 gagaagctgg ctgtatagga ttctaccttc agtttctcac aagcccttg aatccattga
 601 cgaaggccaa gtcactcaca actgggatga agttgatcct gatcctaacc agcttagatg
 661 gaaaccattt gagattccaa aagcatctca gaagaaagta gactttgtga gtggcctgca
 721 taccttgtgt ggagctggag acataaagtc taacaatggg cttgctatcc acattttcct
 781 ctgcaatacc tccatggaga acagatgctt ttacaattca gatggggact tcttgattgt
 841 tccgcagaaa gggaaccttc tcatttacac cgagtttggc aagatgcttg tacagcccaa
 901 tgagatctgc gtcattcaga gaggaatgcg gttcagcata gatgtctttg aggagaccag
 961 gggctacatc ttggaggtct atggtgtcca ctttgagtta cctgaccttg gaccaattgg
1021 ggccaatggc ttggccaatc ctcgtgattt cttgataccc attgcctggt atgaggatcg
1081 ccaagtacca ggtggttaca cggtcattaa taaataccag ggcaagctgt tgctgccaa
1141 acaggatgtc tccccgttca atgttgtggc ctggcacggg aattatacac cctacaagta
1201 caacctgaag aatttcatgg ttatcaactc agtggccttt gaccatgcag acccatccat
1261 tttcacagta ttgactgcta agtctgtccg ccctggagtg gccattgctg attttgtcat
1321 cttcccacct cgatgggggg ttgctgataa gaccttcagg cctccttatt accataggaa
```

```
1381 ctgcatgagt gagttcatgg gactcatccg aggtcactat gaggcaaagc aaggtgggtt 1441 cctgccaggg ggagggagtc tacacagcac aatgacccc catggacctg atgctgactg 1501 ctttgagaag gccagcaagg tcaagctggc acctgagagg attgccgatg gcaccatggc 1561 atttatgttt gaatcatctt taagtctggc ggtcacaaag tggggactca aggcctccag 1621 gtgtttggat gagaactacc acaagtgctg ggagccactc aagagccact tcactcccaa 1681 ctccaggaac ccagcagaac ctaattgaga ctggaacatt gctaccataa ttaagagtag 1741 atttgtgaag atttcttcag aatctcatgc tttctggtag tattggagga ggggttggt 1801 taaaatgaaa attcactttt catagtcaag taactcagaa cttttatgga aacgcatttg 1861 caaagttcta tggctgtcac cttaattact caataaactt gctggtgttc tgtggacgta
```

One example of a nucleic acid sequence for human HMGA2 is available as NCBI accession number NM_003483 (gi: 62912480). This sequence is recited below for easy reference as SEQ ID NO:143.

```
   1 cttgaatctt ggggcaggaa ctcagaaaac ttccagcccg ggcagcgcgc gcttggtgca 61 agactcagga gctagcagcc cgtccccctc cgactctccg gtgccgccgc tgcctgctcc 121 cgccacccta ggaggcgcgg tgccacccac tactctgtcc tctgcctgtg ctccgtgccc 181 gaccctatcc cggcggagtc tccccatcct ccttTgcttt ccgactgccc aaggcacttt 241 caatctcaat ctcttctctc tctctctctc tctctctctc tctctctctc tctctctctc 301 tctctctctc gcagggtggg gggaagagga ggaggaattc tttccccgcc taacatttca 361 agggacacaa ttcactccaa gtctcttccc tttccaagcc gcttccgaag tgctcccggt 421 gcccgcaact cctgatccca acccgcgaga ggagcctctg cgacctcaaa gcctctcttc 481 cttctccctc gcttccctcc tcctcttgct acctccacct ccaccgccac ctccacctcc 541 ggcaccccacc caccgccgcc gccgccaccg gcagcgcctc ctcctctcct cctcctcctc 601 ccctcttctc tttttggcag ccgctggacg tccggtgttg atggtggcag cggcggcagc 661 ctaagcaaca gcagccctcg cagcccgcca gctcgcgctc gccccgccgg cgtcccagc 721 cctatcacct catctcccga aaggtgctgg gcagctccgg ggcggtcgag gcgaagcggc 781 tgcagcggcg gtagcggcgg cgggaggcag gatgagcgca cgcggtgagg gcgcggggca 841 gccgtccact tcagcccagg gacaacctgc cgccccagcg cctcagaaga gaggacgcgg 901 ccgccccagg aagcagcagc aagaaccaac cggtgagccc tctcctaaga gacccagggg 961 aagacccaaa ggcagcaaaa acaagagtcc ctctaaagca gctcaaaaga aagcagaagc 1021 cactggagaa aaacggccaa gaggcagacc taggaaatgg ccacaacaag ttgttcagaa 1081 gaagcctgct caggaggaaa ctgaagagac atcctcacaa gagtctgccg aagaggacta 1141 gggggcgcca acgttcgatt tctacctcag cagcagttgg atcttttgaa gggagaagac 1201 actgcagtga ccacttattc tgtattgcca tggtctttcc actttcatct ggggtggggt 1261 ggggtggggt ggggagggg ggggtggggt gggagaaaat cacataacct taaaaaggac 1321 tatattaatc accttctttg taatcccttc acagtcccag gtttagtgaa aaactgctgt 1381 aaacacaggg gacacagctt aacaatgcaa cttttaatta ctgtttttctt ttttcttaac 1441 ctactaatag tttgttgatc tgataagcaa gagtgggcgg gtgagaaaaa ccgaattggg 1501 tttagtcaat cactgcactg catgcaaaca agaaacgtgt cacacttgtg acgtcgggca 1561 ttcatatagg aagaacgcgg tgtgtaacac tgtgtacacc tcaaatacca ccccaaccca 1621 ctccctgtag tgaatcctct gtttagaaca ccaaagataa ggactagata ctacttctc 1681 ttttttcgtat aatcttgtag acacttactt gatgattttt aacttttat ttctaaatga
```

-continued

```
1741 gacgaaatgc tgatgtatcc tttcattcag ctaacaaact agaaaaggtt atgttcattt
1801 ttcaaaaagg gaagtaagca aacaaatatt gccaactctt ctatttatgg atatcacaca
1861 tatcagcagg agtaataaat ttactcacag cacttgtttt caggacaaca cttcattttc
1921 aggaaatcta cttcctacag agccaaaatg ccatttagca ataaataaca cttgtcagcc
1981 tcagagcatt taaggaaact agacaagtaa aattatcctc tttgtaattt aatgaaaagg
2041 tacaacagaa taatgcatga tgaactcacc taattatgag gtgggaggag cgaaatctaa
2101 atttcttttg ctatagttat acatcaattt aaaaagcaaa aaaaaaaag ggggggcaa
2161 tctctctctg tgtctttctc tctctctctt cctctccctc tctcttttca ttgtgtatca
2221 gtttccatga aagacctgaa taccacttac ctcaaattaa gcatatgtgt tacttcaagt
2281 aatacgtttt gacataagat ggttgaccaa ggtgcttttc ttcggcttga gttcaccatc
2341 tcttcattca aactgcactt ttagccagag atgcaatata tccccactac tcaatactac
2401 ctctgaatgt tacaacgaat ttacagtcta gtacttatta catgctgcta tacacaagca
2461 atgcaagaaa aaaacttact gggtaggtga ttctaatcat ctgcagttct ttttgtacac
2521 ttaattacag ttaaagaagc aatctcctta ctgtgtttca gcatgactat gtattttcct
2581 atgtttttt aattaaaaat ttttaaaata cttgtttcag cttctctgct agatttctac
2641 attaacttga aaattttta accaagtcgc tcctaggttc ttaaggataa ttttcctcaa
2701 tcacactaca catcacacaa gatttgactg taatatttaa atattaccct ccaagtctgt
2761 acctcaaatg aattctttaa ggagatggac taattgactt gcaaagacct acctccagac
2821 ttcaaaagga atgaacttgt tacttgcagc attcatttgt tttttcaatg tttgaaatag
2881 ttcaaactgc agctaaccct agtcaaaact attttgtaa aagacatttg atagaaagga
2941 acacgttttt acatactttt gcaaaataag taaataataa ataaaataaa gccaaccttt
3001 caaagaaact tgaagctttg taggtgagat gcaacaagcc ctgcttttgc ataatgcaat
3061 caaaaatatg tgttttaag attagttgaa tataagaaaa tgcttgacaa atattttcat
3121 gtatttaca caaatgtgat ttttgtaata tgtctcaacc agatttattt taaacgcttc
3181 ttatgtagag tttttatgcc tttctctcct agtgagtgtg ctgacttttt aacatggtat
3241 tatcaactgg gccaggaggt agtttctcat gacggctttt gtcagtatgg cttttagtac
3301 tgaagccaaa tgaaactcaa aaccatctct cttccagctg cttcagggag gtagtttcaa
3361 aggccacata cctctctgag actggcagat cgctcactgt tgtgaatcac caaggagct
3421 atggagagaa ttaaaactca acattactgt taactgtgcg ttaaataagc aaataaacag
3481 tggctcataa aaataaaagt cgcattccat atctttggat gggccttta gaaacctcat
3541 tggccagctc ataaaatgga agcaattgct catgttggcc aaacatggtg caccgagtga
3601 tttccatctc tggtaaagtt acacttttat ttcctgtatg ttgtacaatc aaaacacact
3661 actacctctt aagtcccagt atacctcatt tttcatactg aaaaaaaaag cttgtggcca
3721 atggaacagt aagaacatca taaaatttt atatatatag tttatttttg tgggagataa
3781 attttatagg actgttcttt gctgttgttg gtcgcagcta cataagactg gacatttaac
3841 ttttctacca tttctgcaag ttaggtatgt ttgcaggaga aaagtatcaa gacgtttaac
3901 tgcagttgac tttctccctg ttcctttgag tgtcttctaa ctttattctt tgttcttttat
3961 gtagaattgc tgtctatgat tgtactttga atcgcttgct tgttgaaaat atttctctag
```

```
4021 tgtattatca ctgtctgttc tgcacaataa acataacagc ctctgtgatc cccatgtgtt 4081 ttgattcctg ctctttgtta cagttccatt aaatgagtaa taaagtttgg tcaaaacaga 4141 aaaaaaaaaa
```

One example of a nucleic acid sequence for human IGFBP6 is available as NCBI accession number NM_002178 (gi: 49574524). This sequence is recited below for easy reference as SEQ ID NO:144.

```
  1 gcggcggcgg gcagcagctg cgctgcgact gctctggaag gagaggacgg ggcacaaacc 61 ctgaccatga cccccacag gctgctgcca ccgctgctgc tgctgctagc tctgctgctc 121 gctgccagcc caggaggcgc cttggcgcgg tgcccaggct gcgggcaagg ggtgcaggcg 181 ggttgtccag ggggctgcgt ggaggaggag gatgggggt cgccagccga gggctgcgcg 241 gaagctgagg gctgtctcag gagggagggg caggagtgcg gggtctacac ccctaactgc 301 gccccaggac tgcagtgcca tccgcccaag gacgacgagg cgcctttgcg ggcgctgctg 361 ctcggccgag gccgctgcct tccggcccgc gcgcctgctg ttgcagagga gaatcctaag 421 gagagtaaac cccaagcagg cactgcccgc ccacaggatg tgaaccgcag agaccaacag 481 aggaatccag gcacctctac cacgcccctcc cagcccaatt ctgcgggtgt ccaagacact 541 gagatgggcc catgccgtag acatctggac tcagtgctgc agcaactcca gactgaggtc 601 taccgagggg ctcaaacact ctacgtgccc aattgtgacc atcgaggctt ctaccggaag 661 cggcagtgcc gctcctccca ggggcagcgc cgaggtccct gctggtgtgt ggatcggatg 721 ggcaagtccc tgccagggtc tccagatggc aatggaagct cctcctgccc cactgggagt 781 agcggctaaa gctggggat agaggggctg cagggccact ggaaggaaca tggagctgtc 841 atcactcaac aaaaaaccga ggccctcaat ccaccttcag gccccgcccc atgggcccct 901 caccgctggt tggaaagagt gttggtgttg gctggggtgt caataaagct gtgcttgggg 961 tcgctgaaaa aaaaaaaaaa
```

One example of a nucleic acid sequence for human KIT is available as NCBI accession number NM_000222 (gi: 148005048). This sequence is recited below for easy reference as SEQ ID NO:145.

```
  1 tctgggggct cggctttgcc gcgctcgctg cacttgggcg agagctggaa cgtggaccag 61 agctcggatc ccatcgcagc taccgcgatg agaggcgctc gcggcgcctg ggattttctc 121 tgcgttctgc tcctactgct tcgcgtccag acaggctctt ctcaaccatc tgtgagtcca 181 ggggaaccgt ctccaccatc catccatcca ggaaaatcag acttaatagt ccgcgtgggc 241 gacgagatta ggctgttatg cactgatccg ggctttgtca aatggacttt tgagatcctg 301 gatgaaacga atgagaataa gcagaatgaa tggatcacgg aaaaggcaga agccaccaac 361 accggcaaat acacgtgcac caacaaacac ggcttaagca attccattta tgtgtttgtt 421 agagatcctg ccaagctttt ccttgttgac cgctccttgt atgggaaaga agacaacgac 481 acgctggtcc gctgtcctct cacagaccca gaagtgacca attattccct caagggggtgc 541 caggggaagc ctcttcccaa ggacttgagg tttattcctg accccaaggc gggcatcatg 601 atcaaaagtg tgaaacgcgc ctaccatcgg ctctgtctgc attgttctgt ggaccaggag 661 ggcaagtcag tgctgtcgga aaaattcatc ctgaaagtga ggccagcctt caaagctgtg 721 cctgttgtgt ctgtgtccaa agcaagctat cttcttaggg aagggggaaga attcacagtg 781 acgtgcacaa taaagatgt gtctagttct gtgtactcaa cgtggaaaag agaaaacagt
```

-continued

```
 841 cagactaaac tacaggagaa atataatagc tggcatcacg gtgacttcaa ttatgaacgt
 901 caggcaacgt tgactatcag ttcagcgaga gttaatgatt ctggagtgtt catgtgttat
 961 gccaataata cttttggatc agcaaatgtc acaacaacct tggaagtagt agataaagga
1021 ttcattaata tcttccccat gataaacact acagtatttg taaacgatgg agaaaatgta
1081 gatttgattg ttgaatatga agcattcccc aaacctgaac accagcagtg gatctatatg
1141 aacagaacct tcactgataa atgggaagat tatcccaagt ctgagaatga agtaatatc
1201 agatacgtaa gtgaacttca tctaacgaga ttaaaaggca ccgaaggagg cacttacaca
1261 ttcctagtgt ccaattctga cgtcaatgct gccatagcat ttaatgttta tgtgaataca
1321 aaaccagaaa tcctgactta cgacaggctc gtgaatggca tgctccaatg tgtggcagca
1381 ggattcccag agcccacaat agattggtat ttttgtccag gaactgagca gagatgctct
1441 gcttctgtac tgccagtgga tgtgcagaca ctaaactcat ctgggccacc gtttggaaag
1501 ctagtggttc agagttctat agattctagt gcattcaagc acaatggcac ggttgaatgt
1561 aaggcttaca cgatgtggg caagacttct gcctatttta actttgcatt taaaggtaac
1621 aacaaagagc aaatccatcc ccacaccctg ttcactcctt tgctgattgg tttcgtaatc
1681 gtagctggca tgatgtgcat tatttgtatg attctgacct acaaatattt acagaaaccc
1741 atgtatgaag tacagtggaa ggttgttgag gagataaatg aaacaatta tgtttacata
1801 gacccaacac aacttcctta tgatcacaaa tgggagtttc ccagaaacag gctgagtttt
1861 gggaaaaccc tgggtgctgg agcttcgggg aaggttgttg aggcaactgc ttatggctta
1921 attaagtcag atgcggccat gactgtcgct gtaaagatgc tcaagccgag tgcccatttg
1981 acagaacggg aagccctcat gtctgaactc aaagtcctga gttaccttgg taatcacatg
2041 aatattgtga atctacttgg agcctgcacc attggagggc ccaccctggt cattacagaa
2101 tattgttgct atggtgatct tttgaatttt ttgagaagaa aacgtgattc atttatttgt
2161 tcaaagcagg aagatcatgc agaagctgca ctttataaga atcttctgca ttcaaaggag
2221 tcttcctgca gcgatagtac taatgagtac atggacatga aacctggagt ttcttatgtt
2281 gtcccaacca aggccgacaa aaggagatct gtgagaatag gctcatacat agaaagagat
2341 gtgactcccg ccatcatgga ggatgacgag ttggccctag acttagaaga cttgctgagc
2401 ttttcttacc aggtggcaaa gggcatggct ttcctcgcct ccaagaattg tattcacaga
2461 gacttggcag ccagaaatat cctccttact catggtcgga tcacaaagat ttgtgatttt
2521 ggtctagcca gagacatcaa gaatgattct aattatgtgg ttaaaggaaa cgctcgacta
2581 cctgtgaagt ggatggcacc tgaaagcatt ttcaactgtg tatacacgtt tgaaagtgac
2641 gtctggtcct atgggatttt ctttgggag ctgttctctt taggaagcag ccccatcct
2701 ggaatgccgg tcgattctaa gttctacaag atgatcaagg aaggcttccg gatgctcagc
2761 cctgaacacg cacctgctga atgtatgac ataatgaaga cttgctggga tgcagatccc
2821 ctaaaaagac caacattcaa gcaaattgtt cagctaattg agaagcagat tcagagagc
2881 accaatcata tttactccaa cttagcaaac tgcagcccca accgacagaa gcccgtggta
2941 gaccattctg tgcggatcaa ttctgtcggc agcaccgctt cctcctccca gcctctgctt
3001 gtgcacgacg atgtctgagc agaatcagtg tttgggtcac ccctccagga atgatctctt
3061 cttttggctt ccatgatggt tatttctttt tctttcaact tgcatccaac tccaggatag
3121 tgggcacccc actgcaatcc tgtctttctg agcacacttt agtggccgat gattttgtc
3181 atcagccacc atcctattgc aaaggttcca actgtatata ttcccaatag caacgtagct
3241 tctaccatga acagaaaaca ttctgatttg gaaaagagag gggaggtatg gactgggggc
```

-continued

```
3301 cagagtcctt tccaaggctt ctccaattct gcccaaaaat atggttgata gtttacctga
3361 ataaatggta gtaatcacag ttggccttca gaaccatcca tagtagtatg atgatacaag
3421 attagaagct gaaaacctaa gtcctttatg tggaaaacag aacatcatta gaacaaagga
3481 cagagtatga acacctgggc ttaagaaatc tagtatttca tgctgggaat gagacatagg
3541 ccatgaaaaa aatgatcccc aagtgtgaac aaaagatgct cttctgtgga ccactgcatg
3601 agcttttata ctaccgacct ggttttttaaa tagagtttgc tattagagca ttgaattgga
3661 gagaaggcct ccctagccag cacttgtata tacgcatcta taaattgtcc gtgttcatac
3721 atttgagggg aaaacaccat aaggtttcgt ttctgtatac aaccctggca ttatgtccac
3781 tgtgtataga agtagattaa gagccatata agtttgaagg aaacagttaa taccattttt
3841 taaggaaaca atataaccac aaagcacagt ttgaacaaaa tctcctcttt tagctgatga
3901 acttattctg tagattctgt ggaacaagcc tatcagcttc agaatggcat tgtactcaat
3961 ggatttgatg ctgtttgaca aagttactga ttcactgcat ggctcccaca ggagtgggaa
4021 aacactgcca tcttagtttg gattcttatg tagcaggaaa taaagtatag gtttagcctc
4081 cttcgcaggc atgtcctgga caccgggcca gtatctatat atgtgtatgt acgtttgtat
4141 gtgtgtagac aaatatttgg aggggtattt ttgccctgag tccaagaggg tcctttagta
4201 cctgaaaagt aacttggctt tcattattag tactgctctt gtttcttttc acatagctgt
4261 ctagagtagc ttaccagaag cttccatagt ggtgcagagg aagtggaagg catcagtccc
4321 tatgtatttg cagttcacct gcacttaagg cactctgtta tttagactca tcttactgta
4381 cctgttcctt agaccttcca taatgctact gtctcactga aacatttaaa tttacccttt
4441 tagactgtag cctggatatt attcttgtag tttacctctt taaaaacaaa acaaaacaaa
4501 acaaaaaact ccccttcctc actgcccaat ataaaaggca aatgtgtaca tggcagagtt
4561 tgtgtgttgt cttgaaagat tcaggtatgt tgcctttatg gtttcccccct tctacatttc
4621 ttagactaca tttagagaac tgtggccgtt atctggaagt aaccatttgc actggagttc
4681 tatgctctcg cacctttcca aagttaacag attttggggt tgtgttgtca cccaagagat
4741 tgttgtttgc catactttgt ctgaaaaatt cctttgtgtt tctattgact tcaatgatag
4801 taagaaaagt ggttgttagt tatagatgtc taggtacttc aggggcactt cattgagagt
4861 tttgtcttgg atattcttga aagtttatat ttttataatt ttttcttaca tcagatgttt
4921 ctttgcagtg gcttaatgtt tgaaattatt ttgtggcttt ttttgtaaat attgaaatgt
4981 agcaataatg tcttttgaat attcccaagc ccatgagtcc ttgaaaatat tttttatata
5041 tacagtaact ttatgtgtaa atacataagc ggcgtaagtt taaaggatgt tggtgttcca
5101 cgtgttttat tcctgtatgt tgtccaattg ttgacagttc tgaagaattc taataaaatg
5161 tacatatata aatcaaaaaa aaaaaaaaaa
```

One example of a nucleic acid sequence for human LRP4 is available as NCBI accession number NM_002334 (gi: 157384997). This sequence is recited below for easy reference as SEQ ID NO:146.

```
  1 gcggcggcgg cccgagggcg acttgcgggg cgcgcaggcc gccgtgcacc cgggacgctt
 61 ccccctcggg gaccctccgc gggcttctcc gccgcgccgt ccggcgggag ccggcgggac
121 cccgggcgag cggcgcgggc ggcaccatga ggcggcagtg gggcgcgctg ctgcttggcg
181 ccctgctctg cgcacacggc ctggccagca gccccgagtg tgcttgtggt cggagccact
```

-continued

```
 241 tcacatgtgc agtgagtgct cttggagagt gtacctgcat ccctgcccag tggcagtgtg
 301 atggagacaa tgactgcggg gaccacagcg atgaggatgg atgtatacta cctacctgtt
 361 cccctcttga ctttcactgt gacaatggca agtgcatccg ccgctcctgg gtgtgtgacg
 421 gggacaacga ctgtgaggat gactcggatg agcaggactg tcccccccgg gagtgtgagg
 481 aggacgagtt tccctgccag aatggctact gcatccggag tctgtggcac tgcgatggtg
 541 acaatgactg tggcgacaac agcgatgagc agtgtgacat gcgcaagtgc tccgacaagg
 601 agttccgctg tagtgacgga agctgcattg ctgagcattg gtactgcgac ggtgacaccg
 661 actgcaaaga tggctccgat gaggagaact gtccctcagc agtgccagcg ccccctgca
 721 acctggagga gttccagtgt gcctatggac gctgcatcct cgacatctac cactgcgatg
 781 gcgacgatga ctgtggagac tggtcagacg agtctgactg ctcctcccac cagccctgcc
 841 gctctgggga gttcatgtgt gacagtggcc tgtgcatcaa tgcaggctgg cgctgcgatg
 901 gtgacgcgga ctgtgatgac cagtctgatg agcgcaactg caccacctcc atgtgtacgg
 961 cagaacagtt ccgctgtcac tcaggccgct gtgtccgcct gtcctggcgc tgtgatgggg
1021 aggacgactg tgcagacaac agcgatgaag agaactgtga gaatacagga agccccccaat
1081 gtgccttgga ccagttcctg tgttggaatg ggcgctgcat tgggcagagg aagctgtgca
1141 acggggtcaa cgactgtggt gacaacagcg acgaaagccc acagcagaat tgccggcccc
1201 ggacgggtga ggagaactgc aatgttaaca cggtggctg tgcccagaag tgccagatgg
1261 tgcggggggc agtgcagtgt acctgccaca caggctaccg gctcacagag gatgggcaca
1321 cgtgccaaga tgtgaatgaa tgtgccgagg aggggtattg cagccagggc tgcaccaaca
1381 gcgaaggggc tttccaatgc tggtgtgaaa caggctatga actacggccc gaccggcgca
1441 gctgcaaggc tctggggcca gagcctgtgc tgctgttcgc caatcgcatc gacatccggc
1501 aggtgctgcc acaccgctct gagtacacac tgctgcttaa caacctggag aatgccattg
1561 cccttgattt ccaccaccgc cgcgagcttg tcttctggtc agatgtcacc ctggaccgga
1621 tcctccgtgc caacctcaac ggcagcaacg tggaggaggt tgtgtctact gggctggaga
1681 gcccaggggg cctggctgtg gattgggtcc atgacaaact ctactggacc gactcaggca
1741 cctcgaggat tgaggtggcc aatctggatg gggcccaccg gaaagtgttg ctgtggcaga
1801 acctggagaa gccccgggcc attgccttgc atcccatgga gggtaccatt tactggacag
1861 actgggcaa caccccccgt attgaggcct ccagcatgga tggctctgga cgccgcatca
1921 ttgccgatac ccatctcttc tggcccaatg gcctcaccat cgactatgcc gggcgccgta
1981 tgtactgggt ggatgctaag caccatgtca tcgagagggc caatctggat gggagtcacc
2041 gtaaggctgt cattagccag ggcctcccgc atcccttcgc catcacagtg tttgaagaca
2101 gcctgtactg gacagactgg cacaccaaga gcatcaatag cgctaacaaa tttacgggga
2161 agaaccagga aatcattcgc aacaaactcc acttccctat ggacatccac accttgcacc
2221 cccagcgcca acctgcaggg aaaaaccgct gtggggacaa caacggaggc tgcacgcacc
2281 tgtgtctgcc cagtggccag aactacacct gtgcctgccc cactggcttc cgcaagatca
2341 gcagccacgc ctgtgcccag agtcttgaca agttcctgct ttttgcccga aggatggaca
2401 tccgtcgaat cagctttgac acagaggacc tgtctgatga tgtcatccca ctggctgacg
2461 tgcgcagtgc tgtggcccctt gactgggact cccgggatga ccacgtgtac tggacagatg
2521 tcagcactga taccatcagc agggccaagt gggatggaac aggacaggag gtggtagtgg
2581 ataccagttt ggagagccca gctggcctgg ccattgattg ggtcaccaac aaactgtact
2641 ggacagatgc aggtacagac cggattgaag tagccaacac agatggcagc atgagaacag
```

-continued

```
2701 tactcatctg ggagaacctt gatcgtcctc gggacatcgt ggtggaaccc atgggcgggt
2761 acatgtattg gactgactgg ggtgcgagcc ccaagattga acgagctggc atggatgcct
2821 caggccgcca agtcattatc tcttctaatc tgacctggcc taatgggtta gctattgatt
2881 atgggtccca gcgtctatac tgggctgacg ccggcatgaa gacaattgaa tttgctggac
2941 tggatggcag taagaggaag gtgctgattg aagccagct cccccaccca tttgggctga
3001 ccctctatgg agagcgcatc tattggactg actggcagac aagagcata cagagcgctg
3061 accggctgac agggctggac cgggagactc tgcaggagaa cctggaaaac ctaatggaca
3121 tccatgtctt ccaccgccgc cggcccccag tgtctacacc atgtgctatg gagaatggcg
3181 gctgtagcca cctgtgtctt aggtccccaa atccaagcgg attcagctgt acctgcccca
3241 caggcatcaa cctgctgtct gatggcaaga cctgctcacc aggcatgaac agtttcctca
3301 tcttcgccag gaggatagac attcgcatgg tctccctgga catcccttat tttgctgatg
3361 tggtggtacc aatcaacatt accatgaaga acaccattgc cattggagta gacccccagg
3421 aaggaaaggt gtactggtct gacagcacac tgcacaggat cagtcgtgcc aatctggatg
3481 gctcacagca tgaggacatc atcaccacag ggctacagac cacagatggg ctcgcggttg
3541 atgccattgg ccggaaagta tactggacag acacgggaac aaaccggatt gaagtgggca
3601 acctggacgg gtccatgcgg aaagtgttgg tgtggcagaa ccttgacagt ccccgggcca
3661 tcgtactgta ccatgagatg gggtttatgt actggacaga ctgggggag aatgccaagt
3721 tagagcggtc cggaatggat ggctcagacc gcgcggtgct catcaacaac aacctaggat
3781 ggcccaatgg actgactgtg gacaaggcca gctcccaact gctatgggcc gatgcccaca
3841 ccgagcgaat tgaggctgct gacctgaatg gtgccaatcg gcatacattg gtgtcaccgg
3901 tgcagcaccc atatggcctc accctgctcg actcctatat ctactggact gactggcaga
3961 ctcggagcat ccaccgtgct gacaagggta ctggcagcaa tgtcatcctc gtgaggtcca
4021 acctgccagg cctcatggac atgcaggctg tggaccgggc acagccacta ggttttaaca
4081 agtgcggctc gagaaatggc ggctgctccc acctctgctt gcctcggcct tctggcttct
4141 cctgtgcctg ccccactggc atccagctga agggagatgg gaagacctgt gatccctctc
4201 ctgagaccta cctgctcttc tccagccgtg gctccatccg gcgtatctca ctggacacca
4261 gtgaccacac cgatgtgcat gtccctgttc ctgagctcaa caatgtcatc tccctggact
4321 atgacagcgt ggatggaaag gtctattaca cagatgtgtt cctggatgtt atcaggcgag
4381 cagacctgaa cggcagcaac atggagacag tgatcgggcg agggctgaag accactgacg
4441 ggctggcagt ggactgggtg gccaggaacc tgtactggac agacacaggt cgaaatacca
4501 ttgaggcgtc caggctggat ggttcctgcc gcaaagtact gatcaacaat agcctggatg
4561 agccccgggc cattgctgtt tccccagga aggggtacct cttctggaca gactggggcc
4621 acattgccaa gatcgaacgg gcaaacttgg atggttctga gcggaaggtc ctcatcaaca
4681 cagacctggg ttgcccaat ggccttaccc tggactatga tacccgcagg atctactggg
4741 tggatgcgca tctggaccgg atcgagagtg ctgacctcaa tgggaaactg cggcaggtct
4801 tggtcagcca tgtgtcccac ccctttgccc tcacacagca agacaggtgg atctactgga
4861 cagactggca gaccaagtca atccagcgtg ttgacaaata tcaggccgg aacaaggaga
4921 cagtgctggc aaatgtggaa ggactcatgg atatcatcgt ggtttcccct cagcggcaga
4981 cagggaccaa tgcctgtggt gtgaacaatg gtggctgcac ccacctctgc tttgccagag
5041 cctcggactt cgtatgtgcc tgtcctgacg aacctgatag ccggccctgc tcccttgtgc
```

-continued

```
5101 ctggcctggt accaccagct cctagggcta ctggcatgag tgaaaagagc ccagtgctac
5161 ccaacacacc acctaccacc ttgtattctt caaccacccg gacccgcacg tctctggagg
5221 aggtggaagg aagatgctct gaaagggatg ccaggctggg cctctgtgca cgttccaatg
5281 acgctgttcc tgctgctcca ggggaaggac ttcatatcag ctacgccatt ggtggactcc
5341 tcagtattct gctgattttg gtggtgattg cagctttgat gctgtacaga cacaaaaaat
5401 ccaagttcac tgatcctgga atggggaacc tcacctacag caaccoctcc taccgaacat
5461 ccacacagga agtgaagatt gaagcaatcc ccaaaccagc catgtacaac cagctgtgct
5521 ataagaaaga gggagggcct gaccataact acaccaagga gaagatcaag atcgtagagg
5581 gaatctgcct cctgtctggg gatgatgctg agtgggatga cctcaagcaa ctgcgaagct
5641 cacgggggg cctcctccgg gatcatgtat gcatgaagac agacacggtg tccatccagg
5701 ccagctctgg ctccctggat gacacagaga cggagcagct gttacaggaa gagcagtctg
5761 agtgtagcag cgtccatact gcagccactc cagaaagacg aggctctctg ccagacacgg
5821 gctggaaaca tgaacgcaag ctctcctcag agagccaggt ctaaatgccc acattctctt
5881 ccctgcctgc ctgttccttc tcctttatgg acgtctagtc cttgtgctcg cttacaccgc
5941 aggccccgct tctgtgtgct tgtcctcctc ctcctcccac cccataactg ttcctaagcc
6001 ttcaccggag ctgtttacca cgtgagtcca taactacctg tgcacaagaa atgatggcac
6061 atcacgagaa tttagacctg gattttacca tgaacctcac atcttgtact ccatcctggg
6121 ccccctgaaa ctgcttattc gtgattcctc accagcgtag agctccacct cccctttccc
6181 cagtaccctc agtgcctgct tctcagtgct gatgcagctg atgacccagg actgcgctct
6241 gccccatcac agccagcatg actgcttctc tgagagaact tgcccatcag gggctgggac
6301 atggggtgt gggtaaagac agggatgaag gatagaggct gagagaagaa ggaagaatca
6361 gcccagcagg tatgggcatc tgggaaacct ccagcctcaa gtgtgttggt aacatgaaaa
6421 agctttgggg ggtagttgga tctgggtgtc tggtccattg ctggcagtgg acattattct
6481 tgccctaaga gacactgcct tttcagcagc agatactggt gagatggggg tggctcaggc
6541 tgttcttcct cctcctagaa tgtctggagc tgtttctaca ttcagataac tgggtcccct
6601 atcacaaggc tactggctaa taggaattcc ctcctggtgc caccactggc cagtaccttt
6661 cctaagtctt tgctcaaatt aaccaggttg tgagccagtg gcttgagtga atgttaggcc
6721 ttgggggctg agtctctgaa aagtctaaga agctctgcct agaccaaata tggtatacct
6781 cctgaccccT ctctccctca tgtcctggga ttctggggaa gagacctaga aacaagcttt
6841 caaagaaaaa ccagaagttg tcataaatgg tcagaaagaa cgatcaggtt ggagacttgg
6901 gaaacccagg gcctaaagag aagtatccat gagggtcaaa cttcctgttg aacttcctat
6961 gttctttctc aagtgctcag ggatctaagt tagtggacag caagcctgtg gctacggggt
7021 ggtgatgttc ctcttccagc tgtcccctca gctaaggggc ttagtttcca tgtgggatgc
7081 catcacttgg ttcatgctca ttcacacaaa gggcacgtgt ctcagcctgg tatcagggaa
7141 attgagactt attttttgccc taaaacgtct ccctagctgt tcttcgtggg gtttttttgt
7201 ttgttttttt gcctaatttg cttttttctga ccaagccttg tggcaccagc aatctccaaa
7261 gtcctgtggt gggagggctg aataaataaa aatacaaaga ggtgggtaag gagtaggaag
7321 gtagagagca ccactgatga ggccctccta gcccatggca gacccagacc tcttctcccc
7381 caggaattag aagtggcagg agagaacaac aggggctggg aatggagggg agaatttcta
7441 ggggaagttt cctgagttga aacttctcct gtggttactg gtattgagaa atcagctacc
7501 aaagtgaaaa aggacaagat caattctttt ctagtcagtt ctaagactgc tagagagaga
```

-continued

```
7561 taccaggccc ttagccttgc tctcagtagc gtcagcccca gttctgagcc tccccacatt
7621 acacttaaca agcagtaaag gagtgagcac tttgggtcct tagactcatg tctggggagg
7681 aagagcaagt agaaaagtgg cattttcttg attggaaagg gggaaggatc ttattgcact
7741 tgggctgttc agaatgtaga aaggacatat ttgaggaagt atctatttga gcactgattt
7801 actctgtaaa aagcaaaatc tctctgtcct aaactaatgg aagcgattct cccatgctca
7861 tgtgtaatgg ttttaacgtt actcactgga gagattggac tttctggagt tatttaacca
7921 ctatgttcag tattttagga ctttatgata atttaatata aatttagctt ttcttaatca
7981 aaaaaaaaaa aaaaaaaa
```

One example of a nucleic acid sequence for human MATN2 is available as NCBI accession number NM_002380 (gi: 62548859). This sequence is recited below for easy reference as SEQ ID NO:147.

```
   1 gcgagcgaag ggagcgctct gggatgggac ttggagcaag cggcggcggc ggagacagag
  61 gcagaggcag aagctggggc tccgtcctcg cctcccacga gcgatccccg aggagagccg
 121 cggccctcgg cgaggcgaag aggccgacga ggaagacccg ggtggctgcg cccctgcctc
 181 gcttcccagg cgccggcggc tgcagccttg cccctcttgc tcgccttgaa aatggaaaag
 241 atgctcgcag gctgctttct gctgatcctc ggacagatcg tcctcctccc tgccgaggcc
 301 agggagcggt cacgtgggag gtccatctct aggggcagac acgctcggac ccacccgcag
 361 acggcccttc tggagagttc ctgtgagaac aagcgggcag acctggtttt catcattgac
 421 agctctcgca gtgtcaacac ccatgactat gcaaaggtca aggagttcat cgtggacatc
 481 ttgcaattct tggacattgg tcctgatgtc acccgagtgg gcctgctcca atatggcagc
 541 actgtcaaga atgagttctc cctcaagacc ttcaagagga agtccgaggt ggagcgtgct
 601 gtcaagagga tgcggcatct gtccacgggc accatgactg gctggccat ccagtatgcc
 661 ctgaacatcg cattctcaga agcagagggg gcccggcccc tgagggagaa tgtgccacgg
 721 gtcataatga tcgtgacaga tgggagacct caggactccg tggccgaggt ggctgctaag
 781 gcacgggaca cgggcatcct aatctttgcc attggtgtgg gccaggtaga cttcaacacc
 841 ttgaagtcca ttgggagtga gccccatgag gaccatgtct tccttgtggc caatttcagc
 901 cagattgaga cgctgacctc cgtgttccag aagaagttgt gcacggccca catgtgcagc
 961 accctggagc ataactgtgc ccacttctgt atcaacatcc ctggctcata cgtctgcagg
1021 tgcaaacaag gctacattct caactcggat cagacgactt gcagaatcca ggatctgtgt
1081 gccatggagg accacaactg tgagcagctc tgtgtgaatg tgccgggctc cttcgtctgc
1141 cagtgctaca gtggctacgc cctggctgag gatgggaaga ggtgtgtggc tgtggactac
1201 tgtgcctcag aaaaccacgg atgtgaacat gagtgtgtaa atgctgatgg ctcctacctt
1261 tgccagtgcc atgaaggatt tgctcttaac ccagataaaa aaacgtgcac aaagatagac
1321 tactgtgcct catctaatca cggatgtcag cacgagtgtg ttaacacaga tgattcctat
1381 tcctgccact gcctgaaagg ctttaccctg aatccagata agaaaacctg cagaaggatc
1441 aactactgtg cactgaacaa accgggctgt gagcatgagt gcgtcaacat ggagggagagc
1501 tactactgcc gctgccaccg tggctacact ctggacccca atggcaaaac ctgcagccga
1561 gtggaccact gtgcacagca ggaccatggc tgtgagcagc tgtgtctgaa cacggaggat
1621 tccttcgtct gccagtgctc agaaggcttc ctcatcaacg aggacctcaa gacctgctcc
1681 cgggtggatt actgcctgct gagtgaccat ggttgtgaat actcctgtgt caacatggac
```

-continued

```
1741 agatcctttg cctgtcagtg tcctgaggga cacgtgctcc gcagcgatgg gaagacgtgt
1801 gcaaaattgg actcttgtgc tctggggac cacggttgtg aacattcgtg tgtaagcagt
1861 gaagattcgt ttgtgtgcca gtgctttgaa ggttatatac tccgtgaaga tggaaaaacc
1921 tgcagaagga aagatgtctg ccaagctata gaccatggct gtgaacacat ttgtgtgaac
1981 agtgatgact catacacgtg cgagtgcttg gagggattcc ggctcgctga ggatgggaaa
2041 cgctgccgaa ggaaggatgt ctgcaaatca acccaccatg gctgcgaaca catttgtgtt
2101 aataatggga attcctacat ctgcaaatgc tcagagggat ttgttctagc tgaggacgga
2161 agacggtgca agaaatgcac tgaaggccca attgacctgg tctttgtgat cgatggatcc
2221 aagagtcttg gagaagagaa ttttgaggtc gtgaagcagt ttgtcactgg aattatagat
2281 tccttgacaa tttcccccaa agccgctcga gtgggctgc tccagtattc cacacaggtc
2341 cacacagagt tcactctgag aaacttcaac tcagccaaag acatgaaaaa agccgtggcc
2401 cacatgaaat acatgggaaa gggctctatg actgggctgg ccctgaaaca catgtttgag
2461 agaagtttta cccaaggaga aggggccagg cccctttcca caagggtgcc cagagcagcc
2521 attgtgttca ccgacggacg ggctcaggat gacgtctccg agtgggccag taaagccaag
2581 gccaatggta tcactatgta tgctgttggg gtaggaaaag ccattgagga ggaactacaa
2641 gagattgcct ctgagcccac aaacaagcat ctcttctatg ccgaagactt cagcacaatg
2701 gatgagataa gtgaaaaact caagaaaggc atctgtgaag ctctagaaga ctccgatgga
2761 agacaggact ctccagcagg ggaactgcca aaaacggtcc aacagccaac agaatctgag
2821 ccagtcacca taaatatcca agacctactt tcctgttcta attttgcagt gcaacacaga
2881 tatctgtttg aagaagacaa tcttttacgg tctacacaaa gctttccca ttcaacaaaa
2941 ccttcaggaa gccctttgga agaaaaacac gatcaatgca aatgtgaaaa ccttataatg
3001 ttccagaacc ttgcaaacga agaagtaaga aaattaacac agcgcttaga agaaatgaca
3061 cagagaatgg aagccctgga aaatcgcctg agatacagat gaagattaga aatcgcgaca
3121 catttgtagt cattgtatca cggattacaa tgaacgcagt gcagagcccc aaagctcagg
3181 ctattgttaa atcaataatg ttgtgaagta aaacaatcag tactgagaaa cctggtttgc
3241 cacagaacaa agacaagaag tatacactaa cttgtataaa tttatctagg aaaaaaatcc
3301 ttcagaattc taagatgaat ttaccaggtg agaatgaata agctatgcaa ggtattttgt
3361 aatatactgt ggacacaact tgcttctgcc tcatcctgcc ttagtgtgca atctcatttg
3421 actatacgat aaagtttgca cagtcttact tctgtagaac actggccata ggaaatgctg
3481 ttttttttgta ctggactttta ccttgatata tgtatatgga tgtatgcata aaatcatagg
3541 acatatgtac ttgtggaaca agttggattt tttatacaat attaaaattc accacttcag
3601 agaatggtat tcagtgcaaa aattcttagt ttaactttaa atggaagata tgtatgtatg
3661 agaaatggcc aacatgccta tgaaaaaaat gctgaatctc atcagtaatc aggaaaatgc
3721 aggttaaaac aataccattt ttcacccatc agcttagcaa aaatgagtat atttttttaac
3781 aagtgttggt aaggatgtgg aaatgtgagg ttcttgtagt aagaatgcaa atggcactct
3841 ttgtagagta agtctgttga catctcataa aactgaaaat gcacacaacc ctgtaaatct
3901 agcaactgca ctcagttgat ttcagcccat acatacaaag agacctgcat aagaatgtta
3961 ctaggctttg taaaagcaaa aaataaggaa caacttaaac atcatcagaa ggggaactga
4021 taaactctgt tgtaatccat accacagaaa tacaacaccg catgtacagg aatgtgctac
4081 atctatacaa ataaatggtc aaactcaaaa aaaaaaaaaa aa
```

One example of a nucleic acid sequence for human MET is available as NCBI accession number NM_001127500 (gi: 188595715). This sequence is recited below for easy reference as SEQ ID NO:148.

```
   1 gccctcgccg cccgcggcgc cccgagcgct tgtgagcag atgcggagcc gagtggaggg
  61 cgcgagccag atgcggggcg acagctgact tgctgagagg aggcggggag gcgcggagcg
 121 cgcgtgtggt ccttgcgccg ctgacttctc cactggttcc tgggcaccga aagataaacc
 181 tctcataatg aaggcccccg ctgtgcttgc acctggcatc ctcgtgctcc tgtttacctt
 241 ggtgcagagg agcaatgggg agtgtaaaga ggcactagca aagtccgaga tgaatgtgaa
 301 tatgaagtat cagcttccca acttcaccgc ggaaacaccc atccagaatg tcattctaca
 361 tgagcatcac atttttccttg gtgccactaa ctacatttat gttttaaatg aggaagacct
 421 tcagaaggtt gctgagtaca agactgggcc tgtgctggaa cacccagatt gtttcccatg
 481 tcaggactgc agcagcaaag ccaatttatc aggaggtgtt tggaaagata acatcaacat
 541 ggctctagtt gtcgacacct actatgatga tcaactcatt agctgtggca gcgtcaacag
 601 agggacctgc cagcgacatg tctttcccca aatcatact gctgacatac agtcggaggt
 661 tcactgcata ttctccccac agatagaaga gcccagccag tgtcctgact gtgtggtgag
 721 cgccctggga gccaaagtcc tttcatctgt aaaggaccgg ttcatcaact tctttgtagg
 781 caataccata aattcttctt atttcccaga tcatccattg cattcgatat cagtgagaag
 841 gctaaaggaa acgaaagatg gttttatgtt tttgacggac cagtcctaca ttgatgtttt
 901 acctgagttc agagattctt accccattaa gtatgtccat gcctttgaaa gcaacaattt
 961 tatttacttc ttgacggtcc aaagggaaac tctagatgct cagacttttc acacaagaat
1021 aatcaggttc tgttccataa actctggatt gcattcctac atggaaatgc ctctggagtg
1081 tattctcaca gaaaagagaa aaaagagatc cacaaagaag gaagtgttta atatacttca
1141 ggctgcgtat gtcagcaagc ctgggcca gcttgctaga caaataggag ccagcctgaa
1201 tgatgacatt ctttccgggg tgttcgcaca aagcaagcca gattctgccg aaccaatgga
1261 tcgatctgcc atgtgtgcat tccctatcaa atatgtcaac gacttcttca caagatcgt
1321 caacaaaaac aatgtgagat gtctccagca ttttttacgga cccaatcatg agcactgctt
1381 taataggaca cttctgagaa attcatcagg ctgtgaagcg cgccgtgatg aatatcgaac
1441 agagtttacc acagctttgc agcgcgttga cttattcatg ggtcaattca gcgaagtcct
1501 cttaacatct atatccacct tcattaaagg agacctcacc atagctaatc ttgggacatc
1561 agagggtcgc ttcatgcagg ttgtggtttc tcgatcagga ccatcaaccc ctcatgtgaa
1621 ttttctcctg gactcccatc cagtgtctcc agaagtgatt gtggagcata cattaaacca
1681 aaatggctac acactggtta tcactgggaa gaagatcacg aagatcccat tgaatggctt
1741 gggctgcaga catttccagt cctgcagtca atgcctctct gccccaccct ttgttcagtg
1801 tggctggtgc cacgacaaat gtgtgcgatc ggaggaatgc ctgagcggga catggactca
1861 acagatctgt ctgcctgcaa tctacaaggt tttcccaaat agtgcacccc ttgaaggagg
1921 gacaaggctg accatatgtg gctgggactt tggatttcgg aggaataata aatttgattt
1981 aaagaaaact agagttctcc ttggaaatga gactgcacc ttgactttaa gtgagagcac
2041 gatgaataca ttgaaatgca cagttggtcc tgccatgaat aagcatttca atatgtccat
2101 aattatttca aatggccacg ggacaacaca atacagtaca ttctcctatg tggatcctgt
2161 aataacaagt atttcgccga aatacggtcc tatggctggt ggcactttac ttacttaac
2221 tggaaattac ctaaacagtg ggaattctag acacatttca attggtggaa aaacatgtac
```

-continued

```
2281 tttaaaaagt gtgtcaaaca gtattcttga atgttatacc ccagcccaaa ccatttcaac
2341 tgagtttgct gttaaattga aaattgactt agccaaccga gagacaagca tcttcagtta
2401 ccgtgaagat cccattgtct atgaaattca tccaaccaaa tcttttatta gtacttggtg
2461 gaaagaacct ctcaacattg tcagttttct attttgcttt gccagtggtg ggagcacaat
2521 aacaggtgtt gggaaaaacc tgaattcagt tagtgtcccg agaatggtca taaatgtgca
2581 tgaagcagga aggaacttta cagtggcatg tcaacatcgc tctaattcag agataatctg
2641 ttgtaccact ccttccctgc aacagctgaa tctgcaactc cccctgaaaa ccaaagcctt
2701 tttcatgtta gatgggatcc tttccaaata ctttgatctc atttatgtac ataatcctgt
2761 gtttaagcct tttgaaaagc cagtgatgat ctcaatgggc aatgaaaatg tactggaaat
2821 taagggaaat gatattgacc ctgaagcagt taaaggtgaa gtgttaaaag ttggaaataa
2881 gagctgtgag aatatacact tacattctga agccgtttta tgcacggtcc ccaatgacct
2941 gctgaaattg aacagcgagc taaatataga gtggaagcaa gcaatttctt caaccgtcct
3001 tggaaaagta atagttcaac cagatcagaa tttcacagga ttgattgctg gtgttgtctc
3061 aatatcaaca gcactgttat tactacttgg gttttcctg tggctgaaaa agagaaagca
3121 aattaaagat ctgggcagtg aattagttcg ctacgatgca agagtacaca ctcctcattt
3181 ggataggctt gtaagtgccc gaagtgtaag cccaactaca gaaatggttt caaatgaatc
3241 tgtagactac cgagctactt ttccagaaga tcagtttcct aattcatctc agaacggttc
3301 atgccgacaa gtgcagtatc ctctgacaga catgtccccc atcctaacta gtggggactc
3361 tgatatatcc agtccattac tgcaaaatac tgtccacatt gacctcagtg ctctaaatcc
3421 agagctggtc caggcagtgc agcatgtagt gattgggccc agtagcctga ttgtgcatt
3481 caatgaagtc ataggaagag ggcattttgg ttgtgtatat catgggactt tgttggacaa
3541 tgatggcaag aaaattcact gtgctgtgaa atccttgaac agaatcactg acataggaga
3601 agtttcccaa tttctgaccg agggaatcat catgaaagat tttagtcatc ccaatgtcct
3661 ctcgctcctg ggaatctgcc tgcgaagtga agggtctccg ctggtggtcc taccatacat
3721 gaaacatgga gatcttcgaa atttcattcg aaatgagact cataatccaa ctgtaaaaga
3781 tcttattggc tttggtcttc aagtagccaa aggcatgaaa tatcttgcaa gcaaaaagtt
3841 tgtccacaga gacttggctg caagaaactg tatgctggat gaaaaattca cagtcaaggt
3901 tgctgatttt ggtcttgcca gagacatgta tgataaagaa tactatagtg tacacaacaa
3961 aacaggtgca aagctgccag tgaagtggat ggctttggaa agtctgcaaa ctcaaaagtt
4021 taccaccaag tcagatgtgt ggtcctttgg cgtgctcctc tgggagctga tgacaagagg
4081 agccccacct tatcctgacg taaacacctt tgatataact gtttacttgt tgcagggag
4141 aagactccta caacccgaat actgcccaga ccccttatat gaagtaatgc taaaatgctg
4201 gcacccctaaa gccgaaatgc gcccatcctt ttctgaactg tgtcccgga tatcagcgat
4261 cttctctact ttcattgggg agcactatgt ccatgtgaac gctacttatg tgaacgtaaa
4321 atgtgtcgct ccgtatcctt ctctgttgtc atcagaagat aacgctgatg atgaggtgga
4381 cacacgacca gcctccttct gggagacatc atagtgctag tactatgtca aagcaacagt
4441 ccacactttg tccaatggtt ttttcactgc ctgacctta aaaggccatc gatattcttt
4501 gctcttgcca aaattgcact attataggac ttgtattgtt atttaaatta ctggattcta
4561 aggaatttct tatctgacag agcatcagaa ccagaggctt ggtcccacag gccacggacc
4621 aatggcctgc agccgtgaca acactcctgt catattggag tccaaaactt gaattctggg
```

-continued

```
4681 ttgaattttt taaaaatcag gtaccacttg atttcatatg ggaaattgaa gcaggaaata 4741 ttgagggctt cttgatcaca gaaaactcag aagagatagt aatgctcagg acaggagcgg 4801 cagccccaga acaggccact catttagaat tctagtgttt caaaacactt ttgtgtgttg 4861 tatggtcaat aacattttc attactgatg gtgtcattca cccattaggt aaacattccc 4921 ttttaaatgt ttgtttgttt tttgagacag gatctcactc tgttgccagg gctgtagtgc 4981 agtggtgtga tcatagctca ctgcaacctc cacctcccag gctcaagcct cccgaatagc 5041 tgggactaca ggcgcacacc accatccccg gctaattttt gtattttttg tagagacggg 5101 gttttgccat gttgccaagg ctggtttcaa actcctggac tcaagaaatc cacccacctc 5161 agcctcccaa agtgctagga ttacaggcat gagccactgc gcccagccct tataaatttt 5221 tgtatagaca ttcctttggt tggaagaata tttataggca atacagtcaa agtttcaaaa 5281 tagcatcaca caaaacatgt ttataaatga acaggatgta atgtacatag atgacattaa 5341 gaaaatttgt atgaaataat ttagtcatca tgaaatattt agttgtcata taaaaaccca 5401 ctgtttgaga atgatgctac tctgatctaa tgaatgtgaa catgtagatg ttttgtgtgt 5461 attttttaa atgaaaactc aaaataagac aagtaatttg ttgataaata ttttaaaga 5521 taactcagca tgtttgtaaa gcaggataca ttttactaaa aggttcattg gttccaatca 5581 cagctcatag gtagagcaaa gaaagggtgg atggattgaa aagattagcc tctgtctcgg 5641 tggcaggttc ccacctcgca agcaattgga aacaaaactt tgggggagtt ttattttgca 5701 ttagggtgtg ttttatgtta agcaaaacat actttagaaa caaatgaaaa aggcaattga 5761 aaatcccagc tatttcacct agatggaata gccaccctga gcagaacttt gtgatgcttc 5821 attctgtgga attttgtgct tgctactgta tagtgcatgt ggtgtaggtt actctaactg 5881 gttttgtcga cgtaaacatt taagtgtta tatttttat aaaaatgttt attttaatg 5941 atatgagaaa aattttgtta ggccacaaaa acactgcact gtgaacattt tagaaaaggt 6001 atgtcagact gggattaatg acagcatgat tttcaatgac tgtaaattgc gataaggaaa 6061 tgtactgatt gccaatacac cccaccctca ttacatcatc aggacttgaa gccaagggtt 6121 aacccagcaa gctacaaaga gggtgtgtca cactgaaact caatagttga gtttggctgt 6181 tgttgcagga aaatgattat aactaaaagc tctctgatag tgcagagact taccagaaga 6241 cacaaggaat tgtactgaag agctattaca atccaaatat tgccgtttca taaatgtaat 6301 aagtaatact aattcacaga gtattgtaaa tggtggatga caaaagaaaa tctgctctgt 6361 ggaaagaaag aactgtctct accagggtca agagcatgaa cgcatcaata gaaagaactc 6421 ggggaaacat cccatcaaca ggactacaca cttgtatata cattcttgag aacactgcaa 6481 tgtgaaaatc acgtttgcta tttataaact tgtccttaga ttaatgtgtc tggacagatt 6541 gtgggagtaa gtgattcttc taagaattag atacttgtca ctgcctatac ctgcagctga 6601 actgaatggt acttcgtatg ttaatagttg ttctgataaa tcatgcaatt aaagtaaagt 6661 gatgcaacat cttgtaaaaa aaaaaaaaaa aaaaa
```

One example of a nucleic acid sequence for human MYH10 is available as NCBI accession number NM_005964 (gi: 41406063). This sequence is recited below for easy reference as SEQ ID NO:149.

```
  1 actgaggcgc tggatctgtg gtcgcggctg gggacgtgcg cccgcgccac catcttcggc 61 tgaagaggca attgcttttg gatcgttcca tttacaatgg cgcagagaac tggactcgag 121 gatccagaga ggtatctctt tgtggacagg gctgtcatct acaaccctgc cactcaagct 181 gattggacag ctaaaaagct agtgtggatt ccatcagaac gccatggttt tgaggcagct
```

-continued

```
 241 agtatcaaag aagaacgggg agatgaagtt atggtggagt tggcagagaa tggaaagaaa
 301 gcaatggtca acaaagatga tattcagaag atgaacccac ctaagttttc caaggtggag
 361 gatatggcag aattgacatg cttgaatgaa gcttccgttt tacataatct gaaggatcgc
 421 tactattcag gactaatcta tacttattct ggactcttct gtgtagttat aaaccttac
 481 aagaatcttc caatttactc tgagaatatt attgaaatgt acagagggaa gaagcgtcat
 541 gagatgcctc cacacatcta tgctatatct gaatctgctt acagatgcat gcttcaagat
 601 cgtgaggacc agtcaattct ttgcacgggt gagtcaggtg ctgggaagac agaaaataca
 661 aagaaagtta ttcagtacct tgcccatgtt gcttcttcac ataaaggaag aaaggaccat
 721 aatattcctg gggaacttga acggcagctt ttgcaagcaa atccaattct ggaatcattt
 781 ggaaatgcga agactgtgaa aaatgataac tcatctcgtt ttggcaaatt tattcggatc
 841 aactttgatg taactggcta tatcgttggg gccaacattg aaacatacct tctggaaaag
 901 tctcgtgctg ttcgtcaagc aaaagatgaa cgtacttttc atatctttta ccagttgtta
 961 tctggagcag agaacacct aaagtctgat ttgcttcttg aaggatttaa taactacagg
1021 tttctctcca atggctatat tcctattccg ggacagcaag acaaagataa tttccaggag
1081 accatggaag caatgcacat aatgggcttc tcccatgaag agattctgtc aatgcttaaa
1141 gtagtatctt cagtgctaca gtttggaaat atttctttca aaaggagag aaatactgat
1201 caagcttcca tgccagaaaa tacagttgcg cagaagctct gccatcttct tgggatgaat
1261 gtgatggagt ttactcgggc catcctgact ccccggatca aggtcggccg agactatgtg
1321 caaaaagccc agaccaaaga acaggcagat tttgcagtag aagcattggc aaaagctacc
1381 tatgagcggc tctttcgctg gctcgttcat cgcatcaata agctctgga taggaccaaa
1441 cgtcagggag catctttcat tggaatcctg gatattgctg gatttgaaat ttttgagctg
1501 aactcctttg aacaactttg catcaactac accaatgaga agctgcagca gctgttcaac
1561 cacaccatgt ttatcctaga acaagaggaa taccagcgcg aaggcatcga gtggaacttc
1621 atcgatttcg ggctggatct gcagccatgc atcgacctaa tagagagacc tgcgaaccct
1681 cctggtgtac tggcccttt ggatgaagaa tgctggttcc ctaaagccac agataaaacc
1741 tttgttgaaa aactggttca agagcaaggt tcccactcca gtttcagaa acctcgacaa
1801 ttaaaagaca aagctgattt tgcattata cattatgcag ggaaggtgga ctataaggca
1861 gatgagtggc tgatgaagaa tatggacccc ctgaatgaca acgtggccac ccttttgcac
1921 cagtcatcag acagatttgt ggcagagctt tggaaagatg tggaccgtat cgtgggtctg
1981 gatcaagtca ctggtatgac tgagacagct tttggctccg catataaaac caagaagggc
2041 atgtttcgta ccgttgggca actctacaaa gaatctctca ccaagctgat ggcaactctc
2101 cgaaacacca accctaactt tgttcgttgt atcattccaa atcacgagaa gagggctgga
2161 aaattggatc cacacctagt cctagatcag cttcgctgta atggtgtcct ggaagggatc
2221 cgaatctgtc gccagggctt ccctaaccga atagttttcc aggaattcag acagagatat
2281 gagatcctaa ctccaaatgc tattcctaaa ggttttatgg atggtaaaca ggcctgtgaa
2341 cgaatgatcc gggctttaga attggaccca aacttgtaca gaattggaca gagcaagata
2401 ttttcagag ctggagttct ggcacactta gaggaagaaa gagatttaaa aatcaccgat
2461 atcattatct tcttccaggc cgtttgcaga ggttacctgg ccagaaaggc ctttgccaag
2521 aagcagcagc aactaagtgc cttaaaggtc ttgcagcgga actgtgccgc gtacctgaaa
2581 ttacggcact ggcagtggtg gcgagtcttc acaaaggtga agccgcttct acaagtgact
```

-continued

```
2641 cgccaggagg aagaacttca ggccaaagat gaagagctgt tgaaggtgaa ggagaagcag 2701 acgaaggtgg aaggagagct ggaggagatg gagcggaagc accagcagct tttagaagag 2761 aagaatatcc ttgcagaaca actacaagca gagactgagc tctttgctga agcagaagag 2821 atgagggcaa gacttgctgc taaaaagcag gaattagaag agattctaca tgacttggag 2881 tctaggggttg aagaagaaga agaaagaaac caaatcctcc aaaatgaaaa gaaaaaaatg 2941 caagcacata ttcaggacct ggaagaacag ctagacgagg aggaaggggc tcggcaaaag 3001 ctgcagctgg aaaaggtgac agcagaggcc aagatcaaga agatggaaga ggagattctg 3061 cttctcgagg accaaaattc caagttcatc aaagaaaaga aactcatgga agatcgcatt 3121 gctgagtgtt cctctcagct ggctgaagag gaagaaaagg cgaaaaactt ggccaaaatc 3181 aggaataagc aagaagtgat gatctcagat ttagaagaac gcttaaagaa ggaagaaaag 3241 actcgtcagg aactggaaaa ggccaaaaga aaactcgacg gggagacgac cgacctgcag 3301 gaccagatcg cagagctgca ggcgcagatt gatgagctca agctgcagct ggccaagaag 3361 gaggaggagc tgcagggcgc actggccaga ggtgatgatg aaacactcca taagaacaat 3421 gcccttaaag ttgtgcgaga gctacaagcc caaattgctg aacttcagga agactttgaa 3481 tccgagaagg cttcacggaa caaggccgaa agcagaaaa gggacttgag tgaggaactg 3541 gaagctctga aaacagagct ggaggacacg ctggacacca cggcagccca gcaggaacta 3601 cgtacaaaac gtgaacaaga agtggcagag ctgaagaaag ctcttgagga ggaaactaag 3661 aaccatgaag ctcaaatcca ggacatgaga caaagacacg caacagccct ggaggagctc 3721 tcagagcagc tggaacaggc caagcggttc aaagcaaatc tagagaagaa caagcagggc 3781 ctggagacag ataacaagga gctggcgtgt gaggtgaagg tcctgcagca ggtcaaggct 3841 gagtctgagc acaagaggaa gaagctcgac gcgcaggtcc aggagctcca tgccaaggtc 3901 tctgaaggcg acaggctcag ggtggagctg gcggagaaag caagtaagct gcagaatgag 3961 ctagataatg tctccaccct tctggaagaa gcagagaaga agggtattaa atttgctaag 4021 gatgcagcta gtcttgagtc tcaactacag gatacacagg agcttcttca ggaggagaca 4081 cgccagaaac taaacctgag cagtcggatc cggcagctgg aagaggagaa gaacagtctt 4141 caggagcagc aggaggagga ggaggaggcc aggaagaacc tggagaagca agtgctggcc 4201 ctgcagtccc agttggctga taccaagaag aaagtagatg acgacctggg aacaattgaa 4261 agtctggaag aagccaagaa gaagcttctg aaggacgcgg aggccctgag ccagcgcctg 4321 gaggagaagg cactggcgta tgacaaactg gagaagacca agaaccgcct gcagcaggag 4381 ctggacgacc tcacggtgga cctggaccac cagcgccagg tcgcctccaa cttggagaag 4441 aagcagaaga gtttgaccca gctgttagca gaagagaaga gcatctctgc tcgctatgcc 4501 gaagagcggg accgggccga agccgaggcc agagagaaag aaaccaaagc cctgtcactg 4561 gcccggcccc tcgaggaagc cctggaggcc aaggaggagt ttgagaggca gaacaagcag 4621 ctccgagcag acatggaaga cctcatgagc tccaaagatg atgtgggaaa aaacgttcac 4681 gaacttgaaa atccaaacg ggccctagag cagcaggtgg aggaaatgag gacccagctg 4741 gaggagctgg aagacgaact ccaggccacg gaagatgcca agcttcgtct ggaggtcaac 4801 atgcaggcca tgaaggcgca gttcgagaga gacctgcaaa ccagggatga gcagaatgaa 4861 gagaagaagc ggctgctgat caaacaggtg cgggagctcg aggcggagct ggaggatgag 4921 aggaaacagc gggcgcttgc tgtagcttca aagaaaaaga tggagatagg cctgaaggac 4981 ctcgaagccc aaatcgaggc tgcgaacaaa gctcgggatg aggtgattaa gcagctccgc 5041 aagctccagg ctcagatgaa ggattaccaa cgtgaattag aagaagctcg tgcatccaga
```

```
5101 gatgagattt ttgctcaatc caaagagagt gaaagaaat tgaagagtct ggaagcagaa
5161 atccttcaat tgcaggagga acttgcctca tctgagcgag cccgccgaca cgccgagcag
5221 gagagagatg agctggcgga cgagatcacc aacagcgcct ctggcaagtc cgcgctgctg
5281 gatgagaagc ggcgtctgga agctcggatc gcacagctgg aggaggagct ggaagaggag
5341 cagagcaaca tggagctgct caacgaccgc ttccgcaaga ccactctaca ggtggacaca
5401 ctgaacgccg agctagcagc cgagcgcagc gccgcccaga gagtgacaa tgcacgccag
5461 caactggagc ggcagaacaa ggagctgaag gccaagctgc aggaactcga gggtgctgtc
5521 aagtctaagt tcaaggccac catctcagcc ctggaggcca agattgggca gctggaggag
5581 cagcttgagc aggaagccaa ggaacgagca gccgccaaca aattagtccg tcgcactgag
5641 aagaagctga agaaatctt catgcaggtt gaggatgagc gtcgacacgc ggaccagtat
5701 aaagagcaga tggagaaggc caacgctcgg atgaagcagc ttaaacgcca gctggaggaa
5761 gcagaagaag aagcgacgcg tgccaacgca tctcggcgta aactccagcg ggaactggat
5821 gatgccaccg aggccaacga gggcctgagc cgcgaggtca gcaccctgaa gaaccggctg
5881 aggcggggtg gccccatcag cttctcttcc agccgatctg gccggcgcca gctgcacctt
5941 gaaggagctt ccctggagct ctccgacgat gacacagaaa gtaagaccag tgatgtcaac
6001 gagacgcagc caccccagtc agagtaaagt tgcaggaagc cagaggaggc aatacagtgg
6061 gacagttagg aatgcacccg gggcctcctg cagatttcgg aaattggcaa gctacgggat
6121 tccttcctga agatcaact gtgtcttaag gctctccagc ctatgcatac tgtatcctgc
6181 ttcagactta ggtacaattg ctcccctttt tatatataga cacacacagg acacatatat
6241 taaacagatt gtttcatcat tgcatctatt ttccatatag tcatcaagag accattttat
6301 aaaacatggt aagacccttt ttaaaacaaa ctccaggccc ttggttgcgg gtcgctgggt
6361 tattggggca gcgccgtggt cgtcactcag tcgctctgca tgctctctgt catacagaca
6421 ggtaacctag ttctgtgttc acgtggcccc cgactcctca gccacatcaa gtctcctaga
6481 ccactgtgga ctcaaactg cacttgtctc tctcatttcc ttcaaataat gatcaatgct
6541 atttcagtga gcaaactgtg aaaggggctt tggaaagagt aggaggggtg ggctggatcg
6601 gaagcaacac ccatttgggg ttaccatgtc catcccccaa ggggggccct gcccctcgag
6661 tcgatggtgt cccgcatcta ctcatgtgaa ctggccttgg cgagggctgg tctgtgcata
6721 gaagggatag tggccacact gcagctgagg ccccaggtgg cagccatgga tcatgtagac
6781 ttccagatgt ctcccgaac cgcctggctc tgccggcgcc ctcctcacgt caggagcaag
6841 cagccgtgga cccctaagcc gagctggtgg aaggcccctc cctgtcgcca gccgggccct
6901 catgctgacc ttgcaaattc agccgctgct ttgagcccaa aatgggaata ttggttttgt
6961 gtccgaggct tgttccaagt tgtcaatga ggtttatgga gcctccagaa cagatgccat
7021 cttcctgaat gttgacatgc cagtgggtgt gactccttca tttttccttc tcccttccct
7081 ttggacagtg ttacagtgaa cacttagcat cctgtttttg gttggtagtt aagcaaactg
7141 acattacgga aagtgcctta gacactacag tactaagaca atgttgaata tatcattcgc
7201 ctctataaca atttaatgta ttcagttttg actgtgcttc atatcatgta cctctctagt
7261 caaagtggta ttacagacat tcagtgacaa tgaatcagtg ttaattctaa atccttgatc
7321 ctctgcaatg tgcttgaaaa cacaaacctt ttgggttaaa agctttaaca tctattagga
7381 agaatttgtc ctgtgggttt ggaatcttgg attttccccc tttatgaact gtactggctg
7441 ttgaccacca gacacctgac cgcaaatatc ttttcttgta ttcccatatt tctagacaat
```

-continued
```
7501 gatttttgta agacaataaa tttattcatt atagatattt gcgcctgctc tgtttacttg 7561 aagaaaaaag cacccgtgga gaataaagag acctcaataa acaagaataa tcatgtgaa
```

One example of a nucleic acid sequence for human PFAAP5 is available as NCBI accession number AF530063 (gi: 33329092). This sequence is recited below for easy reference as SEQ ID NO:150.

```
   1 atgtcttatg gtgaaattga aggtaaattc ttgggaccta gagaagaagt aacgagtgag 61 ccacgctgta aaaaattgaa gtcaaccaca gagtcgtatg ttttcacaa tcatagtaat 121 gctgattttc acagaatcca agagaaaact ggaaatgatt gggtccctgt gaccatcatt 181 gatgtcagag gacatagtta tttgcaggag aacaaaatca aaactacaga tttgcataga 241 cctttgcatg atgagatgcc tggtaataga ccagatgtta ttgaatccat tgattcacag 301 gttttacagg aagcacgtcc tccattagta tccgcagacg atgagatata tagcacaagt 361 aaagcattta taggacccat ttacaaaccc cctgagaaaa agaaacgtaa tgaagggagg 421 aatgaggcac atgttctaaa tggtataaat gacagaggag acaaaaaga gaaacagaaa 481 tttaactctg aaaaatcaga gattgacaat gaattattcc agttttacaa agaaattgaa 541 gagcttgaaa aggaaaaaga tggttttgag aacagttgta aagaatctga accttctcag 601 gaacaatttg ttccatttta tgagggtcat aataatggtc tcttaaaacc tgatgaagaa 661 aagaaagatc ttagtaataa agctatgcca tcacattgtg attatcagca gaacttgggg 721 aatgagccag acaaatatcc ctgtaatgga caagtaaatac ctacattttg tgacacttca 781 tttacttctt tcaggcctga atggcagtca gtatatcctt ttatagtgcc ctatggtccc 841 cctcttccca gtttgaacta tcatttaaac attcagagat tcagtggtcc accaaatcca 901 ccatcaaata ttttccaagc ccaagatgac tctcagatac aaaatggata ttatgtaaat 961 aattgtcatg ttaactggaa ttgcatgact tttgatcaga acaatgaata tactgactgt 1021 agtgagaata ggagtagtgt tcatccctct ggaaatggct gcagtatgca agatcgatat 1081 gtgagtaatg gtttctgtga agtcagagaa agatgctgga agatcattg tatggacaag 1141 cataatggaa cagacaggtt tgtgaaccag cagtttcaag aggaaaagtt aaataaattg 1201 cagaagttac ttattctttt aagaggtctg cctggttctg ggaaaacaac attgtctcga 1261 attctgcttg gtcagaatcg tgatggcatt gtgttcagca ctgatgacta ttttcaccat 1321 caagatgggt acaggtataa tgttaatcaa cttggtgatg cccatgactg gaaccagaac 1381 agagcaaaac aagctatcga tcagggaaga tctccagtta taatagataa cactaatata 1441 caagcttggg aaatgaagcc atatgtggaa gtggccatag gaaaaggata cagagtagag 1501 tttcatgaac ctgaaacttg gtggaaattt gatcctgaag aattagaaaa gaggaataaa 1561 catggtgtgt ctcgaaagaa gattgctcag atgttggatc gttatgaata tcaaatgtcc 1621 atttctattg taatgaattc agtggaacca tcacacaaaa gcacacaaag acctcctcct 1681 ccacagggga gacagaggtg gggaggctct cttggctcac ataatcgtgt ctgtgtcaca 1741 aataatcatt aa
```

One example of a nucleic acid sequence for human PGF is available as NCBI accession number NM_002632 (gi: 56676307). This sequence is recited below for easy reference as SEQ ID NO:151.

```
  1 ctgctgtctg cggaggaaac tgcatcgacg gacggccgcc cagctacggg aggacctgga 61 gtggcactgg gcgcccgacg gaccatcccc gggacccgcc tgccctcgg cgcccgcc
```

-continued

```
 121 cgccgggccg ctccccgtcg ggttccccag ccacagcctt acctacgggc tcctgactcc
 181 gcaaggcttc cagaagatgc tcgaaccacc ggccggggcc tcggggcagc agtgagggag
 241 gcgtccagcc ccccactcag ctcttctcct cctgtgccag gggctccccg ggggatgagc
 301 atggtggttt ccctcggag ccccctggct cgggacgtct gagaagatgc cggtcatgag
 361 gctgttccct tgcttcctgc agctcctggc cgggctggcg ctgcctgctg tgcccccca
 421 gcagtgggc ttgtctgctg ggaacggctc gtcagaggtg gaagtggtac ccttccagga
 481 agtgtggggc cgcagctact gccgggcgct ggagaggctg gtggacgtcg tgtccgagta
 541 ccccagcgag gtggagcaca tgttcagccc atcctgtgtc tccctgctgc gctgcaccgg
 601 ctgctgcggc gatgagaatc tgcactgtgt gccggtggag acggccaatg tcaccatgca
 661 gctcctaaag atccgttctg ggaccggcc ctcctacgtg gagctgacgt tctctcagca
 721 cgttcgctgc gaatgccggc ctctgcggga gaagatgaag ccggaaagga ggagacccaa
 781 gggcaggggg aagaggagga gagagaagca gagacccaca gactgccacc tgtgcggcga
 841 tgctgttccc cggaggtaac ccaccccttg gaggagagag accccgcacc cggctcgtgt
 901 atttattacc gtcacactct tcagtgactc ctgctggtac ctgccctcta tttattagcc
 961 aactgtttcc ctgctgaatg cctcgctccc ttcaagacga ggggcaggga aggacaggac
1021 cctcaggaat tcagtgcctt caacaacgtg agagaaagag agaagccagc cacagacccc
1081 tgggagcttc cgctttgaaa gaagcaagac acgtggcctc gtgaggggca agctaggccc
1141 cagaggccct ggaggtctcc aggggcctgc agaaggaaag aaggggcccc tgctacctgt
1201 tcttgggcct caggctctgc acagacaagc agcccttgct ttcggagctc ctgtccaaag
1261 tagggatgcg gatcctgctg gggccgccac ggcctggctg gtgggaaggc cggcagcggg
1321 cggaggggat ccagccactt ccccctcttc ttctgaagat cagaacattc agctctggag
1381 aacagtggtt gcctggggc ttttgccact ccttgtcccc cgtgatctcc cctcacactt
1441 tgccatttgc ttgtactggg acattgttct ttccggccaa ggtgccacca ccctgccccc
1501 cctaagagac acatacagag tgggcccccgg gctggagaaa gagctgcctg gatgagaaac
1561 agctcagcca gtggggatga ggtcaccagg ggaggagcct gtgcgtccca gctgaaggca
1621 gtggcagggg agcaggttcc ccaagggccc tggcaccccc acaagctgtc cctgcagggc
1681 catctgactg ccaagccaga ttctcttgaa taaagtattc tagtgtggaa aaaaaaaaa
1741 aaaaaaaaaa aaaaaaa
```

One example of a nucleic acid sequence for human PIP3-E is available as NCBI accession number AJ310566 (gi: 18307480). This sequence is recited below for easy reference as SEQ ID NO:152.

```
  1 gtttaagtag aatcctcaag cttggcctca gagtactatg aggcttctga atccaggaat
 61 aagactgctc ttggatttac tctctttgta ttgcatgtca aaggcaacag aactggacca
121 agaaaattca taacttttg cgtttgtttc tactaagatg acatcataca tggctattga
181 tggcagtgct cttgttccct tgcgtcagaa gcccaggagg aaaactcaag gttttctcac
241 gatgagtcgg aggaggatat cgtgtaaaga tctgggccat gctgactgcc aagggtggct
301 gtataagaaa aaggaaaagg gaagtttcct aagcaacaaa tggaaaaagt tctgggtgat
361 actgaagggg tcgtcactgt actggtatag caatcaaatg gcagagaaag ctgatggatt
421 tgtcaacctg cctgatttca ctgtggaaag agcatctgaa tgcaagaaaa agcatgcttt
481 taagatcagc catccacaga tcaagacctt ttattttgca gctgagaatg tgcaggaaat
541 gaacgtgtgg ttaaataaac ttggatcggc tgtaatccat caggaatcca ctacaaagga
```

-continued

```
 601 tgaagaatgt tacagtgaaa gtgaacagga agatccagaa atagctgcgg agacaccacc
 661 ccctcctcac gcttcccaga ctcagtcttt gactgcacag caggcatctt catcctcacc
 721 cagcctgagt ggaacgtcgt attctttctc ttccctggaa aatacagtga agacacccag
 781 cagttttcct tcctccttat ctaaagagag acaatccttg cctgacacag ttaacagttt
 841 gtctgctgct gaagatgagg gacaaccaat aacgtttgct gtgcaagttc attcacctgt
 901 accctcagag gcaggcatcc acaaggccct ggaaaacagt tttgtcacat cagaaagtgg
 961 attttgaac tctttatcta gtgatgatac ttcttcattg agtagcaatc atgaccatct
1021 tactgtccca gataagcctg ctggatcaaa gatcatggac aaagaagaga caaagtgtc
1081 tgaagatgat gaaatggaga agctgtacaa atcattagag caagctagtc tatctcctct
1141 tggggaccga cgaccttcga ctaaaaagga gttgagaaaa tcctttgtta agcggtgtaa
1201 aaatccatct ataaacgaga aactccacaa aatccgaaca ttgaatagca cattaaagtg
1261 taaagaacat gatctggcca tgattaacca gttgctggat gacccgaagc tgacagccag
1321 gaaatacaga gagtggaaag tcatgaacac cctgctgatc caggacatct atcagcagca
1381 gcgggcttcg cctgccctg atgacactga tgacacccc caggaactca agaaatcacc
1441 ttcttctccc tctgttgaaa attccatttg agacaaagtc agggttttct cctcttatat
1501 tttatcacaa gcaactcttc aagatgttgc aaaagcttac atttttcctt aaaaggaaaa
1561 ctgaaaccca gtccttcaag catcagcttc ccatctaaag atgcacgtta gatgaagata
1621 at
```

One example of a nucleic acid sequence for human PKNOX2 is available as NCBI accession number NM_022062 (gi: 116812643). This sequence is recited below for easy reference as SEQ ID NO:153.

```
   1 gtgtgaaggg ggggtccggg gggcgggtcc ctgtgccgct gacgtcccga gcagtgctgg
  61 gaagtatagg ctgtgttgtc acgccggtgt cagtctgatg aagattggca tcaggtgaag
 121 tctggagcag gacttctgag gctttctatc ctccatgctg ctcactagaa aagggctgt
 181 gaactgtgct ttggctctag cagacaggaa gaaattctgg cccagctgga agtagaaaga
 241 ggggagtgag tctcctgagg accatctcag aggcccggg atcacccgaa cagtcctcca
 301 tgtgaatcaa tcccatgatg caacatgcct ccccagcccc cgctctgacg atgatggcca
 361 cgcagaatgt cccgccccca ccctaccagg acagcccaca gatgacggca accgcccagc
 421 caccctccaa ggcccaggct gtccacatct ctgccccctc agctgctgcc agcacacctg
 481 tgcccagtgc ccccatcgac ccccaggccc agctggaggc tgacaagcga gctgtataca
 541 ggcaccctct tttcccgctc ctgacgctgc tgtttgagaa atgtgaacag gccacccagg
 601 gctctgagtg catcacctcc gccagctttg atgtggacat cgagaacttt gtccaccagc
 661 aggaacagga gcacaaaccc ttcttcagcg atgacccaga actggacaat ctgatggtga
 721 aggcaatcca ggtcctgaga atccacctgc tggagctgga gaaagtcaat gaactctgca
 781 aggacttttg taaccgttac atcacctgcc tcaaaaccaa gatgcacagc gacaacctgc
 841 tcaggaatga tctagggggg ccctactccc caaccagcc ctccatcaac cttcactcac
 901 aggacctcct gcagaattcc cccaattcca tgtccggagt ctccaataac ccccagggga
 961 ttgtggtccc agcctcagcg ctccagcagg gcaacatcgc catgacaacc gtcaactcac
1021 aagttgtgtc aggtggagcc ttataccaac cggttaccat ggtaacctcc cagggtcagg
1081 tggtcaccca agcaatcccc cagggagcca tccagatcca gaacacacag gttaaccttg
```

-continued

```
1141 acctcacctc cctcctggac aatgaggata agaagtccaa gaacaaacga ggagtcttgc 1201 ccaagcatgc caccaatata atgcgttctt ggctcttcca gcatctcatg cacccctacc 1261 ccacggagga tgagaagagg cagatcgcag cccagaccaa cctcaccctc ctgcaagtaa 1321 acaactggtt catcaatgcc cggaggcgca tcctgcagcc catgcttgat gccagcaacc 1381 cagatcctgc ccccaaagcc aagaagatca agtctcagca ccggcccacc caaagattct 1441 ggcccaactc catcgctgcg ggggtgctgc agcagcaggg cggtgcccca gggacaaacc 1501 ccgatggttc catcaacttg acaacctgc agtccctgtc ctcagacagt gccaccatgg 1561 ccatgcagca ggctatgatg gctgcacacg atgactcatt ggatgggaca agaagaagg 1621 atgaggatga gatggaagag gaggaggagg aggagctgga ggaggaggtc gacgagctgc 1681 agacgacaaa tgtcagcgac ctgggcttgg aacacagtga ctccctggag tagtcgggca 1741 gcccagatgg cactgatcac tgagcaggag aggagtgtcg ccgggaggcc ttcagggtgg 1801 gggggaaggg gacatgggca ggaagcaccg agggagttgg gccctagctt ccccaaatca 1861 gtagcttgaa gaaaggcaaa ggagacacct gttccttccc aaccaccgag cttcaatgag 1921 gaccccagcc ccacttccct ggaactgccg aggactctgt ttggcggggc cagtcgagca 1981 gcctgtgtgg aaagacagga gtgagatctg gactcaccaa atccctgagg atagatggca 2041 cccatggccc ccacccacgg aaggacttga gttgtttaca gccctgcac tgaggcagat 2101 tggtgctgtt cgcagagtag gcctttgccc ggggcagac ttagaaggaa ggggagagac 2161 aaaggggac tgagtttcat ccccagaagt ttctcagctc ctttgacaga cattcaaggg 2221 caggagggag ccccaaagca taaccagtgg ccagaggagt gggagggcct gaggcatcac 2281 atcttgcaga tcagaatggg atggaatcca ccaggctcca gctcatccct ccaaggccct 2341 gtctctgcgc acagcaacca tggacatggg agaaagggat gggagccaca gtgcccttca 2401 ctctctcctg gaaaccaact gtaagctggt gggctcaacc tgtgggaggt taagaggagt 2461 cccttctggg ttgactccaa gagccaagga gatggcagac cctgggctag gaaccatatg 2521 gaggtgactt tgaggccaca gctgtcccta ggtgatcaca gaacttagct cctttaacaa 2581 caggacaatg gttttttacc ctagatgttc ccaccttcag tgctccacgc cctccataga 2641 ccttcagaga aggtgaaacc aggttatctg ggaatctttc cagcccgcag gtcgccacgg 2701 ccatccctt gctcccagcc tggctccatc agcctccagc ttcctttctt cattctgtcc 2761 ttcagggaag gcagaagaaa cattggaaag catctagtcc agtgggaagc caggggttgg 2821 agaaggtgct acatccctct tcccatcaat atcctaaatg tggggagggg cccagagaat 2881 ggcacccaag agcctgcggg gatgcccatc ccacacaccc cacccagctg ttctaaccct 2941 gctatccaca gccctggagg aactggggct cctggaagga ggaggaggct ctccactgtc 3001 caccctaaca cataccctcc cacccacctt ccagaccccc ttggttggca ccctctcctc 3061 cggttccctc tcaccccatg gctgtgaatg acaggacagg tcacacgtgt gtttccatt 3121 gggtttaatt taatggacgt gcagtttcat ttgtaaattg tgcattggcc acctccttca 3181 gtggcaggat gtgagtggct acctggctca actggagggg acccttggg ccctctgggg 3241 cttcccctcc cccacctggt tggggtagag caaaaggatg gtcactcttc cgaggtctcc 3301 ctgaaatgaa tgtatttctc ccccaaaaga gctgatattt aatgttttaa taaggatttt 3361 tgagaaacaa ataaccttat ttataatctg ggtgatccaa tcatttttta ctccctttg 3421 atgccataca tagaggaaag tctagctttt ttggcgtgag acttttgcaa tgtgcagtgg 3481 gataaaatgc atttcctttt ctggttcgtt tttcttgtta acacgcgcac acagacacac 3541 acacacaccg ttccactcac cacctggaca ggcgtccccc agcacggaca cactggcaca
```

-continued

```
3601 caggtgccca catctcttcc tctcagcccc tccacctgcc taatgttatg caacctcctt 3661 ctgatgtatc caccaaacca gtactgaatg tggccgagac gttttcagta aatcttatta 3721 cctaccgtaa
```

One example of a nucleic acid sequence for human PRKACB is available as NCBI accession number NM_182948 (gi: 46909585). This sequence is recited below for easy reference as SEQ ID NO:154.

```
   1 acacatgcat agctcttagc ttctgtgtaa gaagttgtga gctccttctg gaaacatttg 61 cagttacatt aagtaaagtg taaatgcaca tgaatggcag cttatagaga accaccttgt 121 aaccagtata caggtacaac tacagctctt cagaaattgg aaggttttgc tagccggtta 181 tttcatagac actctaaagg tactgcacat gatcagaaaa cagctctgga aaatgacagc 241 cttcatttct ctgaacatac tgccttatgg gacagatcaa tgaaagagtt tctagccaaa 301 gccaaagaag acttttgaa aaaatgggag aatccaactc agaataatgc cggacttgaa 361 gattttgaaa ggaaaaaaac ccttggaaca ggttcatttg gaagagtcat gttggtaaaa 421 cacaaagcca ctgaacagta ttatgccatg aagatcttag ataagcagaa ggttgttaaa 481 ctgaagcaaa tagagcatac tttgaatgag aaaagaatat tacaggcagt gaattttcct 541 ttccttgttc gactggagta tgcttttaag gataattcta atttatacat ggttatggaa 601 tatgtccctg ggggtgaaat gttttcacat ctaagaagaa ttggaaggtt cagtgagccc 661 catgcacggt tctatgcagc tcagatagtg ctaacattcg agtacctcca ttcactagac 721 ctcatctaca gagatctaaa acctgaaaat ctcttaattg accatcaagg ctatatccag 781 gtcacagact ttgggtttgc caaaagagtt aaaggcagaa cttggacatt atgtggaact 841 ccagagtatt tggctccaga ataattctc agcaagggct acaataaggc agtggattgg 901 tgggcattag gagtgctaat ctatgaaatg gcagctggct atccccattt ctttgcagac 961 caaccaattc agatttatga aaagattgtt tctggaaagg tccgattccc atcccacttc 1021 agttcagatc tcaaggacct tctacggaac ctgctgcagg tggatttgac caagagattt 1081 ggaaatctaa agaatggtgt cagtgatata aaaactcaca agtggtttgc cacgacagat 1141 tggattgcta tttaccagag gaaggttgaa gctccattca taccaaagtt tagaggctct 1201 ggagatacca gcaactttga tgactatgaa gaagaagata tccgtgtctc tataacagaa 1261 aaatgtgcaa agaatttgg tgaattttaa agaggaacaa gatgacatct gagctcacac 1321 tcagtgtttg cactctgttg agagataagg tagagctgag accgtccttg ttgaagcagt 1381 tacctagttc cttcattcca acgactgagt gaggtcttta ttgccatcat cccgtgtgcg 1441 cactctgcat ccacctatgt aacaaggcac cgctaagcaa gcattgtctg tgccataaca 1501 cagtactaga ccactttctt acttctcttt gggttgtctt tctcctctcc tatatccatt 1561 tcttcctttt ccaatttcat tggttttctc taaacagtgc tccattttat tttgttggtg 1621 tttcagatgg gcagtgttat ggctacgtga tatttgaagg gaaggataag tgttgctttc 1681 agtagttatt gccaatattg ttgttggtca atggcttgaa gataaacttt ctaataatta 1741 ttatttcttt gagtagctca gacttggttt tgccaaaact cttggtaatt tttgaagata 1801 gactgtctta tcaccaagga aatttataca aattaagact aactttcttg gaattcacta 1861 ttctggcaat aaatttggt agactaatac agtacagcta gacccagaaa tttggaaggc 1921 tgtagatcag aggttctagt tccctttccc tcctttata tcctcctctc cttgagtaat 1981 gaagtgacca gcctgtgtag tgtgacaaac gtgtctcatt cagcaggaaa aactaatgat
```

```
-continued
2041 atggatcatc acccagattc tctcacttgg taccagcatt tctgtaggta ttagagaaga 2101 gttctaagtt ttctaaacct taactgttcc ttaaggattt tagccagtat tttaatagaa 2161 catgattaat gaaagtgaca aattttaaat tttctctaat agtcctcatc ataaactttt 2221 taaaggaaaa taagcaaact aaaaagaaca ttggtttaga taaatactta tactttgcaa 2281 agtcaaaaat ggcttgattt ttggaaacaa tatagaggta ttcatattta aatgagggtt 2341 tacatttgtt ttgttttgta accgttaaaa agaagttgtt tccagctaat tattgtggtg 2401 tactatattt gtgagcctag ggtaggggca ctgctgcaac ttctgctttc atcccatgcc 2461 tcatcaatga ggaaagggaa caaagtgtat aaaactgcca caattgtatt ttaattttga 2521 ggtatgatat tttcagatat ttcataattt ctaacctctg ttctctcagt aaacagaatg 2581 tctgatcgat catgcagata caatgttggt atttgagagg ttagtttttt tcctacactt 2641 ttttttgcca actgacttaa caacattgct gtcaggtgga aatttcaagc acttttgcac 2701 atttagttca gtgtttgttg agaatccatg gcttaaccca cttgttttgc tatttttttc 2761 tttgctttta attttcccca tctgatttta tctctgcgtt tcagtgacct accttaaaac 2821 aacacacgag aagagttaaa ctgggttcat tttaatgatc aatttacctg catataaaat 2881 ttatttttaa tcaagctgat cttaatgtat ataatcattc tatttgcttt attatcggtg 2941 caggtaggtc attaacacca cttctttttca tctgtaccac accctggtga aacctttgaa 3001 gacataaaaa aaacctgtct gagatgttct ttctaccaat ctatatgtct ttcggttatc 3061 aagtgtttct gcatggtaat gtcatgtaaa tgctgatatt gatttcactg gtccatctat 3121 atttaaaacg tgcaagaaaa aaataaaata ctctgctcta gcaagttttg tgtaacaaag 3181 gcatatcgtc atgttaataa atttaaaaca tcattcgtat aaaatatttt aattttcttg 3241 tatttcattt agacccaaga acatgctgac caatgtgttc tatatgtaaa ctacaaattc 3301 tatggtagct ttgttgtata ttattgtaaa attattttaa taagtcatgg ggatgacaat 3361 ttgattatta caatttagtt ttcagtaatc aaaaagattt ctatgaattc taaaaaatat 3421 ttttttctat gaaattacta gtgcccagct gtagaatcta ccttaggtag atgatcccta 3481 gacatacgtt ggttttgagg gctattcagc cattcctttt tactctctat ttaaaggccg 3541 tgagcaagct tgtcatgagc aaatatgtca agggagtcaa tttctgacca atcaagtaca 3601 ctaaattaga atattttttaa agtatgtaac attcccagtt tcagccacaa tttagccaag 3661 aataagataa aaacttgaat aagaagtaag tagcataaat cagtatttaa cctaaaatta 3721 catatttgaa acagaagata ttatgttatg ctcagtaaat aattaagaga tggcattgtg 3781 taagaaggag ccctagactg aaagtcaaga catctgaatt tcaggctgga aaactatcag 3841 tatgatctca gcctcagttc tcttgtctgt aaaatggaag aactggatta ggcagtttgt 3901 aagattcctc ctaactttca cagtcgatga caagattgtc ttttttatctg atattttgaa 3961 gggtatattg ctttgaagta agtctcaata aggcaatata ttttagggca tctttcttct 4021 tatctctgac agtgttctta aaattatttg aatatcataa gagccttggt gtctgtccta 4081 attcctttct cactcaccga tgctgaatac ccagttgaat caaactgtca acctaccaaa 4141 aacgatattg tggcttatgg gtattgctgt ctcattcttg gtatattctt gtgttaactg 4201 cccattggcc tgaaaatact cattgtaagc ctgaaaaaaa aaatctttcc cactgttttt 4261 tctgcttgtt gtaagaatca aatgaaataa tgtatgtgaa agcaccttgt aaactgtaac 4321 ctatcaatgt aaaatgttaa ggtgtgttgt tatttcatta attacttctt tgtttagaat 4381 ggaatttcct atgcactact gtagctagga aatgctgaaa caactgtgt ttttttaatta 4441 atcaataact gcaaaattaa agtaccttca atggataaga caaaaaaaaa aaaaaaaa
```

One example of a nucleic acid sequence for human PROS1 is available as NCBI accession number NM_000313 (gi: 223671900). This sequence is recited below for easy reference as SEQ ID NO:155.

```
   1 tttggaaacg tcacactgtg gaggaaaagc agcaactagg gagctggtga agaaggatgt
  61 ctcagcagtg tttactaggc ctccaacact agagcccatc cccagctcc gaaaagcttc
 121 ctggaaatgt ccttgttatc acttcccctc tcgggctggg cgctgggagc gggcggtctc
 181 ctccgccccc ggctgttccg ccgaggctcg ctgggtcgct ggcgccgccg cgcagcacgg
 241 ctcagaccga ggcgcacagg ctcgcagctc cgcggcgcct agcgctccgg tccccgccgc
 301 gacgcgccac cgtccctgcc ggcgcctccg cgcgcttcga aatgagggtc ctgggtgggc
 361 gctgcggggc gctgctggcg tgtctcctcc tagtgcttcc cgtctcagag gcaaactttt
 421 tgtcaaagca acaggcttca caagtcctgg ttaggaagcg tcgtgcaaat tctttacttg
 481 aagaaaccaa acagggtaat cttgaaagag aatgcatcga agaactgtgc aataaagaag
 541 aagccaggga ggtctttgaa aatgacccgg aaacggatta tttttatcca aaatacttag
 601 tttgtcttcg ctcttttcaa actgggttat tcactgctgc acgtcagtca actaatgctt
 661 atcctgacct aagaagctgt gtcaatgcca ttccagacca gtgtagtcct ctgccatgca
 721 atgaagatgg atatatgagc tgcaaagatg gaaaagcttc ttttacttgc acttgtaaac
 781 caggttggca aggagaaaag tgtgaatttg acataaatga atgcaaagat ccctcaaata
 841 taaatggagg ttgcagtcaa atttgtgata atacacctgg aagttaccac tgttcctgta
 901 aaaatggttt tgttatgctt tcaaataaga aagattgtaa agatgtggat gaatgctctt
 961 tgaagccaag catttgtggc acagctgtgt gcaagaacat cccaggagat tttgaatgtg
1021 aatgccccga aggctacaga tataatctca aatcaaagtc ttgtgaagat atagatgaat
1081 gctctgagaa catgtgtgct cagctttgtg tcaattaccc tggaggttac acttgctatt
1141 gtgatgggaa gaaaggattc aaacttgccc aagatcagaa gagttgtgag gttgtttcag
1201 tgtgccttcc cttgaacctt gacacaaagt atgaattact ttacttggcg gagcagtttg
1261 caggggttgt tttatattta aaatttcgtt tgccagaaat cagcagattt tcagcagaat
1321 ttgatttccg gacatatgat tcagaaggcg tgatactgta cgcagaatct atcgatcact
1381 cagcgtggct cctgattgca cttcgtggtg gaaagattga agttcagctt aagaatgaac
1441 atacatccaa aatcacaact ggaggtgatg ttattaataa tggtctatgg aatatggtgt
1501 ctgtggaaga attagaacat agtattagca ttaaaatagc taaagaagct gtgatggata
1561 taaataaacc tggaccccctt tttaagccgg aaaatggatt gctggaaacc aaagtatact
1621 ttgcaggatt ccctcggaaa gtggaaagtg aactcattaa accgattaac cctcgtctag
1681 atggatgtat acgaagctgg aatttgatga gcaaggagc ttctggaata aggaaatta
1741 ttcaagaaaa acaaaataag cattgcctgg ttactgtgga aagggctcc tactatcctg
1801 gttctggaat tgctcaattt cacatagatt ataataatgt atccagtgct gagggttggc
1861 atgtaaatgt gaccttgaat attcgtccat ccacgggcac tggtgttatg cttgccttgg
1921 tttctggtaa caacacagtg ccctttgctg tgtccttggt ggactccacc tctgaaaaat
1981 cacaggatat tctgttatct gttgaaaata ctgtaatata tcggatacag gccctaagtc
2041 tatgttccga tcaacaatct catctggaat ttagagtcaa cagaaacaat ctggagttgt
2101 cgacaccact taaaatagaa accatctccc atgaagacct tcaaagacaa cttgccgtct
2161 tggacaaagc aatgaaagca aaagtggcca catacctggg tggccttcca gatgttccat
2221 tcagtgccac accagtgaat gccttttata atggctgcat ggaagtgaat attaatggtg
2281 tacagttgga tctggatgaa gccatttcta aacataatga tattagagct cactcatgtc
```

-continued

```
2341 catcagtttg gaaaaagaca aagaattctt aaggcatctt ttctctgctt ataataccttt
2401 ttccttgtgt gtaattatac ttatgtttca ataacagctg aagggtttta tttacaatgt
2461 gcagtctttg attattttgt ggtcctttcc tgggattttt aaaaggtcct ttgtcaagga
2521 aaaaaattct gttgtgatat aaatcacagt aaagaaattc ttacttctct tgctatctaa
2581 gaatagtgaa aataacaat tttaaatttg aattttttc ctacaaatga cagtttcaat
2641 ttttgtttgt aaaactaaat tttaatttta tcatcatgaa ctagtgtcta aatacctatg
2701 ttttttttcag aaagcaagga agtaaactca aacaaaagtg cgtgtaatta aatactatta
2761 atcataggca gatactattt tgtttatgtt tttgtttttt tcctgatgaa ggcagaagag
2821 atggtggtct attaaatatg aattgaatgg agggtcctaa tgccttattt caaaacaatt
2881 cctcaggggg aacagctttg gcttcatctt tctcttgtgt ggcttcacat ttaaaccagt
2941 atctttattg aattagaaaa caagtgggac atattttcct gagagcagca caggaatctt
3001 cttcttggca gctgcagtct gtcaggatga gatatcagat taggttggat aggtggggaa
3061 atctgaagtg ggtacatttt ttaaattttg ctgtgtgggt cacacaaggt ctacattaca
3121 aaagacagaa ttcagggatg gaaaggagaa tgaacaaatg tgggagttca tagttttcct
3181 tgaatccaac ttttaattac cagagtaagt tgccaaaatg tgattgttga agtacaaaag
3241 gaactatgaa aaccagaaca aattttaaca aaaggacaac cacagaggga tatagtgaat
3301 atcgtatcat tgtaatcaaa gaagtaagga ggtaagattg ccacgtgcct gctggtactg
3361 tgatgcatt caagtggcag ttttatcacg tttgaatcta ccattcatag ccagatgtgt
3421 atcagatgtt tcactgacag ttttaacaa taaattcttt tcactgtatt ttatatcact
3481 tataataat cggtgtataa ttttaaaatg catgtgaata tctttattat atcaactgtt
3541 tgaataaaac aaaattacat aatagacatt taactcttca aaaaaaaaaa aaaaa
```

35

One example of a nucleic acid sequence for human PSD3 is available as NCBI accession number NM_015310 (gi: 117606359). This sequence is recited below for easy reference as SEQ ID NO:156.

```
  1 aacaaagagc acgcggcgct ggccgccggc actcgcgccc tgaggctgcg gccccggagc
 61 gcccggcggc ggtttcggcg cgcggccggg ctggcgatgg aagatggaag gaaggagcgc
121 agcggcagag acatttgttt gggtgaacaa tgcatctgca cattcccaga gtgttgccaa
181 ggccaaatat gaattttat ttggcagatc tgaagggaaa gctccagata ctagtgatca
241 tggaggaagc actttactcc caccaaatgt cacaaatgaa tttccagaat atgggaccat
301 ggaggaaggt ggagaaggcc taagggcttc tctggaattt gatggtgagg ctctgccatg
361 ccacccacaa gagcagcagg gtgtccagcc tcttactggc tgccactctg ggctcgacag
421 tgttacagaa ggaccaaaag atgtcagaga ggccccctct caaagtcatc tcaaggaaca
481 aagtttacag cccattgact ctttgatttc agctctgaaa gccacagaag ccagaatcat
541 ttccggaaca ttacaggcta caaaggtact ggaccaagat gctgtttcta gttttttcagt
601 tcagcaggtg gaaaaagagc tggacactgc cagtcgtaaa acacagagag tcaacaaaac
661 gctccctgct ggccaaaaaa atttaccaga aatacctctt tcagctgaag taacaacgga
721 ggaaagtttt tatttgagca tccagaaaga tctcaccgcg ctgttaactg gagacactca
781 ggcagagatt tcccagataa tgaataatgg gaggaaaggg gctgtctgtg tgcaggagcc
841 atcttgtcct ttggcctccc tcgggagctc agcagtgacc tgccactctg caggcagtgt
901 tggtttcttg aaagagcaga ggtctgctct tgggagagag cacccagggg gatgtgatcg
```

```
-continued
 961 aagcagctcc atgggacgcc caggccgggt caaacatgtg gaatttcaag gagtggaaat
1021 actgtggaca ggaggagaca agagagagac ccagcatcct atagattttg agacatcact
1081 gcaaagaaca gcctctcctg acagcaaaga gtcttccaaa gtgccacgcc atctcatctc
1141 atcagctggt ttgtgtaatt caagtagttt aactgagaat gtttgggatg aatcctggaa
1201 agctccttca gagaggcctg cactagctc ggggacattt tcccctgtgc gtcttgatga
1261 gagtggagag gatgaagtct tcctacagga aaacaaacag catcttgaga agacacctaa
1321 accagagaga gacagggaaa ggatcagcga acaagaggag cacgttaagg gggaagatga
1381 agacatcctt gggcctggat atacggagga ctccaccgac gtgtacagct cccagtttga
1441 aaccattttg gacaacactt ctttatacta cagtgcagag tccctggaga cattatactc
1501 agagcctgat agctatttta gctttgaaat gcccctcact ccaatgatac aacagcgcat
1561 taaagaaggt ggtcagttct tggagaggac atcaggggga ggacatcagg atatcctgag
1621 tgtgtctgca gatggtggca tcgtgatggg ctattctagt ggcgtcacca atgggctgaa
1681 tgatgccagc gactccatct acacgaaagg cacccccgag attgctttct ggggaagcaa
1741 tgctggggtg aaaacaacac ggctagaagc tcattctgaa atggggagca ctgaaatttt
1801 ggaaaaggag accccagaaa atctcagtaa tggtaccagc agcaatgtgg aagcagccaa
1861 aaggttggcc aaacgccttt atcagctgga cagattcaaa agatcagatg ttgcaaaaca
1921 ccttggcaag aacaacgaat ttagcaaact agttgcagaa gaatatctga gttttttga
1981 ttttacagga atgacgctgg atcagtcact caggtatttc tttaaagcat tctctcttgt
2041 gggagaaact caagaacgag agagagtttt aatacacttc tccaatagat attttttattg
2101 taacccagat accattgctt cacaagatgg agtccattgc cttacctgtg caataatgct
2161 tcttaatacc gatctacatg gccacaatat tggaaagaag atgacctgtc aggagttcat
2221 tgcaaatctg caagggtaa atgagggtgt tgatttctcc aaggatctgc tgaaagctct
2281 gtacaactca atcaagaatg agaagcttga atgggcagta gatgatgaag agaaaaaaaa
2341 gtctccctca gaaagtactg aggagaaagc taacggaaca catccaaaga ccatcagtcg
2401 tattggaagt actactaacc cattttttgga cattcctcat gatccaaatg ctgctgtgta
2461 caaaagtgga ttcttggctc ggaaaattca tgcagatatg gatggaaaga agactccaag
2521 aggaaaacga ggatggaaaa ccttttatgc tgtactgaag ggaacagttc tttacttgca
2581 aaaggatgaa tacaagccag aaaaggcctt gtctgaagag gacttgaaaa acgctgtgag
2641 tgtgcaccac gcattggcat ccaaggccac ggactatgag aagaaaccaa acgtgtttaa
2701 acttaaaact gccgactgga gggtcttgct ttttcaaact cagagcccag aggaaatgca
2761 agggtggata aacaaaatca attgtgtggc agctgtattt tctgcaccac catttccagc
2821 agcaatcggc tctcagaaga agtttagccg cccacttctg cctgccacta caacaaaact
2881 gtctcaggag gagcaactga agtcacatga aagtaagctg aagcagatca ccaccgagct
2941 ggccgagcac cgctcatatc cccccgacaa gaaggtcaaa gccaaggacg tcgatgagta
3001 caaactgaaa gaccactatc tggagtttga gaaacccgc tatgaaatgt atgtcagcat
3061 tctcaaggaa ggaggcaaag agctactgag taacgatgaa agcgaggctg caggactgaa
3121 gaagtcgcac tcgagtcctt cgctgaaccc ggatacttct ccaatcactg ccaaagtcaa
3181 gcgtaacgtg tcagagagga aggatcaccg acctgaaaca ccaagcatta agcaaaaagt
3241 tacttagagt ccatctgcgg ccaggaagtg ctggtcatgg agcaaaatag ggttttcaa
3301 gatctttctg gtaatccgtg aatatattta aaaaaaaaa gtctgtgaca aaacggtgca
```

```
3361 ttagtaattt tttctattgt atattttgt tagtttctgt acagattgtc tttgctcttg
3421 atttcttttg ctttgatgat ttttgcaact tgatagctaa tgcacctttt ctgtgaggag
3481 gagggatcg tgatttcaga atgaattatg tatcccttct cttttggttt tctcttgttt
3541 gcagtctgct cagttgtttt atgtattctc atatcaactg ttaaacttt ttttaaggtt
3601 aaagaattta atccattgtg aaacacttaa ctggacaaac tgtagtttta gtaaattcta
3661 gctggagtta atatacgcct ttatatgtga aatcttgccc agtcacagag gtagaattga
3721 gcactcacag atgctccagt aagaatcaca gtgctgggaa tctagttgct ccaatatgag
3781 gcagcttcat gtgcagctta gcacttgttg ttgagatcgg accctgctgg aagcagggaa
3841 aagaagcgtg aagatcgtag gattgagaac ttagggaagc acattagctt gcttgaagtg
3901 ctgattccat ttcagccaag caagggaaag aggaagtgga gtcattttgc ctttgaaggc
3961 tgaggaaaga ttgatacccca gttaattttg tttgctaaag gatggggggca ataatcggcc
4021 cttgaggagc tgcagcagta ggcatgtgct cagtctgcag gaattgttac ctcactccca
4081 cagggtctag actagaaatc catcatctct atcgttgata tccttccatc caggaataga
4141 tttttcttac tctacatatg tgtgtgtgcg tgcgtgtgtg tgcgtgtgtg ggcatggggt
4201 tgtgtcctgg ttgtgatatt gaggtcttcc ttcctaacaa attaatacta aaatgaaaca
4261 gcttttcttg tgtccttaag acaaaataag gaaggaaaac gtagctgcag ttgtccacga
4321 tggatattgg ttctttaaaa tatatctgaa agtagtagtc agaatgaatt atggttggaa
4381 aactgaggaa tcttctggtt gcaggtgcaa agtgactttg tttattcttg tctcagtctc
4441 cttgatagcc acttcactct gctactactc aactttctcc taaaaatact tcatctattt
4501 tcagtccttt ctttctgtct actcaaaatg gttctattaa ctttgcagtc atgagcttgt
4561 tccagttaca gtcccttga agttcagggt gataaacaga atattcttct gtagaggaag
4621 agaaaggagt gaaagtttag cccactgaga cctagagctt tgtgatttcc taaccttgaa
4681 actctgtaat ccctaaagtt aaaatctccg caagtggcac aacttcagaa ctaatagtat
4741 cactttgatt tttctttttc ctcccttaga aagtttctct agttctatag tttatttgtt
4801 gaaggtacta tgaccaaaga atcagctgct ctacaggaat agcatggttc cagtgaatta
4861 gagaaaacct gctgtaaagc catggtagtg tctaagtggt atgttattat gatgtactag
4921 catttattta cagaattatt tattaacgtt tacttccttc ccctctgtaa atgtccatga
4981 ctattgccca gagaaggctt acccctctct agggttgcag ttgctttctt tgtaataagt
5041 attttgccac acctgtaaaa aaaaaaacct cacttttaac tctctgcctt gtttgggtaa
5101 aggcagtaac taagtttatg tttcagaact gcaaaacaaa caggatagtt accaatatgg
5161 cccatgtatc agattgattt ttgtagcctc tcactgaatc caacatatcc acaagcaagt
5221 tatctgtctt tctacctgat aatctaaatt atcaggatat ttgttttctg cctaaatgtt
5281 tatactaagc cgaggggaga gaggtaccta gaccatgtca tctacaagct tcagtaacta
5341 aagaaaaagg aacttccctg agtggcttga atgtgtttgc ccacagtcta tatctatgta
5401 tatagaatgt ctgtatgtat tttacttatt taatatacat tgaatggtac cttgctacag
5461 tatttctgac atttagagta gtgttgaaat actcggctag catcagcacc actatagcac
5521 tgtccgtgtc atatgagtca ctaatattaa ctccagggac ttctggatag gctaatagat
5581 cattggatac gaagggctct tttgaagctt cagtatacca tgttttgcata gtttatcttt
5641 aaaaacaact ttaaaggttc ttttgtgagc caggatctca gactgccgta gcatgatgct
5701 gtccatcttt agcgcatggg ctgagaacac ctcttccctg aggcttctga aggttgctgt
5761 ctgtcatgag tgcatgaagg aggccaagag tttatgctat gggaggaaac agtcactgat
```

-continued

```
5821  ttgcctagat tctgagagtc tggcccatag ccaaccacat tttcctttgg gataatttat
5881  ttcctgtggc atctagccag aagaaattga ggatgtttcc tttcacagct gctccaagcc
5941  tgttgcccaa ttcacggtac aagggagcac cccttcsctt tcctctgaag gtacgccacc
6001  cacctccgtc gcccacctca gcgcccagga gcttgggac ttccttccat atgataaatc
6061  attcttcttc acgtcaatac acttcatatt aatttctagt acagaaaatc ttgacagcta
6121  tcagaatgcc ttggtcatag tgttgttgca aaattgacca tacaggtggc ccatgtataa
6181  aatctgaatt ttaggggttt gtccccacct cgcatgctgg cttttacagg gaggtgtctg
6241  ggattcctca ttagcaatca aaacttaatt actgggatgc agagtcctta ctttatcgcc
6301  agcccgtagg catttctgaa gtgcactttt ttgaaacatc attttgctaa ctctcagcag
6361  tgtctaatta aactgagcaa tacttttgtg aattttaatt aatctcagca aaaccatgat
6421  gggagagagt cctctgatgg aaatgtagtc cctggattat gtgtaacctt tttattcctc
6481  ttagatgcag aggatagaaa gcattttttg gtgcagtggt cttgtggcaa acacaagacc
6541  ctctatgcgt ctccaactgt tatcctaatc tagaaaatga ggactggccc ctgggcaaaa
6601  gtgacatgag gaatttactc tggaagagga aaatctgggt ggctttccaa ggctaagata
6661  ggtttgtatt tcaccctgtg gccaagctac agaacttctg agattgtgga agaattttttg
6721  caaccagcag ggaaagaggc ctcttactgc ctaaacacaa agttacactg agctttttcta
6781  ctgtcctttg cctattgctc cctctatcat gtaaagatct gggaaggatg agaggcaggg
6841  cctgcttgtc atgagctgca ctctttttctt tttaactaat cattgacaat tggaagaaaa
6901  ttgacgttaa agaagtttct ccattgtctt actaacaaaa ccttttgggt ttcattaatt
6961  gtccttgaaa ttgagttcct ttggcatttt tccttgcagt catcagttaa gcatgttgca
7021  tcctgaattc acagaagttt agctttgcag gtttgaatct ctgtaattta actcccgtgg
7081  acttggtcga gttttcagca ggttgggagc cacctctctt catttcagca gtgagtcatc
7141  ccttgacttt tcaaatgaca gaattttttc caattgtaaa attagcactg taaaacaaag
7201  aaccaaagtg gcatcctaag agttgttaaa cctgaagtct agtttatgag gaattgtcca
7261  agttggagtt taaatagtat ctgcttttgt ctcaaagcat ctaagttatt ctgacagaaa
7321  atggtaagtc agctttgcag gcagatgcgc ctctgggcct cctaccttgc tccacagctt
7381  tctggccatc ttgtctccca ggccatgcca ctgctctgcc acatgtcagc aaatttctttt
7441  ccaccagtct tatagcatct tacatgatca aatcatcaca gaataacccc gtgatagatt
7501  attgatagca atagagaggg gctttgtcac tgattttttct ctcagattcc ttttccatct
7561  ctcatccata aaggaaggac tgaaatccaa aggcattctc cttttgtacc tacagtatcc
7621  agaacccacg tgggcagcct tctgcttatg acaataattg gcccattgca tgcagagaga
7681  atgtcttcat agagagaatg tcattaaata cttgaatctg catgacagtt tgacttgaat
7741  gcaacagcag gaaaattttg caagttacat aattgtatat acagtaggtt ttcttaagtc
7801  tcttcggttc atcctttgta atttgtgtgt gtatctgtag tattgcaggc ttttggagac
7861  tattcttaca ggcagtatgc cagtcatcaa agaaaatgct gtcacctgcc attgttgtat
7921  ttgtgggtat ttatagttgt atgtatgtaa atgcatcagt gtgtagattg catatcagtg
7981  tatggtacat gtacatcaaa attattttttg tccttaatca gtgtgatatg aaaagcaagt
8041  acaacctcat aggactgatt atataatgaa gttgttgaga gtatatatag tggtattgtt
8101  ttattaaact taaactcaaa taatattttg attaaaattt ttaataagac tttatgctag
8161  aaaattcttt gagctttgaa tcaccagggc aaaaatgact ttcaactaac cttgtgaatc
```

-continued

```
8221  ttttgcagtg tactgtgtgc aataccaagg gcatagctcc ctgtaatttg ggaaatacag
8281  aaagaaaaga aaaaaaaaaa aaaaggcagc ctgtgcagtc ttagtaactt tagtattaag
8341  agcacttaaa gtcaaactga caattttggg cttattacaa aatgtgatgc tttaaagcac
8401  acgttcttta ttgttgttgt aattagtcca taaaaaatat agctttcgga agaattaagt
8461  acccaccata tcatttatgt atttgtgtat gttttacggg agatcaaacc actctcgtgg
8521  tgccgcatcc gtactcgctt gacttggaag aaatatcaca agcactaaag tatatcaggg
8581  catcccagga ttgggtactg tatcctaggt ttgcagttgc agaaattagc atctagtgtc
8641  acaggtaaaa gaatttcagg accaggttta aactttattt taaatatttt tatacttagg
8701  tctctttttc ctgcctctcc ccaaagaaga gccactggcc ttagttgttt gagcttactg
8761  cttatattat agagtgtaaa taggtaacta gagactaaaa ttttattaac cagcatgttt
8821  ggtatattta aagcagtgac tgagtgtgtt tgagtgagtg gctgagtgca gtgtcttttg
8881  tttaaacaca ctgcctcgtg tctttgtagc tgattcagag agtttgaatt gtggggtggg
8941  agactaactt cagctccagg ctgcagtaat gtgttggtag ttacacttga ggcattttt
9001  tgttgttgtt aattaactct atagtctcaa actattttg caaatatatc attttccta
9061  attggttctt gacgtgcagt ggactggctc tgtgaatgat tggcagggtc ttagttttgc
9121  gagagtattt ccttctaaga attattgtga tctgcagaaa cagccatttg attcaaaaat
9181  catgtagaaa aggagtagga gaagcaaaac gtttcatttt tgggccttaa ccatttgaaa
9241  tgtttggact ttaaacataa agccatggag tttataaagc caagtaacca tttgatatgg
9301  ataataatat ctactctaga gagagtatat atatgcacat tgatttttaa tgctgttaag
9361  atacttttgt aaaactgtag gaacaagagt aattagacca aattgaagct taggggacag
9421  taaagtggtt gctttccatt tagggtaacc atgcatgtgg ttagtcctct cctcctgaga
9481  ttcagaacca gttgactgtc cccttaggtg tataaggaga aaagttgaca tgtctgggac
9541  ctctgacatg tgtacacatg cttgcacaca tgcacacaca gtgaatgttt taagttatac
9601  aaacataaga ccttaagatg caaagagcca gaatattcta aagaggtgat gaacagaggg
9661  ggtggaaact gcatcacaga tgttttccaa gggccagggt ggaatctgag ctctagtgtc
9721  tgactttgag atgcattata tttttaacac ataaatgagg ggatccatat cacattcttt
9781  cttgtggacc accaaattga aggctttctt gtaattcaca agcagcagct ctccagcatc
9841  tctccgtagc ctgggtgaag tcccagaagc tggtgtgcat cattttccaa ggtggcagag
9901  ctgcttgctc tgcagatcat tcctttgaga gaggagtaca agtgaagaaa caaggaggca
9961  cttcctgtag gagcactgat gtgccttgtc cacactcccc tctgagcttt actggtaaga
10021 gagctccgac tgaacatgct gagcagttga gcacttttcc atcagcaaca acagcgagga
10081 tggaaatgga aaggaaccga actaaaatgc atttcccttt gcagggcaga gagctaagct
10141 cttaggaata gtgttataga aataagcacc ctaacttcaa ttcctgaaaa tgttggttaa
10201 tggagagaat tttggagttt cacttaatat tttcccatcg gtcgccataa ataagtcttc
10261 aggcgctcct agaagagtcc cagcccaagg ctcgattaag gaccacactg caggtctgag
10321 gctcactgct ctgagtcctg aacaccagag ccctgcagag agtggtgata acacatcatc
10381 tctgcaaaga ggaacctctc ccccggccgc cacttcactc aggcttctac tgagcagcaa
10441 ggacagcctg ggtttcaaat gccacttccc ctgctttagg gatccaggtg tcctgatagc
10501 gtgaccctgc tgaggcaagg tatcaactcc gagagtgact gagtcactga gcgtggcaca
10561 tgaacaaacg tcatgacaaa gattctctga gtgaagttaa caccacgtat tttacctttg
10621 caaaaaacaa actggcaccc tgagttctaa ctacggacgg acgatatctt tgcctccaca
```

```
10681 cccagattcc tggaaatggc taacgtttcc tttctagggg aagggtcgag gaatactcaa
10741 gtgctagctt agcagctttg ttcagtccag atcagagctg ttaggtaaag gcctaaccac
10801 ctccctgcag tctcttatat ctcaagcttt aggaacccat ttctaaatgt acactagcgg
10861 agaatttata ttgtcagcct tgattaccat aggacaggca gaaaggcgat aatttgtatc
10921 ttttaatata aaagaagctt ttaactttc cagcctatta taataactga gttatattca
10981 ctgtggctca aactaattgg cattgtggaa catttcttta ccttcaaagt tttctccacc
11041 aatcatttca gttctattgc agtcctggtg ccatatgtcc cctgcaaatt gtgaaagtaa
11101 ttagtgacaa aatagcagcc tgctcctttt caatggcgaa actgtcggca ttagcagttt
11161 tgggtaagct ggcggtacta taacacgtac tggaaacctg ttcctcatca ccacctacca
11221 gattctgaaa atgccgtctt ctagaaaacg atggcgtttg tggtggtctt cttttgaaag
11281 gaacagtaat ttgtgtggat attgttaaag tgtttaaaga atattttgac aattaagttt
11341 acattttaca attgctttat tttttattaa aatagttgta tataaatatt accctatttc
11401 actgttgttc aagtaaatct aaaccttgta gacaagtgag tcatctgata tgtatagaag
11461 ctgtgatata tagagtacat ttattgtgta aatgtttatg aatataattg ttcctgtgtt
11521 tttataagtt ggggatattt tgttgtttta cggcaacaaa atttattgca tttaaatggt
11581 ttttatgtaa tagaaatcac gcaaaatagt gaaggattta aaatatgtat atgatacatg
11641 taaatgtaca aactttagaa agaaataaat ccaacaaatt tcaatca
```

One example of a nucleic acid sequence for human QPCT is available as NCBI accession number NM_012413 (gi:68216098). This sequence is recited below for easy reference as SEQ ID NO:157.

```
   1 ggcgatggga aggcgggcgc agtcgaccca agggtggaga agagggaagg cgaaggacgc
  61 gcgttcccgg gctcgtgacc gccagcggcc cggggaaccc gctcccagac agactcggag
 121 agatggcagg cggaagacac cggcgcgtcg tgggcaccct ccacctgctg ctgctggtgg
 181 ccgccctgcc ctgggcatcc aggggggtca gtccgagtgc ctcagcctgg ccagaggaga
 241 agaattacca ccagccagcc attttgaatt catcggctct tcggcaaatt gcagaaggca
 301 ccagtatctc tgaaatgtgg caaaatgact tacagccatt gctgatagag cgatacccgg
 361 gatcccctgg aagctatgct gctcgtcagc acatcatgca gcgaattcag aggcttcagg
 421 ctgactgggt cttggaaata gacaccttct tgagtcagac accctatggg taccggtctt
 481 tctcaaatat catcagcacc ctcaatccca ctgctaaacg catttggtc ctcgcctgcc
 541 actatgactc caagtatttt tcccactgga acaacagagt gtttgtagga gccactgatt
 601 cagccgtgcc atgtgcaatg atgttggaac ttgctcgtgc cttagacaag aaactccttt
 661 ccttaaagac tgtttcagac tccaagccag atttgtcact ccagctgatc ttctttgatg
 721 gtgaagaggc ttttcttcac tggtctcctc aagattctct ctatgggtct cgacacttag
 781 ctgcaaagat ggcatcgacc ccgcacccac tggagcgag aggcaccagc caactgcatg
 841 gcatggattt attggtctta ttggatttga ttggagctcc aaacccaacg tttcccaatt
 901 tttttccaaa ctcagccagg tggttcgaaa gacttcaagc aattgaacat gaacttcatg
 961 aattgggttt gctcaaggat cactctttgg aggggcggta tttccagaat tacagttatg
1021 gaggtgtgat tcaggatgac catattccat tttaagaag aggtgttcca gttctgcatc
1081 tgataccgtc tcctttccct gaagtctggc acaccatgga tgacaatgaa gaaaatttgg
```

-continued

```
1141 atgaatcaac cattgacaat ctaaacaaaa tcctacaagt ctttgtgttg gaatatcttc
1201 atttgtaata ctctgattta gtttaggata attggttcta gaattgaatt caaaagtcaa
1261 ggcatcattt aaaataatct gatttcagac aaatgctgtg tggaaacatc tatcctatag
1321 atcatcctat tcttatgtgt ctttggttat cagatcaatt acagaataat tgtgttgtga
1381 tattgtgtcc taaattgctc attaattttt atttacagat tgaaaagag ggaccgtgta
1441 aagaaaatgg aaaataaata tctttcaaag actcttttag ataaacacga tgaggcaaaa
1501 tcaggttcat tcattcaacg atagtttctc aacagtactt aaatagcggt tggaaaacgt
1561 agccttcatt ttatgatttt ttcatatgtg gaaatctatt acatgtaata caaaacaaac
1621 atgtagtttg aaggcggtca gatttctttg agaaatcttt gtagagttaa ttttatggaa
1681 attaaaatca gaattaaatg ctaaaaaaaa aaaaaaaa
```

One example of a nucleic acid sequence for human RAB27A is available as NCBI accession number NM_004580 (gi: 34485707). This sequence is recited below for easy reference as SEQ ID NO:158.

```
   1 gtttttgaaag ttgatggagc gaactgcttt tccaaagact cttttgaaaa acttttaag
  61 taggccattc tgactttaac atttctcttt gtcttaacat tagacaaaaa gtaaccttcc
 121 tgaagaggac atgtgattgg aagttgtcaa ttgttgaagc attggtaact ccagtctcta
 181 acgttttaga aaatcataac aagcggttct ctaccctgta aaggtgaact actgagttct
 241 tcattatgtc tgatggagat tatgattacc tcatcaagtt tttagctttg ggagactctg
 301 gtgtagggaa gaccagtgta ctttaccaat atacagatgg taaatttaac tccaaattta
 361 tcacaacagt gggcattgat ttcagggaaa aaagagtggt gtacagagcc agtgggccgg
 421 atggagccac tggcagaggc cagagaatcc acctgcagtt atgggacaca gcagggcagg
 481 agaggtttcg tagcttaacg acagcgttct tcagagatgc tatgggtttt cttctacttt
 541 ttgatctgac aaatgagcaa gtttcctca atgtcagaaa ctggataagc cagctacaga
 601 tgcatgcata ttgtgaaaac ccagatatag tgctgtgtgg aaacaagagt gatctggagg
 661 accagagagt agtgaaagag gaggaagcca tagcactcgc agagaaatat ggaatcccct
 721 actttgaaac tagtgctgcc aatgggacaa acataagcca agcaattgag atgcttctgg
 781 acctgataat gaagcgaatg gaacggtgtg tggacaagtc ctggattcct gaaggagtgg
 841 tgcgatcaaa tggtcatgcc tctacggatc agttaagtga agaaaaggag aaaggggcat
 901 gtggctgttg agaagtcaag taagcgacat agtagttcag gtggcccatg cctgggatct
 961 tctctatgat tgatacatgg cacagtgaga gattaatggg cattgtgtac aaattgcttc
1021 tcaccatccc cattagacct acgaataaag catccggttc taaaattaat ttgttgcagc
1081 tttgtaaata tttctttaag attcagcctg agagttagga gaaatatttc agagccaaaa
1141 gtgccttata caaccttagc ctattatagt aaatcattca aggattcaga attttgcagt
1201 cacagaagag tgtatttatt atgtagaatg aatgagggta ctgtcacctg ccttaatgta
1261 ggtaggccca gagtcttaca tttaagatct tacatgcagt tataaaaccg ccacagtctt
1321 caatccagat ttgaagactc atgccatagg tgacattcta aaataccatt aaagccactt
1381 aaatgttaaa taagaatata catgcacatc agctcaatgt ctttgagtat taattttatg
1441 taagcattct atttaacatg aatataggac aaatcatggc tatatctata gaccttggat
1501 aaactggatt gaccaattat acactcacgg tgactttttt attggtggga aggggattgg
1561 ggtggggcag gctggcttaa tgtaatatga gcaaccaaag tgggacttct gtctccccgc
1621 tatattccca ttgctctgaa tggttgattg aagggtcagg gaactagatt ttatggcttt
```

-continued

```
1681 agttcactgt gattgtacat ttatacttgg cctatgtgct ggccgcacct gaacatagct 1741 ggtgcttatg ccgagttatt tgcgatgagt aaatatttag tttcttttc ttcatattta 1801 taatgttgat ctggcatcct caggctgcag ctttattagc ttataactta ctcatctcta 1861 tctttaccag caggctctgt attgttgata tttgcaactt gttttgcttt tccattggtg 1921 gaattgaaat aattagtttt taattacata agatgcctgt ttgctatttg gtggaagata 1981 gatgttcata ttgaagcagt cacatttgta ctgtagttca ataaaagaaa aatgaagtat 2041 tctgtagcct atatttttca tagagctcat gagcatttac tgtacttgct gggtcttgcc 2101 aagatcattt attccgctgc attgccaaag tgtcttcata ccaaattaaa ggtggtttta 2161 atatatgttt catggaagtt gtttataaaa ttcaaaggta tttcatttag gtgaaaagtc 2221 ttatttatta aagtggtttg aataaagtag atcaaaactt ccagagatct taatggctat 2281 ataggaagaa atatcactca ccataattta aataaagaat aaaaatactt gtattttgtg 2341 gtggcaaatg tttggtagaa ctgtaattag aaaaatacaa gtatatttgc gtgatggtta 2401 cactagaagc ccagacttta cgactacaca atatattcat gtatctaaac tgtacttgta 2461 cccctaaat ttattttaa aaaaggaaaa ataaaagtat catgaaaaaa cctattttt 2521 tttccactgt ccttccacta ctcccataac aaacttatcc atggttggta aaattttaca 2581 tatttctatc cttgaaatga aggcttcttt taaattccaa agaagtcatg gaggcctgtg 2641 catttgaatt gtatatgcta gtgaggaaaa gatttagaca tttcaagagc agggttggcc 2701 aggcgcggtg gctcacacct gtaatcccag cactttggga ggccgaggag ggcggatcac 2761 gaggtcagga gatcgagacc atcctggcta acacagtgaa accccatctc tactaaaaaa 2821 aaaa
```

One example of a nucleic acid sequence for human RXRG is available as NCBI accession number NM_006917 (gi: 58331205). This sequence is recited below for easy reference as SEQ ID NO:159.

```
  1 gtggcaagag tagcggtgac ggcggcggcg gcggcggcgg cagcattatg cgtgattact 61 gacaggcacc agctgctgcc gccacagccg tctcaaacgc actatgtgga ctctccgatc 121 tagaggcaga ttcctgacta atcccagagg gctggcccag cctgtgctcc ccgggctgct 181 aggaagcgat gaccactctt gttagcccaa gttgaagaaa gccgggctgt gcctgggagc 241 cgagagaggc ggtaatattt agaagctgca caggagagga acatgaactg acgagtaaac 301 atgtatggaa attattctca cttcatgaag tttcccgcag gctatggagg ctcccctggc 361 cacactggct ctacatccat gagcccatca gcagccttgt ccacagggaa gccaatggac 421 agccacccca gctacacaga taccccagtg agtgcccac ggactctgag tgcagtgggg 481 accccctca atgccctggg ctctccatat cgagtcatca cctctgccat gggcccaccc 541 tcaggagcac ttgcagcgcc tccaggaatc aacttggttg ccccacccag ctctcagcta 601 aatgtggtca acagtgtcag cagttcagag acatcaagc ccttaccagg gcttcccggg 661 attggaaaca tgaactaccc atccaccagc cccggatctc tggttaaaca catctgtgcc 721 atctgtggag acagatcctc aggaaagcac tacggggtat acagttgtga aggctgcaaa 781 gggttcttca agaggacgat aaggaaggac ctcatctaca cgtgtcggga taataaagac 841 tgcctcattg acaagcgtca gcgcaaccgc tgccagtact gtcgctatca gaagtgcctt 901 gtcatgggca tgaagaggga agctgtgcaa gaagaaagac agaggagccg agagcgagct 961 gagagtgagg cagaatgtgc taccagtggt catgaagaca tgcctgtgga gaggattcta
```

-continued

```
1021 gaagctgaac ttgctgttga accaaagaca gaatcctatg gtgacatgaa tatggagaac
1081 tcgacaaatg accctgttac caacatatgt catgctgctg acaagcagct tttcaccctc
1141 gttgaatggg ccaagcgtat tccccacttc tctgacctca ccttggagga ccaggtcatt
1201 ttgcttcggg cagggtggaa tgaattgctg attgcctctt tctcccaccg ctcagtttcc
1261 gtgcaggatg gcatccttct ggccacgggt ttacatgtcc accggagcag tgcccacagt
1321 gctgggtcg gctccatctt tgacagagtc ctaactgagc tggtttccaa aatgaaagac
1381 atgcagatgg acaagtcgga actgggatgc ctgcgagcca ttgtactctt taacccagat
1441 gccaagggcc tgtccaaccc ctctgaggtg gagactctgc gagagaaggt ttatgccacc
1501 cttgaggcct acaccaagca gaagtatccg gaacagccag gcaggtttgc caagctgctg
1561 ctgcgcctcc cagctctgcg ttccattggc ttgaaatgcc tggagcacct cttcttcttc
1621 aagctcatcg gggacacccc cattgacacc ttcctcatgg agatgttgga accccgctg
1681 cagatcacct gagccccacc agccacagcc tccccaccca ggatgacccc tgggcaggtg
1741 tgtgtggacc cccaccctgc actttcctcc acctcccacc ctgaccccct tcctgtcccc
1801 aaaatgtgat gcttataata aagaaaacct ttctacacat gaaaaaaaaa aaaaaa
```

One example of a nucleic acid sequence for human SDC4 is available as NCBI accession number NM_002999 (gi: 38201674). This sequence is recited below for easy reference as SEQ ID NO:160.

```
   1 actcgccgca gcctgcgcgc cttctccagt ccgcggtgcc atggccccg cccgtctgtt
  61 cgcgctgctg ctgttcttcg taggcggagt cgccgagtcg atccgagaga ctgaggtcat
 121 cgaccccag gacctcctag aaggccgata cttctccgga gccctaccag acgatgagga
 181 tgtagtgggg cccgggcagg aatctgatga cttttgagctg tctggctctg gagatctgga
 241 tgacttggaa gactccatga tcggccctga agttgtccat cccttggtgc ctctagataa
 301 ccatatccct gagagggcag ggtctgggag ccaagtcccc accgaaccca agaaactaga
 361 ggagaatgag gttatcccca agagaatctc acccgttgaa gagagtgagg atgtgtccaa
 421 caaggtgtca atgtccagca ctgtgcaggg cagcaacatc tttgagagaa cggaggtcct
 481 ggcagctctg attgtgggtg gcatcgtggg catcctcttt gccgtcttcc tgatcctact
 541 gctcatgtac cgtatgaaga gaaggatga aggcagctat gacctgggca agaaacccat
 601 ctacaagaaa gcccccacca atgagttcta cgcgtgaagc ttgcttgtgg gcactggctt
 661 ggactttagc ggggagggaa gccagggat tttgaaggg ggacattagg gtagggtgag
 721 gtcaacctaa tactgacttg tcagtatctc cagctctgat tacctttgaa gtgttcagaa
 781 gagacattgt cttctactgt tctgccaggt tcttcttgag ctttgggcct cagttgccct
 841 ggcagaaaaa tggattcaac ttggccttc tgaaggcaag actgggattg gatcacttct
 901 taaacttcca gttaagaatc taggtccgcc ctcaagccca tactgaccat gcctcatcca
 961 gagctcctct gaagccaggg ggctaacgga tgttgtgtgg agtcctggct ggaggtcctc
1021 ccccagtggc cttcctccct tcctttcaca gccggtctct ctgccaggaa atgggggaag
1081 gaactagaac cacctgcacc ttgagatgtt tctgtaaatg ggtacttgtg atcacactac
1141 gggaatctct gtggtatata cctggggcca ttctaggctc tttcaagtga cttttggaaa
1201 tcaaccttt ttatttgggg gggaggatgg ggaaaagagc tgagagttta tgctgaaatg
1261 gatttataga atatttgtaa atctattttt agtgtttgtt cgtttttta actgttcatt
1321 cctttgtgca gagtgtatat ctctgcctgg gcaagagtgt ggaggtgccg aggtgtcttc
```

-continued

```
1381 attctctcgc acatttccac agcacctgct aagtttgtat ttaatggttt ttgttttttgt
1441 ttttgtttgt ttcttgaaaa tgagagaaga gccggagaga tgattttttat taattttttt
1501 tttttttttt ttttttttact atttatagct ttagataggg cctcccttcc cctcttcttt
1561 ctttgttctc tttcattaaa cccctttcccc agttttttttt ttatactttta aaccccgctc
1621 ctcatggcct tggcccttttc tgaagctgct tcctcttata aaatagcttt tgccgaaaca
1681 tagttttttt ttagcagatc ccaaaatata atgaagggga tggtgggata tttgtgtctg
1741 tgttcttata atatattatt attcttcctt ggttctagaa aaatagataa atatatttttt
1801 ttcaggaaat agtgtggtgt ttccagtttg atgttgctgg gtggttgagt gagtgaattt
1861 tcatgtggct gggtgggttt ttgccttttt ctcttgccct gttcctggtg ccttctgatg
1921 gggctggaat agttgaggtg gatggttcta ccctttctgc cttctgtttg ggacccagct
1981 ggtgttcttt ggtttgcttt cttcaggctc tagggctgtg ctatccaata cagtaaccac
2041 atgcggctgt ttaaagttaa gccaattaaa atcacataag attaaaaatt ccttcctcag
2101 ttgcactaac cacgtttcta gaggcgtcac tgtatgtagt tcatggctac tgtactgaca
2161 gcgagagcat gtccatctgt tggacagcac tattctagag aactaaactg gcttaacgag
2221 tcacagcctc agctgtgctg ggacgaccct tgtctccctg ggtaggggg ggggaatggg
2281 ggagggctga tgaggcccca gctggggcct gttgtctggg accctccctc tcctgagagg
2341 ggaggcctgg tggcttagcc tgggcaggtc gtgtctcctc ctgacccccag tggctgcggt
2401 gaggggaacc accctcccctt gctgcaccag tggccattag ctcccgtcac cactgcaacc
2461 cagggtccca gctggctggg tcctcttctg cccccagtgc ccttcccctt gggctgtgtt
2521 ggagtgagca cctcctctgt aggcacctct cacactgttg tctgttactg atttttttttg
2581 ataaaaagat aataaaacct ggtactttct aaaaaaaaaa aaaaaaaaaa aaaaaaaaa
```

One example of a nucleic acid sequence for human SERPINA1 is available as NCBI accession number NM_001127707 (gi: 189163541). This sequence is recited below for easy reference as SEQ ID NO:161.

```
  1 tgggcaggaa ctgggcactg tgcccagggc atgcactgcc tccacgcagc aaccctcaga
 61 gtcctgagct gaaccaagaa ggaggagggg gtcgggcctc cgaggaaggc ctagccgctg
121 ctgctgccag gaattccagg ttggaggggc ggcaacctcc tgccagcctt caggccactc
181 tcctgtgcct gccagaagag acagagcttg aggagagctt gaggagagca ggaaagcctc
241 ccccgttgcc cctctggatc cactgcttaa atacggacga ggacagggcc ctgtctcctc
301 agcttcaggc accaccactg acctgggaca gtgaatcgac aatgccgtct tctgtctcgt
361 ggggcatcct cctgctggca ggcctgtgct gcctggtccc tgtctccctg gctgaggatc
421 cccagggaga tgctgcccag aagacagata catcccacca tgatcaggat cacccaacct
481 tcaacaagat cacccccaac ctggctgagt tcgccttcag cctataccgc cagctggcac
541 accagtccaa cagcaccaat atcttcttct ccccagtgag catcgctaca gcctttgcaa
601 tgctctccct ggggaccaag gctgacactc acgatgaaat cctggagggc ctgaatttca
661 acctcacgga gattccggag gctcagatcc atgaaggctt ccaggaactc ctccgtaccc
721 tcaaccagcc agacagccag ctccagctga ccaccggcaa tggcctgttc ctcagcgagg
781 gcctgaagct agtggataag ttttttggagg atgttaaaaa gttgtaccac tcagaagcct
841 tcactgtcaa cttcggggac accgaagagg ccaagaaaca gatcaacgat tacgtggaga
901 agggtactca agggaaaatt gtggatttgg tcaaggagct tgacagagac acagttttttg
```

```
 961 ctctggtgaa ttacatcttc tttaaaggca aatgggagag acccttttgaa gtcaaggaca
1021 ccgaggaaga ggacttccac gtggaccagg tgaccaccgt gaaggtgcct atgatgaagc
1081 gtttaggcat gtttaacatc cagcactgta agaagctgtc cagctgggtg ctgctgatga
1141 aatacctggg caatgccacc gccatcttct tcctgcctga tgagggaaa ctacagcacc
1201 tggaaaatga actcacccac gatatcatca ccaagttcct ggaaaatgaa gacagaaggt
1261 ctgccagctt acatttaccc aaactgtcca ttactggaac ctatgatctg aagagcgtcc
1321 tgggtcaact gggcatcact aaggtcttca gcaatggggc tgacctctcc ggggtcacag
1381 aggaggcacc cctgaagctc tccaaggccg tgcataaggc tgtgctgacc atcgacgaga
1441 aagggactga agctgctggg gccatgtttt tagaggccat acccatgtct atccccccg
1501 aggtcaagtt caacaaaccc tttgtcttct aatgattga acaaaatacc aagtctcccc
1561 tcttcatggg aaaagtggtg aatcccaccc aaaaataact gcctctcgct cctcaacccc
1621 tcccctccat ccctggcccc ctccctggat gacattaaag aagggttgag ctggtccctg
1681 cctgcatgtg actgtaaatc cctcccatgt tttctctgag tctcccttg cctgctgagg
1741 ctgtatgtgg gctccaggta acagtgctgt cttcgggccc cctgaactgt gttcatggag
1801 catctggctg ggtaggcaca tgctgggctt gaatccaggg gggactgaat cctcagctta
1861 cggacctggg cccatctgtt tctggagggc tccagtcttc cttgtcctgt cttggagtcc
1921 ccaagaagga atcacagggg aggaaccaga taccagccat gaccccaggc tccaccaagc
1981 atcttcatgt ccccctgctc atcccccact ccccccacc cagagttgct catcctgcca
2041 gggctggctg tgcccacccc aaggctgccc tcctgggggc cccagaactg cctgatcgtg
2101 ccgtggccca gttttgtggc atctgcagca acacaagaga gaggacaatg tcctcctctt
2161 gacccgctgt cacctaacca gactcgggcc ctgcacctct caggcacttc tggaaaatga
2221 ctgaggcaga ttcttcctga agcccattct ccatggggca acaaggacac ctattctgtc
2281 cttgtccttc catcgctgcc ccagaaagcc tcacatatct ccgtttagaa tcaggtccct
2341 tctccccaga tgaagaggag ggtctctgct ttgttttctc tatctcctcc tcagacttga
2401 ccaggcccag caggccccag aagaccatta ccctatatcc cttctcctcc ctagtcacat
2461 ggccataggc ctgctgatgg ctcaggaagg ccattgcaag gactcctcag ctatgggaga
2521 ggaagcacat cacccattga ccccgcaac ccctcccttt cctcctctga gtcccgactg
2581 gggccacatg cagcctgact tctttgtgcc tgttgctgtc cctgcagtct tcagagggcc
2641 accgcagctc cagtgccacg gcaggaggct gttcctgaat agcccctgtg gtaagggcca
2701 ggagagtcct tccatcctcc aaggccctgc taaaggacac agcagccagg aagtcccctg
2761 ggccccctagc tgaaggacag cctgctccct ccgtctctac caggaatggc cttgtcctat
2821 ggaaggcact gccccatccc aaactaatct aggaatcact gtctaaccac tcactgtcat
2881 gaatgtgtac ttaaaggatg aggttgagtc ataccaaata gtgatttcga tagttcaaaa
2941 tggtgaaatt agcaattcta catgattcag tctaatcaat ggataccgac tgtttcccac
3001 acaagtctcc tgttctctta agcttactca ctgacagcct ttcactctcc acaaatacat
3061 taaagatatg gccatcacca agccccctag gatgacacca gacctgagag tctgaagacc
3121 tggatccaag ttctgacttt tcccctgac agctgtgtga ccttcgtgaa gtcgccaaac
3181 ctctctgagc cccagtcatt gctagtaaga cctgcctttg agttggtatg atgttcaagt
3241 tagataacaa aatgtttata cccattagaa cagagaataa atagaactac atttcttgca
```

One example of a nucleic acid sequence for human SLC25A15 is available as NCBI accession number NM_014252 (gi: 237649033). This sequence is recited below for easy reference as SEQ ID NO:162.

```
   1 tgggggcggt ggcagggccg gtgggcggtg gcggctcccg gtctcggctc gggcacggcc
  61 ctgggcaggc cgcccgccag ccgcaggggc gctcctgagc ttcgcgggc cgcagtccgg
 121 gatgcctgcg cgaagggagg ggcgaagggc cggccgttgc cgacgtgggt gttaagtggc
 181 cgccccagcc ggcgacccgg agccgagagc gggcggcgga gcctgagctg gacgcggcca
 241 cgccggcgcg gcgggatatg tggtgcctgt cataagctcc agagagctgc cttccacaag
 301 accagcagaa gagtgggcaa acatgaaatc caatcctgct atccaggctg ccattgacct
 361 cacagcgggg gctgcaggag gtacagcatg tgtactgacc gggcagccct ttgacacaat
 421 gaaagtgaag atgcagacgt tccctgacct gtaccggggc ctcaccgact gctgcctgaa
 481 gacttactcc caggtgggct tccgtggctt ctacaagggt accagtccag cactaatcgc
 541 caacatcgct gagaactcag tcctcttcat gtgctacggc ttctgccagc aggtggtgcg
 601 gaaagtggct ggattggaca agcaggcaaa gctgagtgat ctgcagaatg cagccgccgg
 661 ttccttcgcc tctgcctttg ctgcactggt gctctgcccc acggagctcg tgaagtgccg
 721 gctgcagacc atgtatgaga tggagacatc agggaagata gccaagagcc agaatacagt
 781 gtggtctgtc atcaaaagta ttcttaggaa agatggcccc ttggggttct accatggact
 841 ctcaagcact ttacttcgag aagtaccagg ctatttcttc ttcttcggtg gctatgaact
 901 gagccggtcc ttttttgcat cagggagatc aaaagatgaa ttaggccctg tacctttgat
 961 gttaagtggt ggagttggtg ggatttgcct ctggcttgcg gtatacccag tggattgtat
1021 caaatccaga attcaagttc tttccatgtc tggaaaacag gcaggattta tcagaacctt
1081 tataaatgtt gtgaaaaatg aaggaataac ggccttatat tctggactga acctactat
1141 gattcgagca ttccctgcca atggagcact ctttttggcc tacgaatata gcaggaagtt
1201 gatgatgaac cagttggaag catactgaag tgtcttggtg ggcctgagcc aagcacaggt
1261 gtttgaggac tacagttcat ctcagggttt cttggagtac aagaccagtg tgaagttatt
1321 ctgatttctt gggaattttg cttttttgtct tcccttctac cctacatctt aaactttatg
1381 gaagaacctc tattttgcat catatcattt ctgtccataa ttgtactgaa atagaaaagt
1441 gaccgctctt gctcttggta aaatatagag tggtcagtag ccttatgcac ctaattcaaa
1501 aggtggaata tagttctgtc agggctttta cgtaaacctc cacttgtaca tgcaatttgg
1561 acagttatgt gttgagggaa atacagtttg gtaccttgtt tatttcaaat atcagaaaaa
1621 cccagaggtg atcatttctc atgaagatgc ttataaatgg ttgcttaacc cattctagat
1681 gtagggtctg cttaatgtgt gtacttttct aagtggttga ttatttttta ttttttgat
1741 acagagtctc actctgtcac ccagactgga gtgcagtggc acgatctcgg ctcactgcaa
1801 cctccgcctc ctgggttcaa gcgattctct cacctcagcc tcctgagtag ctgggattac
1861 aggtacgcgc caccatgtcc agctaatttt ttttggtatt ttttgtagag acgaggtttc
1921 accatgttgt ccaggttggt ctcgaactcc tgacctcaag tgatccgccc acctcggcct
1981 cccaaagtgc tgggattact ggtgtgagcc accatgccca gccagtggtt gaatttttta
2041 aaaagtgttc atggggtgct tgaaaactaa aatatccttc tagatttgta agacagtata
2101 cctgcatact ggtgtggctt ccacacttga gtaaaagctt cagagtaggt atcctagatt
2161 tccccaagat gctctactct taaaatagtg ccattcattt tctaggtggg atcatattcc
2221 acgctgacta tattgctagg ggtgcccag agggtcaggc ctttgggaaa tagcatggcc
2281 tttaccagct tccccttctct cccaaagaac ttcccttctt gggctttaga ttgaggaagg
```

```
2341 ggctgagtgg taggcggtgc tgctgtgctc tgatgaagac ccatgtggct agcaacagcg 2401 cttaccttt gtctctgggt cctggcctgg ggccatcaat ccactttggg ccactcactg 2461 tctgctctgc ctccaccaat cagaaaccct tccaaggaac agtgagagcc aaagccaaga 2521 gaagccttct tccctgtttg gtgattgtgt gacagtgggt gaacctctct cagagagaac 2581 tagaaagaac tcagtgcttg tactccacag tgagtaatgt caggtctgac ccatcctgaa 2641 gcctgtcttg ccatgctttt acagtgttgg aggcttctac atttggtact tgcagtcagt 2701 aagtcttaat gatgactgta tatgtgatat gagtttataa agcaatggaa cataagaaaa 2761 gcaattgtag gccaggcgca gtggctcacg cctataatcc cagcactttg ggaggctgag 2821 gcgggcgggt cacaaggtca ggagttcgag aacagcctga ccaacatggt gaaaccccat 2881 ctctactaaa aatacaaaaa ttagctgggc gtggtggcac gtgcctgtaa tcccagctac 2941 tcaggaggct gaggcaggag aatcgcttga acccgggagg cagaggttgc agtgaactga 3001 gattgtgcca ctgcactcca gactgggtga cacagcgaga cttcatctca aaaaaaaaa 3061 gaaaagaaaa gcaattgtac ttcactatgc catatgtatg tattcactga ccaaaaattc 3121 actgaccaac caaccaaact ccacacttca tctgatcccc catagacttg gggatggaca 3181 gctgttcttt ggccatatgg tataagagga tcattcttgt cactacttaa gttagcctca 3241 tcattttgtg ctgctccaac accagcaggg tatctcccaa taaagtgttc ctaagcagcc 3301 tgtatactga gtgcaagcag gctatcaatt ttaataatag tccataccat gtatgtgttt 3361 ctgtcagcag aatgtacatg ttgtacaaaa cctccaggtt ccttaagctt tttgctgtcc 3421 atgaatcctc tgtggcaact gtaatcacag agccagaagc cagagggcca gggatatgag 3481 aggctgacaa acatcagggg acatctgggg aggagatccc tgtcatgtct cttgtgccat 3541 ggagctatta tggctggtct tccatttgct tttctttaa gtgaaaacca tttttctact 3601 ttgcttttct ctccatactt aaatggtcag tagctactga gtggtgcttt atctgaatag 3661 gcctggatcg aagtaaaata gaaatgggac tggctttcca caggaagtaa actgcttcag 3721 agcccacagt cccctgctca gtgtccggaa agaagtcagt catccctgtt ggcagtaaat 3781 cttcccacag gccgtccatt agagatttaa ctagatatgt tcaatagaaa gagtctgagg 3841 caagtggaaa tgaggaacgg aaacttaggt tgggagaata ttttttttt attcattctg 3901 tttgcttaat tcagagtaca gtttgtgcta tttcatatct gtactccagg cagaaatata 3961 acttgaaaat actgtgtcta aagaaatttc agtgttctat cattaaatta tttacttaat 4021 aaaaaaaaaa aaaaaaaa
```

One example of a nucleic acid sequence for human SLC4A4 is available as NCBI accession number NM_001098484 (gi: 197927157). This sequence is recited below for easy reference as SEQ ID NO:163.

```
  1 gcggcggcgg ccgcggtggc agcgaaggcg gcggcggcgg cggcagtggc agtggccgct 61 gcagccccac actccgccgc caaactggag gagcgacgga agccagaccc caggaggatg 121 gaggatgaag ctgtcctgga cagaggggct tccttcctca agcatgtgtg tgatgaagaa 181 gaagtagaag gccaccatac catttacatc ggagtccatg tgccgaagag ttacaggaga 241 aggagacgtc acaagagaaa gacagggcac aaagaaaaga aggaaaagga gagaatctct 301 gagaactact ctgacaaatc agatattgaa aatgctgatg aatccagcag cagcatccta 361 aaacctctca tctctcctgc tgcagaacgc atccgattca tcttgggaga ggaggatgac 421 agcccagctc cccctcagct cttcacggaa ctggatgagc tgctggccgt ggatgggcag 481 gagatggagt ggaaggaaac agccaggtgg atcaagtttg aagaaaaagt ggaacagggt
```

-continued

```
 541 ggggaaagat ggagcaagcc ccatgtggcc acattgtccc ttcatagttt atttgagctg
 601 aggacatgta tggagaaagg atccatcatg cttgatcggg aggcttcttc tctcccacag
 661 ttggtggaga tgattgttga ccatcagatt gagacaggcc tattgaaacc tgaacttaag
 721 gataaggtga cctatacttt gctccggaag caccggcatc aaaccaagaa atccaacctt
 781 cggtccctgg ctgacattgg gaagacagtc tccagtgcaa gtaggatgtt taccaaccct
 841 gataatggta gcccagccat gacccatagg aatctgactt cctccagtct gaatgacatt
 901 tctgataaac cggagaagga ccagctgaag aataagttca tgaaaaaatt gccacgtgat
 961 gcagaagctt ccaacgtgct tgttggggag ttgactttt tggatactcc tttcattgcc
1021 tttgttaggc tacagcaggc tgtcatgctg ggtgccctga ctgaagttcc tgtgcccaca
1081 aggttcttgt tcattctctt aggtcctaag gggaaagcca agtcctacca cgagattggc
1141 agagccattg ccaccctgat gtctgatgag gtgttccatg acattgctta taaagcaaaa
1201 gacaggcacg acctgattgc tggtattgat gagttcctag atgaagtcat cgtccttcca
1261 cctggggaat gggatccagc aattaggata gagcctccta agagtcttcc atcctctgac
1321 aaaagaaaga atatgtactc aggtggagag aatgttcaga tgaatgggga tacgccccat
1381 gatggaggtc acggaggagg aggacatggg gattgtgaag aattgcagcg aactggacgg
1441 ttctgtggtg gactaattaa agacataaag aggaaagcgc cattttttgc cagtgatttt
1501 tatgatgctt taaatattca agctctttcg gcaattctct tcatttatct ggcaactgta
1561 actaatgcta tcacttttgg aggactgctt ggggatgcca ctgacaacat gcagggcgtg
1621 ttggagagtt tcctgggcac tgctgtctct ggagccatct tttgcctttt tgctggtcaa
1681 ccactcacta ttctgagcag caccggacct gtcctagttt tgagaggct tctatttaat
1741 ttcagcaagg acaataattt tgactatttg gagtttcgcc tttggattgg cctgtggtcc
1801 gccttcctat gtctcatttt ggtagccact gatgccagct tcttggttca atacttcaca
1861 cgtttcacgg aggagggctt ttcctctctg attagcttca tctttatcta tgatgctttc
1921 aagaagatga tcaagcttgc agattactac cccatcaact ccaacttcaa agtgggctac
1981 aacactctct tttcctgtac ctgtgtgcca cctgacccag ctaatatctc aatatctaat
2041 gacaccacac tggccccaga gtatttgcca actatgtctt ctactgacat gtaccataat
2101 actacctttg actgggcatt tttgtcgaag aaggagtgtt caaaatacgg aggaaacctc
2161 gtcgggaaca actgtaattt tgttcctgat atcacactca tgtcttttat cctcttcttg
2221 ggaacctaca cctcttccat ggctctgaaa aaattcaaaa ctagtcctta ttttccaacc
2281 acagcaagaa aactgatcag tgattttgcc attatcttgt ccattctcat cttttgtgta
2341 atagatgccc tagtaggcgt ggacacccca aaactaattg tgccaagtga gttcaagcca
2401 acaagtccaa accgaggttg gttcgttcca ccgtttggag aaaaccctg tgggtgtgc
2461 cttgctgctg ctatcccggc tttgttggtc actatactga ttttcatgga ccaacaaatt
2521 acagctgtga ttgtaaacag gaaagaacat aaactcaaga aaggagcagg gtatcacttg
2581 gatctctttt gggtggccat cctcatggtt atatgctccc tcatggctct tccgtggtat
2641 gtagctgcta cggtcatctc cattgctcac atcgacagtt tgaagatgga gacagagact
2701 tctgcacctg gagaacaacc aaagtttcta ggagtgaggg aacaaagagt cactggaacc
2761 cttgtgttta ttctgactgg tctgtcagtc tttatggctc ccatcttgaa gtttataccc
2821 atgcctgtac tctatggtgt gttcctgtat atgggagtag catcccttaa tggtgtgcag
2881 ttcatggatc gtctgaagct gcttctgatg cctctgaagc atcagcctga cttcatctac
```

-continued

```
2941 ctgcgtcatg ttcctctgcg cagagtccac ctgttcactt tcctgcaggt gttgtgtctg 3001 gccctgcttt ggatcctcaa gtcaacggtg gctgctatca tttttccagt aatgatcttg 3061 gcacttgtag ctgtcagaaa aggcatggac tacctcttct cccagcatga cctcagcttc 3121 ctggatgatg tcattccaga aaaggacaag aaaaagaagg aggatgagaa gaaaaagaaa 3181 aagaagaagg gaagtctgga cagtgacaat gatgattctg actgcccata ctcagaaaaa 3241 gttccaagta ttaaaattcc aatggacatc atggaacagc aaccttttcct aagcgatagc 3301 aaaccttctg acagagaaag atcaccaaca ttccttgaac gccacacatc atgctgataa 3361 aattcctttc cttcagtcac tcggtatgcc aagtcctcct agaactccag taaaagttgt 3421 gcctcaaatt agaatagaac ttgaacctga agacaatgat tatttctgga ggagcaaggg 3481 aacagaaact acattgtaac ctgtttgtct ttcttaaaac tgacatttgt tgttaatgtc 3541 atttgttttt gtttggctgt ttgtttattt tttaactttt atttcgtctc agttttggt 3601 cacaggccaa ataatacagc gctctctctg cttctctctt gcatagatac aatcaagaca 3661 atagtgcacc gttccttaaa aacagcatct gaggaatccc ccttttgttc ttaaactttc 3721 agatgtgtcc tttgataacc aaattctgtc actcaagaca cagacacgca cagaccctgt 3781 cctttgcctc tattaagcag aggatggaag tattaaggat tttgtaacac ctttttatgaa 3841 aatgttgaag gaacttaaaa ctttagcttt ggagctgtgc ttactggctt gtctttgtct 3901 ggtagaacaa accttgacct ccagacagag tcccttctca cttatagagc tctccaggac 3961 tggaaaagt gctgctattt taacttgctc ttgcttgtaa atcctaatct tagagttatc 4021 aaaagaagaa aaaactgaag gtactttact ccctatagag aaaccattgc catcattgta 4081 gcaagtgctg gaatgtccct tttttcctat gcaacttttt ttaacccttt aatgaactta 4141 tctgttgagt acattgaaga atattttct tcctagattt tgttgtttaa attatggggc 4201 ctaacctgcc acttatttt tgtcaatttt taaaacttt ttttaattac tgtaaagaaa 4261 atgaattttt tcctgcagca ggaaacatag ttttgagtag ttctacctct tatttgtagc 4321 tgccaggctt tctgtaaaaa ttgtattgta tataatgtga ttttacaca tacatacaca 4381 cacaaataca caatctctag ggtaagccag aaggcaagat cagattaaaa acaccatgtt 4441 tctaagcatc cattttttccc tttctttaaa agaaacttaa ctgttctatg aaggagattg 4501 agggagaaga gacaaactcc tatgtcatga gaataaccga tgttctgata atagtagcat 4561 ctaggtacag atgctggttg tattaccacg tcaatgtcct atgcagtatt gttagacatt 4621 ttctcatttt gaaatatttg tgtgtttgtg tatgtgctct gtgccatggc tggtgtatat 4681 atgtgcaatg ttagaaggca aaagagtgat ggtaggcaga gggcaaagtc attgaatctc 4741 ttatgccagt tttcataaaa cccaaaccac atatgaaaaa atccattaag ggtccaagaa 4801 gtctgtccat atgaaaatga gggtaaatat agtttatttc ccaggtatca gtcattataa 4861 ttgatataat agctctaaca tgcaatataa aattcatagg agtattaata gcccatttac 4921 acatctataa aatgtaatgg gattgcagag ctgcagagta cagtgtaaca gtactctcat 4981 gcaatttttt tcaggatgca aaggcaatta ttctttgtaa gcgggacatt tagaatatat 5041 ttgtgtacat attatatgta tgtatatttc aaagtaccac actgaaaatt agacatttat 5101 taaccaaatt taacgtggta tttaaaggta atattttaa tatgatacat tacatattgt 5161 gaatgtatac taaaaaaaca ttttaaatgt taaaattata atttcagatt catataacca 5221 caactgtgat atatcctaac tataaccagt tgttgagggg tatactagaa gcagaatgaa 5281 accacatttt ttggtttgat aatatgcact tattgactcc cactcattgt tatgttaatt 5341 aagttattat tctgtctcct tgtaattttg attacaaaaa ttttattatc ctgagttagc
```

-continued

```
5401 tgttactttt acagtacctg atactcctaa aactttaac ttatacaaat tagtcaataa 5461 tgacccccaat ttttcatta aataatagt ggtgaattat atgttattgt gttaaaacct 5521 cacttgccaa attctggctt cacatttgta tttagggcta tccttaaaat gatgagtcta 5581 tattatctag ctttctatta ccctaatata aactggtata agaagacttt ccttttttct 5641 ttatgcatgg aagcatcaat aaattgttta aaaccatgt atagtaaatt cagcttaacc 5701 cgtgatcttc ttaagttaaa ggtactttg tttataaaa gctctagata aaactttctt 5761 ttctgatcat gaatcaagta tctgtggttt catgcccctc tctatacctt tcaaagaact 5821 cctgaagcaa cttaactcat catttcagcc tctgagtaga ggtaaaacct atgtgtactt 5881 ctgtttatga tccatattga tatttatgac atgaacacag aatagtacct tacatttgct 5941 aaacagacag ttaatatcaa atcctttcaa tattctggga acccagggaa gttttaaaa 6001 atgtcattac tttcaaagga acagaagtag ttaaccaaac taacaagcaa aacctgaggt 6061 ttacctagtg acaccaaatt atcggtattt taactgaatt tacccattga ctaagaatga 6121 accagatttg gtggtggttt tgtttctatg caaactggac acaaattaca acagtaaatt 6181 tttttataag tgcttctccc ttctccatga tgtgacttcc ggagataaag gattcaaaag 6241 ataaagacaa agtacgctca gagttgttaa ccagaaagtc ctggctgtgg ttgcagaaac 6301 actgttggaa gaaagagat gactaagtca agtgtctgcc ttatcaaaag agcaaaaatg 6361 cctctggttt tgtgtttggg agaaaaatat cttggacgca ctgttttcct tgataaaagt 6421 catcttctct actgtgtgaa atgaatactt ggaattctaa ttgttttgtg tgccaggggc 6481 agtaatgtcc ctgcctcttc tcccaatcaa ggttgaggag tggggctggg gagaggactt 6541 aactgactta agaagtagga aaacaaaac ctctctcctc agccttccac ctccaagaga 6601 ggaggaaaaa cagttgtctg ctgtctgtaa ttcagtttgc gtgtatttta tgctcatgca 6661 ccaacccata cagagtaaat cttttatcaa ctatatactg gtgtttaata gagaatgatt 6721 gtcttccgag ttttttggtt ccttttttaa ctgtgttaaa gtacttgaaa tgtattgact 6781 gctgactata ttttaaaaac aaaatgaaat aatttgagtt gtattacaga ggttgacatt 6841 gttcagggat gggacaaagc cttcttcaat cctttcata ctacttaatg attttggtgc 6901 aggaacctga gattttctga tttatatttc atgatatttc acatttgctc ttcacagcat 6961 gagcatgaag cccagtggca ccaaatggct gggtacaatc aagtgatatt ttgtagcacc 7021 tcactatctg aaaggccatg agttttcaga tgatttcatt gagcttcatt gcagcctgaa 7081 attttaaaaa agttgtgtaa tacgccaacc agtcaagttg tgttttggcc agagatttag 7141 atatgtccaa tttcctggct catttcattg tgctctatgg gtacgtataa aaagcaagaa 7201 ttctgtttcc taggcaaaca ttgcaactca gggctaaagt catccagtga aacttttaga 7261 gccagaagta actttgtccc agtcctacaa tgtgaaaaga gtgaatagtt gcctcttttt 7321 agccatttc atggctggta catattcgta cgcattactt ttcagaatca atacgcactt 7381 tcagatattc ttattttat tctcttaagt cttattaac tttggagaga gaaatgatgc 7441 atctttttat tttaaatgaa gtagatcaac atggtggaac aaaatgataa agaacagaaa 7501 acatttcaat atattactaa taactttttc caatataaat cctaaaattc ctataacata 7561 gtattttaca gttttatgaa gcttctatt gtgacttta tggaattaag agatgaagaa 7621 gatgagatat tttagcattt atattttca aaattatatg tatacttaaa aataaagtaa 7681 ctttatgcat tta
```

One example of a nucleic acid sequence for human SLIT1 is available as NCBI accession number NM_003061 (gi: 188528674). This sequence is recited below for easy reference as SEQ ID NO:164.

```
   1 gggagaggga gacgcaggcg gcgaaacggc agaggagccg agcccctcc gcccaaggcg
  61 ccctccctcc gtccgcgcac aggcgccgtc gcttggagga gcaaggtgcc tcccagcccg
 121 caggggcgcc gcgcgcaagc ccgcgggctc ttcggtggct ctgccccggg actgcacctg
 181 gaggcggccc cggacgggga tggtcagcgg ctgctgccgt ctggctcgcg agcgggacgc
 241 tgtgagggca ccatggcgct gactcccggg tggggtcct cggcggggcc ggtccggccg
 301 gagctctggc tgctgctgtg ggcagccgcg tggcgcctgg gtgcctcggc gtgccccgcc
 361 ctctgcacct gcaccggaac cacggtggac tgccacggca cggggctgca ggccattccc
 421 aagaatatac ctcggaacac cgagcgcctg gaactcaatg caacaacat cactcggatc
 481 cataagaatg actttgcggg gctcaagcag ctgcgggtgc tgcagctgat ggagaaccag
 541 attggagcag tggaacgtgg tgcttttgat gacatgaagg agctggagcg gctgcgactg
 601 aaccgaaacc agctgcacat gttaccggaa ctgctgttcc agaacaacca ggctttgtca
 661 agactggact tgagtgagaa cgccatccag gccatcccca ggaaagcttt tcggggagct
 721 acggaccta aaaatttaca gctggacaag aaccagatca gctgcattga ggaagggggcc
 781 ttccgtgctc tgcggggggct ggaggtgctg accctgaaca acaacaatat caccaccatc
 841 cccgtgtcca gcttcaacca tatgcccaag ctacggacct tccgcctgca ctccaaccac
 901 ctgttttgcg actgccacct ggcctggctc tcgcagtggc tgaggcagcg gccaaccatc
 961 gggctcttca cccagtgctc gggcccagcc agcctgcgtg gcctcaatgt ggcagaggtc
1021 cagaagagtg agttcagctg ctcaggccag ggagaagcgg ggcgcgtgcc cacctgcacc
1081 ctgtcctccg gctcctgccc ggccatgtgc acctgcagca atggcatcgt ggactgtcgt
1141 ggaaaaggcc tcactgccat cccggccaac ctgcccgaga ccatgacgga gatacgcctg
1201 gagctgaacg gcatcaagtc catccctcct ggagccttct caccctacag aaagctacgg
1261 aggatagacc tgagcaacaa tcagatcgct gagattgcac ccgacgcctt ccagggcctc
1321 cgctcccctga actcgctggt cctctatgga aacaagatca cagacctccc ccgtggtgtg
1381 tttggaggcc tatacaccct acagtcctg ctcctgaatg ccaacaagat caactgcatc
1441 cggcccgatg ccttccagga cctgcagaac ctctcactgc tctccctgta tgacaacaag
1501 atccagagcc tcgccaaggg cactttcacc tccctgcggg ccatccagac tctgcacctg
1561 gcgcagaacc cttcatttg cgactgtaac ctcaagtggc tggcagactt cctgcgcacc
1621 aatcccatcg agacgagtgg tgcccgctgt gccagtcccc ggcgcctcgc caacaagcgc
1681 atcgggcaga tcaagagcaa gaagttccgg tgctcagcca agagcagta cttcattcca
1741 ggcacggagg attaccagct gaacagcgag tgcaacagcg acgtggtctg tccccacaag
1801 tgccgctgtg aggccaacgt ggtggagtgc tccagcctga gctcaccaa gatccctgag
1861 cgcatccccc agtccacggc agaactgcga ttgaataaca atgagatttc catcctggag
1921 gccactggga tgtttaaaaa acttacacat ctgaagaaaa tcaatctgag caacaacaag
1981 gtgtcagaaa ttgaagatgg ggccttcgag ggcgcagcct ctgtgagcga gctgcaccta
2041 actgccaacc agctggagtc catccggagc ggcatgttcc ggggtctgga tggcttgagg
2101 accctaatgc tgcggaacaa ccgcatcagc tgcatccaca cgacagctt cacgggcctg
2161 cgcaacgtcc ggcctcctct ctctctacgac aaccagatca ccaccgtatc cccaggagcc
2221 ttcgacaccc tccagtccct ctccacactg aatctcctgg ccaacccttt caactgcaac
```

-continued

```
2281  tgccagctgg cctggctagg aggctggcta cggaagcgca agatcgtgac ggggaacccg
2341  cgatgccaga accctgactt tttgcggcag attcccctgc aggacgtggc cttccctgac
2401  ttcaggtgtg aggaaggcca ggaggagggg ggctgcctgc cccgcccaca gtgcccacag
2461  gagtgcgcct gcctggacac cgtggtccga tgcagcaaca agcacctgcg ggccctgccc
2521  aagggcattc ccaagaatgt cacagaactc tatttggacg ggaaccagtt cacgctggtt
2581  ccgggacagc tgtctacctt caagtacctg cagctcgtgg acctgagcaa caacaagatc
2641  agttccttaa gcaattcctc cttcaccaac atgagccagc tgaccactct gatcctcagc
2701  tacaatgccc tgcagtgcat cccgcctttg gccttccagg gactccgctc cctgcgcctg
2761  ctgtctctcc acggcaatga catctccacc ctccaagagg gcatctttgc agacgtgacc
2821  tccctgtctc acctggccat ggtgccaac  ccctatact gtgactgcca cctccgctgg
2881  ctgtccagct gggtgaagac tggctacaag gaaccgggca ttgctcgttg tgctgggccc
2941  caggacatgg agggcaagct gctcctcacc acgcctgcca agaagtttga atgccaaggt
3001  cctccaacgc tggctgtcca ggccaagtgt gatctctgct tgtccagtcc gtgccagaac
3061  cagggcacct gccacaacga cccccttgag gtgtacaggt gcgcctgccc cagcggctat
3121  aagggtcgag actgtgaggt gtccctggac agctgttcca gtggccctg  tgaaaatggg
3181  ggcacctgcc atgcacagga gggcgaggat gccccgttca cgtgctcctg tcccaccggc
3241  tttgaaggac caacctgtgg ggtgaacaca gatgactgtg tggatcatgc ctgtgccaat
3301  gggggcgtct gtgtggatgg tgtgggcaac tacacctgcc agtgcccct  gcagtatgag
3361  ggaaaggcct gtgagcagct ggtggacttg tgctctccgg atctgaaccc atgtcaacac
3421  gaggcccagt gtgtgggcac cccggatggg cccaggtgtg agtgcatgcc aggttatgca
3481  ggtgacaact gcagtgagaa ccaggatgac tgcagggacc accgctgcca gaatggggcc
3541  cagtgtatgg atgaagtcaa cagctactcc tgcctctgtg ctgagggcta cagtggacag
3601  ctctgtgaga tccctcccca tctgcctgcc cccaagagcc cctgtgaggg gactgagtgc
3661  cagaatgggg ccaactgtgt ggaccagggc aacaggcctg tgtgccagtg cctcccaggc
3721  ttcggtggcc ctgagtgtga aagttgctc  agtgtcaact tgtggatcg  ggacacttac
3781  ctgcagttca ctgacctgca aaactggcca cgggccaaca tcacgttgca ggtctccacg
3841  gcagaggaca atgggatcct tctgtacaac ggggacaacg accacattgc agttgagctg
3901  taccagggcc atgtgcgtgt cagctacgac ccaggcagct accccagctc tgccatctac
3961  agtgctgaga cgatcaacga tgggcaattc cacaccgttg agctggttgc ctttgaccag
4021  atggtgaatc tctccattga tggcgggagc cccatgacca tggacaactt ggcaaacat
4081  tacacgctca acagcgaggc gccactctat gtgggaggga tgcccgtgga tgtcaactca
4141  gctgccttcc gctgtggca  gatcctcaac ggcaccggct ccacggttg  catccgaaac
4201  ctgtacatca caaacgagct gcaggacttc accaagacgc agatgaagcc aggcgtggtg
4261  ccaggctgcg aaccctgccg caagctctac tgcctgcatg gcatctgcca gcccaatgcc
4321  accccagggc ccatgtgcca ctgcgaggct ggctgggtgg gcctgcactg tgaccagccc
4381  gctgacggcc cctgccatgg ccacaagtgt gtccatgggc aatgcgtgcc cctcgacgct
4441  ctttcctaca gctgccagtg ccaggatggg tactcgggg  cactgtgcaa ccaggccggg
4501  gccctggcag agccctgcag aggcctgcag tgcctgcatg gcactgcca  ggcctcaggc
4561  accaaggggg cacactgtgt gtgtgacccc ggcttttcgg gcgagctgtg tgagcaagag
4621  tccgagtgcc ggggggaccc tgtccgggac tttcaccagg tccagagggg ctatgccatc
```

-continued

```
4681 tgccagacca cgcgccccct gtcatgggtg gagtgccggg gctcgtgccc aggccagggc 4741 tgctgccagg gccttcggct gaagcggagg aagttcacct ttgagtgcag cgatgggacc 4801 tcttttgccg aggaggtgga aaagcccacc aagtgtggct gtgccctctg cgcatagcgc 4861 tgggcgtgga caggccggtg agggcgggca aggggcccca gccgctgcag cagcggagac 4921 agtcgccagc agctgggctg gggtgcaggt catcacagga cggctcctgg gcagctgggc 4981 cctcctgggt ggggtggtgc cagagcagcc ttttaaaagc aaattgcgcc atagctgggg 5041 gcagcggggg tgggcgaggc ctgagctgcg ggctgccctc tccggaagtg ccttgcacaa 5101 ataggcgctt aataaatatt tgttgagtga atgtgtgcgt gaggtcaggc caagaagtgc 5161 agaacgatga caccccctcct tacctgctat ctgaatctgg agaagaaaaa tgacagcctt 5221 ccaaaccaac ccttcccttt ggcctgtggc ccaggctggc ttggaactgg gtctgtggcc 5281 ccagaagcct cttaccccctc tgcgggcaac catgaagtac tgtcagcctc cccgggaagc 5341 cagcctggtt cattctgctg ctacagaatc tgctggtggt aggccaggct ctggagcggg 5401 ggtgccgcct cctgctggcc agggagggtc ggacccttgc cccctgggct gactggcagc 5461 tctgcagcca cggcttggga acgaggctgt gggtggaggt ggttcttagg accaggcctc 5521 tgaatcctaa agttctagca tgactactgt agctgcgagg gcttatgtgg aggaaacagt 5581 cacaggggct gctcagggtg gcagaccccca ctaaagaggg cagagggttc tttgctctag 5641 ataaacaaac atcatctgcc tccagacact ggccacagta ggagtattgg tcctgggctt 5701 ccccagccac cagtcagcca caagctgtcg gtgaccctatt ggtagaggga ctgggtgtga 5761 gggtctgggc cagggtgctt gacctgggag cagctggttc agagtccttc acaccgcagg 5821 ccagtaggga gcagtggaag ggacagtgct ccaggcattg ggaagtccct gctggctcta 5881 tcactcgggg caaacttctc cccacctggg ccttgggttc ttcagctata aaatggccag 5941 aggtgggggg cgggatgact aaaggaacag tgcagactcc cccactgtgg tcttgggagg 6001 ccagaggagt tagaagacct atctatctat ctatctatct acattgatca catcaaaagt 6061 atttatgtgc ctaacccggg gctggggatt gtggacgttc tggcctaatg gacagatgtg 6121 aactcatccc agagcatcgc aggaatgacc aggatgcccg ggaagagttg agctgagtgg 6181 gggctccagc cacagacagc ggcccaggcc agggagttgc tggcaacgaa ggagccagtg 6241 gtggaagaag aagaggccct gaatatacga ttgcctgccc acgttgtctt ctcttccata 6301 cacagtgaaa atgtagaaag atggtttgtg aggccaaact gtgaatgggc taaagggagg 6361 caaagttgca ctctccttcc ccagagggct caccaagagg gcacacccccc gggggttctg 6421 gtgggcaacg ggggtgagca tgtccctgcc ctggctccct ccatctgtga ccaggaggca 6481 tggctgggtg tatgttcagg tgaggctcag agtggcattg tgtccctgtc ccctgcccag 6541 ggcagtgagg ggagcccttg atgctgatta gaaggctaga actggggtag aggtgcctgg 6601 catgtctcat gccatgggga ctcaatctag caactgtgag tcctggggtc cctgtgatgg 6661 gaagagggca gtgccctgcc caatgtggca ggtgtcctca tggcaggatc tgcccctcac 6721 caggggctg ggatctactt gcttggagct ctgagcaagg ccacaatgcc cgcccccacc 6781 cccaagtaga ctgcagcctg ggcctcatgg ggcttctccc aggcccacat ggcatccctc 6841 tctgagtttc caggccaccg tgggaccctg cagagcatct gcaccgggct ggatagggca 6901 gaaaagctca agggcagcta gcttgcctct tccctggaag aaaggtgctc tgggactcac 6961 caaccctgag aaagatagct ttcctggcca ccaccattcc ccaccaccct ggagaagcca 7021 attcccaggc ttgaagggca ctggctggca ggaggcctct tcattctgca ggaggtggaa 7081 aggacacctg tagacaggtg atgctcaccc ctcacctggc gccatggggc tgggaggtga
```

-continued

```
7141 gcggctggca tgtttgttcc tagggagcac catgtgagct taaggctccc ctgaccggcc 7201 ccaccacatg gcccagcctc ctagcacagc agcgctgacc tcagtgcagt ctgaggattg 7261 gaatccacca tgagatgatg tgagagctgt gtgccccagg atcaactttt tctccaactt 7321 ggccatcagc cagcgagttg ctaaggacct gagtcagcac tcacgttgcc tattcacact 7381 ccgcttgaaa gtccggaagg tggctactgc aaaatcaccc ctctgagaag tcctctctcc 7441 acatcttgtc cccctttgtg aagacccta gttcgctctg cattttaggc atgaagagat 7501 acagcagggt gcgtccggag ggagctgtgg ccttgcaaca ccactggcaa cagggccggg 7561 gctcccggtg aaggtgtcag gaagtggaaa aggctggact ttgtctcctc tttgcctgct 7621 ggtagcctaa ccgcaaaagt atctctttat acagaatact tacagattct aatatatatt 7681 tgtatttcat tttgttacag tatttttata tgttaaagtc aacatccagc gtcttgtttt 7741 gcctttcaga tgctatgtgg tcgtggcacg ttttgttggg ggtttctgta gtcgtcttgt 7801 ttggatcaac tcctagaggc tggtttagaa caggcccatg agggagctgc acctgccctg 7861 gaagtattgt tttagactat gtcgatattg tctgttgtct tccatgtgaa catgacattg 7921 agtcactctg caaaaaaaaa aaaaaaaaa
```

One example of a nucleic acid sequence for human SPTAN1 is available as NCBI accession number NM_001130438 (gi: 194595508). This sequence is recited below for easy reference as SEQ ID NO:165.

```
   1 gccactaccc gctgcggagt gaacggtgtg gagcggaggc cgcggaggct cctcggtcct 61 tcagcacccc tcggcccgac gcacccacgc ccctcacccc ccgagagccg aaaatggacc 121 caagtggggt caaagtgctg gaaacagcag aggacatcca ggagaggcgg cagcaggtcc 181 tagaccgata ccaccgcttc aaggaactct caacccttag gcgtcagaag ctggaagatt 241 cctatcgatt ccagttcttt caaagagatg ctgaagagct ggagaaatgg atacaggaaa 301 aacttcagat tgcatctgat gagaattata agacccaac caacttgcag ggaaagcttc 361 agaagcatca agcatttgaa gctgaagtgc aggccaactc aggagccatt gttaagctgg 421 atgaaactgg aaacctgatg atctcagaag ggcattttgc atctgaaacc atacggaccc 481 gtttgatgga gctgcaccgc cagtgggaat tactttttgga gaagatgcga gaaaaggaa 541 tcaaactgct gcaggcccag aagttggtgc agtacttacg agaatgtgag gacgtgatgg 601 actggatcaa tgacaaggaa gcaattgtta cttctgaaga gctgggccag gatctggagc 661 atgtagaggt tttacagaag aaatttgaag agtttcaaac agatatggct gctcatgaag 721 aaagagttaa tgaagtgaac cagtttgctg ccaaactcat acaggagcag cacccctgagg 781 aggaactgat caagactaag caggatgaag tcaatgcagc ctggcagcgg ctgaagggcc 841 tggctctgca gaggcagggg aagctctttg gggcagcaga agttcagcgc tttaacaggg 901 atgtggatga gactatcagt tggattaagg aaaaggagca gttaatggcc tctgatgatt 961 ttggccgaga cctggcaagt gttcaggctc tgcttcggaa gcacgagggt ctggagagag 1021 atcttgctgc tctagaagac aaggtcaaag ccctgtgtgc tgaggctgac cgcctgcaac 1081 agtcccaccc tctgagtgca acacagattc aagtgaagcg agaggaactg attacaaact 1141 gggagcagat ccgcaccttg gcggcagaga gacatgcacg gctcaatgat tcatacaggc 1201 ttcaacgctt ccttgctgac ttccgtgacc tcaccagctg ggtgactgag atgaaagccc 1261 tcatcaatgc agatgagctt gccagtgatg tggctggggc tgaagccctg ctagatagac 1321 accaagagca caagggtgaa attgatgccc atgaagacag cttcaaatct gcagatgaat
```

-continued

```
1381 ctggacaggc actgcttgct gctggtcact atgcctcaga tgaagtgagg gagaagctga 1441 ccgtcctttc cgaggagaga gcggcgctgc tggagctgtg ggagctgcgc aggcagcagt 1501 acgagcagtg catggacctg cagctcttct accgggacac tgagcaggtg gacaactgga 1561 tgagcaagca ggaggcgttc ctgttgaatg aagacttggg agattccttg gatagtgtgg 1621 aagcgcttct taagaagcac gaagactttg agaaatccct tagtgcccag gaggaaaaga 1681 ttacagcatt agatgaattt gcaaccaagc taattcagaa caaccactat gcaatggaag 1741 atgtggccac tcgccgagat gctctgttga ccgccgcaa tgcccttcac gagagagcca 1801 tgcgtcgccg ggcccagcta gccgattctt ccatctgca gcagttttc cgtgattctg 1861 atgagctcaa gagttgggtc aatgagaaga tgaaaactgc cacagatgaa gcttataaag 1921 atccatccaa cctacaagga aaagtacaga agcatcaggc ttttgaggct gagctctcag 1981 caaaccagag ccgaattgat gccttggaga aagctggcca aaagctgatt gatgtcaacc 2041 actatgccaa ggatgaagtg gcagctcgta tgaatgaggt gatcagtttg tggaagaaac 2101 tgctagaggc cactgaactg aaaggaataa agcttcgtga agccaaccag caacagcaat 2161 ttaatcgcaa tgttgaggat attgaattgt ggctatatga agtagaaggt cacttggctt 2221 cggatgatta cggcaaagat cttaccaatg tgcagaacct ccagaagaaa catgccctgc 2281 tagaggcaga tgtggctgct caccaggacc gaattgatgg catcaccatt caggcccgcc 2341 agttccaaga tgctggccat tttgatgcag aaaacatcaa gagaaacag gaagccctcg 2401 tggctcgcta tgaggcactc aaggagccca tggttgcccg gaagcagaag ctggccgatt 2461 ctctgcggtt gcagcagctc ttccgggatg ttgaggatga ggacgtgg attcgagaga 2521 aagagcccat tgccgcatct accaacagag gtaaggattt aattgggtc cagaatctgc 2581 taaagaaaca tcaagcctta caagcagaaa ttgctggaca tgaaccacgc atcaaagcag 2641 ttacacagaa ggggaatgcc atggtggagg aaggccattt tgctgcagag gatgtgaagg 2701 ccaagcttca cgagctgaac caaaagtggg aggcactgaa agccaaagct tcccagcgtc 2761 ggcaggacct ggaggactct ctgcaggccc agcagtactt tgctgatgct aacgaggctg 2821 aatcctggat gcgggagaag gaacccattg tgggcagcac tgactatggc aaggacgaag 2881 actctgctga ggctctactg aagaaacacg aagctttgat gtcagatctc agtgcctacg 2941 gcagcagcat ccaggctttg cgagaacaag cacagtcctg ccggcaacaa gtggccccca 3001 cggatgatga gactgggaag gagctggtct tggctctcta cgactatcag gagaagagtc 3061 cccgagaggt caccatgaag aagggagata tccttacctt actcaacagc accaacaagg 3121 attggtggaa agtggaagtg aacgatcgtc agggttttgt gccggctgcg tacgtgaaga 3181 aattggaccc cgcccagtca gcctcccggg agaatctcct ggaggagcaa ggcagcatag 3241 cactgcggca ggagcagatt gacaatcaga cacgcataac taaggaggcc ggcagtgtat 3301 ctctgcgtat gaagcaggtg gaagaactat atcattctct gctggaactg ggtgagaagc 3361 gtaaaggcat gttggagaag agttgcaaga agtttatgtt gttccgtgaa gcgaatgaac 3421 tacagcaatg gatcaatgag aaggaagccc tctgacaag tgaggaggtc ggagcagact 3481 tggagcaggt tgaggtgctc cagaagaagt ttgatgactt ccagaaggac ctgaaggcca 3541 atgagtcacg gttgaaggac attaacaagg tagctgaaga cctggagtct gaaggtctca 3601 tggcagagga ggtgcaggct gtgcaacaac aggaagtgta tggcatgatg cccagggatg 3661 aaactgattc caagacagcc tccccgtgga agtctgctcg tctgatggtt cacaccgtgg 3721 ccaccttaa ttccatcaag gagctgaatg agcgctggcg gtccctacag cagctggccg 3781 aggaacggag ccagctcttg ggcagcgccc atgaagtaca gaggttccac agagatgctg
```

```
3841 atgaaaccaa agaatggatt gaagagaaga atcaagctct aaacacagac aattatggac
3901 atgatctcgc cagtgtccag gccctgcaac gcaagcatga gggcttcgag agggaccttg
3961 cggctctcgg tgacaaggta aactcccttg gtgaaacagc agagcgcctg atccagtccc
4021 atcccgagtc agcagaagac ctgcaggaaa agtgcacaga gttaaaccag gcctggagca
4081 gcctggggaa acgtgcagat cagcgcaagg caaagttggg tgactcccac gacctgcagc
4141 gcttccttag cgatttccgg gacctcatgt cttggatcaa tggaatacgg gggttggtgt
4201 cctcagatga gctagccaag gatgtcaccg gagctgaggc attgctggag cgacaccagg
4261 aacaccggac agaaatcgat gccagggctg gcactttcca ggcatttgag cagtttggac
4321 agcagctgtt ggctcacgga cactatgcca gccctgagat caagcagaaa cttgatattc
4381 ttgaccagga gcgtgcagac ctggagaagg cctgggttca gcgcaggatg atgctggatc
4441 agtgccttga actgcagctg ttccatcggg actgtgagca agctgagaac tggatggctg
4501 cccgggaggc cttcttgaat accgaagaca aaggagactc actggacagc gtagaggctc
4561 tgatcaaaaa acatgaagac tttgacaaag cgattaacgt ccaggaagag aagattgctg
4621 ctctgcaggc ctttgccgac cagctcatcg ctgccggcca ttatgccaag ggagacattt
4681 ctagccggcg caatgaggtc ttggacaggt ggcgacgtct gaaagcccag atgattgaga
4741 aaaggtcaaa gctaggagaa tctcaaaccc tccaacagtt cagccgggat gtggatgaga
4801 ttgaggcttg gatcagtgaa aaattgcaaa cagcgagtga tgagtcgtac aaggatccca
4861 ccaacatcca gctttccaag ctgctgagca agcaccagaa gcaccaggct tttgaagcag
4921 agctgcatgc caacgctgac cggatccgtg gggttatcga catgggcaac tccctcattg
4981 aacgtggagc ctgtgccggc agtgaggatg ctgtcaaggc ccgcctggct gccttagctg
5041 accagtggca gttcttggtg caaaagtcag cggaaaagag ccagaaactg aaagaagcca
5101 acaagcagca gaacttcaac acagggatca aggactttga cttctggctg tctgaggtgg
5161 aggccctgct ggcatccgaa gattatggca aagacctggc ttctgtgaac aacctgctga
5221 aaaagcatca actgctggaa gcagatatat ctgcccatga ggatcgcctg aaggacctga
5281 acagccaggc agacagcctg atgaccagca gtgccttcga cacctcccaa gtaaaggaca
5341 agagggacac catcaacggg cgcttccaga agatcaagag catggcggcc tcccggcgag
5401 ccaagctgaa tgaatcccat cgcctgcacc agttcttccg ggacatggat gacgaggagt
5461 cctggatcaa ggagaagaag ctgctggtgg gctcagagga ctacggccgg gacctaaccg
5521 gcgtgcagaa cctgaggaag aagcacaagc ggctggaagc agaactggct gcgcatgagc
5581 cggctattca gggtgtcctg gacactggca agaagctgtc cgatgacaac accatcggga
5641 aagaggagat ccagcagcgg ctggcgcagt tgtgggcagc tggaaagag ctgaagcagc
5701 tggcagctgc ccggggtcag cggctggaag agtccttgga atatcagcag tttgtagcca
5761 atgtggaaga ggaagaagcc tggatcaatg agaaaatgac cctggtggcc agcgaagatt
5821 atggcgacac tcttgccgcc atccagggct tactgaagaa acatgaagct tttgagacag
5881 acttcaccgt ccacaaggat cgcgtgaatg atgtctgcac caatggacaa gacctcatta
5941 agaagaacaa tcaccatgag gagaacatct cttcaaagat gaagggcctg aacgggaaag
6001 tgtcagacct ggagaaagct gcagcccaga gaaaggcgaa gctggatgag aactcggcct
6061 tccttcagtt caactggaag gcggacgtgg tggagtcctg gatcggtgaa aaggagaaca
6121 gcttgaagac agatgattat ggccgagacc tgtcttctgt gcagacgctc ctcaccaaac
6181 aggaaacttt tgacgctggg ctgcaggcct tccagcagga aggcattgcc aacatcactg
```

```
6241 ccctcaaaga tcagcttctc gccgccaaac acgttcagtc caaggccatc gaggcccggc 6301 acgcctccct catgaagagg tggagccagc ttctggccaa ctcagccgcc cgcaagaaga 6361 agcttctgga ggctcagagt cacttccgca aggtggagga cctcttcctg accttcgcca 6421 aaaaggcttc tgccttcaac agctggtttg aaaatgcaga ggaggactta acagaccccg 6481 tgcgctgcaa ctccttggaa gaaatcaaag ctttgcgcga ggcccacgac gccttccgct 6541 cctccctcag ctctgcccag gctgacttca accagctggc cgagctggac cgccagatca 6601 agagcttccg cgtagcctcc aaccccctaca cctggtttac catggaggcc ctggaggaga 6661 cctggaggaa cctacagaaa atcatcaagg agagggagct ggagctgcag aaggaacagc 6721 ggcggcagga ggagaacgac aagctgcgcc aggagtttgc ccagcacgcc aacgccttcc 6781 accagtggat ccaagagacc aggacatacc tcctcgatgg gtcctgtatg gtggaagagt 6841 cggggaccct cgaatcccag cttgaagcta ccaaacgcaa gcaccaggaa atccgagcca 6901 tgagaagtca gctcaaaaag atcgaggacc tggggccgc catggaggag ccctcatcc 6961 tggacaacaa gtacacggag cacagcaccg tgggcctcgc ccagcagtgg gaccagctgg 7021 accagctggg catgcgcatg cagcacaacc tggagcagca gatccaggcc aggaacacaa 7081 caggtgtgac tgaggaggcc ctcaaagaat tcagcatgat gtttaaacac tttgacaagg 7141 acaagtctgg caggctgaac catcaggagt tcaaatcttg cctgcgctcc ctgggctatg 7201 acctgcccat ggtggaggaa ggggaacctg accctgagtt cgaggcaatc ctggacacgg 7261 tggatccgaa cagagatggc catgtctcct tgcaagaata catggctttc atgatcagcc 7321 gcgaaactga gaacgtcaag tccagcgagg agattgagag cgccttccgg gccctcagct 7381 cagagggaaa gccttacgtg accaaggagg agctctacca gaacctgacc cgggaacaag 7441 ccgactactg cgtctcccac atgaagccct acgtggacgg caaggccgc gagctcccca 7501 ccgcgttcga ctacgtggag ttcacccgct cgcttttcgt gaactgagcc actccctggg 7561 tcacccaccc ctcgctgctt gccctgcgtc gccttgctgc atgtccgctc ctctgtgtgc 7621 tctcactttc cactgtaacc ttaagcctgc ttagcttgga ataagactta ggagaaaatg 7681 gtgcttcact aacccgcttc cggtccagtc acaatcatca tgtcactgtg gggacccaga 7741 tctgtgtctt gaagcagctg ccctcattcc gacttcagaa aatcgaagca gctggctcct 7801 ccccttgttc tctctcccac cctcccccaa atctgtttc atgtaaaaga caaataaatg 7861 atgacttccc ccaaaaaaaa aaaaaaaaa aaaaaaaaaa aaaaaaaaa aaaaaaaaa 7921 aaaa
```

One example of a nucleic acid sequence for human TFCP2L1 is available as NCBI accession number NM_014553 (gi: 212276201). This sequence is recited below for easy reference as SEQ ID NO:166.

```
  1 gggttcggag cgcgaagccg ccgctgggtc ctcggcgcgc cccgcgtctg cgcttgctgc 61 cgcgccccgg tcggcgcgct gggagttcca gccatgctct tctggcacac gcagcccgag 121 cactacaacc agcacaactc cggcagctac ctgcgtgatg tgctcgctct gcccatcttc 181 aagcaggagg aacccagct gtcccccgag aacgaggccc gcctgccacc cctgcaatat 241 gtgttgtgtg ctgccacgtc cccagccgtg aagctgcatg aagagacgct gacctacctc 301 aaccaaggtc agtcttatga atccgacta ctggagaatc ggaagctggg agactttcaa 361 gatctgaaca caaatatgt caagagcatc atccgtgtgg tcttccatga ccgccggctg 421 cagtatacgg agcaccagca gctggagggc tggcggtgga tcggccaggg gaccggatc 481 ctggacatcg atattccact gtctgttggt atcttggacc ccagggccag cccgacccag
```

-continued

```
 541 ctgaatgcag tcgagttttt gtgggaccct gcgaagagag cttctgcatt cattcaggta
 601 cactgcatca gcacagaatt cacccccagg aagcacgggg gcgagaaggg agtgcccttt
 661 cgagtccaga ttgacacgtt taagcagaac gagaatgggg agtacacgga gcacctgcac
 721 tcagccagct gccagatcaa ggtgttcaag ccgaagggac ccgatcggaa acagaagact
 781 gaccgggaga agatggagaa aagaactgcc caagagaagg agaaatacca gccgtcctat
 841 gaaaccacca tcctcacaga gtgctctcca tggcccgacg tggcctacca ggtgaacagc
 901 gccccgtccc caagctacaa tggttctcca aacagctttg gcctcggcga aggcaacgcc
 961 tctccgaccc accggtggag ggccctgccc gtgggcagtg accacctgct cccatcagct
1021 tcgatccagg atgcccagca gtggcttcac cgcaacaggt tctcgcagtt ctgccggctc
1081 tttgccagct tctcaggtgc tgacttgctg aagatgtccc gagatgattt ggtccagatc
1141 tgtggtcccg cagatgggat ccggctcttc aacgccatca aaggccggaa tgtgaggcca
1201 aagatgacca tttatgtctg tcaggagctg agcagaatcg agtgcccct gcagcagaag
1261 cgggacggca gtggagacag caacctgtct gtgtaccacg ccatcttcct ggaagagctg
1321 accaccttgg agctgattga gaagatcgcc aacctgtaca gcatctcccc ccagcacatc
1381 caccgagtct accggcaggg ccccacgggc atccatgtgg tggtgagcaa cgagatggtg
1441 cagaacttcc aagatgaatc ctgttttgtc ctcagcacaa ttaaagctga gagcaatgat
1501 ggctaccaca tcatcctgaa atgtggactc tgagcagcag tggacctcat acctgtctcc
1561 agctcccagc cctgtggatc cccgtggatg tagacattgc cccactgtaa gctgtggcct
1621 caccaggcaa gctgaggcca ggagggaccc tgcccagtct gtgaaagcta cagagcacca
1681 accagcagaa gcctgtggac accaagtacg gtgtacagaa agccagtggc tcctttctcc
1741 cttcctcttg gcctccagat tttgaatggt tccttgttct tttctattgg tccaaccctg
1801 acgttctaaa agggcaaaca gtggagacgt ctgctctgaa atccctcatc ccttagttgg
1861 aagctgattg ggtatcttgg tgctgcctgt attggtccct tctgaccact ctcctgcctc
1921 cagagaaagc tctgcttcac cctggaagct ggtacccttta cctcctcctc tgggagttgg
1981 ctgcatggcc agcactgccg acttgatggg agcagtttgc cctcattctc ctgtttcagg
2041 tttgcttccc ttctcagtga ccctggtgag catccgcctt tcctgttctt ggatgaattg
2101 atgggagtgg ggctattctg tgccttctac ctctttcttc tctacgttgt ttctaaggat
2161 ctgctgctgc ggaacccaaa gatgtgctcc tgtctctgca ctggcgcatt ggcatggtag
2221 atgccacaat gtatgtgcac ggcctttctc agagacatta gttctgaggc cctttgtggg
2281 gaggttaggg ggatggtaat agaaaaagac tattttattt cctggcaatc acgggtaagg
2341 aggattagga atgagtattc cattcctagg tgtcatcaga tgaccttgac caccacaata
2401 ccaggccctc ttggatggac ttatagaaag ttagagaaga ccttgttgaa ccgctgctaa
2461 acttgccaca ggagcgatgt gttttctctg agtgcccctc acttacatgt ttatctttgt
2521 ttgtagaggc tatgtttagg atattttgcc tgcatcagaa tgggtgcatc atctttctta
2581 atggcctaac tatcgggaaa tttgagtgtc agtaactgtg gtagactcag aaattcgtct
2641 ttgtcttgcc tctggttcct gggatccagt gatctctact ggcccagggc ttcagctctt
2701 ggttaattta ggttcatggg gaaccctctg accacctgaa tggatgtca tagcttctaa
2761 atggagcttc tgtggaatga agtgctagac tgaaggacta ccagaataaa acagggtcta
2821 caatggggag aacttgtttt atagatgagg aaaccaaggc tcagaggggc aaagtcacct
2881 gcatggtagc acatagtgat agggtagcga tataaattta tcatataaac caggacatct
```

-continued

```
2941 cggaataaaa ggggctctgt tagtcattat gttgggtaat agccgtggca ttcctacaga
3001 acagagtgag gacaggctcc tgattcctct tccttcttta gaggagaagc ggggagtggg
3061 ttaactaaca gctttattga gatgtcattc acatgccatt cagtttaccc attgctagtg
3121 tccaattgta ttcacagaac caccatcaat tcacagaatt acagtcaacg ttggtacatt
3181 ttcatcaccc ccagtaaaac cccgtaccct tggtctgtca ctcctgcttt cctaactcct
3241 gcagtccaag gcagccatga atctactttc tatgtaagat taacctactc tggacatttc
3301 atatatctgg aatcatgtga tatctctttt gtgactggct tcttccactg aatgttttct
3361 agggccgtcc aagttgagga tgtatcagta cttcattctt ttgtattgct gaataatact
3421 tcattgtata gatagaccac atttgtttat tgattcatca gttgatggac atttgtgtgt
3481 ttttactttt tggctactct gaatgatgct gctatgaaca tatttctaca agattttgtg
3541 tggacatatg ttttcatttc ttttagcaat atacatagga gtggaattgc taggtcttac
3601 agtaactccg tgttttaact ttttgagaaa ctgccagact gttttctata gcagctgtac
3661 cattttacat tcccaccagc aatgtatcca ggtttcaatt tgtctacatc ctcatcaaca
3721 cttgctatta tctgtctttt tgcttttagc atcctaatga gtatgaaatg ctatcttgtg
3781 gttttgattt gcattcccct gatggcaact gatgctgagt gtcttttcct gtgcttacgg
3841 gccatgcgta tttctttgga gaaaggtcta tccaggtcct ttgcctattt ttaattgagt
3901 tgtctttttt tttttaagtt ttctgttttc ctaaccacta gactaccagg gatgagcctt
3961 cttttatta ttgagttggg tgagctattt gtatattcta gacgccagtc ttttatcagg
4021 tatatgactg gtaaaaatgt tctccccttc tgtggattgt tttcagtttc ttgttggtgt
4081 cctttgagac acaaaacttt ttaactttga tgatttccaa gatacgtatt tttttttctat
4141 tgtcacttgt gcttttggtg ccatatctag aaaaccattg cctaatccaa ggtcaagaag
4201 attaatgcct gtgttttctt ctaagaacta tacttttagt tctcacaatg gtctttgatc
4261 catttcgagt atatttttat atatgatgtg atgtaggggt ccagcttcat tcttttgctt
4321 gtggatctcc acttgtccca ctgctgatta ttgagaaaaa tatcctttct ccacggaatt
4381 gtcttggcat ccttgctaaa ggcctctgct tcttactgga tcttctttcc tgggacatgg
4441 tgtcgttggg aagcttacct ttttttttttt tttacttagt ctgtgtttgg ttccaccagt
4501 tttatgctgc ctttctactc tgttcttgct gtctccctct ttacctgagt caacggtact
4561 gagtcctatc tctctctgat gttccccagt cttccttggt gcatgttcta gctccacaca
4621 ctagtccttg gaggaaggtt gagaccaatg atttcctgtt atgagtcatg aggaaactga
4681 atcacctaga agtggaataa tgtgctcagg gtcaccatag cccattagtg gaaggaccag
4741 gactagacct ttagtcttct gaggtccagc cccttaggct gtctgtcatc actgtaccca
4801 agtgatgtca ctaccaaggc caaatgatgg tgggctaaat tttaattctc aaaagtgtag
4861 gaggctaata ttgtcttcta agttccaaaa gaagatgtaa taaaagtctg ttaccttaag
4921 tgtgctatta gtagagtctt ccattttct ggcatgcccc tggcatctgc tcttcttacc
4981 ttctcgtggt tgtagttaaa gcttatagct tatgaaagaa tagaaaataa taaataccaa
5041 aaaaaagtac acatggtaat ttggtaccaa aatatctcag ctgcctaatt tagcagctca
5101 tcccttccac agggtcaga tgagctaaag ctccaggttt tattttcat ttgattgaca
5161 tacagaaaag ccatagccct tcccacagct gtccagggtc tttcctgtga gtccggaggt
5221 gctggcctat tgagcaggac agctcttccc agggcattcc caccaacctg tggcttctga
5281 actgtagctt cttttacag tgaacccag agggaaataa gacagacaca tgtgctcagg
5341 ccaccatctt gaactggaag cccaaagctg agttccttac tcttaggtcg tcacggtttt
```

```
5401 tgcggggtat ctgcaaggtt gagataaacc ctttcctgtt taccaggttg tcctttctgg 5461 atgaagggac agaggctgtt gaatggagga ataataggtt tgctggagga ggggcatggt 5521 atgcctgtgg aaaggacagg atggggtggg gaggtcgagg ctttgacttg gggtcctaaa 5581 caaaggtcag gtgttgccct agtgacctct tgcccagaca gcccagagcc ccttacacag 5641 agctattaac ctagggaagg ctttaccagc agtggactgg agccagccag ggtcacaagt 5701 ttccaagtcc agcattgctt caggggctgg cctgagtaac tgaagatctg aaaatcatta 5761 acaagtcgat gaaataaacg aaaagcctc ttaggctgtt gtcagtggag cagagggaga 5821 aagtccctag gcgctcagag ggggtgagaa agcagtggat gattgggcgg gggtgggga 5881 ttagatgttg acactgcctg gggtgtagga agaggaacag agaacccaga gtcagggtcc 5941 tagatcccag accctcgctc agtatgagtc tctttgcctc tctgggtctc tatctcctcc 6001 tcttacaaat acaggcttgg tgatctctga agatggcacc aacctgccat gaaatgaatc 6061 tgagggggttt tcccattttt ccctccatca aaatcgtaca aaaagctgga cgtggtggcc 6121 catgcctcta atcctagcat tttgggaggc cgaggtggga gaatcacttg acgccaagag 6181 ttcgagacca gcctgggcat cgtagtgaga ctccatctct gtcttttttga aaataaaaaa 6241 tctttgaaaa ttgcacaaca ggcaggagac ctttacgtgt gcccatcctg gttgtacaca 6301 gtgccaccag tgctcctgca gtgcaaggcg gcatgcttct tgacatggg cagattgtgt 6361 ccatcgtgtc tttgggaatc agccctagct cctaactggg ctgactactt cctccgcaaa 6421 cttatggggg ctcccagata ttccttgcca gccaggggcc agacacagtg caggcacagt 6481 ctgtgtcatt ggtgcacatg tgcgtgttta catgtgtacc tgggttcctt cccttgccca 6541 tgaatttgcc atgagcacag ccagaagcag cctcagcttg gcaaggtgtg gagatgactg 6601 ctgttccctt cgcatttggg gaaaacaggc tccctcggta gctcgatgat cctcttttga 6661 tcttgtgtga cctcctggag agtggatgaa gctggtggcc ttagcttttc tagacagtgt 6721 aagtggcact gggcaaggcc cccagagcag ggcaaggtct ctagagcggg tctcccacat 6781 gactggcttc acacaggcac ttccgctcgg gttgcatgct ctgtgtcatc ttaccggtcc 6841 agggttgcag gtaggaaatg tttgtaccct cttctgattg ccacctcctt cccatcgccc 6901 cttagggaca gggcttgagg gccagtgagg cgctggtcag gcaccccagg cctccttggg 6961 acctgcccag gggcaccctg agagctcctg aaaccccac ttagcttcca gacctttctg 7021 caaaagctcc tcctggcttt cctccctccc ccaatctatg ggtcacagct aacagatctg 7081 agggcaactg ctgtgctagt ggccagggct gcacctgcca tccccggctc tgccactta 7141 gggccttcta gaggcagtgt ccttaggaag tagctctgag gcatgggttt tctgctcctg 7201 tgcagggcag ctgatgggat aaggtgggga aggacggtca gtgcttgggc cccagctggc 7261 cagcctggcg atggggaaac caaaccatgt cccccagcga agggccagag tgggaacctg 7321 tcctcatgcc cttcgtcctg aggagccctg aggtgggcag caggggccag gggaagtttt 7381 caggccttca tcaaagagaa caacatcctc agctccgcac ccctcatcct gtatcagcac 7441 ttaccggtgt gtgactgccc ttgtcagcta gcatacggtg ggcccacctg gcccactggc 7501 tgtttatgcc actgatttat gatagggaat attatctttg aacccaatga agtgttttct 7561 cccccatcac aaaaaaaaaa attcttattt ttagtagaca tgtatttacc aaaaatatgt 7621 actcaattat tgtattttgg attttatcaa tttaaaaatt gtggaaattt gtttgctctt 7681 acgccaacat aatattgatt ttgcctcttg gctctgaaag cccaaaatat ttaccgtcta 7741 gcccgttaca gaaaaagtct gctgactact gagccagacc tccattacct ccatccctgt
```

```
-continued
7801 tggattattt aaagaaagcc tcagacagta agggctttt taaaagaata aaatgacttg 7861 gtttgcgctt ggaagcaggg gaagcattca gatgagcggt ttctgcatta accctgccta 7921 tcacgcatct cgtgtcctgt gtggctggcg agcccccctt ggaaggttct ggtgcttcag 7981 ctggctcctg cagagtccac cccgcctcgt ggtgggaatg cagagccctt tgctttcctt 8041 cttgccgcct gcttcctgtt cctggggacc cgctgggcct ttggtctgca tcccctggcc 8101 aggtccctca gggttgatgc gtggagaagg actttgagca gtggtgggca gcagtggcct 8161 cctggccagc tcacactctt gtcctgggag gggcagcctg atctcacctc cacctagtac 8221 cttggggact gaggaccttt tggcttctct ggagcctgca agcctcttcc catgtgtcca 8281 gctgctcttc ctgctacaaa ggggactgct cacagtggcc tcagcttggt ggttttgagg 8341 ggccgccccc cggccctcca taagggtatc ctgggcctga gaattctgca tctgccattg 8401 gaggatggac agcctcaaat ggaaggagtc ccacgggaga tgggtccgag gtccggctgt 8461 ggccatccag cccctgtgg cttgtccagc ctctgtgcac ccctggtgtc ttcactccag 8521 gggcagacag cagccactgc agttcctttc ttcgtgagta acagtagtga tagcagctgg 8581 ggctaacagg ctaggctttg tgttctgcgc atttggtcag cttctcactc gatcctccct 8641 aaagcaatgg ggaggccccc actagcccag ttttcaggaa gtcaactggg aggttagatg 8701 ggggccaggg tcccacagct actgatggcc cgagccaggt tgagcttcct ggtgtccagt 8761 ccggatccca cttgcagatc tcatgctctc agataggtgg gacaagttct tttgtcacag 8821 tgctggctct gtcctgaggc ctcattgctg gctgggtgtg ctctgctggg aaaagctttg 8881 cggggcttgc ttggttaacc acagaagaga aggggactgt ttggggtgcc tctctgcagc 8941 ctccccgtgc tgggtggaag cacggttact gtgttctcta atgttcatgt atttaaaatg 9001 atttctttct aaagatgtaa cctccacacc tttctccaga ttgggtgact cttttctaaa 9061 ggtggtggga gtatctgtcg gggtggtgtg gcccttggat gggtcaggtg ggtgtgagag 9121 gtcctgggga ggtgggcgtt gagctcaaag ttgtcctact gccatgtttt tgtacctgaa 9181 ataaagcata tttttgcactt gttactgtac catagtgcgg acgagaagtc tgtatgtggg 9241 atctgtgctt gggttagaat gcaaataaaa ctcacatttg taagaaaaaa aaaaaaaaa 9301 aaaaaa
```

One example of a nucleic acid sequence for human TIAM1 is available as NCBI accession number NM_003253 (gi: 115583669). This sequence is recited below for easy reference as SEQ ID NO:167.

```
  1 gccccgcatc gtgcccggcc ccgtcgcgga gatcccggac gaccgtcgcg ggttgatggt 61 cgcattccag atgtaaacag cttcagaagc ctgacggtca tatggtagaa tcactgtgga 121 ctgagaccca cctttctaga cctgaagccc aggaggagga agaggaggct ggttggtacc 181 atgggcataa tgctctgaat cctagtctct cacctagtat gtgagcagtc cctgcagatg 241 gcccatttgg agatcttgac aaagcctctt ctgtttccaa tggggttttt ggcgcattct 301 cacagactta gatgaaactg tgatggccac cgcagggggc aggtgctgac atcgtcccca 361 gccctgtggc tgttcatccg gacatcattt ccaacctcaa tatctaaatg ccacagtgct 421 cttgagcaa gttgggctgg ggaccactgt tgcctttaa gaccataaaa ccatgggaaa 481 cgcagaaagt caacatgtag agcacgagtt ttatggagaa aagcatgcca gcctggggcg 541 caagcacact tcccgctccc tgcgcctctc gcacaagacg cggaggacca ggcacgcttc 601 ctcggggaag gtgatccaca ggaactccga agtgagcacc cgatccagca gcaccccag 661 catcccccag tccctggctg aaaatggcct ggagcccttc tcccaagatg gtaccctaga
```

-continued

```
 721 agacttcggg agccccatct gggtggaccg agtggacatg ggcttgagac ctgtgtctta
 781 cactgactct tctgtcactc ccagcgtaga cagcagcatc gtcctcacag cagcctctgt
 841 gcagagcatg ccagacactg aggagagcag gctttacggg gatgacgcta catatttggc
 901 tgagggaggc aggaggcagc attcctatac atccaatggg cccactttca tggagacggc
 961 gagctttaag aagaaacgct ccaaatctgc agacatctgg cgggaggaca gcctggaatt
1021 ctcactctct gatctgagcc aagaacattt aacaagcaac gaagaaatct tgggttccgc
1081 cgaagagaag gactgcgagg aggctcgggg gatggaaacg cgggcgagtc cgcggcagct
1141 cagcaccctgt cagagagcca attccttggg tgacttgtat gctcagaaaa actctggagt
1201 gacagcaaac ggggggccgg ggagcaaatt tgcaggctac tgtcggaatt tggtgtctga
1261 tattcccaat cttgcaaacc ataagatgcc accagctgct gctgaagaga ctcctccgta
1321 cagtaattat aacacacttc cctgtaggaa atctcactgt ctctctgaag gtgccaccaa
1381 cccacaaatt agccatagca acagcatgca aggcagaaga gctaaaacaa ctcaggatgt
1441 taatgcaggc gagggcagtg agtttgcaga cagtgggatt gaaggggcca ctaccgacac
1501 ggacctcctg tccaggcgat ctaatgccac caactccagc tactcaccca ccacaggccg
1561 ggcctttgtg ggcagcgaca gcggcagcag ctccaccggg gatgcggctc gtcaggggt
1621 gtacgagaac ttccggcggg agctggagat gagcaccacc aacagcgaga gcctggagga
1681 ggccggctcg gcgcacagcg atgagcagag cagcggcacc ctgagctctc cgggccagtc
1741 ggacatcctg ctgaccgccg cacagggcac ggtgcgcaag gccggcgccc tggccgtcaa
1801 gaacttcctg gtgcacaaga gaacaagaa ggtggagtca gccacccgga ggaagtggaa
1861 gcactactgg gtgtccctga aaggatgcac gctattttc tacgagagcg acggcaggtc
1921 tgggatagac cacaacagca tccccaaaca cgccgtctgg gtggagaaca gcattgtgca
1981 ggcggtgcct gagcacccca agaaggactt tgtcttctgc ctcagcaatt ccctgggtga
2041 tgccttcctt tttcagacca ctagccagac ggagcttgaa aactggatca ccgccatcca
2101 ctctgcctgc gccactgcgg tcgcgaggca ccaccacaag gaagacacgc tccgactcct
2161 gaaatcagag atcaaaaaac tggaacagaa gattgacatg gatgaaaaga tgaagaaaat
2221 gggtgaaatg cagctgtctt cagtcactga ctcaaagaaa aagaaaacaa tattagatca
2281 gatctttgtc tgggagcaaa atctcgagca gttccaaatg gacctgtttc gtttccgctg
2341 ttatttagcc agccttcagg gtggggagct gccaaaccc aaaaggcttc tcgcttttgc
2401 aagtcgacca acgaaagtgg ccatgggccg ccttggaatc ttttcggtat catcgtttca
2461 tgccctggtg gcagcacgca ctggtgaaac tggagtgaga agacgtactc aggccatgtc
2521 cagatccgcg agcaagcgaa ggagcaggtt ttcttctctg tggggtctgg atactacctc
2581 caaaaagaag cagggacggc caagcatcaa tcaggtgttt ggagagggaa ccgaagctgt
2641 aaagaaatct ttagagggaa tatttgatga cattgttcca gatggcaaga gggagaaaga
2701 agtggtctta cctaacgttc accagcacaa ccctgactgc acatttggg tccacgagta
2761 tttcactcca tcctggttct gtctgcccaa taatcagcct gccctgacgg tcgtccggcc
2821 aggcgacact gcacgggaca ccctggagct gatttgcaag acacatcaac tggatcattc
2881 tgctcattac ctgcgcctga aatttctaat agaaaacaaa atgcagctct atgttccaca
2941 gcccgaggaa gacatctatg agctgctgta caagaaatt gaaatctgtc caaagtcac
3001 tcagagcatc cacattgaga agtcagatac agctgctgat acttacgggt tttcactttc
3061 ttctgtggaa gaagatggta ttcgaaggct gtacgtgaat agtgtgaagg aaaccggttt
```

-continued

```
3121 agcttccaag aaaggcctga aagcaggaga tgagattctt gagatcaata atcgtgctgc 3181 tgacgccctg aactcttcta tgctcaaaga tttcctctca cagccctcgc tgggcctcct 3241 ggtgaggacc taccccgagc tggaggaagg agtggagctg ctggaaagcc cgccccaccg 3301 agtggacggc cctgccgacc ttggcgagag ccccctcgcc tttctcacca gcaacccagg 3361 gcacagcctt tgcagcgagc agggcagcag tgctgagacc gctccagagg agaccgaggg 3421 gccagacttg gaatcctcag atgagactga tcacagcagc aagagtacag aacaggtggc 3481 cgcattttgc cgcagtttgc atgagatgaa ccccctctgac cagagcccat ctcctcagga 3541 ctccacgggg cctcagctgg cgaccatgag acaactctcg gatgcagata gctgcgcaa 3601 ggtgatctgc gagctcctgg agacggagcg cacctacgtg aaggatttaa actgtcttat 3661 ggagagatac ctaaagcctc ttcaaaaaga aacttttctc acccaggatg agcttgacgt 3721 gcttttttgga aatttaacgg aaatggtaga gtttcaagta gaattcctta aaactctaga 3781 agatggagtg agactggtac ctgatttgga aaagcttgag aaggttgatc aatttaagaa 3841 agtgctgttc tctctggggg gatcattcct gtattatgct gaccgcttca agctctacag 3901 tgccttctgc gccagccaca caaaagttcc caaggtcctg gtgaaagcca agacagacac 3961 ggctttcaag gcattcttgg atgcccagaa cccgaagcag cagcactcat ccacgctgga 4021 gtcgtacctc atcaagccca tccagaggat cctcaagtac ccacttctgc tcagggagct 4081 gttcgccctg accgatgcgg agagcgagga gcactaccac ctggacgtgg ccatcaagac 4141 catgaacaag gttgccagtc acatcaatga gatgcagaaa atccatgaag agtttgggcc 4201 tgtgtttgac cagctgattg ctgaacagac tggtgagaaa aaagagggttg cagatctgag 4261 catgggagac ctgcttttgc acactaccgt gatctggctg aacccgccgg cctcgctggg 4321 caagtggaaa aaggaaccag agttggcagc attcgtcttc aaaactgctg tggtccttgt 4381 gtataaagat ggttccaaac agaagaagaa acttgtagga tctcacaggc tttccattta 4441 tgaggactgg gacccctttca gatttcgaca catgatcccc acggaagcgc tgcaggttcg 4501 agctttggcg agtgcagatg cagaggcaaa tgccgtgtgt gaaattgtcc atgtaaaatc 4561 cgagtctgaa gggaggccgg agagggtctt tcacttgtgc tgcagctccc cagagagccg 4621 aaaggatttc ctaaaggctg tgcattcaat cctgcgtgat aagcacagaa gacagctcct 4681 caaaaccgag agccttccct catcccagca atatgtccct tttggaggca aaagattgtg 4741 tgcactgaag ggggccaggc cggccatgag cagggcagtg tctgccccaa gcaagtctct 4801 tgggaggagg aggcggcggc tggctcgaaa caggtttacc attgattctg atgccgtctc 4861 cgcaagcagc ccggagaaag agtcccagca gccccccggt ggtggggaca ctgaccgatg 4921 ggtagaggag cagtttgatc ttgctcagta tgaggagcaa gatgacatca aggagacaga 4981 catcctcagt gacgatgatg agttctgtga gtccgtgaag ggtgcctcag tggacagaga 5041 cctgcaggag cggcttcagg ccacctccat cagtcagcgg gaaagaggcc ggaaaaccct 5101 ggatagtcac gcgtcccgca tggcacagct caagaagcaa gctgccctgt cggggatcaa 5161 tggaggcctg gagagcgcaa gcgaggaagt catttgggtt aggcgtgaag actttgcccc 5221 ctccaggaaa ctgaacactg agatctgact gcgtcacctg ccccgtagag aatgtgtgta 5281 gatacttcct gccctaactc tgcccaccct cctgtaccgt cgacaagaat gtccccttag 5341 gtcgcgctct tgcacacacg gttttggcag ctgacttggt tctgaagcca tgtagccacc 5401 caactttgtc attttcaaca acatcagaaa gaattgatca gaatcccaaa taagcttgag 5461 tcctatcttg tgtatattac taagggcttt tatttattct caataaatca gggcctgaac 5521 aattaaaaga aaaaagattc tatagcactg gaaagcaaat caccccagga gttaacggat
```

```
-continued
5581 gtacaacaga ttaatttaag ggatagtagc acacacacga tccttctatc tgaaatcagt 5641 ctcctagctg gggaaacctc tttcacacac aaaatgaaat gtgtacagct tgccgtgttc 5701 tgactgtacc cttccctctt ccatgtctga aatctccgt gtattttaag aatgtgtgag 5761 gagagggtgg cgattcatgt ttcaatgagc ctctttttt ttttccttcc tgttttggtc 5821 tatggctggt cttactctgt gtccatgttc ggaagctcta gttttgcata gaattataga 5881 gatgccaaac tctttgaaaa gagatccaaa tttatcgctt gagagaaaga aaagaaacac 5941 tattttttgt attttacctg agatacaggg gcacaaatag atgagaattt tacagtgtta 6001 gtgtatgtat ccctgagcct aaaaaatgag gatataacct tttacagaga gagtgaggcg 6061 tggtggtttt atatttatat atgaaaggcc agcaagctca tgcgaaggat atacttttct 6121 tccaaaaagc ggatttttt tttttaatgt ttgaatctat atttgagatg ggagtttggt 6181 tggattaaac atgacacccc ggtgggcggt gtgtgtgtct gttgcacatg gcagggaggg 6241 gagcctcctt ctcatggggt tgccatggtg atcattggtt tttccatcaa aattgcatct 6301 tcatccatag attaccttcc ccttccctga cagtccataa ccaaacccttt aaacagaaca 6361 acctctttaa aaacttctct tgtgtttaac actttcttca tgccaacgaa acagggtaaa 6421 catgctcaaa acattaacag tctaaacaga tatccaaata ctaagaagaa aaacaagtta 6481 tagcactttc aattttttt ttttttttaa aaaaaggttt atagcttttt cttttcccat 6541 gtcacaatgt ccacttccta agaagggttt aaaatactat gaaaactttc tttttgggga 6601 aaatatctat ttggtgtttg acacatcagt aggtactta aagacctgaa ttttatagta 6661 gctttaggag ttatatttta taaaaatcag ttatgactt atatttccag acaatagaga 6721 gttcagtaca tcatgctctt gtgcctctgc ctgcttttcc tgcgttccca ccctgtattc 6781 cccccgcctt tcgggtttcc agggcttcga gcttgatctt ttgaaagttt tattctatta 6841 aatttttgct atatcttctg gttttctgaa aaagctttag aatggtttct atacccttg 6901 tatcactgca ttttttccata tcatctccgg ttcgatcgcg tccagatgga aaacggaagc 6961 agaggcttct aatcgtcgca tttactggct ccagtgcaac acatccatct gaaaacactc 7021 ggaagtctgg tgcttggaga gggtgccatt gtctcttgta cataaggtca tgacgtgtct 7081 atgtcaaaag ttcttatata tttcttttat aagctgaaag aaggtctatt tttatgtttt 7141 taggtctatg aatggaacgt tgtaaatgct tgtcaaacaa taaaaataac gaaaagtgaa 7201 aaaaaaaaaa aaaaaaaa
```

One example of a nucleic acid sequence for human TIMP1 is available as NCBI accession number NM_003254 (gi: 73858576). This sequence is recited below for easy reference as SEQ ID NO:168.

```
  1 tttcgtcggc ccgccccttg gcttctgcac tgatggtggg tggatgagta atgcatccag 61 gaagcctgga ggcctgtggt ttccgcaccc gctgccaccc ccgcccctag cgtggacatt 121 tatcctctag cgctcaggcc ctgccgccat cgccgcagat ccagcgccca gagagacacc 181 agagaaccca ccatggcccc ctttgagccc ctggcttctg gcatcctgtt gttgctgtgg 241 ctgatagccc ccagcagggc ctgcacctgt gtcccacccc acccacagac ggccttctgc 301 aattccgacc tcgtcatcag gccaagttc gtgggacac cagaagtcaa ccagaccacc 361 ttataccagc gttatgagat caagatgacc aagatgtata agggttcca agccttaggg 421 gatgccgctg acatccggtt cgtctacacc ccgccatgg agagtgtctg cggatacttc 481 cacaggtccc acaaccgcag cgaggagttt ctcattgctg gaaaactgca ggatggactc
```

-continued

```
541 ttgcacatca ctacctgcag ttttgtggct ccctggaaca gcctgagctt agctcagcgc 601 cggggcttca ccaagaccta cactgttggc tgtgaggaat gcacagtgtt tccctgttta 661 tccatcccct gcaaactgca gagtggcact cattgcttgt ggacggacca gctcctccaa 721 ggctctgaaa agggcttcca gtcccgtcac cttgcctgcc tgcctcggga gccagggctg 781 tgcacctggc agtccctgcg gtcccagata gcctgaatcc tgcccggagt ggaagctgaa 841 gcctgcacag tgtccaccct gttcccactc ccatctttct tccggacaat gaaataaaga 901 gttaccaccc agcagaaaaa aaaaaaaaaa a
```

One example of a nucleic acid sequence for human TNS3 is available as NCBI accession number NM_022748 (gi: 134152712). This sequence is recited below for easy reference as SEQ ID NO:169.

```
   1 agaatgggaa actgccttgg gagaagcccc aagtgagccc aagggcgcag agcagaagga 61 ccctggagtg taagagccta gattgcaagc ctggcaggag gagccggaag aattaacctc 121 gagtctgcac gcttttaaga acaaggcctt taaaaaatcc aaagtgtgtg gagtttgcaa 181 acaaattatt gacggtcaag gtatttcatg ccgagcctgc aagtattcct gccacaagaa 241 atgtgaagcc aaggtggtga ttccctgcgg tgtgcaagtc cgactggaac aggctccagg 301 gagttccacg ctgtccagtt ctctctgccg tgataaacct ctgcggcccg tcatcctgag 361 tcccaccatg gaggagggcc atgggctgga cctcacttac atcacggagc gcatcatcgc 421 tgtgtccttc cctgccggct gctctgagga gtcctacctg cacaacctac aggaggtcac 481 gcgcatgctc aagtccaagc acggggacaa ctacctggta ttaaaccttt cagaaaagag 541 atatgacctt acgaagctta acccaaagat catggatgtg ggctggccag agctccacgc 601 accgccctg gataagatgt gtaccatatg caaggcgcag gagtcctggc tgaacagcaa 661 cctccagcat gtggtcgtca ttcactgcag gggcgggaaa ggacgcatag gagtggtcat 721 atcatcctac atgcatttca ccaacgtctc agccagcgcc gaccaggccc ttgacaggtt 781 tgcaatgaag aagtttatg atgacaaagt ttcagcttta atgcagcctt cccaaaaacg 841 gtatgttcag ttcctcagtg ggctcctgtc cggatcggtg aaaatgaatg cctctcccct 901 gttcctgcat tttgtcatcc tccacggcac ccccaacttc gacacaggtg gagtgtgccg 961 gccctttctg aagctctacc aagccatgca gcctgtgtac acctccggga tctacaacgt 1021 tggcccagaa aaccccagca ggatctgcat cgtcatcgag ccggcccagc ttctgaaggg 1081 agatgtcatg gtgaaatgct accacaagaa ataccgctcg gccacccgtg acgtcatttt 1141 ccgcctgcag tttcacactg gggctgtgca gggctacggg ctggtgtttg gaaggagga 1201 tctggacaat gccagcaaag atgaccgttt tcctgactat gggaaggttg aattagtctt 1261 ctctgccacg cctgagaaga ttcaagggtc cgaacacttg tacaacgacc acggtgtgat 1321 tgtggactac aacacaacag acccactgat acgctgggac tcgtacgaga acctcagtgc 1381 agatggagaa gtgctacaca cgcagggccc tgtcgatggc agcctttacg cgaaggtgag 1441 gaagaaaagc tcctcggatc ctggcatccc aggtggcccc caggcaatcc cggccaccaa 1501 cagcccgac cacagtgacc acaccttgtc tgtcagcagt gactccggcc actctacagc 1561 ctctgccagg acggataaga cggaagagcg cctggcccca ggaaccagga ggggcctgag 1621 tgcccaggag aaggcagagt tggaccagct gctcagtggc tttggcctgg aagatcctgg 1681 aagctccctc aaggaaatga ctgatgctcg aagcaagtac agtgggaccc gccacgtggt 1741 gccagcccag gttcacgtga atggagacgc tgctctgaag gatcgggaga cagacattct
```

-continued

```
1801 ggatgacgag atgccccacc acgacctgca cagtgtggac agccttggga ccctgtcctc
1861 ctcggaaggg cctcagtcgg cccacctggg tcccttcacc tgccacaaga gcagccagaa
1921 ctcactccta tctgacggtt ttggcagcaa cgttggtgaa gatccgcagg gcaccctcgt
1981 tccggacctg ggccttggca tggacggccc ctatgagcgg gagcggactt ttgggagtcg
2041 agagcccaag cagccccagc ccctgctgag aaagccctca gtgtccgccc agatgcaggc
2101 ctatgggcag agcagctact ccacacagac ctgggtgcgc cagcagcaga tggttgtagc
2161 tcaccagtat agcttcgccc agatggggga ggcccggctg gtgagccgct gccctgcaga
2221 caatcctggc ctcgtccagg cccagcccag agtgccactc accccaccc gagggaccag
2281 cagtagggtg gctgtccaga ggggtgtagg cagtgggcca catcccctg acacacagca
2341 gccctctccc agcaaagcgt tcaaacccag gtttccagga gaccaggttg tgaatggagc
2401 cggcccagag ctgagcacag gcccctcccc aggctcgccc accctggaca tcgaccagtc
2461 catcgagcag ctcaacaggc tgatcctgga gctggatccc accttcgagc ccatccctac
2521 ccacatgaac gccctcggta gccaggccaa tggctctgtg tctccagaca gcgtgggagg
2581 tgggctccgg gcaagcagca ggctgcctga cacaggagag ggcccagca gggccaccgg
2641 gcggcaaggc tcctctgctg aacagcccct gggcgggaga ctcaggaagc tgagcctggg
2701 gcagtacgac aacgatgctg gggggcagct gcccttctcc aaatgtgcat ggggaaaggc
2761 tggtgtggac tatgccccaa acctgccgcc attcccctca ccagcggacg tcaaagagac
2821 gatgaccccct ggctatcccc aggacctcga tattatcgat ggcagaattt taagtagcaa
2881 ggagtccatg tgttcaactc cagcatttcc tgtgtctcca gagacaccgt atgtgaaaac
2941 agcgctgcgc catcctccgt tcagcccacc tgagccccg ctgagcagcc cagccagtca
3001 gcacaaagga ggacgtgaac cacgaagctg ccctgagacg ctcactcacg ctgtggggat
3061 gtcagagagc cccatcggac ccaaatccac gatgctccgg gctgatgcgt cctcgacgcc
3121 ctcctttcag caggcttttg cttcttcctg caccatttcc agcaacggcc ctgggcagag
3181 gagagagagc tcctcttctg cagaacgcca gtgggtggag agcagcccca agcccatggt
3241 ttccctgctg gggagcggcc ggcccaccgg aagtcccctc agcgctgagt tctccggtac
3301 caggaaggac tccccagtgc tgtcctgctt cccgccgtca gagctccagg ctcctttcca
3361 cagccatgag ctgtccctag cagagccacc ggactccctg gcgcctccca gcagccaggc
3421 cttcctgggc ttcggcaccg ccccagtggg aagtggcctt ccgcccgagg aggacctggg
3481 ggccttgctg gccaattctc atggagcgtc accgacccc agcatcccgc tgacagcgac
3541 aggggctgcc gacaatggct tcctgtccca caactttctc acggtggcgc tggacacag
3601 cagccaccac agtccaggcc tgcagggcca gggtgtgacc ctgcccgggc agccacccct
3661 ccctgagaag aagcgggcct cggaggggga tcgttctttg ggctcagtct ctccctcctc
3721 cagtggcttc tccagcccgc acagcgggag caccatcagt atccccttcc caaatgtcct
3781 tcccgacttt tccaaggctt cagaagcggc ctcacctctg ccagatagtc caggtgataa
3841 acttgtgatc gtgaaatttg ttcaagacac ttccaagttc tggtacaagg cggatatttc
3901 aagagaacaa gccatcgcca tgttgaagga caaggagccg ggctcattca ttgttcgaga
3961 cagccattcc ttccgagggg cctatggcct ggccatgaag gtggccacgc ccccaccttc
4021 agtcctgcag ctgaacaaga aagctggaga tttggccaat gaactcgtcc ggcacttttt
4081 gatcgagtgt accccgaagg gagtgcggtt gaaagggtgc tcgaatgaac catatttcgg
4141 gagcctgacg gccttggtgt gccagcattc catcacgccc ttggccttgc cgtgcaagct
```

```
4201 gcttatccca gagagagatc cattggagga aatagcagaa agttctcccc agacggcagc
4261 caattcagca gctgagctgt tgaagcaggg ggcagcctgc aatgtgtggt acttgaactc
4321 tgtggagatg gagtccctca ccggccacca ggcgatccag aaggccctga gcatcaccct
4381 ggtccaggag cctccacctg tgtccacagt tgtgcacttc aaggtgtcag cccagggcat
4441 caccctgaca gacaatcaga ggaagctctt cttccggagg cattaccccg tgaacagtgt
4501 gattttctgt gccttggacc cacaagacag gaagtggatc aaagatggcc cttcctcaaa
4561 agtctttgga tttgtggccc ggaagcaggg cagtgccacg gataatgtgt gccacctgtt
4621 tgcagagcat gaccctgagc agcctgccag tgccattgtc aacttcgtat caaaggtcat
4681 gattggttcc ccaaagaagg tctgagaact cccctccctc cctgaccca ccgatgcctc
4741 tcgaagccct ggagacagcc gttgggtgag ggtggggccc ccacttttta ccaaactagt
4801 aaacctgaca ttccaggccc atgaggggaa agaggatctt ccagctctgc aaaaacaaga
4861 acaaacaaca tcaccgtgaa ttggccttc ctgaaagtga cttatctgac acatctctgt
4921 agccacatgc tttttgggta gaagaagctg gcatgggtg caccccaccc cctagggtcc
4981 ccatgggaaa gggacatgca aggaaacagc acagaacacg aggtggtccc catgtccctg
5041 gcacactagc attccggggg atgaggaatc cccagccctt gaggcagagg tgccgagtga
5101 ctgccatgct tcgcccgtcc gcatgggcgc ttctgtccag ctgcacccga ggccgggggt
5161 ttccctcacc tcggtcttcc caagatggag atgctaacga aactgagaag ggggcgtatg
5221 tttgacgaag gtttgtgcaa gtcaggccct tctggaacac agcagggcct acaacgaggg
5281 gcctttgcga tgggctgtga ggatgggggt ggtgggaaga attggccacg ttggagaccc
5341 catgccaccc caccatggtg agtgctctgt gcctcctgct cacctgtggt gagctgggcg
5401 agctgggcga gctgggcgag ctgggctggg gagagcctgt gaggaccgag aggagaaatg
5461 agaagaagga acaaaaatat tatttctatg taatttatat tttacttatg ccaaattatt
5521 tatgataatt tgccattgct atactgtacc agtgtcaaat gctgcagcct gccaagctgt
5581 gattttgtga ggcttgtccc tatgtaggat gcaccgcagg cccctggcca ctgaaagagt
5641 gtgcagtgga ctgtgggtct cccatatgcg gtgccgccca aggtggctt tgcctcaagc
5701 aacctaccct gatgttttac tcattggaat gttttctccc gattgtggat gacttctttt
5761 ctgatggaga gagtccagga gggatggaaa actcctggat ttaagctcag catcccccac
5821 atgggctttt cgatcatctt caggcctgaa gctgcacgac ctgaagttcg cctgcattta
5881 tcagccctct ttgtgctgct ccttgccacc ttggggttcc tgctggggac catgtgtggt
5941 tgtggcatgt gtgagcagaa gggaggatga ggaaaaagag aagaaacccc ggtactgaca
6001 agctgttttt gagtgccact gtttgccatc atctaagcca ctgaatcaag tgtatttcag
6061 gcttatttca acattccaat gccctggttt tcctgcttga atctgttcgt ggtcaaaggt
6121 ttgggggaat ttgtgaccct ggaacatccc cagagtgaaa gatggagctg ggccacatca
6181 gaataaggcc ttggccccat cctctcacag cctaggtgct ctgcaggcat gctgactgtc
6241 ctgattgcga tccagcccga aattccctcc tctgctttca aaagtcaaat cccccattct
6301 taggccacac tggtgtcaca agctcctgtc agggagctgg ggtttgggaa tgtgctttgt
6361 gaactctgct ttaaagtgag gggccgagga aaacttagaa acaggcagag ttggaagcag
6421 ccaaatcaca gtgggtgttg tgtgtgtgtg cgtgtgtgca tgcgtgcgtg tatgcgtgtg
6481 tgaaagcagg tggaccattc cactttttag ctcctattga tgcaccaaac caagtgcctc
6541 atttctgtgc caaatgtttg ccttggtcgt tgtggacctc cttctctaac ttgcggtggc
6601 atgactgtca ggaggtgctg gcattttcag cagatcctca tgtgttgacc ctgatgtctt
```

-continued

```
6661 tagcagaggc ctctagcatc tcggtttttc atccactgca ggaatgtggc cacagggagc 6721 agaggtttgt actttcccca agaggtcctc atcctgagac ggtctctacc catgtttaac 6781 ccaaagagtg caggccaggt tccttatcct tctgatgaag gatgagagag ctcatttaga 6841 agtcagagca aactagggtc tcagtattga gaaacgcagc ctgccaggga atcacagaga 6901 catcggggtg cccgcgatgg ccctcatgaa gccatgcctc gacggcattc aggaagccct 6961 gcaaacgtgc tttttgaact cattggccag gtgtgatttt tacacaaggt aaacgtggtc 7021 aagggcatcg gggaatttgc tccaagcaga tagctccctc tgaggaacca aaggaagcaa 7081 gtttccacga tttctgaaga gctggtatag gaagtttctt tcttcctttt gtgttacatg 7141 tgcattaaac agaacaagct gtgtgtcatc acagattgta ctgtgggctc agaaaccgtg 7201 agagagcccc caccgtggac accggctcta gggccacagg aaaaggaacg tttccaggca 7261 ttttgtctcc agggctcccg ctggacaggc acgtactgcc ctggggagta aatgcggaga 7321 gttcacgaac tgtgcccaac gcatgttata gccagggtcc tactaactac tcagtaaaag 7381 aacgtattgt tgtattcctc cagtgttaag ctatagccat gttaaaagtc actgtgcatt 7441 tattctcagc atcaaatacc ttgtaacgtc ttctctgcct tgttagtgca tatttttact 7501 tttctgatac tgtaaagaat atatccagta tgtaaatgaa tgttctataa atcttttgta 7561 tagtcatttt ctctgctcct taaatatcat ctctattcag agtataataa aattatgaac 7621 ttggtaaaaa aaaaaaaaaa aaaaaaaaa aaaaaaaaa aaaaaaaaaa aaaaaaaaaa 7681 aaaaaaaaaa aaaaaaa
```

One example of a nucleic acid sequence for human TSPAN12 is available as NCBI accession number NM_012338 (gi: 48255911). This sequence is recited below for easy reference as SEQ ID NO:170.

```
   1 ggccctggct gccgccgctg cctcgtccgg actcggagag gacttgggag ggacagcggc 61 gctgggaggt ggcttagcag agactttcca gcaactgctg cccaggactt tttttttttt 121 ttttcttttt cccaggaggc ggcgacggcg gcggcggggg gagaggaaga gaaagaagcg 181 tctccagctg aagccaatgc agccctccgg ctctccgcga agaagttccc tgccccgatg 241 agccccgcc gtgcgtcccc gactatcccc aggcgggcgt ggggcaccgg gcccagcgcc 301 gacgatcgct gccgttttgc ccttgggagt aggatgtggt gaaaggatgg ggcttctccc 361 ttacggggct cacaatggcc agagaagatt ccgtgaagtg tctgcgctgc ctgctctacg 421 ccctcaatct gctcttttgg ttaatgtcca tcagtgtgtt ggcagtttct gcttggatga 481 gggactacct aaataatgtt ctcactttaa ctgcagaaac gagggtagag gaagcagtca 541 ttttgactta ctttcctgtg gttcatccgg tcatgattgc tgtttgctgt ttccttatca 601 ttgtggggat gttaggatat tgtggaacgg tgaaaagaaa tctgttgctt cttgcatggt 661 actttggaag tttgcttgtc attttctgtg tagaactggc ttgtggcgtt ggacatatg 721 aacaggaact tatggttcca gtacaatggt cagatatggt cactttgaaa gccaggatga 781 caaattatgg attacctaga tatcggtggc ttactcatgc ttggaatttt tttcagagag 841 agtttaagtg ctgtggagta gtatatttca ctgactggtt ggaaatgaca gagatggact 901 ggcccccaga ttcctgctgt gttagagaat cccaggatg ttccaaacag gcccaccagg 961 aagatctcag tgacctttat caagagggtt gtgggaagaa aatgtattcc tttttgagag 1021 gaaccaaaca actgcaggtg ctgaggtttc tgggaatctc cattggggtg acacaaatcc 1081 tggccatgat tctcaccatt actctgctct gggctctgta ttatgataga agggagccgg
```

-continued

```
1141 ggacagacca aatgatgtcc ttgaagaatg acaactctca gcacctgtca tgtccctcag
1201 tagaactgtt gaaaccaagc ctgtcaagaa tctttgaaca cacatccatg gcaaacagct
1261 ttaatacaca ctttgagatg gaggagttat aaaaagaaat gtcacagaag aaaaccacaa
1321 acttgtttta ctggacttgt gaattttttga gtacatacta tgtgtttcag aaatatgtag
1381 aaataaaaat gttgccataa aataacacct aagcatatac tattctatgc tttaaaatga
1441 ggatggaaaa gtttcatgtc ataagtcacc acctggacaa taattgatgc ccttaaaatg
1501 ctgaagacag atgtcatacc cactgtgtag cctgtgtatg acttttactg aacacagtta
1561 tgttttgagg cagcatggtt tgattagcat ttccgcatcc atgcaaacga gtcacatatg
1621 gtgggactgg agccatagta aaggttgatt tacttctacc aactagtata taaagtacta
1681 attaaatgct aacataggaa gttagaaaat actaataact tttattactc agcgatctat
1741 tcttctgatg ctaaataaat tatatatcag aaaactttca atattggtga ctacctaaat
1801 gtgattttttg ctggttacta aaatattctt accacttaaa agagcaagct aacacattgt
1861 cttaagctga tcagggattt tttgtatata agtctgtgtt aaatctgtat aattcagtcg
1921 atttcagttc tgataatgtt aagaataacc attatgaaaa ggaaaatttg tcctgtatag
1981 catcattatt tttagccttt cctgttaata aagcttact attctgtcct gggcttatat
2041 tacacatata actgttattt aaatacttaa ccactaattt tgaaaattac cagtgtgata
2101 cataggaatc attattcaga atgtagtctg gtctttagga agtattaata agaaaatttg
2161 cacataactt agttgattca gaaaggactt gtatgctgtt tttctcccaa atgaagactc
2221 tttttgacac taaacacttt ttaaaaagct tatctttgcc ttctccaaac aagaagcaat
2281 agtctccaag tcaatataaa ttctacagaa aatagtgttc ttttttctcca gaaaaatgct
2341 tgtgagaatc attaaaacat gtgacaattt agagattctt tgttttattt cactgattaa
2401 tatactgtgg caaattacac agattattaa atttttttac aagagtatag tatatttatt
2461 tgaaatggga aaagtgcatt ttactgtatt ttgtgtattt tgtttatttc tcagaatatg
2521 gaaagaaaat taaaatgtgt caataaatat tttctagaga gtaaaaaaaa aaaaaaaaa
```

40

One example of a nucleic acid sequence for human UPP1 is available as NCBI accession number NM_003364 (gi: 31742506). This sequence is recited below for easy reference as SEQ ID NO:171.

```
  1 ggtcagctga gttcgccggc ccagggcagg cggggcccga gcctagcggt aaccccgggg
 61 cagggcgggg ccgctcgcag actccatatg agattcaccct cgcaggtggt tccctcattc
121 gagtgctccg gcgcacagac ccgcgccccg ccgtctgcga gcctcccgag agccgtccct
181 tcgtccggcc ctggagcatt gcgtttgtcg ccggtgtcgc agtgcgagga tggcgccgcg
241 ggtgtagcgg ctctctgcgc aggccgagtg ggcccagaga agcgaggaac tccgcagctc
301 gtcgacacgt ctcgtctcct gtcccaattc agggcttggt gaggtgactc gcggtcgcgg
361 gtgactcgcc ggcaggacac tgcctggaac gcctggagcg cctcccactg cagacgtctg
421 tccgcctcca gccgctctcc tctgacgggt cctgcctcag ttggcggaat ggcggccacg
481 ggagccaatg cagagaaagc tgaaagtcac aatgattgcc ccgtcagact tttaaatcca
541 aacatagcaa aaatgaaaga agatattctc tatcatttca atctcaccac tagcagacac
601 aatttcccag ccttgtttgg agatgtgaag tttgtgtgtg ttggtggaag cccctcccgg
661 atgaaagcct tcatcaggtg cgttggtgca gagctgggcc ttgactgccc aggtagagac
721 tatcccaaca tctgtgcggg aactgaccgc tatgccatgt ataaagtagg accggtgctg
```

```
 781 tctgtcagtc atggtatggg cattccttct atctcaatca tgttgcatga gctcataaag 841 ctgctgtact atgcccggtg ctccaacgtc actatcatcc gcattggcac ttctggtggg 901 ataggtctgg agcccggcac tgtggtcata acagagcagg cagtggatac ctgcttcaag 961 gcagagtttg agcagattgt cctggggaag cgggtcatcc ggaaaacgga ccttaacaag 1021 aagctggtgc aggagctgtt gctgtgttct gcagagctga gcgagttcac cacagtggtg 1081 gggaacacca tgtgcacctt ggacttctat gaagggcaag gccgtctgga tggggctctc 1141 tgctcctaca cggagaagga caagcaggcg tatctggagg cagcctatgc agccggcgtc 1201 cgcaatatcg agatggagtc ctcggtgttt gccgccatgt gcagcgcctg cggcctccaa 1261 gcggccgtgg tgtgtgtcac cctcctgaac cgcctggaag gggaccagat cagcagccct 1321 cgcaatgtgc tcagcgagta ccagcagagg ccgcagcggc tggtgagcta cttcatcaag 1381 aagaaactga gcaaggcctg agcgctgccc tgcacctccg cagacctgct gtgatgactt 1441 gccattaaaa gcattgtcca aaatcccctg ttgtgtggac tttgagcaca ctttacacaa 1501 gaatctagaa aatcagatcg cgattaagag acagagaatc ttggattaac cgcatgggag 1561 atgttcttcc ttttgaagtt tcattggagc attttcaatg atgttagcct gatttggggt 1621 ttcttcaaga acattctacc aaattttttgt actatttcta gggaaatttt tcagacttta 1681 aaattctaat ggtagtcaga tttcatgtca ctaaacaaga aatctgacaa tagtgccagg 1741 aaactaattt cctgatacat taaaaaaatt ccatgcaaaa aaaaaaaaaa aaaaaa
```

One example of a nucleic acid sequence for human NAUK2 is available as NCBI accession number NM_030952 (gi: 13569921). This sequence is recited below for easy reference as SEQ ID NO:172.

```
   1 gtgctttact gcgcgctctg gtactgctgt ggctccccgt cctggtgcgg gacctgtgcc 61 ccgcgcttca gccctccccg cacagcctac tgattcccct gccgcccttg ctcacctcct 121 gctcgccatg gagtcgctgg ttttcgcgcg gcgctccggc cccactccct cggccgcaga 181 gctagcccgg ccgctggcgg aagggctgat caagtcgccc aagcccctaa tgaagaagca 241 ggcggtgaag cggcaccacc acaagcacaa cctgcggcac cgctacgagt tcctggagac 301 cctgggcaaa ggcacctacg gaaggtgaa gaaggcgcgg gagagctcgg ggcgcctggt 361 ggccatcaag tcaatccgga aggacaaaat caaagatgag caagatctga tgcacatacg 421 gagggagatt gagatcatgt catcactcaa ccaccctcac atcattgcca tccatgaagt 481 gtttgagaac agcagcaaga tcgtgatcgt catggagtat gccagccggg gcgaccttta 541 tgactacatc agcgagcggc agcagctcag tgagcgcgaa gctaggcatt tcttccggca 601 gatcgtctct gccgtgcact attgccatca gaacagagtt gtccaccgag atctcaagct 661 ggagaacatc ctcttggatg ccaatgggaa tatcaagatt gctgacttcg gcctctccaa 721 cctctaccat caaggcaagt tcctgcagac attctgtggg agcccctct atgcctcgcc 781 agagattgtc aatgggaagc cctacacagg cccagaggtg acagctggt ccctgggtgt 841 tctcctctac atcctggtgc atggcaccat gcccttgat gggcatgacc ataagatcct 901 agtgaaacag atcagcaacg gggcctaccg ggagccacct aaaccctctg atgcctgtgg 961 cctgatccgg tggctgttga tggtgaaccc caccgccgg gccaccctgg aggatgtggc 1021 cagtcactgg tgggtcaact ggggctacgc caccccgagtg ggagagcagg aggctccgca 1081 tgagggtggg caccctggca gtgactctgc ccgcgcctcc atggctgact ggctccggcg 1141 ttcctcccgc cccctcctgg agaatggggc caaggtgtgc agcttcttca gcagcatgc
```

```
-continued
1201 acctggtggg ggaagcacca ccctggcct ggagcgccag cattcgctca agaagtcccg 1261 caaggagaat gacatggccc agtctctcca cagtgacacg gctgatgaca ctgcccatcg 1321 ccctggcaag agcaacctca agctgccaaa gggcattctc aagaagaagg tgtcagcctc 1381 tgcagaaggg gtacaggagg accctccgga gctcagccca atccctgcga gcccagggca 1441 ggctgccccg ctgctcccca agaagggcat tctcaagaag cccgacagc gcgagtctgg 1501 ctactactcc tctcccgagc ccagtgaatc tggggagctc ttggacgcag cgacgtgtt 1561 tgtgagtggg gatcccaagg agcagaagcc tccgcaagct tcagggctgc tcctccatcg 1621 caaaggcatc ctcaaactca atggcaagtt ctcccagaca gccttggagc tcgcggcccc 1681 caccaccttc ggctccctgg atgaactcgc cccacctcgc cccctggccc gggccagccg 1741 accctcaggg gctgtgagcg aggacagcat cctgtcctct gagtcctttg accagctgga 1801 cttgcctgaa cggctcccag agcccccact gcggggctgt gtgtctgtgg acaacctcac 1861 ggggcttgag gagccccct cagagggccc tggaagctgc ctgaggcgct ggcggcagga 1921 tcctttgggg gacagctgct tttccctgac agactgccag gaggtgacag cgacctaccg 1981 acaggcactg agggtctgct caaagctcac ctgagtggag taggcattgc cccagcccgg 2041 tcaggctctc agatgcagct ggttgcaccc cgagggggaga tgccttctcc cccacctccc 2101 aggacctgca tcccagctca gaaggctgag agggtttgca gtggagccct gagcagggct 2161 ggatatggga agtaggcaaa tgaaatgcgc caagggttca gtgtctgtct tcagccctgc 2221 tgaacgaaga ggatactaaa gagagggaa cgggaatgcc cgcgacagag tccacattgc 2281 ctgtttcttg tgtacatggg ggggccacag agacctggaa agagaactct cccagggccc 2341 atctcctgca tcccatgaat actctgtaca catggtgcct tctaaggaca gctccttccc 2401 tactcattcc ctgcccaagt ggggccagac ctctttacac acacattccc gttcctacca 2461 accaccagaa ctggatggtg gcacccctaa tgtgcatgag gcatcctggg aatggtctgg 2521 agtaacgctt cgttattttt attttattt ttatttattt atttattttt ttgagacgga 2581 gtttcgctct tggtgcccag gctagagtgc aatggcgcga tctcagctca cctcaacctc 2641 cgcctcccgg gttcaagcga ttctcctgcc tcagcctccc tagtagctgg gattacaggc 2701 gcccgccacc atgcccggct aattttgtat ttttagtaga gacagggttt ctccatgttg 2761 gtcaggctgg tctcaaactc ccgacctcag gtgatccacc cacctcggcc tcccaaagtg 2821 ctgggattac aggcgtgagc caccgcgccc cacctaaccc ttccttattt agcctaggag 2881 taagagaaca caatctctgt ttcttcaatg gttctcttcc cttttccatc ctccaaacct 2941 ggcctgagcc tcctgaagtt gctgctgtga atctgaaaga cttgaaaagc ctccgcctgc 3001 tgtgtggact tcatctcaag gggcccagcc tcctctggac tccaccttgg acctcagtga 3061 ctcagaactt ctgcctctaa gctgctctaa agtccagact atggatgtgt tctctaggcc 3121 ttcaggactc tagaatgtcc atatttattt ttatgttctt ggctttgtgt tttaggaaaa 3181 gtgaatcttg ctgtttcaa taatgtgaat gctatgttct gggaaaatcc actatgacat 3241 ctaagttttg tgtacagaga gatattttg caactatttc cacctcctcc cacaaccccc 3301 cacactccac tccacactct tgagtctctt tacctaatgg tctctaccta atggacctcc 3361 gtggccaaaa agtaccatta aaaccagaaa ggtgattgga aaaaaaaaa aaaaaaaaa 3421 aaaaaaaaaa aaaaaaaaaa aaa
```

REFERENCES

1. Mazzaferri E L. Solitary thyroid nodule. 2. Selective approach to management. Postgrad Med. 1981; 70:107-109, 112, 116.
2. Davies L. Welch H G. Increasing incidence of thyroid cancer in the United States, 1973-2002. JAMA. 2006; 295:2164-2167.
3. Arora N, Scognamiglio T, Zhu B, Fahey T J 3rd. Do benign thyroid nodules have malignant potential? An evidence-based review. World J Surg. 2008; 32:1237-1246.
4. Chan J K. Strict criteria should be applied in the diagnosis of encapsulated follicular variant of papillary thyroid carcinoma. Am J Clin Pathol. 2002; 117:16-18.
5. Franc B, de la Salmoniere P, Lange F, et al. Interobserver and intraobserver reproducibility in the histopathology of follicular thyroid carcinoma. Hum Pathol, 2003; 34:1092-1100.
6. Lloyd R V, Erickson L A, Casey M B, et al. Observer variation in the diagnosis of follicular variant of papillary thyroid carcinoma. Am J Surg Pathol. 2004; 28:1336-1340.
7. Saxen E, Franssila K, Bjarnason O, Normann T, Ringertz N. Observer variation in histologic classification of thyroid cancer. Acta Pathol Microbiol Scand [A]. 1978; 86A:483-486.
8. Hirokawa M, Carney J A, Goellner J R, et al. Observer variation of encapsulated follicular lesions of the thyroid gland. Am J Surg Pathol. 2002; 26:1508-1514.
9. Williams E D. Guest editorial: two proposals regarding the terminology of thyroid tumors. Int J Surg Pathol. 2000; 8:181-183.
10. Miettinen M, Karkkainen P. Differential reactivity of HBME-1 and CD15 antibodies in benign and malignant thyroid tumours. Preferential reactivity with malignant tumours, Virchows Arch. 1996; 429(4-5):213-21.9.
11. Cheung C C, Ezzat S, Freeman J L, Rosen I B, Asa S L. Immunohistochemical diagnosis of papillary thyroid carcinoma. Mod Pathol, 2001; 14:338-342.
12. Choi Y L, Kim M K, Suh J W, et al. Immunoexpression of HBME-1, high molecular weight cytokeratin, cytokeratin 19, thyroid transcription factor-1, and E-cadherin in thyroid carcinomas. J Korean Med Sci. 2005; 20:853-859,
13. de Matos P S, Ferreira A P, de Oliveira Facuri F, Assumpcao L V, Metze K, Ward L S, Usefulness of HBME-1, cytokeratin 19 and galectin-3 immunostaining in the diagnosis of thyroid malignancy. Histopathology. 2005; 47:391-401.
14. Papotti M, Rodriguez J, De Pompa R, Bartolazzi A, Rosai J. Galectin-3 and HBME-1 expression in well differentiated thyroid tumors with follicular architecture of uncertain malignant potential. Mod Pathol. 2005; 18:541-546.
15. Prasad M L, Pellegata N S, Huang Y. Nagaraja H N, de la Chapelle A, Kloos R T. Galectin-3, fibronectin-1, CITED-1, HBME1 and cytokeratin-19 immunohistochemistry is useful for the differential diagnosis of thyroid tumors, Mod Pathol. 2005; 18:48-57.
16. Scognamiglio T, Hyjek E, Kao J, Chen Y T. Diagnostic usefulness of HBME1, galectin-3, CK19, and CITED1 and evaluation of their expression in encapsulated lesions with questionable features of papillary thyroid carcinoma. Am J Clin Pathol. 2006; 126:700-708.
17, Fusco A, Chiappetta G, Hui P. et al. Assessment of RET/PTC oncogene activation and clonality in thyroid nodules with incomplete morphological evidence of papillary carcinoma: a search for the early precursors of papillary cancer. Am J Pathol. 2002; 160:2157-2167.
18. Chevillard S, Ugolin N, Vieth P. et al. Gene expression profiling of differentiated thyroid neoplasms: diagnostic and clinical implications. Clin Cancer Res. 2004; 10:6586-6597.
19. Finley D J, Thu B, Barden C B, Fahey T J 3rd. Discrimination of benign and malignant thyroid nodules by molecular profiling. Ann Surg. 2004; 240:425-436; discussion 436-437.
20. Huang Y, Prasad M, Lemon W J, et al. Gene expression in papillary thyroid carcinoma reveals highly consistent profiles. Proc Natl Acad Sci USA. 2001; 98:15044-15049.
21. Mazzanti C, Zeiger M A, Costouros N G; et al. Using gene expression profiling to differentiate benign versus malignant thyroid tumors. Cancer Res. 2004; 64:2898-2903.
22. Lubitz C C, Ugras S K, Kazam J J, et al. Microarray analysis of thyroid nodule fine-needle aspirates accurately classifies benign and malignant lesions. J Mol Diagn. 2006; 8:490-498; quiz 528.
23. Jarzab B, Wiench M, Fujarewicz K, et al. Gene expression profile of papillary thyroid cancer: sources of variability and diagnostic implications. Cancer Res. 2005; 65:1587-1597.
24. Nikiforova M N, Kimura E T, Gandhi M, et al. BRAF mutations in thyroid tumors are restricted to papillary carcinomas and anaplastic or poorly differentiated carcinomas arising from papillary carcinomas. J Clin Endocrinol Metab. 2003; 88:5399-5404.
25. Fontaine J F, Mirebeau-Prunier D, Franc B, et al. Microarray analysis refines classification of non-medullary thyroid tumours of uncertain malignancy. Oncogene. 2008; 27:2228-2236.
26. Frasca F, Nucera C, Pellegriti C, et al. BRAF(V600E) mutation and the biology of papillary thyroid cancer. Endocr. Relat. Cancer. 2008; 15:191-205.
27. Kebebew E, Weng J, Bauer J, et al. The prevalence and prognostic value of BRAF mutation in thyroid cancer. Ann. Surg. 2007; 246:466-470; discussion 470-471.
28. Trovisco V. Vieira de Castro I, Soares P, et al. BRAF mutations are associated with some histological types of papillary thyroid carcinoma. J Pathol. 2004; 202:247-251.
29. Zhu X L, Zhou X Y, Zhu X Z, [BRAFV599E mutation and RET/PTC rearrangements in papillary thyroid carcinoma]. Zhonghua Bing Li Xue Za Zhi. 2005; 34:270-274.
30. Pennelli N, Pennelli G, Merante Boschin I, Pelizzo M R. Thyroid intrafollicular neoplasia (TIN) as a precursor of papillary microcarcinoma. Ann Ital Chir. 2005; 76:219-224.
31. Vasko V V, Gaudart J, Allasia C, et al. Thyroid follicular adenomas may display features of follicular carcinoma and follicular variant of papillary carcinoma. Eur J Endocrinol. 2004; 1.51:779-786.
32. Prasad M L, Huang Y, Pellegata N S, de la Chapelle A, Kloos R T. Hashimoto's thyroiditis with papillary thyroid carcinoma (PTC)-like nuclear alterations express molecular markers of PTC. Histopathology. 2004; 45:39-46.
33. Arif S, Blanes A, Diaz-Cano S J. Hashimoto's thyroiditis shares features with early papillary thyroid carcinoma. Histopathology. 2002; 41:357-362.
34. Nikiforov Y E. RET/PTC rearrangement—a link between Hashimoto's thyroiditis and thyroid cancer . . . or not. J Clin Endocrinol Metab. 2006; 91:2040-2042.
35. Rhoden K J, Unger K, Salvatore G, et al. RET/papillary thyroid cancer rearrangement in nonneoplastic thyrocytes: follicular cells of Hashimoto's thyroiditis share low-level recombination events with a subset of papillary carcinoma, J. Clin Endocrinol Metab. 2006; 91:2414-2423.
36. Rosai J. Handling of thyroid follicular patterned lesions, Endocr Pathol. 2005; 16:279-283.
37. Liu J, Singh B, Tallini G, et al. Follicular variant of papillary thyroid carcinoma: a clinicopathologic study of a problematic entity. Cancer. 2006; 1.07:1255-1264.
38. Vickery A L Jr, Thyroid papillary carcinoma. Pathological and philosophical controversies. Am J Surg Pathol. 1983; 7: 797-807.
39. Evans H L. Encapsulated papillary neoplasms of the thyroid. A study of 14 cases followed for a minimum of 10 years. Am J Surg Pathol. 1987; 11:592-597.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method comprising:
measuring levels of RNA expression of genes consisting of DPP4, SERPINA1, MATN2, and PROS1 in a test tissue or cell sample from a subject by microarray analysis and/or quantitative polymerase chain reaction using primers or probes, wherein at least one of the primers or probes is SEQ ID NO: 18, 33, 42, or 50; and treating the subject for thyroid cancer when thyroid cancer cells in the test tissue or cell sample have at least a 50% increase in the measured levels of RNA expression of genes consisting of DPP4, SERPINA1, and PROS1 and at least a 50% decrease in the measured level of MATN2 RNA expression compared to RNA expression levels of genes consisting of DPP4, SERPINA1, MATN2, and PROS1 in a benign thyroid standard sample.

2. The method of claim 1, further comprising performing fine needle aspiration to obtain the test tissue or cell sample.

3. The method of claim 1, wherein the test tissue sample or cell sample is an unclassified tumor sample.

4. The method of claim 1, wherein the test tissue or cell sample is a formalin fixed test tissue or cell sample.

5. The method of claim 1, wherein the method detects thyroid cancer cells in the test tissue or cell sample with greater than 80% specificity.

6. The method of claim 1, wherein thyroid cancer cells are detected in the test tissue or cell sample when the RNA expression of DPP4, SERPINA1, MATN2, and PROS1 is at least 2.4 fold different as compared to the RNA expression of DPP4, SERPINA1, MATN2, and PROS1 in the benign thyroid standard sample.

7. A method comprising:

obtaining a test thyroid tissue sample from a subject by fine needle aspirate;

measuring levels of RNA expression of genes consisting of DPP4, SERPINA1, MATN2, and PROS1 in the test thyroid tissue sample using primers or probes, wherein at least one of the primers or probes is SEQ ID NO: 18, 33, 42, or 50; and treating the subject for thyroid cancer when at least a 50% increase in the measured levels of RNA expression of genes consisting of DPP4, SERPINA1, and PROS1 and at least a 50% decrease in the measured level of MATN2 RNA expression are detected in the thyroid tissue sample compared to RNA expression levels of genes consisting of DPP4, SERPINA1, MATN2, and PROS1 in a benign thyroid standard sample.

8. The method of claim 7, wherein thyroid cancer cells are detected in the test thyroid tissue sample when the RNA expression of DPP4, SERPINA1, MATN2, and PROS1 is at least 2.4 fold different as compared to the RNA expression of genes consisting of DPP4, SERPINA1, MATN2, and PROS1 in the benign thyroid standard sample.

9. The method of claim 7, wherein the test tissue sample is an unclassified tumor sample.

10. The method of claim 1, further comprising performing reverse transcription polymerase chain reaction, and/or real time polymerase chain reaction, before or in conjunction with microarray analysis and/or quantitative polymerase chain reaction.

* * * * *